(12) United States Patent
Almstetter et al.

(10) Patent No.: US 9,637,491 B2
(45) Date of Patent: *May 2, 2017

(54) PYRAZOLO[4,3-D]PYRIMIDINES AS KINASE INHIBITORS

(71) Applicant: Origenis GmbH, Martinsried (DE)

(72) Inventors: Michael Almstetter, Martinsried (DE); Michael Thormann, Martinsried (DE); Andreas Treml, Martinsried (DE); Nadine Traube, Martinsried (DE)

(73) Assignee: ORIGENIS GMBH, Martinsried (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/436,145

(22) PCT Filed: Oct. 18, 2013

(86) PCT No.: PCT/EP2013/003146
§ 371 (c)(1),
(2) Date: Apr. 16, 2015

(87) PCT Pub. No.: WO2014/060112
PCT Pub. Date: Apr. 24, 2014

(65) Prior Publication Data
US 2015/0266882 A1    Sep. 24, 2015

Related U.S. Application Data

(60) Provisional application No. 61/795,553, filed on Oct. 19, 2012.

(51) Int. Cl.
| | | |
|---|---|---|
| A01N 43/90 | (2006.01) | |
| A61K 31/519 | (2006.01) | |
| C07D 487/00 | (2006.01) | |
| C07D 487/04 | (2006.01) | |
| C07D 519/00 | (2006.01) | |

(52) U.S. Cl.
CPC .......... *C07D 487/04* (2013.01); *A61K 31/519* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 4,469,868 A | 9/1984 | DeWald | 544/251 |
| 5,723,608 A | 3/1998 | Yuan | 544/118 |
| 6,531,475 B1 | 3/2003 | Haddach et al. | 514/250 |

FOREIGN PATENT DOCUMENTS

| | | | | |
|---|---|---|---|---|
| EP | 1348707 A1 | 10/2003 | | |
| EP | 2123654 A1 | 11/2009 | | |
| EP | WO2012/143144 | * 10/2012 | ........... | C07D 487/04 |
| JP | 2007055940 A | 3/2007 | | |
| WO | WO 98/29413 | 7/1998 | | |
| WO | WO 02/074774 A1 | 9/2002 | | |
| WO | WO 2004/058749 A1 | 7/2004 | | |
| WO | WO 2006/120552 A2 | 11/2006 | | |
| WO | WO2006/126718 | * 11/2006 | ........... | C07D 487/04 |
| WO | WO 2007/054778 A1 | 5/2007 | | |
| WO | WO 2009/102468 A1 | 8/2009 | | |
| WO | WO 2010/068258 A1 | 6/2010 | | |
| WO | WO2010/118367 | * 10/2010 | ........... | C07D 487/04 |
| WO | WO2010/129053 | 11/2010 | | |
| WO | WO 2012/143144 A1 | 10/2012 | | |
| WO | WO 2013/155381 A1 | 10/2013 | | |

OTHER PUBLICATIONS

Nichols et al. "Substrate Specificity and Inhibitors of LRRK2, a Protein Kinase Mutated in Parkinson's Disease" Biochemical Journal 2009 424:47-60.
Yuan et al. "3-Aryl Pyrazolo[4,3-*d*]pyrimidine Derivatives: Nonpeptide CRF-1 Antagonists" Bioorganic & Medicinal Chemistry Letters 2002 12:2133-2136.
XP-002716023 File Registry 1394024-12-4: 2H-Pyrazolo [4,3-d]pyrimidine, 7-chloro-5-ethyl-2-methyl; Princeton BioMolecular Research, Inc. Sep. 12, 2012.
XP-002716024 File Registry 1394021-13-6: 2H-Pyrazolo [4,3-d]pyrimidine, 7-chloro-2,5-dimethyl; Princeton BioMolecular Research, Inc. Sep. 12, 2012.
XP-002716025 File Registry 1211533-12-8: 1H-Pyrazolo [4,3-d]pyrimidine, 7-chloro-5-(trifluoromethyl); ArrayChem, Inc. Mar. 18, 2010.
XP-002716026 File Registry 1211532-55-6: 1H-Pyrazolo [4,3-d]pyrimidine-5-ethanamine; ArrayChem, Inc. Mar. 18, 2010.
XP-002716027 File Registry 1211516-67-4: 1H-Pyrazolo [4,3-d]pyrimidine, 7-chloro-5-cyclopentyl; ArrayChem, Inc. Mar. 18, 2010.
Office Communication dated Jun. 19, 2014 from U.S. Appl. No. 13/506,510, filed Apr. 23, 2012.

(Continued)

*Primary Examiner* — Jeffrey H Murray
(74) *Attorney, Agent, or Firm* — Licata & Tyrrell P.C.

(57) ABSTRACT

The present invention relates to novel compounds of formula (I) that are capable of inhibiting one or more kinases, especially SYK (Spleen Tyrosine Kinase), LRRK2 (Leucine-rich repeat kinase 2) and/or MYLK (Myosin light chain kinase) or mutants thereof. The compounds find applications in the treatment of a variety of diseases. These diseases include autoimmune diseases, inflammatory diseases, bone diseases, metabolic diseases, neurological and neurodegenerative diseases, cancer, cardiovascular diseases, allergies, asthma, alzheimer's disease, parkinson's disease, skin disorders, eye diseases, infectious diseases and hormone-related diseases.

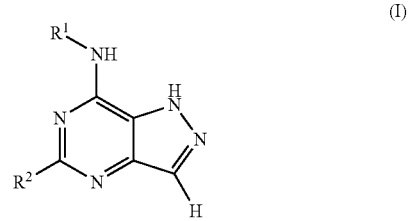

26 Claims, No Drawings

(56) References Cited

OTHER PUBLICATIONS

Office Communication dated Feb. 9, 2015 from U.S. Appl. No. 13/506,510, filed Apr. 23, 2012.
Office Communication dated Jun. 30, 2015 from U.S. Appl. No. 13/506,510, filed Apr. 23, 2012.
EPO Search Report from 11003372.7 dated Aug. 10, 2011.
International Search Report from PCT/EP2012/001737 dated Jul. 2, 2012.
International Search Report from PCT/EP2013/003146 dated Nov. 25, 2013.
Office Communication dated Jul. 28, 2016 from U.S. Appl. No. 13/506,510, filed Apr. 23, 2012.
Office Communication dated Feb. 9, 2016 from U.S. Appl. No. 13/506,510, filed Apr. 23, 2012.
Office Communication dated Nov. 28, 2014 from U.S. Appl. No. 13/506,510, filed Apr. 23, 2012.
Answers 10, 11, 12, 14, 15, 16, 17, 18, 19, 24, 25, 26 and 29 of American Chemical Society on Scientific and Technical Information Network dated Mar. 18-19, 2010 from corresponding Japanese Application JP 2014-50554.

* cited by examiner

PYRAZOLO[4,3-D]PYRIMIDINES AS KINASE INHIBITORS

This patent application is the National Stage of International Application No. PCT/EP2013/003146, filed Oct. 18, 2013, which claims the benefit of priority from U.S. Provisional Patent Application Serial No. 61/795,553 filed Oct. 19, 2012, the teachings of each of which are herein incorporated by reference in their entirety.

The present invention relates to novel compounds that are capable of inhibiting one or more kinases, especially SYK (Spleen Tyrosine Kinase), LRRK2 (Leucine-rich repeat kinase 2) and/or MYLK (Myosin light chain kinase) or mutants thereof. The compounds find applications in the treatment of a variety of diseases. These diseases include autoimmune diseases, inflammatory diseases, bone diseases, metabolic diseases, neurological and neurodegenerative diseases, cancer, cardiovascular diseases, allergies, asthma, alzheimer's disease, parkinson's disease, skin disorders, eye diseases, infectious diseases and hormone-related diseases.

The present invention provides one or more compounds of formula (I):

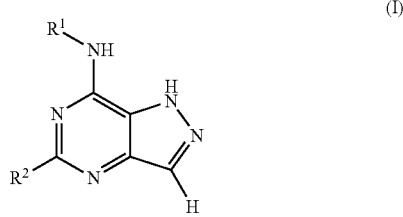

wherein
$R^1$ is an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group; and
$R^2$ is an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group, wherein $R^2$ is bound to the pyrimidine ring of formula (I) via a carbon-carbon bond;
or a pharmaceutically acceptable salt, ester, solvate or hydrate or a pharmaceutically acceptable formulation thereof.

The expression alkyl refers to a saturated, straight-chain or branched hydrocarbon group that contains from 1 to 20 carbon atoms, preferably from 1 to 12 carbon atoms, especially from 1 to 6 (e.g. 1, 2, 3 or 4) carbon atoms, for example a methyl, ethyl, propyl, iso-propyl, n-butyl, iso-butyl, sec-butyl, tert-butyl, n-pentyl, iso-pentyl, n-hexyl, 2,2-dimethylbutyl or n-octyl group.

The expressions alkenyl and alkynyl refer to at least partially unsaturated, straight-chain or branched hydrocarbon groups that contain from 2 to 20 carbon atoms, preferably from 2 to 12 carbon atoms, especially from 2 to 6 (e.g. 2, 3 or 4) carbon atoms, for example an ethenyl (vinyl), propenyl (allyl), iso-propenyl, butenyl, ethinyl, propinyl, butinyl, acetylenyl, propargyl, isoprenyl or hex-2-enyl group. Preferably, alkenyl groups have one or two (especially preferably one) double bond(s), and alkynyl groups have one or two (especially preferably one) triple bond(s).

Furthermore, the terms alkyl, alkenyl and alkynyl refer to groups in which one or more hydrogen atoms have been replaced by a halogen atom (preferably For Cl) such as, for example, a 2,2,2-trichloroethyl or a trifluoromethyl group.

The expression heteroalkyl refers to an alkyl, alkenyl or alkynyl group in which one or more (preferably 1, 2 or 3) carbon atoms have been replaced by an oxygen, nitrogen, phosphorus, boron, selenium, silicon or sulfur atom (preferably by an oxygen, sulfur or nitrogen atom) or by a SO or a $SO_2$ group. The expression heteroalkyl furthermore refers to a carboxylic acid or to a group derived from a carboxylic acid, such as, for example, acyl, acylalkyl, alkoxy-carbonyl, acyloxy, acyloxyalkyl, carboxyalkylamide or alkoxycarbonyloxy.

Preferably, a heteroalkyl group contains from 1 to 12 carbon atoms and from 1 to 4 hetero atoms selected from oxygen, nitrogen and sulphur (especially oxygen and nitrogen). Especially preferably, a heteroalkyl group contains from 1 to 6 (e.g. 1, 2, 3 or 4) carbon atoms and 1, 2 or 3 (especially 1 or 2) hetero atoms selected from oxygen, nitrogen and sulphur (especially oxygen and nitrogen). The term $C_1$-$C_6$ heteroalkyl refers to a heteroalkyl group containing from 1 to 6 carbon atoms and 1, 2 or 3 heteroatoms selected from O, S and/or N (especially O and/or N). The term $C_1$-$C_4$ heteroalkyl refers to a heteroalkyl group containing from 1 to 4 carbon atoms and 1, 2 or 3 heteroatoms selected from O, S and/or N (especially O and/or N). Furthermore, the term heteroalkyl refers to groups in which one or more hydrogen atoms have been replaced by a halogen atom (preferably F or Cl).

Examples of heteroalkyl groups are groups of formulae: $R^a$—O—$Y^a$—, $R^a$—SO—$Y^a$—, $R^a$—$SO_2$—$Y^a$—, $R^a$—N($R^b$)—$Y^a$—, $R^a$—CO—$Y^a$—, $R^a$—O—CO—$Y^a$—, $R^a$—CO—O—$Y^a$—, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—, $R^a$—N($R^b$)—C(NR$^d$)—N($R^c$)—$Y^a$—, $R^a$—CS—$Y^a$—, $R^a$—O—CS—$Y^a$—, $R^a$—CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—CO—S—$Y^a$—, $R^a$—S—CO—N($R^b$)—$Y^a$—, $R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, wherein $R^a$ being a hydrogen atom, a $C_1$-$C_6$ alkyl, a $C_2$-$C_6$ alkenyl or a $C_2$-$C_6$ alkynyl group; $R^b$ being a hydrogen atom, a $C_1$-$C_6$ alkyl, a $C_2$-$C_6$ alkenyl or a $C_2$-$C_6$ alkynyl group; $R^c$ being a hydrogen atom, a $C_1$-$C_6$ alkyl, a $C_2$-$C_6$ alkenyl or a $C_2$-$C_6$ alkynyl group; $R^d$ being a hydrogen atom, a $C_1$-$C_6$ alkyl, a $C_2$-$C_6$ alkenyl or a $C_2$-$C_6$ alkynyl group and $Y^a$ being a bond, a $C_1$-$C_6$ alkylene, a $C_2$-$C_6$ alkenylene or a $C_2$-$C_6$ alkynylene group, wherein each heteroalkyl group contains at least one carbon atom and one or more hydrogen atoms may be replaced by fluorine or chlorine atoms.

Specific examples of heteroalkyl groups are methoxy, trifluoromethoxy, ethoxy, n-propyloxy, isopropyloxy, butoxy, tert-butyloxy, methoxymethyl, ethoxymethyl, —$CH_2CH_2OH$, —$CH_2OH$, —$SO_2Me$, methoxyethyl, 1-methoxyethyl, 1-ethoxyethyl, 2-methoxyethyl or 2-ethoxyethyl, methylamino, ethylamino, propylamino, isopropylamino, dimethylamino, diethylamino, iso-propylethylamino, methylamino methyl, ethylamino methyl, diisopropylamino ethyl, methylthio, ethylthio, isopropylthio, enol ether, dimethylamino methyl, dimethylamino ethyl, acetyl, propionyl, butyryloxy, acetyloxy, methoxycarbonyl, ethoxycarbonyl, propionyloxy, acetylamino or propionylamino, carboxymethyl, carboxyethyl or carboxypropyl, N-ethyl-N-methylcarbamoyl or N-methylcarbamoyl. Further examples of heteroalkyl groups are nitrile, isonitrile, cyanate, thiocyanate, isocyanate, isothiocyanate and alkylnitrile groups.

The expression cycloalkyl refers to a saturated or partially unsaturated (for example, a cycloalkenyl group) cyclic group that contains one or more rings (preferably 1 or 2), and contains from 3 to 14 ring carbon atoms, preferably from 3 to 10 (especially 3, 4, 5, 6 or 7) ring carbon atoms. The expression cycloalkyl refers furthermore to groups in which one or more hydrogen atoms have been replaced by fluorine, chlorine, bromine or iodine atoms or by OH, $=$O, SH, $=$S, $NH_2$, $=$NH, $N_3$ or $NO_2$ groups, thus, for example, cyclic ketones such as, for example, cyclohexanone, 2-cyclohexenone or cyclopentanone. Further specific examples of cycloalkyl groups are a cyclopropyl, cyclobutyl, cyclopentyl, spiro[4,5]decanyl, norbornyl, cyclohexyl, cyclopentenyl, cyclohexadienyl, decalinyl, bicyclo[4.3.0]nonyl, tetraline, cyclopentylcyclohexyl, fluorocyclohexyl or cyclohex-2-enyl group.

The expression heterocycloalkyl refers to a cycloalkyl group as defined above in which one or more (preferably 1, 2 or 3) ring carbon atoms have been replaced by an oxygen, nitrogen, silicon, selenium, phosphorus or sulfur atom (preferably by an oxygen, sulfur or nitrogen atom) or a SO group or a $SO_2$ group. A heterocycloalkyl group has preferably 1 or 2 ring(s) containing from 3 to 10 (especially 3, 4, 5, 6 or 7) ring atoms (preferably secected from C, O, N and S). The expression heterocycloalkyl refers furthermore to groups that are substituted by fluorine, chlorine, bromine or iodine atoms or by OH, $=$O, SH, $=$S, $NH_2$, $=$NH, $N_3$ or $NO_2$ groups. Examples are a piperidyl, prolinyl, imidazolidinyl, piperazinyl, morpholinyl, urotropinyl, pyrrolidinyl, tetrahydrothiophenyl, tetrahydropyranyl, tetrahydrofuryl or 2-pyrazolinyl group and also lactames, lactones, cyclic imides and cyclic anhydrides.

The expression alkylcycloalkyl refers to groups that contain both cycloalkyl and also alkyl, alkenyl or alkynyl groups in accordance with the above definitions, for example alkylcycloalkyl, cycloalkylalkyl, alkylcycloalkenyl, alkenylcycloalkyl and alkynylcycloalkyl groups. An alkylcycloalkyl group preferably contains a cycloalkyl group that contains one or two rings having from 3 to 10 (especially 3, 4, 5, 6 or 7) ring carbon atoms, and one or two alkyl, alkenyl or alkynyl groups (especially alkyl groups) having 1 or 2 to 6 carbon atoms.

The expression heteroalkylcycloalkyl refers to alkylcycloalkyl groups as defined above in which one or more (preferably 1, 2 or 3) carbon atoms have been replaced by an oxygen, nitrogen, silicon, selenium, phosphorus or sulfur atom (preferably by an oxygen, sulfur or nitrogen atom) or a SO group or a $SO_2$ group. A heteroalkylcycloalkyl group preferably contains 1 or 2 rings having from 3 to 10 (especially 3, 4, 5, 6 or 7) ring atoms, and one or two alkyl, alkenyl, alkynyl or heteroalkyl groups (especially alkyl or heteroalkyl groups) having from 1 or 2 to 6 carbon atoms. Examples of such groups are alkylheterocycloalkyl, alkylheterocycloalkenyl, alkenylheterocycloalkyl, alkynylheterocycloalkyl, heteroalkylcycloalkyl, heteroalkylheterocycloalkyl and heteroalkylheterocycloalkenyl, the cyclic groups being saturated or mono-, di- or tri-unsaturated.

The expression aryl refers to an aromatic group that contains one or more rings containing from 6 to 14 ring carbon atoms, preferably from 6 to 10 (especially 6) ring carbon atoms. The expression aryl refers furthermore to groups that are substituted by fluorine, chlorine, bromine or iodine atoms or by OH, SH, $NH_2$, $N_3$ or $NO_2$ groups. Examples are the phenyl, naphthyl, biphenyl, 2-fluorophenyl, anilinyl, 3-nitrophenyl or 4-hydroxyphenyl group.

The expression heteroaryl refers to an aromatic group that contains one or more rings containing from 5 to 14 ring atoms, preferably from 5 to 10 (especially 5 or 6 or 9 or 10) ring atoms, and contains one or more (preferably 1, 2, 3 or 4) oxygen, nitrogen, phosphorus or sulfur ring atoms (preferably O, S or N). The expression heteroaryl refers furthermore to groups that are substituted by fluorine, chlorine, bromine or iodine atoms or by OH, SH, $N_3$, $NH_2$ or $NO_2$ groups. Examples are pyridyl (e.g. 4-pyridyl), imidazolyl (e.g. 2-imidazolyl), phenylpyrrolyl (e.g. 3-phenylpyrrolyl), thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, isoquinolinyl, pyrrolyl, purinyl, carbazolyl, acridinyl, pyrimidyl, 2,3'-bifuryl, pyrazolyl (e.g. 3-pyrazolyl) and isoquinolinyl groups.

The expression aralkyl refers to groups containing both aryl and also alkyl, alkenyl, alkynyl and/or cycloalkyl groups in accordance with the above definitions, such as, for example, arylalkyl, arylalkenyl, arylalkynyl, arylcycloalkyl, arylcycloalkenyl, alkylarylcycloalkyl and alkylarylcycloalkenyl groups. Specific examples of aralkyls are toluene, xylene, mesitylene, styrene, benzyl chloride, o-fluorotoluene, 1H-indene, tetraline, dihydronaphthalene, indanone, phenylcyclopentyl, cumene, cyclohexylphenyl, fluorene and indane. An aralkyl group preferably contains one or two aromatic ring systems (1 or 2 rings) containing from 6 to 10 carbon atoms and one or two alkyl, alkenyl and/or alkynyl groups containing from 1 or 2 to 6 carbon atoms and/or a cycloalkyl group containing 5 or 6 ring carbon atoms.

The expression heteroaralkyl refers to an aralkyl group as defined above in which one or more (preferably 1, 2, 3 or 4) carbon atoms have been replaced by an oxygen, nitrogen, silicon, selenium, phosphorus, boron or sulfur atom (preferably oxygen, sulfur or nitrogen), that is to say to groups containing both aryl or heteroaryl, respectively, and also alkyl, alkenyl, alkynyl and/or heteroalkyl and/or cycloalkyl and/or heterocycloalkyl groups in accordance with the above definitions. A heteroaralkyl group preferably contains one or two aromatic ring systems (1 or 2 rings) containing from 5 or 6 to 10 ring carbon atoms and one or two alkyl, alkenyl and/or alkynyl groups containing 1 or 2 to 6 carbon atoms and/or a cycloalkyl group containing 5 or 6 ring carbon atoms, wherein 1, 2, 3 or 4 of these carbon atoms have been replaced by oxygen, sulfur or nitrogen atoms.

Examples are arylheteroalkyl, arylheterocycloalkyl, arylheterocycloalkenyl, arylalkylheterocycloalkyl, arylalkenylheterocycloalkyl, arylalkynylheterocycloalkyl, arylalkylheterocycloalkenyl, heteroarylalkyl, heteroarylalkenyl, heteroarylalkynyl, heteroarylheteroalkyl, heteroarylcycloalkyl, heteroarylcycloalkenyl, heteroarylheterocycloalkyl, heteroarylheterocycloalkenyl, heteroarylalkylcycloalkyl, heteroarylalkylheterocycloalkenyl, heteroarylheteroalkylcycloalkyl, heteroarylheteroalkylcycloalkenyl and heteroarylheteroalkylhetero-cycloalkyl groups, the cyclic groups being saturated or mono-, di- or tri-unsaturated. Specific examples are a tetrahydroisoquinolinyl, benzoyl, 2- or 3-ethylindolyl, 4-methylpyridino, 2-, 3- or 4-methoxyphenyl, 4-ethoxyphenyl, 2-, 3- or 4-carboxyphenylalkyl group.

As already stated above, the expressions cycloalkyl, heterocycloalkyl, alkylcycloalkyl, heteroalkylcycloalkyl, aryl, heteroaryl, aralkyl and heteroaralkyl also refer to groups that are substituted by fluorine, chlorine, bromine or iodine atoms or by OH, =O, SH, =S, $NH_2$, =NH, $N_3$ or $NO_2$ groups.

The expression "optionally substituted" especially refers to groups that are optionally substituted by fluorine, chlorine, bromine or iodine atoms or by OH, =O, SH, =S, $NH_2$, =NH, $N_3$ or $NO_2$ groups. This expression refers furthermore to groups that may be substituted by one, two, three or more unsubstituted $C_1$-$C_{10}$ alkyl, $C_2$-$C_{10}$ alkenyl, $C_2$-$C_{10}$ alkynyl, $C_1$-$C_{10}$ heteroalkyl, $C_3$-$C_{18}$ cycloalkyl, $C_2$-$C_{17}$ heterocycloalkyl, $C_4$-$C_{20}$ alkylcycloalkyl, $C_2$-$C_{19}$ heteroalkylcycloalkyl, $C_6$-$C_{18}$ aryl, $C_1$-$C_{17}$ heteroaryl, $C_7$-$C_{20}$ aralkyl or $C_2$-$C_{19}$ heteroaralkyl groups. This expression refers furthermore especially to groups that may be substituted by one, two, three or more unsubstituted $C_1$-$C_6$ alkyl, $C_2$-$C_6$ alkenyl, $C_2$-$C_6$ alkynyl, $C_1$-$C_6$ heteroalkyl, $C_3$-$C_{10}$ cycloalkyl, $C_2$-$C_9$ heterocycloalkyl, $C_7$-$C_{12}$ alkylcycloalkyl, $C_2$-$C_{11}$ heteroalkylcycloalkyl, $C_6$-$C_{10}$ aryl, $C_1$-$C_9$ heteroaryl, $C_7$-$C_{12}$ aralkyl or $C_2$-$C_{11}$ heteroaralkyl groups.

Preferred substituents are F, Cl, Br, OH, SH, =O, $NH_2$, $C_{1-4}$ alkyl, $C_{1-4}$ heteroalkyl cyclopropyl, $SF_5$, NO and $NO_2$.

Moreover preferred substituents are F, Cl, Br, OH, SH, =O, $NH_2$, $C_{1-4}$ alkyl (e.g. methyl, ethyl, t-butyl), $NMe_2$, $CONH_2$, $CH_2NMe_2$, $NHSO_2Me$, $C(CH_3)_2CN$, COMe, OMe, SMe, COOMe, COOEt, $CH_2COOH$, $OCH_2COOH$, COOH, SOMe, $SO_2Me$, cyclopropyl, $SO_2NH_2$, $SO_2NHMe$, $SO_2CH_2CH_2OH$, $NHCH_2CH_2OH$, $CH_2CH_2OCH_3$, $SF_5$, $SO_2NMe_2$, NO, $NO_2$, $OCF_3$, $SO_2CF_3$, CN or $CF_3$.

Especially preferred substituents are F, Cl, Br, Me, OMe, CN or $CF_3$.

According to a preferred embodiment, all alkyl, alkenyl, alkynyl, heteroalkyl, aryl, heteroaryl, cycloalkyl, heterocycloalkyl, alkylcycloalkyl, heteroalkylcycloalkyl, aralkyl and heteroaralkyl groups described herein may optionally be substituted.

When an aryl, heteroaryl, cycloalkyl, alkylcycloalkyl, heteroalkylcycloalkyl, heterocycloalkyl, aralkyl or heteroaralkyl group contains more than one ring, these rings may be bonded to each other via a single or double bond or these rings may be annulated.

Preferred are compounds of formula (I) wherein $R^1$ is an aryl, heteroaryl, cycloalkyl, heterocycloalkyl, alkylcycloalkyl, heteroalkylcycloalkyl, aralkyl or heteroaralkyl group, all of which may optionally be substituted.

Further preferred are compounds of formula (I) wherein $R^1$ is an aryl, heteroaryl, $CH_2$-aryl or $CH_2$-heteroaryl group, all of which may optionally be substituted.

Moreover preferred are compounds of formula (I) wherein $R^1$ is an optionally substituted phenyl or naphthyl group or an optionally substituted heteroaryl group having one or two rings containing 5, 6, 7, 8, 9 or 10 ring atoms, or an optionally substituted arylheterocycloalkyl, heteroarylcycloalkyl or heteroarylheterocycloalkyl group containing two or three rings (especially two annullated rings) and 9 to 20 (especially 9 or 10) ring atoms. Preferably, the heteroatoms are selected from S, O and N, especially from N and O. Further preferably, the number of heteroatoms is 1 to 6 (especially 1, 2, 3 or 4).

Especially preferably, $R^1$ is an optionally substituted phenyl group or an optionally substituted heteroaryl group having one ring containing 5 or 6 ring atoms. Preferably this phenyl or heteroaryl group is substituted by one or more (especially one) $C_1$-$C_{10}$ alkyl, $C_2$-$C_{10}$ alkenyl, $C_2$-$C_{10}$ alkynyl, $C_1$-$C_{10}$ heteroalkyl, $C_3$-$C_{18}$ cycloalkyl, $C_2$-$C_{17}$ heterocycloalkyl, $C_4$-$C_{20}$ alkylcycloalkyl, $C_2$-$C_{19}$ heteroalkylcycloalkyl, $C_6$-$C_{18}$ aryl, $C_1$-$C_{17}$ heteroaryl, $C_7$-$C_{20}$ aralkyl or $C_2$-$C_{19}$ heteroaralkyl group(s). Preferably, the heteroatoms are selected from S, O and N, especially from N and O. Especially preferably, the phenyl or heteroaryl group is substituted by one or more (especially one) $C_1$-$C_6$ alkyl, $C_2$-$C_6$ alkenyl, $C_2$-$C_6$ alkynyl, $C_1$-$C_6$ heteroalkyl, $C_3$-$C_{10}$ cycloalkyl, $C_2$-$C_9$ heterocycloalkyl, $C_7$-$C_{12}$ alkylcycloalkyl, $C_2$-$C_{11}$ heteroalkylcycloalkyl, $C_6$-$C_{10}$ aryl, $C_1$-$C_9$ heteroaryl, $C_7$-$C_{12}$ aralkyl or $C_2$-$C_{11}$ heteroaralkyl group(s). Preferably, the heteroatoms are selected from S, O and N, especially from N and O.

Further preferred are compounds of formula (I) wherein $R^1$ is a group of formula —$CH_2$—Ar wherein Ar is an optionally substituted phenyl or naphthyl group or an optionally substituted heteroaryl group having one or two rings containing 5, 6, 7, 8, 9 or 10 ring atoms, or an optionally substituted arylheterocycloalkyl, heteroarylcycloalkyl or heteroarylheterocycloalkyl group containing two or three rings (especially two annullated rings) and 9 to 20 (especially 9 or 10) ring atoms. Preferably, the heteroatoms are selected from S, O and N, especially from N and O. Further preferably, the number of heteroatoms is 1 to 6 (especially 1, 2, 3 or 4).

Especially preferably, Ar is an optionally substituted phenyl group or an optionally substituted heteroaryl group having one ring containing 5 or 6 ring atoms. Preferably this phenyl or heteroaryl group is substituted by one or more (especially one) $C_1$-$C_{10}$ alkyl, $C_2$-$C_{10}$ alkenyl, $C_2$-$C_{10}$ alkynyl, $C_1$-$C_{10}$ heteroalkyl, $C_3$-$C_{18}$ cycloalkyl, $C_2$-$C_{17}$ heterocycloalkyl, $C_4$-$C_{20}$ alkylcycloalkyl, $C_2$-$C_{19}$ heteroalkylcycloalkyl, $C_6$-$C_{18}$ aryl, $C_1$-$C_{17}$ heteroaryl, $C_7$-$C_{20}$ aralkyl or $C_2$-$C_{19}$ heteroaralkyl group(s). Preferably, the heteroatoms are selected from S, O and N, especially from N and O. Especially preferably the phenyl or heteroaryl group is substituted by one or more (especially one) $C_1$-$C_6$ alkyl, $C_2$-$C_6$ alkenyl, $C_2$-$C_6$ alkynyl, $C_1$-$C_6$ heteroalkyl, $C_3$-$C_{10}$ cycloalkyl, $C_2$-$C_9$ heterocycloalkyl, $C_7$-$C_{12}$ alkylcycloalkyl, $C_2$-$C_{11}$ heteroalkylcycloalkyl, $C_6$-$C_{10}$ aryl, $C_1$-$C_9$ heteroaryl, $C_7$-$C_{12}$ aralkyl or $C_2$-$C_{11}$ heteroaralkyl group(s). Preferably, the heteroatoms are selected from S, O and N, especially from N and O.

Further preferably, $R^1$ is a group of formula $X^1$-$L^1$-$Y^1$ or a group of formula $X^1$-$L^1$-yl-$L^2$-$Z^1$ wherein $X^1$ is an optionally substituted phenyl group or an optionally substituted heteroaryl group containing 5 or 6 ring atoms and 1, 2, 3 or 4 heteroatoms selected from O, S and N;

$L^1$ is a bond or a group of formula —$CH_2$—, —C(=O)—, —SO—, —$SO_2$—, —NH—C(=O)—, —C(=O)—NH—, —C(=O)—O—, —O—C(=O)—, —NH—C(=O)—O—, —O—C(=O)—NH—, —NH—$SO_2$—NH—, —$CH_2$—NH—$CH_2$—, —NH—$SO_2$—, —$SO_2$—NH— or —NH—C(=O)—NH— (preferably, $L^1$ is a bond or a group of formula —$CH_2$—, —C(=O)—, —$SO_2$— or —NH—C(=O)—NH—);

$Y^1$ is an optionally substituted phenyl group, an optionally substituted heteroaryl group containing 5 or 6 ring atoms and 1, 2, 3 or 4 heteroatoms selected from O, S and N, an optionally substituted $C_3$-$C_7$ cycloalkyl group or an optionally substituted heterocycloalkyl group containing 3, 4, 5, 6 or 7 ring atoms and 1, 2, 3 or 4 heteroatoms selected from O, S and N (preferably, $Y^1$ is an optionally substituted $C_3$-$C_7$ cycloalkyl group or an optionally substituted heterocycloalkyl group containing 3, 4, 5, 6 or 7 ring atoms and 1, 2, 3 or 4 heteroatoms selected from O, S and N);

L² is a bond or a group of formula —CH₂—, —C(=O)—, —SO—, —SO₂—, —NH—C(=O)—, —C(=O)—NH—; —C(=O)—O—, —O—C(=O)—, —NH—C(=O)—O—, —O—C(=O)—NH—, —NH—SO₂—NH—, —CH₂—NH—CH₂—, —NH—SO₂—, —SO₂—NH— or —NH—C(=O)—NH— (preferably, L² is a bond or a group of formula —CH₂—, —C(=O)—, —SO₂— or NH—C(=O)—NH—; especially preferably, L² is a bond); and Z¹ is an optionally substituted phenyl group, an optionally substituted heteroaryl group containing 5 or 6 ring atoms and 1, 2, 3 or 4 heteroatoms selected from O, S and N, an optionally substituted C₃-C₇ cycloalkyl group or an optionally substituted heterocycloalkyl group containing 3, 4, 5, 6 or 7 ring atoms and 1, 2, 3 or 4 heteroatoms selected from O, S and N (preferably, Z¹ is an optionally substituted C₃-C₇ cycloalkyl group or an optionally substituted heterocycloalkyl group containing 3, 4, 5, 6 or 7 ring atoms and 1, 2, 3 or 4 heteroatoms selected from O, S and N).

Especially preferred are compounds of formula (I) wherein, R¹ is selected from the following groups: 4-morpholinophenyl; 4-(4-methylpiperazino)phenyl; 6-(4-methylpiperazino)-3-pyridyl; 4-piperidinophenyl; 4-pyrrolidinophenyl; 4-carboxyphenyl; 4-(dimethylamino)phenyl; p-amino-carbonylphenyl; 4-cyanophenyl; 4,5 dimethoxyphenyl; 3-hydroxyphenyl; 3-aminophenyl; 3-anisyl; 1,6-benzomorpholinylene; 6-indazolyl; 2H-1,4-benzoxazin-3-on-6-yl; 2-methyl-benzimidazol-6-yl; 6-benzotriazolyl; 5-cyclopropylpyrazol-3-yl; 3-pyrazolyl; 2-aminocyclohexyl; 4-chlorophenyl; 3-dimethylaminophenyl; 3-(aminocarbonyl)phenyl; 2-(aminocarbonyl)phenyl; 4-(N-ethylpiperazino)phenyl; 4-(4-cyclopropyl-1-piperazinyl)phenyl; 4-dimethylaminomethyl-phenyl; 4-(4-methylpiperazinomethyl)phenyl and 4-pyrrolidinomethyl-phenyl.

Especially preferably, R¹ is selected from the following groups:

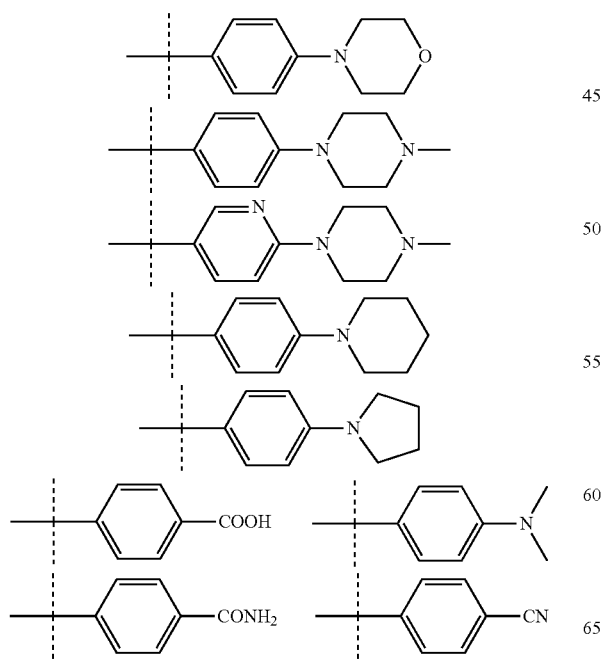

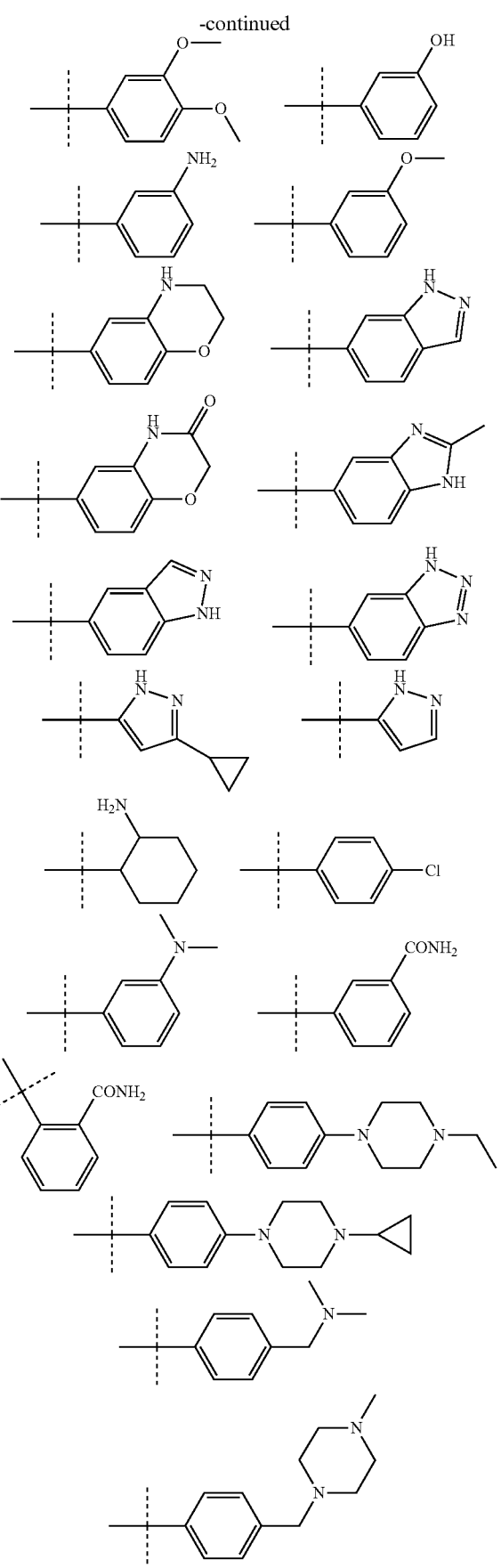

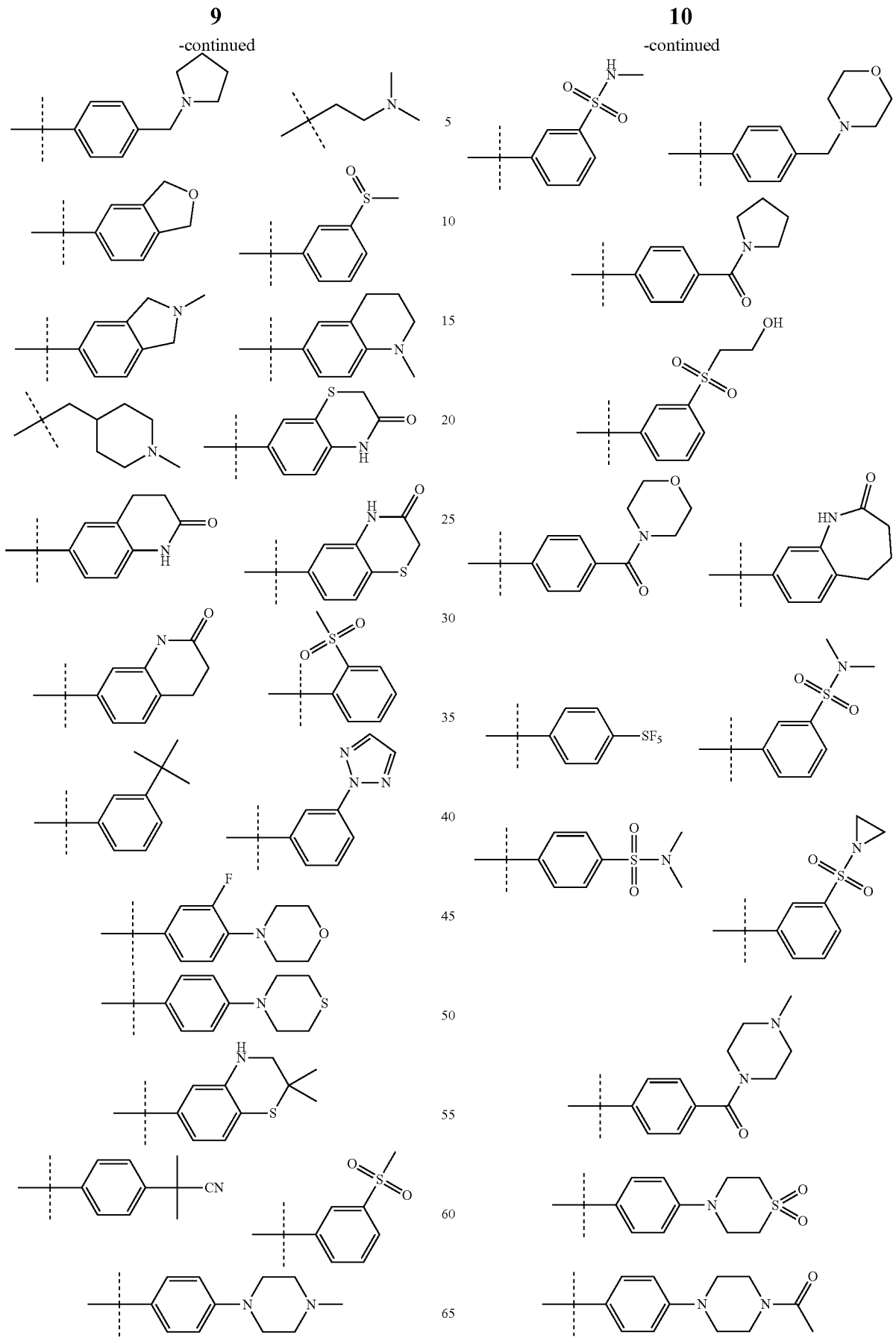

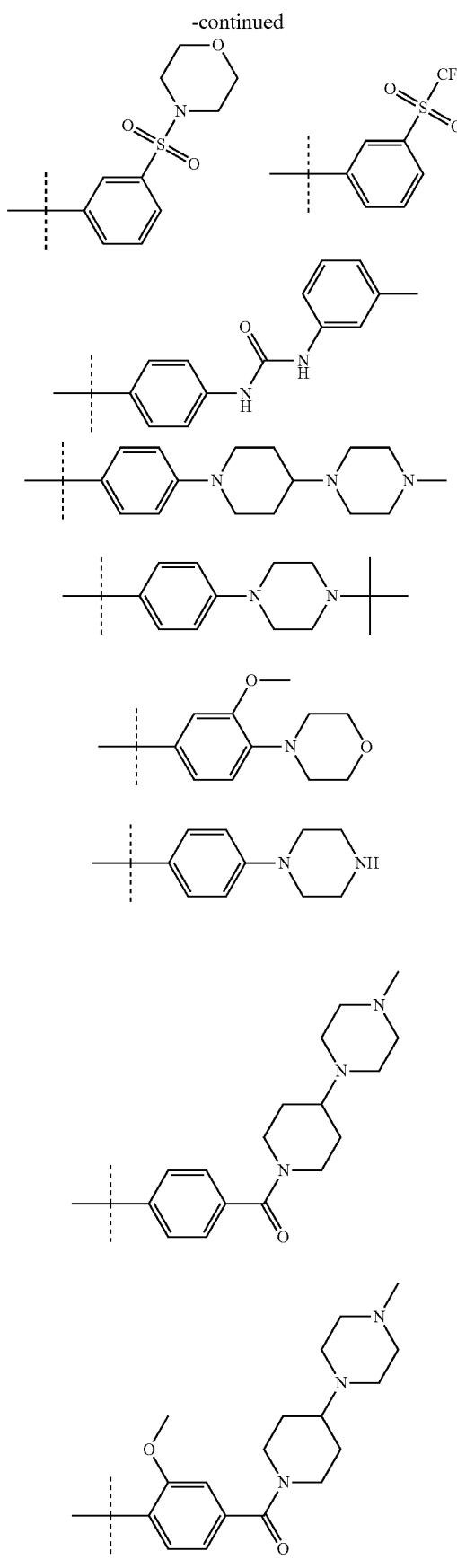
Moreover especially preferably, $R^1$ is selected from the following groups:
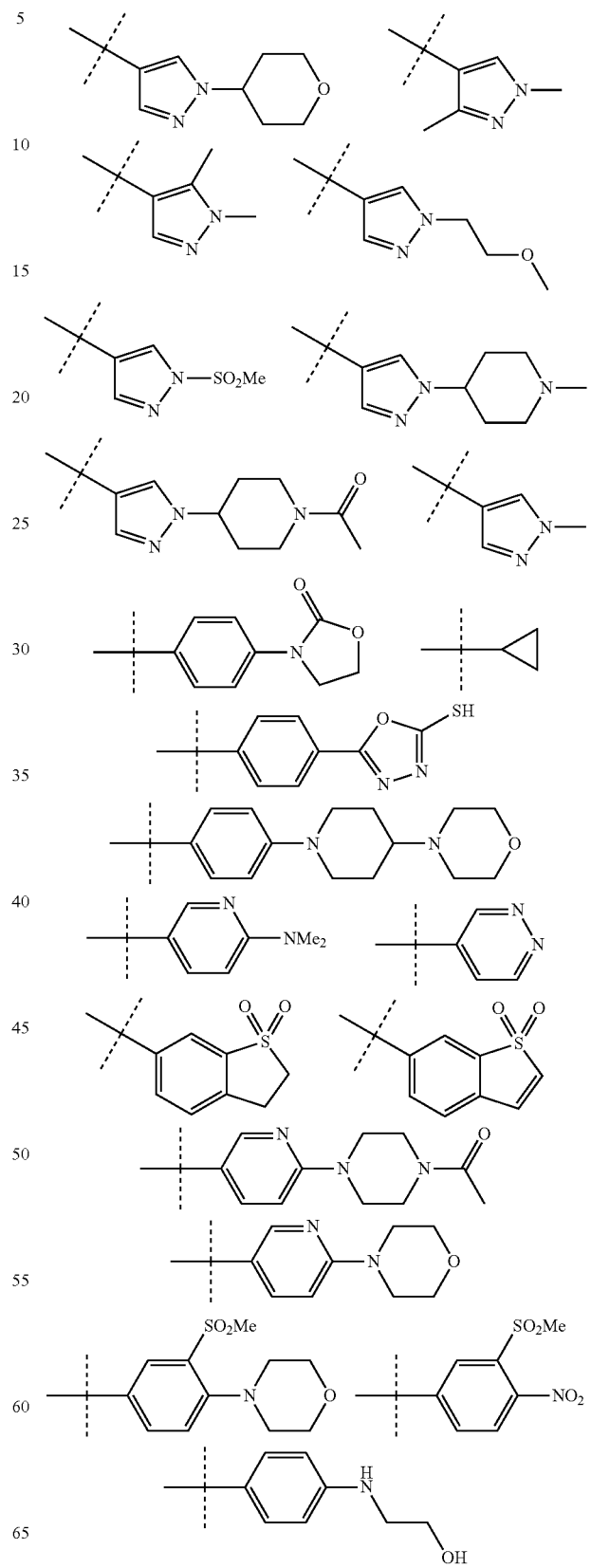

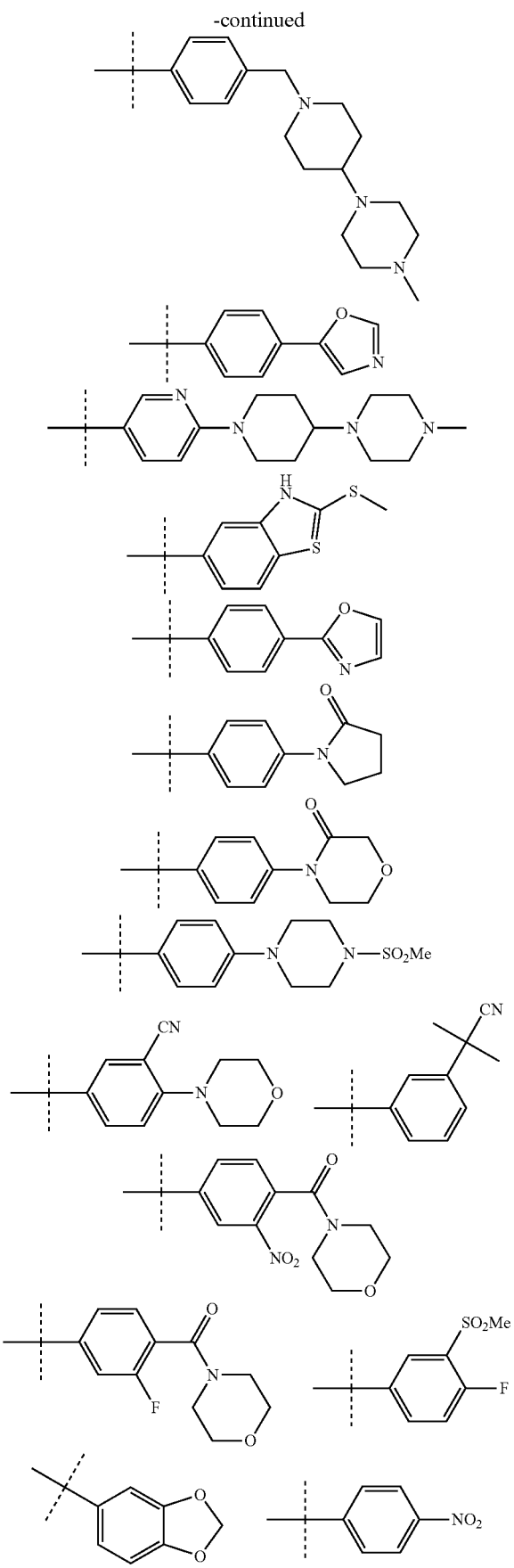
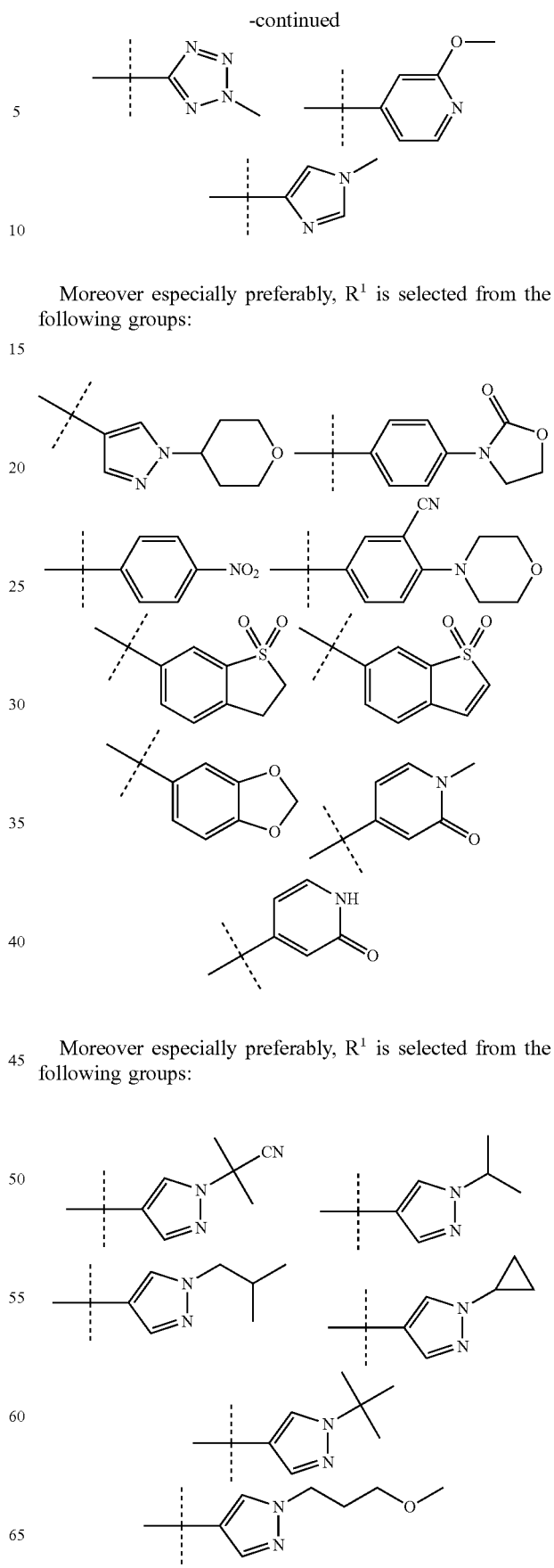
Moreover especially preferably, $R^1$ is selected from the following groups:
Moreover especially preferably, $R^1$ is selected from the following groups:

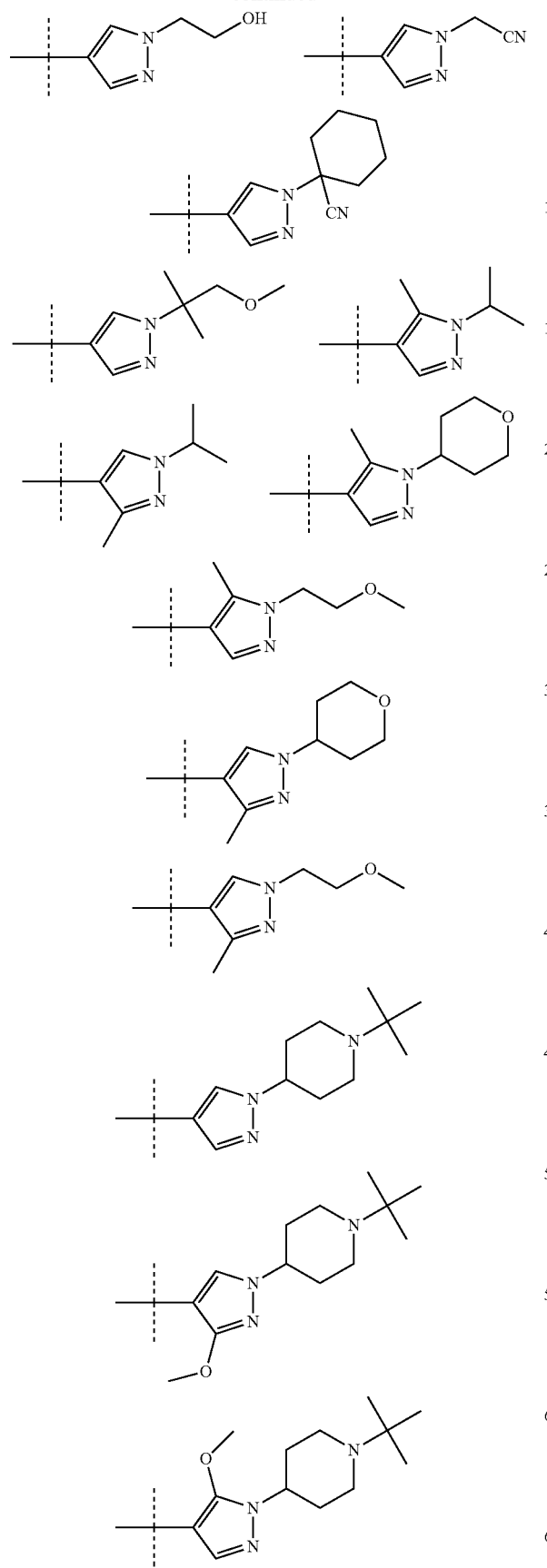
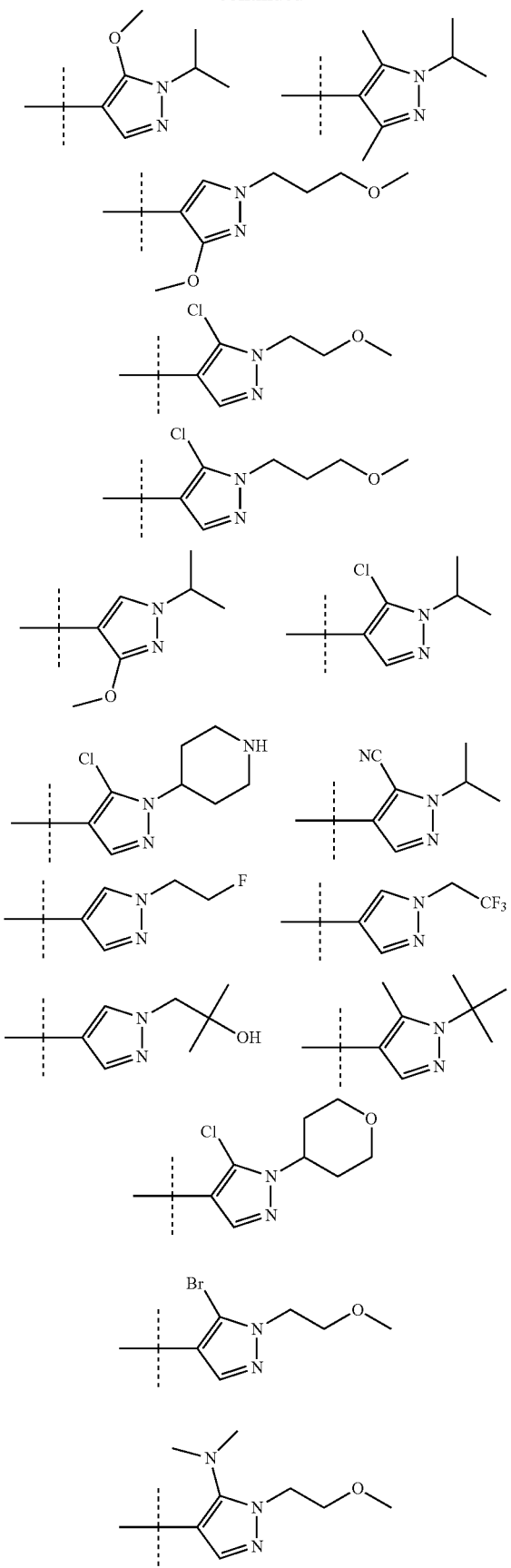

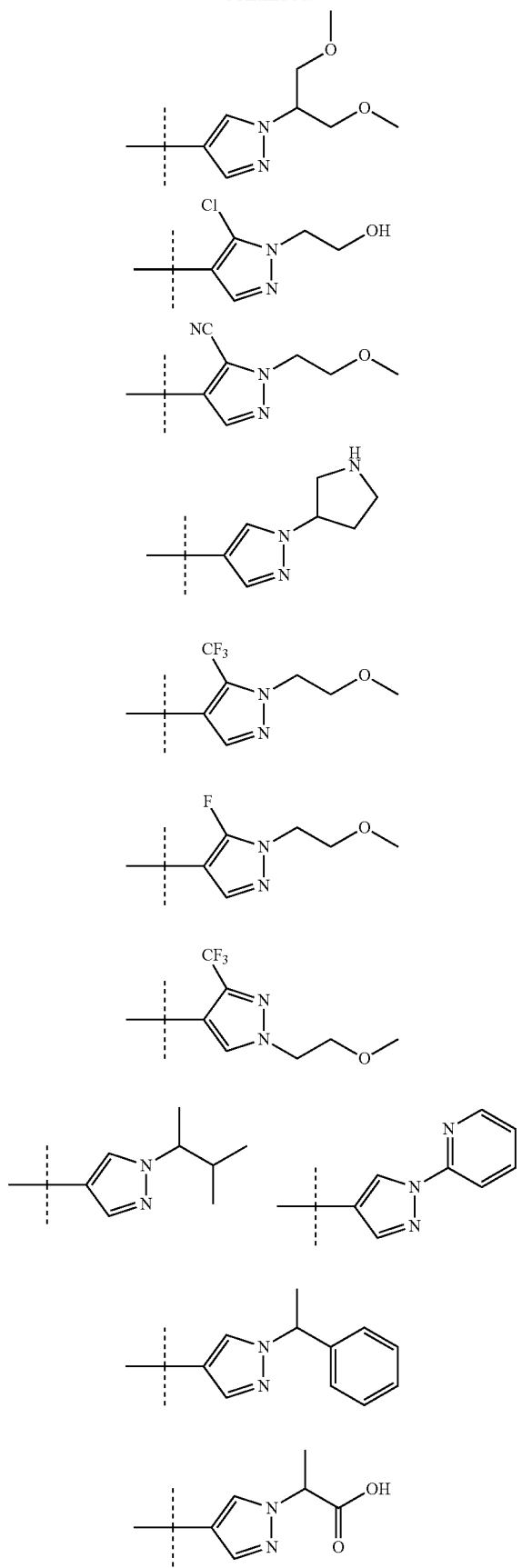
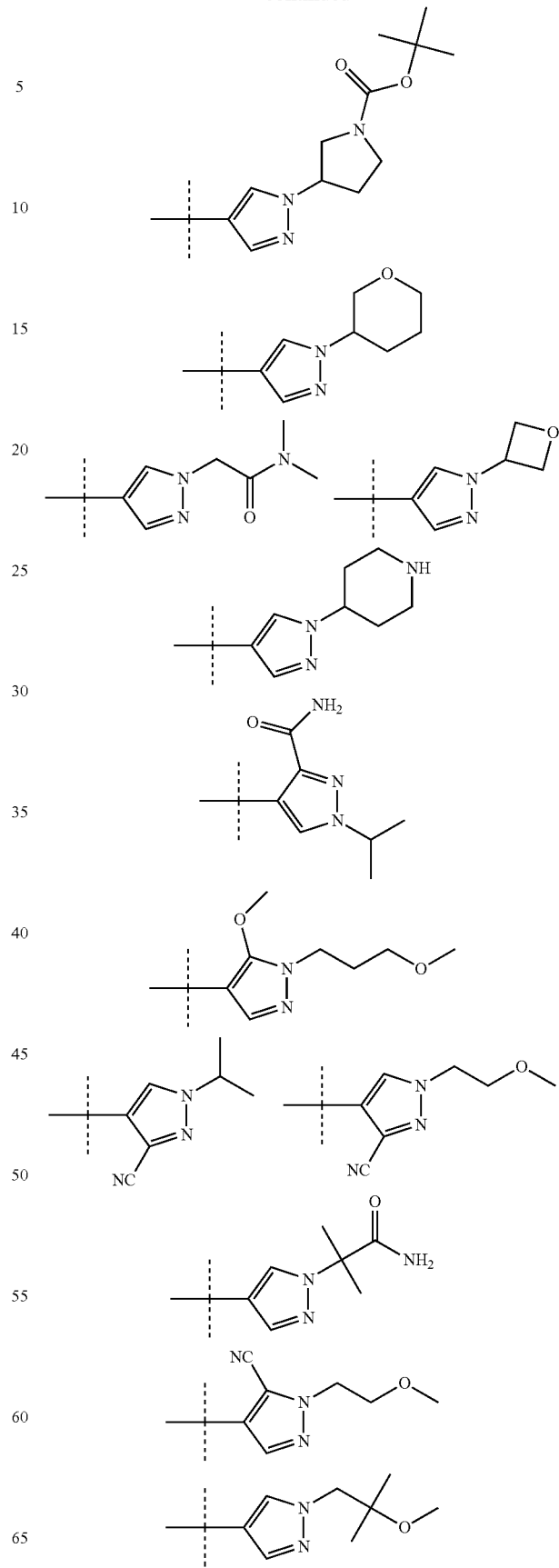

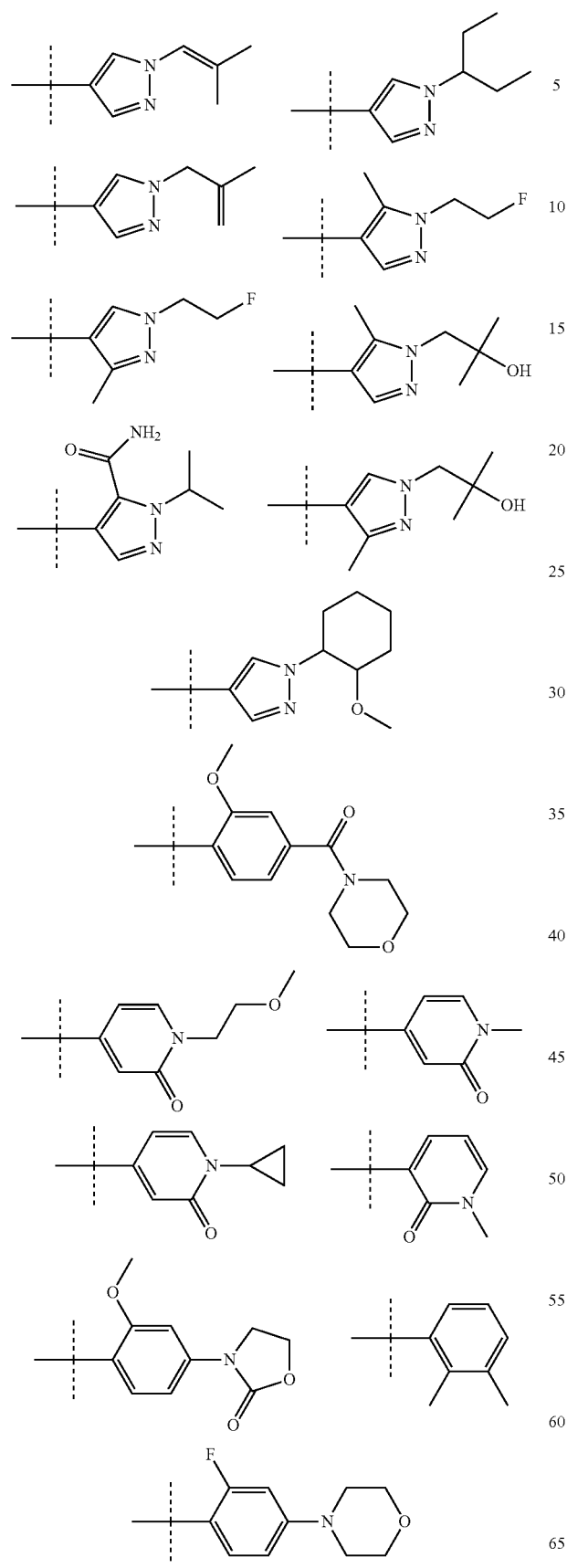
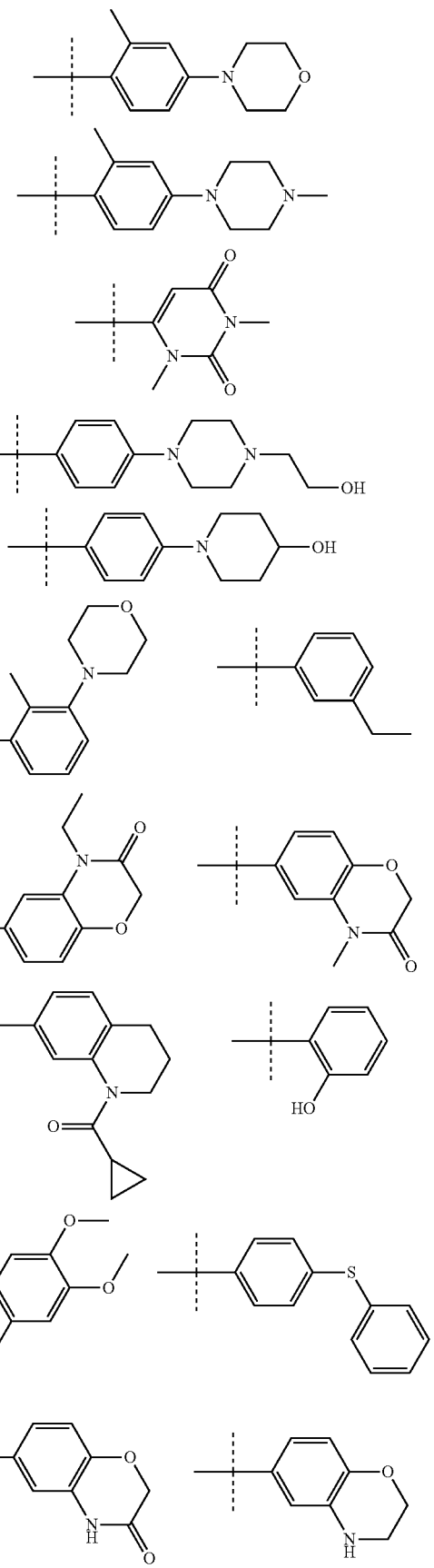

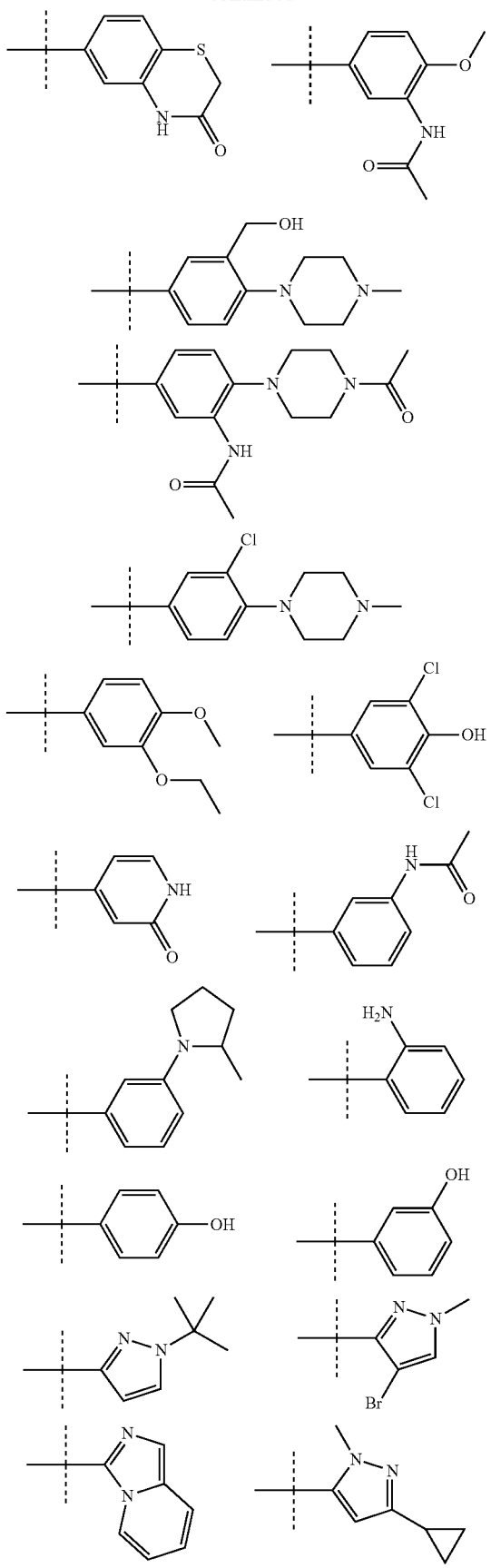

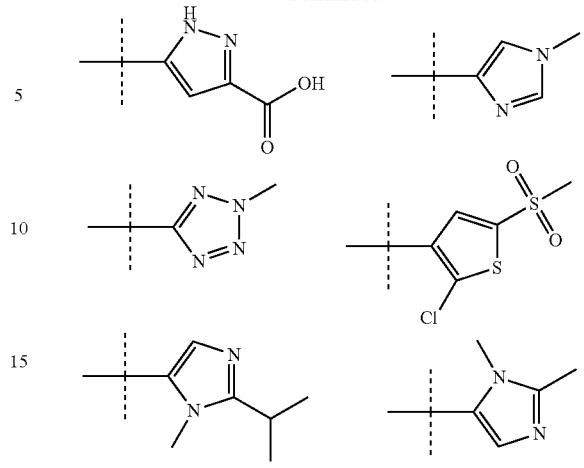

Further preferred are compounds of formula (I) wherein $R^1$ has the following structure:

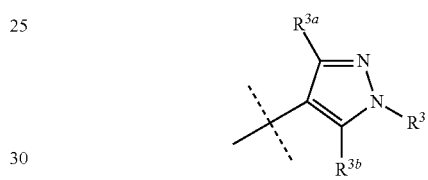

wherein
$R^3$ is hydrogen or an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group;
$R^{3a}$ is hydrogen, halogen, OH, SH, $NH_2$, or an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group (preferably hydrogen or methyl; especially preferably hydrogen); and
$R^{3b}$ is hydrogen, halogen, OH, SH, $NH_2$, or an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group (preferably hydrogen or methyl; especially preferably hydrogen).

Further especially preferred are compounds of formula (I) wherein $R^1$ has the following structure:

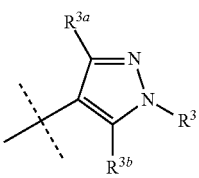

wherein
$R^3$ is hydrogen or a $C_1$-$C_6$ alkyl; a $C_2$-$C_6$ alkenyl, a $C_2$-$C_6$ alkynyl, a $C_1$-$C_6$ alkoxy-$C_1$-$C_6$ alkyl, a $C_1$-$C_6$ heteroalkyl; a $C_3$-$C_7$ cycloalkyl; a $C_1$-$C_4$ alkyl-$C_3$-$C_7$ cycloalkyl; a $C_1$-$C_4$ heteroalkyl-$C_3$-$C_7$ cycloalkyl; a phenyl; a $C_1$-$C_4$ alkyl-phenyl or a $C_1$-$C_4$ heteroalkyl-phenyl group; or a heteroaryl group containing 5 or 6 ring atoms and 1, 2, 3 or 4 heteroatoms selected from O, S and N; a $C_1$-$C_4$ alkyl-heteroaryl or a $C_1$-$C_4$ heteroalkyl-heteroaryl group wherein the heteroaryl group contains 5 or 6 ring atoms and 1, 2, 3 or 4 heteroatoms selected from O, S and N; or a heterocycloalkyl group containing 3, 4, 5, 6 or 7 ring atoms and 1, 2, 3 or 4 heteroatoms selected from O, S and N; or a $C_1$-$C_4$ alkyl-heterocycloalkyl or a $C_1$-$C_4$ heteroalkyl-heterocycloalkyl group wherein the heterocycloalkyl group contains 3, 4, 5, 6 or 7 ring atoms and 1, 2, 3 or 4 heteroatoms selected from O, S and N; all of which groups may optionally be substituted (especially preferably by a halogen or an OH, an =O, a CN, a phenyl, a $C_1$-$C_6$ alkyl or a $C_1$-$C_6$ heteroalkyl (such as e.g. COOH, $CONH_2$ or $OCH_3$) group);

$R^{3a}$ is hydrogen, halogen, a $C_1$-$C_6$ alkyl group (such as e.g. $CH_3$ or $CF_3$), a $C_1$-$C_6$ heteroalkyl group (such as e.g. $OCH_3$, $N(CH_3)_2$, CN or $CONH_2$) or an optionally substituted $C_3$-$C_7$ cycloalkyl group; and $R^{3b}$ is hydrogen, halogen, a $C_1$-$C_6$ alkyl group (such as e.g. $CH_3$ or $CF_3$), a $C_1$-$C_6$ heteroalkyl group (such as e.g. $OCH_3$, $N(CH_3)_2$, CN or $CONH_2$) or an optionally substituted $C_3$-$C_7$ cycloalkyl group.

Moreover preferred are compounds of formula (I) wherein $R^1$ has the following structure:

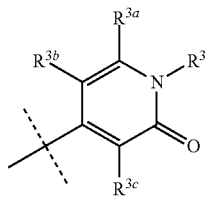

wherein
$R^3$ is hydrogen or an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group;

$R^{3a}$ is hydrogen, halogen, OH, SH, $NH_2$, or an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group (preferably hydrogen or methyl; especially preferably hydrogen);

$R^{3b}$ is hydrogen, halogen, OH, SH, $NH_2$, or an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group (preferably hydrogen or methyl; especially preferably hydrogen); and $R^{3c}$ is hydrogen, halogen, OH, SH, $NH_2$, or an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group (preferably hydrogen or methyl; especially preferably hydrogen).

Especially preferred are compounds of formula (I) wherein $R^1$ has the following structure:

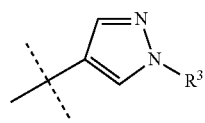

wherein $R^3$ is hydrogen or an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group.

Preferably, $R^3$ is an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group.

Moreover preferably, $R^3$ is an optionally substituted alkyl, heteroalkyl, cycloalkyl, heterocycloalkyl, alkylcycloalkyl or heteroalkylcycloalkyl group.

Especially preferably, $R^3$ is selected from the following groups:

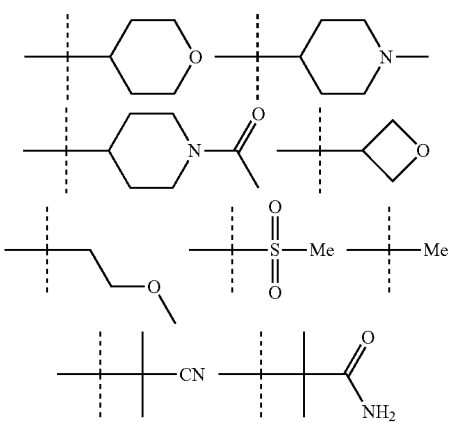

Especially preferred are compounds of formula (I), wherein $R^1$ is derived from the following amines:

m-toluidine; 3-(trifluoromethyl)aniline; 3,4,5-trimethoxyaniline; 1H-indazol-5-amine; aniline; 1H-indazol-6-amine; 3-chloroaniline; 7-methyl-1H-indazol-5-amine; 2-methoxyethan-1-amine; thiophen-2-ylmethanamine; 6-methyl-1H-indazol-5-amine; 2H-indazol-6-amine; methyl 4-aminobenzoate; 1H-benzo[d]imidazol-5-amine; 2H-indazol-7-amine; (1-methyl-1H-pyrrol-2-yl)methanamine; benzo[d][1,3]dioxol-5-amine; pyridin-3-amine; 1-methyl-1H-indazol-6-amine; 6-methoxypyridin-3-amine; 4-(4-methylpiperazin-1-yl)aniline; 4-(4-methyl-1,4-diazepan-1-yl)aniline; pyridin-2-amine; 5-bromopyridin-2-amine; isoquinolin-3-amine; 4-methylpyridin-2-amine; 4,6-dimethylpyridin-2-amine; 1H-indazol-7-amine; benzene-1,3-diamine; 6-amino-2H-benzo[b][1,4]oxazin-3(4H)-one; 1H-benzo[d][1,2,3]triazol-5-amine; 3-aminobenzimidamide; 4-(piperidin-1-yl)aniline; N1,N1-dimethylbenzene-1,4-diamine; 3-aminobenzamide; 3,4-dimethoxyaniline; 4-morpholinoaniline; 2-methyl-1H-benzo[d]imidazol-6-amine; 4-aminobenzoic acid; 4-aminobenzamide; 4-aminobenzonitrile; 3-methoxyaniline; 4-methoxyaniline; 3-aminobenzonitrile; benzo[c][1,2,5]thiadiazol-5-amine; 3-aminopyridin-2(1H)-one; 2-ethoxyaniline; 1H-pyrazol-3-amine; 5-amino-1H-pyrazole-4-carboxamide; 2-phenoxyaniline; 3-phenoxyaniline; 5-amino-1H-benzo[d]imidazol-2(3H)-one; 1H-indol-5-amine; 4-(aminomethyl)aniline; 1H-indol-6-amine; N1,N1-dimethylbenzene-1,3-diamine; 3-phenyl-1H-pyrazol-5-amine; N1,N1-diethylbenzene-1,4-diamine; 4-(pyrrolidin-1-yl)aniline; 4H-1,2,4-triazole-3,5-diamine; 3-morpholinoaniline; 3-cyclobutyl-1H-pyrazol-5-amine; 4-(4,5-dihydro-1H-imidazol-2-yl)aniline; 4-(4-aminophenyl)morpholin-3-one; 2,2-dimethyl-3,4-dihydro-2H-benzo[b][1,4]thiazin-6-amine;

7-amino-3,4-dihydroquinolin-2(1H)-one; 6-amino-2H-benzo[b][1,4]thiazin-3(4H)-one; 5-(tert-butyl)-1H-pyrazol-3-amine; 3-methyl-1H-pyrazol-5-amine; 5-cyclopropyl-1H-pyrazol-3-amine; 4-(1H-tetrazol-5-yl)aniline; 2,3-dihydrobenzo[b][1,4]dioxin-6-amine; 4-(1-methylpiperidin-4-yl)aniline; 6-morpholinopyridin-3-amine; 4-(2-methoxyethoxy)aniline; 4-ethoxy-3-methoxyaniline; 1-(4-aminophenyl)pyrrolidin-2-one; 4-thiomorpholinoaniline; 5-aminobenzo[d]oxazol-2(3H)-one; 3,4-dihydro-2H-benzo[b][1,4]oxazin-6-amine; 7-aminoquinazolin-4-ol; 4-(4-aminophenyl)thiomorpholine 1,1-dioxide; 2-(4-aminophenyl)acetamide; 3-aminophenol; 3,4-diethoxyaniline; 6-amino-1H-benzo[d][1,3]oxazine-2,4-dione; 5-amino-2-methoxyphenol; 3-methoxy-N-methylaniline; N-(3-aminophenyl)acetamide; 1H-pyrazol-4-amine; 4-fluoro-3-methoxyaniline; 3-fluoro-4-methoxyaniline; 1-methyl-1H-benzo[d]imidazol-5-amine; 1-(3-aminophenyl)ethan-1-one; N-(4-aminophenyl)acetamide; 1H-pyrrolo[2,3-b]pyridin-6-amine; 3-aminobenzenesulfonamide; 4-aminobenzenesulfonamide; pyridine-2,6-diamine; 1,2,3-trimethyl-1H-indol-5-amine; pyrimidine-2,4-diamine; 5-(methylthio)-4H-1,2,4-triazol-3-amine; 5-cyclopropyl-4H-1,2,4-triazol-3-amine; N-(5-amino-2-methoxyphenyl)acetamide; 1H-benzo[d]imidazol-2-amine; 1H-imidazol-2-amine; 1-(4-aminophenyl)ethan-1-one; 4H-benzo[d][1,3]dioxin-6-amine; 1,3-dihydroisobenzofuran-5-amine; 1-methyl-1H-benzo[d]imidazol-6-amine; 4,5-dimethylthiazol-2-amine; 2-methyl-4-(4-methylpiperazin-1-yl)aniline; 6-methylpyridin-2-amine; 4-methylthiazol-2-amine; 4,5,6,7-tetrahydrobenzo[d]thiazol-2-amine; 4-phenoxyaniline; 2-methyl-1,2,3,4-tetrahydrobenzo[4,5]imidazo[1,2-a]pyrazin-8-amine; 4-(pyridin-4-ylmethyl)aniline; 4-aminobenzene-1,2-diol; 4-((1-methylpiperidin-4-yl)oxy)aniline; 1-(4-(4-aminophenyl)piperazin-1-yl)ethan-1-one; 6-(4-methylpiperazin-1-yl)pyridin-3-amine; N1,N1,2-trimethylbenzene-1,4-diamine; 4-(4-cyclopropylpiperazin-1-yl)aniline; ammonia; 3-fluoro-4-morpholinoaniline; 7-aminoquinoxalin-2(1H)-one; 3-methyl-4-(4-methylpiperazin-1-yl)aniline; 4-(piperazin-1-yl)aniline; 4-((dimethylamino)methyl)aniline; 2-fluoro-4-morpholinoaniline; 4-(4-ethylpiperazin-1-yl)aniline; 8-amino-4,5-dihydro-1H-benzo[b]azepin-2(3H)-one; 5-amino-1,3-dimethyl-1H-benzo[d]imidazol-2(3H)-one; 4-benzylaniline; 2-methyl-4-morpholinoaniline; N1-methyl-N1-(1-methylpiperidin-4-yl)benzene-1,4-diamine; 4-(2-morpholinoethyl)aniline; 3-chloro-4-(4-methylpiperazin-1-yl)aniline; 1,2,3,4-tetrahydroquinolin-7-amine; cyclohexane-1,2-diamine; pyridin-4-amine; 2-(4-aminophenyl)-N-(4-methoxyphenethyl)acetamide; 3-(piperazin-1-yl)aniline; 4-amino-N-(2-(diethylamino)ethyl)benzamide; 2-(4-methylpiperazin-1-yl)pyrimidin-5-amine, 7-amino-2H-benzo[b][1,4]oxazin-3(4H)-one; 3,4-dihydro-2H-benzo[b][1,4]oxazin-7-amine; 3-(4-methylpiperazin-1-yl)aniline; 3-(2-(piperazin-1-yl)ethoxy)aniline; 6-methyl-5,6,7,8-tetrahydro-1,6-naphthyridin-3-amine, (4-aminophenyl)(pyrrolidin-1-yl)methanone; (4-aminophenyl)(morpholino)methanone; 4-(pyrrolidin-1-ylmethyl)aniline; (4-aminophenyl)(4-methylpiperazin-1-yl)methanone; N2-(2-(dimethylamino)ethyl)pyrimidine-2,5-diamine; 4-(morpholinomethyl)aniline; 4-((4-methylpiperazin-1-yl)methyl)aniline; 4-(4-ethylpiperazin-1-yl)-3-fluoroaniline; 4-(2-(4-benzylpiperazin-1-yl)ethyl)aniline, 4-((4-benzylpiperazin-1-yl)methyl)aniline; p-toluidine; 6-(2-(dimethylamino)ethoxy)pyridin-3-amine; 2-methyl-1H-benzo[d]imidazol-5-amine; N2-(3-(dimethylamino)propyl)pyridine-2,5-diamine; N2-(2-(dimethylamino)ethyl)pyridine-2,5-diamine; 6-((1-methylpiperidin-4-yl)oxy)pyridin-3-amine; 4-(4-cyclopentylpiperazin-1-yl)aniline; 4-(4-isobutylpiperazin-1-yl)aniline; 4-(4-isopropylpiperazin-1-yl)aniline; 4-(4-(cyclopropylmethyl)piperazin-1-yl)aniline; 4-(4-(tert-butyl)piperazin-1-yl)aniline; 2-(4-(4-aminophenyl)piperazin-1-yl)acetic acid; 2-(4-amino-2-methoxyphenoxy)acetic acid; (4-aminophenyl)methanol; 4-(4-(2-(dimethylamino)ethyl)piperazin-1-yl)aniline; 2-(4-aminophenyl)acetic acid; 6-amino-2-naphthoic acid; 3-aminobenzoic acid; 4'-amino-[1,1'-biphenyl]-4-carboxylic acid; 1-(4-aminophenyl)-3-(m-tolyl)urea; 2-(4-aminophenoxyl)acetic acid; 2-methylisoindolin-5-amine; (4-amino-3-methoxyphenyl)(4-(4-methylpiperazin-1-yl)piperidin-1-yl)methanone; 4-amino-N-(2-(dimethylamino)ethyl)-N-methylbenzamide; (4-aminophenyl)(2-(methoxymethyl)pyrrolidin-1-yl)methanone; (4-aminophenyl)(azetidin-1-yl)methanone; 4-amino-N,N-dimethylbenzamide; (4-aminophenyl)(4-methyl-1,4-diazepan-1-yl)methanone; 1-(4-aminobenzoyl)piperidin-4-one; (4-aminophenyl)(1,4-dioxa-8-azaspiro[4.5]decan-8-yl)methanone; (4-aminophenyl)(3-(dimethylamino)pyrrolidin-1-yl)methanone; 1-methyl-1,2,3,4-tetrahydroquinolin-6-amine; 3-aminophenyl sulphur pentafluoride; 4-fluoroaniline; 3,4-difluoroaniline; N-(4-aminophenyl)-2,2,2-trifluoroacetamide; 3-((6-amino-2H-benzo[b][1,4]oxazin-3-yl)amino)propan-1-ol; N3-phenethyl-2H-benzo[b][1,4]oxazine-3,6-diamine; 3,5-difluoroaniline; 3-fluoro-4-methylaniline; 3,4,5-trifluoroaniline; 4-nitroaniline; 3-methoxy-4-morpholinoaniline; 3-(methylsulfonyl)aniline; 2-(4-aminophenyl)-1,1,1,3,3,3-hexafluoropropan-2-ol; 4-(difluoromethoxy)-3-methoxyaniline; 3-fluoro-4-(trifluoromethyl)aniline; 3-fluoro-4-(trifluoromethoxy)aniline; 2,3-dimethoxyaniline; 2,4-dimethoxyaniline; 3,5-dimethoxyaniline; 4-amino-N,N-dimethylbenzenesulfonamide; 3-amino-N-cyclopropylbenzenesulfonamide; 4-(2H-1,2,3-triazol-2-yl)aniline; 3-(methylsulfinyl)aniline; 3-(2H-1,2,3-triazol-2-yl)aniline; 3-amino-N-methylbenzenesulfonamide; 3-(morpholinosulfonyl)aniline; 3-((trifluoromethyl)sulfonyl)aniline; 2-((3-aminophenyl)sulfonyl)ethan-1-ol; N-(4-aminophenyl)-4-fluorobenzamide; 4-morpholino-3-nitroaniline; 2,4-difluoroaniline; 2-aminobenzamide; 4-chloroaniline; N1,N1-dimethylethane-1,2-diamine; (1-methylpiperidin-4-yl)methanamine; 1-methyl-1,2,3,4-tetrahydroquinolin-7-amine; 2-(4-aminophenyl)-2-methylpropanenitrile; 4-aminophenylsulphurpentafluoride; 3-amino-N,N-dimethylbenzenesulfonamide, 2-(methylsulfonyl)aniline; 4-(4-(4-methylpiperazin-1-yl)piperidin-1-yl)aniline; 3-((dimethylamino)methyl)aniline; (4-aminophenyl)(4-(4-methylpiperazin-1-yl)piperidin-1-yl)methanone.

Furthermore $R^1$ can be derived from the following amines:

formamide; 2-aminoethan-1-ol; prop-2-yn-1-amine; N1-methylethane-1,2-diamine; 2-aminoacetonitrile; 3-aminopropan-1-ol; butan-1-amine; cyclopropanamine; propan-2-amine; 3-aminopropanenitrile; 4-aminobutan-1-ol; cyclobutanamine; 2-aminopropan-1-ol; acetamide; cyclopropylmethanamine; 5-aminopentan-1-ol; 2-aminoacetamide; isoxazol-3-amine; thiazol-2-amine; 3-aminopropane-1,2-diol; cyclopentanamine; piperidin-4-amine; piperidin-3-amine; pyrimidin-2-amine; 2-aminocyclopentanol; 3-aminopropanamide; tetrahydro-2H-pyran-4-amine; 2-methylpropan-2-amine; o-toluidine; 2,2,2-trifluoroethan-1-amine; phenylmethanamine; piperidin-4- ylmethanamine; 2-aminocyclohexanol; 4-aminobutanamide; piperidin-3-ylmethanamine; 1-methyl-1H-pyrazol-4-amine; 2-methoxyaniline; 2-chloroaniline; 2-aminopropanamide; 4-methylthiophen-2-amine; 2-phenylethan-1-amine; 1H-pyrazol-5-amine; 5-methylisoxazol-3-amine; 2-morpholinoethan-1-amine; 1-(aminomethyl)-N-methylcyclopropanamine; 1-methyl-1H-pyrrol-3-amine; 5-methylthiazol-2-amine; 5-methylthiophen-2-amine; 4-aminophenol; 3-fluoroaniline; 3,5-dimethylisoxazol-4-amine; 3-morpholinopropan-1-amine; 2-aminobutanamide; 4-iodoaniline; (3-aminophenyl)methanol; 2-aminothiazole-4-carbaldehyde; 3-bromoaniline; 2,6-dimethylaniline; 4-ethylaniline; 3-amino-2-methylphenol; 4-(methylthio)aniline; 3-ethylaniline; 1-phenylethan-1-amine; 2-(4-aminophenyl)ethan-1-ol; 5-aminonicotinaldehyde; 6-aminonicotinaldehyde; 4-aminobenzaldehyde; 3-aminobenzaldehyde; indolin-6-amine; 4-amino-2-methoxyphenol; 2-aminopyrimidine-5-carbaldehyde; 5-aminopyrazine-2-carbaldehyde; 5-aminopicolinaldehyde; 3-methoxy-4-methylaniline; 6-aminopyrazine-2-carbaldehyde; N1,6-dimethylbenzene-1,3-diamine; 5-methyl-1H-pyrazol-3-amine; 4-ethoxyaniline; 2,3-dihydrobenzofuran-5-amine; 3-ethoxyaniline; benzo[d]thiazol-5-amine; benzo[d]thiazol-6-amine; piperidine-3-carboxamide; imidazo[1,2-a]pyridin-6-amine; piperidine-4-carboxamide; benzo[d]thiazol-7-amine; benzo[d]isoxazol-5-amine; 4-methoxy-3-methylaniline; benzo[d]thiazol-2-amine; 4-vinylaniline; benzo[c][1,2,5]thiadiazol-4-amine; 1-aminocyclopropanecarboxamide; 2-phenylcyclopropanamine; 2-aminocyclopentanecarboxamide; 3-vinylaniline; (5-amino-2-methoxyphenyl)methanol; 2-(4-aminophenoxyl)ethan-1-ol; 1,2,3,4-tetrahydroisoquinolin-6-amine; (4-amino-2-methoxyphenyl)methanol; 2-amino-4-methylpyrimidine-5-carbaldehyde; 6-amino-4-methylnicotinaldehyde; 2-isopropoxyaniline; 6-amino-2-methylnicotinaldehyde; 4-amino-2-methylphenol; 5-amino-2-methylphenol; 3-chloro-4-methoxyaniline; 3,5-dimethylaniline; N-(3-aminophenyl)formamide; 2-(3-aminophenoxyl)ethan-1-ol; N-(6-aminopyridin-2-yl)formamide; 4-amino-2-fluorophenol; 5-amino-2-hydroxybenzonitrile; 4-amino-3-fluorophenol; N-(4-aminophenyl)formamide; 2,4-dimethylaniline; 3,4-dimethylaniline; 2-fluoro-5-methylaniline; 2,5-dimethylaniline; quinoxalin-6-amine; quinolin-6-amine; 2-amino-3-methylbutanamide; quinoxalin-5-amine; naphthalen-1-amine; naphthalen-2-amine; 4-fluoro-3-methylaniline; quinolin-5-amine; quinolin-8-amine; 2,6-dimethylpyrimidin-4-amine; 1-(4-aminophenyl)ethan-1-ol; 2,3,4,5-tetrahydrobenzo[b][1,4]oxazepin-7-amine; 3-methoxy-4-(methoxymethyl)aniline; 2-fluoro-4-methoxyaniline; 5-amino-6-methoxypyrazine-2-carbaldehyde; 2-amino-4-methoxypyrimidine-5-carbaldehyde; 6-amino-5-methoxynicotinaldehyde; 3-chloro-4-fluoroaniline; 4H-benzo[b][1,4]oxazin-6-amine; 4-isopropylaniline; 4-amino-2,5-dimethylphenol; 4-amino-2-chlorophenol; 4H-benzo[b][1,4]oxazin-7-amine; 3-(2-methoxyethoxy)aniline; 4-methoxy-2-methylaniline; 5-methoxy-2-methylaniline; 3-(2-(methylamino)ethoxy)aniline; 3-isopropylaniline; 4-amino-2,3-dimethylphenol; N-(5-amino-2-methylphenyl)formamide; 2-amino-4-methylpentanamide; 4-chloro-3-methylaniline; 3-aminocyclopentanecarboxamide; 2-chloro-5-fluoropyrimidin-4-amine; 3,4-dihydroquinolin-6-amine; 2-amino-4-methylpentanethioamide; 2-(isopentyloxy)aniline; 6-amino-5-methylnicotinaldehyde; 5-amino-6-methylpyrazine-2-carbaldehyde; 2-amino-6-methylpyrimidine-4-carbaldehyde; 2-methyl-2H-indazol-6-amine; 5-amino-6-methylpicolinaldehyde; 5-amino-4-methylpicolinaldehyde; 4-isopropoxyaniline; 1-methyl-1H-indazol-5-amine; 3,5-dichloroaniline; 3,4-dichloroaniline; [1,1'-biphenyl]-2-amine; 2,6-dimethoxypyridin-3-amine; 4-methoxy-3,5-dimethylaniline; 2-methyl-2H-indazol-5-amine; 3-(ethyl(hydroxy)amino)aniline; 3-isopropoxyaniline; N1-isopropylbenzene-1,3-diamine; 4-amino-5-chloro-2-methylphenol; 1-methyl-1H-indol-4-amine; 1H-indazol-4-amine; 1-methyl-1H-indazol-4-amine; 2-methyl-2H-indazol-4-amine; 1H-indol-4-amine; 1H-benzo[d]imidazol-6-amine; 1H-benzo[d][1,2,3]triazol-6-amine; 2-methylbenzo[d]thiazol-5-amine; 4-(methylsulfinyl)aniline; 1-methyl-1H-indol-5-amine; 3-(2-aminophenyl)propanamide; 2-((2-aminocyclohexyl)amino)acetic acid; (2,3,6-trifluorophenyl)methanamine; 5-bromo-2-chloropyrimidin-4-amine; 1-methyl-1H-indazol-7-amine; 1-methyl-1H-benzo[d]imidazol-4-amine; 2-methyl-2H-indazol-7-amine; 2-methylbenzo[d]oxazol-7-amine; 4-methyl-3,4-dihydro-2H-benzo[b][1,4]oxazin-7-amine; 4-methyl-3,4-dihydro-2H-benzo[b][1,4]oxazin-6-amine; 4-(4H-1,2,4-triazol-4-yl)aniline; 4-(1H-imidazol-1-yl)aniline; 4-(1H-pyrazol-1-yl)aniline; 5-aminoindolin-2-one; 6-aminoindolin-2-one; 3-methoxy-4-(2-methoxyethoxy)aniline; 3-(4-amino-2-methoxyphenoxy)propan-1-ol; 2-((4-aminophenyl)(methyl)amino)ethan-1-ol; 2-methyl-1,2,3,4-tetrahydroisoquinolin-6-amine; 4-amino-N-methylbenzamide; 3-amino-N-methylbenzamide; 1-(piperidin-4-yl)-1H-pyrazol-4-amine; 4-(oxazol-4-yl)aniline; 4-(pyrrolidin-3-yl)aniline; 2-(trifluoromethoxy)aniline; 3-chloro-4-methoxy-5-methylaniline; 2-((2-aminophenyl)imino)acetic acid; 3-(oxazol-5-yl)aniline; (5-aminobenzofuran-2-yl)methanol; 3,4,5-trimethylaniline; N-(5-amino-2-fluorophenyl)formamide; methyl 4-amino-1-methyl-1H-pyrrole-2-carboxylate; methyl 3-aminobenzoate; N-(3-amino-4-ethoxyphenyl)formamide; 2-((3-aminophenyl)amino)propan-1-ol; 2-methyl-2,3-dihydrobenzo[b][1,4]dioxin-6-amine; 4-(1H-1,2,4-triazol-1-yl)aniline; 3-(1H-pyrazol-1-yl)aniline; 2-amino-2-phenylacetamide; 4-(thiazol-4-yl)aniline; 1,2-dimethyl-1H-indol-4-amine; 4-(oxazol-5-yl)aniline; 1-ethyl-1H-indol-4-amine; 3-(thiazol-2-yl)aniline; 4-(1,2,3-thiadiazol-4-yl)aniline; 3-(isoxazol-3-yl)aniline; 4-(isoxazol-3-yl)aniline; 4-(isoxazol-5-yl)aniline; 4-(thiophen-2-yl)aniline; 3-(1H-tetrazol-1-yl)aniline; 4-(1H-tetrazol-1-yl)aniline; 3-(1H-imidazol-1-yl)aniline; 5-aminobenzofuran-2(3H)-one; 8-methylquinolin-4-amine; 2-amino-2-(pyridin-3-yl)acetamide; 1-phenyl-1H-pyrazol-4-amine; 1-phenyl-1H-pyrrol-3-amine; 3-(2H-tetrazol-2-yl)aniline; 3-(1H-1,2,4-triazol-1-yl)aniline; 3-(1H-1,2,3-triazol-1-yl)aniline; 4-(1H-1,2,3-triazol-1-yl)aniline; 3-(pyrrolidin-1-yl)aniline; 3-(1H-pyrrol-1-yl)aniline; 4-(1H-pyrrol-1-yl)aniline; 4-(1,3,4-oxadiazol-2-yl)aniline; 4-(thiazol-2-yl)aniline; 3-(thiazol-4-yl)aniline; 3-(oxazol-4-yl)aniline; 3-(thiazol-5-yl)aniline; 4-(thiazol-5-yl)aniline; 6-fluoronaphthalen-2-amine; methyl 2-((2-aminocyclohexyl)amino)acetate; 4-isobutoxyaniline; 2-methylquinolin-6-amine; 2-methylquinolin-8-amine; 3-methylcinnolin-5-amine; 2-(4-aminophenyl)propan-2-ol; 2-((4-aminophenyl)(ethyl)amino)ethan-1-ol; 4-(2-(dimethylamino)ethoxy)aniline; 4-(tetrahydro-2H-pyran-4-yl)aniline; 3-methoxy-4-((2-methoxyethoxy)methyl)aniline; N1-(2-methoxyethyl)-N1-methylbenzene-1,4-diamine; 4-isopropoxy-3-methoxyaniline; 4-amino-2-methoxybenzoic acid; 4-(piperidin-4-yl)aniline; 4-amino-N,2-dimethylbenzamide; 6-(tetrahydro-2H-pyran-4-yl)

pyridin-3-amine; 6-(piperidin-4-yl)pyridin-3-amine; 4-(3-(dimethylamino)propyl)aniline; 4-(pyridin-3-yl)aniline; 4-(piperidin-3-yl)aniline; 2-ethyl-1,2,3,4-tetrahydroisoquinolin-6-amine; 3,5-dichloro-4-methoxyaniline; 4-amino-2-chloro-6-methylphenol; 3(4-aminophenoxy) propane-1,2-diol; 3-(tert-butyl)aniline; 2-(5-amino-1H-indazol-1-yl)ethan-1-ol; 2-(6-amino-1H-indazol-1-yl)ethan-1-ol; 4-chloro-2,5-dimethoxyaniline; ethyl 3-aminobenzoate; 4-(tert-butyl)aniline; 4-chloro-3,5-dimethylaniline; N-(3-amino-5-chlorophenyl)formamide; 4-(trifluoromethyl)aniline; [1,1'-biphenyl]-3-amine; 6-amino-2H-chromen-2-one; 7-amino-2H-chromen-2-one; methyl 2-(4-aminophenyl)acetate; methyl 2-(3-aminophenyl)acetate; methyl 5-amino-2-hydroxybenzoate; methyl 4-amino-2-hydroxybenzoate; 5-amino-2-methoxybenzoic acid; 3-(2-(dimethylamino)ethoxy)aniline; 4-methyl-4H-benzo[b][1,4]oxazin-7-amine; 3-amino-4-isopropylphenol; 5-methyl-3-phenylisoxazol-4-amine; 3-(pyrimidin-2-yl)aniline; 3-(pyrimidin-5-yl)aniline; 2,3-dihydro-1H-pyrrolo[1,2-a]indol-8-amine; 4-(pyrimidin-2-yl)aniline; 3-(pyridin-3-yl)aniline; 4-(pyridin-2-yl)aniline; 6-methoxynaphthalen-2-amine; 2-methyl-2H-indol-4-amine; 4-chloronaphthalen-1-amine; 3-(pyridin-4-yl)aniline; 4-amino-2-methoxybenzamide; 3-(5-methyl-1H-tetrazol-1-yl)aniline; 2-fluoro-4-(1H-pyrazol-1-yl)aniline; 2-fluoro-4-(thiazol-4-yl)aniline; 4-(pyrimidin-5-yl)aniline; 3-(pyrazin-2-yl)aniline; 4-(pyrazin-2-yl)aniline; 3-(tetrahydro-2H-pyran-4-yl)aniline; 3-(pyridazin-4-yl)aniline; 4-(pyridazin-4-yl)aniline; 4-(pyridin-4-yl)aniline; 3-(pyridin-2-yl)aniline; [1,1'-biphenyl]-4-amine; 7-chloro-1H-indazol-6-amine; 6-bromonaphthalen-2-amine; 3-(1-methyl-1H-tetrazol-5-yl)aniline; 4-(4-methyl-4H-1,2,4-triazol-3-yl)aniline; 4-(1-methyl-1H-imidazol-2-yl)aniline; 3-(1-methyl-1H-imidazol-2-yl)aniline; 4-(2-methyl-1H-imidazol-1-yl)aniline; 3-(2-methyl-1H-imidazol-1-yl)aniline; 2(4-aminophenyl)-2-methylpropan-1-ol; 1-(4-aminophenyl)azetidin-3-ol; 2-aminoquinazoline-6-carbaldehyde; 1-(4-aminophenyl)-2-methylpropan-2-ol; 2-(4-aminophenoxy)-N-methylacetamide; 4-(1,4-oxazepan-4-yl)aniline; 3-methoxy-4-(pyrrolidin-1-yl)aniline; 4-amino-N-propylbenzamide; 3-aminoquinoline-6-carbaldehyde; 4-((tetrahydrofuran-2-yl)methoxy)aniline; 4-((tetrahydro-2H-pyran-4-yl)oxy)aniline; 4-(pyridin-4-yloxy)aniline; 4-(3-fluoroazetidin-1-yl)aniline; 4-amino-N-(2-hydroxyethyl)benzamide; 1(4-aminophenyl)cyclobutanol; 2-aminoquinoline-6-carbaldehyde; 4-(2-methoxypropan-2-yl)aniline; 2-((4-amino-2-methoxyphenyl)(methyl)amino)ethan-1-ol; 4-methoxy-3-(pyrrolidin-1-yl)aniline; 4-(3-methylazetidin-1-yl)aniline; 2,3-dimethyl-2H-indazol-6-amine; 4-(trifluoromethoxy)aniline; 3-methyl-1H-indazol-6-amine; 1-(2-morpholinoethyl)-1H-pyrazol-4-amine; 3-(trifluoromethoxy)aniline; 4-amino-N-ethoxybenzamide; 3-amino-N-propylbenzamide; 4-((2-methyl-1H-imidazol-1-yl)methyl)aniline; 3-(5-amino-1H-indazol-1-yl)propan-1-ol; 4-amino-2,6-dichlorophenol; 3-(6-amino-1H-indazol-1-yl)propan-1-ol; 2-((3-aminophenyl)imino)acetamide; methyl 5-amino-2-methoxybenzoate; ethyl 2-((2-aminophenyl)imino)acetate; 4-((trifluoromethyl)thio)aniline; 5-amino-2-hydroxybenzoic acid; 4-amino-2-hydroxybenzoic acid; 2-((3-aminophenyl)imino)acetic acid; 2,2'-((3-aminophenypazanediyl)bis(ethan-1-ol); 2,2-difluorobenzo[d][1,3]dioxol-5-amine; 2-((methylamino)methylene)-2,3-dihydrobenzofuran-5-amine; 3-aminophenyl ethylcarbamate; 1-(4-aminophenyl)-3-ethylurea; 1-(3-aminophenyl)-3-ethylurea; 6-amino-2-methyl-2H-benzo[b][1,4]oxazin-3(4H)-one; 4-methyl-[1,1'-biphenyl]-3-amine; 2-methyl-1H-indol-4-amine; 3-(4-aminopiperidin-1-yl)-3-oxopropanenitrile; 4-(pyridin-3-yloxy)aniline; 1-(3-aminophenyl)pyrrolidin-2-one; 4-(5,6-dihydro-4H-1,3-oxazin-2-yl)aniline; 4-(3,6-dihydro-2H-pyran-4-yl)aniline; 6-aminoquinoline-2-carbonitrile; 2-chloro-5-cyclopropylpyrimidin-4-amine; 3-(3-aminopiperidin-1-yl)-3-oxopropanenitrile; 3-((tetrahydro-2H-pyran-4-yl)oxy)aniline; 3-(3,6-dihydro-2H-pyran-4-yl)aniline; dibenzo[b,d]furan-2-amine, 3-methoxy-4-(oxazol-5-yl)aniline; 4-methoxy-3-(2H-1,2,3-triazol-2-yl)aniline; 1-(4-aminophenyl)pyrrolidin-3-ol; 1-(4-aminophenoxy)-2-methylpropan-2-ol; 4-((tetrahydro-2H-pyran-4-yl)methoxy)aniline; (4-(4-aminophenyl)morpholin-3-yl)methanol; 4-(2H-tetrazol-5-yl)aniline; 2-methoxy-N1-(2-methoxyethyl)-N1-methylbenzene-1,4-diamine; 4-(1-methoxy-2-methylpropan-2-yl)aniline; 5-amino-1-methyl-6-oxo-1,6-dihydropyridine-3-carbaldehyde; 2-((4-amino-2-ethoxyphenyl)(methyl)amino)ethan-1-ol; 4-(2-(pyrrolidin-1-yl)ethoxy)aniline; 4-(1-methyl-1H-pyrazol-4-yl)aniline; 4-(1H-imidazol-4-yl)aniline; 4-(methylsulfonyl)aniline; 2-methoxy-[1,1'-biphenyl]-4-amine; 4-(1-methylpyrrolidin-3-yl)aniline; 5-amino-2-methylisoindolin-1-one; 6-amino-2-methylisoindolin-1-one; 3-(2-(pyrrolidin-1-yl)ethoxy)aniline; 2-(2-methoxyethyl)-1,2,3,4-tetrahydroisoquinolin-6-amine; 4-methoxy-3-(trifluoromethyl)aniline; 2-((3-aminophenyl)imino)-N-methylacetamide; 3-(1H-tetrazol-5-yl)aniline; N-(4-aminophenyl)-N-methylacetamide; 3-(benzyloxy)aniline; 3-(1H-pyrazol-3-yl)aniline; 2-amino-7-oxabicyclo[4.2.0]octa-1,3,5-triene-8-carboxylic acid; (5-amino-1H-indol-2-yl)methanol; 6-methoxy-[1,1'-biphenyl]-3-amine; 4-methoxy-[1,1'-biphenyl]-3-amine; ethyl(4-amino-2-hydroxyphenyl)carbamate; 3-fluoro-4-(thiazol-4-yl)aniline; 3-fluoro-4-(1H-pyrazol-1-yl)aniline; 4-amino-N-(3-hydroxypropyl)benzamide; 3-fluoro-4-(1H-imidazol-1-yl)aniline; 1-(4-aminophenyl)pyridin-2(1H)-one; 1-(4-aminophenyl)-1-methylurea; butyl 4-aminobenzoate; 4-(5-methyl-1,2,4-oxadiazol-3-yl)aniline; 3-(2-methylthiazol-4-yl)aniline; 4-(3-methyl-1H-pyrazol-1-yl)aniline; 3-methyl-5-(2H-1,2,3-triazol-2-yl)aniline; 4-methyl-3-(2H-1,2,3-triazol-2-yl)aniline; 2-amino-2-(3-hydroxyphenyl)acetamide; 2-amino-2-(3-fluorophenyl)acetamide; 3-fluoro-5-(2H-1,2,3-triazol-2-yl)aniline; 4-fluoro-3-(2H-1,2,3-triazol-2-yl)aniline; 4-amino-2-(2H-1,2,3-triazol-2-yl)benzonitrile; 3-fluoro-4-(2H-1,2,3-triazol-2-yl)aniline; 3-(2H-tetrazol-5-yl)aniline; 3-chloro-1H-indazol-5-amine; 4-(methylthio)-7H-pyrrolo[2,3-d]pyrimidin-2-amine; 4-(2-(methoxymethyl)pyrrolidin-1-yl)aniline; 2'-methoxy-[1,1'-biphenyl]-3-amine; 4-(1-methyl-1H-pyrazol-3-yl)aniline; 3-(1-methyl-1H-pyrazol-3-yl)aniline; 3-(1-methyl-1H-pyrazol-4-yl)aniline; 4-(5-methyl-1,3,4-thiadiazol-2-yl)aniline; 3-(5-methyl-1,2,4-oxadiazol-3-yl)aniline; 3-(4-methyl-2H-1,2,3-triazol-2-yl)aniline; 3-(4-methyl-1H-1,2,3-triazol-1-yl)aniline; 3-(5-methylisoxazol-3-yl)aniline; 3-methyl-5-(2H-tetrazol-2-yl)aniline; 3-methyl-4-(2H-1,2,3-triazol-2-yl)aniline; 3-methyl-4-(1H-pyrazol-1-yl)aniline; 3-(5-methylfuran-2-yl)aniline; 2-amino-2-(m-tolyl)acetamide; 2-amino-2-(p-tolyl)acetamide; 3-amino-1H-indazole-6-carbaldehyde; 3-ethoxy-4-morpholino aniline; 3-amino-1H-indazole-5-carb aldehyde; 1-(4-aminophenyl)piperidin-3-ol; 3-methoxy-4-((tetrahydro-2H-pyran-4-yl)oxy)aniline; 2-(4-amino-2-methoxyphenoxy)-N-methylacetamide; 2-amino-1H-benzo[d]imidazole-6-carbaldehyde; 2-(4-aminophenoxy)-N-(2-hydroxyethyl)acetamide; 5-amino-2- morpholinobenzonitrile; 1-(4-aminophenyl)piperidin-4-ol; (1-(4-aminophenyl)pyrrolidin-3-yl)methanol; 4-(4-fluoropiperidin-1-yl)aniline; 3-(methoxymethyl)-4-morpholinoaniline; 3-methoxy-4-((tetrahydrofuran-2-yl)methoxy)aniline; 4-(3-(dimethylamino)propoxy)-3-methoxyaniline; 1-(4-amino-2-methoxyphenyl)azetidin-3-ol; 4-amino-N-(2-hydroxyethyl)-2-methoxybenzamide; 1-(4-amino-2-methoxyphenyl)-2-methylpropan-2-ol; 3-(4-aminophenoxy)-2,2-dimethylpropan-1-ol; 4-(2-methylmorpholino)aniline; 6-(2-methylmorpholino)pyridin-3-amine; 3-methyl-4-(piperidin-4-yl)aniline; 4-(2-morpholinoethoxy)aniline; 3-(2-morpholinoethoxy)aniline; 3-methyl-4-morpholinoaniline; (1-(4-aminophenethyl)pyrrolidin-2-yl)methanol; 4-(2-methylpyridin-4-yl)aniline; 6-(1-methylpiperidin-4-yl)pyridin-3-amine; 2-(2-methylmorpholino)pyrimidin-5-amine; 3-methyl-4-(tetrahydro-2H-pyran-4-yl)aniline; 4-amino-N-cyclopropylbenzamide; 4-(1-methylpiperidin-3-yl)aniline; 4-(1-ethylpyrrolidin-3-yl)aniline; 5-methyl-6-morpholinopyridin-3-amine; 4-methyl-3-(trifluoromethyl)aniline; 5-aminobenzofuran-2-carboxylic acid; 2-((dimethylamino)methyl)benzofuran-5-amine; ethyl 2-((3-aminophenyl)imino)acetate; 3-fluoro-5-(trifluoromethyl)aniline; 4-amino-2-(trifluoromethyl)phenol; 5-amino-2,3-dihydrobenzofuran-2-carboxylic acid; N-(4-aminophenyl)methanesulfonamide; 7-amino-4-methyl-2H-benzo[b][1,4]oxazin-3(4H)-one; 6-amino-4-methyl-2H-benzo[b][1,4]oxazin-3(4H)-one; 3-methyl-5-(trifluoromethyl)aniline; 6-amino-1-methyl-3,4-dihydroquinolin-2(1H)-one; methyl(4-aminophenyl)(methyl)carbamate; N-(4-aminophenyl)-2-hydroxy-N-methylacetamide; 6-aminoquinolin-2(1H)-one; 6-amino-1-methylquinolin-2(1H)-one; 4-(ethylsulfonyl)aniline; N-(4-aminophenyl)-N-methylpropionamide; 4-(3,5-dimethyl-1H-pyrazol-1-yl)aniline; 2-amino-2-(3-chlorophenyl)acetamide; 5-fluoro-4-(piperazin-1-yl)pyrimidin-2-amine; 4-(2-(piperidin-1-yl)ethoxy)aniline; 3-chloro-5-(2H-1,2,3-triazol-2-yl)aniline; 4-chloro-3-(2H-1,2,3-triazol-2-yl)aniline; (1-(4-aminophenyl)-1H-1,2,3-triazol-4-yl)methanol; 3-(5-fluoropyrimidin-2-yl)aniline; 4'-fluoro-[1,1'-biphenyl]-3-amine; 3'-fluoro-[1,1'-biphenyl]-3-amine; 4-bromo-3-(2H-1,2,3-triazol-2-yl)aniline; dibenzo[b,d]furan-3-amine; 3-bromo-5-(2H-1,2,3-triazol-2-yl)aniline; 3-methoxy-5-(2H-1,2,3-triazol-2-yl)aniline; 3-methoxy-5-(1H-tetrazol-1-yl)aniline; 2-amino-2-(4-methoxyphenyl)acetamide; 1-(4-aminophenyl)-3-methylazetidin-3-ol; (4-(4-aminophenyl)morpholin-2-yl)methanol; 1-(4-amino-2-methoxyphenyl)pyrrolidin-3-ol; 2-(5-amino-2-morpholinophenoxy)ethan-1-ol; (1-(4-aminophenyl)piperidin-4-yl)methanol; 4-(4-aminophenoxy)cyclohexanol; 4-(4-aminophenyl)piperazin-2-one; 4-(3,3-difluoroazetidin-1-yl)aniline; 2-(1-(4-aminophenyl)pyrrolidin-3-yl)ethan-1-ol; 4-amino-N-(oxetan-3-yl)benzamide; 1-(4-aminophenyl)-2,2,2-trifluoroethan-1-ol; 1-(4-amino-2-methoxyphenoxy)-2-methylpropan-2-ol; 3-methoxy-4-((tetrahydro-2H-pyran-4-yl)methoxy)aniline; 4-amino-N-(2-hydroxyethyl)-N-methylbenzamide; 2-(4-aminophenoxy)-N,N-dimethylacetamide; 4-(3-fluoro-3-methylazetidin-1-yl)aniline; 3-methyl-4-(2-methylmorpholino)aniline; 4-(1-ethylpiperidin-4-yl)aniline; 3-fluoro-4-(2-methylmorpholino)aniline; 3-methyl-4-(1-methylpiperidin-4-yl)aniline; 4-(2,3-dihydroimidazo[2,1-b]thiazol-6-yl)aniline; 3-fluoro-4-(1-methylpiperidin-4-yl)aniline; 5-methyl-6-(2-methylmorpholino)pyridin-3-amine; 3-fluoro-4-(piperazin-1-ylmethyl)aniline; 4'-methoxy-[1,1'-biphenyl]-4-amine; 1-(6-amino-3,4-dihydroisoquinolin-2(1H)-yl)ethan-1-one; 4-amino-N,N-diethylbenzamide; 5-(4-ethylpiperazin-1-yl)pyridin-2-amine; 2-(isopropylsulfonyl)aniline; 3-methyl-4-(1,2,3,6-tetrahydropyridin-4-yl)aniline, 2-methyl-5-(2-morpholinoethoxy)aniline; methyl 5-aminobenzofuran-2-carboxylate; 5-amino-N-methyl-2,3-dihydrobenzofuran-2-carboxamide; methyl 5-amino-2,3-dihydrobenzofuran-2-carboxylate; 3-methoxy-5-(trifluoromethyl)aniline; 5-amino-N-methylbenzofuran-2-carboxamide; 2-((3-aminophenyl)imino)-N-(2-hydroxyethyl)acetamide; 4-chloro-3-(trifluoromethyl)aniline; 3-nitroaniline; methyl 4-amino-2,3-dihydrobenzofuran-7-carboxylate; 6-amino-N-methyl-1H-indole-1-carboxamide; ethyl 2-amino-7-oxabicyclo[4.2.0]octa-1(6),2,4-triene-8-carboxylate; 3-aminophenyl isopropylcarbamate; 3-chloro-4-morpholinoaniline; 2-(6-amino-1H-indazol-1-yl)acetamide; 1-(4-aminophenyl)azetidine-2-carboxamide; 6-amino-2-naphthamide; 3-amino-5-(2H-1,2,3-triazol-2-yl)benzonitrile; 3-amino-5-(1H-1,2,3-triazol-1-yl)benzonitrile; 4-amino-N-cyclobutylbenzamide; 3-(4-methoxypyrimidin-2-yl)aniline; 4-(6-methoxypyridin-3-yl)aniline; 3-(6-methoxypyridin-2-yl)aniline; 3-(6-methoxypyridin-3-yl)aniline; 3'-methoxy-[1,1'-biphenyl]-3-amine; 4'-methoxy-[1,1'-biphenyl]-3-amine; N-(4-aminophenyl)-3-hydroxy-N-methylpropanamide; 9-methyl-9H-carbazol-3-amine; 2-(1-(4-aminophenyl)piperidin-4-yl)ethan-1-ol; 1-(4-amino-2-methoxyphenyl)piperidin-3-ol; 1-(4-aminophenyl)-3-methylpyrrolidin-3-ol; 2-(4-(4-aminophenyl)piperazin-1-yl)ethan-1-ol; 4-(3,3-difluoropyrrolidin-1-yl)aniline; 4-(2-oxa-6-azaspiro[3.3]heptan-6-yl)aniline; 3-(2-methoxyethoxy)-4-morpholinoaniline; 3-(4-amino-2-methoxyphenoxy)-2,2-dimethylpropan-1-ol; 1-(4-amino-2-methoxyphenyl)piperidin-4-ol; (1-(4-amino-2-methoxyphenyl)pyrrolidin-3-yl)methanol; 4-(3-methoxy-3-methylazetidin-1-yl)aniline; 1-(4-amino-2-ethoxyphenoxy)-2-methylpropan-2-ol; 1-(4-amino-2-ethoxyphenyl)pyrrolidin-3-ol; 4-amino-N-ethyl-N-(2-hydroxyethyl)benzamide; 4-((4-ethylpiperazin-1-yl)methyl)aniline; 1-(4-aminophenyl)-3-ethylazetidin-3-ol; 3-methyl-4-(2-(pyrrolidin-1-yl)ethoxy)aniline; 4-methyl-3-(2-(pyrrolidin-1-yl)ethoxy)aniline; 1-(4-aminophenethyl)piperidin-4-ol; 2-(4-(4-aminophenyl)piperidin-1-yl)ethan-1-ol; 3-methyl-4-((1-methylpiperidin-4-yl)oxy)aniline; 2-methoxy-5-methyl-4-(piperidin-4-yl)aniline; 4-(1-(2-methoxyethyl)-1H-pyrazol-4-yl)aniline; 3-fluoro-4-(2-(pyrrolidin-1-yl)ethoxy)aniline; 4-amino-N-cyclopentylbenzamide; 4-(1-(2-methoxyethyl)pyrrolidin-3-yl)aniline; 2-methoxy-4-(4-methylpiperazin-1-yl)aniline; 2-(4-(4-amino-1H-pyrazol-1-yl)piperidin-1-yl)acetonitrile; (4-aminophenyl)(piperazin-1-yl)methanone; 1-(1-(2-methoxyethyl)piperidin-4-yl)-1H-pyrazol-4-amine; 4-(2-(4-methylpiperazin-1-yl)ethyl)aniline; 4-(1,2-dimethylpiperidin-4-yl)-3-fluoroaniline; methyl 2-(5-amino-1H-indazol-1-yl)acetate; methyl 2-(6-amino-1H-indazol-1-yl)acetate; 2-(5-amino-1H-indazol-1-yl)-N-methylacetamide; 3-chloro-4-(trifluoromethoxy)aniline; 4-(4,5-dichloro-1H-imidazol-1-yl)aniline; 2-(6-amino-1H-indazol-1-yl)-N-methylacetamide; (3-aminophenyl)(phenyl)methanone; methyl 3-amino-5-formamidobenzoate; 5-methoxy-2-methyl-[1,1'-biphenyl]-4-amine; 2-((3-aminophenyl)imino)-N,N-dimethylacetamide; 2-((3-aminophenyl)imino)-N-(2-(methylamino)ethyl)acetamide; ethyl 5-aminobenzofuran-2-carboxylate; 1-(4-aminophenyl)pyrrolidine-2-carboxamide; (1-(2-amino-5-fluoropyrimidin-4-yl)piperidin-4-yl)methanol; 4-amino-N-(2-hydroxyethyl)benzenesulfonamide; 4-(2-amino-5- fluoropyrimidin-4-yl)piperazin-2-one; 3-(1H-benzo[d][1,2,3]triazol-1-yl)aniline; 3-(1H-indazol-1-yl)aniline; 3-(2H-benzo[d][1,2,3]triazol-2-yl)aniline; 3-(1H-benzo[d]imidazol-1-yl)aniline; 3-(1H-indazol-2-yl)aniline; 3-(imidazo[1,2-a]pyridin-2-yl)aniline; 3-(4-aminophenyl)pyridin-2(1H)-one; 3-(benzo[d][1,3]dioxol-4-yl)aniline; 3-(benzo[d][1,3]dioxol-5-yl)aniline; 3-(2,3-dihydrobenzofuran-5-yl)aniline; 3-(imidazo[1,2-a]pyridin-6-yl)aniline; 4-(imidazo[1,2-a]pyridin-6-yl)aniline; 6-amino-N-methyl-2-naphthamide; 3-fluoro-4-(4-methyl-1H-pyrazol-1-yl)aniline; 1-(4-aminophenyl)-4-methylpiperidin-4-ol; 1-(4-amino-2-methoxyphenyl)-3-methylazetidin-3-ol; (4-(4-amino-2-methoxyphenyl)morpholin-2-yl)methanol; 2-(4-(4-aminophenyl)piperazin-1-yl)acetaldehyde; 4-(4-(3-fluoropropyl)piperazin-1-yl)aniline; 4-(4,4-difluoropiperidin-1-yl)aniline; 4-(3,3-difluoropiperidin-1-yl)aniline; 4-(8-oxa-3-azabicyclo[3.2.1]octan-3-yl)aniline; 4-amino-N-(tetrahydro-2H-pyran-4-yl)benzamide; (4-aminophenyl)(3-hydroxyazetidin-1-yl)methanone; 3-(4-amino-2-ethoxyphenoxy)-2,2-dimethylpropan-1-ol; 4-(4-ethylpiperazin-1-yl)-3-methoxyaniline; 4-(2,6-dimethylmorpholino)aniline; 1-(4-aminophenyl)-3-methylpiperidin-3-ol; 2-(4-aminophenyl)-N,2-dimethylpropanamide; 4-(1-(2-methoxyethyl)piperidin-4-yl)aniline; 4-(1-(3-fluoropropyl)piperidin-4-yl)aniline; 4-(2-(4-ethylpiperazin-1-yl)ethyl)aniline; 4-amino-N-phenylbenzamide; 3-((dimethylamino)methyl)-1H-indazol-6-amine; 1-(4-aminophenyl)-N,N-dimethylpyrrolidin-3-amine; 4-(4-ethoxypiperidin-1-yl)-3-fluoroaniline; 6-(2,6-dimethylmorpholino)pyridin-3-amine; 6-(1-(2-methoxyethyl)piperidin-4-yl)pyridin-3-amine; 4-methyl-3-(2-morpholinoethoxy)aniline; 6-amino-2,2-dimethyl-2H-benzo[b][1,4]oxazin-3(4H)-one; 3-(5-amino-1H-indazol-1-yl)-N-methylpropanamide; 3-(6-amino-1H-indazol-1-yl)-N-methylpropanamide; 5-amino-N-(2-hydroxyethyl)benzofuran-2-carboxamide; 3-(5-amino-2H-indazol-2-yl)-N-methylpropanamide; N-(3-amino-5-(trifluoromethyl)phenyl)formamide; 4-(benzyloxy)-3-chloroaniline; 6-amino-2,2-difluoro-2H-benzo[b][1,4]oxazin-3(4H)-one; 5-amino-N-(2-hydroxyethyl)-2,3-dihydrobenzofuran-2-carboxamide; 5-amino-1H-indole-2-carboxylic acid; methyl 5-amino-3-oxo-2,3-dihydrobenzofuran-2-carboxylate; methyl 2-amino-8-methyl-7-oxabicyclo[4.2.0]octa-1,3,5-triene-5-carboxylate; 2-methoxy-5-nitroaniline; N-(3-aminophenyl)pivalamide; N-(4-aminophenyl)-N-methylcyclopropanecarboxamide; N-(4-amino-2-chlorophenyl)-N-methylacetamide; 3-((4-aminophenyl)sulfonyl)propanenitrile; 2-morpholinoquinolin-6-amine; 4-amino-N-(2-methoxyethyl)benzenesulfonamide; 4-amino-N-cyclopropyl-N-methylbenzamide; tert-butyl 4-aminopiperidine-1-carboxylate; 1-(4-aminophenyl)piperidine-2-carboxamide; 3,5-difluoro-4-morpholinoaniline; 4-(4-aminophenyl)thiomorpholine-2,3-dione; 3-(2H-benzo[b][1,4]oxazin-4(3H)-yl)aniline; 3-(quinolin-3-yl)aniline; 3-(quinolin-4-yl)aniline; 3',4'-difluoro-[1,1'-biphenyl]-3-amine; 3-(quinolin-5-yl)aniline; 3-(quinolin-8-yl)aniline; 3-(2,3-dihydrobenzo[b][1,4]dioxin-6-yl)aniline; 4-(2,3-dihydrobenzo[b][1,4]dioxin-6-yl)aniline; 3-(quinolin-6-yl)aniline; 4-(methylsulfinyl)-7H-pyrrolo[2,3-d]pyrimidin-2-amine; 4-(4-(2-methoxyethyl)piperazin-1-yl)aniline; 2',4'-dimethoxy-[1,1'-biphenyl]-3-amine; 2',3'-dimethoxy-[1,1'-biphenyl]-3-amine; 3',4'-dimethoxy-[1,1'-biphenyl]-3-amine; 1-(4-aminophenyl)-N-methylpyrrolidine-2-carboxamide; tert-butyl 3-aminopiperidine-1-carboxylate; 2-(4-(4-amino-2-methoxyphenyl)piperazin-1-yl)ethan-1-ol; 1-(4-amino-2-ethoxyphenyl)-3-methylazetidin-3-ol; 4-(2-oxa-7-azaspiro[3.5]nonan-7-yl)aniline; 4-(7-oxa-2-azaspiro[3.5]nonan-2-yl)aniline; 1-(4-amino-2-methoxyphenyl)-3-methylpyrrolidin-3-ol; 1-(4-aminophenyl)-N,N-dimethylpiperidin-4-amine; 2-(aminophenyl)-1,1,1-trifluoropropan-2-ol; 1-(4-amino-2-fluorophenyl)-3-methylazetidin-3-ol; 4-(1-cyclopropylpiperidin-4-yl)aniline; 4-(1-(2-methoxyethyl)piperidin-4-yl)-3-methylaniline; 3-(4-(4-aminophenyl)piperidin-1-yl)propanenitrile; 4-amino-N-(3-methoxypropyl)benzenesulfonamide; 2-fluoro-5-methyl-4-(1-methylpiperidin-4-yl)aniline; 4-(1-isopropylpiperidin-4-yl)aniline; 2-(3-aminophenoxy)-1-morpholinoethan-1-one; 2-(4-(4-amino-2-methylphenyl)piperidin-1-yl)acetonitrile; 4-(1-(3-fluoropropyl)piperidin-4-yl)-3-methylaniline; ethyl 3-(5-amino-1H-indazol-1-yl)propanoate; ethyl 3-(6-amino-1H-indazol-1-yl)propanoate; 5-amino-N,N-dimethyl-2,3-dihydrobenzofuran-2-carboxamide; ethyl 2-(4-aminophenyl)-2-methylpropanoate; ethyl 3-(5-amino-2H-indazol-2-yl)propanoate; 4-fluoro-3-nitroaniline; 2-fluoro-5-nitroaniline; methyl 5-amino-1H-indole-2-carboxylate; tert-butyl (4-aminophenyl)carbamate; tert-butyl (3-aminophenyl)carbamate; 4-methyl-3-nitroaniline; 2-methyl-5-nitroaniline; 1-(4-aminophenyl)-N-methylpiperidine-2-carboxamide; tert-butyl 4-(aminomethyl)piperidine-1-carboxylate; isopropyl(4-aminophenyl)(methyl)carbamate; 2-(morpholinomethyl)quinolin-6-amine; 4-(pyrrolidin-1-yl)-7H-pyrrolo[2,3-d]pyrimidin-2-amine; benzyl 4-aminocyclohexanecarboxylate; 4-amino-N-cyclobutyl-N-methylbenzamide; 1-(4-aminophenyl)-1H-1,2,3-triazole-4-carboxamide; 2-(4-aminophenoxy)-1-morpholinoethan-1-one; 4-amino-N-cyclopropylbenzenesulfonamide; 2'-(pyrrolidin-3-yl)-[1,1'-biphenyl]-3-amine; 1-(methylsulfonyl)-1H-indazol-6-amine; N-(4-aminophenyl)-2-(dimethylamino)-N-methylacetamide; 5-(4-aminophenyl)-N,N-dimethylpyridin-2-amine; 4-(2-methyl-1-morpholinopropan-2-yl)aniline; 1-(4-amino-2-methoxyphenyl)-4-methylpiperidin-4-ol; 5-amino-2-morpholinobenzamide; (4-aminophenyl)(4-hydroxypiperidin-1-yl)methanone; 3-methoxy-4-(4-(2-methoxyethyl)piperazin-1-yl)aniline; 1-(4-amino-2-methoxyphenyl)-3-methylpiperidin-3-ol; 3-(4-aminophenyl)-1,4-dimethylpiperazin-2-one; 1-(4-(4-aminophenyl)piperidin-1-yl)ethan-1-one; 4-(2-(4-(2-methoxyethyl)piperazin-1-yl)ethyl)aniline; 4-amino-N-(2-morpholinoethyl)benzamide; 2-(methylsulfonyl)-1,2,3,4-tetrahydroisoquinolin-6-amine; 1-(4-aminophenethyl)-N,N-dimethylpyrrolidin-3-amine; 3-methyl-4-(3-(4-methylpiperazin-1-yl)propoxy)aniline; 3-((4-(4-amino-2-methylphenyl)piperidin-1-yl)propanenitrile; 3-chloro-4-(2,6-dimethylmorpholino)aniline; ethyl 5-amino-1H-indole-2-carboxylate; 2-((3-aminophenyl)imino)-1-morpholinoethan-1-one; 2-((3-aminophenyl)imino)-N-(2,3-dihydroxypropyl)acetamide; 2-((3-aminophenyl)imino)-1-(piperazin-1-yl)ethan-1-one; 4-chloro-3-nitroaniline; 4-(pyrrolidin-1-ylsulfonyl)aniline; 2,2,3,3-tetrafluoro-2,3-dihydrobenzo[b][1,4]dioxin-6-amine; methyl 5-amino-2-(trifluoromethoxy)benzoate; ethyl 7-amino-1H-indole-2-carboxylate; 5-amino-N-isopropyl-2,3-dihydrobenzofuran-2-carboxamide; 1-(4-(5-aminopyridin-2-yl)piperazin-1-yl)ethan-1-one; benzyl 3-(aminomethyl)piperidine-1-carboxylate; 6-amino-N,N-dimethyl-2-naphthamide; 4-(4-aminophenyl)piperazine-1-carboxamide; 1-(4-aminophenyl)piperidine-3-carboxamide; 4-(piperidin-1-yl)-7H-pyrrolo[2,3-d]pyrimidin-2-amine; 4-amino-N-cyclobutylbenzenesulfonamide; 1-(4-aminophenyl)piperidine-4-carboxylic acid; 1-(4-aminophenyl)-4-hydroxypyrrolidine-2-carboxamide; 1-(4-aminophenyl)piperidine-4-carboxamide; 2'-(piperidin-4-yl)-[1,1'-biphenyl]-3-amine; 2'-(piperidin-3-yl)-[1,1'-biphenyl]-3-amine; 2-phenyl-1H-indol-4-amine; 2',5'-dimethoxy-[1,1'-biphenyl]-3-amine; 1-(4-aminophenyl)-N-methylpyrrolidine-3-carboxamide; tert-butyl 2-(4-aminophenoxyl)acetate; (4-aminophenyl)(2-(hydroxymethyl)morpholino)methanone; 4-amino-N-methyl-N-(tetrahydro-2H-pyran-4-yl)benzamide; 1-(4-amino-2-ethoxyphenyl)-4-methylpiperidin-4-ol; (4-aminophenyl)(3-hydroxy-3-methylazetidin-1-yl)methanone; 3-(4-(4-aminophenyl)piperidin-1-yl)propane-1,2-diol; 1-(4-aminophenethyl)-N,N-dimethylpiperidin-4-amine; 4-(2,2-dimethylmorpholino)-3-methylaniline; 4-amino-N-(1-methylpiperidin-4-yl)benzamide; 4-(2-(tetrahydro-2H-pyran-4-yl)thiazol-4-yl)aniline; 4-(2-(piperidin-3-yl)thiazol-4-yl)aniline; 4-(2-(pyridin-3-yl)thiazol-4-yl)aniline; 4-(1-(piperidin-4-yl)-1H-pyrazol-4-yl)aniline; 4-(1-cyclopentylpiperidin-4-yl)aniline; 3-(1,2,3,6-tetrahydropyridin-4-yl)-1H-indazol-6-amine; 4-(1-ethylpiperidin-4-yl)-2-methoxy-5-methylaniline; methyl 4-(4-aminophenyl)piperazine-1-carboxylate; tert-butyl 2-((3-aminophenyl)imino)acetate; (5-aminobenzofuran-2-yl)(pyrrolidin-1-yl)methanone; methyl 3-amino-5-(trifluoromethyl)benzoate; 2-((3-aminophenyl)imino)-N-(3-(dimethylamino)propyl)acetamide; ethyl 6-amino-4H-benzo[b]imidazo[1,5-d][1,4]oxazine-3-carboxylate; 1-(2-amino-5-fluoropyrimidin-4-yl)piperidine-3-carboxamide; 1-(4-(4-aminophenyl)piperazin-1-yl)propan-1-one; 2-amino-4-(m-tolyl)pyrimidine-5-carboxamide; 2-amino-4-(2-(2-hydroxyethyl)piperidin-1-yl)pyrimidine-5-carboxamide; 4-(morpholinosulfonyl)aniline; 4-((thiazol-4-ylmethyl)sulfonyl)aniline; 4-((tetrahydro-2H-pyran-4-yl)sulfonyl)aniline; 3-(2H-1,2,3-triazol-2-yl)-5-(trifluoromethyl)aniline; 1-(4-aminophenyl)-N-methylpiperidine-3-carboxamide; 1-(4-aminophenyl)-N-methylpiperidine-4-carboxamide; 6-amino-2,2,4-trimethyl-2H-benzo[b][1,4]oxazin-3(4H)-one; 1-(4-(4-aminophenyl)-3-methylpiperazin-1-yl)ethan-1-one; 2-(4-aminophenylsulfonamido)acetamide; 4-(phenylsulfonyl)aniline; 3-(2H-1,2,3-triazol-2-yl)-4-(trifluoromethyl)aniline; 3-morpholino-4-(1H-pyrazol-1-yl)aniline; 3-(1H-1,2,3-triazol-1-yl)-4-(trifluoromethyl)aniline; 4-(3-(trifluoromethyl)-1H-pyrazol-1-yl)aniline; 2-(6-amino-2-oxo-3,4-dihydroquinolin-1(2H)-yl)acetic acid; 1-(4-aminophenyl)-4-hydroxy-N-methylpyrrolidine-2-carboxamide; 1-(4-aminophenyl)-N,N-dimethylpyrrolidine-2-carboxamide; 4-(4-((dimethylamino)methyl)piperidin-1-yl)-5-fluoropyrimidin-2-amine; 7-amino-2,2,4-trimethyl-2H-benzo[b][1,4]oxazin-3(4H)-one; 3-(4-methyl-3,4-dihydro-2H-benzo[b][1,4]oxazin-7-yl)aniline; N-(1-(4-aminophenyl)piperidin-4-yl)acetamide; 1-(4-(4-aminophenyl)-1,4-diazepan-1-yl)ethan-1-one; 1-(4-(4-aminophenyl)-5,6-dihydropyridin-1(2H)-yl)ethan-1-one; 1-(4-(4-aminophenyl)-1,2,3,6-tetrahydropyridin-2-yl)ethan-1-one; 2-(1-(4-aminophenyl)piperidin-4-yl)propan-2-ol; 4-(piperidin-4-yl)-3-(trifluoromethyl)aniline; 4-(1-cyclopropylpiperidin-4-yl)-3-methylaniline; 4-(piperazin-1-yl)-3-(trifluoromethyl)aniline; 1-(4-aminophenyl)piperidine-3-carboxylic acid; 1-(4-aminophenethyl)piperidine-4-carboxylic acid; 4-morpholino-3-(trifluoromethyl)aniline; 4-amino-N-(4-chlorophenyl)benzamide; 4-(4-(4-aminophenyl)piperidin-1-yl)butan-2-one; 4-(4-aminophenyl)-N-ethylpiperidine-1-carboxamide; 4-(1-isopropylpiperidin-4-yl)-3-methylaniline; 2-(4-(4-amino-2-methylphenyl)piperidin-1-yl)acetamide; (5-aminobenzofuran-2-yl)(morpholino)methanone; 5-amino-N-(2,3-dihydroxypropyl)-2,3-dihydrobenzofuran-2-carboxamide; 5-amino-N-(2,3-dihydroxypropyl)benzofuran-2-carboxamide; 5-amino-N-(1,3-dihydroxypropan-2-yl)benzofuran-2-carboxamide; 2-amino-4-(3-methoxyphenyl)pyrimidine-5-carboxamide; 3-amino-N-methoxy-N-phenylbenzamide; 1-(4-aminophenyl)-N,N-dimethylpiperidine-2-carboxamide; 2-amino-4-(3-ethylphenyl)pyrimidine-5-carboxamide; 1-(1-(2-amino-5-fluoropyrimidin-4-yl)piperidin-4-yl)urea; 2-(1-(2-amino-5-fluoropyrimidin-4-yl)piperidin-4-yl)acetamide; 2-amino-4-(3-(hydroxymethyl)piperidin-1-yl)pyrimidine-5-carboxamide; 4-(4-(pyridin-2-yl)piperazin-1-yl)aniline; 3-(4-phenylpiperazin-1-yl)aniline; 3'-morpholino-[1,1'-biphenyl]-3-amine; 4'-morpholino-[1,1'-biphenyl]-3-amine; 3'-morpholino-[1,1'-biphenyl]-4-amine; 4'-morpholino-[1,1'-biphenyl]-4-amine; 2'-(methylsulfonyl)-[1,1'-biphenyl]-3-amine; 1-(4-(4-aminophenyl)piperazin-1-yl)-2-methoxyethan-1-one; 2',3',4'-trimethoxy-[1,1'-biphenyl]-3-amine; 4-acetyl-1-(4-aminophenyl)piperazin-2-one; (2-aminocyclohexyl)(tert-butyl)carbamate; 4-(4-(1-methylcyclopropyl)piperazin-1-yl)aniline; 2-(4-aminophenoxy)-1-(3-hydroxy-3-methylazetidin-1-yl)ethan-1-one; (4-aminophenyl)(4-hydroxy-4-methylpiperidin-1-yl)methanone; 4-(2-(4-(pyrrolidin-1-yl)piperidin-1-yl)ethyl)aniline; 1-(4-(4-amino-2-methylphenyl)piperidin-1-yl)ethan-1-one; 4-(1-(methylsulfonyl)pyrrolidin-3-yl)aniline; 4-(1-(2-morpholinoethyl)-1H-pyrazol-4-yl)aniline; 4-(1-methylpiperidin-4-yl)-3-(trifluoromethyl)aniline; 1-(4-(4-aminophenyl)piperidin-1-yl)-2-(ethylamino)ethan-1-one; 4-(1-(2,2,2-trifluoroethyl)piperidin-4-yl)aniline; 4-(4-aminophenyl)piperidine-1-carboxylate; 1-(4-(4-amino-2-methylphenyl)piperidin-1-yl)-3-methoxypropan-2-ol; 2-(4-(4-amino-2-methylphenyl)piperidin-1-yl)-N-methylacetamide; 4-(4-benzylpiperazin-1-yl)aniline; 2-((3-aminophenyl)imino)-1-(4-methylpiperazin-1-yl)ethan-1-one; 2-((3-aminophenyl)imino)-N-(2-morpholinoethyl)acetamide; (5-aminobenzofuran-2-yl)(1,4-diazepan-1-yl)methanone; (6-aminonaphthalen-2-yl)(morpholino)methanone; 1-(4-(4-amino-3-methylphenyl)piperazin-1-yl)ethan-1-one; 1-((1-(2-amino-5-fluoropyrimidin-4-yl)piperidin-4-yl)methyl)urea; 4-(2-amino-5-fluoropyrimidin-4-yl)piperazine-1-carboxamide; 1-(4-(4-amino-2-fluorophenyl)piperazin-1-yl)ethan-1-one; 1-(4-(4-aminophenyl)-2-methylpiperazin-1-yl)ethan-1-one; 4-(1-(methylsulfonyl)piperidin-4-yl)aniline; 4-(2-(4-morpholinopiperidin-1-yl)ethyl)aniline; 3-methyl-4-(1-(piperidin-4-yl)-1H-pyrazol-4-yl)aniline; 4-(1-(methylsulfonyl)piperidin-3-yl)aniline; 1-(4-(4-amino-2-methylphenyl)piperidin-1-yl)-2-(ethylamino)ethan-1-one; 1-(3-(4-aminophenyl)pyrrolidin-1-yl)-2-(dimethylamino)ethan-1-one; ethyl 3-(4-(4-aminophenyl)piperidin-1-yl)propanoate; tert-butyl 6-amino-3,4-dihydroisoquinoline-2(1H)-carboxylate; 4-(benzyloxy)-3-(trifluoromethyl)aniline; 5-amino-N-(1-hydroxy-2-methylpropan-2-yl)benzofuran-2-carboxamide; 1-((4-aminophenyl)sulfonyl)piperidin-4-ol; 4-(4-(methylsulfonyl)piperidin-1-yl)aniline; 1-(4-aminophenyl)-N,N-dimethylpiperidine-4-carboxamide; 2-amino-4-(4-(2-hydroxyethyl)-1,4-diazepan-1-yl)pyrimidine-5-carboxamide; 4-(4-aminophenyl)-N,N-dimethylpiperazine-1-carboxamide; 1-(4-(4-amino-2-chlorophenyl)piperazin-1-yl)ethan-1-one; 3-(2-amino-5-nitrophenyl)propanamide; 3-(4-(2-amino-5-fluoropyrimidin-4-yl)piperazin-1-yl)-3-oxopropanenitrile; 3-fluoro-4-(3-(trifluoromethyl)-1H-pyrazol-1-yl)aniline; (4-(4-aminophenyl)piperazin-1-yl)(cyclopropyl)methanone; 1-(3'-amino-[1,1'-biphenyl]-4-yl)piperidin-2-one; 1-(3'-amino-[1,1'-biphenyl]-3-yl)pyridin-2(1H)-one; 1-(3'-amino-[1,1'-biphenyl]-4-yl)pyridin-2(1H)-one; 4-(methylsulfonyl)-3-morpholinoaniline; 3'-(methylsulfonyl)-[1,1'-biphenyl]-4-amine; 4'-(methylsulfonyl)[1,1'-biphenyl]-4-amine; 3'-(methylsulfonyl)-[1,1'-biphenyl]-3-amine; 4'-(methylsulfonyl)-[1,1'-biphenyl]-3-amine; methyl 4-(4-aminophenyl)-3-methylpiperazine-1-carboxylate; N-(4-aminophenyl)-2-(benzyloxy)-N-methylacetamide; 2-(4-amino-N-methylphenylsulfonamido)acetic acid; 1-(4-aminophenyl)-4-hydroxy-N,N-dimethylpyrrolidine-2-carboxamide; 1-(4-aminophenyl)-N,N-dimethylpiperidine-3-carboxamide; N-(1-(4-aminophenyl)piperidin-4-yl)-N-methylacetamide; 1-(4-(4-aminophenyl)piperidin-1-yl)-2-(dimethylamino)ethan-1-one; 4-(1-(4,4,4-trifluorobutyl)piperidin-4-yl)aniline; 3-methyl-4-(6-(piperazin-1-yl)pyridin-3-yl)aniline; 1-(1-(2-(methylsulfonyl)ethyl)piperidin-4-yl)-1H-pyrazol-4-amine; 1-(4-(5-aminopyridin-2-yl)piperidin-1-yl)-2-(dimethylamino)ethan-1-one; 4-(1-(ethylsulfonyl)piperidin-4-yl)aniline; 2-((3-aminophenyl)imino)-N-(2-(benzylamino)ethyl)acetamide; 1-(4-(4-aminophenyl)-3-methylpiperazin-1-yl)-2-methoxyethan-1-one; N-(1-(2-amino-5-fluoropyrimidin-4-yl)piperidin-4-yl)-2-cyanoacetamide; 4-((4-(methylsulfonyl)piperazin-1-yl)methyl)aniline; 4-(4-(methylsulfonyl)-1,4-diazepan-1-yl)aniline; 4-(1-(methylsulfonyl)-1,2,3,6-tetrahydropyridin-4-yl)aniline; 4-(2-(methylsulfonyl)-1,2,3,6-tetrahydropyridin-4-yl)aniline; 2-amino-4-(methyl(1-methylpiperidin-4-yl)amino)pyrimidine-5-carboxamide; 4-(4-(ethylsulfonyl)piperazin-1-yl)aniline; 1-(4-(4-aminobenzoyl)piperazin-1-yl)ethan-1-one; 4-(2-methyl-4-(methylsulfonyl)piperazin-1-yl)aniline; 2,6-diisopropyl-4-phenoxyaniline; 2-methyl-4-(4-(methylsulfonyl)piperazin-1-yl)aniline; 3-methyl-4-(1-(2-morpholinoethyl)-1H-pyrazol-4-yl)aniline; 4-(1-(2-(methylsulfonyl)ethyl)piperidin-4-yl)aniline; 1-(4-(4-amino-2-methylphenyl)piperidin-1-yl)-2-(dimethylamino)ethan-1-one; 5-amino-2-(morpholine-4-carbonyl)benzofuran-3(2H)-one; tert-butyl(6-amino-4H-chromen-4-yl)carbamate; 2-amino-4-(3,5-dimethylphenyl)pyrimidine-5-carboxamide; (1-(4-aminophenyl)piperidin-4-yl)(pyrrolidin-1-yl)methanone; 4-acetyl-1-(4-aminophenyl)piperazine-2-carboxamide; 3-(4-(4-aminophenyl)piperidin-1-yl)-1,1,1-trifluoropropan-2-ol; tert-butyl 3-(4-aminophenyl)pyrrolidine-1-carboxylate; ethyl 1-(3-aminobenzoyl)piperidine-4-carboxylate; (1-(4-aminophenyl)piperidin-4-yl)(morpholino)methanone; (1-(4-aminophenyl)piperidin-4-yl)(piperidin-1-yl)methanone; 4-acetyl-1-(4-aminophenyl)-N-methylpiperazine-2-carboxamide; tert-butyl 4-(4-aminophenyl)piperidine-1-carboxylate; butyl 2-(4-amino-N-methylphenylsulfonamido)acetate; 4-(4-(cyclopropylsulfonyl)piperazin-1-yl)aniline; N-(1-(4-aminophenyl)piperidin-4-yl)-N-methylmethanesulfonamide; 4-(4-(ethylsulfonyl)-2-methylpiperazin-1-yl)aniline; 3-methyl-4-(1-(2-(methylsulfonyl)ethyl)piperidin-4-yl)aniline; (4-aminophenyl)(4-(methylsulfonyl)piperazin-1-yl)methanone; 4-(4-(cyclopropylsulfonyl)-2-methylpiper azin-1-yl)aniline; 1-(4-(4-aminophenyl)piperidin-1-yl)-2-(methylsulfonyl)ethan-1-one; methyl 4-((6-amino-2H-indazol-2-yl)methyl)-3-methoxybenzoate; methyl 4-((6-amino-1H-indazol-1-yl)methyl)-3-methoxybenzoate; 4-((6-amino-1H-indazol-1-yl)methyl)-3-methoxy-N-methylbenzamide; 2-isopropyl-5-methylcyclohexyl 5-amino-2,3-dihydrobenzofuran-2-carboxylate; ethyl 4-amino-3-(2-amino-5-nitrobenzyl)-4-oxobutanoate; 3,4-bis(3-(trifluoromethyl)-1H-pyrazol-1-yl)aniline.

Especially preferably, $R^1$ can be derived from the following amines: 4-(4-(4-methylpiperazin-1-yl)piperidin-1-yl)aniline; 3-fluoro-4-morpholino aniline; 4-fluoro-3-(methylsulfonyl)aniline; 3-((dimethylamino)methyl)aniline; (4-aminophenyl)(4-(4-methylpiperazin-1-yl)piperidin-1-yl)methanone; (3-aminophenyl)(morpholino)methanone; 3-(tert-butyl)aniline; 4-morpholinoaniline; 4-(4-cyclopropylpiperazin-1-yl)aniline; 6-morpholinopyridin-3-amine; 6-amino-2,3-dihydrobenzo[b]thiophene 1,1-dioxide; 6-aminobenzo[b]thiophene 1,1-dioxide; (4-aminophenyl)(morpholino)methanone; 4-(morpholinomethyl)aniline; 3-methoxy-4-morpholinoaniline; 1,3-dihydroisobenzofuran-5-amine; 4-((4-(4-methylpiperazin-1-yl)piperidin-1-yl)methyl)aniline; 3-(morpholinomethyl)aniline; 2-(3-aminophenyl)-2-methylpropanenitrile; 3-(4-aminophenyl)oxazolidin-2-one; 5-cyclopropyl-1H-pyrazol-3-amine; (4-amino-2-fluorophenyl)(morpholino)methanone; (4-amino-2-nitrophenyl)(morpholino)methanone; 4-(oxazol-2-yl)aniline; 4-(oxazol-5-yl)aniline; 4-(4-(tert-butyl)piperazin-1-yl)aniline; pyridazin-4-amine; 3-(methylsulfonyl)-4-nitroaniline; 3-(methylsulfonyl)aniline; 3,4-dimethoxyaniline; 1-(4-(4-aminophenyl)piperazin-1-yl)ethan-1-one; 7-amino-3,4-dihydroquinolin-2(1H)-one; 4-((dimethylamino)methyl)aniline; 2-methylisoindolin-5-amine; 2-(methylthio)-1H-benzo[d]imidazol-5-amine; 4-(4-(methylsulfonyl)piperazin-1-yl)aniline; 4-(4-aminophenyl)morpholin-3-one; (4-aminophenyl)(pyrrolidin-1-yl)methanone; (4-aminophenyl)(4-methylpiperazin-1-yl)methanone; 4-aminobenzamide; 1-(4-aminophenyl)pyrrolidin-2-one; 5-amino-2-morpholinobenzonitrile; 8-amino-4,5-dihydro-1H-benzo[b]azepin-2(3H)-one; 6-(4-methylpiperazin-1-yl)pyridin-3-amine; cyclopropanamine; 1-methyl-1H-pyrazol-4-amine; 5-(4-aminophenyl)-1,3,4-oxadiazole-2-thiol; 1-(tetrahydro-2H-pyran-4-yl)-1H-pyrazol-4-amine; 4-(4-morpholinopiperidin-1-yl)aniline; N2,N2-dimethylpyridine-2,5-diamine; 3-(methylsulfonyl)-4-morpholinoaniline; 1-(4-(5-aminopyridin-2-yl)piperazin-1-yl)ethan-1-one; 6-(4-(4-methylpiperazin-1-yl)piperidin-1-yl)pyridin-3-amine; 1,5-dimethyl-1H-pyrazol-4-amine; 1,3-dimethyl-1H-pyrazol-4-amine; 2-((4-aminophenyl)amino)ethan-1-ol; 1-(2-methoxyethyl)-1H-pyrazol-4-amine; 1-(methylsulfonyl)-1H-pyrazol-4-amine; 1-(1-methylpiperidin-4-yl)-1H-pyrazol-4-amine; 1-(4-(4-amino-1H-pyrazol-1-yl)piperidin-1-yl)ethan-1-one; 1-methyl-1H-1,2,3-triazol-4-amine; 2-methyl-2H-1,2,3-triazol-4-amine; 1-methyl-1H-pyrazol-3-amine.

Furthermore preferably, $R^1$ can be derived from the following amines: methanamine; 2-aminoethane-1-thiol; ethane-1,2-diamine; 2-methylpropan-1-amine; furan-2-ylmethanamine; pyrimidin-4-amine; pyridin-4-ylmethanamine; pyridin-2-ylmethanamine; pyridin-3-ylmethanamine; 2-fluoroaniline; 3-methylpyridin-4-amine; 2-(pyridin-4-yl)ethan-1-amine; 1-methyl-1H-pyrazol-3-amine; (2-methoxyphenyl)methanamine; 4-aminocyclohexanol; 6-fluoropyridin-2-amine; (S)-butane-1,2-diamine; 1-amino-3-methylbut-3-en-1-ol; benzene-1,4-diamine; 5-aminopyridin-2-ol; 2-aminobenzonitrile; 2-(1H-imidazol-5-yl)ethan-1-amine; 2-(methylthio)pyrimidin-4-amine;

(2-ethoxyphenyl)methanamine; 2,6-difluoroaniline; 6-chloropyridin-3-amine; 2-methoxypyridin-4-amine; 6-methoxypyridazin-3-amine; 1-ethyl-5-methyl-1H-pyrazol-3-amine; (4-methoxyphenyl)methanamine; (4-chlorophenyl)methanamine; (3-chlorophenyl)methanamine; 2-chloro-6-methylaniline; benzo[d]isoxazol-6-amine; benzo[d]oxazol-5-amine; benzo[d]oxazol-6-amine; 4-((methylamino)methyl)aniline; 3-ethynylaniline; 3-aminopicolinamide; 2-aminonicotinamide; N1-isopropyl-2-methylpropane-1,2-diamine; 2-fluoro-6-methylpyrimidin-4-amine; 4-chloro-3-methoxyaniline; 4-aminonicotinic acid; 2-aminobenzoic acid; 2-((5-aminopyridin-2-yl)oxy)ethan-1-ol; (3-amino-1H-pyrazol-5-yl)methanol; 4-(2-(methylamino)ethyl)aniline; 2-aminothiazole-4-carboxamide; methyl 2-aminonicotinate; 1-(3-aminophenyl)ethan-1-ol; 2-((4-aminobenzyl)amino)ethan-1-ol; methyl 4-aminonicotinate; methyl 2-aminobenzoate; 6-(2-methoxyethoxy)pyridin-3-amine; 4-(2-(methylamino)ethoxy)aniline; 3-ethoxy-4-methoxyaniline; 6-((2-aminoethyl)amino)nicotinonitrile; 5-aminopicolinamide; 6-aminopicolinamide; 2-(methylsulfinyl)pyrimidin-4-amine; 2-methylbenzo[d]oxazol-5-amine; 2-(4-amino-2-methoxyphenoxy)ethan-1-ol; 4-aminobenzimidamide; 3-methoxy-4-propoxyaniline; 4-(((2-methoxyethyl)amino)methyl)aniline; 2,5-dimethoxyaniline; ethyl 2-aminobenzoate; 2-amino-6-((2-aminoethyl)amino)nicotinonitrile; (R)-1-phenylethan-1-amine; 3-cyclopropyl-1H-pyrazol-5-amine; 2-((5-aminopyridin-2-yl)(methyl)amino)ethan-1-ol; 4-amino-N-methylbenzimidamide; 2-(3-aminophenyl)acetic acid; 2-((6-aminopyridin-3-yl)(methyl)amino)ethan-1-ol; 2-(4-amino-2-methoxyphenoxy)acetonitrile; 4-amino-N-hydroxybenzamide; 2,4,6-trifluoroaniline; 4-((2-methoxyethoxy)methoxy)aniline; N2,N2-diethylpyridine-2,5-diamine; 4-((ethyl(methyl)amino)methyl)aniline; ethyl 4-aminobenzoate; 4-amino-2-((2-aminoethyl)amino)thiazole-5-carbonitrile; 2-aminobenzenesulfonamide; ethyl 6-aminonicotinate; 5-morpholinopyridin-2-amine; 4-amino-N,N'-dimethylbenzimidamide; N-(5-amino-2-hydroxyphenyl)acetamide; ethyl 4-aminobenzimidate; 3-(4-aminophenyl)propanoic acid; 2-((4-aminobenzyl)(methyl)amino)ethan-1-ol; 2-morpholinopyrimidin-5-amine; 6-morpholinopyridazin-3-amine; 6-(piperazin-1-yl)pyridin-3-amine; 4-((1H-imidazol-1-yl)methyl)aniline; 4-amino-N-methoxybenzamide; N5-(2-methoxyethyl)-N5-methylpyridine-2,5-diamine; N2-(2-methoxyethyl)-N2-methylpyridine-2,5-diamine; 2-(4-aminophenyl)-N-methylacetimidamide; 3-amino-N,2-dimethylbenzamide; 2,4-diaminobenzamide; 6-((1-aminopropan-2-yl)amino)nicotinonitrile; 6-((2-aminopropyl)amino)nicotinonitrile; (4-aminophenyl)dimethylphosphine oxide; 1-(5-aminopyridin-2-yl)azetidin-3-ol; 3-methyl-1H-indazol-5-amine; 4-amino-N-cyclopropylnicotinamide; 2-(5-aminopyridin-2-yl)-2-methylpropan-1-ol; 4-amino-3-methylbenzamide; 4-amino-3-methylbenzimidamide; 1-(6-aminopyridin-3-yl)azetidin-3-ol; 4-(1,4-diazepan-1-yl)aniline; 4-(piperazin-1-ylmethyl)aniline; methyl 4-amino-2-methoxybenzoate; 4-(((2-methoxyethyl)(methyl)amino)methyl)aniline; 2-(4-aminophenyl)-N,N'-dimethylacetimidamide; 2-amino-5-methoxybenzamide; 1-(6-aminopyridin-2-yl)pyrrolidin-3-ol; 2-(methylsulfonyl)pyrimidin-4-amine; 4-(2-(dimethylamino)ethoxy)-3-methoxyaniline; 4-((1,4-diazepan-1-yl)methyl)aniline; 4-(1H-imidazol-2-yl)aniline; 2-(3-aminophenyl)propanoic acid; 4-amino-N-(4-aminophenyl)butanamide; 4-amino-N-(3-aminophenyl)butanamide; 1-((5-aminopyridin-2-yl)oxy)-2-methylpropan-2-ol; 1-((6-aminopyridin-3-yl)oxy)-2-methylpropan-2-ol; 4-amino-N,N-dimethylbenzimidamide; 2-(4-aminophenyl)propanoic acid; 4-amino-N,3-dimethylbenzamide; (3,4,5-trimethoxyphenyl)methanamine; N2-phenethylpyrimidine-2,4-diamine; N1-(5-(trifluoromethyl)pyridin-2-yl)ethane-1,2-diamine; 4-amino-N-methylbenzenesulfonamide; 3-methoxy-4-(piperidin-4-yloxy)aniline; 3-methyl-4-(piperazin-1-yl)aniline; 4-(3-methylpiperazin-1-yl)aniline; N-(4-aminobenzyl)-N-methylacetamide; 2-(3-aminophenyl)-N,N-dimethylacetamide; 2-(4-aminophenyl)-N,N-dimethylacetimidamide; 4-((1H-tetrazol-5-yl)methyl)aniline; 2-amino-5-isopropylthiazole-4-carboxamide; 1-(4-aminophenyl)-3-methylazetidin-3-amine; (2-aminopropyl)(tert-butyl)carbamic acid; 1-(5-aminopyridin-2-yl)-3-methylazetidin-3-ol; 3-methoxy-4-(1H-pyrazol-5-yl)aniline; 1-(4-aminophenyl)piperidin-4-one; 1-(6-aminopyridin-3-yl)-3-methylazetidin-3-ol; 4-(4-aminophenyl)thiomorpholine 1-oxide; N1-(4-aminobenzyl)-N1,N2,N2-trimethylethane-1,2-diamine; ethyl 2-(4-aminophenyl)propanoate; 4-((3-methylpiperazin-1-yl)methyl)aniline; 3-((3-methylpiperazin-1-yl)methyl)aniline; (6-aminopyridin-3-yl)(morpholino)methanone; 1-(2-amino-6-((2-aminoethyl)amino)pyridin-3-yl)propan-1-one; methyl 2-amino-6-((2-aminoethyl)amino)nicotinate; 4-(4-aminobenzyl)piperazin-2-one; N-(3-aminophenyl)tetrahydrofuran-2-carboxamide; 4-(1H-imidazol-2-yl)-3-methylaniline; 2-(4-aminobenzamido)acetic acid; 2-(4-aminophenyl)-N-(2-hydroxyethyl)-N-methylacetamide; N-(2-(4-aminophenoxyl)ethyl)-N-methylacetamide; 4-((((methylsulfonyl)methyl)amino)methyl)aniline; N-(3-aminophenyl)furan-2-carboxamide; N-(4-aminophenyl)furan-2-carboxamide; 4-(imino(morpholino)methyl)aniline; 4-((4-methyl-1,4-diazepan-1-yl)methyl)aniline; (S)-1-(4-aminophenyl)pyrrolidin-3-ol; (S)-2-(3-aminopyrrolidin-1-yl)pyrimidin-4-amine; (S)-4-((tetrahydrofuran-2-yl)methoxy)aniline; N1-(5-nitrothiazol-2-yl)ethane-1,2-diamine; (S)-1-(4-aminopyrimidin-2-yl)pyrrolidin-3-ol; ethyl 2-amino-6-((2-aminoethyl)amino)nicotinate; N2-(1-phenylpropan-2-yl)pyrimidine-2,4-diamine; 1-(5-aminopyridin-2-yl)-4-methylpiperidin-4-ol; 2-(3-aminophenyl)-1-morpholinoethan-1-one; 2-(4-aminophenyl)-1-morpholino ethan-1-one; 2-(3-amino-1H-pyrazol-5-yl)-N-cyclopropylacetamide; 1-(5-aminopyridin-2-yl)-3-methylpiperidin-3-ol; N-(4-aminophenyl)isonicotinamide; N-(4-aminophenyl)benzamide; 4-(3,5-dimethylpiperazin-1-yl)aniline; (4-aminophenyl)(1,4-diazepan-1-yl)methanone; 4-((5,6-dihydroimidazo[1,2-a]pyrazin-7(8H)-yl)methyl)aniline; 1-(4-aminobenzyl)pyrrolidine-2-carboxylic acid; 4-(2-imino-2-morpholinoethyl)aniline; methyl 2-(4-aminobenzamido)acetate; (S)-1-(4-aminophenyl)piperidin-3-ol; (S)-(1-(4-aminophenyl)pyrrolidin-3-yl)methanol; (R)-(4-(4-aminophenyl)morpholin-3-yl)methanol; 2-amino-4-(trifluoromethyl)thiazole-5-carboxamide; N1-(5-nitropyridin-2-yl)ethane-1,2-diamine; 6,6-diphenylhex-5-en-1-amine; tert-butyl(4-aminophenyl)carbamate; methyl 1-(4-aminobenzyl)pyrrolidine-2-carboxylate; (4-amino-2-methoxyphenyl)(morpholino)methanone; 6-(4-isopropylpiperazin-1-yl)pyridin-3-amine; tert-butyl(3-aminophenyl)carbamate; 2-amino-N-(4-aminophenyl)benzamide; 4-amino-N-benzylbenzamide; 3-((3,5-dimethylpiperazin-1-yl)methyl)aniline; (S)-(4-(4-aminophenyl)morpholin-2-yl)methanol; (S)-1-(4-amino-2-methoxyphenyl)pyrrolidin-3-ol; N2-(2-aminoethyl)-5-nitropyridine-2,6-diamine; 6-((2-aminoethyl)thio)-3-nitropyridin-2-amine; (S)-3-methoxy-4-((tetrahydrofuran-2-yl)methoxy)aniline; 6-(2-aminoethoxy)-3-nitropyridin-2-amine; (6-aminopyridin-3-yl)(4-methylpiperazin-1-yl)methanone; (S)-(4-(5-aminopyridin-2-yl)morpholin-2-yl)methanol; 1-(4-aminobenzyl)-3-isopropyl-1-methylurea; (S)-1-(4-amino-2- methoxyphenyl)piperidin-3-ol; (R)-1-(4-aminophenyl)-3-methylpyrrolidin-3-ol; (R)-N2-(1-phenylethyl)pyrimidine-2,4-diamine; (S)-(1-(4-amino-2-methoxyphenyl)pyrrolidin-3-yl)methanol; (S)-1-(4-amino-2-ethoxyphenyl)pyrrolidin-3-ol; N2-(3-aminopropyl)-5-nitropyridine-2,6-diamine; 1-(4-(4-aminobenzyl)piperazin-1-yl)ethan-1-one; 4-(4-aminobenzoyl)piperazin-2-one; 4-amino-N-(4-aminophenyl)benzamide; 2-(4-aminophenyl)-N-cyclooctylacetamide; 5-(aminomethyl)-N-(4-aminophenyl)furan-2-carboxamide; 4-((3-methyl-5,6-dihydro-[1,2,4]triazolo[4,3-a]pyrazin-7 (8H)-yl)methyl)aniline; 2-(4-aminophenyl)-1-morpholinopropan-1-one; 2-(4-aminophenyl)-1-(4-methylpiperazin-1-yl)ethan-1-one; 2-(3-aminophenyl)-1-(4-methylpiperazin-1-yl)ethan-1-one; (4-aminophenyl)(4-ethylpiperazin-1-yl)methanone; (R)-1-(4-aminophenyl)-3-methylpiperidin-3-ol; (S)-(4-(4-amino-2-methoxyphenyl)morpholin-2-yl)methanol; 4-(aminomethyl)-N-(4-aminophenyl)benzamide; (R)-1-(5-aminopyridin-2-yl)-3-methylpiperidin-3-ol; (4-aminophenyl)(5,6-dihydroimidazo[1,2-a]pyrazin-7(8H)-yl)methanone; N-(aminomethyl)-N-(4-aminophenyl) benzamide; 2-(aminomethyl)-N-(4-aminophenyl) isonicotinamide; 5-(aminomethyl)-N-(4-aminophenyl) nicotinamide; 4-(aminomethyl)-N-(4-aminophenyl) picolinamide; 5-(aminomethyl)-N-(4-aminophenyl) picolinamide; 6-(aminomethyl)-N-(4-aminophenyl) picolinamide; 6-(aminomethyl)-N-(4-aminophenyl) nicotinamide; 3-(aminomethyl)-N-(4-aminophenyl) benzamide; 3-(aminomethyl)-N-(3-aminophenyl) benzamide; 4-(aminomethyl)-N-(3-aminophenyl) benzamide; N4-((1H-indol-5-yl)methyl)pyrimidine-2,4-diamine; ethyl 4-(4-aminophenyl)piperazine-1-carboxylate; 1-(2-amino-6-((2-aminoethyl)amino)pyridin-3-yl)-2,2,2-trifluoroethan-1-one; (R)-1-(4-amino-2-methoxyphenyl)-3-methylpyrrolidin-3-ol; N2-(2-aminopropyl)-5-nitropyridine-2,6-diamine; 2-((1R,4S)-2,5-diazabicyclo[2.2.1] heptan-2-yl)pyrimidin-4-amine; N2-(1-aminopropan-2-yl)-5-nitropyridine-2,6-diamine; 4-(2-aminoethyl)-N-(4-aminophenyl)benzamide; 4-(2-aminoethyl)-N-(3-aminophenyl)benzamide; N-(4-aminophenyl)-2-(3-chlorophenyl)acetamide; (4-aminophenyl)(hexahydro-1H-pyrido[1,2-a]pyrazin-2(6H)-yl)methanone; 2-(4-aminophenyl)-N,N-diisopropylacetamide; N-(4-aminophenyl)-2-(4-methoxyphenyl)acetamide; N-(3-aminophenyl)-2-(4-methoxyphenyl)acetamide; N-(4-aminophenyl)-4-((methylamino)methyl)benzamide; N-(3-aminophenyl)-4-((methylamino)methyl)benzamide; (R)—N2-methyl-N2-(1-phenylethyl)pyrimidine-2,4-diamine; N-(4-aminophenyl)-1,2,3,4-tetrahydroisoquinoline-6-carboxamide; 4'-fluoro-5-(trifluoromethoxy)[1,1'-biphenyl]-2-amine; N-(3-aminophenyl)-1,2,3,4-tetrahydroisoquinoline-6-carboxamide; N-(3-aminophenyl)-1,2,3,4-tetrahydroisoquinoline-7-carboxamide; N-(4-aminophenyl)-1,2,3,4-tetrahydroisoquinoline-7-carboxamide; (S)-3-(4-aminophenyl)-1,4-dimethylpiperazin-2-one; (4-aminophenyl)(3-methyl-5,6-dihydro-[1,2,4]triazolo[4,3-a]pyrazin-7(8H)-yl)methanone; N-(4-aminophenyl)-4-(((2-hydroxyethyl)amino)methyl)benzamide; 4-(aminomethyl)-N-(4-aminophenyl)-2-fluorobenzamide; 4-(aminomethyl)-N-(3-aminophenyl)-2-fluorobenzamide; N-(4-aminophenyl)-3,4-dichlorobenzamide; N-(4-aminophenyl)-4-((dimethylamino)methyl)benzamide; 4-((2R,6R)-2,6-dimethylmorpholino)aniline; N-(4-aminophenyl)-4-guanidinobenzamide; 2-(4-aminophenyl)-1-(hexahydro-1H-pyrido[1,2-a]pyrazin-2(6H)-yl)propan-1-one; tert-butyl 4-(4-aminophenyl)piperazine-1-carboxylate; N-(3-aminophenyl)-4-(2-aminopropan-2-yl)benzamide; N-(4-aminophenyl)-4-(2-aminopropan-2-yl)benzamide; N-(3-aminophenyl)-4-(tert-butyl)benzamide; N-(4-aminophenyl)-4-(tert-butyl)benzamide; N-(3-aminophenyl)-4-(piperidin-3-yl)benzamide; 3-amino-4-methyl-N-(3-(trifluoromethyl)phenyl)benzamide; N-(3-amino-4-methylphenyl)-3-(trifluoromethyl)benzamide; 3-amino-N-(3-aminophenyl)-2-(3,4-dichlorophenyl)propanamide; 4-amino-N-(4-aminophenyl)-2-(3,4-dichlorophenyl)butanamide; N-(4-aminophenyl)-4-(4-methylpiperazin-1-yl)methyl) benzamide; N-(3-amino-4-methylphenyl)-4-methoxy-3-(trifluoromethyl)benzamide; N-(4-aminophenyl)-4-(((2-(methylsulfonyl)ethyl)amino)methyl)benzamide; tert-butyl ((5-((4-aminophenyl)carbamoyl)furan-2-yl)methyl) carbamate; tert-butyl(4-((4-aminophenyl)carbamoyl)benzyl)carbamate; tert-butyl((2-((4-aminophenyl)carbamoyl)pyridin-4-yl)methyl)carbamate; tert-butyl(4-((4-aminophenyl)carbamoyl)phenethyl)carbamate; tert-butyl 6-(4-aminophenyl)carbamoyl)-3,4-dihydroisoquinoline-2 (1H)-carboxylate; tert-butyl(2-(4-((3-aminophenyl)carbamoyl)phenyl)propan-2-yl)carbamate; tert-butyl(3-((3-aminophenyl)amino)-2-(3,4-dichlorophenyl)-3-oxopropyl) carbamate; tert-butyl(4-((4-aminophenyl)amino)-3-(3,4-dichlorophenyl)-4-oxobutyl)carbamate; tert-butyl(4-((4-aminophenyl)carbamoyl)benzyl)(2-((tetrahydro-2H-pyran-2-yl)oxy)ethyl)carbamate.

Furthermore preferably, $R^1$ can be derived from the following compounds (e.g. ureas, amides):
urea; 1-methylurea; propionamide; 1-ethylurea; 1-(2-hydroxyethyl)urea; 1-propylurea; cyclopropanecarboxamide; 1-(3-hydroxypropyl)urea; 1-isopropylurea; 1-(2-cyanoethyl)urea; ethanesulfonamide; thiazole-4-carboxamide; furan-2-carboxamide; 1,2,3-thiadiazole-4-carboxamide; thiazole-5-carboxamide; isoxazole-3-carboxamide; 1-isobutylurea; thiophene-3-carboxamide; furan-3-carboxamide; picolinamide; cyclohexanecarboxamide; 1-methyl-1H-pyrazole-5-carboxamide; nicotinamide; 1-methyl-1H-imidazole-2-carboxamide; 1-methyl-1H-pyrrole-2-carboxamide; benzamide; 1-methyl-1H-1,2,4-triazole-5-carboxamide; 2-methylfuran-3-carboxamide; 1-(3-(dimethylamino)propyl)urea; 2-morpholinoacetamide; 3-fluoropicolinamide; 3-methylpicolinamide; 2-methylnicotinamide; 2-methylbenzamide; 1-(tert-butyl)urea; 2-(pyridin-2-yl)acetamide; 5-bromothiazole-4-carboxamide; 2-fluorobenzamide; 4-methoxythiophene-3-carboxamide; 2-(piperidin-1-yl) acetamide; 2-(tetrahydro-2H-pyran-4-yl)acetamide; 2-chlorofuran-3-carboxamide; 1-ethyl-1H-pyrazole-5-carboxamide; 2-methylthiazole-4-carboxamide; 3-phenylpropanamide; 3-chloropicolinamide; 3-bromopicolinamide; 1H-pyrazole-3-carboxamide; 2-methoxynicotinamide; 3-methoxypicolinamide; 1H-imidazole-2-carboxamide; 1-(2-fluoroethyl)-1H-pyrazole-5-carboxamide; 1-methyl-1H-1,2,4-triazole-3-carboxamide; 1-methyl-1H-imidazole-4-carboxamide; 2-methyloxazole-4-carboxamide; 4-methylthiophene-2-carboxamide; 1H-imidazole-4-carboxamide; 1H-pyrazole-5-carboxamide; 2-methoxybenzamide; 1-methyl-1H-pyrazole-3-carboxamide; 1-vinyl-1H-pyrazole-5-carboxamide; 5-methylisoxazole-3-carboxamide; 5-methylfuran-2-carboxamide; 6-methylpicolinamide; 6-fluoropicolinamide; 4-methylmorpholine-2-carboxamide; 5-methylpicolinamide; 5-oxopyrrolidine-3-carboxamide; 1-(3-(1H-imidazol-1-yl)propyl)urea; 5-chlorofuran-2-carboxamide; 5-fluoropicolinamide; 1,3-dimethyl-1H-pyrazole-5-carboxamide; 2-ethoxynicotinamide; 2-ethoxybenzamide; 1-ethyl-1H-pyrazole-3-carboxamide; 2-(3-methyl-1H-pyrazol-1-yl) acetamide; 3-methylbenzamide; 4-morpholinobutanamide; 1,4-dimethyl-1H-pyrazole-5-carboxamide; 1-methylpiperidine-4-carboxamide; 1-isopropyl-1H-pyrazole-5-carboxamide; 6-(methylamino)picolinamide; 5-isopropylthiazole-4-carboxamide; 4-(methylamino)picolinamide; 1-isopropyl-1H-1,2,4-triazole-5-carboxamide; 1-isopropyl-1H-1,2,3-triazole-5-carboxamide; 6-methoxypicolinamide; 6-chloropicolinamide; 5-bromopicolinamide; 1-(3-thiomorpholinopropyl)urea; 5-isopropyloxazole-4-carboxamide; 1-isopropyl-1H-imidazole-2-carboxamide; 5-isopropylisoxazole-4-carboxamide; 1-(difluoromethyl)-1H-pyrazole-5-carboxamide; 1-(2-fluoroethyl)-1H-pyrazole-3-carboxamide; 2,3-difluorobenzamide; 6-methoxypyrazine-2-carboxamide; 4-chloro-1-methyl-1H-pyrazole-5-carboxamide; 6-bromopicolinamide; 1-(3-morpholinopropyl)urea; 2,6-difluorobenzamide; 1-ethyl-4-fluoro-1H-pyrazole-5-carboxamide; 1-ethyl-3-methyl-1H-pyrazole-5-carboxamide; 1,4-dimethyl-1H-pyrazole-3-carboxamide; 4-chloro-1-ethyl-1H-pyrazole-5-carboxamide; 2,5-dimethyloxazole-4-carboxamide; 3-isopropylpicolinamide; 6-(ethylamino)picolinamide; 1,5-dimethyl-1H-pyrazole-3-carboxamide; 4-cyanobenzamide; 2-methoxy-3-methylbenzamide; 2-methoxy-4-methylbenzamide; 2-methoxy-5-methylbenzamide; 4-fluoro-1-methyl-1H-pyrazole-3-carboxamide; 2,5-dimethylthiazole-4-carboxamide; 5-methyl-1H-pyrazole-3-carboxamide; pyrazolo[1,5-a]pyridine-2-carboxamide; 3-methyl-1H-pyrazole-5-carboxamide; 2-isopropyl-2H-1,2,3-triazole-4-carboxamide; 3-(prop-1-en-2-yl)picolinamide; isoquinoline-1-carboxamide; 4-chloro-1H-pyrazole-5-carboxamide; 3,5-difluoropicolinamide; 2,5-difluorobenzamide; 2,4-difluorobenzamide; 3-ethyl-1H-pyrazole-5-carboxamide; 1-isopropyl-1H-pyrazole-3-carboxamide; 2-(difluoromethoxy)benzamide; 3-(dimethylamino)benzamide; 6-(dimethylamino)picolinamide; 6-chloro-3-fluoropicolinamide; 4-bromo-1,3-dimethyl-1H-pyrazole-5-carboxamide; 2-acetylthiazole-4-carboxamide; 3-cyclopropyl-1-methyl-1H-pyrazole-5-carboxamide; 6-oxo-1,6-dihydropyridine-2-carboxamide; 5-adimethylamino)methyl)furan-2-carboxamide; 1-(3-(4-methylpiperazin-1-yl)propyl)urea; 4-fluoro-1-isopropyl-1H-pyrazole-5-carboxamide; 1H-indazole-1-carboxamide; 4-(trifluoromethyl)thiazole-5-carboxamide; 6-(cyclopropylamino)picolinamide; 6-((dimethylamino)methyl)picolinamide; 6-(isopropylamino)picolinamide; 1H-benzo[d]imidazole-2-carboxamide; 1-(2,2,2-trifluoroethyl)-1H-pyrazole-5-carboxamide; 1H-indole-2-carboxamide; 3,6-dichloropicolinamide; 4-chloro-1-isopropyl-1H-pyrazole-3-carboxamide; 1-acetylpiperidine-4-carboxamide; 4-((dimethylamino)methyl)-5-methylisoxazole-3-carboxamide; 4-acetylmorpholine-2-carboxamide; 1-ethyl-3-isopropyl-1H-pyrazole-5-carboxamide; 4-chloro-1-isopropyl-1H-pyrazole-5-carboxamide; 1-((tetrahydro-2H-pyran-4-yl)methyl)-1H-pyrazole-5-carboxamide; 2-(pyrrolidin-1-yl)isonicotinamide; 6-(pyrrolidin-1-yl)picolinamide; 6-(diethylamino)picolinamide; 3-isopropyl-1-methyl-1H-pyrazole-5-carboxamide; 5-isopropyl-2-methylthiazole-4-carboxamide; 2-(trifluoromethyl)thiazole-4-carboxamide; 2-phenylthiazole-4-carboxamide; 5-(trifluoromethyl)furan-2-carboxamide; 1-ethyl-3-isobutyl-1H-pyrazole-5-carboxamide; 5-(pyrrolidin-1-ylmethyl)furan-2-carboxamide; 3-isopropyl-1H-pyrazole-5-carboxamide; 2-(piperidin-1-ylmethyl)thiazole-4-carboxamide; 2-(morpholinomethyl)thiazole-4-carboxamide; 5-(morpholinomethyl)isoxazole-3-carboxamide; 1-methyl-4-(trifluoromethyl)-1H-pyrazole-5-carboxamide; 3-(methylsulfonyl)picolinamide; 6-morpholinopicolinamide; 5-morpholinopicolinamide; 5-(piperidin-1-yl)picolinamide; 2-benzylthiazole-4-carboxamide; 1-isopropyl-5-oxopyrrolidine-3-carboxamide; 1-methyl-3-(trifluoromethyl)-1H-pyrazole-5-carboxamide; 3-(tert-butyl)-1-methyl-1H-pyrazole-5-carboxamide; 1-((tetrahydro-2H-pyran-4-yl)methyl)-1H-pyrazole-3-carboxamide; 2'-chloro-[1,1'-biphenyl]-2-carboxamide; 2-chloro-5-isopropylthiazole-4-carboxamide; 3-isobutyl-1-methyl-1H-pyrazole-5-carboxamide; 5-acetyl-2-methylthiazole-4-carboxamide; 5-methyl-4-(pyrrolidin-1-ylmethyl)isoxazole-3-carboxamide; 3-isobutyl-1H-pyrazole-5-carboxamide; 6-(morpholinomethyl)picolinamide; 6-(piperidin-1-ylmethyl)picolinamide; 6-((tetrahydro-2H-pyran-4-yl)oxy)picolinamide; 3-(dimethylamino)-6-(methylamino)picolinamide; 2-((1,4-oxazepan-4-yl)methyl)thiazole-4-carboxamide; 6-((tetrahydro-2H-pyran-4-yl)amino)picolinamide; 3-chloro-6-(dimethylamino)picolinamide; 6-chloro-3-(dimethylamino)picolinamide; 5-(2-methylthiazol-4-yl)isoxazole-3-carboxamide; 5-methyl-4-(morpholinomethyl)isoxazole-3-carboxamide; 1-methyl-3-(morpholinomethyl)-1H-pyrazole-5-carboxamide; 5-methyl-4-(piperidin-1-ylmethyl)isoxazole-3-carboxamide; 3-chloro-6-morpholinopicolinamide; 3-chloro-6-(piperidin-1-yl)picolinamide; 3-(dimethylamino)-6-(ethylamino)picolinamide; 1-(methylsulfonyl)piperidine-4-carboxamide; 2-methyl-5-(trifluoromethyl)oxazole-4-carboxamide; 1-(tert-butyl)-3-methyl-1H-pyrazole-5-carboxamide; 2-((2-methylmorpholino)methyl)thiazole-4-carboxamide; 6-(4-methylpiperazin-1-yl)picolinamide; 1-methyl-5-(morpholinomethyl)-1H-pyrazole-3-carboxamide; 6-((1-methylpiperidin-4-yl)amino)picolinamide; 2-((2-ethylmorpholino)methyl)thiazole-4-carboxamide; 6-(methyl(tetrahydro-2H-pyran-4-yl)amino)picolinamide; 6-((4-methylpiperazin-1-yl)methyl)picolinamide; 6-chloro-3-morpholinopicolinamide; 6-chloro-3-(piperidin-1-yl)picolinamide; (1R,2S)-2-phenylcyclopropanecarboxamide; 5-isopropyl-2-(morpholinomethyl)thiazole-4-carboxamide; 6-(2-methoxy-5-methylphenyl)picolinamide; 3-(dimethylamino)-6-morpholinopicolinamide; 3-(dimethylamino)-6-(piperidin-1-yl)picolinamide; 1-isopropyl-3-(morpholinomethyl)-1H-pyrazole-5-carboxamide; 2-((hexahydro-2H-benzo[b][1,4]oxazin-4(3H)-yl)methyl)thiazole-4-carboxamide; 6-((4-methyl-3-oxopiperazin-1-yl)methyl)picolinamide; 2-(2,2-dimethylmorpholino)methyl)thiazole-4-carboxamide; 2-((hexahydro-1H-pyrido[1,2-a]pyrazin-2(6H)-yl)methyl)thiazole-4-carboxamide; 2-((3,3-dimethylpiperidin-1-yl)methyl)thiazole-4-carboxamide; 2-((4,4-dimethylpiperidin-1-yl)methyl)thiazole-4-carboxamide; tert-butyl 4-carbamoyl-3-methyl-1H-pyrazole-1-carboxylate; 1-(3-(4-(methylsulfonyl)piperazin-1-yl)propyl)urea; 2-((4-isopropylpiperazin-1-yl)methyl)thiazole-4-carboxamide; 6-((4,4-difluoropiperidin-1-yl)methyl)picolinamide; 6-((hexahydro-2H-benzo[b][1,4]oxazin-4(3H)-yl)methyl)picolinamide; 6-((hexahydro-1H-pyrido[1,2-a]pyrazin-2(6H)-yl)methyl)picolinamide; 6-((3,3-dimethylpiperidin-1-yl)methyl)picolinamide; 6-((4,4-dimethylpiperidin-1-yl)methyl)picolinamide; 1-methyl-3-(morpholine-4-carbonyl)-1H-pyrazole-5-carboxamide; 1-isopropyl-5-(morpholinomethyl)-1H-pyrazole-3-carboxamide; 6-((4-isopropylpiperazin-1-yl)methyl)picolinamide; 2-((4-isopropyl-3-methylpiperazin-1-yl)methyl)thiazole-4-carboxamide; 2-((2-isobutylmorpholino)methyl)thiazole-4-carboxamide;

6-((4-isopropylpiperidin-1-yl)methyl)picolinamide; 2-(6-oxa-9-azaspiro[4.5]decan-9-ylmethyl)thiazole-4-carboxamide; 2-((4-isobutylpiperazin-1-yl)methyl)thiazole-4-carboxamide; 2-((1,1-dioxidothiomorpholino)methyl)thiazole-4-carboxamide; 6-((4-isopropyl-3-methylpiperazin-1-yl)methyl)picolinamide; 6-((1,1-dioxidothiomorpholino)methyl)picolinamide; 6-((4-isobutylpiperazin-1-yl)methyl)picolinamide; 6-((2-isobutylmorpholino)methyl)picolinamide; benzyl 3-carbamoyl-4-hydroxypyrrolidine-1-carboxylate; 2-((4-cyclopentylpiperazin-1-yl)methyl)thiazole-4-carboxamide; 2-((3-(pyridin-3-yl)pyrrolidin-1-yl)methyl)thiazole-4-carboxamide; 6-((4-acetylpiperazin-1-yl)methyl)picolinamide; 2-(1-benzamidoethyl)thiazole-4-carboxamide; 2-((4-(pentan-3-yl)piperazin-1-yl)methyl)thiazole-4-carboxamide; 6-((4-cyclopentylpiperazin-1-yl)methyl)picolinamide; 6-((4-(pentan-3-yl)piperazin-1-yl)methyl)picolinamide; 2-((2-(pyrrolidin-1-ylmethyl)morpholino)methyl)thiazole-4-carboxamide; tert-butyl 4-carbamoyl-3-cyclopropyl-1H-pyrazole-1-carboxylate; 6-((2-(pyrrolidin-1-ylmethyl)morpholino)methyl)picolinamide; 6-((3-phenylpiperidin-1-yl)methyl)picolinamide; 2-(((6S)-2,6-dimethylmorpholino)methyl)thiazole-4-carboxamide; 2-((3-(benzyloxy)piperidin-1-yl)methyl)thiazole-4-carboxamide; 2-((4-(2-morpholinoethyl)piperazin-1-yl)methyl)thiazole-4-carboxamide; 6-((4-(methylsulfonyl)piperazin-1-yl)methyl)picolinamide; 6-((2-(phenoxymethyl)morpholino)methyl)picolinamide; 6-((3-(benzyloxy)piperidin-1-yl)methyl)picolinamide; 6-((4-(2-morpholinoethyl)piperazin-1-yl)methyl)picolinamide; 2-((4-(4-fluorophenyl)piperazin-1-yl)methyl)thiazole-4-carboxamide; 2-(((2R,6R)-2,6-dimethylmorpholino)methyl)thiazole-4-carboxamide; 6-((4-(4-fluorophenyl)piperazin-1-yl)methyl)picolinamide; 2-(((2R,6S)-2,6-dimethylmorpholino)methyl)thiazole-4-carboxamide; 6-(((2R,6R)-2,6-dimethylmorpholino)methyl)picolinamide; 6-(((2R,6S)-2,6-dimethylmorpholino)methyl)picolinamide.

Moreover especially preferably, $R^1$ can be derived from the following amines: 1-ethyl-1H-pyrazol-4-amine; 1,5-dimethyl-1H-pyrazol-4-amine; 3-methyl-1H-pyrazol-4-amine; 2-(4-amino-1H-pyrazol-1-yl)ethan-1-ol; 1-propyl-1H-pyrazol-4-amine; 1-(2-fluoroethyl)-1H-pyrazol-4-amine; 1-ethyl-5-methyl-1H-pyrazol-4-amine; 5-methoxy-1-methyl-1H-pyrazol-4-amine; N5,1-dimethyl-1H-pyrazole-4,5-diamine; 5-chloro-1-methyl-1H-pyrazol-4-amine; 5-(fluoromethyl)-1-methyl-1H-pyrazol-4-amine; 3-(4-amino-1H-pyrazol-1-yl)propan-1-ol; 1-(2-methoxyethyl)-1H-pyrazol-4-amine; 1,3-dimethyl-1H-pyrazol-4-amine; 1-butyl-1H-pyrazol-4-amine; 5-methyl-1-propyl-1H-pyrazol-4-amine; 4-amino-1-methyl-1H-pyrazole-5-carbonitrile; 5-chloro-1-ethyl-1H-pyrazol-4-amine; 1-(2-fluoroethyl)-5-methyl-1H-pyrazol-4-amine; 1-isopropyl-1H-pyrazol-4-amine; 1-(difluoromethyl)-1H-pyrazol-4-amine; 3-(4-amino-1H-pyrazol-1-yl)propanenitrile; 1-ethyl-3-methyl-1H-pyrazol-4-amine; 1-cyclopropyl-1H-pyrazol-4-amine; 1-(2-methoxyethyl)-5-methyl-1H-pyrazol-4-amine; 1,3,5-trimethyl-1H-pyrazol-4-amine; 1-butyl-5-methyl-1H-pyrazol-4-amine; 1-(oxetan-3-yl)-1H-pyrazol-4-amine; 1-(cyclopropylmethyl)-1H-pyrazol-4-amine; 1-isopropyl-3-methyl-1H-pyrazol-4-amine; 1-(difluoromethyl)-3-methyl-1H-pyrazol-4-amine; 1-(difluoromethyl)-5-methyl-1H-pyrazol-4-amine; 3-methyl-1-propyl-1H-pyrazol-4-amine; 1-isopropyl-5-methyl-1H-pyrazol-4-amine; 5-cyclopropyl-1-methyl-1H-pyrazol-4-amine; 1-(2-fluoroethyl)-3-methyl-1H-pyrazol-4-amine; N5,N5,1-trimethyl-1H-pyrazole-4,5-diamine; 5-isopropyl-1-methyl-1H-pyrazol-4-amine; 3-(4-amino-5-methyl-1H-pyrazol-1-yl)propanenitrile; 1-(tetrahydrofuran-3-yl)-1H-pyrazol-4-amine; 3-methyl-1-(oxetan-3-yl)-1H-pyrazol-4-amine; 1-(2-methoxyethyl)-3-methyl-1H-pyrazol-4-amine; 1-(1-methoxypropan-2-yl)-1H-pyrazol-4-amine; 1-(2-methoxypropyl)-1H-pyrazol-4-amine; 5-cyclobutyl-1-methyl-1H-pyrazol-4-amine; 5-methyl-1-(oxetan-3-yl)-1H-pyrazol-4-amine; 1-(cyclopropylmethyl)-3-methyl-1H-pyrazol-4-amine; 5-chloro-1-cyclopropyl-1H-pyrazol-4-amine; 5-chloro-1-isopropyl-1H-pyrazol-4-amine; 1-(cyclopropylmethyl)-5-methyl-1H-pyrazol-4-amine; 1-(tetrahydro-2H-pyran-4-yl)-1H-pyrazol-4-amine; 1-(pyridin-2-yl)-1H-pyrazol-4-amine; 2-(4-amino-1H-pyrazol-1-yl)cyclopentanol; 1-(pyrimidin-5-yl)-1H-pyrazol-4-amine; 1-(tetrahydro-2H-pyran-3-yl)-1H-pyrazol-4-amine; 2-(4-amino-1H-pyrazol-1-yl)-N-methylacetamide; 1-(pyrimidin-2-yl)-1H-pyrazol-4-amine; 1-(piperidin-3-yl)-1H-pyrazol-4-amine; 3-(4-amino-3-methyl-1H-pyrazol-1-yl)propanenitrile; 5-methyl-1-(tetrahydrofuran-3-yl)-1H-pyrazol-4-amine; 3-methyl-1-(tetrahydrofuran-3-yl)-1H-pyrazol-4-amine; 3-isopropyl-1-methyl-1H-pyrazol-4-amine; 3-cyclopropyl-1-methyl-1H-pyrazol-4-amine; 5-chloro-1-(cyclopropylmethyl)-1H-pyrazol-4-amine; 5-chloro-1-(oxetan-3-yl)-1H-pyrazol-4-amine; 1-(4-amino-1H-pyrazol-1-yl)-2-methylpropan-2-ol; 1-(2,2,2-trifluoroethyl)-1H-pyrazol-4-amine; 2-(4-amino-1H-pyrazol-1-yl)-2-methylpropan-1-ol; 1-(pyridin-3-ylmethyl)-1H-pyrazol-4-amine; 1-(pyrimidin-2-ylmethyl)-1H-pyrazol-4-amine; 1-(pyrazin-2-ylmethyl)-1H-pyrazol-4-amine; 1-(pyrimidin-4-ylmethyl)-1H-pyrazol-4-amine; 1-(pyridazin-3-ylmethyl)-1H-pyrazol-4-amine; 1-(pyridin-2-ylmethyl)-1H-pyrazol-4-amine; 1-(3-methylpyridin-4-yl)-1H-pyrazol-4-amine; 3-methyl-1-(tetrahydro-2H-pyran-4-yl)-1H-pyrazol-4-amine; 5-methyl-1-(tetrahydro-2H-pyran-4-yl)-1H-pyrazol-4-amine; 5-methyl-1-phenyl-1H-pyrazol-4-amine; 3-methyl-1-phenyl-1H-pyrazol-4-amine; 1-(3-fluoropiperidin-4-yl)-1H-pyrazol-4-amine; 1-(2-methoxycyclopentyl)-1H-pyrazol-4-amine; 3-methyl-1-(pyridin-2-yl)-1H-pyrazol-4-amine; 3-cyclobutyl-1-methyl-1H-pyrazol-4-amine; 5-methyl-1-(tetrahydro-2H-pyran-3-yl)-1H-pyrazol-4-amine; 3-methyl-1-(pyrimidin-2-yl)-1H-pyrazol-4-amine; 3-methyl-1-(pyrimidin-5-yl)-1H-pyrazol-4-amine; 3-methyl-1-(tetrahydro-2H-pyran-3-yl)-1H-pyrazol-4-amine; 3-methyl-1-(piperidin-3-yl)-1H-pyrazol-4-amine; 2-(4-amino-5-methyl-1H-pyrazol-1-yl)-N-methylacetamide; 2-(4-amino-1H-pyrazol-1-yl)-2-methylpropanenitrile; 1-(methylsulfonyl)-1H-pyrazol-4-amine; 1-((3-methyloxetan-3-yl)methyl)-1H-pyrazol-4-amine; 1-(1-methoxy-2-methylpropan-2-yl)-1H-pyrazol-4-amine; 1-(4-amino-1H-pyrazol-1-yl)cyclopropanecarbonitrile; 1-(4-amino-1H-pyrazol-1-yl)-3-methylbutan-2-ol; 1'-methyl-1'H-[1,4'-bipyrazol]-amine; 2-(4-amino-1H-pyrazol-1-yl)pentan-3-ol; 1-(4-amino-3-methyl-1H-pyrazol-1-yl)-2-methylpropan-2-ol; 3-methyl-1-(2,2,2-trifluoroethyl)-1H-pyrazol-4-amine; 1-(2-methoxy-2-methylpropyl)-1H-pyrazol-4-amine; 1-(1-methylpyrrolidin-3-yl)-1H-pyrazol-4-amine; 5-chloro-1-(tetrahydro-2H-pyran-4-yl)-1H-pyrazol-4-amine; 5-methyl-1-(2,2,2-trifluoroethyl)-1H-pyrazol-4-amine; 1-(4-amino-5-methyl-1H-pyrazol-1-yl)-2-methylpropan-2-ol; 5-methyl-1-(pyrimidin-2-ylmethyl)-1H-pyrazol-4-amine; 5-methyl-1-(pyrazin-2-ylmethyl)-1H-pyrazol-4-amine; 5-methyl-1-(pyrimidin-4-ylmethyl)-1H-pyrazol-4-amine; 5-methyl-1-(pyridazin-3-ylmethyl)-1H-pyrazol-4-amine; 5-methyl-1-(pyridin-3-ylmethyl)-1H-pyrazol-4-amine; 5-methyl-1-(pyridin-2-ylmethyl)-1H-pyrazol-4-amine; 3-methyl-1-(pyrimidin-2-ylmethyl)-1H-pyrazol-4-amine; 3-methyl-1-(pyrazin-2-ylmethyl)-1H-pyrazol-4-amine; 3-methyl-1-

(pyrimidin-4-ylmethyl)-1H-pyrazol-4-amine; 3-methyl-1-(pyridazin-3-ylmethyl)-1H-pyrazol-4-amine; 3-methyl-1-(pyridin-3-ylmethyl)-1H-pyrazol-4-amine; 3-methyl-1-(pyridin-2-ylmethyl)-1H-pyrazol-4-amine; 1-(1-methylpiperidin-4-yl)-1H-pyrazol-4-amine; 1-(4-fluorophenyl)-1H-pyrazol-4-amine; 3-(4-amino-1H-pyrazol-1-yl)-2,2-dimethylpropanenitrile; 1-(2-methylpyridin-4-yl)-1H-pyrazol-4-amine; 1-(ethylsulfonyl)-1H-pyrazol-4-amine; (R)-1-(2-methoxypropyl)-1H-pyrazol-4-amine; 1-(4-amino-1H-pyrazol-1-yl)cyclobutanecarbonitrile; 1-((1-methyl-1H-pyrazol-3-yl)methyl)-1H-pyrazol-4-amine; 1-(1-methylpiperidin-3-yl)-1H-pyrazol-4-amine; 3-methyl-1-(methylsulfonyl)-1H-pyrazol-4-amine; 2-(4-amino-1H-pyrazol-1-yl)-N,N-dimethylacetamide; 3-methyl-1-((3-methyloxetan-3-yl)methyl)-1H-pyrazol-4-amine; 1-(3-methoxycyclopentyl)-1H-pyrazol-4-amine; 2-(4-amino-3-methyl-1H-pyrazol-1-yl)cyclopentanol; 2-(4-amino-5-methyl-1H-pyrazol-1-yl)-2-methylpropanenitrile; 5-methyl-1-((3-methyloxetan-3-yl)methyl)-1H-pyrazol-4-amine; 1-(4-amino-3-chloro-1H-pyrazol-1-yl)-2-methylpropan-2-ol; 1-(4-amino-5-chloro-1H-pyrazol-1-yl)-2-methylpropan-2-ol; 1-(4-amino-5-methyl-1H-pyrazol-1-yl)-3-methylbutan-2-ol; 2-(4-amino-5-chloro-1H-pyrazol-1-yl)-2-methylpropan-2-ol; 5-methyl-1-(methylsulfonyl)-1H-pyrazol-4-amine; 1-(1-methoxy-2-methylpropan-2-yl)-5-methyl-1H-pyrazol-4-amine; 2-(4-amino-3-methyl-1H-pyrazol-1-yl)-N-methylacetamide; 1',5-dimethyl-1'H-[1,4'-bipyrazol]-4-amine; 2-(4-amino-5-methyl-1H-pyrazol-1-yl)pentan-3-ol; 1-(4-chlorophenyl)-1H-pyrazol-4-amine; 5-(4-amino-1H-pyrazol-1-yl)piperidin-2-one; (S)-1-(1-methoxypropan-2-yl)-1H-pyrazol-4-amine; (S)-2-(4-amino-1H-pyrazol-1-yl)propanenitrile; 1-(1-(pyridin-2-yl)ethyl)-1H-pyrazol-4-amine; 1-((6-methylpyridin-2-yl)methyl)-1H-pyrazol-4-amine; (S)-2-(4-amino-5-methyl-1H-pyrazol-1-yl)propanenitrile; 1-(4-amino-5-methyl-1H-pyrazol-1-yl)cyclobutanecarbonitrile; 1-(4-fluorophenyl)-5-methyl-1H-pyrazol-4-amine; (R)-1-(2-methoxypropyl)-5-methyl-1H-pyrazol-4-amine; 5-methyl-1-(1-methylpiperidin-4-yl)-1H-pyrazol-4-amine; 1-(ethylsulfonyl)-5-methyl-1H-pyrazol-4-amine; 3-methyl-1-(3-methylpyridin-4-yl)-1H-pyrazol-4-amine; 2-(4-amino-5-chloro-1H-pyrazol-1-yl)-2-methylpropanenitrile; 3-(4-amino-5-methyl-1H-pyrazol-1-yl)-2,2-dimethylpropanenitrile; 1-(4-amino-5-chloro-1H-pyrazol-1-yl)cyclopropanecarbonitrile; 1-(3-fluoropiperidin-4-yl)-3-methyl-1H-pyrazol-4-amine; 1-(2-methoxycyclopentyl)-3-methyl-1H-pyrazol-4-amine; 5-methyl-1-((1-methyl-1H-pyrazol-3-yl)methyl)-1H-pyrazol-4-amine; 5-methyl-1-(1-methylpiperidin-3-yl)-1H-pyrazol-4-amine; 5-chloro-1-((3-methyloxetan-3-yl)methyl)-1H-pyrazol-4-amine; 2-(4-amino-3-ethyl-1H-pyrazol-1-yl)-2-methylpropanenitrile; 5-methyl-1-(2-methylpytidin-4-yl)-1H-pyrazol-4-amine; 4-(4-amino-1H-pyrazol-1-yl)benzonitrile; 1-(1-(2-fluoroethyl)piperidin-4-yl)-1H-pyrazol-4-amine; 2-(4-amino-1H-pyrazol-1-yl)-2-methylpropanamide; 1-(1-isopropylazetidin-3-yl)-1H-pyrazol-4-amine; 2-(4-amino-3-methyl-1H-pyrazol-1-yl)-2-methylpropanenitrile; 3-(4-amino-5-chloro-1H-pyrazol-1-yl)-2,2-dimethylpropanenitrile; 1-(4-chlorophenyl)-5-methyl-1H-pyrazol-4-amine; (S)-1-(1-methoxypropan-2-yl)-5-methyl-1H-pyrazol-4-amine; 5-(4-amino-5-methyl-1H-pyrazol-1-yl)piperidin-2-one; 1-(4-amino-3-methyl-1H-pyrazol-1-yl)cyclopropanecarbonitrile; 5-methyl-1-(1-(pyridin-2-yl)ethyl)-1H-pyrazol-4-amine; 3-methyl-1-(1-(pyridin-2-yl)ethyl)-1H-pyrazol-4-amine; 1-(1-methoxy-2-methylpropan-2-yl)-3-methyl-1H-pyrazol-4-amine; 1',3-dimethyl-1'H-[1,4'-bipyrazol]-4-amine; 2-(4-amino-3-methyl-1H-pyrazol-1-yl)pentan-3-ol; 1-(4-amino-3-methyl-1H-pyrazol-1-yl)-3-methylbutan-2-ol; 5-methyl-1-((6-methylpyridin-2-yl)methyl)-1H-pyrazol-4-amine; 2-(4-amino-1H-pyrazol-1-yl)-N,2-dimethylpropanamide; 1-(isopropylsulfonyl)-1H-pyrazol-4-amine; 1-(cyclopropylsulfonyl)-1H-pyrazol-4-amine; 1-(3,5-difluorophenyl)-1H-pyrazol-4-amine; methyl 2-(4-amino-1H-pyrazol-1-yl)-2-methylpropanoate; 1-(3-fluoro-1-methylpiperidin-4-yl)-1H-pyrazol-4-amine; 1-(2,2-dimethyl-1,3-dioxan-5-yl)-1H-pyrazol-4-amine; 1-(2,6-dimethyltetrahydro-2H-pyran-4-yl)-1H-pyrazol-4-amine; 1-(4,4-difluorocyclohexyl)-1H-pyrazol-4-amine; 4-(4-amino-5-methyl-1H-pyrazol-1-yl)benzonitrile; 1-(1-(oxetan-3-yl)azetidin-3-yl)-1H-pyrazol-4-amine; 1-(4-amino-3-cyclopropyl-1H-pyrazol-1-yl)-2-methylpropan-2-ol; 1-(1-(2-fluoroethyl)piperidin-4-yl)-5-methyl-1H-pyrazol-4-amine; 1-(4-fluorophenyl)-3-methyl-1H-pyrazol-4-amine; (R)-1-(2-methoxypropyl)-3-methyl-1H-pyrazol-4-amine; (S)-1-(1-methoxypropan-2-yl)-3-methyl-1H-pyrazol-4-amine; 3-methyl-1-(1-methylpiperidin-4-yl)-1H-pyrazol-4-amine; 1-(ethylsulfonyl)-3-methyl-1H-pyrazol-4-amine; 2-(4-amino-3-methyl-1H-pyrazol-1-yl)-N,N-dimethylacetamide; (S)-2-(4-amino-3-methyl-1H-pyrazol-1-yl)propanenitrile; 2-(4-amino-3-chloro-1H-pyrazol-1-yl)-2-methylpropanenitrile; 3-(4-amino-3-methyl-1H-pyrazol-1-yl)-2,2-dimethylpropanenitrile; 1-(4-amino-3-methyl-1H-pyrazol-1-yl)cyclobutanecarbonitrile; 2-(4-amino-3-methyl-1H-pyrazol-1-yl)-2-methylpropanamide; 1-(3-methoxycyclopentyl)-3-methyl-1H-pyrazol-4-amine; 3-methyl-1-((1-methyl-1H-pyrazol-3-yl)methyl)-1H-pyrazol-4-amine; 3-methyl-1-(1-methylpiperidin-3-yl)-1H-pyrazol-4-amine; 1-(1-isopropylazetidin-3-yl)-5-methyl-1H-pyrazol-4-amine; 3-methyl-1-(2-methylpyridin-4-yl)-1H-pyrazol-4-amine; 2-(4-amino-1H-pyrazol-1-yl)-N-ethyl-2-methylpropanamide; 1-(1-ethyl-3-fluoropiperidin-4-yl)-1H-pyrazol-4-amine; 1-(sec-butylsulfonyl)-1H-pyrazol-4-amine; 1-(2-(1-methyl-1H-pyrazol-5-yl)propan-2-yl)-1H-pyrazol-4-amine; 5-(4-amino-1H-pyrazol-1-yl)-1-methylpiperidin-2-one; (R)-1-(1-methylpiperidin-3-yl)-1H-pyrazol-4-amine; 1-(cyclopropylsulfonyl)-3-methyl-1H-pyrazol-4-amine; 1-(2-(4-methyl-4H-1,2,4-triazol-3-yl)propan-2-yl)-1H-pyrazol-4-amine; methyl 2-(4-amino-5-methyl-1H-pyrazol-1-yl)-2-methylpropanoate; 1-(4-chlorophenyl)-3-methyl-1H-pyrazol-4-amine; 1-(isopropylsulfonyl)-5-methyl-1H-pyrazol-4-amine; 1-(isopropylsulfonyl)-3-methyl-1H-pyrazol-4-amine; 1-(3,5-difluorophenyl)-5-methyl-1H-pyrazol-4-amine; 1-(1-(2-methoxyethyl)piperidin-4-yl)-5-methyl-1H-pyrazol-4-amine; 2-(4-amino-5-methyl-1H-pyrazol-1-yl)-N,2-dimethylpropanamide; 5-(4-amino-3-methyl-1H-pyrazol-1-yl)piperidin-2-one; 3-(4-amino-3-chloro-1H-pyrazol-1-yl)-2,2-dimethylpropanenitrile; 1-(cyclopropylsulfonyl)-5-methyl-1H-pyrazol-4-amine; 1-(2,2-dimethyl-1,3-dioxan-5-yl)-3-methyl-1H-pyrazol-4-amine; 3-methyl-1-(1-(oxetan-3-yl)azetidin-3-yl)-1H-pyrazol-4-amine; 1-(4,4-difluorocyclohexyl)-3-methyl-1H-pyrazol-4-amine; 1-(2,6-dimethyltetrahydro-2H-pyran-4-yl)-5-methyl-1H-pyrazol-4-amine; 1-(4,4-difluorocyclohexyl)-5-methyl-1H-pyrazol-4-amine; 3-methyl-1-((6-methylpyridin-2-yl)methyl)-1H-pyrazol-4-amine; 1-(4-(4-amino-1H-pyrazol-1-yl)piperidin-1-yl)ethan-1-one; 1-(1-(oxetan-3-yl)piperidin-4-yl)-1H-pyrazol-4-amine; 1-(2-methyl-2-morpholinopropyl)-1H-pyrazol-4-amine; 1-(2-methyl-1-morpholinopropan-2-yl)-1H-pyrazol-4-amine; 4-(4-amino-3-methyl-1H-pyrazol-1-yl)benzonitrile; 4-(4-amino-1H-pyrazol-1-yl)tetrahydro-2H-thiopyran 1,1-dioxide; 1-(4-amino-1H-pyrazol-1-yl)-N-ethylcyclobutanecarboxamide; 1-(1-isobutylpiperidin-4-yl)-1H-pyrazol-4-amine; 3-methyl-1-(2-(1-methyl-1H-pyrazol-5-yl)propan-2- yl)-1H-pyrazol-4-amine; 1-(1-(2-fluoroethyl)piperidin-4-yl)-3-methyl-1H-pyrazol-4-amine; 5-chloro-1-(3-fluoro-1-methylpiperidin-4-yl)-1H-pyrazol-4-amine; 3-methyl-1-(2-(4-methyl-4H-1,2,4-triazol-3-yl)propan-2-yl)-1H-pyrazol-4-amine; 2-(4-amino-5-chloro-1H-pyrazol-1-yl)-N,2-dimethylpropanamide; (R)-5-methyl-1-(1-methylpiperidin-3-yl)-1H-pyrazol-4-amine; 1-(1-isopropylazetidin-3-yl)-3-methyl-1H-pyrazol-4-amine; 1-(sec-butylsulfonyl)-5-methyl-1H-pyrazol-4-amine; 2-(4-amino-5-ethyl-1H-pyrazol-1-yl)-N,2-dimethylpropanamide; 1-(3-fluoro-1-(oxetan-3-yl)piperidin-4-yl)-1H-pyrazol-4-amine; 1-(2-(4H-1,2,4-triazol-3-yl)propan-2-yl)-1H-pyrazol-4-amine; 1-(1-((1,3-dioxolan-2-yl)methyl)pyrrolidin-3-yl)-1H-pyrazol-4-amine; 1-(2-(1-methyl-1H-pyrazol-4-yl)propan-2-yl)-1H-pyrazol-4-amine; 1-(2-(1-methyl-1H-pyrazol-3-yl)propan-2-yl)-1H-pyrazol-4-amine; 2-(4-amino-3-methyl-1H-pyrazol-1-yl)-N,2-dimethylpropanamide; 2-(4-amino-1H-pyrazol-1-yl)-N,N,2-trimethylpropanamide; 1-(2-(5-methyl-1,3,4-oxadiazol-2-yl)propan-2-yl)-1H-pyrazol-4-amine; 1-(2-(1-methyl-1H-1,2,4-triazol-3-yl)propan-2-yl)-1H-pyrazol-4-amine; 1-(1-(2,2,2-trifluoroethyl)azetidin-3-yl)-1H-pyrazol-4-amine; 2-(4-amino-3-cyclopropyl-1H-pyrazol-1-yl)-2-methylpropanenitrile; 3-methyl-1-(2-methyl-1-morpholinopropan-2-yl)-1H-pyrazol-4-amine; 1-(3,5-difluorophenyl)-3-methyl-1H-pyrazol-4-amine; methyl 2-(4-amino-3-methyl-1H-pyrazol-1-yl)-2-methylpropanoate; 1-(1-(2-methoxyethyl)piperidin-4-yl)-3-methyl-1H-pyrazol-4-amine; 1-(4-amino-5-(trifluoromethyl)-1H-pyrazol-1-yl)-2-methylpropan-2-ol; 1-(4-amino-3-(trifluoromethyl)-1H-pyrazol-1-yl)-2-methylpropan-2-ol; 3-methyl-1-(2-methyl-2-morpholinopropyl)-1H-pyrazol-4-amine; 1-(4-amino-3-(tert-butyl)-1H-pyrazol-1-yl)-2-methylpropan-2-ol; 3-methyl-1-(1-(oxetan-3-yl)piperidin-4-yl)-1H-pyrazol-4-amine; 1-(3-fluoro-1-methylpiperidin-4-yl)-3-methyl-1H-pyrazol-4-amine; 1-(4-(4-amino-5-methyl-1H-pyrazol-1-yl)piperidin-1-yl)ethan-1-one; 2-(4-amino-5-ethyl-1H-pyrazol-1-yl)-N-ethyl-2-methylpropanamide; 1-(4-amino-5-methyl-1H-pyrazol-1-yl)-N-ethylcyclobutanecarboxamide; 5-chloro-1-(1-ethyl-3-fluoropiperidin-4-yl)-1H-pyrazol-4-amine; 1-(1-isobutylpiperidin-4-yl)-5-methyl-1H-pyrazol-4-amine; 1-(2,6-dimethyltetrahydro-2H-pyran-4-yl)-3-methyl-1H-pyrazol-4-amine; 5-methyl-1-(2-methyl-2-morpholinopropyl)-1H-pyrazol-4-amine; 4-(4-amino-5-methyl-1H-pyrazol-1-yl)tetrahydro-2H-thiopyran 1,1-dioxide; 5-methyl-1-(1-(oxetan-3-yl)piperidin-4-yl)-1H-pyrazol-4-amine; (R)-2-(4-amino-1H-pyrazol-1-yl)-N,N-dimethylpropanamide; 1-(1-(((1,3-dioxolan-2-yl)methyl)piperidin-4-yl)-1H-pyrazol-4-amine; 2-(4-amino-1H-pyrazol-1-yl)-N-isopropyl-2-methylpropanamide; 1-(2-(4H-1,2,4-triazol-3-yl)propan-2-yl)-3-methyl-1H-pyrazol-4-amine; 1-(1-(methylsulfonyl)azetidin-3-yl)-1H-pyrazol-4-amine; 2-(4-amino-3-methyl-1H-pyrazol-1-yl)-N-ethyl-2-methylpropanamide; 1-(1-((1,3-dioxolan-2-yl)methyl)pyrrolidin-3-yl)-5-methyl-1H-pyrazol-4-amine; 2-(4-amino-5-methyl-1H-pyrazol-1-yl)-N,N,2-trimethylpropanamide; 3-methyl-1-(1-(2,2,2-trifluoroethyl)azetidin-3-yl)-1H-pyrazol-4-amine; 1-(1-((1,3-dioxolan-2-yl)methyl)pyrrolidin-3-yl)-3-methyl-1H-pyrazol-4-amine; 5-methyl-1-(2-(1-methyl-1H-pyrazol-4-yl)propan-2-yl)-1H-pyrazol-4-amine; (R)-3-methyl-1-(1-methylpiperidin-3-yl)-1H-pyrazol-4-amine; 1-(sec-butylsulfonyl)-3-methyl-1H-pyrazol-4-amine; 1-(1-(2,2,2-trifluoroethyl)piperidin-4-yl)-1H-pyrazol-4-amine; 2-(4-amino-1H-pyrazol-1-yl)-N-(cyclopropylmethyl)-2-methylpropanamide; 2-(4-amino-1H-pyrazol-1-yl)-2-methyl-1-(pyrrolidin-1-yl)propan-1-one; 5-chloro-1-(3-fluoro-1-(oxetan-3-yl)piperidin-4-yl)-1H-pyrazol-4-amine; 1-(1-(((1,3-dioxolan-2-yl)methyl)piperidin-4-yl)-5-methyl-1H-pyrazol-4-amine; 3-methyl-1-(1-(methylsulfonyl)azetidin-3-yl)-1H-pyrazol-4-amine; 1-(1-(((1,3-dioxolan-2-yl)methyl)piperidin-4-yl)-3-methyl-1H-pyrazol-4-amine; 3-cyclopropyl-1-(cyclopropylsulfonyl)-1H-pyrazol-4-amine; 1-(4-(4-amino-3-methyl-1H-pyrazol-1-yl)piperidin-1-yl)ethan-1-one; 2-(4-amino-5-methyl-1H-pyrazol-1-yl)-N-isopropyl-2-methylpropanamide; (4-(4-amino-1H-pyrazol-1-yl)piperidin-1-yl)(cyclopropyl)methanone; 1-(4-(methylsulfonyl)phenyl)-1H-pyrazol-4-amine; 1-(4-(4-amino-1H-pyrazol-1-yl)piperidin-1-yl)-2-methylpropan-1-one; (R)-1-(1-(oxetan-3-yl)pyrrolidin-3-yl)-1H-pyrazol-4-amine; 4-(4-amino-1H-pyrazol-1-yl)-N,N-dimethylbenzamide; (R)-2-(4-amino-1H-pyrazol-1-yl)-1-(pyrrolidin-1-yl)propan-1-one; 1-(2-(5-methyl-4H-1,2,4-triazol-3-yl)propan-2-yl)-1H-pyrazol-4-amine; 3-methyl-1-(1-(2,2,2-trifluoroethyl)piperidin-4-yl)-1H-pyrazol-4-amine; 5-methyl-1-(1-(2,2,2-trifluoroethyl)piperidin-4-yl)-1H-pyrazol-4-amine; 1-(3-fluoro-1-(oxetan-3-yl)piperidin-4-yl)-3-methyl-1H-pyrazol-4-amine; (R)-2-(4-amino-5-methyl-1H-pyrazol-1-yl)-N,N-dimethylpropanamide; 3-methyl-1-(2-(1-methyl-1H-pyrazol-3-yl)propan-2-yl)-1H-pyrazol-4-amine; 2-(4-amino-5-methyl-1H-pyrazol-1-yl)-N-(cyclopropylmethyl)-2-methylpropanamide; 2-(4-amino-3-methyl-1H-pyrazol-1-yl)-N-(cyclopropylmethyl)-2-methylpropanamide; 2-(4-amino-5-methyl-1H-pyrazol-1-yl)-2-methyl-1-(pyrrolidin-1-yl)propan-1-one; 3-methyl-1-(2-(1-methyl-1H-pyrazol-4-yl)propan-2-yl)-1H-pyrazol-4-amine; 3-methyl-1-(2-(1-methyl-1H-1,2,4-triazol-3-yl)propan-2-yl)-1H-pyrazol-4-amine, 2-(4-amino-3-ethyl-1H-pyrazol-1-yl)-N-isopropyl-2-methylpropanamide; 3-methyl-1-(2-(5-methyl-1,3,4-oxadiazol-2-yl)propan-2-yl)-1H-pyrazol-4-amine; (R)-1-(1-(oxetan-3-yl)piperidin-3-yl)-1H-pyrazol-4-amine; 2-(4-amino-1H-pyrazol-1-yl)-N-(tert-butyl)-2-methylpropanamide; 5-methyl-1-(4-(methylsulfonyl)phenyl)-1H-pyrazol-4-amine; 3-methyl-1-(4-(methylsulfonyl)phenyl)-1H-pyrazol-4-amine; 1-(4-(4-amino-5-methyl-1H-pyrazol-1-yl)piperidin-1-yl)-2-methylpropan-1-one; 4-(4-amino-5-methyl-1H-pyrazol-1-yl)-N,N-dimethylbenzamide; (4-(4-amino-5-methyl-1H-pyrazol-1-yl)piperidin-1-yl)(cyclopropyl)methanone; (R)-2-(4-amino-5-methyl-1H-pyrazol-1-yl)-1-(pyrrolidin-1-yl)propan-1-one; (R)-5-methyl-1-(1-(oxetan-3-yl)pyrrolidin-3-yl)-1H-pyrazol-4-amine; (R)-3-methyl-1-(1-(oxetan-3-yl)pyrrolidin-3-yl)-1H-pyrazol-4-amine; (R)-2-(4-amino-3-methyl-1H-pyrazol-1-yl)-N,N-dimethylpropanamide; 2-(4-amino-1H-pyrazol-1-yl)-2-methyl-N-(2,2,2-trifluoroethyl)propanamide; (R)-5-methyl-1-(1-(oxetan-3-yl)piperidin-3-yl)-1H-pyrazol-4-amine; (R)-3-methyl-1-(1-(oxetan-3-yl)piperidin-3-yl)-1H-pyrazol-4-amine; 2-(4-amino-5-methyl-1H-pyrazol-1-yl)-N-(tert-butyl)-2-methylpropanamide; 2-(4-amino-3-methyl-1H-pyrazol-1-yl)-N-(tert-butyl)-2-methylpropanamide; (4-(4-amino-1H-pyrazol-1-yl)piperidin-1-yl)(1-methylcyclopropyl)methanone; 1-((1R,5R)-8-oxabicyclo[3.2.1]octan-3-yl)-1H-pyrazol-4-amine; 1-(4-(4-amino-3-methyl-1H-pyrazol-1-yl)piperidin-1-yl)-2-methylpropan-1-one; (4-(4-amino-3-methyl-1H-pyrazol-1-yl)piperidin-1-yl)(cyclopropyl)methanone; 4-(4-amino-3-methyl-1H-pyrazol-1-yl)-N,N-dimethylbenzamide; 2-(4-amino-5-methyl-1H-pyrazol-1-yl)-2-methyl-N-(2,2,2-trifluoroethyl)propanamide; 3-methyl-1-(2-(5-methyl-4H-1,2,4-triazol-3-yl)propan-2-yl)-1H-pyrazol-4-amine; 1-(4-(cyclopropylsulfonyl)phenyl)-1H-pyrazol-4-amine; (R)-2-(4-amino-3-methyl-1H-pyrazol-1-yl)-1-(pyrrolidin-1-yl)propan-1-one; (4-(4-amino-3-methyl-1H-pyrazol-1-yl)piperidin-1-yl)(1-methylcyclopropyl)methanone; 1-((1R,5R)-8-oxabicyclo[3.2.1]octan-3-yl)-3-methyl-1H-pyrazol- 4-amine; (4-(4-amino-5-methyl-1H-pyrazol-1-yl)piperidin-1-yl)(1-methylcyclopropyl)methanone; 1-(4-(cyclopropylsulfonyl)phenyl)-3-methyl-1H-pyrazol-4-amine; 1-(4-(cyclopropylsulfonyl)phenyl)-5-methyl-1H-pyrazol-4-amine.

Further preferred, R¹ can be derived from the following compounds (e.g. amines): thiazol-5-amine; isothiazol-4-amine; pyrimidin-5-amine; pyridazin-4-amine; 3-methylisothiazol-5-amine; 3-methylisoxazol-5-amine; 6-methylpyridin-3-amine; 2-fluoropyridin-4-amine; 4-iodo-3-methylisothiazol-5-amine; 2-methylpyridin-4-amine; 5-fluoropyridin-3-amine; 3-ethylisothiazol-5-amine; 5-methylpyridin-3-amine; 6-fluoropyridin-3-amine; 4-fluoro-3-methylisothiazol-5-amine; 3,4-dimethylisothiazol-5-amine; (5-aminoisothiazol-3-yl)methanol; 3-(aminomethyl)aniline; 6-ethylpyridin-3-amine; thieno[2,3-c]isothiazol-3-amine; 5-chloropyridin-3-amine; 3-(methoxymethyl)isothiazol-5-amine; 5-methoxypyridin-3-amine; thieno[3,2-c]isothiazol-3-amine; 4-bromo-3-methylisothiazol-5-amine; 2-ethylpyridin-4-amine; 4-chloro-3-methylisothiazol-5-amine; 2-methoxypyrimidin-5-amine; 2,3-dimethylaniline; thieno[2,3-b]pyridin-3-amine; pyrazolo[1,5-a]pyridin-3-amine; 2,3-dihydro-1H-inden-5-amine; 6-methoxy-5-methylpyridin-3-amine; isothiazolo[3,4-b]pyridin-3-amine; 6-ethoxypyridin-3-amine; benzo[c]isothiazol-3-amine; isothiazolo[3,4-b]pyrazin-3-amine; imidazo[1,2-a]pyridin-7-amine; 5-aminopicolinonitrile; thiazolo[5,4-b]pyridin-6-amine; p-toluidine; 3-methoxypyridine-2,6-diamine; benzo[b]thiophen-5-amine; thieno[3,2-c]pyridin-3-amine; 3-(4-aminophenyl)propan-1-ol; 4-(2-aminoethoxy)aniline; 4-(3-fluoropropyl)aniline; isoquinolin-7-amine; 1,5-naphthyridin-3-amine; quinolin-7-amine; 1,8-naphthyridin-4-amine; quinolin-3-amine; isoquinolin-6-amine; 3-cyclopropylisothiazol-5-amine; 2,6-dimethylpyridin-4-amine; 1,8-naphthyridin-3-amine; quinolin-4-amine; isoquinolin-5-amine; 1,6-naphthyridin-3-amine; 3-isopropylisothiazol-5-amine; quinazolin-6-amine; 3-cyclopropylisoxazol-5-amine; isoquinolin-8-amine; isoquinolin-4-amine; isochroman-7-amine; isochroman-6-amine; 2-(4-aminophenyl)acetonitrile; 5-amino-2-fluorobenzonitrile; quinolin-2-amine; 5-amino-2-methylbenzonitrile; 1,2,3,4-tetrahydroquinolin-6-amine; 3,4-diaminopicolinonitrile; 5,6-dimethoxypyridin-2-amine; 3-fluoro-5-methylaniline; pyrido[2,3-b]pyrazin-7-amine; 5-methoxyindolin-6-amine; 4-(prop-2-yn-1-yloxy)aniline; 3-(4-aminophenoxyl)propan-1-ol; N2,N2-dimethylpyridine-2,5-diamine; N2,N2-dimethylpyridine-2,4-diamine; 2-cyclopropylpyridin-4-amine; 6-cyclopropylpyridin-3-amine; (3-amino-5-iodophenyl)methanol; 3-bromo-5-methylaniline; 4-(4-aminophenyl)butan-1-ol; 2-(3-aminophenoxyl)acetonitrile; 2-(4-aminophenoxyl)acetonitrile; 3-(4-aminophenyl)propanenitrile; 4-(4-fluorobutyl)aniline; N1-(prop-2-yn-1-yl)benzene-1,4-diamine; 3-(prop-2-yn-1-yloxy)aniline; 4-amino-6-chloronicotinonitrile; 3-amino-5-bromopicolinonitrile; 3-fluoro-5-methoxyaniline; 3-chloro-5-fluoroaniline; 4-(difluoromethoxy)aniline; 6-(azetidin-1-yl)pyridin-3-amine; 5-aminopicolinic acid; 3,5-dibromoaniline; 2-(4-amino-2-methylphenoxy)acetonitrile; methyl 5-aminothiophene-2-carboxylate; 3-fluoro-4-(prop-2-yn-1-yloxy)aniline; 3-(4-amino-2-fluorophenyl)propanenitrile; 3-methyl-4-(prop-2-yn-1-yloxy)aniline; 2-(4-amino-2-fluorophenoxy)acetonitrile; 3-(4-amino-2-methylphenyl)propanenitrile; 4-(but-2-yn-1-yloxy)aniline; 1-methyl-1H-pyrrolo[2,3-b]pyridin-4-amine; 6-aminobenzo[d]thiazol-2-ol; 3-(difluoromethoxy)aniline; 1H-pyrrolo[3,2-b]pyridin-6-amine; 6-fluoroquinolin-3-amine; 3-(oxazol-2-yl)aniline; 8-fluoroquinolin-6-amine; 7-fluoroquinolin-3-amine; 8-fluoroquinolin-3-amine; 2,3-dibromo-4-methylaniline; 3-(tert-butyl)isothiazol-5-amine; 4-(oxazol-2-yl)aniline; 2-cyclobutoxypyridin-4-amine; 3-phenylisothiazol-5-amine; 3-phenylisoxazol-5-amine; 5-aminobicyclo[4.2.0]octa-1,3,5-triene-2-carbonitrile; 2-(4-amino-2-(hydroxymethyl)phenoxy)acetonitrile; 2-(4-amino-2-chlorophenoxy)acetonitrile; 3-chloro-4-(prop-2-yn-1-yloxy)aniline; 3-(4-amino-2-chlorophenyl)propanenitrile; 5-(1H-pyrazol-1-yl)pyridin-3-amine; 5-chlorothiazolo[5,4-d]pyrimidin-7-amine; 6-chloro-[1,2,4]triazolo[1,5-a]pyridin-8-amine; 5-(2H-1,2,3-triazol-2-yl)pyridin-3-amine; 5-(1H-imidazol-1-yl)pyridin-3-amine; 6-(1H-pyrazol-1-yl)pyridin-3-amine; 2-(1H-pyrazol-1-yl)pyridin-4-amine; 5-(thiazol-2-yl)pyridin-3-amine; 6-chloroimidazo[1,2-a]pyridin-8-amine; 6-amino-3,4-dihydroquinolin-2(1H)-one; 6-amino-2H-pyrido[3,2-b][1,4]oxazin-3(4H)-one; [2,3'-bipyridin]-5-amine; N2,N2,3-trimethylpyridine-2,5-diamine; 5-(pyrimidin-2-yl)pyridin-3-amine; 3-methyl-4-(pyrimidin-5-yl)isothiazol-5-amine; 2-(trifluoromethyl)pyridin-4-amine; 3-methyl-4-(pyridin-3-yl)isothiazol-5-amine; 3-(morpholinomethyl)isothiazol-5-amine; 5-(trifluoromethyl)pyridin-3-amine; 3-methyl-4-phenylisothiazol-5-amine; 6-(trifluoromethyl)pyridin-3-amine; 1-(3-aminobenzyl)urea; 2-(4-aminophenoxyl)propanenitrile; 2-(3-aminophenoxyl)acetamide; 4-aminopyridine-3-sulfonamide; 1-(4-aminobenzyl)urea; 5-aminobenzofuran-2-carbonitrile; 2-(4-aminophenoxyl)acetamide; 2-(4-aminophenyl)-2-oxoethanethial; 3-(2,3-dihydro-1H-1,2,3-triazol-1-yl)aniline; 4-amino-1-methylindolin-2-one; 3-amino-N'-(2-aminoethyl)picolinohydrazide; N3-(1-aminobutan-2-yl)pyridine-3,5-diamine; 2-amino-N,N-dimethylbenzamide; 4-(pyrimidin-4-yl)aniline; 3-(pyrimidin-4-yl)aniline; 1-isopropyl-1H-indol-4-amine; 6-bromo-5-methylimidazo[1,2-a]pyridin-8-amine; 4-amino-2,6-dibromophenol; 2,2'-((4-aminophenypazanediyl)bis(ethan-1-ol); 4-(piperidin-4-yloxy)aniline; 1-(2-(piperazin-1-yl)ethyl)-1H-pyrazol-4-amine; 3-(5-aminopyridin-2-yl)oxazolidin-2-one; 2-(2-methylmorpholino)aniline; 3-(4-aminophenyl)oxazolidin-2-one; 5-amino-N,N-dimethylisothiazole-3-carboxamide; 3-(morpholinomethyl)aniline; 3-methyl-1H-pyrazolo[3,4-b]pyridin-5-amine; 3-bromo-5-(difluoromethyl)aniline; 1-(2-methoxyethyl)-1H-indazol-5-amine; 2-(4-amino-2,6-dimethylphenoxy)acetonitrile; 3-aminobenzyl methylcarbamate; 4-aminophenethyl carbamate; 1-(prop-2-yn-1-yl)-1H-indol-6-amine; N-(4-aminobenzyl)propionamide; 1-(4-aminophenethyl)urea; 2-(4-amino-2-fluorophenoxy)acetamide; 1-(prop-2-yn-1-yl)-1H-indol-5-amine; 2-(4-amino-2-methylphenoxy)acetamide; 2-(4-amino-2-methylphenoxy)propanenitrile; 2-((1-methylpyrrolidin-3-yl)oxy)aniline; methyl 2-(4-aminophenoxyl)acetate; 3-(1,4,5,6-tetrahydropyrimidin-2-yl)aniline; 3,5-diaminopicolinamide, 2-amino-N-cyclopropylbenzamide; 6-bromo-5-chloroimidazo[1,2-a]pyridin-8-amine; 2-methoxy-4-(piperazin-1-yl)aniline; 2-methoxy-4-(piperidin-4-yl)aniline; 2-methoxy-5-(piperazin-1-yl)aniline; 2-(5-aminoindolin-3-ylidene)acetonitrile; 4-(4-aminophenoxy)butanoic acid; 4-(2-(diethylamino)ethoxy)aniline; 2-(4-aminophenoxy)-2-methylpropan-1-ol; 4-(2-(piperazin-1-yl)ethyl)aniline; 6-(3-methylenemorpholino)pyridin-3-amine; 5-methoxy-6-morpholinopyridin-3-amine; 6-(3-methoxyazetidin-1-yl)pyridin-3-amine; 4-((3-aminopyridin-4-yl)amino)cyclohexanol; N2,N2-dimethylbenzo[d]oxazole-2,6-diamine; 6-(2,2,2-trifluoroethoxyl)pyridin-3-amine; 5-amino-N,N-dimethylpicolinamide; 3-amino-5-methylpyridine 1-oxide; 3-amino-N,N-dimethylbenzamide; 1-(4-aminophenyl)piperidin-2-one; 5-amino-1-methylindolin-2-one; 3-methyl-5-(thiazol-5-yl)aniline; 3-(1H-pyrazol-5-yl)aniline; 2-(4-amino-2-methoxyphenoxy)acetamide;

2-(4-amino-2-chlorophenoxy)acetamide; 2-(4-amino-2-fluorophenoxy)-N-methylacetamide; N-(4-aminophenyl)-2-cyanoacetamide; 4-aminophenethyl methylcarbamate; 1-(3-aminobenzyl)-3-ethylurea; 6-amino-4-methylquinolin-2-ol; 1-(3-methoxypropyl)-1H-indazol-5-amine; 2-(6-aminoindolin-3-ylidene)acetonitrile; 4-(pyridin-3-ylmethoxy)aniline; 2-(7-aminoindolin-3-ylidene)acetonitrile; 1-(4-aminobenzyl)-3-ethylurea; 2-(4-amino-2-(hydroxymethyl)phenoxy)acetamide; 2-(3-aminophenyl)-2H-1,2,3-triazol-4-ol; 3-(2-(methoxymethyl)pyrrolidin-1-yl)aniline; (2-aminophenyl)(pyrrolidin-1-yl)methanone; 3-amino-5-fluoropyridine 1-oxide; 2-(4-amino-3-methoxyphenyl)propane-1,3-diol; (3-aminophenyl)methanesulfonamide; 6-(2-(piperazin-1-yl)ethoxy)pyridin-3-amine, 4-(2-(piperazin-1-yl)ethoxy)aniline; 4-(2-ethyl-2H-tetrazol-5-yl)aniline; 1-(5-aminopyridin-2-yl)piperidin-3-ol; 4-(2-(piperidin-4-yl)ethoxy)aniline; 1-(5-aminopyridin-2-yl)piperidin-4-ol; 4-(3-(piperazin-1-yl)propyl)aniline; 5-fluoro-6-morpholinopyridin-3-amine; 1-(4-aminophenyl)piperidin-4-amine; (4-(4-amino-2-fluorophenyl)morpholin-3-yl)methanol; (5-aminopyridin-2-yl)(azetidin-1-yl)methanone; 4-((methylsulfonyl)methyl)aniline; 2-(azetidin-1-yl)benzo[d]oxazol-6-amine; (3-aminophenyl)(azetidin-1-yl)methanone; 3-bromo-5-(thiazol-5-yl)aniline; 4-(4-(aminomethyl)-1H-1,2,3-triazol-1-yl)aniline; 4-(4-aminophenyl)pyridin-2-amine; 6-amino-4-methyl-2H-benzo[b][1,4]thiazin-3(4H)-one; 1-(4-aminophenethyl)-3-ethylurea; 4-((1H-1,2,4-triazol-3-yl)methyl)aniline; 2-(4-aminophenoxy)propanamide; 2-(4-amino-2-chlorophenoxy)-N-methylacetamide; 5-aminobenzofuran-2-carboxamide; 2-(5-amino-2,3-dimethoxyphenoxy)acetonitrile; 2-(4-aminophenoxy)-2-methylpropanenitrile; 4-((1H-1,2,3-triazol-4-yl)methyl)aniline; N1,N1-di(prop-2-yn-1-yl)benzene-1,4-diamine; 2-amino-6-methylbenzenesulfonamide; 1-isobutyl-1H-indol-4-amine; 6-bromo-5-ethylimidazo[1,2-a]pyridin-8-amine; 2-(4-amino-3-methoxybenzyl)propane-1,3-diol; 1-(4-aminophenyl)-N-methylmethanesulfonamide; prop-2-yn-1-yl(4-aminobenzyl)carbamate; 6-amino-5-fluoro-1,3-dihydrobenzo[c]isothiazole 2,2-dioxide; 6-(4-ethylpiperazin-1-yl)pyridin-3-amine; 4-(2-(1,4-diazepan-1-yl)ethoxy)aniline; 1-(2-(4-methylpiperazin-1-yl)ethyl)-1H-pyrazol-4-amine; (1-(4-aminophenyl)piperidin-3-yl)methanol; 4-(3-(piperazin-1-yl)propoxy)aniline; 2-(5-(4-aminophenyl)-2H-tetrazol-2-yl)ethan-1-ol; 4-(4-methoxypiperidin-1-yl)aniline; N2-methyl-N2-(tetrahydro-2H-pyran-4-yl)pyridine-2,5-diamine; 6-(4-methoxypiperidin-1-yl)pyridin-3-amine; 2,4,4a,5-tetrahydro-1H-benzo[b][1,4]oxazino[4,3-d][1,4]oxazin-8-amine; 6-(3-(ethoxymethyl)morpholino)pyridin-3-amine; (3-aminophenyl)(pyrrolidin-1-yl)methanone; 3-amino-4-methoxy-N,N-dimethylbenzamide; 5-amino-2-methoxy-N,N-dimethylbenzamide; (R)-2-methyl-2H-indol-4-amine; 4(4-(aminomethyl)piperidin-1-yl)aniline; N2-cyclopropylquinoline-2,6-diamine; 4-amino-2-methoxybenzenesulfonamide; 2-(7-amino-1H-indol-3-yl)acetonitrile; 2-(5-amino-2H-indol-2-ylidene)acetonitrile; 5-amino-N,2-dimethylbenzenesulfonamide; 2-(4-amino-2,6-dimethylphenoxy)propanenitrile; N-(4-amino-2-chlorophenyl)-2-cyanoacetamide; 2-(6-amino-1H-indol-3-yl)acetonitrile; 4-((5-methyl-1,2,4-oxadiazol-3-yl)methoxy)aniline; 5-amino-2-methoxybenzenesulfonamide; 2-(5-amino-1H-indol-3-yl)acetonitrile; N-(3-aminobenzyl)cyclopropanecarboxamide; 6-amino-1,2-dihydrobenzo[b]cyclobuta[d]thiophene-1-carbonitrile; N-(4-aminobenzyl)cyclopropanecarboxamide; 2-(4-amino-2,6-dimethylphenoxy)acetamide; 4-((1-methylpiperidin-3-yl)oxy)aniline; 2-(4-amino-2-methylphenoxy)propanamide; 3-((1-methylpiperidin-3-yl)oxy)aniline; N44-amino-3-methylphenyl)acrylamide; 3-((1-methylpiperidin-4-yl)oxy)aniline; 2-(5-amino-1-methyl-1H-indol-3-yl)acetonitrile; 3-chloro-4-(trifluoromethyl)aniline; N-allyl-2(4-aminophenoxy)acetamide; 4-((5-methyl-1,3,4-oxadiazol-2-yl)methoxy)aniline; 2-amino-6-methoxybenzenesulfonamide; 2-amino-N,N-dimethylbenzenesulfonamide; 1-(6-amino-5-methoxyindolin-1-yl)ethan-1-one; N-(4-aminobenzyl)ethanesulfonamide; 5-amino-2-methylbenzenesulfonamide; N-(3-aminobenzyl)ethanesulfonamide; 4-(4-(2-aminoethyl)piperazin-1-yl)aniline; 4-(4-(2-fluoroethyl)piperazin-1-yl)aniline; 4-(4-(2-fluoroethyl)piperidin-1-yl)aniline; 2-(1-(5-aminopyridin-2-yl)piperidin-4-yl)ethan-1-ol; 2-(1-(4-aminophenyl)piperidin-3-yl)ethan-1-ol; 1-(2-(4-ethylpiperazin-1-yl)ethyl)-1H-pyrazol-4-amine; 1-(4-aminophenyl)piperidine-4-carbonitrile; 6-(1,4-diazabicyclo[3.2.2]nonan-4-yl)pyridin-3-amine; 6-(4-ethoxypiperidin-1-yl)pyridin-3-amine; 2-(4-(4-aminophenyl)morpholin-2-yl)ethan-1-ol; (R)-6-(3-methylmorpholino)pyridin-3-amine; 6-amino-4-propyl-2H-pyrido[3,2-b][1,4]oxazin-3(4H)-one; 4-(4-(methoxymethyl)piperidin-1-yl)aniline; 4-(4-ethoxypiperidin-1-yl)aniline; 5-amino-2-fluoro-N,N-dimethylbenzamide; 4-(4-amino-2-fluorophenyl)morpholin-3-one; 3-amino-4-fluoro-N,N-dimethylbenzamide; 3-amino-N-(isoxazol-3-yl)benzamide; 2-(5-amino-3-chloro-2-methyl-1H-indol-1-yl)ethan-1-ol; 3-chloro-2-methyl-1-propyl-1H-indol-5-amine; 5-amino-2-fluorobenzenesulfonamide; (4-aminophenyl)(thiomorpholino)methanone; 4-amino-2-methoxy-N-methylbenzenesulfonamide; 4-aminophenethyl dimethylcarbamate; S-(2-(4-aminophenyl)-2-oxoethyl) ethanethioate; 3-methyl-4-(pyridin-2-ylmethoxy)aniline; 2-((4-aminobenzyl)amino)butanamide; N-(4-aminophenyl)-2-cyano-N-methylacetamide; 4-(methylsulfonyl)benzene-1,3-diamine; (R)-4-((tetrahydrofuran-2-yl)methoxy)aniline; 2,4-dichloro-5-(2H-1,2,3-triazol-2-yl)aniline; (S)-3-(2-methylpyrrolidin-1-yl)aniline; N-(3-amino-4-methoxyphenyl)-2-(dimethylamino)acetamide; N-(4-aminophenethyl)ethanesulfonamide; 2-(1-(4-aminophenyl)piperidin-4-yl)acetonitrile; 4-(4-aminophenyl)-1-ethylpiperazin-2-one; 2-(4-(4-aminophenoxy)piperidin-1-yl)ethan-1-ol; 1-(2-(4-aminophenoxy)ethyl)piperidin-4-ol; 1-(3-(4-aminophenyl)propyl)piperidin-4-ol; 2-(4-(4-aminophenyl)-1,4-diazepan-1-yl)ethan-1-ol; 2-(4-(4-aminophenyl)piperazin-1-yl)acetonitrile; 3-(4-(4-aminophenyl)piperazin-1-yl)propan-1-ol; 3-(1-(4-aminophenyl)piperidin-4-yl)propan-1-ol; 2-(1-(5-aminopyridin-2-yl)piperidin-4-yl)acetonitrile; 2-(4-aminophenoxy)-2-methylpropanoic acid; 4-(2-(4-methylpiperazin-1-yl)ethoxy)aniline; (S)-6-(3-methylmorpholino)pyridin-3-amine; 6-amino-2,2-dimethyl-2H-pyrido[3,2-b][1,4]oxazin-3(4H)-one; 6-(2,2-dimethylmorpholino)pyridin-3-amine; (S)-2-(2-methylmorpholino)aniline; (S)-4-(3-methylmorpholino)aniline; 4-(2,2-dimethylmorpholino)aniline; 3-(difluoromethoxy)-4-morpholinoaniline; 3-isopropoxy-4-morpholinoaniline; (S)-1-(5-aminopyridin-2-yl)pyrrolidin-3-ol; 6-(2,5-dimethylmorpholino)pyridin-3-amine; 4-amino-2-chloro-N,N-dimethylbenzamide; 3-cyclopropyl-5-(thiazol-5-yl)aniline; 3-amino-N-phenylbenzamide; 5-amino-2-chlorobenzenesulfonamide; 3-amino-N-(prop-2-yn-1-yl)benzenesulfonamide; 3-amino-N-butylbenzenesulfonamide; 5-(3-methyl-1,2,4-oxadiazol-5-yl)bicyclo[4.2.0]octa-1,3,5-trien-2-amine; 2-(4-aminophenoxy)-2-methylpropanamide; 2-(6-amino-3-oxo-2H-benzo[b][1,4]oxazin-4(3H)-yl)acetonitrile; 2-(6-amino-3-oxo-2H-benzo[b][1,4]thiazin-4(3H)-yl)acetonitrile; 3-chloro-4-((1-methylpiperidin-3-yl)oxy)aniline; 4-amino-N-(prop-2-yn-1-yl)benzenesulfonamide; 6-amino-1H-indole-3-carboxamide;

3-chloro-4-((1-methylpiperidin-4-yl)oxy)aniline; (S)-(4-(4-aminophenyl)morpholin-3-yl)methanol; 1-(2,2,2-trifluoroethyl)pindolin-4-amine; 2-(3-aminophenyl)-2H-1,2,3-triazole 1-oxide; 2-(pyrrolidin-1-ylsulfonyl)aniline; 2-(4-(4-aminophenethyl)piperazin-1-yl)ethan-1-ol; 4-(2-(4-aminophenoxyl)ethyl)piperazin-2-one; 4-(2-(4-ethylpiperazin-1-yl)ethoxy)aniline; (1-(2-(4-aminophenoxyl)ethyl)piperidin-4-yl)methanol; (R)-6-(3-fluoropyrrolidin-1-yl)pyridin-3-amine; 1-(5-aminopyridin-2-yl)pyrrolidine-3-carboxamide; (R)-6-(2-methylmorpholino)pyridin-3-amine; (R)-4-(2-methylmorpholino)aniline; (R)-1-(5-aminopyridin-2-yl)pyrrolidin-3-ol; 5-fluoro-N2-(6-methylpyridin-3-yl)pyrimidine-2,4-diamine; (S)-(1-(5-aminopyridin-2-yl)pyrrolidin-3-yl)methanol; (3-amino-4-fluorophenyl)(pyrrolidin-1-yl)methanone; 5-amino-2-methoxy-3-methylbenzenesulfonamide; 2-(4-amino-2-fluorophenoxy)-N,N-dimethylacetamide; (4-aminophenyl)(pyridin-4-yl)methanolate; (R)-1-(4-aminophenyl)pyrrolidin-3-ol; (R)-3-methoxy-4-((tetrahydrofuran-2-yl)methoxy)aniline; 3-ethoxy-4-(4-ethylpiperazin-1-yl)aniline; 4-(((3-(ethylsulfonyl)propyl)amino)methyl)aniline; N-(6-amino-2,3-dihydro-1H-inden-1-yl)methanesulfonamide; N-(4-aminobenzyl)cyclopropanesulfonamide; 7-amino-3,4-dihydroisoquinoline-2(1H)-sulfonamide; 4-(2-oxa-7-azaspiro[3.5]nonan-7-ylmethyl)aniline; 2-(4-(2-(4-aminophenoxyl)ethyl)piperazin-1-yl)ethan-1-ol; 2-(5-(4-aminophenyl)-2H-tetrazol-2-yl)acetic acid; (6-(4-aminophenyl)-6-azaspiro[2.5]octan-1-yl)methanol; 4-(2-(diisopropylamino)ethoxy)aniline; 1-(4-aminophenethyl)-4-methylpiperidin-4-ol; 4-(2-((dimethylamino)methyl)morpholino)aniline; (S)-6-(2-methylmorpholino)pyridin-3-amine; 4-(4-isopropoxypiperidin-1-yl)aniline; 2-(pyridin-4-yl)-1H-benzo[d]imidazol-6-amine; N2-(1-((R)-tetrahydrofuran-2-yl)ethyl)pyridine-2,5-diamine; 6-(3-(diethylamino)pyrrolidin-1-yl)pyridin-3-amine; 6-(2-oxa-8-azaspiro[4.5]decan-8-yl)pyridin-3-amine; ethyl 4-(2-aminophenyl)piperazine-1-carboxylate; 4-(1-oxa-8-azaspiro[4.5]decan-8-yl)aniline; 4-(2-oxa-8-azaspiro[4.5]decan-8-yl)aniline; (R)-6-(3-methoxypyrrolidin-1-yl)pyridin-3-amine; 3,5-di(1H-pyrazol-1-yl)aniline; 3,5-di(1H-1,2,3-triazol-1-yl)aniline; 3-(1H-pyrazol-1-yl)-5-(2H-1,2,3-triazol-2-yl)aniline; 1-(5-aminopicolinoyl)azetidine-3-carbonitrile; 3-(1H-1,2,3-triazol-1-yl)-5-(2H-1,2,3-triazol-2-yl)aniline; 3,5-di(2H-1,2,3-triazol-2-yl)aniline; 7-amino-5-methyl-2H-benzo[e][1,2,4]thiadiazine 1,1-dioxide; N-(6-amino-3-methoxypyridin-2-yl)pivalamide; 5-amino-2-fluoro-3-methylbenzenesulfonamide; 4-(pyridin-3-ylmethyl)-4H-benzo[b][1,4]oxazin-7-amine; 2-(4-amino-2-chlorophenoxy)-N,N-dimethylacetamide; (R)-1-(4-aminophenyl)piperidin-3-ol; (S)-1-(4-aminophenyl)-3-methylpyrrolidin-3-ol; (R)-(1-(4-aminophenyl)pyrrolidin-3-yl)methanol; methyl 8-amino-6-bromoimidazo[1,2-a]pyridine-5-carboxylate; (S)-1-(4-aminophenyl)pyrrolidine-2-carboxamide; 5-(9-oxa-3,7-diazabicyclo[3.3.1]nonan-3-yl)-2-methoxyaniline; 1-(6-amino-5-methoxyindolin-1-yl)-2-(methylamino)ethan-1-one; 2-(4-(4-amino-3-methoxyphenyl)piperazin-1-yl)ethan-1-ol; 4-(9-oxa-3,7-diazabicyclo[3.3.1]nonan-3-yl)-2-methoxyaniline; N-(4-aminophenethyl)cyclopropanesulfonamide; 2-amino-1-(4-(4-aminophenyl)piperazin-1-yl)ethan-1-one; 3-(4-(4-aminophenyl)piperazin-1-yl)propane-1,2-diol; 2-(1-(5-aminopyridin-2-yl)piperidin-3-yl)acetic acid; 2-(1-(4-aminophenyl)piperidin-4-yl)acetic acid; 2-(1-(5-aminopyridin-2-yl)piperidin-4-yl)acetic acid; 2-(4-(4-aminophenyl)cyclohexyl)acetic acid; 1-(4-aminobenzyl)piperidine-4-carboxylic acid; 2-(4-(4-aminophenyl)piperidin-1-yl)acetic acid; 2-(1-(4-aminophenyl)piperidin-3-yl)acetic acid; 2-(1-(5-aminopyridin-2-yl)piperidin-4-yl)acetamide; 1-(2-(4-aminophenoxyl)ethyl)-4-methylpiperidin-4-ol; 2-(4-(5-aminopyridin-2-yl)piperazin-1-yl)acetic acid; 2-(1-(4-aminophenyl)piperidin-4-yl)acetamide; dimethylmorpholino)-5-methylpyridin-3-amine; 6-(2,2-dimethylmorpholino)-5-fluoropyridin-3-amine; 6-(4-(diethylamino)piperidin-1-yl)pyridin-3-amine; 6-(3-morpholinopyrrolidin-1-yl)pyridin-3-amine; N2-(1-((S)-tetrahydrofuran-2-yl)ethyl)pyridine-2,5-diamine; difluoropiperidin-1-yl)-3-fluoroaniline; 1-(4-aminophenyl)-N,N-diethylpiperidin-4-amine; (R)-6-(3-(ethyl amino)pyrrolidin-1-yl)pyridin-3-amine; (R)-6-(2-(fluoromethyl)morpholino)pyridin-3-amine; (R)-6-(3-ethoxypyrrolidin-1-yl)pyridin-3-amine; 1-(4-(4-aminophenyl)piperidin-1-yl)propan-1-one; 3-morpholino-5-(1H-pyrazol-1-yl)aniline; 3-morpholino-5-(2H-1,2,3-triazol-2-yl)aniline, 3-(1H-pyrazol-1-yl)-5-(pyrimidin-2-yl)aniline; 3-(pyrimidin-2-yl)-5-(2H-1,2,3-triazol-2-yl)aniline; (5-aminopyridin-2-yl)(3,3-difluoroazetidin-1-yl)methanone; 3-(pyrimidin-2-yl)-5-(1H-1,2,4-triazol-1-yl)aniline; 3-amino-N-(3-fluorophenyl)benzamide; 5-amino-2-isopropylbenzenesulfonamide; 5-amino-3-chloro-2-methylbenzenesulfonamide; 5-amino-2-chloro-3-methylbenzenesulfonamide; 2-(4-amino-2,6-dimethylphenoxy)propanamide; 3-(piperidin-1-ylsulfonyl)aniline; 4-(4-aminobenzyl)thiomorpholine 1,1-dioxide; N-((3-aminophenyl)sulfonyl)propionamide; 2-(ethylsulfonyl)-1,2,3,4-tetrahydroisoquinolin-6-amine; N44-aminophenyl)sulfonyl)propionamide; (S)-1-(4-aminophenyl)-3-methylpiperidin-3-ol; (R)-(4-(4-aminophenyl)morpholin-2-yl)methanol; (R)-1-(4-amino-2-methoxyphenyl)pyrrolidin-3-ol; (S)-1-(5-aminopyridin-2-yl)-3-methylpiperidin-3-ol; (R)-(4-(5-aminopyridin-2-yl)morpholin-2-yl)methanol; (S)-3-methoxy-5-(2-methylpyrrolidin-1-yl)aniline; 1-(6-amino-5-methoxyindolin-1-yl)-2-(dimethylamino)ethan-1-one, 1-(4-(4-amino-3-methoxyphenyl)piperazin-1-yl)ethan-1-one; 1-(4-(4-amino-3-methoxyphenyl)piperidin-1-yl)ethan-1-one; 2-(1-(4-aminobenzyl)piperidin-4-yl)acetic acid; 3-(1-(4-aminophenyl)piperidin-4-yl)propanoic acid; 3-(4-(4-aminophenyl)piperazin-1-yl)propanoic acid; 2-(4-aminophenoxy)-1-(4-methylpiperazin-1-yl)ethan-1-one; 2-(4-(4-aminophenoxyl)piperidin-1-yl)acetic acid; 2-(4-(4-aminophenyl)-1,4-diazepan-1-yl)acetic acid; (S)-4-(2-(ethoxymethyl)morpholino)aniline; 4-(4-morpholinopiperidin-1-yl)aniline; 6-(4-morpholinopiperidin-1-yl)pyridin-3-amine; (S)-6-(2-(ethoxymethyl)morpholino)pyridin-3-amine; 3,5-di(pyrimidin-2-yl)aniline; 4-amino-N-methyl-N-(2,2,2-trifluoroethyl)benzamide; 3-morpholino-5-(pyrimidin-2-yl)aniline; 2'-amino-[1,1'-biphenyl]-4-sulfonamide; 3-amino-N-(3-chlorophenyl)benzamide; 3-amino-N-(4-chlorophenyl)benzamide; N-((5-amino-2-methylphenyl)sulfonyl)propionamide; 2-(4-amino-2-(1-(cyanomethyl)-1H-pyrazol-3-yl)phenoxy)acetonitrile; 5-amino-N,N-diethyl-2-methoxybenzenesulfonamide; (R)-1-(4-amino-2-methoxyphenyl)piperidin-3-ol; (S)-1-(4-amino-2-methoxyphenyl)-3-methylpyrrolidin-3-ol; (R)-1-(4-amino-2-ethoxyphenyl)pyrrolidin-3-ol; N-(4-aminobenzyl)pyridine-3-sulfonamide; 2-(4-aminophenoxy)-1-(4-ethylpiperazin-1-yl)ethan-1-one; 2-(4-(4-aminophenyl)piperazin-1-yl)-2-methylpropan-1-ol; 3-(4-(4-aminophenyl)piperazin-1-yl)-3-oxopropanenitrile; 7-(4-aminophenyl)-1,7-diazaspiro[3.5]nonan-2-one; 1-(2-(4-aminophenoxyl)ethyl)piperidine-4-carboxylic acid; 3-(4-(5-aminopyridin-2-yl)piperazin-1-yl)-3-oxopropanenitrile; (R)-6-(2-(ethoxymethyl)morpholino)pyridin-3-amine; N2-(6-(dimethylamino)pyridin-3-yl)-5-fluoropyrimidine-2,4-diamine; 4-morpholino-3-(trifluoromethoxy)aniline; 3-methyl-4-(2-oxa-8-azaspiro[4.5]decan-8-yl)aniline;

5-amino-N,N-dimethylisoindoline-2-sulfonamide; methyl 2-(((3-aminophenyl)sulfonyl)imino)acetate; 3-((4-aminophenoxy)methyl)-1H-1,2,4-triazol-5(4H)-one; (R)-(4-(4-amino-2-methoxyphenyl)morpholin-2-yl)methanol; 2-(2-(3-aminophenyl)-2H-1,2,3-triazol-4-yl)acetate; 4-amino-3-(pyrrolidin-1-ylsulfonyl)phenol; 4-fluoro-2-(pyrrolidin-1-ylsulfonyl)aniline; 1-(4-(4-amino-2-methylphenyl)piperazin-1-yl)ethan-1-one; N-(6-amino-2,3-dihydro-1H-inden-1-yl)cyclopropanesulfonamide; (S)-N-(6-amino-2,3-dihydro-1H-inden-1-yl)methanesulfonamide; 6-(4-aminophenyl)-6-azaspiro[2.5]octane-1-carboxylic acid; 2-(1-(4-aminophenyl)piperidin-4-yl)-N-(2-hydroxyethyl)acetamide; 6-(5-aminopyridin-2-yl)-6-azaspiro[2.5]octane-1-carboxylic acid; 2-(4-(2-(4-aminophenoxy)ethyl)piperazin-1-yl)acetic acid; 2-(1-(2-(4-aminophenoxyl)ethyl)piperidin-4-yl)acetic acid; 6-(4-aminophenyl)spiro[2.5]octane-1-carboxylic acid; 2-(4-(4-aminophenyl)-1,4-diazepan-1-yl)-2-methylpropan-1-ol; 2-(1-(4-aminophenyl)piperidin-4-yl)-2-methylpropanenitrile; 2-(4-(4-aminophenyl)piperazin-1-yl)-2-methylpropanenitrile; 4-((1S,4S)-2-oxa-5-azabicyclo[2.2.1]heptan-5-yl)aniline; (R)-3-(5-aminopyridin-2-yl)-4-isopropyloxazolidin-2-one; 6-((1S,4S)-2-oxa-5-azabicyclo[2.2.1]heptan-5-yl)pyridin-3-amine; 7-amino-N,N-dimethyl-3,4-dihydroisoquinoline-2(1H)-sulfonamide; 4-((1-methylpiperidin-4-yl)oxy)-3-(trifluoromethyl)aniline; 4-((4-methylpiperazin-1-yl)sulfonyl)aniline; 3-((4-methylpiperazin-1-yl)sulfonyl)aniline; (5-amino-2-methyl-7-oxabicyclo[4.2.0]octa-1(6),2,4-trien-8-yl)(morpholino)methanone; N-((5-amino-2-chlorophenyl)sulfonyl)acetamide; (R)-3-(4-aminophenyl)-1,4-dimethylpiperazin-2-one; 4-fluoro-2-(morpholinosulfonyl)aniline; 4-chloro-2-(pyrrolidin-1-ylsulfonyl)aniline; 4-(4-aminophenyl)-1-methylpiperidine 1-oxide; (3-aminobenzyl)(tert-butyl)carbamate; 2-(4-(4-amino-3-methoxyphenyl)piperazin-1-yl)-2-methylpropan-1-ol; 1-(4-(4-amino-3-methoxyphenyl)piperidin-1-yl)-2-hydroxyethan-1-one; 1-(4-(4-amino-3-methoxyphenyl)piperazin-1-yl)-2-hydroxyethan-1-one; (R)—N-(6-amino-2,3-dihydro-1H-inden-1-yl)methanesulfonamide; 6-(4-((2H-tetrazol-5-yl)methyl)piperidin-1-yl)pyridin-3-amine; 4-(4-((2H-tetrazol-5-yl)methyl)piperidin-1-yl)aniline; 4-((4-(2H-tetrazol-5-yl)piperidin-1-yl)methyl)aniline; 6-(4-aminobenzyl)-6-azaspiro[2.5]octane-1-carboxylic acid; 2-(1-(4-aminophenyl)piperidin-4-yl)cyclopropanecarboxylic acid; 2-(1-(3-(4-aminophenoxyl)propyl)piperidin-4-yl)acetic acid; (S)-3-(5-aminopyridin-2-yl)-4-isopropyloxazolidin-2-one; (6-amino-3-oxo-2H-pyrido[3,2-b][1,4]oxazin-4(3H)-yl)methyl dihydrogen phosphate; (5-amino-2-(pyrrolidin-1-yl)phenyl)(pyrrolidin-1-yl)methanone; (4-aminophenyl)(1,1-dioxidothiomorpholino)methanone; 5-amino-2-(4-methylpiperazin-1-yl)benzenesulfonamide; 3-amino-N-(4-methylpiperidin-1-yl)benzenesulfonamide; tert-butyl(6-aminochroman-4-yl)carbamate; (S)-1-(4-aminophenyl)-N-methylpiperidine-3-carboxamide; 1-(4-(3-amino-4-methoxyphenyl)piperazin-1-yl)-2-(methylamino)ethan-1-one; 1-(4-(4-amino-3-methoxyphenyl)piperazin-1-yl)-2-(methylamino)ethan-1-one; 1-(4-(4-amino-3-methoxyphenyl)piperidin-1-yl)-2-(methylamino)ethan-1-one; 4-((4-((2H-tetrazol-5-yl)methyl)piperidin-1-yl)methyl)aniline; ethyl 6-(4-aminophenyl)-6-azaspiro[2.5]octane-1-carboxylate; 4-((2S,6R)-2,6-dimethylmorpholino)aniline; 6-((2S,6R)-2,6-dimethylmorpholino)pyridin-3-amine; 5-amino-2-methyl-N-(1-methylpiperidin-4-yl)benzenesulfonamide; 3-((1R,5S)-8-oxa-3-azabicyclo[3.2.1]octan-3-yl)aniline; 1-(4-(3-amino-4-methoxyphenyl)piperazin-1-yl)-2-(dimethylamino)ethan-1-one; 6-(2-(4-aminophenoxyl)ethyl)-6-azaspiro[2.5]octane-1-carboxylic acid; 1-(4-(4-aminophenyl)piperazin-1-yl)-2-hydroxy-2-methylpropan-1-one; 1-(4-(5-aminopyridin-2-yl)piperazin-1-yl)-2-hydroxy-2-methylpropan-1-one; 2-(4-(4-aminophenyl)piperazin-1-yl)-2-methylpropanoic acid; 2-(4-(2-(4-aminophenoxy)ethyl)piperazin-1-yl)-2-methylpropanenitrile; 2-(1-(4-aminophenyl)piperidin-4-yl)-2-methylpropanoic acid; 6-(4-amino-2-fluorophenyl)-6-azaspiro[2.5]octane-1-carboxylic acid; ((2S,5S)-5-((4-aminophenoxy)methyl)-1,4-dioxan-2-yl)methanol; 1-(1-(4-aminophenyl)piperidin-4-yl)-2-hydroxy-2-methylpropan-1-one; 2-(4-(4-aminophenyl)piperazin-1-yl)-2-methylpropanamide; 6-(4-aminophenyl)-6-azaspiro[2.5]octane-1-carboxylate; 4-((1S,4S)-2-oxa-5-azabicyclo[2.2.1]heptan-5-yl)-3-methylaniline; (S)-1-(3-(4-amino-3-methoxyphenyl)azetidin-1-yl)-2-hydroxypropan-1-one; 1-(4-(4-aminobenzyl)piperazin-1-yl)-2-hydroxy-2-methylpropan-1-one; 3-fluoro-5-(4,4,5,5-tetramethyl-1,3,2-dioxaborolan-2-yl)aniline; 3-methyl-5-(4,4,5,5-tetramethyl-1,3,2-dioxaborolan-2-yl)aniline; (R)-1-(3-(4-amino-3-methoxyphenyl)azetidin-1-yl)-2-hydroxypropan-1-one; 2-(1-(4-aminophenyl)piperidin-4-yl)-N,N-bis(2-hydroxyethyl)acetamide; tert-butyl 4-(4-aminobenzyl)piperazine-1-carboxylate; 2-((1s,4s)-4-(4-aminophenyl)cyclohexyl)acetic acid; 3-bromo-5-(4,4,5,5-tetramethyl-1,3,2-dioxaborolan-2-yl)aniline; 6-amino-2,2,4-trimethyl-2H-benzo[b][1,4]thiazin-3(4H)-one 1,1-dioxide; (S)-1-(4-(4-amino-3-methoxyphenyl)piperazin-1-yl)-2-hydroxypropan-1-one; (S)-1-(4-(4-amino-3-methoxyphenyl)piperidin-1-yl)-2-hydroxypropan-1-one; 1-(4-(2-(4-aminophenoxyl)ethyl)piperazin-1-yl)-2-hydroxy-2-methylpropan-1-one; 2-((1r,4r)-4-(4-aminophenyl)cyclohexyl)acetic acid; 6-amino-4-(4-methoxybenzyl)-2-methyl-2H-benzo[b][1,4]oxazin-3(4H)-one; (R)-1-(4-(4-amino-3-methoxyphenyl)piperidin-1-yl)-2-hydroxypropan-1-one; (R)-1-(4-(4-amino-3-methoxyphenyl)piperazin-1-yl)-2-hydroxypropan-1-one; (2R,5S)-5-((4-aminophenoxy)methyl)-1,4-dioxane-2-carboxylic acid; (6-amino-2,2-dimethyl-3-oxo-2H-pyrido[3,2-b][1,4]oxazin-4(3H)-yl)methyl dihydrogen phosphate; 3-(difluoromethyl)-5-(4,4,5,5-tetramethyl-1,3,2-dioxaborolan-2-yl)aniline; 4-((5-(3-amino-5-methylphenyl)thiazol-2-yl)methyl)cyclohexanecarboxylic acid; (phosphonooxy)methyl 6-(4-aminophenyl)-6-azaspiro[2.5]octane-1-carboxylate; ethyl 4-((5-(3-amino-5-methylphenyl)thiazol-2-yl)methyl)cyclohexanecarboxylate; 4-((5-(3-amino-5-methylphenyl)thiazol-2-yl)(hydroxy)methyl)-3,3-dimethylcyclohexanol; (R)-6-amino-4-(4-methoxybenzyl)-2-methyl-2H-benzo[b][1,4]thiazin-3(4H)-one; ethyl 4-((5-(3-amino-5-methylphenyl)thiazol-2-yl)methylene)cyclohexanecarboxylate; 4-(amino(5-(3-amino-5-methylphenyl)thiazol-2-yl)methyl)cyclohexanecarboxylic acid; (5-(3-amino-5-methylphenyl)-4-(1,2-dioxaspiro[4.5]decan-8-yl)thiazol-2-yl)methanol; 4-((5-(3-amino-5-methylphenyl)thiazol-2-yl)(hydroxy)methyl)cyclohexanecarboxylic acid; 4-((5-(3-amino-5-methylphenyl)thiazol-2-yl)methyl)-4-hydroxycyclohexanecarboxylic acid; 5-(3-amino-5-methylphenyl)-4-(1,2-dioxaspiro[4.5]decan-8-yl)thiazole-2-carbaldehyde; methyl 4-((5-(3-amino-5-methylphenyl)thiazol-2-yl)(hydroxy)methyl)cyclohexanecarboxylate; 4-(1-(5-(3-amino-5-methylphenyl)thiazol-2-yl)-1-hydroxyethyl)-1-methylcyclohexanol; 4-(3-(5-(3-aminophenyl)thiazol-2-yl)-1-hydroxy-2-methylpropyl)cyclohexanecarboxylic acid; 4-((5-(3-amino-5-methylphenyl)thiazol-2-yl)(hydroxy)methyl)-4-hydroxycyclohexanecarboxylic acid; 4-(1-(5-(3-amino-5-methylphenyl)thiazol-2-yl)-1,2-dihydroxyethyl)cyclohexanecarboxylic acid; 4-(1-(5-(3-amino-5-methylphenyl)thiazol-2-yl)-2-fluoro-1-hydroxyethyl)cyclohexanecarboxylic acid; butyl 4-(1-(5-(3-aminophenyl)thiazol-2-yl)-1-hydroxyethyl)cyclohexanecarboxylate; 4-(1-

(5-(3-aminophenyl)thiazol-2-yl)-1-hydroxy-2-methylpropyl)cyclohexanecarboxylic acid; 3-(1-(5-(3-amino-5-methylphenyl)thiazol-2-yl)-1-hydroxyethyl) bicyclo[3.1.0]hexane-6-carboxylic acid; 4-(5-(3-amino-5-methylphenyl)thiazol-2-yl)-2,2-dimethylcyclohex-3-enecarboxylate; 4-(3-(5-(3-amino-5-methylphenyl)thiazol-2-yl)-3,4-dihydroxybutyl)cyclohexanecarboxylic acid; 4-(1-(5-(3-amino-5-methylphenyl)thiazol-2-yl)-1-hydroxyethyl) cyclohexanecarboxylate; 4-(1-(5-(3-amino-5-methylphenyl) thiazol-2-yl)-3,4-dihydroxybutyl)cyclohexanecarboxylic acid; 7-(5-(3-amino-5-methylphenyl)thiazol-2-yl)-3-ethylbicyclo[4.1.0]heptane-3-carboxylate; butyl 4-(1-(5-(3-amino-5-methylphenyl)thiazol-2-yl)-1-hydroxyethyl)cyclohexanecarboxylate; 4-(1-(5-(3-amino-5-methylphenyl) thiazol-2-yl)-2,2,2-trifluoro-1-hydroxyethyl) cyclohexanecarboxylic acid; 3-(((tert-butyldimethylsilyoxy)methyl)-5-(4,4,5,5-tetramethyl-1,3,2-dioxaborolan-2-yl)aniline.

Moreover especially preferred, $R^1$ is derived from the following amines: 2-(4-amino-1H-pyrazol-1-yl)-2-methylpropanenitrile; 4-amino-1-methylpyridin-2(1H)-one; 1-(tert-butyl)-1H-pyrazol-4-amine; 1-(4-amino-1H-pyrazol-1-yl)cyclohexanecarbonitrile; 1-isopropyl-1H-pyrazol-4-amine; 1-(3-methoxypropyl)-1H-pyrazol-4-amine; 4-amino-1-(2-methoxyethyl)pyridin-2(1H)-one; (4-amino-3-methoxyphenyl)(morpholino)methanone; 1-isobutyl-1H-pyrazol-4-amine; 2-(4-amino-1H-pyrazol-1-yl)ethan-1-ol; 2-(4-amino-1H-pyrazol-1-yl)acetonitrile; 1-cyclopropyl-1H-pyrazol-4-amine; 3-amino-1-methylpyridin-2(1H)-one; 1-(tert-butyl)-1H-pyrazol-3-amine; 4-bromo-1-methyl-1H-pyrazol-3-amine; 1-(1-methoxy-2-methylpropan-2-yl)-1H-pyrazol-4-amine; 1-(2-methoxyethyl)-3-methyl-1H-pyrazol-4-amine, 1-(2-methoxyethyl)-5-methyl-1H-pyrazol-4-amine; 1-isopropyl-3-methyl-1H-pyrazol-4-amine; 1-isopropyl-5-methyl-1H-pyrazol-4-amine; 1-(1-(tert-butyl) piperidin-4-yl)-1H-pyrazol-4-amine; 3-methyl-1-(tetrahydro-2H-pyran-4-yl)-1H-pyrazol-4-amine; 5-methyl-1-(tetrahydro-2H-pyran-4-yl)-1H-pyrazol-4-amine; 4-amino-1-cyclopropylpyridin-2(1H)-one; 5-chloro-1-isopropyl-1H-pyrazol-4-amine; 1-isopropyl-3-methoxy-1H-pyrazol-4-amine; 1-(1-(tert-butyl)piperidin-4-yl)-3-methoxy-1H-pyrazol-4-amine; 1-isopropyl-5-methoxy-1H-pyrazol-4-amine; 1-(1-(tert-butyl)piperidin-4-yl)-5-methoxy-1H-pyrazol-4-amine; 5-chloro-1-(3-methoxypropyl)-1H-pyrazol-4-amine; 1-isopropyl-3,5-dimethyl-1H-pyrazol-4-amine; imidazo[1,2-a]pyridin-3-amine; 3-cyclopropyl-1-methyl-1H-pyrazol-5-amine; 3-(4-amino-3-methoxyphenyl) oxazolidin-2-one; 3-methoxy-1-(3-methoxypropyl)-1H-pyrazol-4-amine; 5-chloro-1-(2-methoxyethyl)-1H-pyrazol-4-amine; 1-(tert-butyl)-5-methyl-1H-pyrazol-4-amine; 6-amino-1,3-dimethylpyrimidine-2,-((1H,3H)-dione; 1-(2-fluoroethyl)-1H-pyrazol-4-amine; 5-chloro-1-(piperidin-4-yl)-1H-pyrazol-4-amine; 5-chloro-1-(tetrahydro-2H-pyran-4-yl)-1H-pyrazol-4-amine; 1-(4-amino-1H-pyrazol-1-yl)-2-methylpropan-2-ol; 2-fluoro-4-morpholinoaniline; 2,3-dimethylaniline; 2-methyl-4-morpholinoaniline; 2-methyl-4-(4-methylpiperazin-1-yl)aniline; 1-(2,2,2-trifluoroethyl)-1H-pyrazol-4-amine; 4-amino-1-isopropyl-1H-pyrazole-5-carbonitrile; 1-(2-methoxyethyl)-3-(trifluoromethyl)-1H-pyrazol-4-amine; 1-(2-methoxyethyl)-5-(trifluoromethyl)-1H-pyrazol-4-amine; 2-(4-amino-5-chloro-1H-pyrazol-1-yl)ethan-1-ol; 5-bromo-1-(2-methoxyethyl)-1H-pyrazol-4-amine; 5-fluoro-1-(2-methoxyethyl)-1H-pyrazol-4-amine; 2-methyl-3-morpholino aniline; 5-ethynyl-1-(2-methoxyethyl)-1H-pyrazol-4-amine; 1-(2-methoxyethyl)-N5,N5-dimethyl-1H-pyrazole-4,5-diamine; 2-(4-(4-aminophenyl) piperazin-1-yl)ethan-1-ol; 1-(4-aminophenyl)piperidin-4-ol; 1-(pyrrolidin-3-yl)-1H-pyrazol-4-amine; 1-(1,3-dimethoxypropan-2-yl)-1H-pyrazol-4-amine; 2-(4-amino-1H-pyrazol-1-yl)-N,N-dimethylacetamide; tert-butyl 3-(4-amino-1H-pyrazol-1-yl)pyrrolidine-1-carboxylate; 1-(pyridin-2-yl)-1H-pyrazol-4-amine; 1-(3-methylbutan-2-yl)-1H-pyrazol-4-amine; 6-amino-4-methyl-2H-benzo[b][1,4]oxazin-3(4H)-one; 6-amino-4-ethyl-2H-benzo[b][1,4]oxazin-3(4H)-one; 1-(1-phenylethyl)-1H-pyrazol-4-amine; 3-ethylaniline; (7-amino-3,4-dihydroquinolin-1(2H)-yl)(cyclopropyl) methanone; 1-(tetrahydro-2H-pyran-3-yl)-1H-pyrazol-4-amine; 2-(4-amino-1H-pyrazol-1-yl)propanoic acid; 5-amino-1H-pyrazole-3-carboxylic acid; 2-aminophenol; 4,5-dimethoxybenzene-1,2-diamine; 4-(phenylthio)aniline; 6-amino-2H-benzo[b][1,4]oxazin-3(4H)-one; 6-amino-2H-benzo[b][1,4]thiazin-3(4H)-one; N-(5-amino-2-methoxyphenyl)acetamide; (5-amino-2-(4-methylpiperazin-1-yl) phenyl)methanol; 3,4-dihydro-2H-benzo[b][1,4]oxazin-6-amine; N-(2-(4-acetylpiperazin-1-yl)-5-aminophenyl) acetamide; 3-chloro-4-(4-methylpiperazin-1-yl)aniline; 4-amino-2,6-dichlorophenol; 3-ethoxy-4-methoxyaniline; 2-(4-amino-1H-pyrazol-1-yl)-2-methylpropanamide; 2-methyl-2H-tetrazol-5-amine; 1-methyl-1H-imidazol-4-amine; 1-(oxetan-3-yl)-1H-pyrazol-4-amine; 4-aminopyridin-2(1H)-one; 2-chloro-5-(methylsulfonyl)thiophen-3-amine; 5-methoxy-1-(3-methoxypropyl)-1H-pyrazol-4-amine; 1-(piperidin-4-yl)-1H-pyrazol-4-amine; 4-amino-1-isopropyl-1H-pyrazole-3-carbonitrile; 4-amino-1-(2-methoxyethyl)-1H-pyrazole-3-carbonitrile; 4-amino-1-(2-methoxyethyl)-1H-pyrazole-5-carbonitrile; 4-amino-1-isopropyl-1H-pyrazole-3-carboxamide; 4-amino-1-isopropyl-1H-pyrazole-5-carboxamide; 1-(2-methylallyl)-1H-pyrazol-4-amine; 1-(2-methylprop-1-en-1-yl)-1H-pyrazol-4-amine; 1,2-dimethyl-1H-imidazol-5-amine; 1-(2-fluoroethyl)-3-methyl-1H-pyrazol-4-amine; 1-(2-fluoroethyl)-5-methyl-1H-pyrazol-4-amine; 2-isopropyl-1-methyl-1H-imidazol-5-amine; 1-(2-methoxy-2-methylpropyl)-1H-pyrazol-4-amine; 1-(4-amino-3-methyl-1H-pyrazol-1-yl)-2-methylpropan-2-ol; 1-(4-amino-5-methyl-1H-pyrazol-1-yl)-2-methylpropan-2-ol; 1-(pentan-3-yl)-1H-pyrazol-4-amine; N-(3-aminophenyl)acetamide; 3-(2-methylpyrrolidin-1-yl)aniline; benzene-1,2-diamine; 4-aminophenol; 1-(2-methoxycyclohexyl)-1H-pyrazol-4-amine.

Further preferred, $R^1$ can be derived from the following compounds (e.g. amines): 1-methyl-1H-pyrazol-5-amine; 1-ethyl-1H-pyrazol-3-amine; 4-methyl-1H-pyrazol-5-amine; 1-isopropyl-1H-pyrazol-5-amine; 1-isopropyl-1H-pyrazol-3-amine; 4-bromo-2-methoxyaniline; 6-chloro-4-methoxypyridin-3-amine; 3-cyclopropyl-1-methyl-1H-pyrazol-5-amine; 4-amino-3-methoxybenzonitrile; 5-amino-1-methyl-1H-pyrazole-3-carboxylic acid; 3-isopropyl-1-methyl-1H-pyrazol-5-amine; 4-amino-3-chlorobenzonitrile; 4-amino-3-methoxybenzoic acid; 4-amino-3-methoxy-2-methylbenzonitrile; 4-amino-2-fluoro-5-methoxybenzonitrile; 4-amino-5-methoxy-2-methylbenzonitrile; 4-amino-5-chloro-2-methylbenzonitrile; 4-bromo-2-chloro-5-methoxyaniline; 4-amino-3-methoxybenzamide; methyl 5-amino-1-methyl-1H-pyrazole-3-carboxylate; 4-methoxy-6-(thiazol-4-yl)pyridin-3-amine; 4-methoxy-6-(thiazol-5-yl) pyridin-3-amine; 4-methoxy-6-(oxazol-2-yl)pyridin-3-amine; 4-(isoxazol-4-yl)-2-methoxyaniline; 4-amino-3-ethoxybenzoic acid; 2-methoxy-4-(trifluoromethyl)aniline; 2-methoxy-4-morpholinoaniline; 2-methoxy-4-(1-methyl-1H-imidazol-5-yl)aniline; 2-chloro-4-(1-methyl-1H-tetrazol-5-yl)aniline; 2-methoxy-4-(1-methyl-1H-tetrazol-5-yl) aniline; 2-methoxy-4-(4-methyl-4H-1,2,4-triazol-3-yl) aniline; 2-methoxy-4-(1-methyl-1H-imidazol-2-yl)aniline;

2-methoxy-4-(1-methyl-1H-pyrazol-5-yl)aniline; 2-bromo-4-morpholinoaniline; (R)-1-(1-methoxypropan-2-yl)-5-methyl-1H-pyrazol-4-amine; 3-(5-amino-1-methyl-1H-pyrazol-3-yl)morpholine-4-carbaldehyde; 5-fluoro-2-methoxy-4-(oxetan-3-yl)aniline; 4-amino-3-methoxy-N-methylbenzamide; 4-amino-2-fluoro-5-methoxybenzoic acid; (R)-2-(4-amino-5-methyl-1H-pyrazol-1-yl)propanenitrile; (S)-1-(2-methoxypropyl)-5-methyl-1H-pyrazol-4-amine; 2-methoxy-4-(methylsulfonyl)aniline; 4-amino-2-chloro-5-methoxybenzoic acid; 2-ethoxy-4-(morpholinomethyl)aniline; 2-chloro-4-(methylsulfonyl)aniline; 2-methoxy-4-(1-methyl-1H-pyrazol-4-yl)aniline; 4-amino-5-chloro-2-methoxybenzoic acid; 2-chloro-4-(2H-tetrazol-5-yl)aniline; 2-methoxy-4-(2-methyl-2H-tetrazol-5-yl)aniline; 4-(2-fluoroethoxy)-6-morpholinopyridin-3-amine; 4-amino-N-ethyl-3-methoxybenzamide; 4-amino-3-methoxy-N,N-dimethylbenzamide; 4-amino-5-chloro-2-methoxybenzamide; 4-amino-3-(difluoromethoxy)benzoic acid; 4-amino-2-fluoro-5-methoxy-N-methylbenzamide; 6-amino-4-chloro-3-methylbenzo[d]oxazol-2(3H)-one; 6-amino-5-chloro-3-methylbenzo[d]oxazol-2(3H)-one; 5-amino-6-chloro-2-methylisoindolin-1-one; 5-amino-6-methoxy-2-methylisoindolin-1-one; 6-amino-6-methoxy-2-methylisoindolin-1-one; 1-(4-amino-3-isopropyl-1H-pyrazol-1-yl)-2-methylpropan-2-ol; 4-methyl-1-(1-methylpiperidin-4-yl)-1H-pyrazol-3-amine; 5-(4-amino-5-methyl-1H-pyrazol-1-yl)-1-methylpiperidin-2-one; 2-(2-fluoroethoxy)-4-(morpholinomethyl)aniline; 5-fluoro-2-methoxy-4-(1-methyl-1H-tetrazol-5-yl)aniline; 5-fluoro-2-methoxy-4-(5-methyl-1H-tetrazol-1-yl)aniline; 4-(3,5-dimethylisoxazol-4-yl)-2-methoxyaniline; 4-(1,5-dimethyl-1H-pyrazol-4-yl)-2-methoxyaniline; 4-(1,3-dimethyl-1H-pyrazol-4-yl)-2-methoxyaniline; 4-amino-N-isopropyl-3-methoxybenzamide; 4-amino-5-chloro-2-methoxy-N-methylbenzamide; (4-amino-3-methoxyphenyl)(azetidin-1-yl)methanone; 4-amino-N,N,3-trimethylbenzamide; 4-amino-N-cyclopropyl-3-methoxybenzamide; 6-amino-7-methoxy-2-methyl-1,2-dihydroisoquinolin-3(4H)-one; 5-amino-2-ethyl-4-methoxyisoindolin-1-one; 6-amino-7-methoxy-2-methylphthalazin-1(2H)-one; 8-amino-N-methyl-2,3-dihydrobenzo[b][1,4]dioxine-5-carboxamide; (R)-1-(1-methoxypropan-2-yl)-3-methyl-1H-pyrazol-4-amine; (S)-1-(2-methoxypropyl)-3-methyl-1H-pyrazol-4-amine; 5-fluoro-2-methoxy-4-(morpholinomethyl)aniline; 2-(2-fluoroethoxy)-4-(methylsulfonyl)aniline; 1-(4-amino-2-fluoro-5-methoxyphenyl)pyrrolidin-2-one; 2-chloro-5-methoxy-4-(1-methyl-1H-imidazol-2-yl)aniline; 2-chloro-4-(3-methyl-1,2,4-oxadiazol-5-yl)aniline; 2-chloro-4-(2-methyl-2H-tetrazol-5-yl)aniline; 2-chloro-5-methoxy-4-(1-methyl-1H-pyrazol-5-yl)aniline; 2-chloro-5-methoxy-4-(1-methyl-1H-imidazol-5-yl)aniline; 4-amino-N-(3-aminopropyl)-3-methoxybenzamide; 4-amino-3-methoxy-N-(2-methoxyethyl)benzamide; 5-ethoxy-2-fluoro-4-morpholinoaniline; (4-amino-3-methoxyphenyl)(pyrrolidin-1-yl)methanone; 4-amino-3-methoxy-N-(oxetan-3-yl)benzamide; 4-amino-N-(cyclopropylmethyl)-3-methoxybenzamide; 4-amino-N-(2,2-difluoroethyl)-3-methoxybenzamide; 6-amino-5-chlorobenzo[d]oxazol-2(3H)-one; 5-amino-4-methoxy-2-methylisoindolin-1-one; 8-amino-7-chloro-4-methyl-3,4-dihydrobenzo[f][1,4]oxazepin-5(2H)-one; 8-amino-N-ethyl-2,3-dihydrobenzo[b][1,4]dioxine-5-carboxamide; 5-(4-amino-3-methyl-1H-pyrazol-1-yl)-1-methylpiperidin-2-one; (5-amino-1-methyl-1H-pyrazol-3-yl)(morpholino)methanone; 2-methoxy-5-methyl-4-(methylsulfonyl)aniline; 4-(4-amino-2-fluoro-5-methoxyphenyl)morpholin-3-one; 1-(4-amino-2-fluoro-5-methoxyphenyl)piperidin-2-one; 5-fluoro-2-methoxy-4-(methylsulfonyl)aniline; 5-fluoro-2-methoxy-4-(5-methyl-1,3,4-oxadiazol-2-yl)aniline; 2-methoxy-4-(5-(methoxymethyl)-1H-tetrazol-1-yl)-5-methylaniline; 5-fluoro-2-methoxy-4-(3-methyl-1,2,4-oxadiazol-5-yl)aniline; (4-amino-3-methoxyphenyl)(morpholino)methanone; 4-amino-3-cyclobutoxybenzoic acid; 4-amino-N-ethyl-3-methoxy-N-methylbenzamide; (4-amino-3-methoxyphenyl)(piperidin-1-yl)methanone; (4-amino-3-methoxyphenyl)(2-methylpyrrolidin-1-yl)methanone; 4-amino-2-fluoro-5-methoxy-N,N-dimethylbenzamide; methyl 4-amino-3-(difluoromethoxy)benzoate; 4-amino-5-chloro-N-(2-hydroxyethyl)-2-methoxybenzamide; (4-amino-3-methoxyphenyl)(piperazin-1-yl)methanone; 6-amino-N,N-dimethylbenzofuran-2-carboxamide; 5-amino-6-chloro-1,3-dimethyl-1H-benzo[d]imidazol-2(3H)-one; (S)-5-methyl-1-(1-methylpiperidin-3-yl)-1H-pyrazol-4-amine; 5-fluoro-2-(2-fluoroethoxy)-4-(morpholinomethyl)aniline; 4-(ethylsulfonyl)-2-methoxy-5-methylaniline; 5-chloro-2-methoxy-4-(methylsulfonyl)aniline; 2-isopropoxy-4-(methylsulfonyl)aniline; 2-chloro-5-methoxy-4-(1-methyl-1H-pyrazol-4-yl)aniline; 2-chloro-5-methoxy-4-(5-methyl-1,3,4-oxadiazol-2-yl)aniline; (4-amino-3-hydroxyphenyl)(morpholino)methanone; 4-amino-5-chloro-2-methoxy-N,N-dimethylbenzamide; 4-amino-5-chloro-2-methoxy-N-(2-methoxyethyl)benzamide; 4-amino-3-methoxy-N-(tetrahydro-2H-pyran-3-yl)benzamide; (4-amino-3-ethoxyphenyl)(morpholino)methanone; 4-amino-N-(tert-butyl)-3-methoxybenzamide; 4-amino-N-isopropyl-3-methoxy-N-methylbenzamide; (4-amino-3-methoxyphenyl)(3-fluoroazetidin-1-yl)methanone; 4-amino-N,N-diethyl-3-methoxybenzamide; (4-amino-3-methylphenyl)(morpholino)methanone; 2-(4-amino-3-methoxyphenyl)-1-morpholinoethan-1-one; 4-amino-N-(3-aminopropyl)-5-chloro-2-methoxybenzamide; (4-amino-3-methoxyphenyl)(2-hydroxypiperidin-1-yl)methanone; (4-amino-3-methoxyphenyl)(2-methylpiperidin-1-yl)methanone; (4-amino-3-fluorophenyl)(morpholino)methanone; (4-amino-3-(2-fluoroethoxy)phenyl)(morpholino)methanone; (4-amino-2-fluoro-5-hydroxyphenyl)(morpholino)methanone; 4-amino-5-(fluoromethoxy)-2-methoxy-N,N-dimethylbenzamide; 4-amino-5-chloro-N-cyclopropyl-2-methoxybenzamide; (4-amino-3-methoxyphenyl)(3-hydroxypyrrolidin-1-yl)methanone; (4-amino-3-chlorophenyl)(morpholino)methanone; (4-amino-3-bromophenyl)(morpholino)methanone; 4-amino-3-methoxy-N-(2-methoxyethyl)-N-methylbenzamide; 6-amino-5-methoxy-N,N-dimethylbenzofuran-3-carboxamide; 5-amino-6-methoxy-2-(oxetan-3-yl)isoindolin-1-one; 6-amino-5-methoxy-N,N-dimethylbenzofuran-2-carboxamide; (4-amino-2,5-dimethylphenyl)(morpholino)methanone; (4-amino-2,3-difluorophenyl)(morpholino)methanone; (4-amino-2,5-difluorophenyl)(morpholino)methanone; (4-amino-5-fluoro-2-methylphenyl)(morpholino)methanone; 8-amino-N-isopropyl-2,3-dihydrobenzo[b][1,4]dioxine-5-carboxamide; (4-amino-2-fluoro-5-methylphenyl)(morpholino)methanone; (S)-3-methyl-1-(1-methylpiperidin-3-yl)-1H-pyrazol-4-amine; (S)-2-(4-amino-5-methyl-1H-pyrazol-1-yl)-N,N-dimethylpropanamide; 5-fluoro-2-methoxy-4-(5-(methoxymethyl)-3-methyl-1H-pyrazol-1-yl)aniline; (4-amino-5-fluoro-2-(fluoromethoxy)phenyl)(pyrrolidin-1-yl)methanone; (4-amino-5-(fluoromethoxy)-2-methylphenyl)(pyrrolidin-1-yl)methanone; (4-amino-2-fluoro-5-methoxyphenyl)(morpholino)methanone; (4-amino-2-fluoro-5-(fluoromethoxy)phenyl)(pyrrolidin-1-yl)methanone; (4-amino-3-methoxyphenyl)(4-methylpiperidin-1-yl)methanone; (4-amino-2-fluoro-3- methoxyphenyl)(morpholino)methanone; 4-amino-5-chloro-2-methoxy-N-(oxetan-3-yl)benzamide; (4-amino-3-methoxyphenyl)(4-fluoropiperidin-1-yl)methanone; 4-amino-5-chloro-N-(2-hydroxyethyl)-2-methoxy-N-methylbenzamide; (4-amino-5-fluoro-2-methoxyphenyl)(morpholino)methanone; (4-amino-3-methoxyphenyl)(4-hydroxypiperidin-1-yl)methanone; 4-amino-2-fluoro-5-methoxy-N-(2-methoxyethyl)-N-methylbenzamide; 4-amino-3-(2,2,2-trifluoroethoxyl)benzoic acid; 4-amino-5-chloro-N-(2-hydroxypropyl)-2-methoxybenzamide; (4-amino-5-chloro-2-methoxyphenyl)(pyrrolidin-1-yl)methanone; (4-amino-3-methoxyphenyl)(2-oxa-5-azabicyclo[2.2.1]heptan-5-yl)methanone; (4-amino-3-methoxyphenyl)(4-methylpiperazin-1-yl)methanone; (4-amino-3-methoxyphenyl)(3-methylpiperidin-1-yl)methanone; (4-amino-3-methoxyphenyl)(2-methylmorpholino)methanone; 5-amino-2-cyclopropyl-4-methoxyisoindolin-1-one; (4-amino-5-chloro-2-methylphenyl)(morpholino)methanone; (4-amino-3-chloro-2-fluorophenyl)(morpholino)methanone; (4-amino-5-chloro-2-hydroxyphenyl)(morpholino)methanone; (4-amino-5-methoxy-2-methylphenyl)(morpholino)methanone; (4-amino-3-methoxy-2-methylphenyl)(morpholino)methanone; (4-amino-5-chloro-2-fluorophenyl)(morpholino)methanone; (4-amino-2-chloro-5-methylphenyl)(morpholino)methanone; (4-amino-2-methoxy-5-methylphenyl)(morpholino)methanone; (4-amino-2-chloro-5-fluorophenyl)(morpholino)methanone; (8-amino-2,3-dihydrobenzo[b][1,4]dioxin-5-yl)(pyrrolidin-1-yl)methanone; (S)-5-methyl-1-(1-(oxetan-3-yl)pyrrolidin-3-yl)-1H-pyrazol-4-amine; (S)-3-methyl-1-(1-(oxetan-3-yl)pyrrolidin-3-yl)-1H-pyrazol-4-amine; 2-methoxy-4-(morpholinosulfonyl)aniline; N'-acetyl-4-amino-5-chloro-2-methoxybenzohydrazide; (4-amino-5-(fluoromethoxy)-2-methylphenyl)(morpholino)methanone; (4-amino-2-fluoro-5-(fluoromethoxy)phenyl)(morpholino)methanone; (4-amino-5-chloro-2-(fluoromethoxy)phenyl)(pyrrolidin-1-yl)methanone; (4-amino-5-(fluoromethoxy)-2-methoxyphenyl)(pyrrolidin-1-yl)methanone; (4-amino-3-methoxyphenyl)(3-(hydroxymethyl)morpholino)methanone; (4-amino-5-chloro-2-methoxyphenyl)(morpholino)methanone, (4-amino-2-chloro-5-methoxyphenyl)(morpholino)methanone; (4-amino-3-isopropoxyphenyl)(morpholino)methanone; (4-amino-3-methylphenyl)(4-hydroxypiperidin-1-yl)methanone; (4-amino-5-ethoxy-2-fluorophenyl)(morpholino)methanone; (4-amino-2-ethoxy-5-fluorophenyl)(morpholino)methanone; (4-amino-3-methoxyphenyl)(3-oxa-8-azabicyclo[3.2.1]octan-8-yl)methanone; (4-amino-3-methoxyphenyl)(3,3-dimethylmorpholino)methanone; 4-amino-5-chloro-2-methoxy-N-(2-methoxyethyl)-N-methylbenzamide; (4-amino-3-methoxyphenyl)(3,3-difluoroazetidin-1-yl)methanone; (4-amino-5-chloro-2-methoxyphenyl)(piperazin-1-yl)methanone; 4-amino-3-methoxy-N-(1-methylpiperidin-4-yl)benzamide; 4-amino-N-ethyl-2-fluoro-5-methoxy-N-(2-methoxyethyl)benzamide; (4-amino-3-(difluoromethoxy)phenyl)(morpholino)methanone; 5-amino-4-methoxy-2-(oxetan-3-yl)isoindolin-1-one; 5-amino-2-(2-hydroxypropan-2-yl)-4-methoxyisoindolin-1-one; (4-amino-5-ethoxy-2-methylphenyl)(morpholino)methanone; (4-amino-2,5-dimethoxyphenyl)(morpholino)methanone; (8-amino-2,3-dihydrobenzo[b][1,4]dioxin-5-yl)(morpholino)methanone; (7-amino-5-fluoro-2,3-dihydrobenzofuran-4-yl)(morpholino)methanone; (4-amino-5-bromo-2-methoxyphenyl)(morpholino)methanone; (S)-5-methyl-1-(1-(oxetan-3-yl)piperidin-3-yl)-1H-pyrazol-4-amine; (S)-3-methyl-1-(1-(oxetan-3-yl)piperidin-3-yl)-1H-pyrazol-4-amine; (S)-2-(4-amino-3-methyl-1H-pyrazol-1-yl)-N,N-dimethylpropanamide; 5-fluoro-2-methoxy-4-(1-(oxetan-3-yl)-1H-pyrazol-4-yl)aniline; 2-chloro-5-methoxy-4-(1,3,5-trimethyl-1H-pyrazol-4-yl)aniline; (4-amino-5-(2-fluoroethoxy)-2-methoxyphenyl)(pyrrolidin-1-yl)methanone; (4-amino-5-chloro-2-(fluoromethoxy)phenyl)(morpholino)methanone; (4-amino-5-(2-fluoroethoxy)-2-methylphenyl)(morpholino)methanone; (4-amino-2-fluoro-5-(2-fluoroethoxyl)phenyl)(morpholino)methanone; (4-amino-5-(fluoromethoxy)-2-methoxyphenyl)(piperidin-1-yl)methanone; (4-amino-3-methoxyphenyl)(2-oxa-6-azaspiro[3.3]heptan-6-yl)methanone; 2-(4-amino-2,5-dimethoxyphenyl)-1-morpholino ethan-1-one; (4-amino-5-chloro-2-ethoxyphenyl)(morpholino)methanone; (4-amino-3-cyclopropylphenyl)(morpholino)methanone; (4-amino-3-methoxyphenyl)(3,3-difluoropyrrolidin-1-yl)methanone; (R)-(4-amino-3-methoxyphenyl)(3-methylmorpholino)methanone; 4-amino-N-(tert-butyl)-5-chloro-2-methoxybenzamide; (4-amino-5-chloro-2-methoxyphenyl)(3-hydroxyazetidin-1-yl)methanone; 4-amino-N-(3,3-difluorocyclobutyl)-3-methoxybenzamide; (4-amino-5-chloro-2-methoxyphenyl)(1,4-oxazepan-4-yl)methanone; 5-amino-2-(2-hydroxy-2-methylpropyl)-6-methoxyisoindolin-1-one; (6-amino-5-methoxybenzofuran-3-yl)(morpholino)methanone; 4-amino-5-fluoro-N-(2-hydroxy-2-methylpropyl)-2-methoxybenzamide; 4-amino-2-fluoro-N-(2-hydroxy-2-methylpropyl)-3-methoxybenzamide; 4-amino-2-fluoro-N-(1-(hydroxymethyl)cyclopropyl)-5-methoxybenzamide; 4-amino-2-fluoro-N-(1-hydroxy-2-methylpropan-2-yl)-5-methoxybenzamide; 4-amino-N-(2-hydroxy-2-methylpropyl)-5-methoxy-2-methylbenzamide; 4-amino-2-fluoro-N-(2-hydroxy-2-methylpropyl)-5-methoxybenzamide; 4-amino-2-fluoro-N-((1-hydroxycyclopropyl)methyl)-5-methoxybenzamide; (S)-2-(4-amino-5-methyl-1H-pyrazol-1-yl)-1-(pyrrolidin-1-yl)propan-1-one; (4-amino-3-methoxyphenyl)(4,4-difluoropiperidin-1-yl)methanone; (4-amino-3-methoxyphenyl)(4-ethylpiperazin-1-yl)methanone; (4-amino-3-methoxyphenyl)(3,3-difluoropiperidin-1-yl)methanone; (4-amino-3-methoxyphenyl)(8-oxa-3-azabicyclo[3.2.1]octan-3-yl)methanone; (4-amino-3-methoxyphenyl)(4-(hydroxymethyl)piperidin-1-yl)methanone; (4-amino-3-methoxyphenyl)(2,6-dimethylmorpholino)methanone; 4-amino-5-chloro-N-(2-hydroxy-2-methylpropyl)-2-methoxybenzamide; (4-amino-3-(cyclobutylmethoxy)phenyl)(morpholino)methanone; (4-amino-3-methoxyphenyl)(3,5-dimethylpiperidin-1-yl)methanone; (4-amino-3-methoxyphenyl)(4-methoxypiperidin-1-yl)methanone; (4-amino-2-fluoro-5-methoxyphenyl)(3-methoxypyrrolidin-1-yl)methanone; (S)-(4-amino-3-methoxyphenyl)(3-methylmorpholino)methanone; (4-amino-3-methoxyphenyl)(2-(hydroxymethyl)morpholino)methanone; (4-amino-5-chloro-2-methoxyphenyl)(3-hydroxypyrrolidin-1-yl)methanone; (4-amino-3-methoxyphenyl)(4,4-dimethylpiperidin-1-yl)methanone; (4-amino-3-cyclopropoxyphenyl)(morpholino)methanone; (4-amino-3-methoxyphenyl)(3-methoxypiperidin-1-yl)methanone; (4-amino-3-methoxyphenyl)(hexahydro-1H-pyrido[1,2-a]pyrazin-2(6H)-yl)methanone; (S)-(4-amino-3-methoxyphenyl)(3-fluoropyrrolidin-1-yl)methanone; 4-amino-5-chloro-2-methoxy-N-(1-methylcyclobutyl)benzamide; (4-amino-2,6-difluoro-3-methoxyphenyl)(morpholino)methanone; (4-amino-3-methoxyphenyl)(2,2-dimethylmorpholino)methanone; (S)-2-(4-amino-3-methyl-1H-pyrazol-1-yl)-1-(pyrrolidin-1-yl)propan-1-one; (R)-(4-amino-3-methoxyphenyl)(3-fluoropyrrolidin-1-yl)methanone; (4-amino-3-cyclobutoxyphenyl)(morpholino)methanone; (4-amino-3-methoxyphenyl)(4-

(dimethylamino)piperidin-1-yl)methanone; (4-amino-5-chloro-2-methoxyphenyl)(3-methoxypyrrolidin-1-yl)methanone; 1-(4-amino-3-methoxybenzoyl)piperidine-4-carbonitrile; (4-amino-3-(oxetan-3-yloxy)phenyl)(morpholino)methanone; (4-amino-2-fluoro-3-isopropoxyphenyl)(morpholino)methanone; (4-amino-3-methoxyphenyl)(4-(2-hydroxyethyl)piperazin-1-yl)methanone; 1-(4-amino-2-fluoro-5-methoxybenzoyl)pyrrolidine-3-carbonitrile; (4-amino-5-chloro-2-methoxyphenyl)(4-hydroxypiperidin-1-yl)methanone; 4-amino-5-chloro-N-(1-cyanocyclopropyl)-2-methoxybenzamide; (R)-(4-amino-3-methoxyphenyl)(3-hydroxypyrrolidin-1-yl)methanone; (4-amino-3-methoxyphenyl)(4-isopropylpiperazin-1-yl)methanone; (4-amino-3-(cyclopropylmethoxy)phenyl)(morpholino)methanone; 4-amino-N-(4,4-difluorocyclohexyl)-3-methoxybenzamide; (4-amino-5-isopropoxy-2-methylphenyl)(morpholino)methanone; (4-amino-3-fluoro-2,6-dimethoxyphenyl)(morpholino)methanone; (S)-(4-amino-3-fluorophenyl)(3-fluoropyrrolidin-1-yl)methanone; 1-((1S,5S)-8-oxabicyclo[3.2.1]octan-3-yl)-3-methyl-1H-pyrazol-4-amine; (4-amino-3-methoxyphenyl)(4-cyclobutylpiperazin-1-yl)methanone; 1-(4-amino-5-chloro-2-methoxybenzoyl)pyrrolidine-3-carbonitrile; (4-amino-3-methoxyphenyl)(3-morpholino azetidin-1-yl)methanone; 4-amino-5-chloro-2-methoxy-N-(1-methylpiperidin-4-yl)benzamide; (4-amino-3-methoxyphenyl)(2,2-di ethylmorpholino)methanone; 1-(4-(4-amino-3-methoxybenzoyl)piperazin-1-yl)ethan-1-one; (4-amino-3-methoxyphenyl)(2-isobutylmorpholino)methanone; (4-amino-3-methoxyphenyl)(4-(oxetan-3-yl)piperazin-1-yl)methanone; (4-amino-5-chloro-2-methoxyphenyl)(2-(hydroxymethyl)morpholino)methanone; 4-amino-2-fluoro-N-(2-hydroxy-2-methylpropyl)-5-methoxy-N-methylbenzamide; (4-amino-3-(cyclopentyloxy)phenyl)(morpholino)methanone; (6-amino-5-methoxy-1-methyl-1H-indol-3-yl)(morpholino)methanone; (4-amino-5-chloro-2-(difluoromethoxy)phenyl)(morpholino)methanone; (S)-(4-amino-3-chlorophenyl)(3-fluoropyrrolidin-1-yl)methanone; (4-amino-5-(cyclopropylmethoxy)-2-methylphenyl)(morpholino)methanone; 4-amino-5-fluoro-N-(2-hydroxy-2-methylpropyl)-2-methoxy-N-methylbenzamide; (4-amino-3-chloro-2,6-dimethoxyphenyl)(morpholino)methanone; (4-amino-2-fluoro-5-methoxyphenyl)(hexahydropyrrolo[1,2-a]pyrazin-2(1H)-yl)methanone; (4-amino-2-fluoro-5-methoxyphenyl)(1-oxa-6-azaspiro[3.3]heptan-6-yl)methanone; (4-amino-2,5-dimethoxyphenyl)(3,3-difluoropyrrolidin-1-yl)methanone; (4-amino-3-methoxyphenyl)(3-(trifluoromethyl)pyrrolidin-1-yl)methanone; (4-amino-3-(trifluoromethoxy)phenyl)(morpholino)methanone; 4-amino-5-chloro-N-(2-hydroxy-2-methylpropyl)-2-methoxy-N-methylbenzamide; 1-(4-amino-5-chloro-2-methoxybenzoyl)piperidine-4-carbonitrile; (4-amino-3-(difluoromethoxy)phenyl)(4-hydroxypiperidin-1-yl)methanone; (4-amino-2-fluoro-5-methoxyphenyl)(2,2-dimethylmorpholino)methanone; (8-amino-2,3-dihydrobenzo[b][1,4]dioxin-5-yl)(3,3-difluoropyrrolidin-1-yl)methanone; (S)-(4-amino-5-chloro-2-methylphenyl)(3-fluoropyrrolidin-1-yl)methanone; (4-amino-5-chloro-2-methoxyphenyl)(1-oxa-6-azaspiro[3.3]heptan-6-yl)methanone; (4-amino-5-chloro-2-methoxyphenyl)(3,3-difluoropyrrolidin-1-yl)methanone; (S)-(4-amino-5-methoxy-2-methylphenyl)(3-fluoropyrrolidin-1-yl)methanone; (4-amino-5-chloro-2-methoxyphenyl)(2-oxa-6-azaspiro[3.3]heptan-6-yl)methanone; (S)-(4-amino-2-fluoro-5-methoxyphenyl)(3-fluoropyrrolidin-1-yl)methanone; (S)-(4-amino-2-fluoro-5-methoxyphenyl)(3-fluoropyrrolidin-1-yl)methanone; 4-(4-amino-2-fluoro-5-methoxyphenyl)-N,N,1-trimethyl-1H-pyrazole-5-carboxamide; (4-amino-5-(fluoromethoxy)-2-methoxyphenyl)(3,3-difluoropyrrolidin-1-yl)methanone; (4-amino-3-methoxyphenyl)(4-(2-hydroxypropan-2-yl)piperidin-1-yl)methanone; (4-amino-5-chloro-2-methoxyphenyl)(2,6-dimethylmorpholino)methanone; (4-amino-3-methoxyphenyl)(4-(tert-butyl)piperidin-1-yl)methanone; (S)-(4-amino-2-fluoro-5-methoxyphenyl)(2-(methoxymethyl)pyrrolidin-1-yl)methanone; (4-amino-5-chloro-2-methoxyphenyl)(4,4-difluoropiperidin-1-yl)methanone; (4-amino-3-(2,2,2-trifluoroethoxy)phenyl)(morpholino)methanone; (4-amino-3-methoxyphenyl)(4-(piperidin-4-yl)piperazin-1-yl)methanone; (4-amino-3-methoxyphenyl)(3-(trifluoromethyl)piperidin-1-yl)methanone; (S)-(4-amino-5-chloro-2-methoxyphenyl)(3-fluoropyrrolidin-1-yl)methanone; 4-amino-5-chloro-2-methoxy-N-methyl-N-(1-methyl-1H-pyrazol-4-yl)benzamide; (4-amino-5-chloro-2-methoxyphenyl)(4-(2-methoxyethyl)piperazin-1-yl)methanone; 4-amino-2-fluoro-5-methoxy-N-methyl-N-(1-methylpiperidin-4-yl)benzamide; (4-amino-5-methoxy-2-(trifluoromethyl)phenyl)(morpholino)methanone; (4-amino-5-(2-fluoroethoxy)-2-methoxyphenyl)(3,3-difluoropyrrolidin-1-yl)methanone; (4-amino-5-chloro-2-methoxyphenyl)(4-(dimethylamino)piperidin-1-yl)methanone; (4-amino-3-methoxyphenyl)(4-(2,2,2-trifluoroethyl)piperazin-1-yl)methanone; (4-amino-5-methoxy-2-(trifluoromethoxy)phenyl)(morpholino)methanone; (4-(4-amino-3-methoxybenzoyl)piperazin-1-yl)(cyclopropyl)methanone; (4-amino-3-methoxyphenyl)(2,2,6,6-tetrafluoromorpholino)methanone; (4-amino-3-methoxyphenyl)(4-(methylsulfonyl)piperazin-1-yl)methanone; (4-amino-5-chloro-2-methoxyphenyl)(3-morpholinoazetidin-1-yl)methanone; (4-amino-5-chloro-2-methoxyphenyl)(4-(oxetan-3-yl)piperazin-1-yl)methanone; (4-amino-3-methoxyphenyl)(4-(1-methylpiperidin-4-yl)piperazin-1-yl)methanone; (4-amino-3-(cyclopentyloxy)phenyl)(2-oxa-6-azaspiro[3.3]heptan-6-yl)methanone; (6-amino-5-chloro-1-methyl-1H-indol-3-yl)(4-methylpiperazin-1-yl)methanone; (4-amino-2-fluoro-5-methoxyphenyl)(4-morpholinopiperidin-1-yl)methanone; (4-amino-3-methoxyphenyl)((3S,4S)-3,4-difluoropyrrolidin-1-yl)methanone; (6-amino-5-chloro-1-methyl-1H-indol-3-yl)(4-ethylpiperazin-1-yl)methanone; (4-amino-2-fluoro-3-methoxyphenyl)((1S,4S)-2-oxa-5-azabicyclo[2.2.1]heptan-5-yl)methanone; (4-amino-2-fluoro-5-methoxyphenyl)((1S,4S)-2-oxa-5-azabicyclo[2.2.1]heptan-5-yl)methanone; (4-amino-5-chloro-2-methoxyphenyl)((1S,4S)-2-oxa-5-azabicyclo[2.2.1]heptan-5-yl)methanone; (4-amino-2-fluoro-5-methoxyphenyl)((3S,4S)-3,4-difluoropyrrolidin-1-yl)methanone; (4-amino-2-fluoro-5-methoxyphenyl)((2S,6R)-2,6-dimethylmorpholino)methanone; (4-amino-2-fluoro-5-methoxyphenyl)((1R,5S)-8-oxa-3-azabicyclo[3.2.1]octan-3-yl)methanone; (4-amino-5-chloro-2-methoxyphenyl)((2S,6R)-2,6-dimethylmorpholino)methanone; (4-amino-5-chloro-2-methoxyphenyl)((3S,5R)-3,5-dimethylpiperazin-1-yl)methanone; (6-amino-5-chloro-1-methyl-1H-indol-3-yl)((1S,4S)-2-oxa-5-azabicyclo[2.2.1]heptan-5-yl)methanone.

Further preferred are compounds of formula (I) wherein $R^2$ is an optionally substituted aryl, heteroaryl, cycloalkyl, heterocycloalkyl, alkylcycloalkyl, heteroalkylcycloalkyl, aralkyl or heteroaralkyl group.

Moreover preferred are compounds of formula (I) wherein $R^2$ is an optionally substituted phenyl or naphthyl group or an optionally substituted heteroaryl group having one or two rings containing 5, 6, 7, 8, 9 or 10 ring atoms, or an optionally substituted arylheterocycloalkyl, heteroarylcycloalkyl or heteroarylheterocycloalkyl group containing two or three (especially two) rings and from 9 to 20 (especially 9 or 10) ring atoms. Preferably, the heteroatoms are selected from S, O and N. Further preferably, the number of heteroatoms is from 1 to 6 (especially 1, 2, 3 or 4).

As already mentioned above, according to the present invention, $R^2$ is bound to the pyrimidine ring of formula (I) via a carbon-carbon bond. In other words, $R^2$ is bound to the pyrimidine moiety of formula (I) via a carbon atom, i.e. a carbon atom of group $R^2$ is bound to the pyrimidine moiety.

Especially preferred are compounds of formula (I) wherein, $R^2$ is selected from the following groups: phenyl; 3-anisyl; 4-anisyl; 2-anisyl; 4,5 dimethoxyphenyl; 6-hydroxyphenyl; 4-pyridyl; 6-pyrrolidinyl-3-pyridinyl; 3-pyrid-3-ylphenyl; 3-morpholinophenyl; 1-methyl-4-piperidyl; 2-thienyl; 3-thienyl; 3-pyrazolyl; 2-benzthiazolyl; imidazo[1,2-a]pyridin-2-yl; 3,6 dimethoxyphenyl; benzimidaz-2-yl and 1-methyl-2-benzimidazolyl.

Especially preferably, $R^2$ is selected from the following groups:

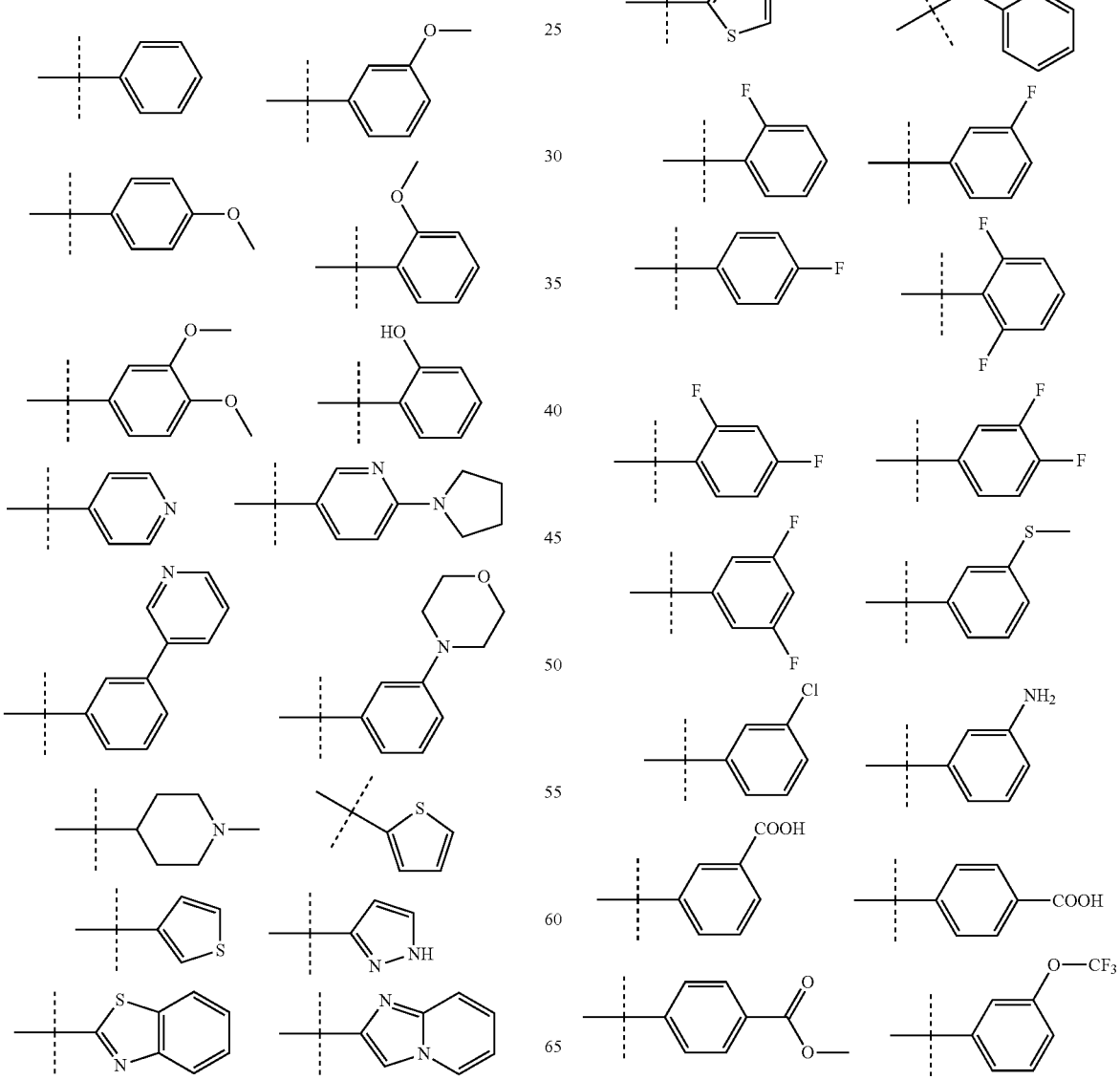

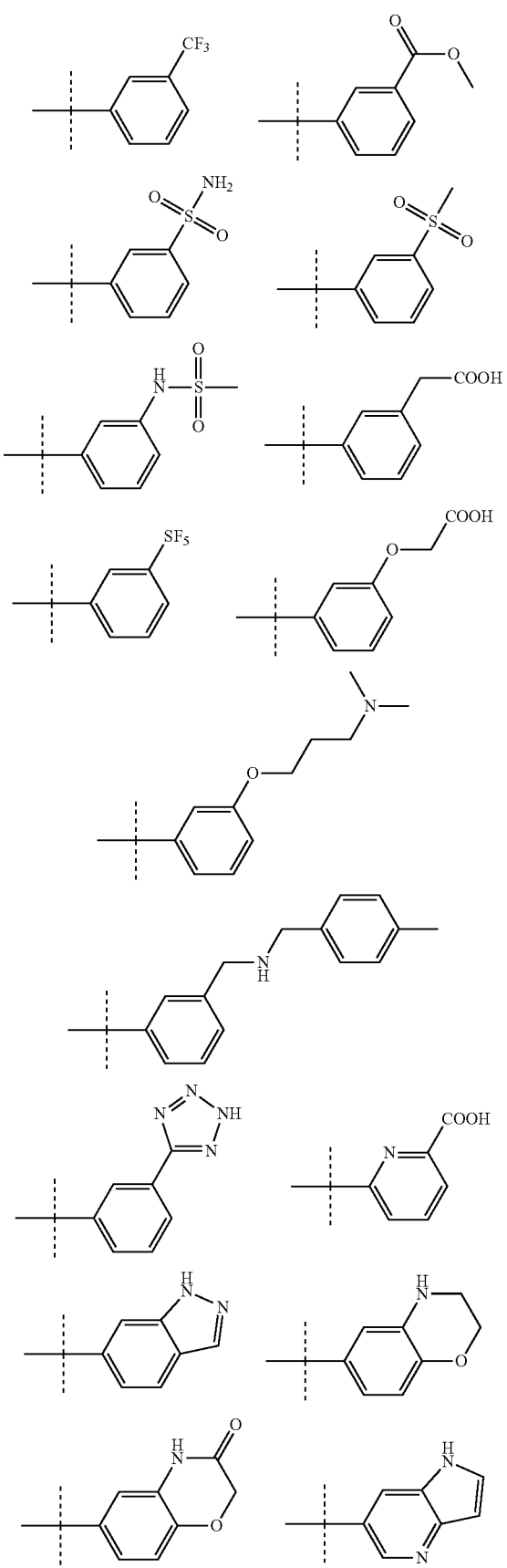
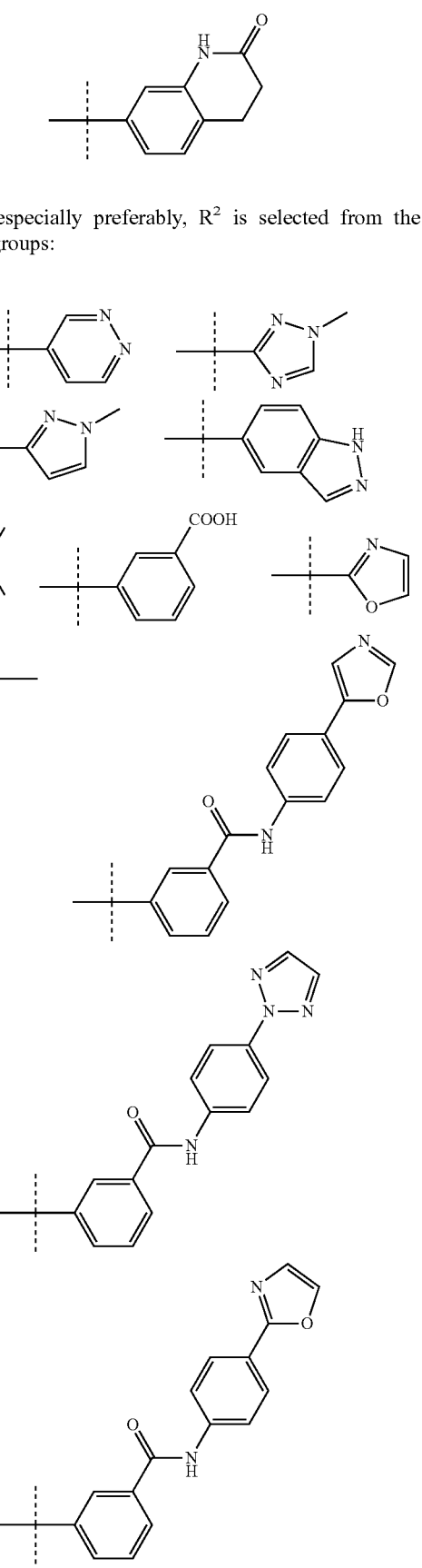
Further especially preferably, $R^2$ is selected from the following groups:

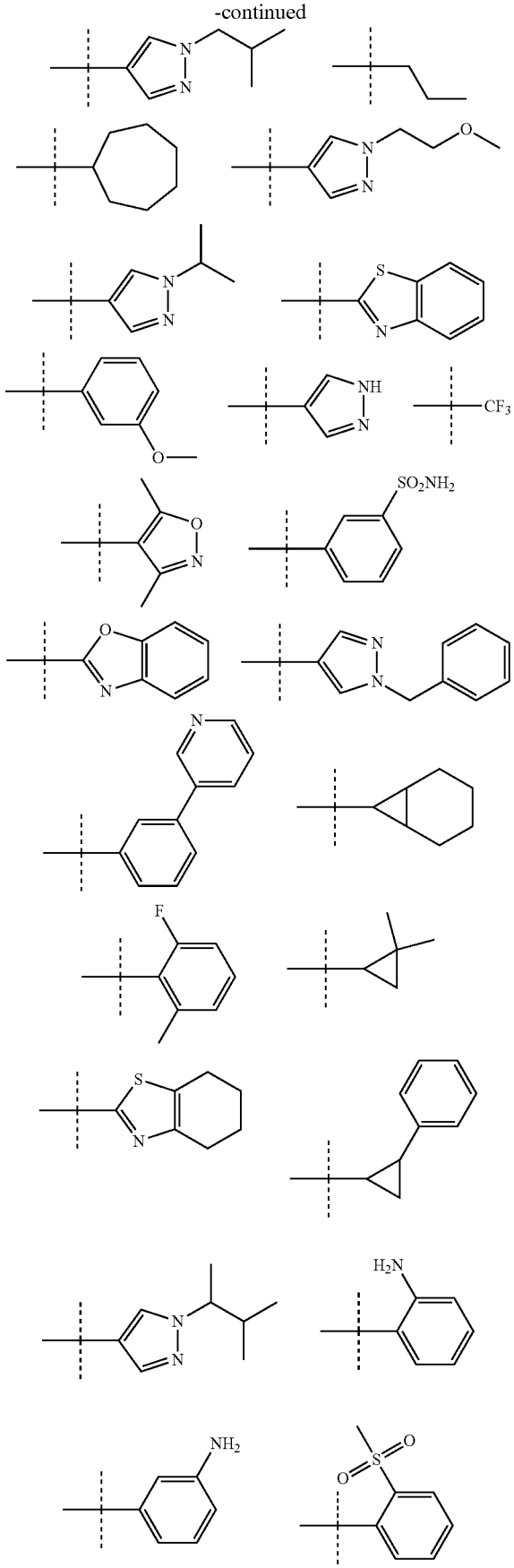

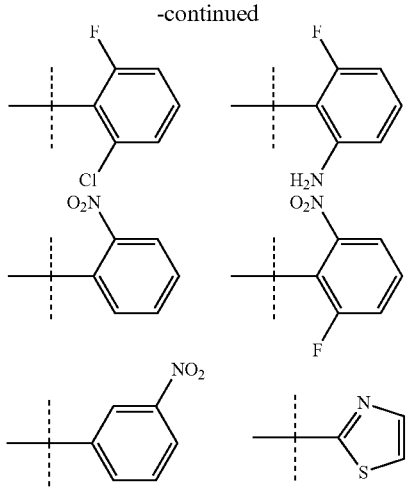

Further preferably, $R^2$ is a group of formula $X^2$-$L^3$-$Y^2$ or a group of formula $X^2$-$L^3$-$Y^2$-$L^4$-$Z^2$ wherein $X^2$ is an optionally substituted phenyl group or an optionally substituted heteroaryl group containing 5 or 6 ring atoms and 1, 2, 3 or 4 heteroatoms selected from O, S and N;

$L^3$ is a bond or a group of formula —CH$_2$—, —C(=O)—, —SO—, —SO$_2$—, —NH—C(=O)—, —C(=O)—NH—; —C(=O)—O—, —O—C(=O)—, —NH—C(=O)—O—, —O—C(=O)—NH—, —NH—SO$_2$—NH—, —CH$_2$—NH—CH$_2$—, —NH—SO$_2$—, —SO$_2$—NH— or —NH—C(=O)—NH— (preferably, $L^3$ is a bond or a group of formula —CH$_2$—, —C(=O)—, —SO$_2$— or —NH—C(=O)—NH—);

$Y^2$ is an optionally substituted phenyl group, an optionally substituted heteroaryl group containing 5 or 6 ring atoms and 1, 2, 3 or 4 heteroatoms selected from O, S and N, an optionally substituted $C_3$-$C_7$ cycloalkyl group or an optionally substituted heterocycloalkyl group containing 3, 4, 5, 6 or 7 ring atoms and 1, 2, 3 or 4 heteroatoms selected from O, S and N (preferably, $Y^2$ is an optionally substituted $C_3$-$C_7$ cycloalkyl group or an optionally substituted heterocycloalkyl group containing 3, 4, 5, 6 or 7 ring atoms and 1, 2, 3 or 4 heteroatoms selected from O, S and N);

$L^4$ is a bond or a group of formula —CH$_2$—, —C(=O)—, —SO—, —SO$_2$—, —NH—C(=O)—, —C(=O)—NH—; —C(=O)—O—, —O—C(=O)—, —NH—C(=O)—O—, —O—C(=O)—NH—, —NH—SO$_2$—NH—, —CH$_2$—NH—CH$_2$—, —NH—SO$_2$—, —SO$_2$—NH— or —NH—C(=O)—NH— (preferably, $L^4$ is a bond or a group of formula —CH$_2$—, —C(=O)—, —SO$_2$— or —NH—C(=O)—NH—; especially preferably, $L^4$ is a bond); and $Z^2$ is an optionally substituted phenyl group, an optionally substituted heteroaryl group containing 5 or 6 ring atoms and 1, 2, 3 or 4 heteroatoms selected from O, S and N, an optionally substituted $C_3$-$C_7$ cycloalkyl group or an optionally substituted heterocycloalkyl group containing 3, 4, 5, 6 or 7 ring atoms and 1, 2, 3 or 4 heteroatoms selected from O, S and N (preferably, $Z^2$ is an optionally substituted $C_3$-$C_7$ cycloalkyl group or an optionally substituted heterocycloalkyl group containing 3, 4, 5, 6 or 7 ring atoms and 1, 2, 3 or 4 heteroatoms selected from O, S and N).

Further preferably, $R^2$ is an optionally substituted alkyl, heteroalkyl, cycloalkyl, heterocycloalkyl, alkylcycloalkyl or heteroalkylcycloalkyl group.

Moreover preferably, $R^2$ is a heteroalkyl group containing from 1 to 6 carbon atoms and 1, 2 or 3 heteroatoms selected from O, S and N, or an optionally substituted $C_3$-$C_7$ cycloalkyl group, or an optionally substituted heterocycloalkyl group containing from 2 to 6 carbon atoms and 1, 2 or 3 heteroatoms selected from O, S and N, or an optionally substituted $C_4$-$C_{10}$ alkylcycloalkyl group, or an optionally substituted heteroalkylcycloalkyl group containing from 3 to 10 carbon atoms and from 1 to 4 heteroatoms selected from O, S and N.

Further especially preferably, $R^2$ is selected from the following groups:

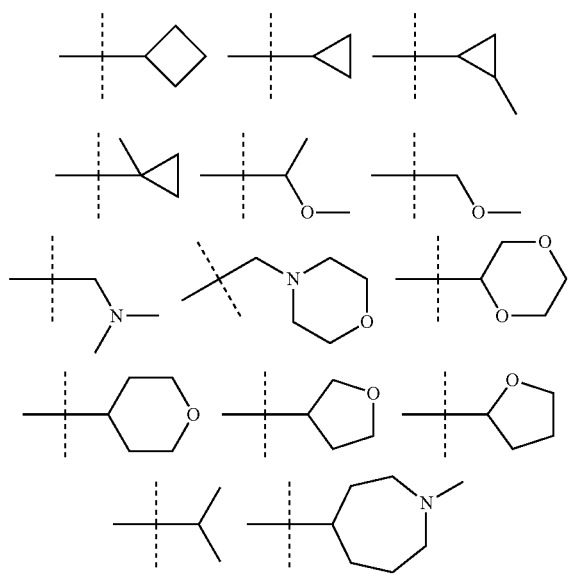

Moreover especially preferably, $R^2$ is selected from the following groups:

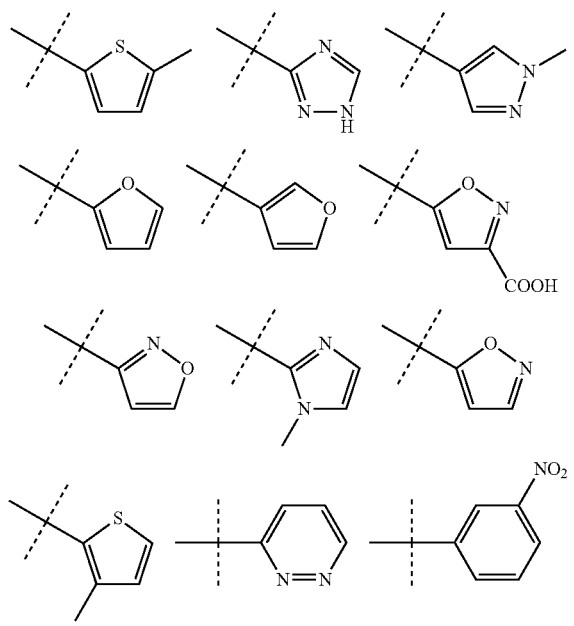

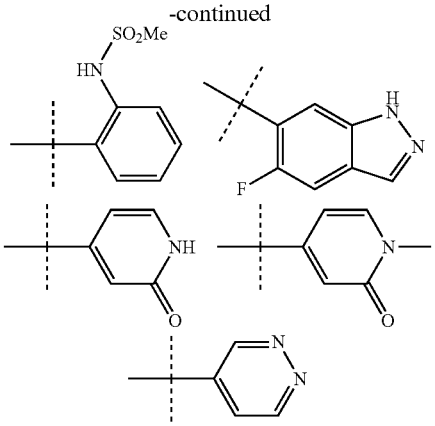

Especially preferably, $R^2$ is a cyclopropyl group.

Moreover preferably, $R^2$ is derived from the following aldehydes:

benzaldehyde; isonicotinaldehyde; 6-(pyrrolidin-1-yl)nicotinaldehyde; 3,4-dimethoxybenzaldehyde; 1-methylpiperidine-4-carbaldehyde; 1H-pyrazole-3-carbaldehyde; 4-methoxybenzaldehyde; 3-methoxybenzaldehyde; thiophene-2-carbaldehyde; thiophene-3-carbaldehyde; benzo[d]thiazole-2-carbaldehyde; 3-(pyridin-3-yl)benzaldehyde; 2-hydroxybenzaldehyde; 3-morpholinobenzaldehyde; 2-methoxybenzaldehyde; 2,5-dimethoxybenzaldehyde; N-(2-aminoethyl)-3-formylbenzamide; imidazo[1,2-a]pyridine-2-carbaldehyde; 1H-benzo[d]imidazole-2-carbaldehyde; 1-methyl-1H-benzo[d]imidazole-2-carbaldehyde; 1H-imidazole-5-carbaldehyde; 1H-imidazole-2-carbaldehyde; 3-(2H-tetrazol-5-yl)benzaldehyde; 2-oxo-2-phenylacetaldehyde; 3-formylbenzoic acid; 2-(3-formylphenoxyl)acetic acid; 5-formylthiophene-3-carboxylic acid; 2-(3-formylphenyl)acetic acid; 6-formylpicolinic acid; thiazole-2-carbaldehyde; 3-(((4-methylbenzyl)amino)methyl)benzaldehyde; 3-(3-(dimethylamino)propoxy)benzaldehyde; 3-formylbenzenesulfonamide; N-(3-formylphenyl)methanesulfonamide; thiazole-4-carbaldehyde; oxazole-4-carbaldehyde; oxazole-2-carbaldehyde; methyl 3-formylbenzoate; methyl 4-formylbenzoate; 3-(pentafluorosulfanyl)benzaldehyde; 3-(methylthio)benzaldehyde; 3-(trifluoromethoxy)benzaldehyde; 3-(trifluoromethyl)benzaldehyde; 3-chlorobenzaldehyde; 2-fluorobenzaldehyde; 3-fluorobenzaldehyde; 4-formylbenzoic acid; 3-(methylsulfonyl)benzaldehyde; 1H-indazole-6-carbaldehyde; 1H-pyrrolo[3,2-b]pyridine-6-carbaldehyde; 4-fluorobenzaldehyde; 3,4-difluorobenzaldehyde; 3,5-difluorobenzaldehyde; 2,6-difluorobenzaldehyde; 2,4-difluorobenzaldehyde; 3-oxo-3,4-dihydro-2H-benzo[b][1,4]oxazine-6-carbaldehyde.

Especially preferably, $R^2$ is derived from the following aldehydes: furan-3-carbaldehyde; thiazole-5-carbaldehyde; furan-2-carbaldehyde; nicotinaldehyde; picolinaldehyde; pyrazine-2-carbaldehyde; pyrimidine-5-carbaldehyde; 1-methyl-1H-pyrrole-2-carbaldehyde; 2-aminobenzaldehyde; 4-methylnicotinaldehyde; 1-methyl-1H-pyrazole-4-carbaldehyde; 2-(hydroxymethyl)benzaldehyde; 1H-pyrazole-4-carbaldehyde; 4-methylthiazole-2-carbaldehyde; 2-chlorobenzaldehyde; benzaldehyde; 4-methylthiophene-2-carbaldehyde; benzaldehyde; 5-methylthiophene-2-carbaldehyde; 3-aminobenzaldehyde; 3-hydroxybenzaldehyde; 2-ethoxybenzaldehyde; 2-aminopyrimidine-5-carbaldehyde; 6-aminonicotinaldehyde; 3-methylbenzaldehyde;

5-chlorothiophene-2-carbaldehyde; 4-hydroxybenzaldehyde; 6-methylpicolinaldehyde; 4-methylbenzaldehyde; 3,5-dimethylisoxazole-4-carbaldehyde; 2-fluoroisonicotinaldehyde; 4-aminobenzaldehyde; 4-iodobenzaldehyde; 5-methylpicolinaldehyde; 5-aminonicotinaldehyde; 3-methyl-1H-pyrazole-4-carbaldehyde; 4-methylpicolinaldehyde; 5-methylnicotinaldehyde; 5-bromothiophene-2-carbaldehyde; 2-aminoisonicotinaldehyde; 3-amino-2-methylbenzaldehyde; 4-fluoro-2-methylbenzaldehyde; 4-bromobenzaldehyde; 6-methoxynicotinaldehyde; 4-chlorobenzaldehyde; 4-(hydroxymethyl)benzaldehyde; 5-methoxynicotinaldehyde; 5-(methylamino)nicotinaldehyde; 3-(aminomethyl)benzaldehyde; 5-chloronicotinaldehyde; 2,3-diaminobenzaldehyde; 2,3-difluorobenzaldehyde; 5-(hydroxymethyl)nicotinaldehyde; 3-(hydroxymethyl)benzaldehyde; 3-bromobenzaldehyde; 3-ethylbenzaldehyde; benzo[d]thiazole-5-carbaldehyde; indoline-6-carbaldehyde; benzo[d]oxazole-6-carbaldehyde; 5-chloro-2-fluorobenzaldehyde; benzo[d][1,3]dioxole-5-carbaldehyde; benzo[d]thiazole-6-carbaldehyde; benzo[d]oxazole-5-carbaldehyde; benzo[d][1,3]dioxole-4-carbaldehyde; terephthalaldehyde; 4-formylbenzonitrile; 3-formylbenzonitrile; 3-chloro-2-fluorobenzaldehyde; 2,3-dihydrobenzofuran-5-carbaldehyde; 2,3-dihydro-1H-indazole-5-carbaldehyde; 2,3-dihydro-1H-benzo[d]imidazole-5-carbaldehyde; benzofuran-2-carbaldehyde; 3-((methylamino)methyl)benzaldehyde; 3-(ethylthio)benzaldehyde; benzofuran-5-carbaldehyde; furo[3,2-b]pyridine-6-carbaldehyde; 5-amino-6-methoxynicotinaldehyde; 4-(chloromethyl)benzaldehyde; 5-chloro-2-hydroxybenzaldehyde; 2-chloro-4-fluorobenzaldehyde; imidazo[1,2-a]pyridine-6-carbaldehyde; 3,4-dihydro-2H-benzo[b][1,4]oxazine-6-carbaldehyde; 3,4-dihydro-2H-benzo[b][1,4]oxazine-7-carbaldehyde; 2,3-dihydrobenzo[b][1,4]dioxine-6-carbaldehyde; 1,2,3,4-tetrahydroisoquinoline-7-carbaldehyde; 2,3-dihydro-1H-pyrido[2,3-b][1,4]oxazine-7-carbaldehyde; 1,2,3,4-tetrahydroisoquinoline-6-carbaldehyde; 5-((2-hydroxyethyl)amino)nicotinaldehyde; 1,5-naphthyridine-3-carbaldehyde; quinoxaline-2-carbaldehyde; quinoline-3-carbaldehyde; 4-fluoro-3-methylbenzaldehyde; 3-fluoro-4-methylbenzaldehyde; quinoline-5-carbaldehyde; 2,3-dihydro-1H-pyrido[2,3-b][1,4]oxazine-6-carbaldehyde; quinoxaline-6-carbaldehyde; quinoline-6-carbaldehyde; 4-((ethylamino)methyl)benzaldehyde; 3-((ethylamino)methyl)benzaldehyde; 3-propoxybenzaldehyde; 2,4-dichlorobenzaldehyde; isoquinoline-4-carbaldehyde; 3-hydroxy-4-methylbenzaldehyde; 3,4-dimethylbenzaldehyde; isoquinoline-5-carbaldehyde; 2-(3-formylphenyl)acetonitrile; 3-ethoxy-2-fluorobenzaldehyde; 6-chloro-5-(hydroxymethyl)nicotinaldehyde; 4-hydroxy-3-methylbenzaldehyde; 3,5-dimethylbenzaldehyde; 1-isobutyl-1H-pyrazole-4-carbaldehyde; 6-oxo-1,6-dihydropyridine-3-carbaldehyde; 4-chloro-3-methylbenzaldehyde; 3-chloro-4-methylbenzaldehyde; N-(2-formylphenyl)acetamide; 4-isopropylbenzaldehyde; 1,2,3,5-tetrahydrobenzo[e][1,4]oxazepine-8-carbaldehyde; 2-oxo-1,2-dihydropyridine-4-carbaldehyde; 5-amino-6-chloronicotinaldehyde; 3-(dimethylamino)benzaldehyde; 4-chloro-3-hydroxybenzaldehyde; 4-formylbenzamide; 1H-indole-6-carbaldehyde; 1-methyl-1H-benzo[d]imidazole-6-carbaldehyde; 1H-indazole-4-carbaldehyde; 1H-benzo[d]imidazole-6-carbaldehyde; 1-methyl-1H-benzo[d]imidazole-5-carbaldehyde; 1-methyl-1H-indazole-6-carbaldehyde; 1-methyl-1H-indazole-5-carbaldehyde; 1H-indazole-5-carbaldehyde; 5-formylnicotinamide; 1H-benzo[d][1,2,3]triazole-6-carbaldehyde; 1H-indole-6-carbaldehyde; 5-formylpicolinamide; 1H-indazole-7-carbaldehyde; 2-methylbenzofuran-7-carbaldehyde; 1H-indole-5-carbaldehyde; 1H-pyrrolo[2,3-b]pyridine-5-carbaldehyde; 1H-indole-2-carbaldehyde; 3-aminobenzo[d]isoxazole-5-carbaldehyde; 1-isopentyl-1H-pyrazole-4-carbaldehyde; 1-methyl-1H-pyrrolo[3,2-b]pyridine-6-carbaldehyde; 3-isopropoxybenzaldehyde; 3-formylbenzamide; 2-methylbenzo[d]thiazole-5-carbaldehyde; 1H-benzo[d]imidazole-5-carbaldehyde; 3-aminobenzo[d]isoxazole-6-carbaldehyde; 1-methyl-1H-indole-6-carbaldehyde; 1H-imidazo[4,5-b]pyridine-6-carbaldehyde; 1H-pyrrolo[2,3-b]pyridine-4-carbaldehyde; 1H-pyrazolo[3,4-b]pyridine-5-carbaldehyde; 1H-pyrrolo[2,3-c]pyridine-4-carbaldehyde; 3-acetylbenzaldehyde; 7H-pyrrolo[2,3-d]pyrimidine-4-carbaldehyde; 1H-pyrazolo[3,4-b]pyridine-4-carbaldehyde; 5-formylnicotinic acid; 1H-benzo[d]imidazole-4-carbaldehyde; 1-methyl-1H-indole-4-carbaldehyde; 1-methyl-1H-indole-5-carbaldehyde; 1H-pyrrolo[2,3-b]pyridine-3-carbaldehyde; 1H-pyrrolo[2,3-c]pyridine-3-carbaldehyde; 2-oxoindoline-6-carbaldehyde; 2-aminoquinazoline-6-carbaldehyde; 5-fluoro-1H-indazole-6-carbaldehyde; 4-methyl-3,4-dihydro-2H-benzo[b][1,4]oxazine-6-carbaldehyde; 3-aminoquinoline-6-carbaldehyde; 4-methyl-3,4-dihydro-2H-benzo[b][1,4]oxazine-7-carbaldehyde; 6-hydroxy-2-naphthaldehyde; 3-hydroxyquinoxaline-6-carbaldehyde; N-(3-formylphenyl)acetamide; 3-fluoro-4-formylbenzamide; 4-fluoro-3-formylbenzamide; 4-formyl-3-methylbenzamide; 3-formyl-4-methylbenzamide; 3-formyl-N-methylbenzamide; N-(5-formylpyridin-3-yl)acetamide; 3-formyl-2-methylbenzamide; 3-(ethylsulfinyl)benzaldehyde; N-(4-formylphenyl)acetamide; 3-(thiazol-2-yl)benzaldehyde; 4-(thiazol-2-yl)benzaldehyde; 3-(oxazol-2-yl)benzaldehyde; 4-(oxazol-2-yl)benzaldehyde; 2-oxoindoline-5-carbaldehyde; 2-aminoquinoline-6-carbaldehyde; 2-hydroxyquinoline-7-carbaldehyde; 2-oxoindoline-4-carbaldehyde; 3-(furan-2-yl)benzaldehyde; 4-(furan-2-yl)benzaldehyde; 3-(pyrrolidin-1-yl)benzaldehyde; 2-oxo-2,3-dihydro-1H-pyrido[2,3-b][1,4]oxazine-7-carbaldehyde; [1,1'-biphenyl]-3-carbaldehyde; [1,1'-biphenyl]-4-carbaldehyde; 1-benzyl-1H-pyrazole-4-carbaldehyde; 6-phenylnicotinaldehyde; 4-morpholinobenzaldehyde; 3-(1-methyl-1H-imidazol-5-yl)benzaldehyde; 4-formyl-2-methoxybenzamide; 5-formyl-2-methoxybenzamide; N-ethyl-4-formylbenzamide; 2-ethyl-1,2,3,4-tetrahydroisoquinoline-6-carbaldehyde; 2-ethyl-1,2,3,4-tetrahydroisoquinoline-7-carbaldehyde; 1-(2-hydroxyethyl)-1H-indazole-6-carbaldehyde; 2-(2-hydroxyethyl)-2H-indazole-6-carbaldehyde; 1-(pyridin-2-ylmethyl)-1H-pyrazole-4-carbaldehyde; 5-amino-1-methyl-6-oxo-1,6-dihydropyridine-3-carbaldehyde; 3-oxo-3,4-dihydro-2H-pyrido[3,2-b][1,4]oxazine-7-carbaldehyde; 3-(2-(dimethylamino)ethoxy)benzaldehyde; N-(3-formylbenzyl)acetamide; 3-(((cyclopropylmethyl)amino)methyl)benzaldehyde; 3-(3-formylphenyl)propanoic acid; 3-(2-hydroxypropan-2-yl)benzaldehyde; 4-(2-hydroxypropan-2-yl)benzaldehyde; 3-oxo-3,4-dihydro-2H-pyrido[3,2-b][1,4]oxazine-6-carbaldehyde; 2-oxo-2,3-dihydro-1H-pyrido[2,3-b][1,4]oxazine-6-carbaldehyde; 3-oxo-3,4-dihydro-2H-benzo[b][1,4]oxazine-7-carbaldehyde; 3-oxo-1,2,3,4-tetrahydroquinoxaline-6-carbaldehyde; 2-oxo-1,2,3,4-tetrahydroquinoline-7-carbaldehyde; 6-methoxy-2-naphthaldehyde; 1-(4-formylphenyl)-3-methylurea; 1-(3-formylphenyl)-3-methylurea; 4-(trifluoromethyl)benzaldehyde; dibenzo[b,d]furan-4-carbaldehyde; 4-fluoro-1H-indazole-6-carbaldehyde; 3-amino-1H-indazole-6-carbaldehyde; 3-amino-1H-indazole-5-carbaldehyde; 2-methyl-1H-benzo[d]imidazole-6-carbaldehyde; 4-formyl-N-(2-hydroxyethyl)benzamide; 3-fluoro-5-formylbenzamide; 4-fluoro-1H-indole-6-carbaldehyde; 2-fluoro- 5-formylbenzamide; 2-fluoro-4-formylbenzamide; 4-formyl-2-methylbenzamide; 3-(piperazin-1-ylmethyl)benzaldehyde; 3-formyl-5-methylbenzamide; 5-formyl-2-methylbenzamide; 3-methyl-1H-indazole-6-carbaldehyde; 2,3-dimethyl-2H-indazole-6-carbaldehyde; 3-methyl-1H-indazole-5-carbaldehyde; 4-(2-hydroxyethyl)-3,4-dihydro-2H-benzo[b][1,4]oxazine-6-carbaldehyde; 1-(2-morpholinoethyl)-1H-pyrazole-4-carbaldehyde; 1-(2-(piperidin-1-yl)ethyl)-1H-pyrazole-4-carbaldehyde; 1-phenethyl-1H-pyrazole-4-carbaldehyde; 3-(piperidin-1-ylmethyl)benzaldehyde; N-(2-formylphenyl)methanesulfonamide; 4-(morpholinomethyl)benzaldehyde; 4-(piperazin-1-ylmethyl)benzaldehyde; 3-(3-methylpyridin-4-yl)benzaldehyde; 2'-fluoro-[1,1'-biphenyl]-4-carbaldehyde; 2,3-dimethyl-2H-indazole-5-carbaldehyde; 2-methyl-1H-benzo[d]imidazole-5-carbaldehyde; 2-amino-1H-benzo[d]imidazole-6-carbaldehyde; 3,3-dimethylindoline-6-carbaldehyde; methyl 3-(3-formylphenyl)propanoate; 6-ethoxy-2-naphthaldehyde; 6-fluoro-1H-indole-4-carbaldehyde; 2-methyl-1H-pyrrolo[2,3-b]pyridine-4-carbaldehyde; 6-methyl-1H-indole-4-carbaldehyde; 2-methyl-1H-indole-4-carbaldehyde; 5-fluoro-1H-pyrrolo[2,3-b]pyridine-4-carbaldehyde; 5-(thiophen-3-ylethynyl)thiophene-2-carbaldehyde; 5-(thiophen-3-ylethynyl)thiophene-2-carbaldehyde; 4-phenoxybenzaldehyde; 7-methyl-1H-indole-4-carbaldehyde; 3-methoxy-4-((2-methoxyethyl)(methyl)amino)benzaldehyde; 3-ethyl-1H-indazole-6-carbaldehyde; 2-chloro-4-formylbenzamide; 4-((pyridin-2-ylamino)methyl)benzaldehyde; 2'-methoxy-[1,1'-biphenyl]-4-carbaldehyde; 1,4-dimethyl-1,2,3,4-tetrahydroquinoxaline-6-carbaldehyde; 4-formyl-N-(2-methoxyethyl)benzamide; 4-formyl-N-(2-(methylamino)ethyl)benzamide; 6-(2-hydroxyethoxy)-2-naphthaldehyde; 3-((methylsulfonyl)methyl)-1,2,4-oxadiazole-5-carbaldehyde; 3-(hydroxymethyl)-1H-indazole-6-carbaldehyde; N-cyclopropyl-5-formylthiophene-2-carboxamide; 4-formylbenzenesulfonamide; 4-(methylsulfonyl)benzaldehyde; 3-formyl-N,N-dimethylbenzamide; 3-((2-oxoimidazolidin-1-yl)methyl)benzaldehyde; 4-(1H-imidazol-2-yl)benzaldehyde; 4-(1-methyl-1H-pyrazol-4-yl)benzaldehyde; 3-(1H-imidazol-5-yl)benzaldehyde; 4-(1H-imidazol-5-yl)benzaldehyde; 2-oxo-2,3-dihydrobenzo[d]oxazole-5-carbaldehyde; 1-methyl-2-oxoindoline-6-carbaldehyde; 2-chloro-5-formylnicotinic acid; 5-formylpyridine-3-sulfonamide; 5-(methylsulfonyl)nicotinaldehyde; 6-chloro-1H-indole-4-carbaldehyde, 5-(pyridin-3-ylethynyl)thiophene-2-carbaldehyde; 5-(pyridin-2-ylethynyl)thiophene-2-carbaldehyde; 2-oxo-2,3-dihydrobenzo[d]oxazole-7-carbaldehyde; 5-((3-methylthiophen-2-yl)ethynyl)thiophene-2-carbaldehyde; 5-(phenylethynyl)thiophene-2-carbaldehyde; 6-methoxy-1H-indole-4-carbaldehyde; 3-(ethylsulfonyl)benzaldehyde; 4'-fluoro-[1,1'-biphenyl]-4-carbaldehyde; 3-(2-hydroxyethyl)-1H-indazole-6-carbaldehyde; 3-(2-hydroxyethyl)-1H-indol-6-carbaldehyde; 2-((4-formyl-1H-pyrazol-1-yl)methyl)benzonitrile; 3-formyl-N-isopropylbenzamide; 1-(3-aminobenzyl)-1H-pyrazole-4-carbaldehyde; 4-(2-morpholinoethoxy)benzaldehyde; N-(4-formylphenyl)methanesulfonamide; 3-(2-amino-4-methylthiazol-5-yl)benzaldehyde; 3-(5-amino-2-methylthiophen-3-yl)benzaldehyde; 3-(3,5-dimethylisoxazol-4-yl)benzaldehyde; 3'-fluoro-[1,1'-biphenyl]-4-carbaldehyde; 4-methyl-3-oxo-3,4-dihydro-2H-benzo[b][1,4]oxazine-6-carbaldehyde; 2-methyl-3-oxo-3,4-dihydro-2H-benzo[b][1,4]oxazine-6-carbaldehyde; 3-oxo-3,4-dihydroquinoxaline-6-carbaldehyde; 1-methyl-3-oxo-1,2,3,4-tetrahydroquinoxaline-6-carbaldehyde; 2-oxo-1,2-dihydroquinoline-7-carbaldehyde; 6-(2-methoxyethoxy)-2-naphthaldehyde; 3-(ethylamino)-1H-indazole-6-carbaldehyde; 4-formyl-1H-indole-6-carbonitrile; N-(5-formylpyridin-3-yl)methanesulfonamide; 3-formyl-N-methylbenzenesulfonamide; (3-formylphenyl)methanesulfonamide; 5-formyl-N-methylpyridine-3-sulfonamide; 5-((2-fluorophenyl)ethynyl)thiophene-2-carbaldehyde; 1-acetylindoline-4-carbaldehyde; 5-(o-tolylethynyl)thiophene-2-carbaldehyde; 3'-methoxy-[1,1'-biphenyl]-4-carbaldehyde; 3-methoxy-4-morpholinobenzaldehyde; 3-nitrobenzaldehyde; 4'-methoxy-[1,1'-biphenyl]-4-carbaldehyde; 4'-methoxy-[1,1'-biphenyl]-3-carbaldehyde; N-(3-formylbenzyl)cyclopropanecarboxamide; (R)-2-(hydroxymethyl)-3,4-dihydro-2H-benzo[b][1,4]oxazine-6-carbaldehyde; N,N-diethyl-4-formylbenzamide; 3'-methoxy-[1,1'-biphenyl]-3-carbaldehyde; 1-(1-phenylpropan-2-yl)-1H-pyrazole-4-carbaldehyde; N-(3-formylbenzyl)methanesulfonamide; 2-(3-formylphenyl)-N-isopropylacetamide; N-cyclopropyl-2-(3-formylphenyl)acetamide; 3-((ethylsulfonyl)methyl)benzaldehyde; 3-formyl-N-isobutylbenzamide; 4-((4-methylpiperazin-1-yl)methyl)benzaldehyde; 2-acetyl-1,2,3,4-tetrahydroisoquinoline-6-carbaldehyde; 2-acetyl-1,2,3,4-tetrahydroisoquinoline-7-carbaldehyde; 1-(3-methoxybenzyl)-1H-pyrazole-4-carbaldehyde; 1-(4-methoxybenzyl)-1H-pyrazole-4-carbaldehyde; 5-((2-chlorophenyl)ethynyl)thiophene-2-carbaldehyde; N,N-diethyl-3-formylbenzamide; 3-(pyrrolidine-1-carbonyl)benzaldehyde; 5-((2-methylthiazol-4-yl)ethynyl)thiophene-2-carbaldehyde; N-cyclopropyl-3-formyl-4-methylbenzamide; 3,3-dimethyl-2-oxoindoline-6-carbaldehyde; 4-ethoxy-3-formylbenzenesulfonamide; 4-(piperidine-1-carbonyl)benzaldehyde; 1-methyl-2-oxo-2,3-dihydro-1H-benzo[d]imidazole-5-carbaldehyde; 2-oxo-2,3-dihydro-1H-benzo[d]imidazole-5-carbaldehyde; N-(4-fluoro-3-formylbenzyl)cyclopropanecarboxamide; N-(2-(dimethylamino)ethyl)-4-formylbenzamide; 4-(morpholine-4-carbonyl)benzaldehyde; 3-(piperazine-1-carbonyl)benzaldehyde; 4-(piperazine-1-carbonyl)benzaldehyde; 3-formyl-N-(2-hydroxyethyl)benzenesulfonamide; 3-((4-formyl-1H-pyrazol-1-yl)methyl)benzonitrile; 1-(3-formyl-2-methylphenyl)-3-isopropylurea; 1-cyclopropyl-3-(3-formyl-2-methylphenyl)urea; N-(3-formyl-2-methylphenyl)azetidine-1-carboxamide; N-(3-formylbenzyl)azetidine-3-carboxamide; N-(3-formylbenzyl)cyclobutanecarboxamide; 2-(3-formylphenyl)-N-isobutylacetamide; N-(3-formylphenyl)-1,2,3-thiadiazole-4-carboxamide; N-(3-formylphenyl)isoxazole-5-carboxamide; N-cyclopentyl-3-formylbenzamide; N,N-diethyl-2-(4-formylphenyl)acetamide; 3-methyl-2-oxo-2,3-dihydro-1H-benzo[d]imidazole-5-carbaldehyde; 3-(1-hydroxyethyl)-1H-indazole-6-carbaldehyde; 2'-oxospiro[cyclopropane-1,3'-indoline]-6'-carbaldehyde; 1,3-dimethyl-2-oxo-2,3-dihydro-1H-benzo[d]imidazole-5-carbaldehyde, 2,2-dimethyl-3-oxoindoline-6-carbaldehyde; N-(2-aminoethyl)-3-formylbenzenesulfonamide; 3-((3-aminopropyl)sulfonyl)benzaldehyde; N-(sec-butyl)-2-(3-formylphenyl)acetamide; 1-(2-cyanoethyl)-3-(3-formyl-2-methylphenyl)urea; 2-cyclopropyl-1H-pyrrolo[2,3-b]pyridine-4-carbaldehyde; 5-((3-fluorophenyl)ethynyl)thiophene-2-carbaldehyde; N-(5-formyl-2-methoxypyridin-3-yl)-2-hydroxypropanamide; 5-(morpholine-4-carbonyl)nicotinaldehyde; 5-(m-tolylethynyl)thiophene-2-carbaldehyde; 3-formyl-N-phenylbenzamide; N-(3-formyl-2-methylphenyl)pyrrolidine-1-carboxamide; N-(3-formylbenzyl)cyclopentanecarboxamide; 3-(1,4-diazepane-1-carbonyl)benzaldehyde; 4-(1,4-diazepane-1-carbonyl)benzaldehyde; 3-(2-morpholino-2-oxoethyl)benzaldehyde; 2-(3-formylphenyl)-N-(1-methoxypropan-2-yl)acetamide; N-(2,3-dihydroxypropyl)-2-(3-formylphenyl)acetamide; 2-(4-formyl-1H-pyrazol-1-yl)-N-phenylacetamide; 4-fluoro-2-((4-formyl-1H-pyrazol-1-yl)methyl)benzonitrile; 1-(2,5-dichlorobenzyl)-1H-pyrazole-4-carbaldehyde; 1-(quinolin-8-ylmethyl)-1H-pyrazole-4-carbaldehyde; 1-(3-formyl-2-methylphenyl)-3-isobutylurea; N-(3-formyl-2-methylphenyl)-1,2,3-thiadiazole-4-carboxamide; N-(3-formyl-2-methylphenyl)isoxazole-5-carboxamide; N-(3-formylphenyl)isonicotinamide; N-(3-formylphenyl) nicotinamide; N-(3-formylphenyl)benzamide; 3-formyl-N-(pyrrolidin-3-ylmethyl)benzamide; 3-formyl-N-(pyrrolidin-2-ylmethyl)benzamide; 3-formyl-N-(piperidin-4-yl)benzamide; 3-((2,5-dioxoimidazolidin-1-yl)methyl)benzaldehyde; 3-(3,5-dimethyl-1H-pyrazol-4-yl)benzaldehyde; 3-(1,3,5-trimethyl-1H-pyrazol-4-yl)benzaldehyde; 2,2-difluoro-3-oxo-3,4-dihydro-2H-benzo[b][1,4]oxazine-6-carbaldehyde; 2,2-dimethyl-3-oxo-3,4-dihydro-2H-benzo[b][1,4]oxazine-6-carbaldehyde; 1-(2-hydroxy-2-methylpropyl)-1H-indazole-6-carbaldehyde; 6-formyl-1H-indazole-3-carboxamide; 2-((6-formylnaphthalen-2-yl)oxy)acetic acid; 1-(2,3-dimethoxybenzyl)-1H-pyrazole-4-carb aldehyde; 3-(4-methyl-2-(methylamino)thiazol-5-yl)benzaldehyde; 1,1-diethyl-3-(3-formyl-2-methylphenyl)urea; 2-(3-formylphenyl)-N-(pentan-3-yl)acetamide; 1-(sec-butyl)-3-(3-formyl-2-methylphenyl)urea; 5-formylpyridin-3-yl 2,2,2-trifluoroacetate; 3-((4-methoxybenzyl)amino)benzaldehyde; N-(5-formyl-2-methylpyridin-3-yl)methanesulfonamide; 5-((3-chlorophenypethynyl)thiophene-2-carbaldehyde; 4-((4-methoxybenzyl)amino)benzaldehyde; 3-(3,4-dichlorophenyl)isonicotinaldehyde; N-(3-formyl-2-methylphenyl)morpholine-4-carboxamide; N-(3-formyl-2-methylphenyl)nicotinamide; 3-formyl-N-(pyridin-4-ylmethyl)benzamide; 4-formyl-N-(pyridin-3-ylmethyl)benzamide; 3-(2-(5,6-dihydropyridin-1(2H)-yl)-2-oxoethyl)benzaldehyde; 1-(3-formyl-2-methylphenyl)-3-(1-methoxypropan-2-yl)urea; 5-formyl-N-(2-hydroxyethyl)-2-methoxybenzenesulfonamide; 2-(3-formylphenyl)-N,N-bis(2-hydroxyethyl)acetamide; N-(3-formyl-2-methylphenyl)-2,5-dihydro-1H-pyrrole-1-carboxamide; N-(3-formylphenyl)-2-phenylacetamide; N-(3-formyl-2-methylphenyl)picolinamide; 2-(3-formylphenyl)-N-(furan-2-ylmethyl)acetamide; N-ethyl-N-(3-formylphenyl)methanesulfonamide; N-benzyl-3-formylbenzamide; 3-(2-(azepan-1-yl)-2-oxoethypbenzaldehyde; 3-(2-(2-methylpiperidin-1-yl)-2-oxoethypbenzaldehyde; 3-(diethylamino)-1H-indazole-6-carbaldehyde; 1-(3-formyl-2-methylphenyl)-3-(pentan-3-yl)urea; N-(5-formyl-2-methoxypyridin-3-yl)methanesulfonamide; N-(2-chloro-5-formylpyridin-3-yl)methanesulfonamide; 1-(3-formylphenyl)-3-phenylurea, N-cyclopropyl-3-formylbenzenesulfonamide; N-(2-chloro-5-formylphenyl)methanesulfonamide; 1-(4-formylphenyl)-3-phenylurea; N-(5-formyl-2-methoxypyridin-3-yl)propane-1-sulfonamide; 6-(benzyloxy)-2-naphthaldehyde; 3-(4-hydroxypiperidine-1-carbonyl)benzaldehyde; 1-(ethylsulfonyl)-1H-indole-6-carbaldehyde; 3-(3-formyl-2-methylphenyl)-1,1-bis(2-hydroxyethyl)urea; N-(3-formyl-2-methylphenypazepane-1-carboxamide; 4-formyl-N-(2-(pyridin-4-yl)ethyl)benzamide; 3-(4-methylpiperazine-1-carbonyl)benzaldehyde; 2-(3-formylphenyl)-N-(1-hydroxy-2-methylpropan-2-yl)acetamide; 3-(2-(3-hydroxypyrrolidin-1-yl)-2-oxoethyl)benzaldehyde; (R)-3-hydroxy-3-methyl-2-oxoindoline-6-carbaldehyde; (S)-3-hydroxy-2,2-dimethylindoline-6-carbaldehyde; 1-(3-formyl-2-methylphenyl)-3-(tetrahydro-2H-pyran-4-yl)urea; 1-cyclohexyl-3-(3-formyl-2-methylphenyl)urea; 1-(3-formyl-2-methylphenyl)-3-phenylurea; N-(3-formyl-2-methylphenyl)-5,6-dihydropyridine-1(2H)-carboxamide; N-(3-formylbenzyl)cyclopropanesulfonamide; 3-(pyrrolidin-1-ylsulfonyl)benzaldehyde; 3-(thiazol-2-ylsulfonyl) benzaldehyde; N-(3-formylbenzyl)-N-methylethanesulfonamide; 2-(3-formylphenyl)-N-(tert-pentyl)acetamide; 3-(1H-pyrrolo[2,3-b]pyridin-4-yl)benzaldehyde; 3-(2-hydroxypropan-2-yl)-1H-indazole-6-carbaldehyde; 2-(methylsulfonyl)-1,2,3,4-tetrahydroisoquinoline-7-carbaldehyde; 1-(3,5-dimethoxybenzyl)-1H-pyrazole-4-carbaldehyde; N1-ethyl-N4-(3-formylphenyl)succinamide; 3-((diethylamino)methyl)-1H-indazole-6-carbaldehyde; N,N-diethyl-5-formylpyridine-3-sulfonamide; N-(5-formyl-2-methoxypyridin-3-yl)ethanesulfonamide; 2-(tert-butyl)-1H-pyrrolo[2,3-b]pyridine-4-carbaldehyde; 4-(2-amino-1-hydroxy-2-(pyridin-3-yl)ethypbenzaldehyde; N-(3-formylphenyl)-2-methoxybenzamide; N-(4'-formyl-[1,1'-biphenyl]-3-yl)acetamide; (S)-2-(3-formylphenyl)-N-(1-hydroxypropan-2-yl)acetamide; 1-(3-formylphenyl)-3-(2-(methylthio)phenyl)urea; 1-(3-formyl-2-methylphenyl)-3-(tert-pentyl)urea; 3-((4-acetylpiperazin-1-yl)methyl)benzaldehyde; 3-formyl-N-(1-methylpiperidin-4-yl)benzamide; 3-formyl-N-(6-hydroxypyridin-3-yl)benzamide; N-(4-fluorophenyl)-3-formylbenzamide; 3-formyl-N-(p-tolyl)benzamide; 3-(3-oxopiperazine-1-carbonyl)benzaldehyde; N-(2-(dimethylamino)ethyl)-2-(3-formylphenyl)-N-methylacetamide; 3-(2-(4-methylpiperazin-1-yl)-2-oxoethyl)benzaldehyde; 3-(2-(4-hydroxypiperidin-1-yl)-2-oxoethypbenzaldehyde; 3-(2-(3-hydroxypiperidin-1-yl)-2-oxoethypbenzaldehyde; N-(3'-formyl-[1,1'-biphenyl]-3-yl)acetamide; 1-(2-cyanoethyl)-1-ethyl-3-(3-formyl-2-methylphenyl)urea; 1-(4-(1H-pyrazol-1-yl)benzyl)-1H-pyrazole-4-carbaldehyde; methyl 4-((4-formyl-1H-pyrazol-1-yl)methyl)benzoate; 1-(2-(trifluoromethoxy)benzyl)-1H-pyrazole-4-carbaldehyde; 1-(3-(1H-pyrrol-1-yl)benzyl)-1H-pyrazole-4-carbaldehyde; 1-(3-formyl-2-methylphenyl)-3-(2,2,2-trifluoroethyl)urea; 1-(3-formyl-2-methylphenyl)-3-(1-hydroxy-2-methylpropan-2-yl)urea; N-(3-formyl-2-methylphenyl)-3-hydroxypyrrolidine-1-carboxamide; 4-((3-formylphenyl)amino)cyclohexanecarboxylic acid; N-(3-formyl-2-methylphenyl)-2-(hydroxymethyl)piperidine-1-carboxamide; (S)-2-(3-formylphenyl)-N-(2-hydroxypropyl)acetamide; 3-formyl-N-(thiazol-2-yl)benzenesulfonamide; 3-formyl-N-(pyrrolidin-1-yl)benzenesulfonamide; 3-(piperazin-1-ylsulfonyl)benzaldehyde; 4-fluoro-N-(3-formylphenyl)benzamide; N-(3-formylphenyl)-4-methylbenzamide; 4-((4-acetylpiperazin-1-yl)methyl)benzaldehyde; 3-(2-(4-methylpiperidin-1-yl)-2-oxoethyl)benzaldehyde; methyl 3-((4-formyl-1H-pyrazol-1-yl)methyl)benzoate; 2-ethyl-N-(3-formyl-2-methylphenyl)piperidine-1-carboxamide; 1-(2-chlorophenyl)-3-(4-formylphenyl)urea; 5-(morpholinosulfonyl)nicotinaldehyde; 3-(morpholinosulfonyl)benzaldehyde; 1-(4-formylphenyl)-3-(2-methoxyphenyl)urea; N-(3-formyl-2-methylphenyl)-3-(pyridin-3-yl)acrylamide; 6-chloro-N-(3-formylphenyl)nicotinamide; 3-formyl-N-((6-hydroxypyridin-3-yl)methyl)benzamide; 3-(indoline-1-carbonyl)benzaldehyde; 3-(3-formyl-2-methylphenyl)-1,1-bis(2-methoxyethyl)urea; 3-(2-(4-methoxypiperidin-1-yl)-2-oxoethyl)benzaldehyde; 4-ethyl-N-(3-formylphenyl)benzamide; (S)-1-(3-formyl-2-methylphenyl)-3-(2-hydroxypropyl)urea; 3-(4-(2-hydroxyethyl)piperazine-1-carbonyl)benzaldehyde; 1-(2-(dimethylamino)ethyl)-3-(3-formyl-2-methylphenyl)-1-methylurea; 1-(3-formyl-2-methylphenyl)-3-(4-methyloxazol-2-yl)urea; 1-(3-formyl-2-methylphenyl)-3-(1H-pyrazol-3-yl)urea; N-(3-formyl-2-methylphenyl)-4-methylpiperazine-1-carboxamide; N-(3- formyl-2-methylphenyl)-4-hydroxypiperidine-1-carboxamide; N-(3-formyl-2-methylphenyl)-3-hydroxypiperidine-1-carboxamide; N-(3-formyl-2-methylphenyl)-4-methylpiperidine-1-carboxamide; N-(3-formyl-2-methylphenyl)-6-hydroxynicotinamide; N-(3-formyl-2-methylphenyl)-1,3-dimethyl-1H-pyrazole-5-carboxamide; N-(4-fluorophenyl)-2-(3-formylphenyl)acetamide; 3-formyl-N-phenylbenzenesulfonamide; N-(3-formylphenyl)-N-methylcyclopropanesulfonamide; N-(3-formylphenyl)-4-hydroxy-6-methylnicotinamide; 3-(2-(2,5-dimethyl-2,5-dihydro-1H-pyrrol-1-yl)-2-oxoethyl)benzaldehyde; 3-(5-cyclopropyl-3-methyl-1H-pyrazol-4-yl)benzaldehyde; 6-formyl-N,N-dimethyl-1H-indazole-3-carboxamide; 6-formyl-N,N-dimethyl-1H-indole-3-carboxamide; 6-(2-((tetrahydro-2H-pyran-2-yl)oxy)ethoxy)-2-naphthaldehyde; N-ethyl-3-((4-formyl-1H-pyrazol-1-yl)methyl)benzamide; N-ethyl-4-((4-formyl-1H-pyrazol-1-yl)methyl)benzamide; 3-(2-(4-ethylpiperazin-1-yl)-2-oxoethyl)benzaldehyde; N-(5-formylpyridin-3-yl)benzenesulfonamide; N-(4-formylphenyl)-3-methoxybenzamide; N-(5-formyl-2-hydroxypyridin-3-yl)cyclopropanesulfonamide; 3-(methylsulfonyl)-1H-pyrazolo[3,4-b]pyridine-5-carbaldehyde; 1-(3-formylphenyl)-3-(m-tolyl)urea; N-(3-formylphenyl)benzenesulfonamide; N-(3-formylphenyl)-3-methoxybenzamide; 1-(4-chlorophenyl)-3-(3-formylphenyl)urea; 1-(3-formyl-2-methylphenyl)-3-(4-hydroxycyclohexyl)urea; 1-(4-fluorophenyl)-3-(3-formyl-2-methylphenyl)urea; N-(3-formyl-2-methylphenyl)-2,5-dimethyl-2,5-dihydro-1H-pyrrole-1-carboxamide; (S)-N-(3-formylbenzyl)pyrrolidine-2-carboxamide; N-(4,4-dimethylpent-2-yn-1-yl)-2-(3-formylphenyl)acetamide; N-(4-cyanophenyl)-3-formylbenzamide; 3-formyl-N-(4-((methylamino)methyl)phenyl)benzamide; 1-(cyclopropylmethyl)-3-(3-formyl-2-methylphenyl)-1-propylurea; (S)-1-(3-formyl-2-methylphenyl)-3-(1-hydroxypropan-2-yl)urea; N-(3-formyl-2-methylphenyl)-4-(hydroxymethyl)piperidine-1-carboxamide; N-(3-formyl-2-methylphenyl)-3-(hydroxymethyl)piperidine-1-carboxamide; 3-(3-formyl-2-methylphenyl)-1-methyl-1-phenylurea; 1-(3-formyl-2-methylphenyl)-3-(1-(hydroxymethyl)cyclopentyl)urea; N-(3-formyl-2-methylphenyl)-4-methyl-1,4-diazepane-1-carboxamide; N-(3-formyl-2-methylphenyl)-2-hydroxy-6-methylnicotinamide; 3-formyl-N-(2,2,2-trifluoroethyl)benzenesulfonamide; 3-((3-aminopyrrolidin-1-yl)sulfonyl)benzaldehyde; N-(3-chlorobenzyl)-3-formylbenzamide; 3-(1,2,3,4-tetrahydroisoquinoline-2-carbonyl)benzaldehyde; 2-(3-formylphenyl)-N,N-diisopropylacetamide; 4-cyano-N-(3-formylphenyl)benzamide; N-(3-formyl-2-methylphenyl)-4-(methylthio)benzamide; N-(3-((4-formyl-1H-pyrazol-1-yl)methyl)phenyl)-2-methoxyacetamide; 4-ethyl-N-(3-formyl-2-methylphenyl)piperazine-1-carboxamide; 1-(4-chlorophenyl)-3-(4-formylphenyl)urea; 1-(3-chlorophenyl)-3-(3-formylphenyl)urea; 3-(2-(isoindolin-2-yl)-2-oxoethyl)benzaldehyde; N-(5-formyl-2-methoxypyridin-3-yl)cyclopropanesulfonamide; N-(5-formyl-2-methoxypyridin-3-yl)propane-2-sulfonamide; N-(2-chloro-5-formylpyridin-3-yl)cyclopropanesulfonamide; N-benzyl-3-formylbenzenesulfonamide; 1-(4-formylphenyl)-3-(3-methoxyphenyl)urea; N-(4-formyl-1H-indol-6-yl)methanesulfonamide; N-(3-formyl-2-methylphenyl)-4-methoxybenzamide; 1-(2-(1H-imidazol-5-yl)ethyl)-3-(3-formyl-2-methylphenyl)urea; 1-(3-chlorophenyl)-3-(3-formylphenyl)urea; 1-(3-formylphenyl)-3-(2-methoxy-5-methylphenyl)urea; 6-formyl-N-(2-hydroxyethyl)-N-methyl-1H-indazole-3-carboxamide; 6-formyl-N-(2-hydroxyethyl)-N-methyl-1H-indole-3-carboxamide; 1-(4-(methylsulfonyl)benzyl)-1H-pyrazole-4-carbaldehyde; 1-(3-chloro-2-fluorophenyl)-3-(3-formylphenyl)urea; 1-(3-formylphenyl)-3-(2-methoxy-6-methylphenyl)urea; N-(3-formyl-2-methylphenyl)benzofuran-2-carboxamide; 3-formyl-N-(3-(pyrrolidin-1-yl)propyl)benzenesulfonamide; 3-((4-methylpiperazin-1-yl)sulfonyl)benzaldehyde; 4'-carbamoyl-2'-formyl-[1,1'-biphenyl]-2-carboxylic acid; N-(6-formyl-1H-indol-3-yl)ethanesulfonamide; 3-((3-(methylamino)pyrrolidin-1-yl)sulfonyl)benzaldehyde; 1-ethyl-3-(3-formyl-2-methylphenyl)-1-phenylurea; N-butyl-N-(3-formylphenyl)benzamide; 4,4-dimethylpent-2-yn-1-yl(3-formyl-2-methylphenyl)carbamate; 1-(4,4-dimethylpent-2-yn-1-yl)-3-(3-formyl-2-methylphenyl)urea; N-(3-formyl-2-methylphenyl)isoindoline-2-carboxamide; 4-ethoxy-N-(3-formyl-2-methylphenyl)benzamide; N-(3-formylphenyl)-4-isopropylbenzamide; (S)-2-(3-formylphenyl)-N-(1-hydroxy-3-methylbutan-2-yl)acetamide; 3-formyl-N-(4-(1-hydroxyethyl)phenyl)benzamide; 1-(3-formylbenzoyl)piperidine-4-carboxylic acid; (S)-N-(3-formyl-2-methylphenyl)-2-(hydroxymethyl)pyrrolidine-1-carboxamide; 4-methoxy-3-(morpholinosulfonyl)benzaldehyde; 4-methoxy-3-((tetrahydro-2H-pyran-4-yl)sulfonyl)benzaldehyde; 1-(2,3-dihydro-1H-inden-1-yl)-3-(3-formyl-2-methylphenyl)urea; N-(3-formyl-2-methylphenyl)-2,6-dimethylmorpholine-4-carboxamide; N-(3-formyl-2-methylphenyl)-3,5-dimethylpiperidine-1-carboxamide; N-(3-formyl-2-methylphenyl)-3,4-dihydroquinoline-1(2H)-carboxamide; N-(3-formyl-2-methylphenyl)quinoline-3-carboxamide; 3-formyl-N-(p-tolyl)benzenesulfonamide; (S)-3-(pyrrolidin-3-ylsulfonyl)benzaldehyde; 6-(dimethylamino)-N-(3-formylphenyl)nicotinamide; 4-bromo-N-(3-formylphenyl)-3-methylbenzamide; (E)-2-oxo-3-(thiazol-4-ylmethylene)indoline-6-carbaldehyde; 1-(3-formyl-2-methylphenyl)-3-(1-phenylpropyl)urea; N-(2-ethoxy-5-formylpyridin-3-yl)benzenesulfonamide; 1-(5-chloro-2-methoxyphenyl)-3-(3-formylphenyl)urea; N-(5-formyl-2-methoxypyridin-3-yl)thiophene-2-sulfonamide; N-(5-formyl-2-hydroxypyridin-3-yl)benzenesulfonamide; N-(3-formylphenyl)-4-methylbenzenesulfonamide; N-(3-formyl-2-methylphenyl)-3-isopropoxyazetidine-1-carboxamide; N-(3-formyl-2-methylphenyl)-4-propoxybenzamide; 1-(3-chloro-4-fluorophenyl)-3-(3-formylphenyl)urea; 3'-nitro-[1,1'-biphenyl]-4-carbaldehyde; 4-(3-formylbenzamido)benzoic acid; 4-((3-formylphenyl)carbamoyl)benzoic acid; 5-(3-formylbenzamido)picolinic acid; 3-(3-formylbenzamido)benzoic acid; 3-(4-formylbenzamido)benzoic acid; N-(4-carbamoylphenyl)-3-formylbenzamide; N-(4-acetylphenyl)-3-formylbenzamide; N-(1H-benzo[d][1,2,3]triazol-5-yl)-3-formylbenzamide; 3-formyl-N-(1H-indazol-5-yl)benzamide; N-(1H-benzo[d]imidazol-5-yl)-3-formylbenzamide; N-(1H-benzo[d]imidazol-6-yl)-3-formylbenzamide; 3-formyl-N-(1H-indazol-6-yl)benzamide; 2-methyl-5-((5-methyl-1H-pyrazol-3-yl)amino)imidazo[1,2-c]pyrimidine-7-carbaldehyde; 1-(3-nitrobenzyl)-1H-pyrazole-4-carbaldehyde; N-(3-formyl-2-methylphenyl)-3-azabicyclo[3.2.2]nonane-3-carboxamide; N-(3-formyl-2-methylphenyl)-4-isopropylbenzamide; 4-acetyl-N-(3-formylphenyl)benzamide; 4-(3-formylbenzamido)cyclohexanecarboxylic acid; 4-(4-formylbenzamido)benzoic acid; N-(4-((dimethylamino)methyl)phenyl)-3-formylbenzamide; 2-(4-(3-formylbenzoyl)piperazin-1-yl)acetic acid; 3-(2-oxo-2-(1,4-dioxa-8-azaspiro[4.5]decan-8-yl)ethyp)benzaldehyde; tert-butyl 2-((6-formylnaphthalen-2-yl)oxy)acetate; (E)-2-oxo-3-(pyridin-4-ylmethylene)indoline-6-carbaldehyde; 4-(dimethylamino)-N-(3-formyl-2-methylphenyl)benzamide; N-(2-chloro-5- formylpyridin-3-yl)benzenesulfonamide; 6-chloro-5-((phenylsulfonyl)methyl)nicotinaldehyde; N-(5-formyl-2-methoxypyridin-3-yl)cyclohexanesulfonamide; 3-formyl-N-(4-(methylcarbamoyl)phenyl)benzamide; 4-cyclopropyl-N-(3-formyl-2-(hydroxymethyl)phenyl)benzamide; 5-formyl-N-(4-(methylcarbamoyl)phenyl)nicotinamide; 3-formyl-N-(4-(hydroxycarbamoyl)phenyl)benzamide; 4-(3-formylbenzamido)-3-methylbenzoic acid; 4-formyl-N-(4-(methylcarbamoyl)phenyl)picolinamide; 4-(3-formyl-2-methylbenzamido)benzoic acid; methyl 4-((3-formylphenyl)carbamoyl)benzoate; N1-(3-formylphenyl)-N4-methylterephthalamide; 4-((3-formylbenzamido)methyl)benzoic acid; 5-(3-formylbenzamido)-N-methylpicolinamide; (S)-1-(3-formyl-2-methylphenyl)-3-(1-hydroxy-3-methylbutan-2-yl)urea; 3-((4-formyl-1H-pyrazol-1-yl)methyl)-N-(thiazol-2-yl)benzamide; N-(3-formylphenyl)-2-(3-isopropylphenoxyl)acetamide; N-(3-formyl-2-methylphenyl)-1H-indole-3-carboxamide; N-(3-formyl-2-methylphenyl)-1-methyl-1H-indole-3-carboxamide; (S)-3-((3-hydroxypyrrolidin-1-yl)sulfonyl)benzaldehyde; methyl 4-(3-formylbenzamido)benzoate; 2-(4-(3-formylbenzamido)phenyl)acetic acid; 2,2,2-trifluoro-N-(5-formyl-2-methoxypyridin-3-yl)ethane-1-sulfonamide; 1-(5-chloro-2-(2-hydroxyethoxyl)phenyl)-3-(3-formylphenyl)urea; N-(2-chloro-5-formylpyridin-3-yl)-2-methylbenzenesulfonamide; 3-(2-(3-(tert-butoxy)azetidin-1-yl)-2-oxoethyl)benzaldehyde; N-(3-formyl-2-methylphenyl)-4-isopropoxybenzamide; 4-(tert-butyl)-N-(3-formylphenyl)benzamide; N-(3-formylphenyl)-4-(trifluoromethyl)benzamide; 3-formyl-N-(4-(piperazin-1-yl)phenyl)benzamide; N-(4-(tert-butyl)phenyl)-3-formylbenzamide; 3-((dimethylamino)methyl)-1-(ethylsulfonyl)-1H-indole-6-carbaldehyde; 1-benzyl-1-(2-cyanoethyl)-3-(3-formyl-2-methylphenyl)urea; 3-formyl-N-(4-(2-(methylamino)-2-oxoethyl)phenyl)benzamide; 4-(tert-butyl)-N-(5-formylpyridin-3-yl)benzamide; (R)-1-(3-formyl-2-methylphenyl)-3-(1-phenylethyl)urea; 1-(3-formyl-2-methylphenyl)-3-(2-(trifluoromethyl)phenyl)urea; N-(3-formyl-2-methylphenyl)-4-(pyrrolidin-1-yl)piperidine-1-carboxamide; 5-(tert-butyl)-N-(3-formyl-2-methylphenyl)oxazole-2-carboxamide; 6-(tert-butyl)-N-(3-formylphenyl)nicotinamide; N-(3-formylphenyl)-4-(2-hydroxypropan-2-yl)benzamide; 4-(3-formylbenzamido)-2-methoxybenzoic acid; 2-(3-formylphenyl)-N-(1-(4-methoxyphenyl)propan-2-yl)acetamide; ethyl 4-(3-formylbenzamido)benzoate; 3-(tert-butoxy)-N-(3-formyl-2-methylphenyl)azetidine-1-carboxamide; 1-(5-chloro-2-(2-(methylamino)ethoxy)phenyl)-3-(3-formylphenyl)urea; 3,3,3-trifluoro-N-(5-formyl-2-methoxypyridin-3-yl)propane-1-sulfonamide; N-(5-formyl-2-methoxypyridin-3-yl)-1H-pyrazole-4-sulfonamide; N-(5-formyl-2-methoxypyridin-3-yl)-1H-imidazole-4-sulfonamide; N-(5-formyl-2-methoxypyridin-3-yl)-2-methoxybenzenesulfonamide; 1-(5-chloro-2-(3-hydroxypropoxyl)phenyl)-3-(3-formylphenyl)urea; N-(3-formyl-2-methylphenyl)-4-isobutoxybenzamide; N-(5-formyl-2-methoxypyridin-3-yl)-4-methoxybenzenesulfonamide; 4-(tert-butyl)-N-(3-formyl-2-methylphenyl)benzamide; 1-(3-formylphenyl)-3-(3-(trifluoromethyl)phenyl)urea; 6-(tert-butyl)-N-(3-formyl-2-methylphenyl)nicotinamide; 3-(6-cyclopropyl-1-oxo-3,4-dihydroisoquinolin-2(1H)-yl)-2-(hydroxymethyl)benzaldehyde; (S)-N-(4-(1-aminoethyl)phenyl)-3-formylbenzamide; 1-(3-formyl)-3-(4-(trifluoromethyl)phenyl)urea; 2-fluoro-4-(3-formylbenzamido)benzoic acid; 4-(3-formylbenzamido)-2-methylbenzoic acid; N-(2-(2-(dimethylamino)ethoxy)-5-formylphenyl)cyclopropanesulfonamide; (S)-1-(3-formyl-2-methylphenyl)-3-(1-hydroxy-3,3-dimethylbutan-2-yl)urea; 4-(tert-butyl)-N-(2-fluoro-3-formylphenyl)benzamide; 4-(tert-butyl)-N-(3-formyl-4-methylphenyl)benzamide; 1-(3-formyl-2-methylphenyl)-3-(1-(4-methoxyphenyl)propan-2-yl)urea; N-(3-formyl-2-methylphenyl)-4-(2-hydroxypropan-2-yl)benzamide; N-(5-formyl-2-methoxypyridin-3-yl)-1,2-dimethyl-1H-imidazole-5-sulfonamide; N-(2-chloro-5-formylpyridin-3-yl)-N-methylbenzenesulfonamide; benzyl(2-chloro-5-formylpyridin-3-yl)carbamate; 6-chloro-5-(fluoro(phenylsulfonyl)methyl)nicotinaldehyde; 3-(benzyloxy)-N-(3-formyl-2-methylphenyl)azetidine-1-carboxamide; N-(4-(1H-pyrazol-4-yl)phenyl)-3-formylbenzamide; 5-formyl-2-methyl-N-(4-(methylcarbamoyl)phenyl)benzamide; N-(4-(1H-pyrazol-4-yl)phenyl)-5-formylnicotinamide; 3-fluoro-5-formyl-N-(4-(methylcarbamoyl)phenyl)benzamide; 1-(4-(tert-butyl)phenyl)-3-(3-formyl-2-methylphenyl)urea; N-(3-formyl-2-methylphenyl)-4-(3-methylazetidin-3-yl)benzamide; 2-(3-formylphenyl)-N-(5,5,5-trifluoro-4-hydroxy-4-methylpent-2-yn-1-yl)acetamide; 3-formyl-5-methyl-N-(4-(methylcarbamoyl)phenyl)benzamide; 4-(3-formylphenylsulfonamido)benzoic acid; N-(4-(1H-tetrazol-5-yl)phenyl)-3-formylbenzamide; N-(4-(1H-1,2,4-triazol-3-yl)phenyl)-3-formylbenzamide; N-(4-(1H-imidazol-2-yl)phenyl)-3-formylbenzamide; N-(4-(1H-imidazol-4-yl)phenyl)-3-formylbenzamide; N-(4-(1H-pyrazol-5-yl)phenyl)-3-formylbenzamide; N-(3-formyl-2-methylphenyl)-4-(3-methyloxetan-3-yl)benzamide; N1-(3-formylphenyl)-N4,N4-dimethylterephthalamide; N-(3-formylphenyl)-4-(1H-imidazol-2-yl)benzamide; 3-(7-(tert-butyl)-4-oxoquinazolin-3(4H)-yl)benzaldehyde; methyl 4-(3-formylbenzamido)-3-methylbenzoate; 2,4-difluoro-N-(5-formyl-2-methoxypyridin-3-yl)benzenesulfonamide; N-(2-chloro-5-formylpyridin-3-yl)-5-fluoro-2-methylbenzenesulfonamide; N-(2-chloro-5-formylpyridin-3-yl)-2,5-dimethylbenzenesulfonamide; N-(3-formyl-2-methylphenyl)-4-(trifluoromethoxy)benzamide; N-(4-formyl-1H-indol-6-yl)benzenesulfonamide; N-(5-formyl-2-methoxypyridin-3-yl)-3-methoxybenzenesulfonamide; N-(3-formyl-2-methylphenyl)-4-phenoxybenzamide; 4-(tert-butyl)-N-(5-formyl-2-methylphenyl)benzamide; 1-(2-chloro-5-(trifluoromethyl)phenyl)-3-(3-formylphenyl)urea; 3-formyl-N-(2-methyl-4-(1H-pyrazol-4-yl)phenyl)benzamide; 4-(tert-butyl)-N-(2-fluoro-5-formylphenyl)benzamide; 3-formyl-N-(3-(N-methylsulfamoyl)phenyl)benzamide; 3-formyl-N-(4-(N-methylsulfamoyl)phenyl)benzamide; N-(2-fluoro-5-formylphenyl)-4,5,6,7-tetrahydro-4,7-methanobenzo[b]thiophene-2-carboxamide; N-(3-formyl-2-methylphenyl)-4-(methylsulfonyl)benzamide; N-(3-formyl-2-methylphenyl)-4-(1H-imidazol-2-yl)benzamide; 3-(7-(tert-butyl)-4-oxoquinazolin-3(4H)-yl)-2-methylbenzaldehyde; 3-(2-((2R,6S)-2,6-dimethylpiperidin-1-yl)-2-oxoethyp)benzaldehyde; 1-(3-formyl-2-methylphenyl)-3-(2S,3R)-1-hydroxy-3-methylpentan-2-yl)urea; 4-(2-cyanopropan-2-yl)-N-(3-formyl-2-methylphenyl)benzamide; 1-(5-chloro-2-(2-(dimethylamino)ethoxy)phenyl)-3-(3-formylphenyl)urea; N-(5-formyl-2-methoxypyridin-3-yl)-2-(4-methylpiperazin-1-yl)ethane-1-sulfonamide; N-(5-formyl-2-methoxypyridin-3-yl)-2-methyl-1H-imidazole-4-sulfonamide; N-(2-chloro-5-formylpyridin-3-yl)-2-methoxy-5-methylbenzenesulfonamide; 4-(2-(dimethylamino)-2-oxoethyl)-N-(3-formyl-2-methylphenyl)piperazine-1-carboxamide; N-(5-formyl-2-(2-morpholinoethoxy)phenyl)cyclopropanesulfonamide; 4-(tert-butyl)-N-(5-formyl-2-methoxyphenyl)benzamide; 1-(3-formyl-2-methylphenyl)-3-(4-(methylsulfonyl)cyclohexyl)urea; N-(3-formyl-2- methylphenyl)-4-(trimethylsilyl)benzamide; 1-(2-(1,3-dioxolan-2-yl)methoxy)-5-chlorophenyl)-3-(3-formylphenyl)urea; 3-formyl-N-(3-methyl-4-(1H-pyrazol-4-yl)phenyl)benzamide; 1-(3-formylphenyl)-3-(2-(2-hydroxyethoxy)-5-(trifluoromethyl)phenyl)urea; 4-(4-chlorobenzyl)-N-(3-formyl-2-methylphenyl)piperazine-1-carboxamide; 4-(1-(3-formylbenzamido)-2-methylpropan-2-yl)benzoic acid; 1-(3-formylphenyl)-3-(2-(3-hydroxypropoxy)-5-(trifluoromethyl)phenyl)urea; 3-(N-(5-formyl-2-methoxypyridin-3-yl)sulfamoyl)benzoic acid; 4-(N-(5-formyl-2-methoxypyridin-3-yl)sulfamoyl)benzoic acid; 1-(3-formylphenyl)-3-(2-(2-methoxyethoxy)-5-(trifluoromethyl)phenyl)urea; 1-(3-formylphenyl)-3-(2-(2-(methylamino)ethoxy)-5-(trifluoromethyl)phenyl)urea, (4aS,8aS)-N-(3-formyl-2-methylphenyl)octahydroisoquinoline-2(1H)-carboxamide; benzyl 4-(3-formylbenzamido)benzoate; 3-((1-(4-(tert-butyl)phenyl)-2,2,2-trifluoroethyl)amino)-2-methylbenzaldehyde; 1-(2,4-dimethoxy-5-(trifluoromethyl)phenyl)-3-(3-formylphenyl)urea; 1-(3-formylphenyl)-3-(2-(3-(methylamino)propoxy)-5-(trifluoromethyl)phenyl)urea; 1-(3-formylphenyl)-3-(2-isopropoxy-5-(trifluoromethyl)phenyl)urea; 1-(3-formylphenyl)-3-(2-methoxy-5-nitrophenyl)urea; 3-formyl-N-(4-((methylsulfonyl)carbamoyl)phenyl)benzamide; N-(3-formyl-2-methylphenyl)-4-(1,1,1-trifluoro-2-hydroxypropan-2-yl)benzamide; 2-(2-(3-(3-formylphenyl)ureido)-4-(trifluoromethyl)phenoxy)acetic acid; 1-(2-(2-(dimethylamino)ethoxy)-5-(trifluoromethyl)phenyl)-3-(3-formylphenyl)urea; 1-(2,4-diethoxy-5-(trifluoromethyl)phenyl)-3-(3-formylphenyl)urea; N-(3-formyl-2-methylphenyl)-4-(2-(trifluoromethyl)benzyl)piperazine-1-carboxamide; 3-(2-(3-((1,1,1,3,3,3-hexafluoropropan-2-yl)oxy)azetidin-1-yl)-2-oxoethyl)benzaldehyde; N-(3-formyl-2-methylphenyl)-3-((1,1,1,3,3,3-hexafluoropropan-2-yl)oxy)azetidine-1-carboxamide; 1-(3-formylphenyl)-3-(2-(2-(pyrrolidin-1-yl)ethoxy)-5-(trifluoromethyl)phenyl)urea; 1-(3-formylphenyl)-3-(2-(2-morpholinoethoxy)-5-(trifluoromethyl)phenyl)urea; 4-chloro-N-(5-formyl-2-methoxypyridin-3-yl)-3-(trifluoromethyl)benzenesulfonamide; 1-(3-formylphenyl)-3-(2-(2-(piperazin-1-yl)ethoxy)-5-(trifluoromethyl)phenyl)urea; 4-(3-formylbenzamido)-2-(2-morpholinoethyl)benzoate; N-(3-formyl-2-methylphenyl)-4-(1,1,1,3,3,3-hexafluoro-2-hydroxypropan-2-yl)benzamide.

Furthermore preferably, $R^2$ may be derived from the corresponding nitriles, carboxylic acids, and carboxylic acid halides (e.g. carboxylic acid chlorides) instead of the above named aldehydes.

Moreover preferably, $R^2$ may be derived from the following compounds (e.g. aldehydes, nitriles, carboxylic acids or carboxylic acid halides):
ethyl carbonocyanidate; pyridazine-4-carbaldehyde; 1-methyl-1H-1,2,4-triazole-3-carbonitrile; 1-methyl-1H-pyrazole-3-carbaldehyde; 1H-indazole-5-carbaldehyde; isobutyric acid; 3-formylbenzoic acid; oxazole-2-carbaldehyde; pivalic acid; 3-formyl-N-(4-(oxazol-5-yl)phenyl)benzamide; N-(4-(2H-1,2,3-triazol-2-yl)phenyl)-3-formylbenzamide; 3-formyl-N-(4-(oxazol-2-yl)phenyl)benzamide; 1-isobutyl-1H-pyrazole-4-carboxylic acid; butyric acid; cycloheptanecarboxylic acid; 1-(2-methoxyethyl)-1H-pyrazole-4-carboxylic acid; 1H-pyrazole-4-carbaldehyde; 3-methoxybenzaldehyde; benzo[d]thiazole-2-carbaldehyde; 1-isopropyl-1H-pyrazole-4-carboxylic acid; 3-formylbenzenesulfonamide; 3,5-dimethylisoxazole-4-carbaldehyde; 2,2,2-trifluoroacetic acid; benzo[d]oxazole-2-carbaldehyde; 1-benzyl-1H-pyrazole-4-carboxylic acid; 3-(pyridin-3-yl)benzaldehyde; bicyclo[4.1.0]heptane-7-carboxylic acid; 2-fluoro-6-methylbenzaldehyde; 2,2-dimethylcyclopropanecarboxylic acid; 4,5,6,7-tetrahydrobenzo[d]thiazole-2-carboxylic acid; 2-phenylcyclopropanecarboxylic acid; 1-(3-methylbutan-2-yl)-1H-pyrazole-4-carboxylic acid; 2-chloro-6-fluorobenzaldehyde; 2-(methylsulfonyl)benzaldehyde; 3-aminobenzaldehyde; 2-aminobenzaldehyde; 2-amino-6-fluorobenzaldehyde; 3-nitrobenzaldehyde; 2-nitrobenzaldehyde; 2-fluoro-6-nitrobenzaldehyde; thiazole-2-carbaldehyde.

Especially preferred are compounds of formula (I) that are selected from: N-(2-(7-((4-morpholinophenyl)amino)-1H-pyrazolo[4,3-d]pyrimidin-5-yl)phenyl)methanesulfonamide; N-(2-(7-((3,4-dimethoxyphenyl)amino)-1H-pyrazolo[4,3-d]pyrimidin-5-yl)phenyl)methanesulfonamide; N-(2-(7-((3-(methylsulfonyl)phenyl)amino)-1H-pyrazolo[4,3-d]pyrimidin-5-yl)phenyl)methanesulfonamide; N-(1H-indazol-6-yl)-5-(3-nitrophenyl)-1H-pyrazolo[4,3-d]pyrimidin-7-amine; N-(4-morpholinophenyl)-5-(3-nitrophenyl)-1H-pyrazolo[4,3-d]pyrimidin-7-amine; 1-(4-(4-((5-(3-nitrophenyl)-1H-pyrazolo[4,3-d]pyrimidin-7-yl)amino)phenyl)piperazin-1-yl)ethan-1-one; 5-(3-aminophenyl)-N-(3,4-dimethoxyphenyl)-1H-pyrazolo[4,3-d]pyrimidin-7-amine; N-(3,4-dimethoxyphenyl)-5-(5-methylthiophen-2-yl)-1H-pyrazolo[4,3-d]pyrimidin-7-amine; 5-(5-methylthiophen-2-yl)-N-(4-morpholinophenyl)-1H-pyrazolo[4,3-d]pyrimidin-7-amine; N-(4-(4-(tert-butyl)piperazin-1-yl)phenyl)-5-(2,6-difluorophenyl)-1H-pyrazolo[4,3-d]pyrimidin-7-amine; 5-(2,6-difluorophenyl)-N-(3-fluoro-4-morpholinophenyl)-1H-pyrazolo[4,3-d]pyrimidin-7-amine; 5-(2,6-difluorophenyl)-N-(3-methoxy-4-morpholinophenyl)-1H-pyrazolo[4,3-d]pyrimidin-7-amine; 1-(4-(4-((5-(2,6-difluorophenyl)-1H-pyrazolo[4,3-d]pyrimidin-7-yl)amino)phenyl)piperazin-1-yl)ethan-1-one; 1-(4-(4-((5-(3-aminophenyl)-1H-pyrazolo[4,3-d]pyrimidin-7-yl)amino)phenyl)piperazin-1-yl)ethan-1-one; methyl 3-(7-(benzo[d][1,3]dioxol-5-ylamino)-1H-pyrazolo[4,3-d]pyrimidin-5-yl)benzoate; N-(benzo[d][1,3]dioxol-5-yl)-5-(3-nitrophenyl)-1H-pyrazolo[4,3-d]pyrimidin-7-amine; 6-((5-(thiophen-2-yl)-1H-pyrazolo[4,3-d]pyrimidin-7-yl)amino)-2,3-dihydrobenzo[b]thiophene 1,1-dioxide; 5-cyclopropyl-N-(4-morpholinophenyl)-1H-pyrazolo[4,3-d]pyrimidin-7-amine; 5-cyclopropyl-N-(3,4-dimethoxyphenyl)-1H-pyrazolo[4,3-d]pyrimidin-7-amine; 5-cyclopropyl-N-(3-(methylsulfonyl)phenyl)-1H-pyrazolo[4,3-d]pyrimidin-7-amine; 6-((5-cyclopropyl-1H-pyrazolo[4,3-d]pyrimidin-7-yl)amino)-2H-benzo[b][1,4]oxazin-3(4H)-one; 7-((5-cyclopropyl-1H-pyrazolo[4,3-d]pyrimidin-7-yl)amino)-3,4-dihydroquinolin-2(1H)-one; N-(4-(4-(tert-butyl)piperazin-1-yl)phenyl)-5-(2-fluorophenyl)-1H-pyrazolo[4,3-d]pyrimidin-7-amine; N-(3-fluoro-4-morpholinophenyl)-5-(2-fluorophenyl)-1H-pyrazolo[4,3-d]pyrimidin-7-amine; 5-(2-fluorophenyl)-N-(3-methoxy-4-morpholinophenyl)-1H-pyrazolo[4,3-d]pyrimidin-7-amine; 1-(4-(4-((5-(2-fluorophenyl)-1H-pyrazolo[4,3-d]pyrimidin-7-yl)amino)phenyl)piperazin-1-yl)ethan-1-one; 2-(4-((5-(2-fluorophenyl)-1H-pyrazolo[4,3-d]pyrimidin-7-yl)amino)phenyl)-2-methylpropanenitrile; 2-(4-(5-(2,6-difluorophenyl)-1H-pyrazolo[4,3-d]pyrimidin-7-yl)amino)phenyl)-2-methylpropanenitrile; N-(2-(7-((4-(4-(4-methylpiperazin-1-yl)piperidin-1-yl)phenyl)amino)-1H-pyrazolo[4,3-d]pyrimidin-5-yl)phenyl)methanesulfonamide; N-(2-(7-((3-oxo-3,4-dihydro-2H-benzo[b][1,4]oxazin-6-yl)amino)-1H-pyrazolo[4,3-d]pyrimidin-5-yl)phenyl)methanesulfonamide; N-(2-(7-((2-oxo-1,2,3,4-tetrahydroquinolin-6-yl)amino)-1H-pyrazolo[4,3-d]pyrimidin-5-yl)phenyl)methanesulfonamide; 5-cyclopropyl-N-(4-(4-(4-methylpiperazin-1-yl)piperidin- 1-yl)phenyl)-1H-pyrazolo[4,3-d]pyrimidin-7-amine; 1-(4-(4-((5-cyclopropyl-1H-pyrazolo[4,3-d]pyrimidin-7-yl)amino)phenyl)piperazin-1-yl)ethan-1-one; 5-cyclopropyl-N-(3-fluoro-4-morpholinophenyl)-1H-pyrazolo[4,3-d]pyrimidin-7-amine; 5-cyclopropyl-N-(3-methoxy-4-morpholinophenyl)-1H-pyrazolo[4,3-d]pyrimidin-7-amine; 6-((5-(thiophen-2-yl)-1H-pyrazolo[4,3-d]pyrimidin-7-yl)amino)benzo[b]thiophene 1,1-dioxide; N-(3-methoxy-4-morpholinophenyl)-5-(thiophen-2-yl)-1H-pyrazolo[4,3-d]pyrimidin-7-amine; 3-(4-((5-(thiophen-2-yl)-1H-pyrazolo[4,3-d]pyrimidin-7-yl)amino)phenyl)oxazolidin-2-one; N-(3-(7-((4-(4-(tert-butyl)piperazin-1-yl)phenyl)amino)-1H-pyrazolo[4,3-d]pyrimidin-5-yl)phenyl)methanesulfonamide; N-(3-(7-((3-fluoro-4-morpholinophenyl)amino)-1H-pyrazolo[4,3-d]pyrimidin-5-yl)phenyl)methanesulfonamide; N-(3-(7-((3-methoxy-4-morpholinophenyl)amino)-1H-pyrazolo[4,3-d]pyrimidin-5-yl)phenyl)methanesulfonamide; N-(3-(7-((4-morpholinophenyl)amino)-1H-pyrazolo[4,3-d]pyrimidin-5-yl)phenyl)methanesulfonamide; N-(3-(7-((4-(morpholine-4-carbonyl)phenyl)amino)-1H-pyrazolo[4,3-d]pyrimidin-5-yl)phenyl)methanesulfonamide; N-(3-(7-((4-(2-oxooxazolidin-3-yl)phenyl)amino)-1H-pyrazolo[4,3-d]pyrimidin-5-yl)phenyl)methanesulfonamide; N-(4-(4-(tert-butyl)piperazin-1-yl)phenyl)-5-(1H-indazol-6-yl)-1H-pyrazolo[4,3-d]pyrimidin-7-amine; N-(3-fluoro-4-morpholinophenyl)-5-(1H-indazol-6-yl)-1H-pyrazolo[4,3-d]pyrimidin-7-amine; N-(3-methoxy-4-morpholinophenyl)-5-(oxazol-4-yl)-1H-pyrazolo[4,3-d]pyrimidin-7-amine; N-(4-morpholinophenyl)-5-(oxazol-4-yl)-1H-pyrazolo[4,3-d]pyrimidin-7-amine; N-(4-(4-(tert-butyl)piperazin-1-yl)phenyl)-5-(oxazol-4-yl)-1H-pyrazolo[4,3-d]pyrimidin-7-amine; 1-(4-(4-((5-(1H-indazol-6-yl)-1H-pyrazolo[4,3-d]pyrimidin-7-yl)amino)phenyl)piperazin-1-yl)ethan-1-one; N-(3,4-dimethoxyphenyl)-5-(3-methylthiophen-2-yl)-1H-pyrazolo[4,3-d]pyrimidin-7-amine; 5-(3-methylthiophen-2-yl)-N-(4-morpholinophenyl)-1H-pyrazolo[4,3-d]pyrimidin-7-amine; (4-((5-cyclopropyl-1H-pyrazolo[4,3-d]pyrimidin-7-yl)amino)phenyl)(4-(4-methylpiperazin-1-yl)piperidin-1-yl)methanone; 5-(1H-indazol-6-yl)-N-(3-methoxy-4-morpholinophenyl)-1H-pyrazolo[4,3-d]pyrimidin-7-amine; 5-cyclopropyl-N-(4-(piperazin-1-yl)phenyl)-1H-pyrazolo[4,3-d]pyrimidin-7-amine; N-(4-morpholinophenyl)-5-(tetrahydrofuran-2-yl)-1H-pyrazolo[4,3-d]pyrimidin-7-amine; N-(3-fluoro-4-morpholinophenyl)-5-(oxazol-4-yl)-1H-pyrazolo[4,3-d]pyrimidin-7-amine; 3-(4-((5-(oxazol-4-yl)-1H-pyrazolo[4,3-d]pyrimidin-7-yl)amino)phenyl)oxazolidin-2-one; 5-(methoxymethyl)-N-(4-morpholinophenyl)-1H-pyrazolo[4,3-d]pyrimidin-7-amine; N-(3,4-dimethoxyphenyl)-5-(methoxymethyl)-1H-pyrazolo[4,3-d]pyrimidin-7-amine; 5-(methoxymethyl)-N-(4-(4-(4-methylpiperazin-1-yl)piperidin-1-yl)phenyl)-1H-pyrazolo[4,3-d]pyrimidin-7-amine; 5-(methoxymethyl)-N-(3-(methylsulfonyl)phenyl)-1H-pyrazolo[4,3-d]pyrimidin-7-amine; 1-(4-(4-((5-(methoxymethyl)-1H-pyrazolo[4,3-d]pyrimidin-7-yl)amino)phenyl)piperazin-1-yl)ethan-1-one; 5-(1-methoxyethyl)-N-(4-morpholinophenyl)-1H-pyrazolo[4,3-d]pyrimidin-7-amine; 1-(4-(4-((5-(1-methoxyethyl)-1H-pyrazolo[4,3-d]pyrimidin-7-yl)amino)phenyl)piperazin-1-yl)ethan-1-one; N-(3,4-dimethoxyphenyl)-5-(1-methoxyethyl)-1H-pyrazolo[4,3-d]pyrimidin-7-amine; 1-(4-(4-((5-(isoxazol-5-yl)-1H-pyrazolo[4,3-d]pyrimidin-7-yl)amino)phenyl)piperazin-1-yl)ethan-1-one; N-(3,4-dimethoxyphenyl)-5-(isoxazol-5-yl)-1H-pyrazolo[4,3-d]pyrimidin-7-amine; 5-(isoxazol-5-yl)-N-(4-morpholinophenyl)-1H-pyrazolo[4,3-d]pyrimidin-7-amine; N-(3-fluoro-4-morpholinophenyl)-5-(isoxazol-5-yl)-1H-pyrazolo[4,3-d]pyrimidin-7-amine; 5-(isoxazol-5-yl)-N-(3-methoxy-4-morpholinophenyl)-1H-pyrazolo[4,3-d]pyrimidin-7-amine; 1-(4-(4-((5-(isoxazol-3-yl)-1H-pyrazolo[4,3-d]pyrimidin-7-yl)amino)phenyl)piperazin-1-yl)ethan-1-one; N-(3,4-dimethoxyphenyl)-5-(isoxazol-3-yl)-1H-pyrazolo[4,3-d]pyrimidin-7-amine; 5-(isoxazol-3-yl)-N-(4-morpholinophenyl)-1H-pyrazolo[4,3-d]pyrimidin-7-amine; N-(3-fluoro-4-morpholinophenyl)-5-(isoxazol-3-yl)-1H-pyrazolo[4,3-d]pyrimidin-7-amine; 5-(isoxazol-3-yl)-N-(3-methoxy-4-morpholinophenyl)-1H-pyrazolo[4,3-d]pyrimidin-7-amine; 5-(5-fluoro-1H-indazol-6-yl)-N-(4-morpholinophenyl)-1H-pyrazolo[4,3-d]pyrimidin-7-amine; N-(3,4-dimethoxyphenyl)-5-(tetrahydrofuran-2-yl)-1H-pyrazolo[4,3-d]pyrimidin-7-amine; N-(4-morpholinophenyl)-5-(tetrahydrofuran-3-yl)-1H-pyrazolo[4,3-d]pyrimidin-7-amine; N-(3,4-dimethoxyphenyl)-5-(tetrahydrofuran-3-yl)-1H-pyrazolo[4,3-d]pyrimidin-7-amine; N-(3,4-dimethoxyphenyl)-5-(tetrahydro-2H-pyran-4-yl)-1H-pyrazolo[4,3-d]pyrimidin-7-amine; N-(4-morpholinophenyl)-5-(tetrahydro-2H-pyran-4-yl)-1H-pyrazolo[4,3-d]pyrimidin-7-amine; N-(3,4-dimethoxyphenyl)-5-(1,4-dioxan-2-yl)-1H-pyrazolo[4,3-d]pyrimidin-7-amine; dioxan-2-yl)-N-(4-morpholinophenyl)-1H-pyrazolo[4,3-d]pyrimidin-7-amine; 5-((5-(1H-indazol-6-yl)-1H-pyrazolo[4,3-d]pyrimidin-7-yl)amino)-2-morpholinobenzonitrile; 5-(furan-2-yl)-N-(4-morpholinophenyl)-1H-pyrazolo[4,3-d]pyrimidin-7-amine; N-(3,4-dimethoxyphenyl)-5-(furan-2-yl)-1H-pyrazolo[4,3-d]pyrimidin-7-amine; 5-(1H-indazol-6-yl)-N-(4-nitrophenyl)-1H-pyrazolo[4,3-d]pyrimidin-7-amine; (4-methylpiperazin-1-yl)(4-((5-(3-nitrophenyl)-1H-pyrazolo[4,3-d]pyrimidin-7-yl)amino)phenyl)methanone, 5-(1-methyl-1H-imidazol-2-yl)-N-(4-morpholinophenyl)-1H-pyrazolo[4,3-d]pyrimidin-7-amine; 1-(4-(4-((5-(1-methyl-1H-imidazol-2-yl)-1H-pyrazolo[4,3-d]pyrimidin-7-yl)amino)phenyl)piperazin-1-yl)ethan-1-one; 5-(morpholinomethyl)-N-(4-morpholinophenyl)-1H-pyrazolo[4,3-d]pyrimidin-7-amine; 1-(4-(4-((5-(morpholinomethyl)-1H-pyrazolo[4,3-d]pyrimidin-7-yl)amino)phenyl)piperazin-1-yl)ethan-1-one; 5-(furan-3-yl)-N-(4-morpholinophenyl)-1H-pyrazolo[4,3-d]pyrimidin-7-amine; N-(3,4-dimethoxyphenyl)-5-(furan-3-yl)-1H-pyrazolo[4,3-d]pyrimidin-7-amine; 1-(4-(4-((5-(furan-3-yl)-1H-pyrazolo[4,3-d]pyrimidin-7-yl)amino)phenyl)piperazin-1-yl)ethan-1-one; N-(4-(tert-butyl)piperazin-1-yl)phenyl)-5-(furan-3-yl)-1H-pyrazolo[4,3-d]pyrimidin-7-amine; 3-(4-((5-(furan-3-yl)-1H-pyrazolo[4,3-d]pyrimidin-7-yl)amino)phenypoxazolidin-2-one; 5-(1-methylcyclopropyl)-N-(4-morpholinophenyl)-1H-pyrazolo[4,3-d]pyrimidin-7-amine; 1-(4-(4-((5-(1-methylcyclopropyl)-1H-pyrazolo[4,3-d]pyrimidin-7-yl)amino)phenyl)piperazin-1-yl)ethan-1-one; 5-(2-methylcyclopropyl)-N-(4-morpholinophenyl)-1H-pyrazolo[4,3-d]pyrimidin-7-amine; 1-(4-(4-((5-(2-methylcyclopropyl)-1H-pyrazolo[4,3-d]pyrimidin-7-yl)amino)phenyl)piperazin-1-yl)ethan-1-one; 5-(2-methylcyclopropyl)-N-(1-(tetrahydro-2H-pyran-4-yl)-1H-pyrazol-4-yl)-1H-pyrazolo[4,3-d]pyrimidin-7-amine; 5-((dimethylamino)methyl)-N-(4-morpholinophenyl)-1H-pyrazolo[4,3-d]pyrimidin-7-amine; 5-(7-((4-morpholinophenyl)amino)-1H-pyrazolo[4,3-d]pyrimidin-5-yl)isoxazole-3-carboxylic acid; 5-(furan-3-yl)-N-(4-(4-(4-methylpiperazin-1-yl)piperidin-1-yl)phenyl)-1H-pyrazolo[4,3-d]pyrimidin-7-amine; 8-((5-(furan-3-yl)-1H-pyrazolo[4,3-d]pyrimidin-7-yl)amino)-4,5-dihydro-1H-benzo[b]azepin-2(3H)-one; 5-(furan-3-yl)-N-(6-(4-methylpiperazin-1-yl)pyridin-3-yl)-1H-pyrazolo[4,3-d]pyrimidin-7-amine; 5-(furan-3-yl)-N-(3-(methylsulfonyl)phenyl)-1H-pyrazolo

[4,3-d]pyrimidin-7-amine; 5-(furan-3-yl)-N-(1-(tetrahydro-2H-pyran-4-yl)-1H-pyrazol-4-yl)-1H-pyrazolo[4,3-d]pyrimidin-7-amine; 1-(4-(4-((5-(furan-2-yl)-1H-pyrazolo[4,3-d]pyrimidin-7-yl)amino)phenyl)piperazin-1-yl)ethan-1-one; N-(4-(4-(tert-butyl)piperazin-1-yl)phenyl)-5-(furan-2-yl)-1H-pyrazolo[4,3-d]pyrimidin-7-amine; 8-((5-(furan-2-yl)-1H-pyrazolo[4,3-d]pyrimidin-7-yl)amino)-4,5-dihydro-1H-benzo[b]azepin-2(3H)-one; 5-(furan-2-yl)-N-(6-(4-methylpiperazin-1-yl)pyridin-3-yl)-1H-pyrazolo[4,3-d]pyrimidin-7-amine; 3-(4-((5-(furan-2-yl)-1H-pyrazolo[4,3-d]pyrimidin-7-yl)amino)phenyl)oxazolidin-2-one; 5-(furan-2-yl)-N-(3-(methylsulfonyl)phenyl)-1H-pyrazolo[4,3-d]pyrimidin-7-amine; 5-(furan-2-yl)-N-(1-(tetrahydro-2H-pyran-4-yl)-1H-pyrazol-4-yl)-1H-pyrazolo[4,3-d]pyrimidin-7-amine; 5-cyclopropyl-N-(1-(tetrahydro-2H-pyran-4-yl)-1H-pyrazol-4-yl)-1H-pyrazolo[4,3-d]pyrimidin-7-amine; 5-cyclobutyl-N-(1-(tetrahydro-2H-pyran-4-yl)-1H-pyrazol-4-yl)-1H-pyrazolo[4,3-d]pyrimidin-7-amine; 5-cyclobutyl-N-(4-morpholinophenyl)-1H-pyrazolo[4,3-d]pyrimidin-7-amine; 5-(1-methyl-1H-pyrazol-4-yl)-N-(4-morpholinophenyl)-1H-pyrazolo[4,3-d]pyrimidin-7-amine; 5-(1-methyl-1H-pyrazol-4-yl)-N-(1-(tetrahydro-2H-pyran-4-yl)-1H-pyrazol-4-yl)-1H-pyrazolo[4,3-d]pyrimidin-7-amine; N-(4-morpholinophenyl)-5-(1H-1,2,4-triazol-3-yl)-2H-pyrazolo[4,3-d]pyrimidin-7-amine; 5-(pyridazin-3-yl)-N-(1-(tetrahydro-2H-pyran-4-yl)-1H-pyrazol-4-yl)-1H-pyrazolo[4,3-d]pyrimidin-7-amine; N-(4-morpholinophenyl)-5-(pyridazin-3-yl)-1H-pyrazolo[4,3-d]pyrimidin-7-amine; N-(6-morpholinopyridin-3-yl)-5-(pyridin-3-yl)-1H-pyrazolo[4,3-d]pyrimidin-7-amine; 5-(oxazol-4-yl)-N-(1-(tetrahydro-2H-pyran-4-yl)-1H-pyrazol-4-yl)-1H-pyrazolo[4,3-d]pyrimidin-7-amine; N-(1-(2-methoxyethyl)-1H-pyrazol-4-yl)-5-(oxazol-4-yl)-1H-pyrazolo[4,3-d]pyrimidin-7-amine; N-(1-(1-methylpiperidin-4-yl)-1H-pyrazol-4-yl)-5-(oxazol-4-yl)-1H-pyrazolo[4,3-d]pyrimidin-7-amine; 1-(4-(4-((5-(oxazol-4-yl)-1H-pyrazolo[4,3-d]pyrimidin-7-yl)amino)-1H-pyrazol-1-yl)piperidin-1-yl)ethan-1-one; 5-(1H-indazol-6-yl)-N-(1-(2-methoxyethyl)-1H-pyrazol-4-yl)-1H-pyrazolo[4,3-d]pyrimidin-7-amine; 5-(1H-indazol-6-yl)-N-(1-(1-methylpiperidin-4-yl)-1H-pyrazol-4-yl)-1H-pyrazolo[4,3-d]pyrimidin-7-amine; 1-(4-(4-((5-(1H-indazol-6-yl)-1H-pyrazolo[4,3-d]pyrimidin-7-yl)amino)-1H-pyrazol-1-yl)piperidin-1-yl)ethan-1-one; 5-(1H-indazol-6-yl)-N-(1-(tetrahydro-2H-pyran-4-yl)-1H-pyrazol-4-yl)-1H-pyrazolo[4,3-d]pyrimidin-7-amine.

Moreover especially preferred are compounds of formula (I) that are selected from: 5-(1-methylcyclopropyl)-N-(4-morpholinophenyl)-1H-pyrazolo[4,3-d]pyrimidin-7-amine; 1-(4-(4-((5-(1-methylcyclopropyl)-1H-pyrazolo[4,3-d]pyrimidin-7-yl)amino)phenyl)piperazin-1-yl)ethan-1-one; 5-(2-methylcyclopropyl)-N-(4-morpholinophenyl)-1H-pyrazolo[4,3-d]pyrimidin-7-amine; 1-(4-(4-((5-(2-methylcyclopropyl)-1H-pyrazolo[4,3-d]pyrimidin-7-yl)amino)phenyl)piperazin-1-yl)ethan-1-one; 5-(2-methylcyclopropyl)-N-(1-(tetrahydro-2H-pyran-4-yl)-1H-pyrazol-4-yl)-1H-pyrazolo[4,3-d]pyrimidin-7-amine; 5-((dimethylamino)methyl)-N-(4-morpholinophenyl)-1H-pyrazolo[4,3-d]pyrimidin-7-amine; 5-(7-((4-morpholinophenyl)amino)-1H-pyrazolo[4,3-d]pyrimidin-5-yl)isoxazole-3-carboxylic acid; 5-(furan-2-yl)-N-(4-(4-(4-methylpiperazin-1-yl)piperidin-1-yl)phenyl)-1H-pyrazolo[4,3-d]pyrimidin-7-amine; 8-((5-(furan-3-yl)-1H-pyrazolo[4,3-d]pyrimidin-7-yl)amino)-4,5-dihydro-1H-benzo[b]azepin-2(3H)-one; 5-(furan-3-yl)-N-(6-(4-methylpiperazin-1-yl)pyridin-3-yl)-1H-pyrazolo[4,3-d]pyrimidin-7-amine; 5-(furan-3-yl)-N-(3-(methylsulfonyl)phenyl)-1H-pyrazolo[4,3-d]pyrimidin-7-amine; N-(4-morpholinophenyl)-5-(pyridazin-4-yl)-1H-pyrazolo[4,3-d]pyrimidin-7-amine; 5-(1-methyl-1H-1,2,4-triazol-3-yl)-N-(4-morpholinophenyl)-2H-pyrazolo[4,3-d]pyrimidin-7-amine; 5-(1-methyl-1H-pyrazol-3-yl)-N-(4-morpholinophenyl)-1H-pyrazolo[4,3-d]pyrimidin-7-amine; 5-(1-methyl-1H-pyrazol-3-yl)-N-(1-(tetrahydro-2H-pyran-4-yl)-1H-pyrazol-4-yl)-1H-pyrazolo[4,3-d]pyrimidin-7-amine; 2-(4-((5-cyclopropyl-1H-pyrazolo[4,3-d]pyrimidin-7-yl)amino)-1H-pyrazol-1-yl)-2-methylpropanenitrile; 5-(1H-indazol-5-yl)-N-(1-(tetrahydro-2H-pyran-4-yl)-1H-pyrazol-4-yl)-1H-pyrazolo[4,3-d]pyrimidin-7-amine; 5-(1H-indazol-5-yl)-N-(4-morpholinophenyl)-1H-pyrazolo[4,3-d]pyrimidin-7-amine; 1-(4-(4-((5-isopropyl-1H-pyrazolo[4,3-d]pyrimidin-7-yl)amino)phenyl)piperazin-1-yl)ethan-1-one; 5-isopropyl-N-(4-morpholinophenyl)-1H-pyrazolo[4,3-d]pyrimidin-7-amine; 5-isopropyl-N-(1-(tetrahydro-2H-pyran-4-yl)-1H-pyrazol-4-yl)-1H-pyrazolo[4,3-d]pyrimidin-7-amine; (2-fluoro-4-((5-isopropyl-1H-pyrazolo[4,3-d]pyrimidin-7-yl)amino)phenyl)(morpholino)methanone; 5-isopropyl-N-(1-(1-methylpiperidin-4-yl)-1H-pyrazol-4-yl)-1H-pyrazolo[4,3-d]pyrimidin-7-amine; 5-isopropyl-N-(1-(2- methoxyethyl)-1H-pyrazol-4-yl)-1H-pyrazolo[4,3-d]pyrimidin-7-amine; 1-(4-(4-((5-isopropyl-1H-pyrazolo[4,3-d]pyrimidin-7-yl)amino)-1H-pyrazol-1-yl)piperidin-1-yl)ethan-1-one; 1-(4-(4-((5-(1-methyl-1H-pyrazol-4-yl)-1H-pyrazolo[4,3-d]pyrimidin-7-yl)amino)phenyl)piperazin-1-yl)ethan-1-one; N-(1-(2-methoxyethyl)-1H-pyrazol-4-yl)-5-(1-methyl-1H-pyrazol-4-yl)-1H-pyrazolo[4,3-d]pyrimidin-7-amine; 1-(4-(4-((5-(1-methyl-1H-pyrazol-4-yl)-1H-pyrazolo[4,3-d]pyrimidin-7-yl)amino)-1H-pyrazol-1-yl)piperidin-1-yl)ethan-1-one; 5-(1-methyl-1H-pyrazol-4-yl)-N-(1-(1-methylpiperidin-4-yl)-1H-pyrazol-4-yl)-1H-pyrazolo[4,3-d]pyrimidin-7-amine; 5-cyclobutyl-N-(1-(2-methoxyethyl)-1H-pyrazol-4-yl)-1H-pyrazolo[4,3-d]pyrimidin-7-amine; 1-(4-(4-((5-cyclobutyl-1H-pyrazolo[4,3-d]pyrimidin-7-yl)amino)phenyl)piperazin-1-yl)ethan-1-one; (4-((5-cyclobutyl-1H-pyrazolo[4,3-d]pyrimidin-7-yl)amino)-2-fluorophenyl)(morpholino)methanone; 5-cyclopropyl-N-(1-(2-methoxyethyl)-1H-pyrazol-4-yl)-1H-pyrazolo[4,3-d]pyrimidin-7-amine; 5-(furan-2-yl)-N-(1-(2-methoxyethyl)-1H-pyrazol-4-yl)-1H-pyrazolo[4,3-d]pyrimidin-7-amine; 1-(4-(4-((5-(furan-2-yl)-1H-pyrazolo[4,3-d]pyrimidin-7-yl)amino)-1H-pyrazol-1-yl)piperidin-1-yl)ethan-1-one; (2-fluoro-4-((5-(furan-2-yl)-1H-pyrazolo[4,3-d]pyrimidin-7-yl)amino)phenyl)(morpholino)methanone; 5-(furan-2-yl)-N-(1-(1-methylpiperidin-4-yl)-1H-pyrazol-4-yl)-1H-pyrazolo[4,3-d]pyrimidin-7-amine; 5-(furan-3-yl)-N-(1-(2-methoxyethyl)-1H-pyrazol-4-yl)-1H-pyrazolo[4,3-d]pyrimidin-7-amine; 1-(4-(4-((5-(furan-3-yl)-1H-pyrazolo[4,3-d]pyrimidin-7-yl)amino)-1H-pyrazol-1-yl)piperidin-1-yl)ethan-1-one; (2-fluoro-4-((5-(furan-3-yl)-1H-pyrazolo[4,3-d]pyrimidin-7-yl)amino)phenyl)(morpholino)methanone; 5-(furan-3-yl)-N-(1-(1-methylpiperidin-4-yl)-1H-pyrazol-4-yl)-1H-pyrazolo[4,3-d]pyrimidin-7-amine; 2-(4-((5-(furan-3-yl)-1H-pyrazolo[4,3-d]pyrimidin-7-yl)amino)-1H-pyrazol-1-yl)-2-methylpropanenitrile; 1-(4-(4-((5-cyclopropyl-1H-pyrazolo[4,3-d]pyrimidin-7-yl)amino)-1H-pyrazol-1-yl)piperidin-1-yl)ethan-1-one; 1-(4-(4-((5-cyclobutyl-1H-pyrazolo[4,3-d]pyrimidin-7-yl)amino)-1H-pyrazol-1-yl)piperidin-1-yl)ethan-1-one; 5-cyclobutyl-N-(1-(1-methylpiperidin-4-yl)-1H-pyrazol-4-yl)-1H-pyrazolo[4,3-d]pyrimidin-7-amine; 5-cyclopropyl-N-(1-(1-methylpiperidin-4-yl)-1H-pyrazol-4-yl)-1H-pyrazolo[4,3-d]pyrimidin-7-amine; (4-((5-cyclopropyl-1H-pyrazolo[4,3-d]pyrimidin-7-yl)amino)-2-fluorophenyl)(morpholino)methanone; 4-((5-cyclobutyl-1H-pyrazolo[4,3-d]pyrimidin-7-yl)amino)-1-methylpyridin-2(1H)-one; 4-((5-cyclopropyl-1H-pyrazolo[4,3-d]pyrimidin-7-yl)amino)-1-methylpyridin-2(1H)-one; 2-(4-((5-(furan-2-yl)-1H-pyrazolo[4,3-d]pyrimidin-7-yl)amino)-1H-pyrazol-1-yl)-2-methylpropanenitrile; N-(1-(tert-butyl)-1H-pyrazol-4-yl)-5-(furan-2-yl)-1H-pyrazolo[4,3-d]pyrimidin-7-amine; 1-(4-((5-(furan-2-yl)-1H-pyrazolo[4,3-d]pyrimidin-7-yl)amino)-1H-pyrazol-1-yl)cyclohexanecarbonitrile; 5-(furan-2-yl)-N-(1-isopropyl-1H-pyrazol-4-yl)-1H-pyrazolo[4,3-d]pyrimidin-7-amine; 5-(furan-2-yl)-N-(1-(3-methoxypropyl)-1H-pyrazol-4-yl)-1H-pyrazolo[4,3-d]pyrimidin-7-amine; methyl 3-(7-((1-(tetrahydro-2H-pyran-4-yl)-1H-pyrazol-4-yl)amino)-1H-pyrazolo[4,3-d]pyrimidin-5-yl)benzoate; 3-(7-((1-(tetrahydro-2H-pyran-4-yl)-1H-pyrazol-4-yl)amino)-1H-pyrazolo[4,3-d]pyrimidin-5-yl)benzoic acid; N-(1-(tert-butyl)-1H-pyrazol-4-yl)-5-(furan-3-yl)-1H-pyrazolo[4,3-d]pyrimidin-7-amine; 1-(4-((5-(furan-3-yl)-1H-pyrazolo[4,3-d]pyrimidin-7-yl)amino)-1H-pyrazol-1-yl)cyclohexanecarbonitrile; 5-(furan-3-yl)-N-(1-isopropyl-1H-pyrazol-4-yl)-1H-pyrazolo[4,3-d]pyrimidin-7-amine; 5-(furan-3-yl)-N-(1-(3-methoxypropyl)-1H-pyrazol-4-yl)-1H-pyrazolo[4,3-d]pyrimidin-7-amine; N-(1-(tert-butyl)-1H-pyrazol-4-yl)-5-cyclobutyl-1H-pyrazolo[4,3-d]pyrimidin-7-amine; 5-cyclobutyl-N-(1-isopropyl-1H-pyrazol-4-yl)-1H-pyrazolo[4,3-d]pyrimidin-7-amine; 5-cyclobutyl-N-(1-(3-methoxypropyl)-1H-pyrazol-4-yl)-1H-pyrazolo[4,3-d]pyrimidin-7-amine; 2-(4-((5-cyclobutyl-1H-pyrazolo[4,3-d]pyrimidin-7-yl)amino)-1H-pyrazol-1-yl)-2-methylpropanenitrile; 4-((5-cyclobutyl-1H-pyrazolo[4,3-d]pyrimidin-7-yl)amino)-1-(2-methoxyethyl)pyridin-2(1H)-one; (4-((5-cyclobutyl-1H-pyrazolo[4,3-d]pyrimidin-7-yl)amino)-3-methoxyphenyl)(morpholino)methanone; N-(1-(tert-butyl)-1H-pyrazol-4-yl)-5-cyclopropyl-1H-pyrazolo[4,3-d]pyrimidin-7-amine; 5-cyclopropyl-N-(1-isopropyl-1H-pyrazol-4-yl)-1H-pyrazolo[4,3-d]pyrimidin-7-amine; 5-cyclopropyl-N-(1-(3-methoxypropyl)-1H-pyrazol-4-yl)-1H-pyrazolo[4,3-d]pyrimidin-7-amine; 4-((5-cyclopropyl-1H-pyrazolo[4,3-d]pyrimidin-7-yl)amino)-1-(2-methoxyethyl)pyridin-2(1H)-one; (4-((5-cyclopropyl-1H-pyrazolo[4,3-d]pyrimidin-7-yl)amino)-3-methoxyphenyl)(morpholino)methanone; 5-cyclopropyl-N-(1-isobutyl-1H-pyrazol-4-yl)-1H-pyrazolo[4,3-d]pyrimidin-7-amine; 5-cyclobutyl-N-(1-isobutyl-1H-pyrazol-4-yl)-1H-pyrazolo[4,3-d]pyrimidin-7-amine; 5-cyclopropyl-N-(1,5-dimethyl-1H-pyrazol-4-yl)-1H-pyrazolo[4,3-d]pyrimidin-7-amine; 5-cyclopropyl-N-(1,3-dimethyl-1H-pyrazol-4-yl)-1H-pyrazolo[4,3-d]pyrimidin-7-amine; 1-(4-(5-((5-cyclopropyl-1H-pyrazolo[4,3-d]pyrimidin-7-yl)amino)pyridin-2-yl)piperazin-1-yl)ethan-1-one; 5-(furan-2-yl)-N-(1-isobutyl-1H-pyrazol-4-yl)-1H-pyrazolo[4,3-d]pyrimidin-7-amine; 2-(4-((5-(furan-2-yl)-1H-pyrazolo[4,3-d]pyrimidin-7-yl)amino)-1H-pyrazol-1-yl)ethan-1-ol; 5-(furan-3-yl)-N-(1-isobutyl-1H-pyrazol-4-yl)-1H-pyrazolo[4,3-d]pyrimidin-7-amine; 2-(4-((5-(furan-3-yl)-1H-pyrazolo[4,3-d]pyrimidin-7-yl)amino)-1H-pyrazol-1-yl)acetonitrile; 2-(4-((5-(furan-3-yl)-1H-pyrazolo[4,3-d]pyrimidin-7-yl)amino)-1H-pyrazol-1-yl)ethan-1-ol; N-(1-(tert-butyl)-1H-pyrazol-4-yl)-5-(oxazol-4-yl)-1H-pyrazolo[4,3-d]pyrimidin-7-amine; N-(1-isopropyl-1H-pyrazol-4-yl)-5-(oxazol-4-yl)-1H-pyrazolo[4,3-d]pyrimidin-7-amine; N-(1-(3-methoxypropyl)-1H-pyrazol-4-yl)-5-(oxazol-4-yl)-1H-pyrazolo[4,3-d]pyrimidin-7-amine; N-(1-isobutyl-1H-pyrazol-4-yl)-5-(oxazol-4-yl)-1H-pyrazolo[4,3-d]pyrimidin-7-amine; 2-(4-((5-(oxazol-4-yl)-1H-pyrazolo[4,3-d]pyrimidin-7-yl)amino)-1H-pyrazol-1-yl)ethan-1-ol; (4-((5-(furan-3-yl)-1H-pyrazolo[4,3-d]pyrimidin-7-yl)amino)-3-methoxyphenyl)(morpholino)methanone; N-(1-(tert-butyl)-1H-pyrazol-4-yl)-5-(oxazol-2-yl)-1H-pyrazolo[4,3-d]pyrimidin-7-amine; N-(1-isopropyl-1H-pyrazol-4-yl)-5-(oxazol-2-yl)-1H-pyrazolo[4,3-d]pyrimidin-7-amine; N-(1-(3-methoxypropyl)-1H-pyrazol-4-yl)-5-(oxazol-2-yl)-1H-pyrazolo[4,3-d]pyrimidin-7-amine; N-(1-isobutyl-1H-pyrazol-4-yl)-5-(oxazol-2-yl)-1H-pyrazolo[4,3-d]pyrimidin-7-amine; 2-(4-((5-(oxazol-2-yl)-1H-pyrazolo[4,3-d]pyrimidin-7-yl)amino)-1H-pyrazol-1-yl)ethan-1-ol; 5-(oxazol-2-yl)-N-(1-(tetrahydro-2H-pyran-4-yl)-1H-pyrazol-4-yl)-1H-pyrazolo[4,3-d]pyrimidin-7-amine; N-(1-(1-methylpiperidin-4-yl)-1H-pyrazol-4-yl)-5-(oxazol-2-yl)-1H-pyrazolo[4,3-d]pyrimidin-7-amine; N-(1-(2-methoxyethyl)-1H-pyrazol-4-yl)-5-(oxazol-2-yl)-1H-pyrazolo[4,3-d]pyrimidin-7-amine; 1-(4-(4-((5-(oxazol-2-yl)-1H-pyrazolo[4,3-d]pyrimidin-7-yl)amino)-1H-pyrazol-1-yl)piperidin-1-yl)ethan-1-one; N-(3-(7-((1-(tert-butyl)-1H-pyrazol-4-yl)amino)-1H-pyrazolo[4,3-d]pyrimidin-5-yl)phenyl)methanesulfonamide; N-(3-(7-((1-isopropyl-1H-pyrazol-4-yl)amino)-1H-pyrazolo[4,3-d]pyrimidin-5-yl)phenyl)methanesulfonamide; N-(3-(7-((1-(3-methoxypropyl)-1H-pyrazol-4-yl)amino)-1H-pyrazolo[4,3-d]pyrimidin-5-yl)phenyl)methanesulfonamide; N-(3-(7-((1- isobutyl-1H-pyrazol-4-yl)amino)-1H-pyrazolo[4,3-d]pyrimidin-5-yl)phenyl)methanesulfonamide; N-(3-(7-((1-(2-hydroxyethyl)-1H-pyrazol-4-yl)amino)-1H-pyrazolo[4,3-d]pyrimidin-5-yl)phenyl)methanesulfonamide; N-(3-(7-((1-(tetrahydro-2H-pyran-4-yl)-1H-pyrazol-4-yl)amino)-1H-pyrazolo[4,3-d]pyrimidin-5-yl)phenyl) methanesulfonamide; N-(3-(7-((1-(1-methylpiperidin-4-yl)-1H-pyrazol-4-yl)amino)-1H-pyrazolo[4,3-d]pyrimidin-5-yl)phenyl)methanesulfonamide; N-(3-(7-((1-(2-methoxyethyl)-1H-pyrazol-4-yl)amino)-1H-pyrazolo[4,3-d]pyrimidin-5-yl)phenyl)methanesulfonamide; N-(3-(7-((1-(1-acetylpiperidin-4-yl)-1H-pyrazol-4-yl)amino)-1H-pyrazolo[4,3-d]pyrimidin-5-yl)phenyl) methanesulfonamide; 5-cyclobutyl-N-(1-cyclopropyl-1H-pyrazol-4-yl)-1H-pyrazolo[4,3-d]pyrimidin-7-amine; 5-(tert-butyl)-N-(1-isobutyl-1H-pyrazol-4-yl)-1H-pyrazolo[4,3-d]pyrimidin-7-amine; 5-(tert-butyl)-N-(1-isopropyl-1H-pyrazol-4-yl)-1H-pyrazolo[4,3-d]pyrimidin-7-amine; 5-(tert-butyl)-N-(1-(3-methoxypropyl)-1H-pyrazol-4-yl)-1H-pyrazolo[4,3-d]pyrimidin-7-amine; 5-(tert-butyl)-N-(1,5-dimethyl-1H-pyrazol-4-yl)-1H-pyrazolo[4,3-d]pyrimidin-7-amine; 5-(tert-butyl)-N-(1,3-dimethyl-1H-pyrazol-4-yl)-1H-pyrazolo[4,3-d]pyrimidin-7-amine; 5-(tert-butyl)-N-(1-cyclopropyl-1H-pyrazol-4-yl)-1H-pyrazolo[4,3-d]pyrimidin-7-amine; 2-(4-((5-(tert-butyl)-1H-pyrazolo[4,3-d]pyrimidin-7-yl)amino)-1H-pyrazol-1-yl)-2-methylpropanenitrile; (4-((5-(tert-butyl)-1H-pyrazolo[4,3-d]pyrimidin-7-yl)amino)-3-methoxyphenyl)(morpholino)methanone; 3-((5-(furan-2-yl)-1H-pyrazolo[4,3-d]pyrimidin-7-yl)amino)-1-methylpyridin-2(1H)-one; N-(1-(tert-butyl)-1H-pyrazol-3-yl)-5-(furan-2-yl)-1H-pyrazolo[4,3-d]pyrimidin-7-amine; N-(1-cyclopropyl-1H-pyrazol-4-yl)-5-(furan-2-yl)-1H-pyrazolo[4,3-d]pyrimidin-7-amine; N-(4-bromo-1-methyl-1H-pyrazol-3-yl)-5-(furan-2-yl)-1H-pyrazolo[4,3-d]pyrimidin-7-amine; N-(1,5-dimethyl-1H-pyrazol-4-yl)-5-(furan-2-yl)-1H-pyrazolo[4,3-d]pyrimidin-7-amine; N-(1,3-dimethyl-1H-pyrazol-4-yl)-5-(furan-2-yl)-1H-pyrazolo[4,3-d]pyrimidin-7-amine; 5-cyclopropyl-N-(1-cyclopropyl-1H-pyrazol-4-yl)-1H-pyrazolo[4,3-d]pyrimidin-7-amine; 5-cyclopropyl-N-(1-(1-methoxy-2-methylpropan-2-yl)-1H-pyrazol-4-yl)-1H-pyrazolo[4,3-d]pyrimidin-7-amine; 5-cyclopropyl-N-(1-(2-methoxyethyl)-3-methyl-1H-pyrazol-4-yl)-1H-pyrazolo[4,3-d]pyrimidin-7-amine; 5-cyclopropyl-N-(1-(2-methoxyethyl)-5-methyl-1H-pyrazol-4-yl)-1H-pyrazolo[4,3-d]pyrimidin-7-amine; 5-cyclopropyl-N-(1-isopropyl-3-methyl-1H-pyrazol-4-yl)-1H-pyrazolo[4,3-d]pyrimidin-7-amine; 5-cyclopropyl-N-(1-isopropyl-5-methyl-1H-pyrazol-4-yl)-1H-pyrazolo[4,3-d]pyrimidin-7-amine; 5-(furan-3-yl)-N-(1-(2-methoxyethyl)-3-methyl-1H-pyrazol-4-yl)-1H-pyrazolo[4,3-d]pyrimidin-7-amine; 5-(furan-3-yl)-N-(1-(2-methoxyethyl)-5-methyl-1H-pyrazol-4-yl)-1H-pyrazolo[4,3-d]pyrimidin-7-amine; 5-(furan-3-yl)-N-(1-(1-methoxy-2-methylpropan-2-yl)-1H-pyrazol-4-yl)-1H-pyrazolo[4,3-d]pyrimidin-7-amine; N-(1-(1-(tert-butyl)piperidin-4-yl)-1H-pyrazol-4-yl)-5-(furan-3-yl)-1H-pyrazolo[4,3-d]pyrimidin-7-amine; 5-(furan-3-yl)-N-(1-isopropyl-3-methyl-1H-pyrazol-4-yl)-1H-pyrazolo[4,3-d]pyrimidin-7-amine; 5-(furan-3-yl)-N-(1-isopropyl-5-methyl-1H-pyrazol-4-yl)-1H-pyrazolo[4,3-d]pyrimidin-7-amine; 5-(furan-3-yl)-N-(3-methyl-1-(tetrahydro-2H-pyran-4-yl)-1H-pyrazol-4-yl)-1H-pyrazolo[4,3-d]pyrimidin-7-amine; 5-(furan-3-yl)-N-(5-methyl-1-(tetrahydro-2H-pyran-4-yl)-1H-pyrazol-4-yl)-1H-pyrazolo[4,3-d]pyrimidin-7-amine; 1-cyclopropyl-4-((5-cyclopropyl-1H-pyrazolo[4,3-d]pyrimidin-7-yl)amino)pyridin-2(1H)-one; N-(5-chloro-1-isopropyl-1H-pyrazol-4-yl)-5-cyclopropyl-1H-pyrazolo[4,3-d]pyrimidin-7-amine; 5-(furan-2-yl)-N-(1-(2-methoxyethyl)-3-methyl-1H-pyrazol-4-yl)-1H-pyrazolo[4,3-d]pyrimidin-7-amine; 5-(furan-2-yl)-N-(1-(2-methoxyethyl)-5-methyl-1H-pyrazol-4-yl)-1H-pyrazolo[4,3-d]pyrimidin-7-amine; 5-(furan-2-yl)-N-(1-isopropyl-3-methyl-1H-pyrazol-4-yl)-1H-pyrazolo[4,3-d]pyrimidin-7-amine; 5-(furan-2-yl)-N-(1-isopropyl-5-methyl-1H-pyrazol-4-yl)-1H-pyrazolo[4,3-d]pyrimidin-7-amine; 5-(furan-2-yl)-N-(1-isopropyl-3-methoxy-1H-pyrazol-4-yl)-1H-pyrazolo[4,3-d]pyrimidin-7-amine; 5-(furan-2-yl)-N-(1-isopropyl-3-methyl-1H-pyrazol-4-yl)-1H-pyrazolo[4,3-d]pyrimidin-7-amine; 5-(furan-2-yl)-N-(1-isopropyl-5-methyl-1H-pyrazol-4-yl)-1H-pyrazolo[4,3-d]pyrimidin-7-amine; N-(1-(1-(tert-butyl)piperidin-4-yl)-3-methoxy-1H-pyrazol-4-yl)-5-(furan-2-yl)-1H-pyrazolo[4,3-d]pyrimidin-7-amine; 5-(furan-3-yl)-N-(1-isopropyl-3-methoxy-1H-pyrazol-4-yl)-1H-pyrazolo[4,3-d]pyrimidin-7-amine; 5-(furan-3-yl)-N-(1-isopropyl-3-methyl-1H-pyrazol-4-yl)-1H-pyrazolo[4,3-d]pyrimidin-7-amine; 5-(furan-3-yl)-N-(1-isopropyl-5-methyl-1H-pyrazol-4-yl)-1H-pyrazolo[4,3-d]pyrimidin-7-amine; N-(1-(1-(tert-butyl)piperidin-4-yl)-3-methoxy-1H-pyrazol-4-yl)-5-(furan-3-yl)-1H-pyrazolo[4,3-d]pyrimidin-7-amine; 5-cyclobutyl-N-(1-isopropyl-3-methoxy-1H-pyrazol-4-yl)-1H-pyrazolo[4,3-d]pyrimidin-7-amine; 5-cyclobutyl-N-(1-isopropyl-5-methoxy-1H-pyrazol-4-yl)-1H-pyrazolo[4,3-d]pyrimidin-7-amine; N-(5-chloro-1-isopropyl-1H-pyrazol-4-yl)-5-cyclobutyl-1H-pyrazolo[4,3-d]pyrimidin-7-amine; 5-cyclopropyl-N-(5-methyl-1-(tetrahydro-2H-pyran-4-yl)-1H-pyrazol-4-yl)-1H-pyrazolo[4,3-d]pyrimidin-7-amine; 5-cyclopropyl-N-(3-methyl-1-(tetrahydro-2H-pyran-4-yl)-1H-pyrazol-4-yl)-1H-pyrazolo[4,3-d]pyrimidin-7-amine; 5-cyclopropyl-N-(1-isopropyl-3-methoxy-1H-pyrazol-4-yl)-1H-pyrazolo[4,3-d]pyrimidin-7-amine; 5-cyclopropyl-N-(1-isopropyl-5-methoxy-1H-pyrazol-4-yl)-1H-pyrazolo[4,3-d]pyrimidin-7-amine; N-(1-(1-(tert-butyl)piperidin-4-yl)-3-methoxy-1H-pyrazol-4-yl)-5-cyclopropyl-1H-pyrazolo[4,3-d]pyrimidin-7-amine; N-(1-(1-(tert-butyl)piperidin-4-yl)-5-methoxy-1H-pyrazol-4-yl)-5-cyclopropyl-1H-pyrazolo[4,3-d]pyrimidin-7-amine; 3-(7-((3,4-dimethoxyphenyl)amino)-1H-pyrazolo[4,3-d]pyrimidin-5-yl)-N-(4-(oxazol-5-yl)phenyl)benzamide; N-(4-(2H-1,2,3-triazol-2-yl)phenyl)-3-(7-(3,4-dimethoxyphenyl)amino)-1H-pyrazolo[4,3-d]pyrimidin-5-yl)benzamide; 3-(7-((3,4-dimethoxyphenyl)amino)-1H-pyrazolo[4,3-d]pyrimidin-5-yl)-N-(4-(oxazol-2-yl)phenyl)benzamide; N-(5-chloro-1-(3-methoxypropyl)-1H-pyrazol-4-yl)-5-(furan-3-yl)-1H-pyrazolo[4,3-d]pyrimidin-7-amine; N-(5-chloro-1-isopropyl-1H-pyrazol-4-yl)-5-(furan-3-yl)-1H-pyrazolo[4,3-d]pyrimidin-7-amine; 5-cyclobutyl-N-(1-isopropyl-3-methyl-1H-pyrazol-4-yl)-1H-pyrazolo[4,3-d]pyrimidin-7-amine; 5-cyclobutyl-N-(1-isopropyl-5-methyl-1H-pyrazol-4-yl)-1H-pyrazolo[4,3-d]pyrimidin-7-amine; 5-cyclobutyl-N-(1-isopropyl-3,5-dimethyl-1H-pyrazol-4-yl)-1H-pyrazolo[4,3-d]pyrimidin-7-amine; N-(5-chloro-1-(3-methoxypropyl)-1H-pyrazol-4-yl)-5-cyclobutyl-1H-pyrazolo[4,3-d]pyrimidin-7-amine; N-(1-(1-(tert-butyl)piperidin-4-yl)-1H-pyrazol-4-yl)-5-cyclopropyl-1H-pyrazolo[4,3-d]pyrimidin-7-amine; 5-cyclopropyl-N-(1-isopropyl-3,5-dimethyl-1H-pyrazol-4-yl)-1H-pyrazolo[4,3-d]pyrimidin-7-amine; N-(5-chloro-1-(3-methoxypropyl)-1H-pyrazol-4-yl)-5-cyclopropyl-1H-pyrazolo[4,3-d]pyrimidin-7-amine; 5-cyclobutyl-N-(imidazo[1,2-a]pyridin-3-yl)-1H-pyrazolo[4,3-d]pyrimidin-7-amine; 5-(furan-2-yl)-N-(1-isopropyl-3,5-dimethyl-1H-pyrazol-4-yl)-1H-pyrazolo[4,3-d]pyrimidin-7-amine; N-(3-cyclopropyl-1-methyl-1H-pyrazol-5-yl)-5-(furan-2-yl)-1H-pyrazolo[4,3-d]pyrimidin-7-amine; N-(5-chloro-1-(3-methoxypropyl)-1H-pyrazol-4-yl)-5-(furan-2-yl)-1H-pyrazolo[4,3-d]pyrimidin- 7-amine; 3-(4-((5-(furan-2-yl)-1H-pyrazolo[4,3-d]pyrimidin-7-yl)amino)-3-methoxyphenyl)oxazolidin-2-one; 5-(furan-3-yl)-N-(1-isopropyl-3,5-dimethyl-1H-pyrazol-4-yl)-1H-pyrazolo[4,3-d]pyrimidin-7-amine, N-(3-cyclopropyl-1-methyl-1H-pyrazol-5-yl)-5-(furan-3-yl)-1H-pyrazolo[4,3-d]pyrimidin-7-amine; 5-(furan-3-yl)-N-(3-methoxy-1-(3-methoxypropyl)-1H-pyrazol-4-yl)-1H-pyrazolo[4,3-d]pyrimidin-7-amine; 5-(furan-3-yl)-N-(imidazo[1,2-a]pyridin-3-yl)-1H-pyrazolo[4,3-d]pyrimidin-7-amine; 3-(4-((5-(furan-3-yl)-1H-pyrazolo[4,3-d]pyrimidin-7-yl)amino)-3-methoxyphenypoxazolidin-2-one; N-(5-chloro-1-(2-methoxyethyl)-1H-pyrazol-4-yl)-5-cyclobutyl-1H-pyrazolo[4,3-d]pyrimidin-7-amine; N-(5-chloro-1-(2-methoxyethyl)-1H-pyrazol-4-yl)-5-cyclopropyl-1H-pyrazolo[4,3-d]pyrimidin-7-amine; N-(1-(tert-butyl)-5-methyl-1H-pyrazol-4-yl)-5-cyclopropyl-1H-pyrazolo[4,3-d]pyrimidin-7-amine; 5-cyclopropyl-N-(imidazo[1,2-a]pyridin-3-yl)-1H-pyrazolo[4,3-d]pyrimidin-7-amine; 3-(4-((5-cyclobutyl-1H-pyrazolo[4,3-d]pyrimidin-7-yl)amino)-3-methoxyphenypoxazolidin-2-one; 5-(furan-2-yl)-N-(3-methoxy-1-(3-methoxypropyl)-1H-pyrazol-4-yl)-1H-pyrazolo[4,3-d]pyrimidin-7-amine; N-(5-chloro-1-isopropyl-1H-pyrazol-4-yl)-5-(furan-2-yl)-1H-pyrazolo[4,3-d]pyrimidin-7-amine; 5-(furan-2-yl)-N-(imidazo[1,2-a]pyridin-3-yl)-1H-pyrazolo[4,3-d]pyrimidin-7-amine; N-(5-chloro-1-(2-methoxyethyl)-1H-pyrazol-4-yl)-5-(furan-2-yl)-1H-pyrazolo[4,3-d]pyrimidin-7-amine; N-(1-(tert-butyl)-5-methyl-1H-pyrazol-4-yl)-5-(oxazol-4-yl)-1H-pyrazolo[4,3-d]pyrimidin-7-amine; N-(5-chloro-1-(2-methoxyethyl)-1H-pyrazol-4-yl)-5-(oxazol-4-yl)-1H-pyrazolo[4,3-d]pyrimidin-7-amine; N-(5-chloro-1-isopropyl-1H-pyrazol-4-yl)-5-(oxazol-4-yl)-1H-pyrazolo[4,3-d]pyrimidin-7-amine; N-(1-isopropyl-5-methyl-1H-pyrazol-4-yl)-5-(oxazol-4-yl)-1H-pyrazolo[4,3-d]pyrimidin-7-amine; N-(1-(tert-butyl)-5-methyl-1H-pyrazol-4-yl)-5-(oxazol-2-yl)-1H-pyrazolo[4,3-d]pyrimidin-7-amine; N-(5-chloro-1-(2-methoxyethyl)-1H-pyrazol-4-yl)-5-(oxazol-2-yl)-1H-pyrazolo[4,3-d]pyrimidin-7-amine; N-(5-chloro-1-isopropyl-1H-pyrazol-4-yl)-5-(oxazol-2-yl)-1H-pyrazolo[4,3-d]pyrimidin-7-amine; N-(1-isopropyl-5-methyl-1H-pyrazol-4-yl)-5-(oxazol-2-yl)-1H-pyrazolo[4,3-d]pyrimidin-7-amine; 6-((5-(furan-3-yl)-1H-pyrazolo[4,3-d]pyrimidin-7-yl)amino)-1,3-dimethylpyrimidine-2,-((1H,3H)-dione; N-(5-chloro-1-(2-methoxyethyl)-1H-pyrazol-4-yl)-5-(furan-3-yl)-1H-pyrazolo[4,3-d]pyrimidin-7-amine; N-(1-(2-fluoroethyl)-1H-pyrazol-4-yl)-5-(furan-3-yl)-1H-pyrazolo[4,3-d]pyrimidin-7-amine; 5-cyclopropyl-N-(1-(2-fluoroethyl)-1H-pyrazol-4-yl)-1H-pyrazolo[4,3-d]pyrimidin-7-amine; 5-cyclobutyl-N-(1-(2-fluoroethyl)-1H-pyrazol-4-yl)-1H-pyrazolo[4,3-d]pyrimidin-7-amine; N-(5-chloro-1-(piperidin-4-yl)-1H-pyrazol-4-yl)-5-cyclobutyl-1H-pyrazolo[4,3-d]pyrimidin-7-amine; (4-((5-(furan-2-yl)-1H-pyrazolo[4,3-d]pyrimidin-7-yl)amino)-3-methoxyphenyl)(morpholino)methanone; 6-((5-(furan-2-yl)-1H-pyrazolo[4,3-d]pyrimidin-7-yl)amino)-1,3-dimethylpyrimidine-2,4(1H,3H)-dione; N-(1-(2-fluoroethyl)-1H-pyrazol-4-yl)-5-(furan-2-yl)-1H-pyrazolo[4,3-d]pyrimidin-7-amine; N-(5-chloro-1-(tetrahydro-2H-pyran-4-yl)-1H-pyrazol-4-yl)-5-(furan-2-yl)-1H-pyrazolo[4,3-d]pyrimidin-7-amine; 1-(4-((5-(furan-2-yl)-1H-pyrazolo[4,3-d]pyrimidin-7-yl)amino)-1H-pyrazol-1-yl)-2-methylpropan-2-ol; 5-cyclopropyl-N-(2-fluoro-4-morpholinophenyl)-1H-pyrazolo[4,3-d]pyrimidin-7-amine; 5-cyclopropyl-N-(2,3-dimethylphenyl)-1H-pyrazolo[4,3-d]pyrimidin-7-amine; 5-cyclopropyl-N-(2-methyl-4-morpholinophenyl)-1H-pyrazolo[4,3-d]pyrimidin-7-amine, 5-cyclopropyl-N-(2-methyl-4-(4-methylpiperazin-1-yl)phenyl)-1H-pyrazolo[4,3-d]pyrimidin-7-amine; 5-cyclopropyl-N-(1-(2,2,2-trifluoroethyl)-1H-pyrazol-4-yl)-1H-pyrazolo[4,3-d]pyrimidin-7-amine; 5-(furan-3-yl)-N-(1-(2,2,2-trifluoroethyl)-1H-pyrazol-4-yl)-1H-pyrazolo[4,3-d]pyrimidin-7-amine; 5-(furan-3-yl)-N-(2-methyl-4-morpholinophenyl)-1H-pyrazolo[4,3-d]pyrimidin-7-amine; 5-(furan-2-yl)-N-(1-(2,2,2-trifluoroethyl)-1H-pyrazol-4-yl)-1H-pyrazolo[4,3-d]pyrimidin-7-amine; 5-(furan-2-yl)-N-(2-methyl-4-morpholinophenyl)-1H-pyrazolo[4,3-d]pyrimidin-7-amine; 5-(furan-2-yl)-N-(2-methyl-4-(4-methylpiperazin-1-yl)phenyl)-1H-pyrazolo[4,3-d]pyrimidin-7-amine; 4-((5-(furan-2-yl)-1H-pyrazolo[4,3-d]pyrimidin-7-yl)amino)-1-isopropyl-1H-pyrazole-5-carbonitrile; 5-(furan-2-yl)-N-(1-(2-methoxyethyl)-3-(trifluoromethyl)-1H-pyrazol-4-yl)-1H-pyrazolo[4,3-d]pyrimidin-7-amine; 5-(furan-2-yl)-N-(1-(2-methoxyethyl)-5-(trifluoromethyl)-1H-pyrazol-4-yl)-1H-pyrazolo[4,3-d]pyrimidin-7-amine; 5-(1-isobutyl-1H-pyrazol-4-yl)-N-(4-morpholinophenyl)-1H-pyrazolo[4,3-d]pyrimidin-7-amine; (3-methoxy-4-((5-propyl-1H-pyrazolo[4,3-d]pyrimidin-7-yl)amino)phenyl)(morpholino)methanone; N-(3,4-dimethoxyphenyl)-5-propyl-1H-pyrazolo[4,3-d]pyrimidin-7-amine; N-(4-morpholinophenyl)-5-propyl-1H-pyrazolo[4,3-d]pyrimidin-7-amine, (4-((5-cycloheptyl-1H-pyrazolo[4,3-d]pyrimidin-7-yl)amino)-3-methoxyphenyl)(morpholino)methanone; 5-cycloheptyl-N-(3,4-dimethoxyphenyl)-1H-pyrazolo[4,3-d]pyrimidin-7-amine; 5-cycloheptyl-N-(4-morpholinophenyl)-1H-pyrazolo[4,3-d]pyrimidin-7-amine; 2-(5-chloro-4-((5-cyclopropyl-1H-pyrazolo[4,3-d]pyrimidin-7-yl)amino)-1H-pyrazol-1-yl)ethan-1-ol; 5-cyclopropyl-N-(1-(2-methoxyethyl)-3-(trifluoromethyl)-1H-pyrazol-4-yl)-1H-pyrazolo[4,3-d]pyrimidin-7-amine; 5-cyclopropyl-N-(1-(2-methoxyethyl)-5-(trifluoromethyl)-1H-pyrazol-4-yl)-1H-pyrazolo[4,3-d]pyrimidin-7-amine; 5-(1-(2-methoxyethyl)-1H-pyrazol-4-yl)-N-(4-morpholinophenyl)-1H-pyrazolo[4,3-d]pyrimidin-7-amine; N-(4-morpholinophenyl)-5-(1H-pyrazol-4-yl)-1H-pyrazolo[4,3-d]pyrimidin-7-amine; 4-((5-(furan-3-yl)-1H-pyrazolo[4,3-d]pyrimidin-7-yl)amino)-1-isopropyl-1H-pyrazole-5-carbonitrile; 5-(furan-3-yl)-N-(1-(2-methoxyethyl)-3-(trifluoromethyl)-1H-pyrazol-4-yl)-1H-pyrazolo[4,3-d]pyrimidin-7-amine; 5-(furan-3-yl)-N-(1-(2-methoxyethyl)-5-(trifluoromethyl)-1H-pyrazol-4-yl)-1H-pyrazolo[4,3-d]pyrimidin-7-amine; N-(5-bromo-1-(2-methoxyethyl)-1H-pyrazol-4-yl)-5-(furan-3-yl)-1H-pyrazolo[4,3-d]pyrimidin-7-amine; N-(5-fluoro-1-(2-methoxyethyl)-1H-pyrazol-4-yl)-5-(furan-3-yl)-1H-pyrazolo[4,3-d]pyrimidin-7-amine; 5-cyclopropyl-N-(2-methyl-3-morpholinophenyl)-1H-pyrazolo[4,3-d]pyrimidin-7-amine; 5-cyclopropyl-N-(5-ethynyl-1-(2-methoxyethyl)-1H-pyrazol-4-yl)-1H-pyrazolo[4,3-d]pyrimidin-7-amine; N-(5-bromo-1-(2-methoxyethyl)-1H-pyrazol-4-yl)-5-(furan-2-yl)-1H-pyrazolo[4,3-d]pyrimidin-7-amine; N-(5-fluoro-1-(2-methoxyethyl)-1H-pyrazol-4-yl)-5-(furan-2-yl)-1H-pyrazolo[4,3-d]pyrimidin-7-amine; N4-(5-(furan-2-yl)-1H-pyrazolo[4,3-d]pyrimidin-7-yl)-1-(2-methoxyethyl)-N5,N5-dimethyl-1H-pyrazole-4,5-diamine; 5-(furan-2-yl)-N-(2-methyl-3-morpholinophenyl)-1H-pyrazolo[4,3-d]pyrimidin-7-amine; N-(1-cyclopropyl-1H-pyrazol-4-yl)-5-(3-methoxyphenyl)-1H-pyrazolo[4,3-d]pyrimidin-7-amine; N-(1-(1-(tert-butyl)piperidin-4-yl)-1H-pyrazol-4-yl)-5-(3-methoxyphenyl)-1H-pyrazolo[4,3-d]pyrimidin-7-amine; 5-(3-methoxyphenyl)-N-(1-(3-methoxypropyl)-1H-pyrazol-4-yl)-1H-pyrazolo[4,3-d]pyrimidin-7-amine; 5-(3-methoxyphenyl)-N-(1-(tetrahydro-2H-pyran-4-yl)-1H-pyrazol-4-yl)-1H-pyrazolo[4,3-d]pyrimidin-7-amine; 5-(benzo[d]thiazol-2-yl)-N-(1-cyclopropyl-1H-pyrazol-4-yl)-1H-pyrazolo[4,3-d]

pyrimidin-7-amine; 5-(benzo[d]thiazol-2-yl)-N-(1-(1-(tert-butyl)piperidin-4-yl)-1H-pyrazol-4-yl)-1H-pyrazolo[4,3-d]pyrimidin-7-amine; 5-(benzo[d]thiazol-2-yl)-N-(1-(3-methoxypropyl)-1H-pyrazol-4-yl)-1H-pyrazolo[4,3-d]pyrimidin-7-amine; 5-(benzo[d]thiazol-2-yl)-N-(1-(tetrahydro-2H-pyran-4-yl)-1H-pyrazol-4-yl)-1H-pyrazolo[4,3-d]pyrimidin-7-amine; 5-(1H-indazol-6-yl)-N-(1-isopropyl-1H-pyrazol-4-yl)-1H-pyrazolo[4,3-d]pyrimidin-7-amine; N-(1-(tert-butyl)-1H-pyrazol-4-yl)-5-(1H-indazol-6-yl)-1H-pyrazolo[4,3-d]pyrimidin-7-amine; 2-(4-((5-(1H-indazol-6-yl)-1H-pyrazolo[4,3-d]pyrimidin-7-yl)amino)-1H-pyrazol-1-yl)-2-methylpropanenitrile; N-(1-(2-fluoroethyl)-1H-pyrazol-4-yl)-5-(1H-indazol-6-yl)-1H-pyrazolo[4,3-d]pyrimidin-7-amine; N-(1-cyclopropyl-1H-pyrazol-4-yl)-5-(1H-indazol-6-yl)-1H-pyrazolo[4,3-d]pyrimidin-7-amine; 5-(1H-indazol-6-yl)-N-(1-(3-methoxypropyl)-1H-pyrazol-4-yl)-1H-pyrazolo[4,3-d]pyrimidin-7-amine; N-(1-isopropyl-1H-pyrazol-4-yl)-5-(1-methyl-1H-pyrazol-4-yl)-1H-pyrazolo[4,3-d]pyrimidin-7-amine; 5-(1-isopropyl-1H-pyrazol-4-yl)-N-(4-morpholinophenyl)-1H-pyrazolo[4,3-d]pyrimidin-7-amine; 2-(4-(4-((5-(1H-indazol-6-yl)-1H-pyrazolo[4,3-d]pyrimidin-7-yl)amino)phenyl)piperazin-1-yl)ethan-1-ol; 5-(1H-indazol-6-yl)-N-(1-isobutyl-1H-pyrazol-4-yl)-1H-pyrazolo[4,3-d]pyrimidin-7-amine; 3-(7-((1-(3-methoxypropyl)-1H-pyrazol-4-yl)amino)-1H-pyrazolo[4,3-d]pyrimidin-5-yl)benzenesulfonamide; 3-(7-((1-(tetrahydro-2H-pyran-4-yl)-1H-pyrazol-4-yl)amino)-1H-pyrazolo[4,3-d]pyrimidin-5-yl)benzenesulfonamide; 3-(7-((1-isopropyl-1H-pyrazol-4-yl)amino)-1H-pyrazolo[4,3-d]pyrimidin-5-yl)benzenesulfonamide; 3-(7-((1-(1-acetylpiperidin-4-yl)-1H-pyrazol-4-yl)amino)-1H-pyrazolo[4,3-d]pyrimidin-5-yl)benzenesulfonamide; 3-(7-((1-isobutyl-1H-pyrazol-4-yl)amino)-1H-pyrazolo[4,3-d]pyrimidin-5-yl)benzenesulfonamide; N-(1-(3-methoxypropyl)-1H-pyrazol-4-yl)-5-(thiophen-2-yl)-1H-pyrazolo[4,3-d]pyrimidin-7-amine; N-(1-(tetrahydro-2H-pyran-4-yl)-1H-pyrazol-4-yl)-5-(thiophen-2-yl)-1H-pyrazolo[4,3-d]pyrimidin-7-amine; N-(1-isopropyl-1H-pyrazol-4-yl)-5-(thiophen-2-yl)-1H-pyrazolo[4,3-d]pyrimidin-7-amine; N-(1-isobutyl-1H-pyrazol-4-yl)-5-(thiophen-2-yl)-1H-pyrazolo[4,3-d]pyrimidin-7-amine; N-(1-(1-methylpiperidin-4-yl)-1H-pyrazol-4-yl)-5-(thiophen-2-yl)-1H-pyrazolo[4,3-d]pyrimidin-7-amine; 5-(3,5-dimethylisoxazol-4-yl)-N-(4-morpholinophenyl)-1H-pyrazolo[4,3-d]pyrimidin-7-amine; 5-(3-methylthiophen-2-yl)-N-(1-(tetrahydro-2H-pyran-4-yl)-1H-pyrazol-4-yl)-1H-pyrazolo[4,3-d]pyrimidin-7-amine; N-(1-(3-methoxypropyl)-1H-pyrazol-4-yl)-5-(1-methyl-1H-pyrazol-4-yl)-1H-pyrazolo[4,3-d]pyrimidin-7-amine; N-(1-isobutyl-1H-pyrazol-4-yl)-5-(1-methyl-1H-pyrazol-4-yl)-1H-pyrazolo[4,3-d]pyrimidin-7-amine; N-(4-morpholinophenyl)-5-(trifluoromethyl)-1H-pyrazolo[4,3-d]pyrimidin-7-amine; 5-(2,6-difluorophenyl)-N-(1-(tetrahydro-2H-pyran-4-yl)-1H-pyrazol-4-yl)-1H-pyrazolo[4,3-d]pyrimidin-7-amine; difluorophenyl)-N-(1-isobutyl-1H-pyrazol-4-yl)-1H-pyrazolo[4,3-d]pyrimidin-7-amine; N4-(5-(furan-3-yl)-1H-pyrazolo[4,3-d]pyrimidin-7-yl)-1-(2-methoxyethyl)-N5,N5-dimethyl-1H-pyrazole-4,5-diamine; 2-(4-(4-((5-(furan-3-yl)-1H-pyrazolo[4,3-d]pyrimidin-7-yl)amino)phenyl)piperazin-1-yl)ethan-1-ol; 1-(4-((5-(furan-3-yl)-1H-pyrazolo[4,3-d]pyrimidin-7-yl)amino)phenyl)piperidin-4-ol; 2-(4-((5-(benzo[d]oxazol-2-yl)-1H-pyrazolo[4,3-d]pyrimidin-7-yl)amino)-1H-pyrazol-1-yl)ethan-1-ol; 5-(benzo[d]oxazol-2-yl)-N-(1-(1-methylpiperidin-4-yl)-1H-pyrazol-4-yl)-1H-pyrazolo[4,3-d]pyrimidin-7-amine; 5-(benzo[d]oxazol-2-yl)-N-(1-(tetrahydro-2H-pyran-4-yl)-1H-pyrazolo[4,3-d]pyrimidin-7-amine; 5-(1H-indazol-6-yl)-N-(1-(pyrrolidin-3-yl)-1H-pyrazol-4-yl)-1H-pyrazolo[4,3-d]pyrimidin-7-amine; N-(1-(1,3-dimethoxypropan-2-yl)-1H-pyrazol-4-yl)-5-(1H-indazol-6-yl)-1H-pyrazolo[4,3-d]pyrimidin-7-amine; 1-(4-((5-(1H-indazol-6-yl)-1H-pyrazolo[4,3-d]pyrimidin-7-yl)amino)-1H-pyrazol-1-yl)-2-methylpropan-2-ol; 1-(4-((5-(furan-2-yl)-1H-pyrazolo[4,3-d]pyrimidin-7-yl)amino)phenyl)piperidin-4-ol; 1-(4-((5-(furan-2-yl)-1H-pyrazolo[4,3-d]pyrimidin-7-yl)amino)-1H-pyrazol-1-yl)-2-methylpropan-2-ol; 2-(4-((5-(furan-2-yl)-1H-pyrazolo[4,3-d]pyrimidin-7-yl)amino)-1H-pyrazol-1-yl)-N,N-dimethylacetamide; tert-butyl 3-(4-((5-(furan-2-yl)-1H-pyrazolo[4,3-d]pyrimidin-7-yl)amino)-1H-pyrazol-1-yl)pyrrolidine-1-carboxylate; N-(1-cyclopropyl-1H-pyrazol-4-yl)-5-(furan-2-yl)-1H-pyrazolo[4,3-d]pyrimidin-7-amine; N-(1-(1,3-dimethoxypropan-2-yl)-1H-pyrazol-4-yl)-5-(furan-2-yl)-1H-pyrazolo[4,3-d]pyrimidin-7-amine; 5-(benzo[d]thiazol-2-yl)-N-(1-(2-methoxyethyl)-1H-pyrazol-4-yl)-1H-pyrazolo[4,3-d]pyrimidin-7-amine; 5-(benzo[d]thiazol-2-yl)-N-(1-isobutyl-1H-pyrazol-4-yl)-1H-pyrazolo[4,3-d]pyrimidin-7-amine; 1-(4-(4-((5-(benzo[d]thiazol-2-yl)-1H-pyrazolo[4,3-d]pyrimidin-7-yl)amino)-1H-pyrazol-1-yl)piperidin-1-yl)ethan-1-one; 5-(benzo[d]thiazol-2-yl)-N-(1-(1-methylpiperidin-4-yl)-1H-pyrazol-4-yl)-1H-pyrazolo[4,3-d]pyrimidin-7-amine; 5-(1-benzyl-1H-pyrazol-4-yl)-N-(4-morpholinophenyl)-1H-pyrazolo[4,3-d]pyrimidin-7-amine; 2-(4-((5-cyclobutyl-1H-pyrazolo[4,3-d]pyrimidin-7-yl)amino)-1H-pyrazol-1-yl)-N,N-dimethylacetamide; 5-cyclobutyl-N-(1-(pyrrolidin-3-yl)-1H-pyrazol-4-yl)-1H-pyrazolo[4,3-d]pyrimidin-7-amine; 5-cyclobutyl-N-(1-(1,3-dimethoxypropan-2-yl)-1H-pyrazol-4-yl)-1H-pyrazolo[4,3-d]pyrimidin-7-amine; N-(1-(pyridin-2-yl)-1H-pyrazol-4-yl)-5-(3-(pyridin-3-yl)phenyl)-1H-pyrazolo[4,3-d]pyrimidin-7-amine; 5-(3-(pyridin-3-yl)phenyl)-N-(1-(pyrrolidin-3-yl)-1H-pyrazol-4-yl)-1H-pyrazolo[4,3-d]pyrimidin-7-amine; N,N-dimethyl-2-(4-((5-(3-(pyridin-3-yl)phenyl)-1H-pyrazolo[4,3-d]pyrimidin-7-yl)amino)-1H-pyrazol-1-yl)acetamide; N-(1-(1,3-dimethoxypropan-2-yl)-1H-pyrazol-4-yl)-5-(3-(pyridin-3-yl)phenyl)-1H-pyrazolo[4,3-d]pyrimidin-7-amine; N-(1-(1-(tert-butyl)piperidin-4-yl)-1H-pyrazol-4-yl)-5-(1H-indazol-6-yl)-1H-pyrazolo[4,3-d]pyrimidin-7-amine; 5-(1H-indazol-6-yl)-N-(1-(3-methylbutan-2-yl)-1H-pyrazol-4-yl)-1H-pyrazolo[4,3-d]pyrimidin-7-amine; 6-((5-(1H-indazol-6-yl)-1H-pyrazolo[4,3-d]pyrimidin-7-yl)amino)-4-methyl-2H-benzo[b][1,4]oxazin-3(4H)-one; 6-((5-(1H-indazol-6-yl)-1H-pyrazolo[4,3-d]pyrimidin-7-yl)amino)-4-ethyl-2H-benzo[b][1,4]oxazin-3(4H)-one; 5-(1H-indazol-6-yl)-N-(1-(pyridin-2-yl)-1H-pyrazol-4-yl)-1H-pyrazolo[4,3-d]pyrimidin-7-amine; 5-(bicyclo[4.1.0]heptan-7-yl)-N-(1-(tetrahydro-2H-pyran-4-yl)-1H-pyrazol-4-yl)-1H-pyrazolo[4,3-d]pyrimidin-7-amine; 5-(bicyclo[4.1.0]heptan-7-yl)-N-(1-(pyrrolidin-3-yl)-1H-pyrazol-4-yl)-1H-pyrazolo[4,3-d]pyrimidin-7-amine; 5-(bicyclo[4.1.0]heptan-7-yl)-N-(3-methoxy-4-morpholinophenyl)-1H-pyrazolo[4,3-d]pyrimidin-7-amine; 2-(4-((5-(1H-indazol-6-yl)-1H-pyrazolo[4,3-d]pyrimidin-7-yl)amino)-1H-pyrazol-1-yl)ethan-1-ol; 5-(1H-indazol-6-yl)-N-(1-(1-phenylethyl)-1H-pyrazol-4-yl)-1H-pyrazolo[4,3-d]pyrimidin-7-amine; N-(3-ethylphenyl)-5-(1H-indazol-6-yl)-1H-pyrazolo[4,3-d]pyrimidin-7-amine; (7-((5-(1H-indazol-6-yl)-1H-pyrazolo[4,3-d]pyrimidin-7-yl)amino)-3,4-dihydroquinolin-1(2H)-yl)(cyclopropyl)methanone; N-(3,4-dimethoxyphenyl)-5-(2-fluoro-6-methylphenyl)-1H-pyrazolo[4,3-d]pyrimidin-7-amine; 5-(2-fluoro-6-methylphenyl)-N-(3-methoxy-4-morpholinophenyl)-1H-pyrazolo[4,3-d]pyrimidin-7-amine; 5-(furan-3-yl)-N-(1-(3-methylbutan-2-yl)-1H-pyrazol-4- yl)-1H-pyrazolo[4,3-d]pyrimidin-7-amine; 5-(furan-3-yl)-N-(1-(tetrahydro-2H-pyran-3-yl)-1H-pyrazol-4-yl)-1H-pyrazolo[4,3-d]pyrimidin-7-amine; 5-(furan-3-yl)-N-(1-(pyridin-2-yl)-1H-pyrazol-4-yl)-1H-pyrazolo[4,3-d]pyrimidin-7-amine; 4-ethyl-6-((5-(furan-3-yl)-1H-pyrazolo[4,3-d]pyrimidin-7-yl)amino)-2H-benzo[b][1,4]oxazin-3(4H)-one; 2-(4-((5-(furan-3-yl)-1H-pyrazolo[4,3-d]pyrimidin-7-yl)amino)-1H-pyrazol-1-yl)propanoic acid; 5-(furan-3-yl)-N-(1-(1-phenylethyl)-1H-pyrazol-4-yl)-1H-pyrazolo[4,3-d]pyrimidin-7-amine; 6-((5-(furan-3-yl)-1H-pyrazolo[4,3-d]pyrimidin-7-yl)amino)-4-methyl-2H-benzo[b][1,4]oxazin-3(4H)-one; N-(3-ethylphenyl)-5-(furan-3-yl)-1H-pyrazolo[4,3-d]pyrimidin-7-amine; cyclopropyl(7-((5-(furan-3-yl)-1H-pyrazolo[4,3-d]pyrimidin-7-yl)amino)-3,4-dihydroquinolin-1(2H)-yl)methanone; 5-(2,2-dimethylcyclopropyl)-N-(1-(tetrahydro-2H-pyran-4-yl)-1H-pyrazol-4-yl)-1H-pyrazolo[4,3-d]pyrimidin-7-amine; dimethylcyclopropyl)-N-(3-methoxy-4-morpholinophenyl)-1H-pyrazolo[4,3-d]pyrimidin-7-amine; 2-(4-((5-(1H-indazol-6-yl)-1H-pyrazolo[4,3-d]pyrimidin-7-yl)amino)-1H-pyrazol-1-yl)propanoic acid; 5-((5-(1H-indazol-6-yl)-1H-pyrazolo[4,3-d]pyrimidin-7-yl)amino)-1H-pyrazole-3-carboxylic acid; N-(1-(1-(tert-butyl)piperidin-4-yl)-1H-pyrazol-4-yl)-5-(4,5,6,7-tetrahydrobenzo[d]thiazol-2-yl)-1H-pyrazolo[4,3-d]pyrimidin-7-amine; N-(1-(tetrahydro-2H-pyran-4-yl)-1H-pyrazol-4-yl)-5-(4,5,6,7-tetrahydrobenzo[d]thiazol-2-yl)-1H-pyrazolo[4,3-d]pyrimidin-7-amine; 6-((5-cyclopropyl-1H-pyrazolo[4,3-d]pyrimidin-7-yl)amino)-4-methyl-2H-benzo[b][1,4]oxazin-3(4H)-one; 5-cyclopropyl-N-(1-(3-methylbutan-2-yl)-1H-pyrazol-4-yl)-1H-pyrazolo[4,3-d]pyrimidin-7-amine; 5-((5-cyclopropyl-1H-pyrazolo[4,3-d]pyrimidin-7-yl)amino)-1H-pyrazole-3-carboxylic acid; (4-((5-(2,6-difluorophenyl)-1H-pyrazolo[4,3-d]pyrimidin-7-yl)amino)phenyl)(4-methylpiperazin-1-yl)methanone; 2-(4-(4-((5-(2,6-difluorophenyl)-1H-pyrazolo[4,3-d]pyrimidin-7-yl)amino)phenyl)piperazin-1-yl)ethan-1-ol; 5-((5-(2,6-difluorophenyl)-1H-pyrazolo[4,3-d]pyrimidin-7-yl)amino)-2-morpholinobenzonitrile; cyclopropyl(7-((5-cyclopropyl-1H-pyrazolo[4,3-d]pyrimidin-7-yl)amino)-3,4-dihydroquinolin-1(2H)-yl)methanone; 2-(4-((5-cyclopropyl-1H-pyrazolo[4,3-d]pyrimidin-7-yl)amino)-1H-pyrazol-1-yl)propanoic acid; 5-(1H-indazol-6-yl)-N-(1-(tetrahydro-2H-pyran-4-yl)-1H-pyrazol-4-yl)-1H-pyrazolo[4,3-d]pyrimidin-7-amine; 2-((5-(1H-indazol-6-yl)-1H-pyrazolo[4,3-d]pyrimidin-7-yl)amino)phenol; N1-(5-(1H-indazol-6-yl)-1H-pyrazolo[4,3-d]pyrimidin-7-yl)-4,5-dimethoxybenzene-1,2-diamine; N-(3-methoxy-4-morpholinophenyl)-5-((1S,2S)-2-phenylcyclopropyl)-1H-pyrazolo[4,3-d]pyrimidin-7-amine; N-(3,4-dimethoxyphenyl)-5-(1S,2S)-2-phenylcyclopropyl)-1H-pyrazolo[4,3-d]pyrimidin-7-amine; N-(4-morpholinophenyl)-5-((1S,2S)-2-phenylcyclopropyl)-1H-pyrazolo[4,3-d]pyrimidin-7-amine; N-(3,4-dimethoxyphenyl)-5-(1-(3-methylbutan-2-yl)-1H-pyrazol-4-yl)-1H-pyrazolo[4,3-d]pyrimidin-7-amine; N-(3-methoxy-4-morpholinophenyl)-5-(1-(3-methylbutan-2-yl)-1H-pyrazol-4-yl)-1H-pyrazolo[4,3-d]pyrimidin-7-amine; 5-(2-chloro-6-fluorophenyl)-N-(3,4-dimethoxyphenyl)-1H-pyrazolo[4,3-d]pyrimidin-7-amine; 5-(2-chloro-6-fluorophenyl)-N-(3-methoxy-4-morpholinophenyl)-1H-pyrazolo[4,3-d]pyrimidin-7-amine; 5-(1H-indazol-6-yl)-N-(4-(phenylthio)phenyl)-1H-pyrazolo[4,3-d]pyrimidin-7-amine; 8-((5-(1H-indazol-6-yl)-1H-pyrazolo[4,3-d]pyrimidin-7-yl)amino)-4,5-dihydro-1H-benzo[b]azepin-2(3H)-one; 5-(1H-indazol-6-yl)-N-(1-(2,2,2-trifluoroethyl)-1H-pyrazol-4-yl)-1H-pyrazolo[4,3-d]pyrimidin-7-amine; 1-(4-((5-(1H-indazol-6-yl)-1H-pyrazolo[4,3-d]pyrimidin-7-yl)amino)phenyl)piperidin-4-ol; 6-((5-(1H-indazol-6-yl)-1H-pyrazolo[4,3-d]pyrimidin-7-yl)amino)-2H-benzo[b][1,4]oxazin-3(4H)-one; 6-((5-(1H-indazol-6-yl)-1H-pyrazolo[4,3-d]pyrimidin-7-yl)amino)-2H-benzo[b][1,4]thiazin-3(4H)-one; 8-((5-(2,6-difluorophenyl)-1H-pyrazolo[4,3-d]pyrimidin-7-yl)amino)-4,5-dihydro-1H-benzo[b]azepin-2(3H)-one; 1-(4-((5-(2,6-difluorophenyl)-1H-pyrazolo[4,3-d]pyrimidin-7-yl)amino)phenyl)piperidin-4-ol; N-(5-((5-(2,6-difluorophenyl)-1H-pyrazolo[4,3-d]pyrimidin-7-yl)amino)-2-methoxyphenyl)acetamide; 5-(2,6-difluorophenyl)-N-(1-(2,2,2-trifluoroethyl)-1H-pyrazol-4-yl)-1H-pyrazolo[4,3-d]pyrimidin-7-amine; 3-(7-((2-oxo-2,3,4,5-tetrahydro-1H-benzo[b]azepin-8-yl)amino)-1H-pyrazolo[4,3-d]pyrimidin-5-yl)benzenesulfonamide; 3-(7-((1-(2-hydroxyethyl)-1H-pyrazol-4-yl)amino)-1H-pyrazolo[4,3-d]pyrimidin-5-yl)benzenesulfonamide; 5-(2-(methylsulfonyl)phenyl)-N-(4-morpholinophenyl)-1H-pyrazolo[4,3-d]pyrimidin-7-amine; 8-((5-(2-(methylsulfonyl)phenyl)-1H-pyrazolo[4,3-d]pyrimidin-7-yl)amino)-4,5-dihydro-1H-benzo[b]azepin-2(3H)-one; N-(3-(7-((2-oxo-2,3,4,5-tetrahydro-1H-benzo[b]azepin-8-yl)amino)-1H-pyrazolo[4,3-d]pyrimidin-5-yl)phenyl)methanesulfonamide, 5-(3-aminophenyl)-N-(1-(tetrahydro-2H-pyran-4-yl)-1H-pyrazol-4-yl)-1H-pyrazolo[4,3-d]pyrimidin-7-amine; 5-(2-aminophenyl)-N-(1-(tetrahydro-2H-pyran-4-yl)-1H-pyrazol-4-yl)-2H-pyrazolo[4,3-d]pyrimidin-7-amine; 5-(2-amino-6-fluorophenyl)-N-(1-(tetrahydro-2H-pyran-4-yl)-1H-pyrazol-4-yl)-1H-pyrazolo[4,3-d]pyrimidin-7-amine; N-(1-(1-methylpiperidin-4-yl)-1H-pyrazol-4-yl)-5-(2-(methylsulfonyl)phenyl)-1H-pyrazolo[4,3-d]pyrimidin-7-amine; 5-(2-(methylsulfonyl)phenyl)-N-(1-(tetrahydro-2H-pyran-4-yl)-1H-pyrazol-4-yl)-1H-pyrazolo[4,3-d]pyrimidin-7-amine; N-(1-(1-methylpiperidin-4-yl)-1H-pyrazol-4-yl)-5-(thiazol-2-yl)-1H-pyrazolo[4,3-d]pyrimidin-7-amine; (5-((5-(1H-indazol-6-yl)-1H-pyrazolo[4,3-d]pyrimidin-7-yl)amino)-2-(4-methylpiperazin-1-yl)phenyl)methanol; N-(5-(2,6-difluorophenyl)-1H-pyrazolo[4,3-d]pyrimidin-7-yl)-3,4-dihydro-2H-benzo[b][1,4]oxazin-6-amine; N-(2-(4-acetylpiperazin-1-yl)-5-((5-(2,6-difluorophenyl)-1H-pyrazolo[4,3-d]pyrimidin-7-yl)amino)phenyl)acetamide; N-(3-chloro-4-(4-methylpiperazin-1-yl)phenyl)-5-(2,6-difluorophenyl)-1H-pyrazolo[4,3-d]pyrimidin-7-amine; 2,6-dichloro-4-((5-(2,6-difluorophenyl)-1H-pyrazolo[4,3-d]pyrimidin-7-yl)amino)phenol; 5-(2,6-difluorophenyl)-N-(3-ethoxy-4-methoxyphenyl)-1H-pyrazolo[4,3-d]pyrimidin-7-amine.

Preferably, the following compounds are excluded from the scope of the present application:

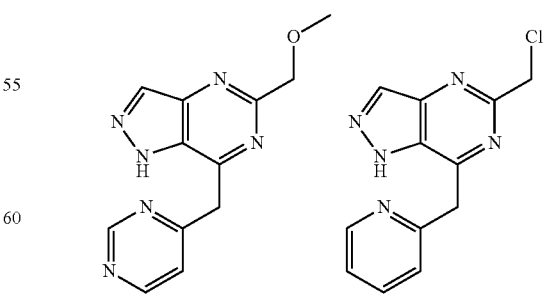

The present invention further provides pharmaceutical compositions comprising one or more compounds of formula (I) as defined herein or a pharmaceutically acceptable ester, prodrug, hydrate, solvate or salt thereof, optionally in combination with a pharmaceutically acceptable carrier.

It is a further object of the present invention to provide a compound of formula (I) as defined herein or a pharmaceutical composition as defined herein for the preparation of a medicament for the treatment of one or more diseases mentioned herein.

Preferably the compounds of the present invention may be used for the treatment and/or prevention of the following conditions:

respiratory tract/obstructive airways diseases and disorders including:

rhinorrhea, tracheal constriction, airway contraction, acute-, allergic, atrophic rhinitis or chronic rhinitis (such as rhinitis caseosa, hypertrophic rhinitis, rhinitis purulenta, rhinitis sicca), rhinitis medicamentosa, membranous rhinitis (including croupous, fibrinous and pseudomembranous rhinitis), scrofulous rhinitis, perennial allergic rhinitis, seasonal rhinitis (including rhinitis nervosa (hay fever) and vasomotor rhinitis), pollinosis, asthma (such as bronchial, atopic, allergic, intrinsic, extrinsic, exercise-induced, cold air-induced, occupational, bacterial infection-induced, and dust asthma particularly chronic or inveterate asthma (e.g. late asthma and airways hyper-responsiveness)), bronchitis (including chronic, acute, arachidic, catarrhal, croupus, phthinoid and eosinophilic bronchitis), cardiobronchitis, pneumoconiosis, chronic inflammatory disease of the lung which result in interstitial fibrosis, such as interstitial lung disease (ILD) (e.g., idiopathic pulmonary fibrosis, or ILD associated with rheumatoid arthritis, or other autoimmune conditions), acute lung injury (ALI), adult respiratory distress syndrome (ARDS), chronic obstructive pulmonary, airways or lung disease (CORD, COAD, COLD or COPD, such as irreversible COPD), chronic sinusitis, conjunctivitis (e.g. allergic conjunctivitis), cystic fibrosis, extrinsic allergic alveolitis (like farmer's lung and related diseases), fibroid lung, hypersensitivity lung diseases, hypersensitivity pneumonitis, idiopathic interstitial pneumonia, nasal congestion, nasal polyposis, otitis media, and cough (chronic cough associated with inflammation or iatrogenic induced), pleurisy, pulmonary congestion, emphysema, bronchiectasis, sarcoidosis, lung fibrosis, including cryptogenic fibrosing alveolitis, fibrosis complicating antineoplastic therapy and chronic infection, including tuberculosis and aspergillosis and other fungal infections, vasculitic and thrombotic disorders of the lung vasculature, and pulmonary hypertension, acute viral infection including the common cold, and infection due to respiratory syncytial virus, influenza, coronavirus (including SARS) and adenovirus, allergic bronchopulmonary mycosis, emphysema, diffuse panbronchiolitis, systemic anaphylaxis or hypersensitivity responses, drug allergies (e.g., to penicillin, cephalosporins), insect sting allergies, and food related allergies which may have effects remote from the gut (such as migraine, rhinitis and eczema), anaphylactic shock, vascular spasms;

bone and joint related diseases and disorders including:

osteoporosis, arthritis (including rheumatic, infectious, autoimmune, chronic, malignant), seronegative spondyloarthropathies (such as ankylosing spondylitis, rheumatoid spondylitis, psoriatic arthritis, enthesopathy, Bechet's disease, Marie-Strümpell arthritis, arthritis of inflammatory bowel disease, and Reiter's disease), systemic sclerosis, osteoarthritis, osteoarthrosis, both primary and secondary to e.g. congenital hip dysplasia, cervical and lumbar spondylitis, and low back and neck pain, Still's disease, reactive arthritis and undifferentiated spondarthropathy, septic arthritis and other infection-related arthropathies and bone disorders such as tuberculosis, including Pott's disease and Poncet's syndrome, acute and chronic crystal-induced synovitis including urate gout, calcium pyrophosphate deposition disease, and calcium apatite related tendon, bursar and synovial inflammation, primary and secondary Sjogren's syndrome, systemic sclerosis and limited scleroderma, mixed connective tissue disease, and undifferentiated connective tissue disease, inflammatory myopathies including, polymalgia rheumatica, juvenile arthritis including idiopathic inflammatory arthritides of whatever joint distribution and associated syndromes, other joint disease (such as intervertebral disc degeneration or temporomandibular joint degeneration), rheumatic fever and its systemic complications, vasculitides including giant cell arteritis, Takayasu's arteritis, polyarteritis nodosa, microscopic polyarteritis, and vasculitides to associated with viral infection, hypersensitivity reactions, cryoglobulins, paraproteins, low back pain, Familial Mediterranean fever, Muckle-Wells syndrome, and Familial Hibenian Fever, Kikuchi disease, drug-induced arthalgias, tendonititides, polychondritis, and myopathies, osteoporosis, osteomalacia like osteoporosis, osteopenia, osteogenesis imperfects, osteopetrosis, osteofibrosis, osteonecrosis, Paget's disease of bone, hypophosphatemia, Felty's syndrome, Still's disease, slack of artificial joint implant, sprain or strain of muscle or joint, tendinitis, fasciitis, periarthritis humeroscapularis, cervico-omo-brachial syndrome, tenosynovitis;

skin and eye related diseases and disorders including:

glaucoma, ocular hypertension, cataract, retinal detachment, psoriasis (including psoriasis vulgaris, pustular psoriasis, arthritic psoriasis, erythroderma psoriaticum), palmoplantar pustulosis, xerodoma, eczematous diseases (like atopic dermatitis, ultraviolet radiation dermatitis, contact dermatitis, and seborrheic dermatitis), phytodermatitis, photodermatitis, cutaneous eosinophilias, chronic skin ulcers, cutaneous lupus erythematosus, contact hypersensitivity/allergic contact dermatitis (including sensitivity to poison ivy, sumac, or oak), and eosinophilic folliculitis (Ofuji's disease), pruritus, drug eruptions, urticaria (acute or chronic, allergic or non-allergic), acne, erythema, dermatitis herpetiformis, scleroderma, vitiligo, lichen planus, lichen sclerosus et atrophica, pyodenna gangrenosum, skin sarcoid, pemphigus, ocular pemphigus, pemphigoid, epidennolysis bullosa, angioedema, vasculitides, toxic erythemas, cutaneous eosinophilias, alopecia areata, male-pattern baldness, Sweet's syndrome, Stevens-Johnson syndrome, Weber-Christian syndrome, erythema multiforme, cellulitis, botl, infective and non infective, panniculitis, cutaneous Lymphomas, non-melanoma skin cancer and other dysplastic lesions, blepharitis, iritis, anterior and posterior uveitis, choroiditis, autoimmune, degenerative or inflammatory disorders affecting the retina, ophthalmitis including sympathetic ophthalmitis, sarcoidosis, xerosis infections including viral, fungal, and bacterial, allergic conjunctivitis, increased fibrosis, keloids, keloplasty, post-surgical scars, epidermolysis bullosa, dry eye, ocular inflammation, allergic conjunctivitis, vernal conjunctivitis, vernal keratoconjunctivitis, and giant papillary conjunctivitis, ocular angiogenesis, cornea damage and scar, all forms of macular degeneration, macular edema, macular dystrophy, abnormal wound healing, scleritis, episcleritis, pachydermia, peripheral ulcerative keratitis, fungal keratitis, herpetic keratitis, invasive aspergillosis; conical cornea, dystorphia epithelialis corneae, severe intraocular inflammation;

gastrointestinal tract and abdominal related diseases and disorders including:

celiac/coeliac disease (e.g. celiac sprue), cholecystitis, enteritis (including infectious, ischemic, radiation, drug-induced, and eosinophilic gastroenteritis), eosinophilic esophagitis, eosinophilic gastrointestinal inflammation, allergen induced diarrhea, enteropathy associated with seronegative arthropathies, gastritis, autoimmune atrophic gastritis, ischemic bowel disease, inflammatory bowel disease (Crohn's disease and ulcerative colitis), colitis, Mooren's ulcer, irritable bowel syndrome, necrotizing enterocolitis, gut ischemia, glossitis, gingivitis, periodontitis, oesophagitis, including reflux, proctitis, fibrosis and cirrhosis of the liver, pancreatitis, both acute and chronic, pancreatic fibrosis, pancreatic sclerosis, pancreatolithiasis, hepatic cirrhosis, hepatitis (congestive, autoimmune, acute, fulminant, chronic, drug-induced, alcoholic, lupoid, steatohepatitis and chronic viral), fatty liver, primary biliary cirrhosis, hepatic porphyria, and gastrointestinal related allergic disorders, spastic colon, diverticulitis, gastroenteric bleeding, Behcet's disease; partial liver resection, acute liver necrosis (e.g. necrosis caused by toxins, viral hepatitis, shock or anoxia), hemolytic uremic syndrome;

hematological disorders including:

anemias, coagulation, myeloproliferative disorders, hemorrhagic disorders, leukopenia, eosinophilic disorders, leukemias (e.g. myelogenous, lymphomas, plasma cell dyscrasias, disorders of the spleen, Banti's disease, hemophilia, purpura (including idiopathic thrombocytopenic purpura), Wiskott-Aldrich syndrome;

metabolic disorders including:

obesity, amyloidosis, disturbances of the amino and acid metabolism like branched chain disease, hyperaminoacidemia, hyperaminoaciduria, disturbances of the metabolism of urea, hyperammonemia, mucopolysaccharidoses e.g. Maroteaux-Lamy syndrome, storage disease like glycogen storage diseases and lipid storage diseases, glycogenosis I diseases like Cori's disease, malabsorption diseases like intestinal carbohydrate malabsorption, oligosaccharidase deficiency like maltase-, lactase-, sucrase-insufficiency, disorders of the metabolism of fructose, disorders of the metabolism of galactose, galactosaemia, disturbances of carbohydrate utilization like diabetes, hypoglycemia, disturbances of pyruvate metabolism, hypolipidemia, hypolipoproteinemia, hyperlipidemia, hyperlipoproteinemia, carnitine or carnitine acyltransferase deficiency, disturbances of the porphyrin metabolism, porphyrins, disturbances of the purine metabolism, lysosomal diseases, metabolic diseases of nerves and nervous systems like gangliosidoses, sphingolipidoses, sulfatidoses, leucodystrophies, Lesch-Nyhan syndrome;

cerebellar dysfunction, disturbances of brain metabolism like:

dementia, Alzheimer's disease, Huntington's chores, Parkinson's disease, Pick's disease, toxic encepha-lopathy, demyelinating neuropathies like inflammatory neuropathy, Guillain-Barre syndrome; Meniere's disease and radiculopathy, primary and secondary metabolic disorders associated with hormonal defects like any disorder stemming from either an hyperfunction or hypofunction of some hormone-secreting endocrine gland and any combination thereof. Sipple's syndrome, pituitary gland dysfunction and its effects on other endocrine glands, such as the thyroid, adrenals, ovaries, and testes, acromegaly, hyper- and hypothyroidism, euthyroid goiter, euthyroid sick syndrome, thyroiditis, and thyroid cancer, over or underproduction of the adrenal steroid hormones, adrenogenital syndrome, Cushing's syndrome, Addison's disease of the adrenal cortex, Addison's pernicious anemia, primary and secondary aldosteronism, diabetes insipidus, diabetes mellitus, carcinoid syndrome, disturbances caused by the dysfunction of the parathyroid glands, pancreatic islet cell dysfunction, diabetes, disturbances of the endocrine system of the female like estrogen deficiency, resistant ovary syndrome; muscle weakness, myotonia. Duchenne's and other muscular dystrophies, dystrophia myotonica of Steinert, mitochondrial myopathies like I disturbances of the catabolic metabolism in the muscle, carbohydrate and lipid storage myopathies, glycogenoses, myoglobinuria, malignant hyperthermia, polymyalgia rheumatics, dermatomyositis, multiple myositis, primary myocardial disease, cardiomyopathy; disorders of the ectoderm, neurofibromatosis, scleroderma and polyar teritis, Louis-Bar syndrome, von Hippel-Lindau disease, Sturge-Weber syndrome, tuberous sclerosis, amyloidosis, porphyria; sexual dysfunction of the male and female; confused states and seizures due to inappropriate secretion of antidiuretic hormone from the pituitary gland, Liddle's syndrome, Bartter's syndrome, Fanconi's I syndrome, and renal electrolyte wasting;

transplant rejection related conditions including:

acute and chronic allograft rejection following solid organ transplant, for example, transplantation of kidney, heart, liver, lung, and cornea, chronic graft versus host disease, skin graft rejection, and bone marrow transplant rejection, immunosuppresion;

genitourinary related conditions including:

nephritis (interstitial, acute interstitial (allergic), and glomerulonephritis), nephrotic syndrome, cystitis including acute and chronic (interstitial) cystitis and Hunner's ulcer, acute and chronic urethritis, prostatitis, epididymitis, oophoritis, salpingitis, vulvo vaginitis, vulvovaginal candidiasis, Peyronie's disease, and erectile dysfunction, renal disease, renal fibrosis, nephropyelitis, secondary contracted kidney, steroid dependent and steroid-resistant nephrosis, Goodpasture's syndrome;

CNS related diseases and disorders including:

neurodegenerative diseases, Alzheimer's disease and other cementing disorders including CJD and nvCJD, amyloidosis, and other demyelinating syndromes, cerebral atherosclerosis and vasculitis, temporal arteritis, myasthenia gravis, acute and chronic so pain (acute, intermittent or persistent, whether of central or peripheral origin) including post-operative, visceral pain, headache, migraine, neuralgia (including trigeminal), atypical facial pain, joint and bone pain, pain arising from cancer and tumor invasion, neuropathic pain syndromes including diabetic, post-herpetic, and HIV-associated neuropathies, neurosarcoidosis, to brain injuries, cerebrovascular diseases and their consequences, Parkinson's disease, corticobasal degeneration, motor neuron disease, dementia, including ALS (Amyotrophic lateral sclerosis), multiple sclerosis, traumatic brain injury, stroke, post-stroke, post-traumatic brain injury, and small-vessel cerebrovascular disease, dementias, vascular dementia, dementia with Lewy bodies, frontotemporal dementia and Parkinsonism linked 1 to chromosome 17, frontotemporal dementias, including Pick's disease, progressive supranuclear palsy, corticobasal degeneration, Huntington's disease, thalamic degeneration, HIV dementia, schizophrenia with dementia, and Korsakoff's psychosis, within the meaning of the definition are also considered to be CNS disorders central and peripheral nervous system complications of malignant, infectious or autoimmune processes, algesia, cerebral infarction, attack, cerebral ischemia, head injury, spinal cord injury, myelopathic muscular atrophy, Shy-Drager syndrome, Reye's syndrome, progressive multifocal leukoencephalopathy, normal pressure hydrocephalus, sclerosing panencephalitis, frontal lobe type dementia, acute anterior poliomyelitis (poliomyelitis), poliomyelitis neurosis, viral encephalitis, allergic encephalomyelitis, epileptic encephalopathies, Creutzfeldt-Jakob disease, Kuru disease, bovine spongiform encephalopathy (mad cow disease), scrapie, epilepsy, cerebral amyloid angiopathy, depression, mania, manic-depressive psychosis, hereditary cerebellar ataxia, peripheral neuropathy, Nasu-Hakola syndrome, Machado-Joseph disease;

inflammatory or immunological diseases or disorders including:

general inflammation (of the ocular, nasal, pulmonary, and gastrointestinal passages), mastocytosis/mast cell disorders (cutaneous, systemic, mast cell activation syndrome, and pediatric mast cell diseases), mastitis (mammary gland), vaginitis, vasculitis (e.g., necrotizing, cutaneous, and hypersensitivity vasculitis), Wegener granulamatosis, myyositis (including polyinyositis, dermatomyositis), basophil related diseases including basophilic leukemia and basophilic leukocytosis, and eosinophil related diseases such as Churg-Strauss syndrome, eosinophilic granuloma, lupus erythematosus (such as, systemic lupus erythematosus, subacute cutaneous lupus erythematosus, and discoid lupus erythematosus), chronic thyroiditis, Hashimoto's thyroiditis, Grave's disease, type I diabetes, complications arising from diabetes mellitus, other immune disorders, eosinophilia fasciitis, hyper IgE syndrome, Addison's disease, antiphospholipid syndrome, immunodeficiency disease, acquired immune deficiency syndrome (AIDS), leprosy, Sezary syndrome, paraneoplastic syndromes, and other autoimmune disorders, fervescence, myositis, nervous diseases selected from multiple myositis, bursitis, Evans syndrome, leukotriene B4-mediated diseases, idiopathic hypoparathyroidism, nephrotic syndrome lupus, immunosuppression;

cardiovascular diseases and disorders including:

congestive heart failure, myocardial infarction, ischemic diseases of the heart, all kinds of atrial and ventricular arrhythmias, hypertension, cerebral trauma, occlusive vascular disease, stroke, cerebrovascular disorder, atherosclerosis, restenosis, affecting the coronary and peripheral is circulation, pericarditis, myocarditis, inflammatory and auto-immune cardiomyopathies including myocardial sarcoid, endocarditis, valvulitis, and aortitis including infective (e.g. syphilitic), hypertensive vascular diseases, peripheral vascular diseases, and atherosclerosis, vasculitides, disorders of the proximal and peripheral veins including phlebitis and thrombosis, including deep vein thrombosis and complications of varicose veins, aortic aneurism, periarteritis nodosa, cardiac fibrosis, post-myocardial infarction, idiopathic cardiomyopathy; angioplasty;

oncological diseases and disorders including:

common cancers (prostate, breast, lung, ovarian, pancreatic, bowel and colon, abdomen, stomach (and any other digestive system cancers), liver, pancreas, peritoneum, endocrine glands (adrenal, parathyroid, pituitary, testicles, ovary, thymus, thyroid), eye, head, neck, nervous system (central and peripheral), lymphatic system, blood, pelvic, skin, bone, soft tissue, spleen, thoracic, urogenital, and brain tumors), breast cancer, genitourinary cancer, lung cancer, gastrointestinal cancer, epidermoid cancer, melanoma, ovarian cancer, pancreas cancer, neuroblastoma, malignancies affecting the bone marrow (including the leukaemias) and lymphoproliferative systems, such as Hodgkin's and non-Hodgkin's lymphoma, B-cell lymphoma, follicular lymphoma, metastatic disease and tumour recurrences, and paraneoplastic syndromes, as well as hypergammaglobulinemia, lymphoproliferative diseases, disorders, and/or conditions, paraproteinemias, purpura (including idiopathic thrombocytopenic purpura), Waldenstron's Macroglobulinemia, Gaucher's Disease, histiocytosis, retinoblastoma and any other hyperproliferative disease, sarcomata, cachexia, tumor growth, tumor invasion, metastasis, AIDS-related lymphomas, malignant immunoproliferative diseases, multiple myeloma and malignant plasma cell neoplasms, lymphoid leukemia, acute or chronic myeloid leukemia, acute or chronic lymphocytic leukemia, monocytic leukemia, other leukemias of specified cell type, leukemia of unspecified cell type, other and unspecified malignant neoplasms of lymphoid, haematopoietic and related tissues, for example diffuse large cell lymphoma, T-cell lymphoma or cutaneous T-cell lymphoma). Myeloid cancer includes e.g. acute or chronic myeloid leukaemia, keratoleukoma and other diseases and disorders including:

pain, migraine, sleep disorders, fever, sepsis, idiopathic thrombocytopenia pupura, post-operative adhesions, flushing, ischemic/reperfusion injury in the heart, brain, peripheral limbs, bacterial infection, viral infection, fungal infection, thrombosis, endotoxin shock, septic shock, thermal regulation including fever, Raynaud's disease, gangrene, diseases requiring anti-coagulation therapy, congestive heart failure, mucus secretion disorders, pulmonary hypotension, prostanoid-induced smooth muscle contract associated with dysmenorrhea and premature labor, premature delivery, reperfusion injury, burn, thermal injury, hemorrhage or traumatic shock, menstrual pain, menstrual cramp, dysmenorrhea, periodontosis, rickettsial infectious disease, protozoal disease, reproduction disease, toothache, pain after tooth extraction, Herpes zoster, Herpes simplex, retroperitoneal fibrosis, various radiation injuries and the like.

The present invention furthermore provides a method of treatment of a disease mediated by kinase-activity comprising the administration, to a patient in need thereof, of a therapeutically effective amount of a compound or a pharmaceutical composition described herein. Preferably, the kinase is selected from SYK (Spleen Tyrosine Kinase), LRRK2 (Leucine-rich repeat kinase 2) and/or Myosin light chain kinase (MYLK or MLCK) or mutants thereof. Further preferably, said treatment is systemic. Moreover preferably, said administration is topical. Moreover preferably, said topical administration is to the skin, the eye or intranasal or by inhalation.

Preferably, the disease is selected from the group consisting of an inflammatory disease, an autoimmune disease, an allergic disorder, and an ocular disorder.

Especially preferably, the disease is selected from the group consisting of pruritus, eczema, asthma, rhinitis, dry eye, ocular inflammation, allergic conjunctivitis, vernal conjunctivitis, vernal keratoconjunctivitis, giant papillary conjunctivitis, fungal keratitis and uveitis.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage may be adjusted to the individual requirements in each particular case including the specific compound being administered, the route of administration, the condition being treated, as well as the patient being treated.

Examples of pharmacologically acceptable salts of sufficiently basic compounds of formula (I) are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleic and salicylic acid. Further, a sufficiently acidic compound of formula (I) may form alkali or earth alkali metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts; all of which are also further examples of salts of formula (I). Compounds of formula (I) may be solvated, especially hydrated. The hydratization/hydration may occur during the process of production or as a consequence of the hygroscopic nature of the initially water free compounds of formula (I). The solvates and/or hydrates may e.g. be present in solid or liquid form.

It should be appreciated that certain compounds of formula (I) may have tautomeric forms from which only one might be specifically mentioned or depicted in the following description, different geometrical isomers (which are usually denoted as cis/trans isomers or more generally as (E) and (Z) isomers) or different optical isomers as a result of one or more chiral carbon atoms (which are usually nomenclatured under the Cahn-Ingold-Prelog or R/S system). All these tautomeric forms, geometrical or optical isomers (as well as racemates and diastereomers) and polymorphous forms are included in the invention. Since the compounds of formula (I) may contain asymmetric C-atoms, they may be present either as achiral compounds, mixtures of diastereomers, mixtures of enantiomers or as optically pure compounds. The present invention comprises both all pure enantiomers and all pure diastereomers, and also the mixtures thereof in any mixing ratio.

According to a further embodiment of the present invention, one or more hydrogen atoms of the compounds of the present invention may be replaced by deuterium. Deuterium modification improves the metabolic properties of a drug with little or no change in its intrinsic pharmacology. Deuterium substitution at specific molecular positions improves metabolic stability, reduces formation of toxic metabolites and/or increases the formation of desired active metabolites. Accordingly, the present invention also encompasses the partially and fully deuterated compounds of formula (I). The term hydrogen also encompasses deuterium.

The therapeutic use of compounds according to formula (I), their pharmacologically acceptable salts, solvates and hydrates, respectively, as well as formulations and pharmaceutical compositions also lie within the scope of the present invention.

The pharmaceutical compositions according to the present invention preferably comprise at least one compound of formula (I) as an active ingredient and, optionally, carrier substances and/or adjuvants.

The present invention also relates to pro-drugs which are composed of a compound of formula (I) and at least one pharmacologically acceptable protective group which will be cleaved off under physiological conditions, such as an alkoxy-, arylalkyloxy-, acyl-, acyloxymethyl group (e.g. pivaloyloxymethyl), an 2-alkyl-, 2-aryl- or 2-arylalkyl-oxycarbonyl-2-alkylidene ethyl group or an acyloxy group as defined herein, e.g. ethoxy, benzyloxy, acetyl or acetyloxy or, especially for a compound of formula (I), carrying a hydroxy group (—OH): a sulfate, a phosphate (—OPO$_3$ or —OCH$_2$OPO$_3$) or an ester of an amino acid. Especially preferred are pro-drugs of the hydroxy group of a compound of formula (I).

As used herein, the term pharmaceutically acceptable ester especially refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

Preferably, the present invention also relates to a prodrug, a biohydrolyzable ester, a biohydrolyzable amide, a polymorph, tautomer, stereoisomer, metabolite, N-oxide, biohydrolyzable carbamate, biohydrolyzable ether, physiologically functional derivative, atropisomer, or in vivo-hydrolysable precursor, diastereomer or mixture of diastereomers, chemically protected form, affinity reagent, complex, chelate and a stereoisomer of the compounds of formula (I).

As mentioned above, therapeutically useful agents that contain compounds of formula (I), their solvates, salts or formulations are also comprised in the scope of the present invention. In general, compounds of formula (I) will be administered by using the known and acceptable modes known in the art, either alone or in combination with any other therapeutic agent.

For oral administration such therapeutically useful agents can be administered by one of the following routes: oral, e.g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystals or as a spray (e.g. liquid aerosol), transdermal, for example via an transdermal delivery system (TDS) such as a plaster containing the active ingredient or intranasal. For the production of such tablets, pills, semisolids, coated tablets, dragees and hard, e.g. gelatine, capsules the therapeutically useful product may be mixed with pharmaceutically inert, inorganic or organic excipients as are e.g. lactose, sucrose, glucose, gelatine, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, polyols. For the production of liquid solutions, emulsions or suspensions or syrups one may use as excipients e.g. water, alcohols, aqueous saline, aqueous dextrose, polyols, glycerin, lipids, phospholipids, cyclodextrins, vegetable, petroleum, animal or synthetic oils. Especially preferred are lipids and more preferred are phospholipids (preferred of natural origin; especially preferred with a particle size between 300 to 350 nm) preferred in phosphate buffered saline (pH=7 to 8, preferred 7.4). For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilization, e.g. UV stabilizers, emulsifiers, sweetener, aromatizers, salts to change the osmotic pressure, buffers, coating additives and antioxidants.

In general, in the case of oral or parenteral administration to adult humans weighing approximately 80 kg, a daily dosage of about 10 mg to about 10,000 mg, preferably from about 20 mg to about 1,000 mg, should be appropriate, although the upper limit may be exceeded when indicated. The daily dosage can be administered as a single dose or in divided doses, or for parenteral administration, it may be given as continuous infusion or subcutaneous injection.

The present invention refers furthermore to compounds of formulas (II), (IIIa) and/or (IIIb) wherein $R^2$ is defined as above and PG is a protecting group.

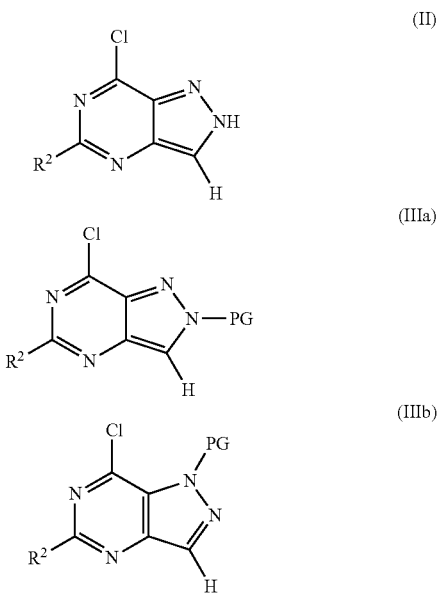

Protecting groups are known to a person skilled in the art and e.g. described in P. J. Kocienski, Protecting Groups, Georg Thieme Verlag, Stuttgart, 1994 and in T. W. Greene, P. G. M. Wuts, Protective Groups in Organic Synthesis, John Wiley & Sons, New York, 1999.

Preferably, PG is a 4-methoxy benzyl group or a carboxybenzyl (Cbz or Z) group; especially preferably, PG is a 4-methoxy benzyl group.

Preferred compounds of formula (II) are: N-(2-(7-chloro-2H-pyrazolo[4,3-d]pyrimidin-5-yl)phenyl)methanesulfonamide; 7-chloro-5-(3-nitrophenyl)-2H-pyrazolo[4,3-d]pyrimidine; 7-chloro-5-(5-methylthiophen-2-yl)-2H-pyrazolo[4,3-d]pyrimidine; 7-chloro-5-(2,6-difluorophenyl)-2H-pyrazolo[4,3-d]pyrimidine; methyl 3-(7-chloro-2H-pyrazolo[4,3-d]pyrimidin-5-yl)benzoate; 7-chloro-5-(thiophen-2-yl)-2H-pyrazolo[4,3-d]pyrimidine; 7-chloro-5-cyclopropyl-2H-pyrazolo[4,3-d]pyrimidine; 7-chloro-5-(2-fluorophenyl)-2H-pyrazolo[4,3-d]pyrimidine; N-(3-(7-chloro-2H-pyrazolo[4,3-d]pyrimidin-5-yl)phenyl)methanesulfonamide; 7-chloro-5-(1H-indazol-6-yl)-2H-pyrazolo[4,3-d]pyrimidine; 4-(7-chloro-2H-pyrazolo[4,3-d]pyrimidin-5-yl)oxazole; 7-chloro-5-(3-methylthiophen-2-yl)-2H-pyrazolo[4,3-d]pyrimidine; 7-chloro-5-(tetrahydrofuran-2-yl)-2H-pyrazolo[4,3-d]pyrimidine; 7-chloro-5-(methoxymethyl)-2H-pyrazolo[4,3-d]pyrimidine; 7-chloro-5-(1-methoxyethyl)-2H-pyrazolo[4,3-d]pyrimidine; 5-(7-chloro-2H-pyrazolo[4,3-d]pyrimidin-5-yl)isoxazole; 3-(7-chloro-2H-pyrazolo[4,3-d]pyrimidin-5-yl)isoxazole; 7-chloro-5-(5-fluoro-1H-indazol-6-yl)-2H-pyrazolo[4,3-d]pyrimidine; 7-chloro-5-(tetrahydrofuran-3-yl)-2H-pyrazolo[4,3-d]pyrimidine; 7-chloro-5-(tetrahydro-2H-pyran-4-yl)-2H-pyrazolo[4,3-d]pyrimidine; 7-chloro-5-(1,4-dioxan-2-yl)-2H-pyrazolo[4,3-d]pyrimidine; 7-chloro-5-(furan-2-yl)-2H-pyrazolo[4,3-d]pyrimidine; 7-chloro-5-(1-methyl-1H-imidazol-2-yl)-2H-pyrazolo[4,3-d]pyrimidine; 4-((7-chloro-2H-pyrazolo[4,3-d]pyrimidin-5-yl)methyl)morpholine; 7-chloro-5-(furan-3-yl)-2H-pyrazolo[4,3-d]pyrimidine; 7-chloro-5-(1-methylcyclopropyl)-2H-pyrazolo[4,3-d]pyrimidine; 7-chloro-5-(2-methylcyclopropyl)-2H-pyrazolo[4,3-d]pyrimidine; 1-(7-chloro-2H-pyrazolo[4,3-d]pyrimidin-5-yl)-N,N-dimethylmethanamine; 5-(7-chloro-2H-pyrazolo[4,3-d]pyrimidin-5-yl)isoxazole-3-carboxylic acid ethyl ester; 7-chloro-5-cyclobutyl-2H-pyrazolo[4,3-d]pyrimidine; 7-chloro-5-(1-methyl-1H-pyrazol-4-yl)-2H-pyrazolo[4,3-d]pyrimidine; 7-chloro-5-(1H-1,2,4-triazol-3-yl)-2H-pyrazolo[4,3-d]pyrimidine; 7-chloro-5-(pyridazin-3-yl)-2H-pyrazolo[4,3-d]pyrimidine; 7-chloro-5-(pyridin-3-yl)-2H-pyrazolo[4,3-d]pyrimidine.

Further preferred compounds of formula (II) are: 7-chloro-5-(pyridazin-4-yl)-2H-pyrazolo[4,3-d]pyrimidine; 7-chloro-5-(1-methyl-1H-1,2,4-triazol-3-yl)-2H-pyrazolo[4,3-d]pyrimidine; 7-chloro-5-(1-methyl-1H-pyrazol-3-yl)-2H-pyrazolo[4,3-d]pyrimidine; 7-chloro-5-(1H-indazol-5-yl)-2H-pyrazolo[4,3-d]pyrimidine; 7-chloro-5-isopropyl-2H-pyrazolo[4,3-d]pyrimidine; 3-(7-chloro-2H-pyrazolo[4,3-d]pyrimidin-5-yl)benzoic acid; 2-(7-chloro-2H-pyrazolo[4,3-d]pyrimidin-5-yl)oxazole; 5-(tert-butyl)-7-chloro-2H-pyrazolo[4,3-d]pyrimidine; 3-(7-chloro-2H-pyrazolo[4,3-d]pyrimidin-5-yl)-N-(4-(oxazol-5-yl)phenyl)benzamide; N-(4-(2H-1,2,3-triazol-2-yl)phenyl)-3-(7-chloro-2H-pyrazolo[4,3-d]pyrimidin-5-yl)benzamide; 3-(7-chloro-2H-pyrazolo[4,3-d]pyrimidin-5-yl)-N-(4-(oxazol-2-yl)phenyl)benzamide; 7-chloro-5-(1-isobutyl-1H-pyrazol-4-yl)-2H-pyrazolo[4,3-d]pyrimidine; 7-chloro-5-propyl-2H-pyrazolo[4,3-d]pyrimidine; 7-chloro-5-cycloheptyl-2H-pyrazolo[4,3-d]pyrimidine; 7-chloro-5-(1-(2-methoxyethyl)-1H-pyrazol-4-yl)-2H-pyrazolo[4,3-d]pyrimidine; 7-chloro-5-(1H-pyrazol-4-yl)-2H-pyrazolo[4,3-d]pyrimidine; 7-chloro-5-(3-methoxyphenyl)-2H-pyrazolo[4,3-d]pyrimidine; 2-(7-chloro-2H-pyrazolo[4,3-d]pyrimidin-5-yl)benzo[d]thiazole; 7-chloro-5-(1-isopropyl-1H-pyrazol-4-yl)-2H-pyrazolo[4,3-d]pyrimidine; 3-(7-chloro-2H-pyrazolo[4,3-d]pyrimidin-5-yl)benzenesulfonamide; 4-(7-chloro-2H-pyrazolo[4,3-d]pyrimidin-5-yl)-3,5-dimethylisoxazole; 7-chloro-5-(trifluoromethyl)-2H-pyrazolo[4,3-d]pyrimidine; 2-(7-chloro-2H-pyrazolo[4,3-d]pyrimidin-5-yl)benzo[d]oxazole; 5-(1-benzyl-1H-pyrazol-4-yl)-7-chloro-2H-pyrazolo[4,3-d]pyrimidine; 7-chloro-5-(3-(pyridin-3-yl)phenyl)-2H-pyrazolo[4,3-d]pyrimidine; 5-(bicyclo[4.1.0]heptan-7-yl)-7-chloro-2H-pyrazolo[4,3-d]pyrimidine; 7-chloro-5-(2-fluoro-6-methylphenyl)-2H-pyrazolo[4,3-d]pyrimidine; 7-chloro-5-(2,2-dimethylcyclopropyl)-2H-pyrazolo[4,3-d]pyrimidine; 2-(7-chloro-2H-pyrazolo[4,3-d]pyrimidin-5- yl)-4,5,6,7-tetrahydrobenzo[d]thiazole; 7-chloro-5-(2-phenylcyclopropyl)-2H-pyrazolo[4,3-d]pyrimidine; 7-chloro-5-(1-(3-methylbutan-2-yl)-1H-pyrazol-4-yl)-2H-pyrazolo[4,3-d]pyrimidine; 7-chloro-5-(2-chloro-6-fluorophenyl)-2H-pyrazolo[4,3-d]pyrimidine; 7-chloro-5-(2-(methylsulfonyl)phenyl)-2H-pyrazolo[4,3-d]pyrimidine; 3-(7-chloro-2H-pyrazolo[4,3-d]pyrimidin-5-yl)aniline; 2-(7-chloro-2H-pyrazolo[4,3-d]pyrimidin-5-yl)aniline; 2-(7-chloro-2H-pyrazolo[4,3-d]pyrimidin-5-yl)-3-fluoroaniline; 2-(7-chloro-2H-pyrazolo[4,3-d]pyrimidin-5-yl)thiazole.

Preferred compounds of formula (IIIa) and (IIIb) are: N-(2-(7-chloro-2-(4-methoxybenzyl)-2H-pyrazolo[4,3-d]pyrimidin-5-yl)phenyl)methanesulfonamide; 7-chloro-2-(4-methoxybenzyl)-5-(3-nitrophenyl)-2H-pyrazolo[4,3-d]pyrimidine; 7-chloro-5-(2,6-difluorophenyl)-2-(4-methoxybenzyl)-2H-pyrazolo[4,3-d]pyrimidine; methyl 3-(7-chloro-2-(4-methoxybenzyl)-2H-pyrazolo[4,3-d]pyrimidin-5-yl)benzoate; 7-chloro-2-(4-methoxybenzyl)-5-(thiophen-2-yl)-2H-pyrazolo[4,3-d]pyrimidine; 7-chloro-5-(2-fluorophenyl)-2-(4-methoxybenzyl)-2H-pyrazolo[4,3-d]pyrimidine; N-(3-(7-chloro-2-(4-methoxybenzyl)-2H-pyrazolo[4,3-d]pyrimidin-5-yl)phenyl)methanesulfonamide; 7-chloro-5-(1H-indazol-6-yl)-2-(4-methoxybenzyl)-2H-pyrazolo[4,3-d]pyrimidine; 4-(7-chloro-2-(4-methoxybenzyl)-2H-pyrazolo[4,3-d]pyrimidin-5-yl)oxazole; 7-chloro-2-(4-methoxybenzyl)-5-(3-methylthiophen-2-yl)-2H-pyrazolo[4,3-d]pyrimidine; 5-(7-chloro-2-(4-methoxybenzyl)-2H-pyrazolo[4,3-d]pyrimidin-5-yl)isoxazole; 3-(7-chloro-2-(4-methoxybenzyl)-2H-pyrazolo[4,3-d]pyrimidin-5-yl)isoxazole; 7-chloro-5-(5-fluoro-1H-indazol-6-yl)-2-(4-methoxybenzyl)-2H-pyrazolo[4,3-d]pyrimidine; 7-chloro-5-(furan-2-yl)-2-(4-methoxybenzyl)-2H-pyrazolo[4,3-d]pyrimidine; 7-chloro-2-(4-methoxybenzyl)-5-(1-methyl-1H-imidazol-2-yl)-2H-pyrazolo[4,3-d]pyrimidine; 7-chloro-2-(4-methoxybenzyl)-5-(1-methyl-1H-imidazol-2-yl)-2H-pyrazolo[4,3-d]pyrimidine; 7-chloro-5-(furan-3-yl)-2-(4-methoxybenzyl)-2H-pyrazolo[4,3-d]pyrimidine; 5-(7-chloro-2-(4-methoxybenzyl)-2H-pyrazolo[4,3-d]pyrimidin-5-yl)isoxazole-3-carboxylic acid ethyl ester; 7-chloro-2-(4-methoxybenzyl)-5-(1-methyl-1H-pyrazol-4-yl)-2H-pyrazolo[4,3-d]pyrimidine; 7-chloro-2-(4-methoxybenzyl)-5-(pyridazin-3-yl)-2H-pyrazolo[4,3-d]pyrimidine; 7-chloro-5-cyclopropyl-2-(4-methoxybenzyl)-2H-pyrazolo[4,3-d]pyrimidine; 7-chloro-2-(4-methoxybenzyl)-5-(tetrahydrofuran-2-yl)-2H-pyrazolo[4,3-d]pyrimidine; 7-chloro-2-(4-methoxybenzyl)-5-(methoxymethyl)-2H-pyrazolo[4,3-d]pyrimidine; 7-chloro-2-(4-methoxybenzyl)-5-(1-methoxyethyl)-2H-pyrazolo[4,3-d]pyrimidine; 7-chloro-2-(4-methoxybenzyl)-5-(tetrahydrofuran-3-yl)-2H-pyrazolo[4,3-d]pyrimidine; 7-chloro-2-(4-methoxybenzyl)-5-(tetrahydro-2H-pyran-4-yl)-2H-pyrazolo[4,3-d]pyrimidine; 7-chloro-5-(1,4-dioxan-2-yl)-2-(4-methoxybenzyl)-2H-pyrazolo[4,3-d]pyrimidine; 4-((7-chloro-2-(4-methoxybenzyl)-2H-pyrazolo[4,3-d]pyrimidin-5-yl)methyl)morpholine; 7-chloro-2-(4-methoxybenzyl)-5-(1-methylcyclopropyl)-2H-pyrazolo[4,3-d]pyrimidine; 7-chloro-2-(4-methoxybenzyl)-5-(2-methylcyclopropyl)-2H-pyrazolo[4,3-d]pyrimidine; 1-(7-chloro-2-(4-methoxybenzyl)-2H-pyrazolo[4,3-d]pyrimidin-5-yl)-N,N-dimethylmethanamine; 7-chloro-5-cyclobutyl-2-(4-methoxybenzyl)-2H-pyrazolo[4,3-d]pyrimidine; 7-chloro-2-(4-methoxybenzyl)-5-(5-methylthiophen-2-yl)-2H-pyrazolo[4,3-d]pyrimidine; 7-chloro-2-(4-methoxybenzyl)-5-(3-methylthiophen-2-yl)-2H-pyrazolo[4,3-d]pyrimidine; 7-chloro-2-(4-methoxybenzyl)-5-(1H-1,2,4-triazol-3-yl)-2H-pyrazolo[4,3-d]pyrimidine; 7-chloro-2-(4-methoxybenzyl)-5-(pyridin-3-yl)-2H-pyrazolo[4,3-d]pyrimidine.

Further preferred compounds of formula (IIIa) and (IIIb) are: 7-chloro-2-(4-methoxybenzyl)-5-(pyridazin-4-yl)-2H-pyrazolo[4,3-d]pyrimidine; 7-chloro-2-(4-methoxybenzyl)-5-(1-methyl-1H-1,2,4-triazol-3-yl)-2H-pyrazolo[4,3-d]pyrimidine; 7-chloro-2-(4-methoxybenzyl)-5-(1-methyl-1H-pyrazol-3-yl)-2H-pyrazolo[4,3-d]pyrimidine; 7-chloro-5-(1H-indazol-5-yl)-2-(4-methoxybenzyl)-2H-pyrazolo[4,3-d]pyrimidine; 7-chloro-5-isopropyl-2-(4-methoxybenzyl)-2H-pyrazolo[4,3-d]pyrimidine, 3-(7-chloro-2-(4-methoxybenzyl)-2H-pyrazolo[4,3-d]pyrimidin-5-yl)benzoic acid; 2-(7-chloro-2-(4-methoxybenzyl)-2H-pyrazolo[4,3-d]pyrimidin-5-yl)oxazole; 5-(tert-butyl)-7-chloro-2-(4-methoxybenzyl)-2H-pyrazolo[4,3-d]pyrimidine; 3-(7-chloro-2-(4-methoxybenzyl)-2H-pyrazolo[4,3-d]pyrimidin-5-yl)-N-(4-(oxazol-5-yl)phenyl)benzamide; N-(4-(2H-1,2,3-triazol-2-yl)phenyl)-3-(7-chloro-2-(4-methoxybenzyl)-2H-pyrazolo[4,3-d]pyrimidin-5-yl)benzamide; 3-(7-chloro-2-(4-methoxybenzyl)-2H-pyrazolo[4,3-d]pyrimidin-5-yl)-N-(4-(oxazol-2-yl)phenyl)benzamide; 7-chloro-5-(1-isobutyl-1H-pyrazol-4-yl)-2-(4-methoxybenzyl)-2H-pyrazolo[4,3-d]pyrimidine; 7-chloro-2-(4-methoxybenzyl)-5-propyl-2H-pyrazolo[4,3-d]pyrimidine; 7-chloro-5-cycloheptyl-2-(4-methoxybenzyl)-2H-pyrazolo[4,3-d]pyrimidine; 7-chloro-2-(4-methoxybenzyl)-5-(1-(2-methoxyethyl)-1H-pyrazol-4-yl)-2H-pyrazolo[4,3-d]pyrimidine; 7-chloro-2-(4-methoxybenzyl)-5-(1H-pyrazol-4-yl)-2H-pyrazolo[4,3-d]pyrimidine; 7-chloro-2-(4-methoxybenzyl)-5-(3-methoxyphenyl)-2H-pyrazolo[4,3-d]pyrimidine; 2-(7-chloro-2-(4-methoxybenzyl)-2H-pyrazolo[4,3-d]pyrimidin-5-yl)benzo[d]thiazole; 7-chloro-5-(1-isopropyl-1H-pyrazol-4-yl)-2-(4-methoxybenzyl)-2H-pyrazolo[4,3-d]pyrimidine; 3-(7-chloro-2-(4-methoxybenzyl)-2H-pyrazolo[4,3-d]pyrimidin-5-yl)benzenesulfonamide, 4-(7-chloro-2-(4-methoxybenzyl)-2H-pyrazolo[4,3-d]pyrimidin-5-yl)-3,5-dimethylisoxazole; 7-chloro-2-(4-methoxybenzyl)-5-(trifluoromethyl)-2H-pyrazolo[4,3-d]pyrimidine; 2-(7-chloro-2-(4-methoxybenzyl)-2H-pyrazolo[4,3-d]pyrimidin-5-yl)benzo[d]oxazole; 5-(1-benzyl-1H-pyrazol-4-yl)-7-chloro-2-(4-methoxybenzyl)-2H-pyrazolo[4,3-d]pyrimidine; 7-chloro-2-(4-methoxybenzyl)-5-(3-(pyridin-3-yl)phenyl)-2H-pyrazolo[4,3-d]pyrimidine; 5-(bicyclo[4.1.0]heptan-7-yl)-7-chloro-2-(4-methoxybenzyl)-2H-pyrazolo[4,3-d]pyrimidine; 7-chloro-5-(2-fluoro-6-methylphenyl)-2-(4-methoxybenzyl)-2H-pyrazolo[4,3-d]pyrimidine; 7-chloro-5-(2,2-dimethylcyclopropyl)-2-(4-methoxybenzyl)-2H-pyrazolo[4,3-d]pyrimidine; 2-(7-chloro-2-(4-methoxybenzyl)-2H-pyrazolo[4,3-d]pyrimidin-5-yl)-4,5,6,7-tetrahydrobenzo[d]thiazole; 7-chloro-2-(4-methoxybenzyl)-5-(2-phenylcyclopropyl)-2H-pyrazolo[4,3-d]pyrimidine; 7-chloro-2-(4-methoxybenzyl)-5-(1-(3-methylbutan-2-yl)-1H-pyrazol-4-yl)-2H-pyrazolo[4,3-d]pyrimidine; 7-chloro-5-(2-chloro-6-fluorophenyl)-2-(4-methoxybenzyl)-2H-pyrazolo[4,3-d]pyrimidine; 7-chloro-2-(4-methoxybenzyl)-5-(2-(methylsulfonyl)phenyl)-2H-pyrazolo[4,3-d]pyrimidine; 3-(7-chloro-2-(4-methoxybenzyl)-2H-pyrazolo[4,3-d]pyrimidin-5-yl)aniline; 2-(7-chloro-2-(4-methoxybenzyl)-2H-pyrazolo[4,3-d]pyrimidin-5-yl)aniline; 2-(7-chloro-2-(4-methoxybenzyl)-2H-pyrazolo[4,3-d]pyrimidin-5-yl)-3-fluoroaniline; 2-(7-chloro-2-(4-methoxybenzyl)-2H-pyrazolo[4,3-d]pyrimidin-5-yl)thiazole.

GENERAL SYNTHESIS

The procedures shown in the following synthesis schemes may be used to provide chloride intermediates. The chloride intermediates may then be used in an amination reaction with various amines and a subsequent deprotection to provide the final products.
Step 1:

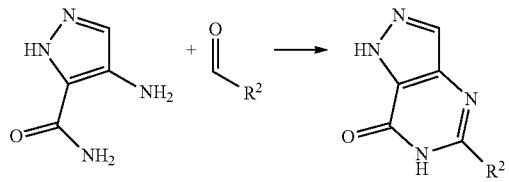

4-Amino-2H-pyrazole-3-carboxylic acid amide is reacted with an aldehyde in the presence of an oxidant esp. 2,3-Dichloro-5,6-dicyano-1,4-benzoquinone to result in the formation of 5-substituted 1,6-dihydro-pyrazolo[4,3-d]pyrimidin-7-one.

As an alternative one can use a two step approach with carboxylic acids:

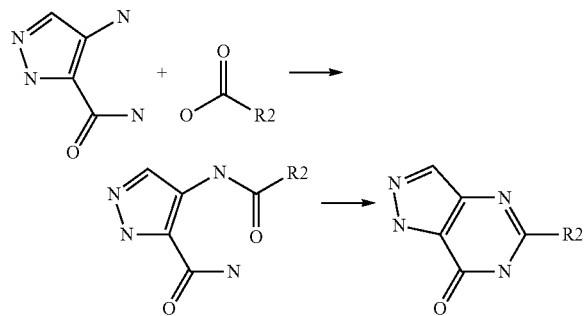

Amino-2H-pyrazole-3-carboxylic acid amide is reacted with a carboxylic acid under amide-coupling conditions. In an subsequent step the ringclosure is forced under strong basic conditions, e.g. in tBuOH/tBuOK and will result in the formation of 5-substituted 1,6-dihydro-pyrazolo[4,3-d]pyrimidin-7-one.

It is also possible to use acidchlorides in the first step, this will lead to an intermediate protection of the pyrazole, which is reverted under the ringclosure conditions in the subsequent step.

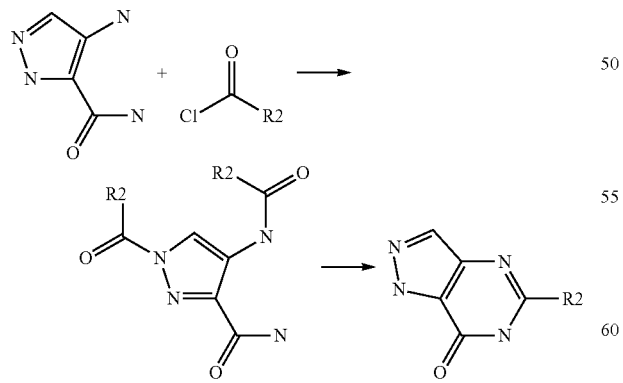

A third alternative towards 5-substituted 1,6-dihydro-pyrazolo[4,3-d]pyrimidin-7-one is the reaction of nitriles with 4-Amino-1-(4-methoxy-benzyl)-1H-pyrazole-3-carboxylic acid methyl esters.

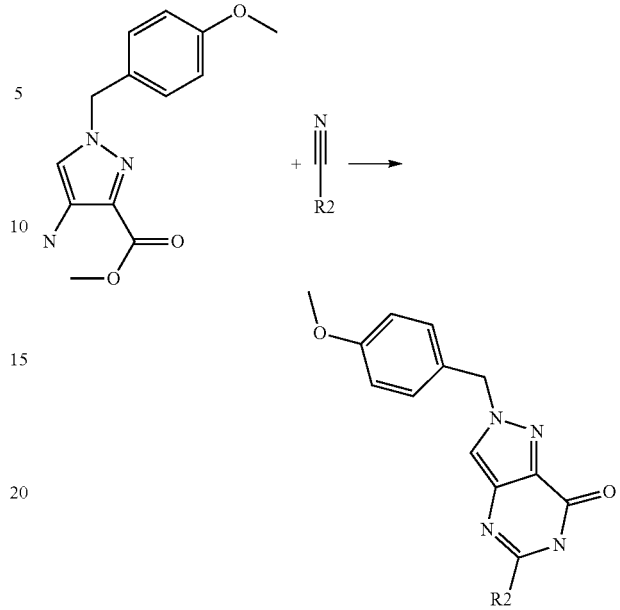

The 4-Amino-1-(4-methoxy-benzyl)-1H-pyrazole-3-carboxylic acid methyl ester is reacted with a nitrile under acidic conditions resulting in an already para-methoxy-benzyl protected group containing 5-substituted 1,6-dihydro-pyrazolo[4,3-d]pyrimidin-7-one.

Step 2:

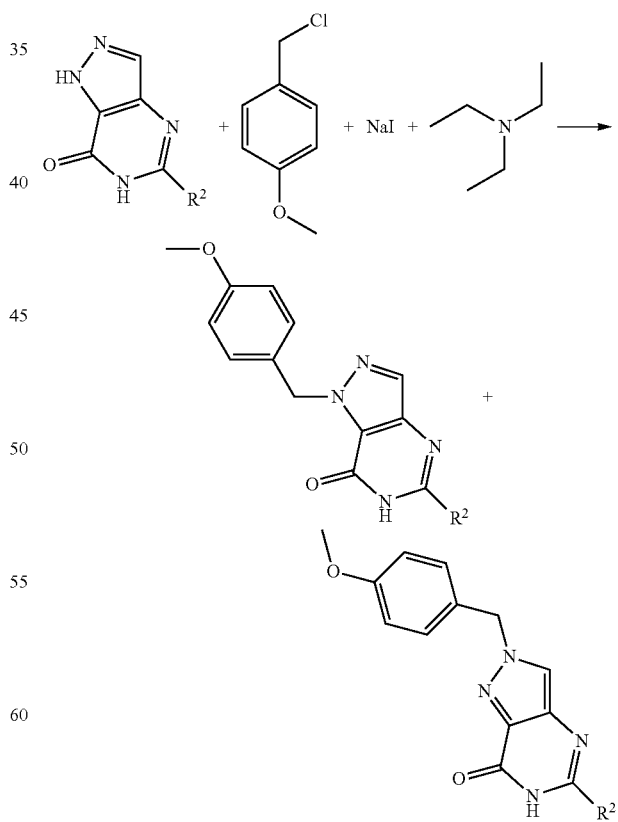

The pyrazole is protected e.g. with a para-methoxy-benzyl protection group. This step results in the formation of two isomers 5-substituted 1-(4-Methoxy-benzyl)-1,6-dihydro-pyrazolo[4,3-d]pyrimidin-7-one and 5-substituted 2-(4-Methoxy-benzyl)-2,6-dihydro-pyrazolo[4,3-d]pyrimidin-7-one. Both isomers can be used in the following steps.

Step 3:

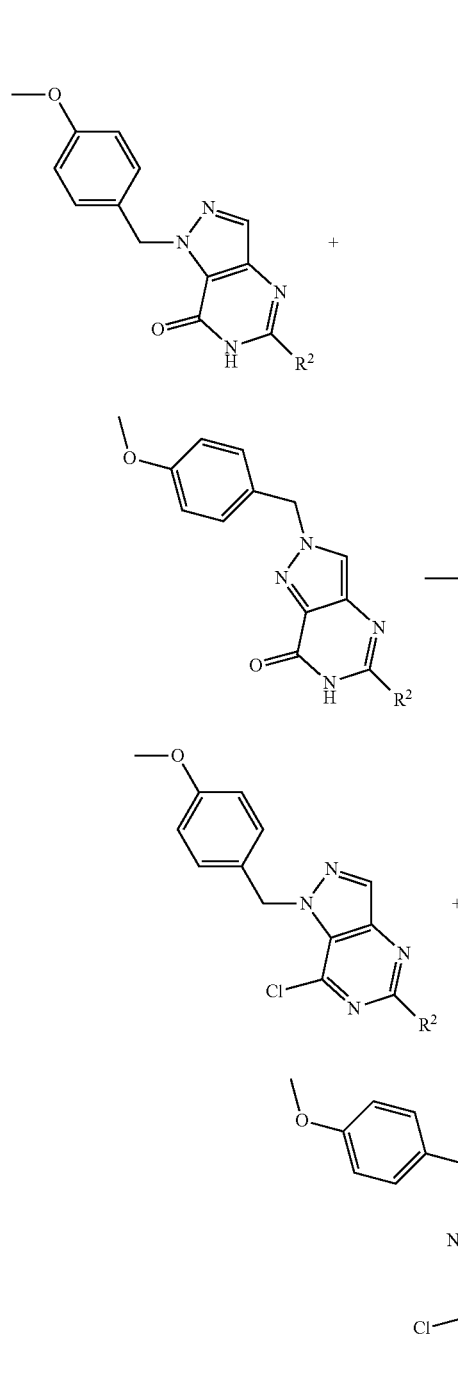

5-substituted 1-(4-Methoxy-benzyl)-1,6-dihydro-pyrazolo[4,3-d]pyrimidin-7-one and 5-substituted 2-(4-Methoxy-benzyl)-2,6-dihydro-pyrazolo[4,3-d]pyrimidin-7-one are chlorinated e.g. with POCl$_3$ resulting in the formation of 5-substituted 7-Chloro-1-(4-methoxy-benzyl)-1H-pyrazolo[4,3-d]pyrimidine and 5-substituted 7-Chloro-2-(4-methoxy-benzyl)-2H-pyrazolo[4,3-d]pyrimidine.

Step 4:

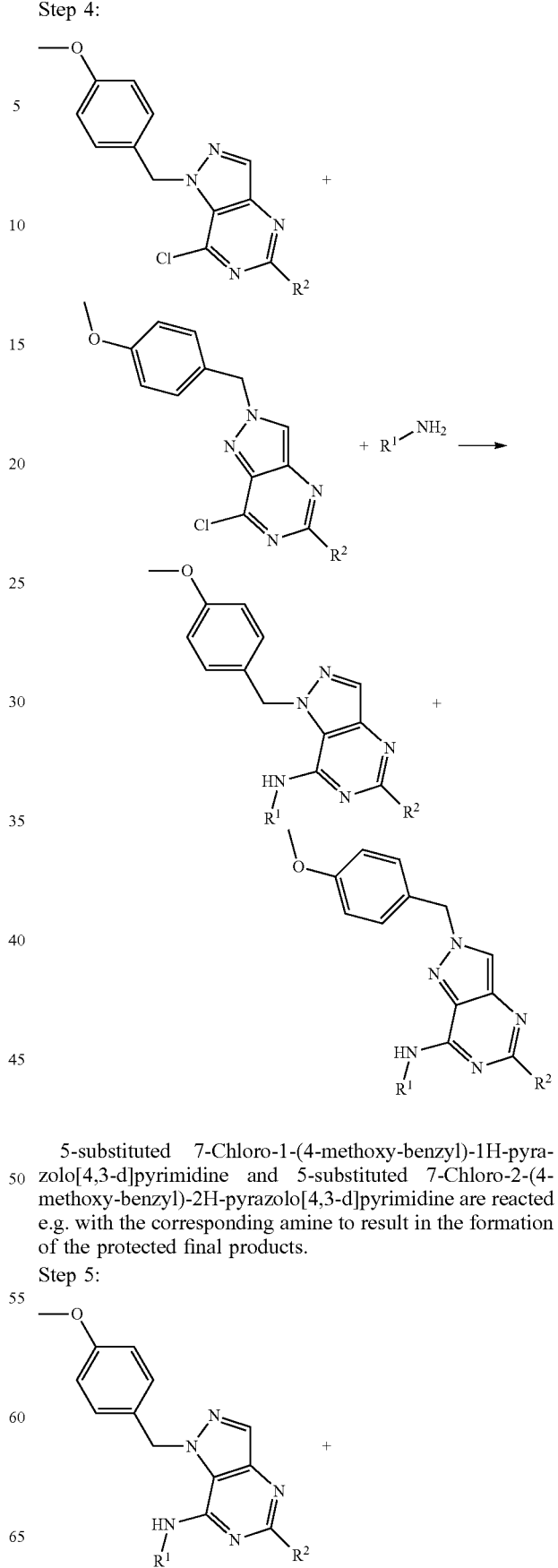

5-substituted 7-Chloro-1-(4-methoxy-benzyl)-1H-pyrazolo[4,3-d]pyrimidine and 5-substituted 7-Chloro-2-(4-methoxy-benzyl)-2H-pyrazolo[4,3-d]pyrimidine are reacted e.g. with the corresponding amine to result in the formation of the protected final products.

Step 5:

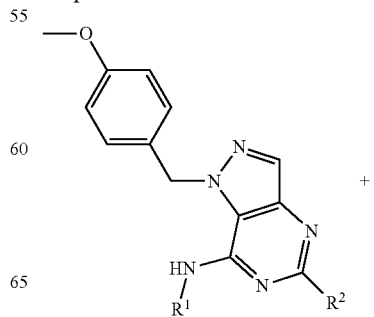

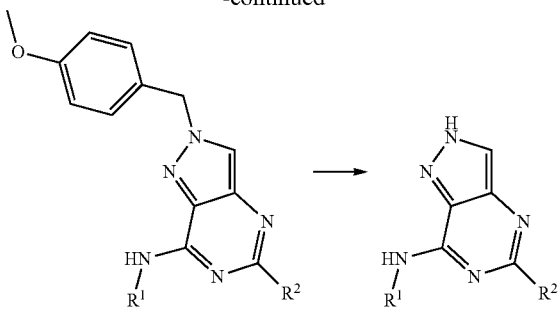

In a final step the para-methoxy-benzyl protection group is removed e.g. with trifluoroacetic acid to provide the final product for biological characterisation.

EXAMPLES

Materials and Methods
Biological Assays—Protein Kinase Assays
SYK Assay

In the assay OMNIA® KINASE ASSAY by Invitrogen Corporation (Carlsbad) the effect of invention of a compound on the phosphorylation is determined by measurement of fluorescence intensity of a chelation-enhanced fluorophore called SOX. Upon phosphorylation of the peptide by the kinase of interest, Mg2+ is chelated to form a bridge between the SOX moiety and the phosphate group that is transferred to the specific tyrosine on the peptide. The fluorescence intensity is directly proportional to the amount of peptide phosphorylation.

To the wells of an 384 well small volume plate (Greiner, Frickenhausen) are added (i) the compound under test in 5% DMSO/distilled water (2 µl), (ii) 16 µl of the master mix containing ATP, DTT, Kinase Reaction Buffer, Omina Peptide Substrate Tyr 7 resulting in a final concentration of 1 mM ATP, 0.2 mM DTT and 10 µM Peptide Substrate. The Master Mix and the assay plate was incubated to reaction temperature before the measurement (30° C.). The reaction was started with addition of (iii) 2 µl 4 µg/ml SYK kinase (Invitrogen, Carlsbad). During measurement fluorescence intensitiy readings were collected using a TECAN M1000 at a wavelength of λex 360/λem 485 nm every 30 s for 30 minutes. The reaction velocity was plotted versus the inhibitor concentration to determine the IC50 using XLFit 5.0 (IDBS, Guildford) to fit to a sigmoidal dose response curve.

The ATP dependency was determined according to Lai C-J-, Wu J C A Simple Kinetic Method for Rapid Mechanistic Analysis of Reversible Enzyme Inhibitors. Assays and Drug Dev. Technologies. 2003; 1(4):527-535. To demonstrate a competition effect of the test compounds towards ATP the corresponding test compound was used at the 50% inhibitory concentration. Assay conditions as described previously were maintained. ATP concentrations used was 1000, 333, 100, 33.3, 10, 3.3, 1 µM.

LRRK2—LRRK2 G2019S—Assay

In the assay LanthaScreen™ Eu Kinase Binding Assay by Invitrogen Corporation (Carlsbad) the effect of invention of a compound on the phosphorylation is determined by measurement of fluorescence intensity emission ratio based on the binding and displacement of a proprietary, Alexa Fluor® 647-labeled, ATP-competitive kinase inhibitor scaffold (kinase tracer) to the kinase of interest. Binding of the tracer to the kinase is detected using a europium-labeled anti-tag antibody, which binds to the kinase of interest. Simultaneous binding of both the tracer and antibody to the kinase results in a high degree of FRET (fluorescence resonance energy transfer) from the europium (Eu) donor fluorophore to the Alexa Fluor® 647 acceptor fluorophore on the kinase tracer. Binding of an inhibitor to the kinase competes for binding with the tracer, resulting in a loss of FRET. The fluorescence intensity ratio is directly proportional to the amount of peptide phosphorylation. To the wells of an 384 well small volume plate (Greiner, Frickenhausen) are added (i) the compound under test in 5% DMSO/distilled water (5 µl), (ii) 5 µl of the kinase antibody mixture resulting in a final concentration 5 nM LRRK2 or their mutants, 2 nM EU-Anti-GST antibody in 1× kinase buffer A. The reaction was started with addition of (iii) 5 µl resulting in a final concentration of 10 nM tracer 236. The assay plate was incubated at RT for 1 h and fluorescence intensitiy readings were collected using a TECAN M1000 at two wavelengthes of λex 340/λem 615 nm and λex 340/λem 665 nm with a delay time of 100 µs and an integration time of 200 µs after 60 minutes. The emission ratio was calculated by division of the acceptor/tracer emission (665 nM) by the antibody/donor emission (615 nM). The inhibitor concentration was plotted versus the emission ratio to determine the IC50 using XLFit 5.0 (IDBS, Guildford) to fit to a sigmoidal dose response curve with a variable slope.

General Procedures for Synthesis of Compounds
Chromatography

The compound verification via analytical HPLC-MS was done after purification using the following instrumentation, column and method:
Analytical Method for Compound Purity
Instrumentation:
Agilent MSD 1100
Analytical Methods:
Solvents:
A: acetonitrile
B: H2O
C: 2% HCOOH in acetonitrile
D: 0.1% NEt3 in acetonitrile The following analytical methods were used:
Method A
Column YMC TriArt C18 2.0×50 mm, 1.9 µm, #TA12SP90502WT
thermostated@40° C.
Gradient:

| Time [min] | % B | % C | % D | Flow [mL/min] |
|---|---|---|---|---|
| 0 | 90 | 5 | 0 | 0.45 |
| 0.5 | 90 | 5 | 0 | 0.45 |
| 4.5 | 10 | 5 | 0 | 0.45 |
| 5.5 | 10 | 5 | 0 | 0.45 |
| 5.6 | 90 | 5 | 0 | 0.45 |

Stoptime@10min
MS:ESIpositive,Massscanfrom100to800
gradientfragmentation: 50to125V
UV: detection @ 220 and 254 nm
Purification and Characterisation:

The resulting crude reaction products were purified in an automatic process using a semi-preparative HPLC-MS with mass-triggered sampling of the desired peak:
Purification Via Semi-preparative HPLC-MS
Instrumentation:
2× Varian PrepStar SD-1
1× Dionex P580 Pump 1 Channel(MakeUP I)
1× Dionex AXP-MS (MakeUP II)

1x Dionex MSQ
1x Dionex UVD 340V Prep Flow Cell
Gilson 215 Liquid Handler
Column:
SunFire Prep C18 OBD 5 μm 19×50 mm
Method:
Column Flow: 30 ml/min
Solvent A: methanol, 0.3% acetic acid
Solvent B: water, 0.3% acetic acid
Time Table for Gradient:

| Time (min) | Solv. A | Solv. B |
|---|---|---|
| 0.0 | 30.00 | 70.00 |
| 10.0 | 100.00 | 0.00 |
| 14.0 | 100.00 | 0.00 |
| 14.4 | 30.00 | 70.00 |
| 16.4 | 30.00 | 70.00 |

Detection:
UV 254 nm, Mass Spectrometer Detector (API-ES, positive)
Compound Preparation Where the preparation of starting materials is not described, these are commercially available, known in the literature, or readily obtainable by those skilled in the art using standard procedures. Where it is stated that compounds were prepared analogously to earlier examples or intermediates, it will be appreciated by the skilled person that the reaction time, number of equivalents of reagents and temperature can be modified for each specific reaction and that it may be necessary or desirable to employ different workup or purification techniques. Where reactions are carried out using microwave irradiation, the microwave used is an Initiator 60 supplied by Biotage. The actual power supplied varies during the course of the reaction in order to maintain a constant temperature.

Abbreviations
DCM=Dichloromethane
DIPEA=N,N-Diisopropylethylamine
DMF=N,N-Dimethylformamide
DDQ=2,3-Dichloro-5,6-dicyano-1,4-benzoquinone
THF=Tetrahydrofuran
MeOH=Methanol
tBuOH=2-Methyl-2-propanol
tBuOK=Potassium tertiary butoxide
T3P=Propane phosphonic acid anhydride
TFA=Trifluoroacetic acid
TEA=Triethylamine
rm=Reaction mixture
rt=Room temperature
AcOH=Acetic acid
MeCN=Acetonitrile
EtOH=Ethanol
EtOAc=Ethyl Acetate
LCMS=Mass spectrometry directed high pressure liquid chromatography
UV=Ultraviolet
DMSO=Dimethylsulphoxide
Intermediates
Route A:

Preparation of 7-chloro-2-(4-methoxybenzyl)-5-phenyl-2H-pyrazolo[4,3-d]pyrimidine Step 1: 5-Phenyl-1,6-dihydro-pyrazolo[4,3-d]pyrimidin-7-one
4-Amino-2H-pyrazole-3-carboxylic acid amide (5 mmol) and benzaldehyde (5 mmol) were dissolved in acetic acid (14 ml). Subsequently DDQ (3.75 mmol) were added and the reaction mixture was heated in the microwave to 180° C. for 30 minutes. The precipitate was filtered and washed with Et2O.

Step 2: Protection of Pyrazole with 1-Chloromethyl-4-methoxy-benzene
5-Phenyl-1,6-dihydro-pyrazolo[4,3-d]pyrimidin-7-one (3.9 mmol) was dissolved in 14 ml acetonitrile. 1-Chloromethyl-4-methoxy-benzene (4.7 mmol), 1.2 eq triethylamine (4.7 mmol) and sodiumiodide (0.39 mmol) was added subsequently. The reaction mixture was heated in the microwave for 30 min at 160° C. After cooling down the reaction the resulting precipitate was filtered and washed with Et2O.
The reaction is leading to two isomers (1-(4-Methoxy-benzyl)-5-phenyl-1,6-dihydro-pyrazolo[4,3-d]pyrimidin-7-one and 2-(4-Methoxy-benzyl)-5-phenyl-2,6-dihydro-pyrazolo[4,3-d]pyrimidin-7-one).
Both isomers can be used for the next steps.

Step 3: Chlorination
The mixture of 1-(4-Methoxy-benzyl)-5-phenyl-1,6-dihydro-pyrazolo[4,3-d]pyrimidin-7-one and 2-(4-Methoxy-benzyl)-5-phenyl-2,6-dihydro-pyrazolo[4,3-d]pyrimidin-7-one (0.18 mmol) was suspended in POCl3. The mixture was heated to 100° C. in a reaction vessel. After 0.5 h-24 h LC-MS showed reaction completion. The mixture was cooled to rt. The mixture was concentrated to dryness, cooled to 0° C., and quenched with ice/water. The mixture was extracted with DCM. The organic layer was washed with NaHCO3 sat. aq. and water, dried (Na2SO4) filtered and concentrated.

The product was used without further purification.
The product is an isomeric mixture of 7-Chloro-1-(4-methoxy-benzyl)-5-phenyl-1H-pyrazolo[4,3-d]pyrimidine and 7-Chloro-2-(4-methoxy-benzyl)-5-phenyl-2H-pyrazolo[4,3-d]pyrimidine
Both isomers can be used for the next steps.

The following Chlorides and Isomers were synthezised according to ROUTE A: N-(2-(7-chloro-2-(4-methoxybenzyl)-2H-pyrazolo[4,3-d]pyrimidin-5-yl)phenyl)methanesulfonamide; 7-chloro-2-(4-methoxybenzyl)-5-(3-nitrophenyl)-2H-pyrazolo[4,3-d]pyrimidine; 7-chloro-5-(2,6-difluorophenyl)-2-(4-methoxybenzyl)-2H-pyrazolo[4,3-d]pyrimidine; methyl 3-(7-chloro-2-(4-methoxybenzyl)-2H-pyrazolo[4,3-d]pyrimidin-5-yl)benzoate; 7-chloro-2-(4-methoxybenzyl)-5-(thiophen-2-yl)-2H-pyrazolo[4,3-d]pyrimidine; 7-chloro-5-(2-fluorophenyl)-2-(4-methoxybenzyl)-2H-pyrazolo[4,3-d]pyrimidine; N-(3-(7-chloro-2-(4-methoxybenzyl)-2H-pyrazolo[4,3-d]pyrimidin-5-yl)phenyl)methanesulfonamide; 7-chloro-5-(1H-indazol-6-yl)-2-(4-methoxybenzyl)-2H-pyrazolo[4,3-d]pyrimidine; 4-(7-chloro-2-(4-methoxybenzyl)-2H-pyrazolo[4,3-d]pyrimidin-5-yl)oxazole; 7-chloro-2-(4-methoxybenzyl)-5-(3-methylthiophen-2-yl)-2H-pyrazolo[4,3-d]pyrimidine; 5-(7-chloro-2-(4-methoxybenzyl)-2H-pyrazolo[4,3-d]pyrimidin-5-yl)isoxazole; 3-(7-chloro-2-(4-methoxybenzyl)-2H- pyrazolo[4,3-d]pyrimidin-5-yl)isoxazole; 7-chloro-5-(5-fluoro-1H-indazol-6-yl)-2-(4-methoxybenzyl)-2H-pyrazolo[4,3-d]pyrimidine; 7-chloro-5-(furan-2-yl)-2-(4-methoxybenzyl)-2H-pyrazolo[4,3-d]pyrimidine; 7-chloro-2-(4-methoxybenzyl)-5-(1-methyl-1H-imidazol-2-yl)-2H-pyrazolo[4,3-d]pyrimidine; 7-chloro-2-(4-methoxybenzyl)-5-(1-methyl-1H-imidazol-2-yl)-2H-pyrazolo[4,3-d]pyrimidine; 7-chloro-5-(furan-3-yl)-2-(4-methoxybenzyl)-2H-pyrazolo[4,3-d]pyrimidine; 5-(7-chloro-2-(4-methoxybenzyl)-2H-pyrazolo[4,3-d]pyrimidin-5-yl) isoxazole-3-carboxylic acid ethyl ester; 7-chloro-2-(4-methoxybenzyl)-5-(1-methyl-1H-pyrazol-4-yl)-2H-pyrazolo[4,3-d]pyrimidine; 7-chloro-2-(4-methoxybenzyl)-5-(pyridazin-3-yl)-2H-pyrazolo[4,3-d]pyrimidine; 7-chloro-2-(4-methoxybenzyl)-5-(pyridazin-4-yl)-2H-pyrazolo[4,3-d]pyrimidine; 7-chloro-2-(4-methoxybenzyl)-5-(1-methyl-1H-pyrazol-3-yl)-2H-pyrazolo[4,3-d]pyrimidine; 7-chloro-5-(1H-indazol-5-yl)-2-(4-methoxybenzyl)-2H-pyrazolo[4,3-d]pyrimidine; 3-(7-chloro-2-(4-methoxybenzyl)-2H-pyrazolo[4,3-d]pyrimidin-5-yl)benzoic acid; 2-(7-chloro-2-(4-methoxybenzyl)-2H-pyrazolo[4,3-d]pyrimidin-5-yl) oxazole; 3-(7-chloro-2-(4-methoxybenzyl)-2H-pyrazolo[4,3-d]pyrimidin-5-yl)-N-(4-(oxazol-5-yl)phenyl)benzamide; N-(4-(2H-1,2,3-triazol-2-yl)phenyl)-3-(7-chloro-2-(4-methoxybenzyl)-2H-pyrazolo[4,3-d]pyrimidin-5-yl)benzamide; 3-(7-chloro-2-(4-methoxybenzyl)-2H-pyrazolo[4,3-d]pyrimidin-5-yl)-N-(4-(oxazol-2-yl)phenyl)benzamide; 7-chloro-2-(4-methoxybenzyl)-5-(1-(2-methoxyethyl)-1H-pyrazol-4-yl)-2H-pyrazolo[4,3-d]pyrimidine; 7-chloro-2-(4-methoxybenzyl)-5-(1H-pyrazol-4-yl)-2H-pyrazolo[4,3-d]pyrimidine; 7-chloro-2-(4-methoxybenzyl)-5-(3-methoxyphenyl)-2H-pyrazolo[4,3-d]pyrimidine; 2-(7-chloro-2-(4-methoxybenzyl)-2H-pyrazolo[4,3-d]pyrimidin-5-yl)benzo[d]thiazole; 3-(7-chloro-2-(4-methoxybenzyl)-2H-pyrazolo[4,3-d]pyrimidin-5-yl)benzenesulfonamide; 4-(7-chloro-2-(4-methoxybenzyl)-2H-pyrazolo[4,3-d]pyrimidin-5-yl)-3,5-dimethylisoxazole; 2-(7-chloro-2-(4-methoxybenzyl)-2H-pyrazolo[4,3-d]pyrimidin-5-yl)benzo[d]oxazole; 7-chloro-2-(4-methoxybenzyl)-5-(3-(pyridin-3-yl)phenyl)-2H-pyrazolo[4,3-d]pyrimidine; 7-chloro-5-(2-fluoro-6-methylphenyl)-2-(4-methoxybenzyl)-2H-pyrazolo[4,3-d]pyrimidine; 7-chloro-5-(2-chloro-6-fluorophenyl)-2-(4-methoxybenzyl)-2H-pyrazolo[4,3-d]pyrimidine; 7-chloro-2-(4-methoxybenzyl)-5-(2-(methylsulfonyl)phenyl)-2H-pyrazolo[4,3-d]pyrimidine; 3-(7-chloro-2-(4-methoxybenzyl)-2H-pyrazolo[4,3-d]pyrimidin-5-yl)aniline; 2-(7-chloro-2-(4-methoxybenzyl)-2H-pyrazolo[4,3-d]pyrimidin-5-yl)aniline; 2-(7-chloro-2-(4-methoxybenzyl)-2H-pyrazolo[4,3-d]pyrimidin-5-yl)-3-fluoro aniline; 2-(7-chloro-2-(4-methoxybenzyl)-2H-pyrazolo[4,3-d]pyrimidin-5-yl)thiazole Route B:

Preparation of 7-chloro-5-cyclopropyl-2-(4-methoxybenzyl)-2H-pyrazolo[4,3-d]pyrimidine Step 1: 5-cyclopropyl-1,6-dihydro-pyrazolo[4,3-d]pyrimidin-7-one 4-amino-2H-pyrazole-3-carboxylic acid amide (5 mmol) and DIPEA (7.5 mmol) were dissolved in DCM (30 mL). The solution was stirred at 0° C. followed by dropwise addition of cyclopropanecarbonyl chloride (10 mmol) in DCM (20 mL). After stirring over night at rt, the mixture was concentrated. After addition of water, the pH was adjusted to pH=6 and the product was extracted with DCM. The crude product—2-cyclopropanecarbonyl-4-(cyclopropanecarbonyl-amino)-2H-pyrazole-3-carboxylic acid amide—was used directly without further purification.

2-cyclopropanecarbonyl-4-(cyclopropanecarbonyl-amino)-2H-pyrazole-3-carboxylic acid amide (3 mmol) was dissolved in tBuOH (20 mL). tBuOK (6eq.) in tBuOHA11 was added. the reaction mixture was heated in the microwave to 150° C. for 30 minutes. The reaction mixture was concentrated. After addition of cold water, the solution was adjusted to pH=5. The product was extracted with EtOAc. The combined organic layers were dried over Na2SO4 and evaporated. The crude product—5-cyclopropyl-1,6-dihydro-pyrazolo[4,3-d]pyrimidin-7-one—was used directly without further purification Step 2 and Step 3, according to the steps described in ROUTE A, will result in the formation of the intermediate 7-chloro-5-cyclopropyl-2-(4-methoxybenzyl)-2H-pyrazolo[4,3-d]pyrimidine Route C:

Preparation of 7-chloro-2-(4-methoxybenzyl)-5-(1-methylcyclopropyl)-2H-pyrazolo[4,3-d]pyrimidine Step 1: 5-(1-methylcyclopropyl)-1,6-dihydro-pyrazolo[4,3-d]pyrimidin-7-one 4-amino-2H-pyrazole-3-carboxylic acid amide (3.5 mmol), 1-methyl-cyclopropanecarboxylic acid (3.5 mmol) and TEA (21 mmol) were dissolved in DCM (30 mL). After addition of T3P (5.25 mmol) the reaction mixture was stirred at rt over night. After addition of 5 mL 0.5 N NaOG (aq.) and 75 mL water, the product was extracted with EtOAc. The combined organic layers were dried over Na2SO4 and evaporated. The crude product—4-[(1-methyl-cyclopropanecarbonyl)-amino]-2H-pyrazole-3-carboxylic acid amide—was used directly without further purification.

4-[(1-methyl-cyclopropanecarbonyl)-amino]-2H-pyrazole-3-carboxylic acid amide (3 mmol) was dissolved in tBuOH (20 mL). tBuOK (6eq.) in tBuOHA11 was added. the reaction mixture was heated in the microwave to 150° C. for 30 minutes. The reaction mixture was concentrated. After addition of cold water, the solution was adjusted to pH=5. The product was extracted with EtOAc. The combined organic layers were dried over Na2SO4 and evaporated. The crude product—5-cyclopropyl-1,6-dihydro-pyrazolo[4,3-d]pyrimidin-7-one—was used directly without further purification Step 2 and Step 3, as described in ROUTE A, will result in the formation of the intermediate 7-chloro-2-(4-methoxybenzyl)-5-(1-methylcyclopropyl)-2H-pyrazolo[4,3-d]pyrimidine The following Chlorides and Isomers were synthezised according to ROUTE C:
7-chloro-2-(4-methoxybenzyl)-5-(tetrahydrofuran-2-yl)-2H-pyrazolo[4,3-d]pyrimidine; 7-chloro-2-(4-methoxybenzyl)-5-(methoxymethyl)-2H-pyrazolo[4,3-d]pyrimidine; 7-chloro-2-(4-methoxybenzyl)-5-(1-methoxyethyl)-2H-pyrazolo[4,3-d]pyrimidine; 7-chloro-2-(4-methoxybenzyl)-5-(tetrahydrofuran-3-yl)-2H-pyrazolo[4,3-d]pyrimidine; 7-chloro-2-(4-methoxybenzyl)-5-(tetrahydro-2H-pyran-4-yl)-2H-pyrazolo[4,3-d]pyrimidine; 7-chloro-5-(1,4-dioxan-2-yl)-2-(4-methoxybenzyl)-2H-pyrazolo[4,3-d]pyrimidine; 4-((7-chloro-2-(4-methoxybenzyl)-2H-pyrazolo[4,3-d]pyrimidin-5-yl)methyl)morpholine; 7-chloro-2-(4-methoxybenzyl)-5-(1-methylcyclopropyl)-2H-pyrazolo[4,3-d]pyrimidine; 7-chloro-2-(4-methoxybenzyl)-5-(2-methylcyclopropyl)-2H-pyrazolo[4,3-d]pyrimidine; 1-(7-chloro-2-(4-methoxybenzyl)-2H-pyrazolo[4,3-d]pyrimidin-5-yl)-N,N-dimethylmethanamine; 7-chloro-5-cyclobutyl-2-(4-methoxybenzyl)-2H-pyrazolo[4,3-d]

pyrimidine; 7-chloro-2-(4-methoxybenzyl)-5-(5-methylthiophen-2-yl)-2H-pyrazolo[4,3-d]pyrimidine; 7-chloro-2-(4-methoxybenzyl)-5-(3-methylthiophen-2-yl)-2H-pyrazolo[4,3-d]pyrimidine; 7-chloro-5-isopropyl-2-(4-methoxybenzyl)-2H-pyrazolo[4,3-d]pyrimidine; 5-(tert-butyl)-7-chloro-2-(4-methoxybenzyl)-2H-pyrazolo[4,3-d]pyrimidine; 7-chloro-5-(1-isobutyl-1H-pyrazol-4-yl)-2-(4-methoxybenzyl)-2H-pyrazolo[4,3-d]pyrimidine; 7-chloro-2-(4-methoxybenzyl)-5-propyl-2H-pyrazolo[4,3-d]pyrimidine; 7-chloro-5-cycloheptyl-2-(4-methoxybenzyl)-2H-pyrazolo[4,3-d]pyrimidine; 7-chloro-2-(4-methoxybenzyl)-5-(1-(2-methoxyethyl)-1H-pyrazol-4-yl)-2H-pyrazolo[4,3-d]pyrimidine; 7-chloro-5-(1-isopropyl-1H-pyrazol-4-yl)-2-(4-methoxybenzyl)-2H-pyrazolo[4,3-d]pyrimidine; 4-(7-chloro-2-(4-methoxybenzyl)-2H-pyrazolo[4,3-d]pyrimidin-5-yl)-3,5-dimethylisoxazole; 7-chloro-2-(4-methoxybenzyl)-5-(trifluoromethyl)-2H-pyrazolo[4,3-d]pyrimidine; 5-(1-benzyl-1H-pyrazol-4-yl)-7-chloro-2-(4-methoxybenzyl)-2H-pyrazolo[4,3-d]pyrimidine; 5-(bicyclo[4.1.0]heptan-7-yl)-7-chloro-2-(4-methoxybenzyl)-2H-pyrazolo[4,3-d]pyrimidine; 7-chloro-5-(2,2-dimethylcyclopropyl)-2-(4-methoxybenzyl)-2H-pyrazolo[4,3-d]pyrimidine; 2-(7-chloro-2-(4-methoxybenzyl)-2H-pyrazolo[4,3-d]pyrimidin-5-yl)-4,5,6,7-tetrahydrobenzo[d]thiazole; 7-chloro-2-(4-methoxybenzyl)-5-(2-phenylcyclopropyl)-2H-pyrazolo[4,3-d]pyrimidine; 7-chloro-2-(4-methoxybenzyl)-5-(1-(3-methylbutan-2-yl)-1H-pyrazol-4-yl)-2H-pyrazolo[4,3-d]pyrimidine;
Route D:

Preparation of 7-chloro-2-(4-methoxybenzyl)-5-(1H-1,2,4-triazol-3-yl)-2H-pyrazolo[4,3-d]pyrimidine Step 1
4-Amino-1-(4-methoxy-benzyl)-1H-pyrazole-3-carboxylic acid methyl ester (0.3 mmol) and 1H-[1,2,4]triazole-3-carbonitrile (0.45 mmol) were dissolved in 2.5 mL 4N HCl in dioxane. The reaction mixture was heated in the microwave to 140° C. for 10 minutes. After completition the solvent was evaporated. The crude product—2-(4-Methoxybenzyl)-5-(1H-[1,2,4]triazol-3-yl)-2,6-dihydro-pyrazolo[4,3-d]pyrimidin-7-one—was used directly without further purification.

Step 3, as described in ROUTE A, will result the in the formation of the intermediate 7-chloro-2-(4-methoxybenzyl)-5-(1H-1,2,4-triazol-3-yl)-2H-pyrazolo[4,3-d]pyrimidine The following Chlorides and Isomers were synthezised according to ROUTE D: 7-chloro-2-(4-methoxybenzyl)-5-(1H-1,2,4-triazol-3-yl)-2H-pyrazolo[4,3-d]pyrimidine: 7-chloro-2-(4-methoxybenzyl)-5-(pyridin-3-yl)-2H-pyrazolo[4,3-d]pyrimidine; 7-chloro-2-(4-methoxybenzyl)-5-(1-methyl-1H-1,2,4-triazol-3-yl)-2H-pyrazolo[4,3-d]pyrimidine
Products Example 1

N-(2-(7-((4-morpholinophenyl)amino)-1H-pyrazolo[4,3-d]pyrimidin-5-yl)phenyl)methanesulfonamide N-(2-(7-chloro-2-(4-methoxybenzyl)-2H-pyrazolo[4,3-d]pyrimidin-5-yl)phenyl)methanesulfonamide (0.16 mmol) and 4-morpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 465.1913 g/mol

HPLC-MS: analytical method A rt: 4.87 min—found mass: 466.2 (m/z+H)

The following examples were synthesized according to the protocol of Example 1:

Example 2

N-(2-(7-((3,4-dimethoxyphenyl)amino)-1H-pyrazolo[4,3-d]pyrimidin-5-yl)phenyl)methanesulfonamide Example 3

N-(2-(7-((3-(methylsulfonyl)phenyl)amino)-1H-pyrazolo[4,3-d]pyrimidin-5-yl)phenyl)methanesulfonamide Example 4

N-(1H-indazol-6-yl)-5-(3-nitrophenyl)-1H-pyrazolo[4,3-d]pyrimidin-7-amine

Example 5

N-(4-morpholinophenyl)-5-(3-nitrophenyl)-1H-pyrazolo[4,3-d]pyrimidin-7-amine

Example 6

1-(4-(4-((5-(3-nitrophenyl)-1H-pyrazolo[4,3-d]pyrimidin-7-yl)amino)phenyl)piperazin-1-yl)ethan-1-one Example 8

N-(3,4-dimethoxyphenyl)-5-(5-methylthiophen-2-yl)-1H-pyrazolo[4,3-d]pyrimidin-7-amine Example 9

5-(5-methylthiophen-2-yl)-N-(4-morpholinophenyl)-1H-pyrazolo[4,3-d]pyrimidin-7-amine Example 10

N-(4-(4-(tert-butyl)piperazin-1-yl)phenyl)-5-(2,6-difluorophenyl)-1H-pyrazolo[4,3-d]pyrimidin-7-amine

Example 11

5-(2,6-difluorophenyl)-N-(3-fluoro-4-morpholinophenyl)-1H-pyrazolo[4,3-d]pyrimidin-7-amine

Example 12

5-(2,6-difluorophenyl)-N-(3-methoxy-4-morpholinophenyl)-1H-pyrazolo[4,3-d]pyrimidin-7-amine

Example 13

1-(4-(4-((5-(2,6-difluorophenyl)-1H-pyrazolo[4,3-d]pyrimidin-7-yl)amino)phenyl)piperazin-1-yl)ethan-1-one

Example 15 methyl 3-(7-(benzo[d][1,3]dioxol-5-ylamino)-1H-pyrazolo[4,3-d]pyrimidin-5-yl)benzoate

Example 16

N-(benzo[d][1,3]dioxol-5-yl)-5-(3-nitrophenyl)-1H-pyrazolo[4,3-d]pyrimidin-7-amine

Example 17

6-((5-(thiophen-2-yl)-1H-pyrazolo[4,3-d]pyrimidin-7-yl)amino)-2,3-dihydrobenzo[b]thiophene 1,1-dioxide

Example 18

5-cyclopropyl-N-(4-morpholinophenyl)-1H-pyrazolo[4,3-d]pyrimidin-7-amine

Example 19

5-cyclopropyl-N-(3,4-dimethoxyphenyl)-1H-pyrazolo[4,3-d]pyrimidin-7-amine

Example 20

5-cyclopropyl-N-(3-(methylsulfonyl)phenyl)-1H-pyrazolo[4,3-d]pyrimidin-7-amine

Example 21

6-((5-cyclopropyl-1H-pyrazolo[4,3-d]pyrimidin-7-yl)amino)-2H-benzo[b][1,4]oxazin-3(4H)-one

Example 22

7-((5-cyclopropyl-1H-pyrazolo[4,3-d]pyrimidin-7-yl)amino)-3,4-dihydroquinolin-2(1H)-one

Example 23

N-(4-(4-(tert-butyl)piperazin-1-yl)phenyl)-5-(2-fluorophenyl)-1H-pyrazolo[4,3-d]pyrimidin-7-amine

Example 24

N-(3-fluoro-4-morpholinophenyl)-5-(2-fluorophenyl)-1H-pyrazolo[4,3-d]pyrimidin-7-amine

Example 25

5-(2-fluorophenyl)-N-(3-methoxy-4-morpholinophenyl)-1H-pyrazolo[4,3-d]pyrimidin-7-amine

Example 26

1-(4-(4-((5-(2-fluorophenyl)-1H-pyrazolo[4,3-d]pyrimidin-7-yl)amino)phenyl)piperazin-1-yl)ethan-1-one

Example 27

2-(4-((5-(2-fluorophenyl)-1H-pyrazolo[4,3-d]pyrimidin-7-yl)amino)phenyl)-2-methylpropanenitrile

Example 28

2-(4-((5-(2,6-difluorophenyl)-1H-pyrazolo[4,3-d]pyrimidin-7-yl)amino)phenyl)-2-methylpropanenitrile

Example 29

N-(2-(7-((4-(4-(4-methylpiperazin-1-yl)piperidin-1-yl)phenyl)amino)-1H-pyrazolo[4,3-d]pyrimidin-5-yl)phenyl)methanesulfonamide

Example 30

N-(2-(7-(3-oxo-3,4-dihydro-2H-benzo[b][1,4]oxazin-6-yl)amino)-1H-pyrazolo[4,3-d]pyrimidin-5-yl)phenyl)methanesulfonamide

Example 31

N-(2-(7-((2-oxo-1,2,3,4-tetrahydroquinolin-7-yl)amino)-1H-pyrazolo[4,3-d]pyrimidin-5-yl)phenyl)methanesulfonamide

Example 32

5-cyclopropyl-N-(4-(4-(4-methylpiperazin-1-yl)piperidin-1-yl)phenyl)-1H-pyrazolo[4,3-d]pyrimidin-7-amine

Example 33

1-(4-(4-((5-cyclopropyl-1H-pyrazolo[4,3-d]pyrimidin-7-yl)amino)phenyl)piperazin-1-yl)ethan-1-one

Example 34

5-cyclopropyl-N-(3-fluoro-4-morpholinophenyl)-1H-pyrazolo[4,3-d]pyrimidin-7-amine

Example 35

5-cyclopropyl-N-(3-methoxy-4-morpholinophenyl)-1H-pyrazolo[4,3-d]pyrimidin-7-amine

Example 36

6-((5-(thiophen-2-yl)-1H-pyrazolo[4,3-d]pyrimidin-7-yl)amino)benzo[b]thiophene 1,1-dioxide

Example 37

N-(3-methoxy-4-morpholinophenyl)-5-(thiophen-2-yl)-1H-pyrazolo[4,3-d]pyrimidin-7-amine

Example 38

3-(4-((5-(thiophen-2-yl)-1H-pyrazolo[4,3-d]pyrimidin-7-yl)amino)phenypoxazolidin-2-one

Example 39

N-(3-(7-(4-(4-(tert-butyl)piperazin-1-yl)phenyl)amino)-1H-pyrazolo[4,3-d]pyrimidin-5-yl)phenyl)methanesulfonamide

Example 40

N-(3-(7-((3-fluoro-4-morpholinophenyl)amino)-1H-pyrazolo[4,3-d]pyrimidin-5-yl)phenyl)methanesulfonamide

Example 41

N-(3-(7-((3-methoxy-4-morpholinophenyl)amino)-1H-pyrazolo[4,3-d]pyrimidin-5-yl)phenyl)methanesulfonamide

Example 42

N-(3-(7-((4-morpholinophenyl)amino)-1H-pyrazolo[4,3-d]pyrimidin-5-yl)phenyl)methanesulfonamide

Example 43

N-(3-(7-(4-(morpholine-4-carbonyl)phenyl)amino)-1H-pyrazolo[4,3-d]pyrimidin-5-yl)phenyl)methanesulfonamide

Example 44

N-(3-(7-((4-(2-oxooxazolidin-3-yl)phenyl)amino)-1H-pyrazolo[4,3-d]pyrimidin-5-yl)phenyl)methanesulfonamide

Example 45

N-(4-(4-(tert-butyl)piperazin-1-yl)phenyl)-5-(1H-indazol-6-yl)-1H-pyrazolo[4,3-d]pyrimidin-7-amine

Example 46

N-(3-fluoro-4-morpholinophenyl)-5-(1H-indazol-6-yl)-1H-pyrazolo[4,3-d]pyrimidin-7-amine

Example 47

N-(3-methoxy-4-morpholinophenyl)-5-(oxazol-4-yl)-1H-pyrazolo[4,3-d]pyrimidin-7-amine

Example 48

N-(4-morpholinophenyl)-5-(oxazol-4-yl)-1H-pyrazolo[4,3-d]pyrimidin-7-amine

Example 49

N-(4-(4-(tert-butyl)piperazin-1-yl)phenyl)-5-(oxazol-4-yl)-1H-pyrazolo[4,3-d]pyrimidin-7-amine

Example 50

1-(4-(4-((5-(1H-indazol-6-yl)-1H-pyrazolo[4,3-d]pyrimidin-7-yl)amino)phenyl)piperazin-1-yl)ethan-1-one

Example 51

N-(3,4-dimethoxyphenyl)-5-(3-methylthiophen-2-yl)-1H-pyrazolo[4,3-d]pyrimidin-7-amine

Example 52

5-(3-methylthiophen-2-yl)-N-(4-morpholinophenyl)-1H-pyrazolo[4,3-d]pyrimidin-7-amine

Example 53

(4-((5-cyclopropyl-1H-pyrazolo[4,3-d]pyrimidin-7-yl)amino)phenyl)(4-(4-methylpiperazin-1-yl)piperidin-1-yl)methanone

Example 54

5-(1H-indazol-6-yl)-N-(3-methoxy-4-morpholinophenyl)-1H-pyrazolo[4,3-d]pyrimidin-7-amine

Example 55

5-cyclopropyl-N-(4-(piperazin-1-yl)phenyl)-1H-pyrazolo[4,3-d]pyrimidin-7-amine

Example 56

N-(4-morpholinophenyl)-5-(tetrahydrofuran-2-yl)-1H-pyrazolo[4,3-d]pyrimidin-7-amine

Example 57

N-(3-fluoro-4-morpholinophenyl)-5-(oxazol-4-yl)-1H-pyrazolo[4,3-d]pyrimidin-7-amine

Example 58

3-(4-((5-(oxazol-4-yl)-1H-pyrazolo[4,3-d]pyrimidin-7-yl)amino)phenypoxazolidin-2-one

Example 59

5-(methoxymethyl)-N-(4-morpholinophenyl)-1H-pyrazolo[4,3-d]pyrimidin-7-amine

Example 60

N-(3,4-dimethoxyphenyl)-5-(methoxymethyl)-1H-pyrazolo[4,3-d]pyrimidin-7-amine

Example 61

5-(methoxymethyl)-N-(4-(4-(4-methylpiperazin-1-yl)piperidin-1-yl)phenyl)-1H-pyrazolo[4,3-d]pyrimidin-7-amine

Example 62

5-(methoxymethyl)-N-(3-(methylsulfonyl)phenyl)-1H-pyrazolo[4,3-d]pyrimidin-7-amine

Example 63

1-(4-(4-((5-(methoxymethyl)-1H-pyrazolo[4,3-d]pyrimidin-7-yl)amino)phenyl)piperazin-1-yl)ethan-1-one

Example 64

5-(1-methoxyethyl)-N-(4-morpholinophenyl)-1H-pyrazolo[4,3-d]pyrimidin-7-amine

Example 65

1-(4-(4-((5-(1-methoxyethyl)-1H-pyrazolo[4,3-d]pyrimidin-7-yl)amino)phenyl)piperazin-1-yl)ethan-1-one

Example 66

N-(3,4-dimethoxyphenyl)-5-(1-methoxyethyl)-1H-pyrazolo[4,3-d]pyrimidin-7-amine

Example 67

1-(4-(4-((5-(isoxazol-5-yl)-1H-pyrazolo[4,3-d]pyrimidin-7-yl)amino)phenyl)piperazin-1-yl)ethan-1-one

Example 68

N-(3,4-dimethoxyphenyl)-5-(isoxazol-5-yl)-1H-pyrazolo[4,3-d]pyrimidin-7-amine

Example 69

5-(isoxazol-5-yl)-N-(4-morpholinophenyl)-1H-pyrazolo[4,3-d]pyrimidin-7-amine

Example 70

N-(3-fluoro-4-morpholinophenyl)-5-(isoxazol-5-yl)-1H-pyrazolo[4,3-d]pyrimidin-7-amine

Example 71

5-(isoxazol-5-yl)-N-(3-methoxy-4-morpholinophenyl)-1H-pyrazolo[4,3-d]pyrimidin-7-amine

Example 72

1-(4-(4-((5-(isoxazol-3-yl)-1H-pyrazolo[4,3-d]pyrimidin-7-yl)amino)phenyl)piperazin-1-yl)ethan-1-one

Example 73

N-(3,4-dimethoxyphenyl)-5-(isoxazol-3-yl)-1H-pyrazolo[4,3-d]pyrimidin-7-amine

Example 74

5-(isoxazol-3-yl)-N-(4-morpholinophenyl)-1H-pyrazolo[4,3-d]pyrimidin-7-amine

Example 75

N-(3-fluoro-4-morpholinophenyl)-5-(isoxazol-3-yl)-1H-pyrazolo[4,3-d]pyrimidin-7-amine

Example 76

5-(isoxazol-3-yl)-N-(3-methoxy-4-morpholinophenyl)-1H-pyrazolo[4,3-d]pyrimidin-7-amine

Example 77

5-(5-fluoro-1H-indazol-6-yl)-N-(4-morpholinophenyl)-1H-pyrazolo[4,3-d]pyrimidin-7-amine

Example 78

N-(3,4-dimethoxyphenyl)-5-(tetrahydrofuran-2-yl)-1H-pyrazolo[4,3-d]pyrimidin-7-amine

Example 79

N-(4-morpholinophenyl)-5-(tetrahydrofuran-3-yl)-1H-pyrazolo[4,3-d]pyrimidin-7-amine

Example 80

N-(3,4-dimethoxyphenyl)-5-(tetrahydrofuran-3-yl)-1H-pyrazolo[4,3-d]pyrimidin-7-amine

Example 81

N-(3,4-dimethoxyphenyl)-5-(tetrahydro-2H-pyran-4-yl)-1H-pyrazolo[4,3-d]pyrimidin-7-amine

Example 82

N-(4-morpholinophenyl)-5-(tetrahydro-2H-pyran-4-yl)-1H-pyrazolo[4,3-d]pyrimidin-7-amine

Example 83

N-(3,4-dimethoxyphenyl)-5-(1,4-dioxan-2-yl)-1H-pyrazolo[4,3-d]pyrimidin-7-amine

Example 84

5-(1,4-dioxan-2-yl)-N-(4-morpholinophenyl)-1H-pyrazolo[4,3-d]pyrimidin-7-amine

Example 85

5-((5-(1H-indazol-6-yl)-1H-pyrazolo[4,3-d]pyrimidin-7-yl)amino)-2-morpholinobenzonitrile

Example 86

5-(furan-2-yl)-N-(4-morpholinophenyl)-1H-pyrazolo[4,3-d]pyrimidin-7-amine

Example 87

N-(3,4-dimethoxyphenyl)-5-(furan-2-yl)-1H-pyrazolo[4,3-d]pyrimidin-7-amine

Example 88

5-(1H-indazol-6-yl)-N-(4-nitrophenyl)-1H-pyrazolo[4,3-d]pyrimidin-7-amine

Example 89

(4-methylpiperazin-1-yl)(4-((5-(3-nitrophenyl)-1H-pyrazolo[4,3-d]pyrimidin-7-yl)amino)phenyl)methanone

Example 90

5-(1-methyl-1H-imidazol-2-yl)-N-(4-morpholinophenyl)-1H-pyrazolo[4,3-d]pyrimidin-7-amine

Example 91

1-(4-(4-((5-(1-methyl-1H-imidazol-2-yl)-1H-pyrazolo[4,3-d]pyrimidin-7-yl)amino)phenyl)piperazin-1-yl)ethan-1-one

Example 92

5-(morpholinomethyl)-N-(4-morpholinophenyl)-1H-pyrazolo[4,3-d]pyrimidin-7-amine

Example 93

1-(4-(4-((5-(morpholinomethyl)-1H-pyrazolo[4,3-d]pyrimidin-7-yl)amino)phenyl)piperazin-1-yl)ethan-1-one

Example 94

5-(furan-3-yl)-N-(4-morpholinophenyl)-1H-pyrazolo[4,3-d]pyrimidin-7-amine

Example 95

N-(3,4-dimethoxyphenyl)-5-(furan-3-yl)-1H-pyrazolo[4,3-d]pyrimidin-7-amine

Example 96

1-(4-(4-((5-(furan-3-yl)-1H-pyrazolo[4,3-d]pyrimidin-7-yl)amino)phenyl)piperazin-1-yl)ethan-1-one

Example 97

N-(4-(4-(tert-butyl)piperazin-1-yl)phenyl)-5-(furan-3-yl)-1H-pyrazolo[4,3-d]pyrimidin-7-amine

Example 98

3-(4-((5-(furan-3-yl)-1H-pyrazolo[4,3-d]pyrimidin-7-yl)amino)phenypoxazolidin-2-one

Example 99

5-(1-methylcyclopropyl)-N-(4-morpholinophenyl)-1H-pyrazolo[4,3-d]pyrimidin-7-amine

Example 100

1-(4-(4-((5-(1-methylcyclopropyl)-1H-pyrazolo[4,3-d]pyrimidin-7-yl)amino)phenyl)piperazin-1-yl)ethan-1-one

Example 101

5-(2-methylcyclopropyl)-N-(4-morpholinophenyl)-1H-pyrazolo[4,3-d]pyrimidin-7-amine

Example 102

1-(4-(4-((5-(2-methylcyclopropyl)-1H-pyrazolo[4,3-d]pyrimidin-7-yl)amino)phenyl)piperazin-1-yl)ethan-1-one

Example 103

5-(2-methylcyclopropyl)-N-(1-(tetrahydro-2H-pyran-4-yl)-1H-pyrazol-4-yl)-1H-pyrazolo[4,3-d]pyrimidin-7-amine

Example 104

5-((dimethylamino)methyl)-N-(4-morpholinophenyl)-1H-pyrazolo[4,3-d]pyrimidin-7-amine

Example 106

5-(furan-3-yl)-N-(4-(4-(4-methylpiperazin-1-yl)piperidin-1-yl)phenyl)-1H-pyrazolo[4,3-d]pyrimidin-7-amine

Example 107

8-((5-(furan-3-yl)-1H-pyrazolo[4,3-d]pyrimidin-7-yl)amino)-4,5-dihydro-1H-benzo[b]azepin-2(3H)-one

Example 108

5-(furan-3-yl)-N-(6-(4-methylpiperazin-1-yl)pyridin-3-yl)-1H-pyrazolo[4,3-d]pyrimidin-7-amine

Example 109

5-(furan-3-yl)-N-(3-(methylsulfonyl)phenyl)-1H-pyrazolo[4,3-d]pyrimidin-7-amine

Example 110

5-(furan-3-yl)-N-(1-(tetrahydro-2H-pyran-4-yl)-1H-pyrazol-4-yl)-1H-pyrazolo[4,3-d]pyrimidin-7-amine

Example 111

1-(4-(4-((5-(furan-2-yl)-1H-pyrazolo[4,3-d]pyrimidin-7-yl)amino)phenyl)piperazin-1-yl)ethan-1-one

Example 112

N-(4-(4-(tert-butyl)piperazin-1-yl)phenyl)-5-(furan-2-yl)-1H-pyrazolo[4,3-d]pyrimidin-7-amine

Example 113

8-((5-(furan-2-yl)-1H-pyrazolo[4,3-d]pyrimidin-7-yl)amino)-4,5-dihydro-1H-benzo[b]azepin-2(3H)-one

Example 114

5-(furan-2-yl)-N-(6-(4-methylpiperazin-1-yl)pyridin-3-yl)-1H-pyrazolo[4,3-d]pyrimidin-7-amine

Example 115

3-(4-((5-(furan-2-yl)-1H-pyrazolo[4,3-d]pyrimidin-7-yl)amino)phenyl)oxazolidin-2-one

Example 116

5-(furan-2-yl)-N-(3-(methylsulfonyl)phenyl)-1H-pyrazolo[4,3-d]pyrimidin-7-amine

Example 117

5-(furan-2-yl)-N-(1-(tetrahydro-2H-pyran-4-yl)-1H-pyrazol-4-yl)-1H-pyrazolo[4,3-d]pyrimidin-7-amine

Example 118

5-cyclopropyl-N-(1-(tetrahydro-2H-pyran-4-yl)-1H-pyrazol-4-yl)-1H-pyrazolo[4,3-d]pyrimidin-7-amine

Example 119

5-cyclobutyl-N-(1-(tetrahydro-2H-pyran-4-yl)-1H-pyrazol-4-yl)-1H-pyrazolo[4,3-d]pyrimidin-7-amine

Example 120

5-cyclobutyl-N-(4-morpholinophenyl)-1H-pyrazolo[4,3-d]pyrimidin-7-amine

Example 121

5-(1-methyl-1H-pyrazol-4-yl)-N-(4-morpholinophenyl)-1H-pyrazolo[4,3-d]pyrimidin-7-amine

Example 122

5-(1-methyl-1H-pyrazol-4-yl)-N-(1-(tetrahydro-2H-pyran-4-yl)-1H-pyrazol-4-yl)-1H-pyrazolo[4,3-d]pyrimidin-7-amine

Example 123

N-(4-morpholinophenyl)-5-(1H-1,2,4-triazol-3-yl)-2H-pyrazolo[4,3-d]pyrimidin-7-amine

Example 124

5-(pyridazin-3-yl)-N-(1-(tetrahydro-2H-pyran-4-yl)-1H-pyrazol-4-yl)-1H-pyrazolo[4,3-d]pyrimidin-7-amine

Example 125

N-(4-morpholinophenyl)-5-(pyridazin-3-yl)-1H-pyrazolo[4,3-d]pyrimidin-7-amine

Example 126

N-(6-morpholinopyridin-3-yl)-5-(pyridin-3-yl)-1H-pyrazolo[4,3-d]pyrimidin-7-amine

Example 127

5-(oxazol-4-yl)-N-(1-(tetrahydro-2H-pyran-4-yl)-1H-pyrazol-4-yl)-1H-pyrazolo[4,3-d]pyrimidin-7-amine

Example 128

N-(1-(2-methoxyethyl)-1H-pyrazol-4-yl)-5-(oxazol-4-yl)-1H-pyrazolo[4,3-d]pyrimidin-7-amine

Example 129

N-(1-(1-methylpiperidin-4-yl)-1H-pyrazol-4-yl)-5-(oxazol-4-yl)-1H-pyrazolo[4,3-d]pyrimidin-7-amine

Example 130

1-(4-(4-((5-(oxazol-4-yl)-1H-pyrazolo[4,3-d]pyrimidin-7-yl)amino)-1H-pyrazol-1-yl)piperidin-1-yl)ethan-1-one

Example 131

5-(1H-indazol-6-yl)-N-(1-(2-methoxyethyl)-1H-pyrazol-4-yl)-1H-pyrazolo[4,3-d]pyrimidin-7-amine

Example 132

5-(1H-indazol-6-yl)-N-(1-(1-methylpiperidin-4-yl)-1H-pyrazol-4-yl)-1H-pyrazolo[4,3-d]pyrimidin-7-amine

Example 133

1-(4-(4-((5-(1H-indazol-6-yl)-1H-pyrazolo[4,3-d]pyrimidin-7-yl)amino)-1H-pyrazol-1-yl)piperidin-1-yl)ethan-1-one

Example 134

5-(1H-indazol-6-yl)-N-(1-(tetrahydro-2H-pyran-4-yl)-1H-pyrazol-4-yl)-1H-pyrazolo[4,3-d]pyrimidin-7-amine

Example 135

5-(1-methylcyclopropyl)-N-(4-morpholinophenyl)-1H-pyrazolo[4,3-d]pyrimidin-7-amine

Example 136

1-(4-(4-((5-(1-methylcyclopropyl)-1H-pyrazolo[4,3-d]pyrimidin-7-yl)amino)phenyl)piperazin-1-yl)ethan-1-one

Example 137

5-(2-methylcyclopropyl)-N-(4-morpholinophenyl)-1H-pyrazolo[4,3-d]pyrimidin-7-amine

Example 138

1-(4-(4-((5-(2-methylcyclopropyl)-1H-pyrazolo[4,3-d]pyrimidin-7-yl)amino)phenyl)piperazin-1-yl)ethan-1-one

Example 139

5-(2-methylcyclopropyl)-N-(1-(tetrahydro-2H-pyran-4-yl)-1H-pyrazol-4-yl)-1H-pyrazolo[4,3-d]pyrimidin-7-amine

Example 140

5-((dimethylamino)methyl)-N-(4-morpholinophenyl)-1H-pyrazolo[4,3-d]pyrimidin-7-amine

Example 142

5-(furan-3-yl)-N-(4-(4-(4-methylpiperazin-1-yl)piperidin-1-yl)phenyl)-1H-pyrazolo[4,3-d]pyrimidin-7-amine

Example 143

8-((5-(furan-3-yl)-1H-pyrazolo[4,3-d]pyrimidin-7-yl)amino)-4,5-dihydro-1H-benzo[b]azepin-2(3H)-one

Example 144

5-(furan-3-yl)-N-(6-(4-methylpiperazin-1-yl)pyridin-3-yl)-1H-pyrazolo[4,3-d]pyrimidin-7-amine

Example 145

5-(furan-3-yl)-N-(3-(methylsulfonyl)phenyl)-1H-pyrazolo[4,3-d]pyrimidin-7-amine

Example 146

5-(furan-3-yl)-N-(1-(tetrahydro-2H-pyran-4-yl)-1H-pyrazol-4-yl)-1H-pyrazolo[4,3-d]pyrimidin-7-amine

Example 147

1-(4-(4-((5-(furan-2-yl)-1H-pyrazolo[4,3-d]pyrimidin-7-yl)amino)phenyl)piperazin-1-yl)ethan-1-one

Example 148

N-(4-(4-(tert-butyl)piperazin-1-yl)phenyl)-5-(furan-2-yl)-1H-pyrazolo[4,3-d]pyrimidin-7-amine

Example 149

8-((5-(furan-2-yl)-1H-pyrazolo[4,3-d]pyrimidin-7-yl)amino)-4,5-dihydro-1H-benzo[b]azepin-2(3H)-one

Example 150

5-(furan-2-yl)-N-(6-(4-methylpiperazin-1-yl)pyridin-3-yl)-1H-pyrazolo[4,3-d]pyrimidin-7-amine

Example 151

3-(4-((5-(furan-2-yl)-1H-pyrazolo[4,3-d]pyrimidin-7-yl)amino)phenyl)oxazolidin-2-one

Example 152

5-(furan-2-yl)-N-(3-(methylsulfonyl)phenyl)-1H-pyrazolo[4,3-d]pyrimidin-7-amine

Example 153

5-(furan-2-yl)-N-(1-(tetrahydro-2H-pyran-4-yl)-1H-pyrazol-4-yl)-1H-pyrazolo[4,3-d]pyrimidin-7-amine

Example 154

5-cyclopropyl-N-(1-(tetrahydro-2H-pyran-4-yl)-1H-pyrazol-4-yl)-1H-pyrazolo[4,3-d]pyrimidin-7-amine

Example 155

5-cyclobutyl-N-(1-(tetrahydro-2H-pyran-4-yl)-1H-pyrazol-4-yl)-1H-pyrazolo[4,3-d]pyrimidin-7-amine

Example 156

5-cyclobutyl-N-(4-morpholinophenyl)-1H-pyrazolo[4,3-d]pyrimidin-7-amine

Example 157

5-(1-methyl-1H-pyrazol-4-yl)-N-(4-morpholinophenyl)-1H-pyrazolo[4,3-d]pyrimidin-7-amine

Example 158

5-(1-methyl-1H-pyrazol-4-yl)-N-(1-(tetrahydro-2H-pyran-4-yl)-1H-pyrazol-4-yl)-1H-pyrazolo[4,3-d]pyrimidin-7-amine

Example 159

N-(4-morpholinophenyl)-5-(1H-1,2,4-triazol-3-yl)-2H-pyrazolo[4,3-d]pyrimidin-7-amine

Example 160

5-(pyridazin-3-yl)-N-(1-(tetrahydro-2H-pyran-4-yl)-1H-pyrazol-4-yl)-1H-pyrazolo[4,3-d]pyrimidin-7-amine

Example 161

N-(4-morpholinophenyl)-5-(pyridazin-3-yl)-1H-pyrazolo[4,3-d]pyrimidin-7-amine

Example 162

N-(4-morpholinophenyl)-5-(pyridin-3-yl)-2H-pyrazolo[4,3-d]pyrimidin-7-amine

Example 163

5-(oxazol-4-yl)-N-(1-(tetrahydro-2H-pyran-4-yl)-1H-pyrazol-4-yl)-1H-pyrazolo[4,3-d]pyrimidin-7-amine

Example 164

N-(1-(2-methoxyethyl)-1H-pyrazol-4-yl)-5-(oxazol-4-yl)-1H-pyrazolo[4,3-d]pyrimidin-7-amine

Example 165

N-(1-(1-methylpiperidin-4-yl)-1H-pyrazol-4-yl)-5-(oxazol-4-yl)-1H-pyrazolo[4,3-d]pyrimidin-7-amine

Example 166

1-(4-(4-((5-(oxazol-4-yl)-1H-pyrazolo[4,3-d]pyrimidin-7-yl)amino)-1H-pyrazol-1-yl)piperidin-1-yl)ethan-1-one

Example 167

5-(1H-indazol-6-yl)-N-(1-(2-methoxyethyl)-1H-pyrazol-4-yl)-1H-pyrazolo[4,3-d]pyrimidin-7-amine

Example 168

5-(1H-indazol-6-yl)-N-(1-(1-methylpiperidin-4-yl)-1H-pyrazol-4-yl)-1H-pyrazolo[4,3-d]pyrimidin-7-amine

Example 169

1-(4-(4-((5-(1H-indazol-6-yl)-1H-pyrazolo[4,3-d]pyrimidin-7-yl)amino)-1H-pyrazol-1-yl)piperidin-1-yl)ethan-1-one

Example 170

5-(1H-indazol-6-yl)-N-(1-(tetrahydro-2H-pyran-4-yl)-1H-pyrazol-4-yl)-1H-pyrazolo[4,3-d]pyrimidin-7-amine

Example 172

N-(4-morpholinophenyl)-5-(pyridazin-4-yl)-1H-pyrazolo[4,3-d]pyrimidin-7-amine

Example 173

5-(1-methyl-1H-1,2,4-triazol-3-yl)-N-(4-morpholinophenyl)-2H-pyrazolo[4,3-d]pyrimidin-7-amine

Example 175

5-(1-methyl-1H-pyrazol-3-yl)-N-(4-morpholinophenyl)-1H-pyrazolo[4,3-d]pyrimidin-7-amine

Example 176

5-(1-methyl-1H-pyrazol-3-yl)-N-(1-(tetrahydro-2H-pyran-4-yl)-1H-pyrazol-4-yl)-1H-pyrazolo[4,3-d]pyrimidin-7-amine

Example 177

2-(4-((5-cyclopropyl-1H-pyrazolo[4,3-d]pyrimidin-7-yl)amino)-1H-pyrazol-1-yl)-2-methylpropanenitrile

Example 178

5-(1H-indazol-5-yl)-N-(1-(tetrahydro-2H-pyran-4-yl)-1H-pyrazol-4-yl)-1H-pyrazolo[4,3-d]pyrimidin-7-amine

Example 179

5-(1H-indazol-5-yl)-N-(4-morpholinophenyl)-1H-pyrazolo[4,3-d]pyrimidin-7-amine

Example 180

1-(4-(4-((5-isopropyl-1H-pyrazolo[4,3-d]pyrimidin-7-yl)amino)phenyl)piperazin-1-yl)ethan-1-one

Example 181

5-isopropyl-N-(4-morpholinophenyl)-1H-pyrazolo[4,3-d]pyrimidin-7-amine

Example 182

5-isopropyl-N-(1-(tetrahydro-2H-pyran-4-yl)-1H-pyrazol-4-yl)-1H-pyrazolo[4,3-d]pyrimidin-7-amine

Example 183

(2-fluoro-4-((5-isopropyl-1H-pyrazolo[4,3-d]pyrimidin-7-yl)amino)phenyl)(morpholino)methanone

Example 184

5-isopropyl-N-(1-(1-methylpiperidin-4-yl)-1H-pyrazol-4-yl)-1H-pyrazolo[4,3-d]pyrimidin-7-amine

Example 185

5-isopropyl-N-(1-(2-methoxyethyl)-1H-pyrazol-4-yl)-1H-pyrazolo[4,3-d]pyrimidin-7-amine

Example 186

1-(4-(4-((5-isopropyl-1H-pyrazolo[4,3-d]pyrimidin-7-yl)amino)-1H-pyrazol-1-yl)piperidin-1-yl)ethan-1-one

Example 187

1-(4-(4-((5-(1-methyl-1H-pyrazol-4-yl)-1H-pyrazolo[4,3-d]pyrimidin-7-yl)amino)phenyl)piperazin-1-yl)ethan-1-one

Example 188

N-(1-(2-methoxyethyl)-1H-pyrazol-4-yl)-5-(1-methyl-1H-pyrazol-4-yl)-1H-pyrazolo[4,3-d]pyrimidin-7-amine

Example 189

1-(4-(4-((5-(1-methyl-1H-pyrazol-4-yl)-1H-pyrazolo[4,3-d]pyrimidin-7-yl)amino)-1H-pyrazol-1-yl)piperidin-1-yl)ethan-1-one

Example 190

5-(1-methyl-1H-pyrazol-4-yl)-N-(1-(1-methylpiperidin-4-yl)-1H-pyrazol-4-yl)-1H-pyrazolo[4,3-d]pyrimidin-7-amine

Example 191

5-cyclobutyl-N-(1-(2-methoxyethyl)-1H-pyrazol-4-yl)-1H-pyrazolo[4,3-d]pyrimidin-7-amine

Example 192

1-(4-(4-((5-cyclobutyl-1H-pyrazolo[4,3-d]pyrimidin-7-yl)amino)phenyl)piperazin-1-yl)ethan-1-one

Example 193

(4-((5-cyclobutyl-1H-pyrazolo[4,3-d]pyrimidin-7-yl)amino)-2-fluorophenyl)(morpholino)methanone

Example 194

5-cyclopropyl-N-(1-(2-methoxyethyl)-1H-pyrazol-4-yl)-1H-pyrazolo[4,3-d]pyrimidin-7-amine

Example 195

5-(furan-2-yl)-N-(1-(2-methoxyethyl)-1H-pyrazol-4-yl)-1H-pyrazolo[4,3-d]pyrimidin-7-amine

Example 196

1-(4-(4-((5-(furan-2-yl)-1H-pyrazolo[4,3-d]pyrimidin-7-yl)amino)-1H-pyrazol-1-yl)piperidin-1-yl)ethan-1-one

Example 197

(2-fluoro-4-((5-(furan-2-yl)-1H-pyrazolo[4,3-d]pyrimidin-7-yl)amino)phenyl)(morpholino)methanone

Example 198

5-(furan-2-yl)-N-(1-(1-methylpiperidin-4-yl)-1H-pyrazol-4-yl)-1H-pyrazolo[4,3-d]pyrimidin-7-amine

Example 199

5-(furan-3-yl)-N-(1-(2-methoxyethyl)-1H-pyrazol-4-yl)-1H-pyrazolo[4,3-d]pyrimidin-7-amine

Example 200

1-(4-(4-((5-(furan-3-yl)-1H-pyrazolo[4,3-d]pyrimidin-7-yl)amino)-1H-pyrazol-1-yl)piperidin-1-yl)ethan-1-one

Example 201

(2-fluoro-4-((5-(furan-3-yl)-1H-pyrazolo[4,3-d]pyrimidin-7-yl)amino)phenyl)(morpholino)methanone

Example 202

5-(furan-3-yl)-N-(1-(1-methylpiperidin-4-yl)-1H-pyrazol-4-yl)-1H-pyrazolo[4,3-d]pyrimidin-7-amine

Example 203

2-(4-((5-(furan-3-yl)-1H-pyrazolo[4,3-d]pyrimidin-7-yl)amino)-1H-pyrazol-1-yl)-2-methylpropanenitrile

Example 204

1-(4-(4-((5-cyclopropyl-1H-pyrazolo[4,3-d]pyrimidin-7-yl)amino)-1H-pyrazol-1-yl)piperidin-1-yl)ethan-1-one

Example 205

1-(4-(4-((5-cyclobutyl-1H-pyrazolo[4,3-d]pyrimidin-7-yl)amino)-1H-pyrazol-1-yl)piperidin-1-yl)ethan-1-one

Example 206

5-cyclobutyl-N-(1-(1-methylpiperidin-4-yl)-1H-pyrazol-4-yl)-1H-pyrazolo[4,3-d]pyrimidin-7-amine

Example 207

5-cyclopropyl-N-(1-(1-methylpiperidin-4-yl)-1H-pyrazol-4-yl)-1H-pyrazolo[4,3-d]pyrimidin-7-amine

Example 208

(4-((5-cyclopropyl-1H-pyrazolo[4,3-d]pyrimidin-7-yl)amino)-2-fluorophenyl)(morpholino)methanone

Example 209

4-((5-cyclobutyl-1H-pyrazolo[4,3-d]pyrimidin-7-yl)amino)-1-methylpyridin-2(1H)-one

Example 210

4-((5-cyclopropyl-1H-pyrazolo[4,3-d]pyrimidin-7-yl)amino)-1-methylpyridin-2(1H)-one

Example 211

2-(4-((5-(furan-2-yl)-1H-pyrazolo[4,3-d]pyrimidin-7-yl)amino)-1H-pyrazol-1-yl)-2-methylpropanenitrile

Example 212

N-(1-(tert-butyl)-1H-pyrazol-4-yl)-5-(furan-2-yl)-1H-pyrazolo[4,3-d]pyrimidin-7-amine

Example 213

1-(4-((5-(furan-2-yl)-1H-pyrazolo[4,3-d]pyrimidin-7-yl)amino)-1H-pyrazol-1-yl)cyclohexanecarbonitrile

Example 214

5-(furan-2-yl)-N-(1-isopropyl-1H-pyrazol-4-yl)-1H-pyrazolo[4,3-d]pyrimidin-7-amine

Example 215

5-(furan-2-yl)-N-(1-(3-methoxypropyl)-1H-pyrazol-4-yl)-1H-pyrazolo[4,3-d]pyrimidin-7-amine

Example 216 methyl 3-(7-((1-(tetrahydro-2H-pyran-4-yl)-1H-pyrazol-4-yl)amino)-1H-pyrazolo[4,3-d]pyrimidin-5-yl)benzoate

Example 218

N-(1-(tert-butyl)-1H-pyrazol-4-yl)-5-(furan-3-yl)-1H-pyrazolo[4,3-d]pyrimidin-7-amine

Example 219

1-(4-((5-(furan-3-yl)-1H-pyrazolo[4,3-d]pyrimidin-7-yl)amino)-1H-pyrazol-1-yl)cyclohexanecarbonitrile

Example 220

5-(furan-3-yl)-N-(1-isopropyl-1H-pyrazol-4-yl)-1H-pyrazolo[4,3-d]pyrimidin-7-amine

Example 221

5-(furan-3-yl)-N-(1-(3-methoxypropyl)-1H-pyrazol-4-yl)-1H-pyrazolo[4,3-d]pyrimidin-7-amine

Example 222

N-(1-(tert-butyl)-1H-pyrazol-4-yl)-5-cyclobutyl-1H-pyrazolo[4,3-d]pyrimidin-7-amine

Example 223

5-cyclobutyl-N-(1-isopropyl-1H-pyrazol-4-yl)-1H-pyrazolo[4,3-d]pyrimidin-7-amine

Example 224

5-cyclobutyl-N-(1-(3-methoxypropyl)-1H-pyrazol-4-yl)-1H-pyrazolo[4,3-d]pyrimidin-7-amine

Example 225

2-(4-((5-cyclobutyl-1H-pyrazolo[4,3-d]pyrimidin-7-yl)amino)-1H-pyrazol-1-yl)-2-methylpropanenitrile

Example 226

4-((5-cyclobutyl-1H-pyrazolo[4,3-d]pyrimidin-7-yl)amino)-1-(2-methoxyethyl)pyridin-2(1H)-one

Example 227

(4-((5-cyclobutyl-1H-pyrazolo[4,3-d]pyrimidin-7-yl)amino)-3-methoxyphenyl)(morpholino)methanone

Example 228

N-(1-(tert-butyl)-1H-pyrazol-4-yl)-5-cyclopropyl-1H-pyrazolo[4,3-d]pyrimidin-7-amine

Example 229

5-cyclopropyl-N-(1-isopropyl-1H-pyrazol-4-yl)-1H-pyrazolo[4,3-d]pyrimidin-7-amine

Example 230

5-cyclopropyl-N-(1-(3-methoxypropyl)-1H-pyrazol-4-yl)-1H-pyrazolo[4,3-d]pyrimidin-7-amine

Example 231

4-((5-cyclopropyl-1H-pyrazolo[4,3-d]pyrimidin-7-yl)amino)-1-(2-methoxyethyl)pyridin-2(1H)-one

Example 232

(4-((5-cyclopropyl-1H-pyrazolo[4,3-d]pyrimidin-7-yl)amino)-3-methoxyphenyl)(morpholino)methanone

Example 233

5-cyclopropyl-N-(1-isobutyl-1H-pyrazol-4-yl)-1H-pyrazolo[4,3-d]pyrimidin-7-amine

Example 234

5-cyclobutyl-N-(1-isobutyl-1H-pyrazol-4-yl)-1H-pyrazolo[4,3-d]pyrimidin-7-amine

Example 235

5-cyclopropyl-N-(1,5-dimethyl-1H-pyrazol-4-yl)-1H-pyrazolo[4,3-d]pyrimidin-7-amine

Example 236

5-cyclopropyl-N-(1,3-dimethyl-1H-pyrazol-4-yl)-1H-pyrazolo[4,3-d]pyrimidin-7-amine

Example 237

1-(4-(5-((5-cyclopropyl-1H-pyrazolo[4,3-d]pyrimidin-7-yl)amino)pyridin-2-yl)piperazin-1-yl)ethan-1-one

Example 238

5-(furan-2-yl)-N-(1-isobutyl-1H-pyrazol-4-yl)-1H-pyrazolo[4,3-d]pyrimidin-7-amine

Example 239

2-(4-((5-(furan-2-yl)-1H-pyrazolo[4,3-d]pyrimidin-7-yl)amino)-1H-pyrazol-1-yl)ethan-1-ol

Example 240

5-(furan-3-yl)-N-(1-isobutyl-1H-pyrazol-4-yl)-1H-pyrazolo[4,3-d]pyrimidin-7-amine

Example 241

2-(4-((5-(furan-3-yl)-1H-pyrazolo[4,3-d]pyrimidin-7-yl)amino)-1H-pyrazol-1-yl)acetonitrile Example 242

2-(4-((5-(furan-3-yl)-1H-pyrazolo[4,3-d]pyrimidin-7-yl)amino)-1H-pyrazol-1-yl)ethan-1-ol Example 243

N-(1-(tert-butyl)-1H-pyrazol-4-yl)-5-(oxazol-4-yl)-1H-pyrazolo[4,3-d]pyrimidin-7-amine Example 244

N-(1-isopropyl-1H-pyrazol-4-yl)-5-(oxazol-4-yl)-1H-pyrazolo[4,3-d]pyrimidin-7-amine Example 245

N-(1-(3-methoxypropyl)-1H-pyrazol-4-yl)-5-(oxazol-4-yl)-1H-pyrazolo[4,3-d]pyrimidin-7-amine Example 246

N-(1-isobutyl-1H-pyrazol-4-yl)-5-(oxazol-4-yl)-1H-pyrazolo[4,3-d]pyrimidin-7-amine Example 247

2-(4-((5-(oxazol-4-yl)-1H-pyrazolo[4,3-d]pyrimidin-7-yl)amino)-1H-pyrazol-1-yl)ethan-1-ol Example 248

(4-((5-(furan-3-yl)-1H-pyrazolo[4,3-d]pyrimidin-7-yl)amino)-3-methoxyphenyl)(morpholino)methanone Example 249

N-(1-(tert-butyl)-1H-pyrazol-4-yl)-5-(oxazol-2-yl)-1H-pyrazolo[4,3-d]pyrimidin-7-amine Example 250

N-(1-isopropyl-1H-pyrazol-4-yl)-5-(oxazol-2-yl)-1H-pyrazolo[4,3-d]pyrimidin-7-amine Example 251

N-(1-(3-methoxypropyl)-1H-pyrazol-4-yl)-5-(oxazol-2-yl)-1H-pyrazolo[4,3-d]pyrimidin-7-amine Example 252

N-(1-isobutyl-1H-pyrazol-4-yl)-5-(oxazol-2-yl)-1H-pyrazolo[4,3-d]pyrimidin-7-amine Example 253

2-(4-((5-(oxazol-2-yl)-1H-pyrazolo[4,3-d]pyrimidin-7-yl)amino)-1H-pyrazol-1-yl)ethan-1-ol Example 254

5-(oxazol-2-yl)-N-(1-(tetrahydro-2H-pyran-4-yl)-1H-pyrazol-4-yl)-1H-pyrazolo[4,3-d]pyrimidin-7-amine Example 255

N-(1-(1-methylpiperidin-4-yl)-1H-pyrazol-4-yl)-5-(oxazol-2-yl)-1H-pyrazolo[4,3-d]pyrimidin-7-amine Example 256

N-(1-(2-methoxyethyl)-1H-pyrazol-4-yl)-5-(oxazol-2-yl)-1H-pyrazolo[4,3-d]pyrimidin-7-amine Example 257

1-(4-(4-((5-(oxazol-2-yl)-1H-pyrazolo[4,3-d]pyrimidin-7-yl)amino)-1H-pyrazol-1-yl)piperidin-1-yl)ethan-1-one Example 258

N-(3-(7-((1-(tert-butyl)-1H-pyrazol-4-yl)amino)-1H-pyrazolo[4,3-d]pyrimidin-5-yl)phenyl)methanesulfonamide Example 259

N-(3-(7-((1-isopropyl-1H-pyrazol-4-yl)amino)-1H-pyrazolo[4,3-d]pyrimidin-5-yl)phenyl)methanesulfonamide Example 260

N-(3-(7-((1-(3-methoxypropyl)-1H-pyrazol-4-yl)amino)-1H-pyrazolo[4,3-d]pyrimidin-5-yl)phenyl)methanesulfonamide Example 261

N-(3-(7-((1-isobutyl-1H-pyrazol-4-yl)amino)-1H-pyrazolo[4,3-d]pyrimidin-5-yl)phenyl)methanesulfonamide Example 262

N-(3-(7-((1-(2-hydroxyethyl)-1H-pyrazol-4-yl)amino)-1H-pyrazolo[4,3-d]pyrimidin-5-yl)phenyl)methanesulfonamide Example 263

N-(3-(7-((1-(tetrahydro-2H-pyran-4-yl)-1H-pyrazol-4-yl)amino)-1H-pyrazolo[4,3-d]pyrimidin-5-yl)phenyl)methanesulfonamide Example 264

N-(3-(7-((1-(1-methylpiperidin-4-yl)-1H-pyrazol-4-yl)amino)-1H-pyrazolo[4,3-d]pyrimidin-5-yl)phenyl)methanesulfonamide Example 265

N-(3-(7-((1-(2-methoxyethyl)-1H-pyrazol-4-yl)amino)-1H-pyrazolo[4,3-d]pyrimidin-5-yl)phenyl)methanesulfonamide

Example 266

N-(3-(7-((1-(1-acetylpiperidin-4-yl)-1H-pyrazol-4-yl)amino)-1H-pyrazolo[4,3-d]pyrimidin-5-yl)phenyl)methanesulfonamide

Example 267

5-cyclobutyl-N-(1-cyclopropyl-1H-pyrazol-4-yl)-1H-pyrazolo[4,3-d]pyrimidin-7-amine

Example 268

5-(tert-butyl)-N-(1-isobutyl-1H-pyrazol-4-yl)-1H-pyrazolo[4,3-d]pyrimidin-7-amine

Example 269

5-(tert-butyl)-N-(1-isopropyl-1H-pyrazol-4-yl)-1H-pyrazolo[4,3-d]pyrimidin-7-amine

Example 270

5-(tert-butyl)-N-(1-(3-methoxypropyl)-1H-pyrazol-4-yl)-1H-pyrazolo[4,3-d]pyrimidin-7-amine

Example 271

5-(tert-butyl)-N-(1,5-dimethyl-1H-pyrazol-4-yl)-1H-pyrazolo[4,3-d]pyrimidin-7-amine

Example 272

5-(tert-butyl)-N-(1,3-dimethyl-1H-pyrazol-4-yl)-1H-pyrazolo[4,3-d]pyrimidin-7-amine

Example 273

5-(tert-butyl)-N-(1-cyclopropyl-1H-pyrazol-4-yl)-1H-pyrazolo[4,3-d]pyrimidin-7-amine

Example 274

2-(4-((5-(tert-butyl)-1H-pyrazolo[4,3-d]pyrimidin-7-yl)amino)-1H-pyrazol-1-yl)-2-methylpropanenitrile

Example 275

(4-((5-(tert-butyl)-1H-pyrazolo[4,3-d]pyrimidin-7-yl)amino)-3-methoxyphenyl)(morpholino)methanone

Example 276

3-((5-(furan-2-yl)-1H-pyrazolo[4,3-d]pyrimidin-7-yl)amino)-1-methylpyridin-2(1H)-one

Example 277

N-(1-(tert-butyl)-1H-pyrazol-3-yl)-5-(furan-2-yl)-1H-pyrazolo[4,3-d]pyrimidin-7-amine

Example 278

N-(1-cyclopropyl-1H-pyrazol-4-yl)-5-(furan-2-yl)-1H-pyrazolo[4,3-d]pyrimidin-7-amine

Example 279

N-(4-bromo-1-methyl-1H-pyrazol-3-yl)-5-(furan-2-yl)-1H-pyrazolo[4,3-d]pyrimidin-7-amine

Example 280

N-(1,5-dimethyl-1H-pyrazol-4-yl)-5-(furan-2-yl)-1H-pyrazolo[4,3-d]pyrimidin-7-amine

Example 281

N-(1,3-dimethyl-1H-pyrazol-4-yl)-5-(furan-2-yl)-1H-pyrazolo[4,3-d]pyrimidin-7-amine

Example 282

5-cyclopropyl-N-(1-cyclopropyl-1H-pyrazol-4-yl)-1H-pyrazolo[4,3-d]pyrimidin-7-amine

Example 283

5-cyclopropyl-N-(1-(1-methoxy-2-methylpropan-2-yl)-1H-pyrazol-4-yl)-1H-pyrazolo[4,3-d]pyrimidin-7-amine

Example 284

5-cyclopropyl-N-(1-(2-methoxyethyl)-3-methyl-1H-pyrazol-4-yl)-1H-pyrazolo[4,3-d]pyrimidin-7-amine

Example 285

5-cyclopropyl-N-(1-(2-methoxyethyl)-5-methyl-1H-pyrazol-4-yl)-1H-pyrazolo[4,3-d]pyrimidin-7-amine

Example 286

5-cyclopropyl-N-(1-isopropyl-3-methyl-1H-pyrazol-4-yl)-1H-pyrazolo[4,3-d]pyrimidin-7-amine

Example 287

5-cyclopropyl-N-(1-isopropyl-5-methyl-1H-pyrazol-4-yl)-1H-pyrazolo[4,3-d]pyrimidin-7-amine

Example 288

5-(furan-3-yl)-N-(1-(2-methoxyethyl)-3-methyl-1H-pyrazol-4-yl)-1H-pyrazolo[4,3-d]pyrimidin-7-amine

Example 289

5-(furan-3-yl)-N-(1-(2-methoxyethyl)-5-methyl-1H-pyrazol-4-yl)-1H-pyrazolo[4,3-d]pyrimidin-7-amine

Example 290

5-(furan-3-yl)-N-(1-(1-methoxy-2-methylpropan-2-yl)-1H-pyrazol-4-yl)-1H-pyrazolo[4,3-d]pyrimidin-7-amine

Example 291

N-(1-(1-(tert-butyl)piperidin-4-yl)-1H-pyrazol-4-yl)-5-(furan-3-yl)-1H-pyrazolo[4,3-d]pyrimidin-7-amine

Example 292

5-(furan-3-yl)-N-(1-isopropyl-3-methyl-1H-pyrazol-4-yl)-1H-pyrazolo[4,3-d]pyrimidin-7-amine

Example 293

5-(furan-3-yl)-N-(1-isopropyl-5-methyl-1H-pyrazol-4-yl)-1H-pyrazolo[4,3-d]pyrimidin-7-amine

Example 294

5-(furan-3-yl)-N-(3-methyl-1-(tetrahydro-2H-pyran-4-yl)-1H-pyrazol-4-yl)-1H-pyrazolo[4,3-d]pyrimidin-7-amine

Example 295

5-(furan-3-yl)-N-(5-methyl-1-(tetrahydro-2H-pyran-4-yl)-1H-pyrazol-4-yl)-1H-pyrazolo[4,3-d]pyrimidin-7-amine

Example 296

1-cyclopropyl-4-((5-cyclopropyl-1H-pyrazolo[4,3-d]pyrimidin-7-yl)amino)pyridin-2(1H)-one

Example 297

N-(5-chloro-1-isopropyl-1H-pyrazol-4-yl)-5-cyclopropyl-1H-pyrazolo[4,3-d]pyrimidin-7-amine

Example 298

5-(furan-2-yl)-N-(1-(2-methoxyethyl)-3-methyl-1H-pyrazol-4-yl)-1H-pyrazolo[4,3-d]pyrimidin-7-amine

Example 299

5-(furan-2-yl)-N-(1-(2-methoxyethyl)-5-methyl-1H-pyrazol-4-yl)-1H-pyrazolo[4,3-d]pyrimidin-7-amine

Example 300

5-(furan-2-yl)-N-(1-isopropyl-3-methyl-1H-pyrazol-4-yl)-1H-pyrazolo[4,3-d]pyrimidin-7-amine

Example 301

5-(furan-2-yl)-N-(1-isopropyl-5-methyl-1H-pyrazol-4-yl)-1H-pyrazolo[4,3-d]pyrimidin-7-amine

Example 302

5-(furan-2-yl)-N-(1-isopropyl-3-methoxy-1H-pyrazol-4-yl)-1H-pyrazolo[4,3-d]pyrimidin-7-amine

Example 303

5-(furan-2-yl)-N-(1-isopropyl-3-methyl-1H-pyrazol-4-yl)-1H-pyrazolo[4,3-d]pyrimidin-7-amine

Example 304

5-(furan-2-yl)-N-(1-isopropyl-5-methyl-1H-pyrazol-4-yl)-1H-pyrazolo[4,3-d]pyrimidin-7-amine

Example 305

N-(1-(1-(tert-butyl)piperidin-4-yl)-3-methoxy-1H-pyrazol-4-yl)-5-(furan-2-yl)-1H-pyrazolo[4,3-d]pyrimidin-7-amine

Example 306

5-(furan-3-yl)-N-(1-isopropyl-3-methoxy-1H-pyrazol-4-yl)-1H-pyrazolo[4,3-d]pyrimidin-7-amine

Example 307

5-(furan-3-yl)-N-(1-isopropyl-3-methyl-1H-pyrazol-4-yl)-1H-pyrazolo[4,3-d]pyrimidin-7-amine

Example 308

5-(furan-3-yl)-N-(1-isopropyl-5-methyl-1H-pyrazol-4-yl)-1H-pyrazolo[4,3-d]pyrimidin-7-amine

Example 309

N-(1-(1-(tert-butyl)piperidin-4-yl)-3-methoxy-1H-pyrazol-4-yl)-5-(furan-3-yl)-1H-pyrazolo[4,3-d]pyrimidin-7-amine

Example 310

5-cyclobutyl-N-(1-isopropyl-3-methoxy-1H-pyrazol-4-yl)-1H-pyrazolo[4,3-d]pyrimidin-7-amine

Example 311

5-cyclobutyl-N-(1-isopropyl-5-methoxy-1H-pyrazol-4-yl)-1H-pyrazolo[4,3-d]pyrimidin-7-amine

Example 312

N-(5-chloro-1-isopropyl-1H-pyrazol-4-yl)-5-cyclobutyl-1H-pyrazolo[4,3-d]pyrimidin-7-amine

Example 313

5-cyclopropyl-N-(5-methyl-1-(tetrahydro-2H-pyran-4-yl)-1H-pyrazol-4-yl)-1H-pyrazolo[4,3-d]pyrimidin-7-amine

Example 314

5-cyclopropyl-N-(3-methyl-1-(tetrahydro-2H-pyran-4-yl)-1H-pyrazol-4-yl)-1H-pyrazolo[4,3-d]pyrimidin-7-amine

Example 315

5-cyclopropyl-N-(1-isopropyl-3-methoxy-1H-pyrazol-4-yl)-1H-pyrazolo[4,3-d]pyrimidin-7-amine

Example 316

5-cyclopropyl-N-(1-isopropyl-5-methoxy-1H-pyrazol-4-yl)-1H-pyrazolo[4,3-d]pyrimidin-7-amine

Example 317

N-(1-(1-(tert-butyl)piperidin-4-yl)-3-methoxy-1H-pyrazol-4-yl)-5-cyclopropyl-1H-pyrazolo[4,3-d]pyrimidin-7-amine

Example 318

N-(1-(1-(tert-butyl)piperidin-4-yl)-5-methoxy-1H-pyrazol-4-yl)-5-cyclopropyl-1H-pyrazolo[4,3-d]pyrimidin-7-amine

Example 319

3-(7-((3,4-dimethoxyphenyl)amino)-1H-pyrazolo[4,3-d]pyrimidin-5-yl)-N-(4-(oxazol-5-yl)phenyl)benzamide

Example 320

N-(4-(2H-1,2,3-triazol-2-yl)phenyl)-3-(7-((3,4-dimethoxyphenyl)amino)-1H-pyrazolo[4,3-d]pyrimidin-5-yl)benzamide

Example 321

3-(7-((3,4-dimethoxyphenyl)amino)-1H-pyrazolo[4,3-d]pyrimidin-5-yl)-N-(4-(oxazol-2-yl)phenyl)benzamide

Example 322

N-(5-chloro-1-(3-methoxypropyl)-1H-pyrazol-4-yl)-5-(furan-3-yl)-1H-pyrazolo[4,3-d]pyrimidin-7-amine

Example 323

N-(5-chloro-1-isopropyl-1H-pyrazol-4-yl)-5-(furan-3-yl)-1H-pyrazolo[4,3-d]pyrimidin-7-amine

Example 324

5-cyclobutyl-N-(1-isopropyl-3-methyl-1H-pyrazol-4-yl)-1H-pyrazolo[4,3-d]pyrimidin-7-amine

Example 325

5-cyclobutyl-N-(1-isopropyl-5-methyl-1H-pyrazol-4-yl)-1H-pyrazolo[4,3-d]pyrimidin-7-amine

Example 326

5-cyclobutyl-N-(1-isopropyl-3,5-dimethyl-1H-pyrazol-4-yl)-1H-pyrazolo[4,3-d]pyrimidin-7-amine

Example 327

N-(5-chloro-1-(3-methoxypropyl)-1H-pyrazol-4-yl)-5-cyclobutyl-1H-pyrazolo[4,3-d]pyrimidin-7-amine

Example 328

N-(1-(1-(tert-butyl)piperidin-4-yl)-1H-pyrazol-4-yl)-5-cyclopropyl-1H-pyrazolo[4,3-d]pyrimidin-7-amine

Example 329

5-cyclopropyl-N-(1-isopropyl-3,5-dimethyl-1H-pyrazol-4-yl)-1H-pyrazolo[4,3-d]pyrimidin-7-amine

Example 330

N-(5-chloro-1-(3-methoxypropyl)-1H-pyrazol-4-yl)-5-cyclopropyl-1H-pyrazolo[4,3-d]pyrimidin-7-amine

Example 331

5-cyclobutyl-N-(imidazo[1,2-a]pyridin-3-yl)-1H-pyrazolo[4,3-d]pyrimidin-7-amine

Example 332

5-(furan-2-yl)-N-(1-isopropyl-3,5-dimethyl-1H-pyrazol-4-yl)-1H-pyrazolo[4,3-d]pyrimidin-7-amine

Example 333

N-(3-cyclopropyl-1-methyl-1H-pyrazol-5-yl)-5-(furan-2-yl)-1H-pyrazolo[4,3-d]pyrimidin-7-amine

Example 334

N-(5-chloro-1-(3-methoxypropyl)-1H-pyrazol-4-yl)-5-(furan-2-yl)-1H-pyrazolo[4,3-d]pyrimidin-7-amine

Example 335

3-(4-((5-(furan-2-yl)-1H-pyrazolo[4,3-d]pyrimidin-7-yl)amino)-3-methoxyphenyl)oxazolidin-2-one

Example 336

5-(furan-3-yl)-N-(1-isopropyl-3,5-dimethyl-1H-pyrazol-4-yl)-1H-pyrazolo[4,3-d]pyrimidin-7-amine

Example 337

N-(3-cyclopropyl-1-methyl-1H-pyrazol-5-yl)-5-(furan-3-yl)-1H-pyrazolo[4,3-d]pyrimidin-7-amine

Example 338

5-(furan-3-yl)-N-(3-methoxy-1-(3-methoxypropyl)-1H-pyrazol-4-yl)-1H-pyrazolo[4,3-d]pyrimidin-7-amine

Example 339

5-(furan-3-yl)-N-(imidazo[1,2-a]pyridin-3-yl)-1H-pyrazolo[4,3-d]pyrimidin-7-amine

Example 340

3-(4-((5-(furan-3-yl)-1H-pyrazolo[4,3-d]pyrimidin-7-yl)amino)-3-methoxyphenyl)oxazolidin-2-one

Example 341

N-(5-chloro-1-(2-methoxyethyl)-1H-pyrazol-4-yl)-5-cyclobutyl-1H-pyrazolo[4,3-d]pyrimidin-7-amine

Example 342

N-(5-chloro-1-(2-methoxyethyl)-1H-pyrazol-4-yl)-5-cyclopropyl-1H-pyrazolo[4,3-d]pyrimidin-7-amine

Example 343

N-(1-(tert-butyl)-5-methyl-1H-pyrazol-4-yl)-5-cyclopropyl-1H-pyrazolo[4,3-d]pyrimidin-7-amine

Example 344

5-cyclopropyl-N-(imidazo[1,2-a]pyridin-3-yl)-1H-pyrazolo[4,3-d]pyrimidin-7-amine

Example 345

3-(4-((5-cyclobutyl-1H-pyrazolo[4,3-d]pyrimidin-7-yl)amino)-3-methoxyphenypoxazolidin-2-one

Example 346

5-(furan-2-yl)-N-(3-methoxy-1-(3-methoxypropyl)-1H-pyrazol-4-yl)-1H-pyrazolo[4,3-d]pyrimidin-7-amine

Example 347

N-(5-chloro-1-isopropyl-1H-pyrazol-4-yl)-5-(furan-2-yl)-1H-pyrazolo[4,3-d]pyrimidin-7-amine

Example 348

5-(furan-2-yl)-N-(imidazo[1,2-a]pyridin-3-yl)-1H-pyrazolo[4,3-d]pyrimidin-7-amine

Example 349

N-(5-chloro-1-(2-methoxyethyl)-1H-pyrazol-4-yl)-5-(furan-2-yl)-1H-pyrazolo[4,3-d]pyrimidin-7-amine

Example 350

6-((9-methoxy-3H-pyrazolo[3,4-c]quinolin-4-yl)amino)-1,3-dimethylpyrimidine-2,4(1H,3H)-dione

Example 351

N-(1-(tert-butyl)-5-methyl-1H-pyrazol-4-yl)-5-(oxazol-4-yl)-1H-pyrazolo[4,3-d]pyrimidin-7-amine

Example 352

N-(5-chloro-1-(2-methoxyethyl)-1H-pyrazol-4-yl)-5-(oxazol-4-yl)-1H-pyrazolo[4,3-d]pyrimidin-7-amine

Example 353

N-(5-chloro-1-isopropyl-1H-pyrazol-4-yl)-5-(oxazol-4-yl)-1H-pyrazolo[4,3-d]pyrimidin-7-amine

Example 354

N-(1-isopropyl-5-methyl-1H-pyrazol-4-yl)-5-(oxazol-4-yl)-1H-pyrazolo[4,3-d]pyrimidin-7-amine

Example 355

N-(1-(tert-butyl)-5-methyl-1H-pyrazol-4-yl)-5-(oxazol-2-yl)-1H-pyrazolo[4,3-d]pyrimidin-7-amine

Example 356

N-(5-chloro-1-(2-methoxyethyl)-1H-pyrazol-4-yl)-5-(oxazol-2-yl)-1H-pyrazolo[4,3-d]pyrimidin-7-amine

Example 357

N-(5-chloro-1-isopropyl-1H-pyrazol-4-yl)-5-(oxazol-2-yl)-1H-pyrazolo[4,3-d]pyrimidin-7-amine

Example 358

N-(1-isopropyl-5-methyl-1H-pyrazol-4-yl)-5-(oxazol-2-yl)-1H-pyrazolo[4,3-d]pyrimidin-7-amine

Example 359

6-((5-(furan-3-yl)-1H-pyrazolo[4,3-d]pyrimidin-7-yl)amino)-1,3-dimethylpyrimidine-2,4(1H,3H)-dione

Example 360

N-(5-chloro-1-(2-methoxyethyl)-1H-pyrazol-4-yl)-5-(furan-3-yl)-1H-pyrazolo[4,3-d]pyrimidin-7-amine

Example 361

N-(1-(2-fluoroethyl)-1H-pyrazol-4-yl)-5-(furan-3-yl)-1H-pyrazolo[4,3-d]pyrimidin-7-amine

Example 362

5-cyclopropyl-N-(1-(2-fluoroethyl)-1H-pyrazol-4-yl)-1H-pyrazolo[4,3-d]pyrimidin-7-amine

Example 363

5-cyclobutyl-N-(1-(2-fluoroethyl)-1H-pyrazol-4-yl)-1H-pyrazolo[4,3-d]pyrimidin-7-amine

Example 364

N-(5-chloro-1-(piperidin-4-yl)-1H-pyrazol-4-yl)-5-cyclobutyl-1H-pyrazolo[4,3-d]pyrimidin-7-amine

Example 365

(4-((5-(furan-2-yl)-1H-pyrazolo[4,3-d]pyrimidin-7-yl)amino)-3-methoxyphenyl)(morpholino)methanone

Example 366

6-((5-(furan-2-yl)-1H-pyrazolo[4,3-d]pyrimidin-7-yl)amino)-1,3-dimethylpyrimidine-2,4(1H,3H)-dione

Example 367

N-(1-(2-fluoroethyl)-1H-pyrazol-4-yl)-5-(furan-2-yl)-1H-pyrazolo[4,3-d]pyrimidin-7-amine

Example 368

N-(5-chloro-1-(tetrahydro-2H-pyran-4-yl)-1H-pyrazol-4-yl)-5-(furan-2-yl)-1H-pyrazolo[4,3-d]pyrimidin-7-amine

Example 369

1-(4-((5-(furan-2-yl)-1H-pyrazolo[4,3-d]pyrimidin-7-yl)amino)-1H-pyrazol-1-yl)-2-methylpropan-2-ol

Example 370

5-cyclopropyl-N-(2-fluoro-4-morpholinophenyl)-1H-pyrazolo[4,3-d]pyrimidin-7-amine

Example 371

5-cyclopropyl-N-(2,3-dimethylphenyl)-1H-pyrazolo[4,3-d]pyrimidin-7-amine

Example 372

5-cyclopropyl-N-(2-methyl-4-morpholinophenyl)-1H-pyrazolo[4,3-d]pyrimidin-7-amine

Example 373

5-cyclopropyl-N-(2-methyl-4-(4-methylpiperazin-1-yl)phenyl)-1H-pyrazolo[4,3-d]pyrimidin-7-amine

Example 374

5-cyclopropyl-N-(1-(2,2,2-trifluoroethyl)-1H-pyrazol-4-yl)-1H-pyrazolo[4,3-d]pyrimidin-7-amine

Example 375

5-(furan-3-yl)-N-(1-(2,2,2-trifluoroethyl)-1H-pyrazol-4-yl)-1H-pyrazolo[4,3-d]pyrimidin-7-amine

Example 376

5-(furan-3-yl)-N-(2-methyl-4-morpholinophenyl)-1H-pyrazolo[4,3-d]pyrimidin-7-amine

Example 377

5-(furan-2-yl)-N-(1-(2,2,2-trifluoroethyl)-1H-pyrazol-4-yl)-1H-pyrazolo[4,3-d]pyrimidin-7-amine

Example 378

5-(furan-2-yl)-N-(2-methyl-4-morpholinophenyl)-1H-pyrazolo[4,3-d]pyrimidin-7-amine

Example 379

5-(furan-2-yl)-N-(2-methyl-4-(4-methylpiperazin-1-yl)phenyl)-1H-pyrazolo[4,3-d]pyrimidin-7-amine

Example 380

4-((5-(furan-2-yl)-1H-pyrazolo[4,3-d]pyrimidin-7-yl)amino)-1-isopropyl-1H-pyrazole-5-carbonitrile

Example 381

5-(furan-2-yl)-N-(1-(2-methoxyethyl)-3-(trifluoromethyl)-1H-pyrazol-4-yl)-1H-pyrazolo[4,3-d]pyrimidin-7-amine

Example 382

5-(furan-2-yl)-N-(1-(2-methoxyethyl)-5-(trifluoromethyl)-1H-pyrazol-4-yl)-1H-pyrazolo[4,3-d]pyrimidin-7-amine

Example 383

5-(1-isobutyl-1H-pyrazol-4-yl)-N-(4-morpholinophenyl)-1H-pyrazolo[4,3-d]pyrimidin-7-amine

Example 384

(3-methoxy-4-((5-propyl-1H-pyrazolo[4,3-d]pyrimidin-7-yl)amino)phenyl)(morpholino)methanone

Example 385

N-(3,4-dimethoxyphenyl)-5-propyl-1H-pyrazolo[4,3-d]pyrimidin-7-amine

Example 386

N-(4-morpholinophenyl)-5-propyl-1H-pyrazolo[4,3-d]pyrimidin-7-amine

Example 387

(4-((5-cycloheptyl-1H-pyrazolo[4,3-d]pyrimidin-7-yl)amino)-3-methoxyphenyl)(morpholino)methanone

Example 388

5-cycloheptyl-N-(3,4-dimethoxyphenyl)-1H-pyrazolo[4,3-d]pyrimidin-7-amine

Example 389

5-cycloheptyl-N-(4-morpholinophenyl)-1H-pyrazolo[4,3-d]pyrimidin-7-amine

Example 390

2-(5-chloro-4-((5-cyclopropyl-1H-pyrazolo[4,3-d]pyrimidin-7-yl)amino)-1H-pyrazol-1-yl)ethan-1-ol

Example 391

5-cyclopropyl-N-(1-(2-methoxyethyl)-3-(trifluoromethyl)-1H-pyrazol-4-yl)-1H-pyrazolo[4,3-d]pyrimidin-7-amine

Example 392

5-cyclopropyl-N-(1-(2-methoxyethyl)-5-(trifluoromethyl)-1H-pyrazol-4-yl)-1H-pyrazolo[4,3-d]pyrimidin-7-amine

Example 393

5-(1-(2-methoxyethyl)-1H-pyrazol-4-yl)-N-(4-morpholinophenyl)-1H-pyrazolo[4,3-d]pyrimidin-7-amine

Example 394

N-(4-morpholinophenyl)-5-(1H-pyrazol-4-yl)-1H-pyrazolo[4,3-d]pyrimidin-7-amine

Example 395

4-((5-(furan-3-yl)-1H-pyrazolo[4,3-d]pyrimidin-7-yl)amino)-1-isopropyl-1H-pyrazole-5-carbonitrile

Example 396

5-(furan-3-yl)-N-(1-(2-methoxyethyl)-3-(trifluoromethyl)-1H-pyrazol-4-yl)-1H-pyrazolo[4,3-d]pyrimidin-7-amine

Example 397

5-(furan-3-yl)-N-(1-(2-methoxyethyl)-5-(trifluoromethyl)-1H-pyrazol-4-yl)-1H-pyrazolo[4,3-d]pyrimidin-7-amine

Example 398

N-(5-bromo-1-(2-methoxyethyl)-1H-pyrazol-4-yl)-5-(furan-3-yl)-1H-pyrazolo[4,3-d]pyrimidin-7-amine

Example 399

N-(5-fluoro-1-(2-methoxyethyl)-1H-pyrazol-4-yl)-5-(furan-3-yl)-1H-pyrazolo[4,3-d]pyrimidin-7-amine

Example 400

5-cyclopropyl-N-(2-methyl-3-morpholinophenyl)-1H-pyrazolo[4,3-d]pyrimidin-7-amine

Example 401

5-cyclopropyl-N-(5-ethynyl-1-(2-methoxyethyl)-1H-pyrazol-4-yl)-1H-pyrazolo[4,3-d]pyrimidin-7-amine

Example 402

N-(5-bromo-1-(2-methoxyethyl)-1H-pyrazol-4-yl)-5-(furan-2-yl)-1H-pyrazolo[4,3-d]pyrimidin-7-amine

Example 403

N-(5-fluoro-1-(2-methoxyethyl)-1H-pyrazol-4-yl)-5-(furan-2-yl)-1H-pyrazolo[4,3-d]pyrimidin-7-amine

Example 404

N4-(5-(furan-2-yl)-1H-pyrazolo[4,3-d]pyrimidin-7-yl)-1-(2-methoxyethyl)-N5,N5-dimethyl-1H-pyrazole-4,5-diamine

Example 405

5-(furan-2-yl)-N-(2-methyl-3-morpholinophenyl)-1H-pyrazolo[4,3-d]pyrimidin-7-amine

Example 406

N-(1-cyclopropyl-1H-pyrazol-4-yl)-5-(3-methoxyphenyl)-1H-pyrazolo[4,3-d]pyrimidin-7-amine

Example 407

N-(1-(1-(tert-butyl)piperidin-4-yl)-1H-pyrazol-4-yl)-5-(3-methoxyphenyl)-1H-pyrazolo[4,3-d]pyrimidin-7-amine

Example 408

5-(3-methoxyphenyl)-N-(1-(3-methoxypropyl)-1H-pyrazol-4-yl)-1H-pyrazolo[4,3-d]pyrimidin-7-amine

Example 409

5-(3-methoxyphenyl)-N-(1-(tetrahydro-2H-pyran-4-yl)-1H-pyrazol-4-yl)-1H-pyrazolo[4,3-d]pyrimidin-7-amine

Example 410

5-(benzo[d]thiazol-2-yl)-N-(1-cyclopropyl-1H-pyrazol-4-yl)-1H-pyrazolo[4,3-d]pyrimidin-7-amine

Example 411

5-(benzo[d]thiazol-2-yl)-N-(1-(1-(tert-butyl)piperidin-4-yl)-1H-pyrazol-4-yl)-1H-pyrazolo[4,3-d]pyrimidin-7-amine

Example 412

5-(benzo[d]thiazol-2-yl)-N-(1-(3-methoxypropyl)-1H-pyrazol-4-yl)-1H-pyrazolo[4,3-d]pyrimidin-7-amine

Example 413

5-(benzo[d]thiazol-2-yl)-N-(1-(tetrahydro-2H-pyran-4-yl)-1H-pyrazol-4-yl)-1H-pyrazolo[4,3-d]pyrimidin-7-amine

Example 414

5-(1H-indazol-6-yl)-N-(1-isopropyl-1H-pyrazol-4-yl)-1H-pyrazolo[4,3-d]pyrimidin-7-amine

Example 415

N-(1-(tert-butyl)-1H-pyrazol-4-yl)-5-(1H-indazol-6-yl)-1H-pyrazolo[4,3-d]pyrimidin-7-amine

Example 416

2-(4-((5-(1H-indazol-6-yl)-1H-pyrazolo[4,3-d]pyrimidin-7-yl)amino)-1H-pyrazol-1-yl)-2-methylpropanenitrile

Example 417

N-(1-(2-fluoroethyl)-1H-pyrazol-4-yl)-5-(1H-indazol-6-yl)-1H-pyrazolo[4,3-d]pyrimidin-7-amine

Example 418

N-(1-cyclopropyl-1H-pyrazol-4-yl)-5-(1H-indazol-6-yl)-1H-pyrazolo[4,3-d]pyrimidin-7-amine

Example 419

5-(1H-indazol-6-yl)-N-(1-(3-methoxypropyl)-1H-pyrazol-4-yl)-1H-pyrazolo[4,3-d]pyrimidin-7-amine

Example 420

N-(1-isopropyl-1H-pyrazol-4-yl)-5-(1-methyl-1H-pyrazol-4-yl)-1H-pyrazolo[4,3-d]pyrimidin-7-amine

Example 421

5-(1-isopropyl-1H-pyrazol-4-yl)-N-(4-morpholinophenyl)-1H-pyrazolo[4,3-d]pyrimidin-7-amine

Example 422

2-(4-(4-((5-(1H-indazol-6-yl)-1H-pyrazolo[4,3-d]pyrimidin-7-yl)amino)phenyl)piperazin-1-yl)ethan-1-ol

Example 423

5-(1H-indazol-6-yl)-N-(1-isobutyl-1H-pyrazol-4-yl)-1H-pyrazolo[4,3-d]pyrimidin-7-amine

Example 424

3-(7-((1-(3-methoxypropyl)-1H-pyrazol-4-yl)amino)-1H-pyrazolo[4,3-d]pyrimidin-5-yl)benzenesulfonamide

Example 425

3-(7-((1-(tetrahydro-2H-pyran-4-yl)-1H-pyrazol-4-yl)amino)-1H-pyrazolo[4,3-d]pyrimidin-5-yl)benzenesulfonamide

Example 426

3-(7-((1-isopropyl-1H-pyrazol-4-yl)amino)-1H-pyrazolo[4,3-d]pyrimidin-5-yl)benzenesulfonamide

Example 427

3-(7-((1-(1-acetylpiperidin-4-yl)-1H-pyrazol-4-yl)amino)-1H-pyrazolo[4,3-d]pyrimidin-5-yl)benzenesulfonamide

Example 428

3-(7-((1-isobutyl-1H-pyrazol-4-yl)amino)-1H-pyrazolo[4,3-d]pyrimidin-5-yl)benzenesulfonamide

Example 429

N-(1-(3-methoxypropyl)-1H-pyrazol-4-yl)-5-(thiophen-2-yl)-1H-pyrazolo[4,3-d]pyrimidin-7-amine

Example 430

N-(1-(tetrahydro-2H-pyran-4-yl)-1H-pyrazol-4-yl)-5-(thiophen-2-yl)-1H-pyrazolo[4,3-d]pyrimidin-7-amine

Example 431

N-(1-isopropyl-1H-pyrazol-4-yl)-5-(thiophen-2-yl)-1H-pyrazolo[4,3-d]pyrimidin-7-amine

Example 432

N-(1-isobutyl-1H-pyrazol-4-yl)-5-(thiophen-2-yl)-1H-pyrazolo[4,3-d]pyrimidin-7-amine

Example 433

N-(1-(1-methylpiperidin-4-yl)-1H-pyrazol-4-yl)-5-(thiophen-2-yl)-1H-pyrazolo[4,3-d]pyrimidin-7-amine

Example 434

5-(3,5-dimethylisoxazol-4-yl)-N-(4-morpholinophenyl)-1H-pyrazolo[4,3-d]pyrimidin-7-amine

Example 435

5-(3-methylthiophen-2-yl)-N-(1-(tetrahydro-2H-pyran-4-yl)-1H-pyrazol-4-yl)-1H-pyrazolo[4,3-d]pyrimidin-7-amine

Example 436

N-(1-(3-methoxypropyl)-1H-pyrazol-4-yl)-5-(1-methyl-1H-pyrazol-4-yl)-1H-pyrazolo[4,3-d]pyrimidin-7-amine

Example 437

N-(1-isobutyl-1H-pyrazol-4-yl)-5-(1-methyl-1H-pyrazol-4-yl)-1H-pyrazolo[4,3-d]pyrimidin-7-amine

Example 438

N-(4-morpholinophenyl)-5-(trifluoromethyl)-1H-pyrazolo[4,3-d]pyrimidin-7-amine

Example 439

5-(2,6-difluorophenyl)-N-(1-(tetrahydro-2H-pyran-4-yl)-1H-pyrazol-4-yl)-1H-pyrazolo[4,3-d]pyrimidin-7-amine

Example 440

5-(2,6-difluorophenyl)-N-(1-isobutyl-1H-pyrazol-4-yl)-1H-pyrazolo[4,3-d]pyrimidin-7-amine

Example 441

N4-(5-(furan-3-yl)-1H-pyrazolo[4,3-d]pyrimidin-7-yl)-1-(2-methoxyethyl)-N5,N5-dimethyl-1H-pyrazole-4,5-diamine

Example 442

2-(4-(4-((5-(furan-3-yl)-1H-pyrazolo[4,3-d]pyrimidin-7-yl)amino)phenyl)piperazin-1-yl)ethan-1-ol

Example 443

1-(4-((5-(furan-3-yl)-1H-pyrazolo[4,3-d]pyrimidin-7-yl)amino)phenyl)piperidin-4-ol

Example 444

2-(4-((5-(benzo[d]oxazol-2-yl)-1H-pyrazolo[4,3-d]pyrimidin-7-yl)amino)-1H-pyrazol-1-yl)ethan-1-ol

Example 445

5-(benzo[d]oxazol-2-yl)-N-(1-(1-methylpiperidin-4-yl)-1H-pyrazol-4-yl)-1H-pyrazolo[4,3-d]pyrimidin-7-amine

Example 446

5-(benzo[d]oxazol-2-yl)-N-(1-(tetrahydro-2H-pyran-4-yl)-1H-pyrazol-4-yl)-1H-pyrazolo[4,3-d]pyrimidin-7-amine

Example 447

5-(1H-indazol-6-yl)-N-(1-(pyrrolidin-3-yl)-1H-pyrazol-4-yl)-1H-pyrazolo[4,3-d]pyrimidin-7-amine

Example 448

N-(1-(1,3-dimethoxypropan-2-yl)-1H-pyrazol-4-yl)-5-(1H-indazol-6-yl)-1H-pyrazolo[4,3-d]pyrimidin-7-amine

Example 449

1-(4-((5-(1H-indazol-6-yl)-1H-pyrazolo[4,3-d]pyrimidin-7-yl)amino)-1H-pyrazol-1-yl)-2-methylpropan-2-ol

Example 450

1-(4-((5-(furan-2-yl)-1H-pyrazolo[4,3-d]pyrimidin-7-yl)amino)phenyl)piperidin-4-ol

Example 451

1-(4-((5-(furan-2-yl)-1H-pyrazolo[4,3-d]pyrimidin-7-yl)amino)-1H-pyrazol-1-yl)-2-methylpropan-2-ol

Example 452

2-(4-((5-(furan-2-yl)-1H-pyrazolo[4,3-d]pyrimidin-7-yl)amino)-1H-pyrazol-1-yl)-N,N-dimethylacetamide

Example 453 tert-butyl 3-(4-((5-(furan-2-yl)-1H-pyrazolo[4,3-d]pyrimidin-7-yl)amino)-1H-pyrazol-1-yl)pyrrolidine-1-carboxylate

Example 454

N-(1-cyclopropyl-1H-pyrazol-4-yl)-5-(furan-2-yl)-1H-pyrazolo[4,3-d]pyrimidin-7-amine

Example 455

N-(1-(1,3-dimethoxypropan-2-yl)-1H-pyrazol-4-yl)-5-(furan-2-yl)-1H-pyrazolo[4,3-d]pyrimidin-7-amine

Example 456

5-(benzo[d]thiazol-2-yl)-N-(1-(2-methoxyethyl)-1H-pyrazol-4-yl)-1H-pyrazolo[4,3-d]pyrimidin-7-amine

Example 457

5-(benzo[d]thiazol-2-yl)-N-(1-isobutyl-1H-pyrazol-4-yl)-1H-pyrazolo[4,3-d]pyrimidin-7-amine

Example 458

1-(4-(4-((5-(benzo[d]thiazol-2-yl)-1H-pyrazolo[4,3-d]pyrimidin-7-yl)amino)-1H-pyrazol-1-yl)piperidin-1-yl)ethan-1-one

Example 459

5-(benzo[d]thiazol-2-yl)-N-(1-(1-methylpiperidin-4-yl)-1H-pyrazol-4-yl)-1H-pyrazolo[4,3-d]pyrimidin-7-amine

Example 460

5-(1-benzyl-1H-pyrazol-4-yl)-N-(4-morpholinophenyl)-1H-pyrazolo[4,3-d]pyrimidin-7-amine

Example 461

2-(4-((5-cyclobutyl-1H-pyrazolo[4,3-d]pyrimidin-7-yl)amino)-1H-pyrazol-1-yl)-N,N-dimethylacetamide

Example 462

5-cyclobutyl-N-(1-(pyrrolidin-3-yl)-1H-pyrazol-4-yl)-1H-pyrazolo[4,3-d]pyrimidin-7-amine

Example 463

5-cyclobutyl-N-(1-(1,3-dimethoxypropan-2-yl)-1H-pyrazol-4-yl)-1H-pyrazolo[4,3-d]pyrimidin-7-amine

Example 464

N-(1-(pyridin-2-yl)-1H-pyrazol-4-yl)-5-(3-(pyridin-3-yl)phenyl)-1H-pyrazolo[4,3-d]pyrimidin-7-amine

Example 465

5-(3-(pyridin-3-yl)phenyl)-N-(1-(pyrrolidin-3-yl)-1H-pyrazol-4-yl)-1H-pyrazolo[4,3-d]pyrimidin-7-amine

Example 466

N,N-dimethyl-2-(4-((5-(3-(pyridin-3-yl)phenyl)-1H-pyrazolo[4,3-d]pyrimidin-7-yl)amino)-1H-pyrazol-1-yl)acetamide

Example 467

N-(1-(1,3-dimethoxypropan-2-yl)-1H-pyrazol-4-yl)-5-(3-(pyridin-3-yl)phenyl)-1H-pyrazolo[4,3-d]pyrimidin-7-amine

Example 468

N-(1-(1-(tert-butyl)piperidin-4-yl)-1H-pyrazol-4-yl)-5-(1H-indazol-6-yl)-1H-pyrazolo[4,3-d]pyrimidin-7-amine

Example 469

5-(1H-indazol-6-yl)-N-(1-(3-methylbutan-2-yl)-1H-pyrazol-4-yl)-1H-pyrazolo[4,3-d]pyrimidin-7-amine

Example 470

6-((5-(1H-indazol-6-yl)-1H-pyrazolo[4,3-d]pyrimidin-7-yl)amino)-4-methyl-2H-benzo[b][1,4]oxazin-3(4H)-one

Example 471

6-((5-(1H-indazol-6-yl)-1H-pyrazolo[4,3-d]pyrimidin-7-yl)amino)-4-ethyl-2H-benzo[b][1,4]oxazin-3(4H)-one

Example 472

5-(1H-indazol-6-yl)-N-(1-(pyridin-2-yl)-1H-pyrazol-4-yl)-1H-pyrazolo[4,3-d]pyrimidin-7-amine

Example 473

5-(bicyclo[4.1.0]heptan-7-yl)-N-(1-(tetrahydro-2H-pyran-4-yl)-1H-pyrazol-4-yl)-1H-pyrazolo[4,3-d]pyrimidin-7-amine

Example 474

5-(bicyclo[4.1.0]heptan-7-yl)-N-(1-(pyrrolidin-3-yl)-1H-pyrazol-4-yl)-1H-pyrazolo[4,3-d]pyrimidin-7-amine

Example 475

5-(bicyclo[4.1.0]heptan-7-yl)-N-(3-methoxy-4-morpholinophenyl)-1H-pyrazolo[4,3-d]pyrimidin-7-amine

Example 476

2-(4-((5-(1H-indazol-6-yl)-1H-pyrazolo[4,3-d]pyrimidin-7-yl)amino)-1H-pyrazol-1-yl)ethan-1-ol

Example 477

5-(1H-indazol-6-yl)-N-(1-(1-phenylethyl)-1H-pyrazol-4-yl)-1H-pyrazolo[4,3-d]pyrimidin-7-amine

Example 478

N-(3-ethylphenyl)-5-(1H-indazol-6-yl)-1H-pyrazolo[4,3-d]pyrimidin-7-amine

Example 479

(7-((5-(1H-indazol-6-yl)-1H-pyrazolo[4,3-d]pyrimidin-7-yl)amino)-3,4-dihydroquinolin-1(2H)-yl)(cyclopropyl)methanone

Example 480

N-(3,4-dimethoxyphenyl)-5-(2-fluoro-6-methylphenyl)-1H-pyrazolo[4,3-d]pyrimidin-7-amine

Example 481

5-(2-fluoro-6-methylphenyl)-N-(3-methoxy-4-morpholinophenyl)-1H-pyrazolo[4,3-d]pyrimidin-7-amine

Example 482

5-(furan-3-yl)-N-(1-(3-methylbutan-2-yl)-1H-pyrazol-4-yl)-1H-pyrazolo[4,3-d]pyrimidin-7-amine

Example 483

5-(furan-3-yl)-N-(1-(tetrahydro-2H-pyran-3-yl)-1H-pyrazol-4-yl)-1H-pyrazolo[4,3-d]pyrimidin-7-amine

Example 484

5-(furan-3-yl)-N-(1-(pyridin-2-yl)-1H-pyrazol-4-yl)-1H-pyrazolo[4,3-d]pyrimidin-7-amine

Example 485

4-ethyl-6-((5-(furan-3-yl)-1H-pyrazolo[4,3-d]pyrimidin-7-yl)amino)-2H-benzo[b][1,4]oxazin-3(4H)-one

Example 486

2-(4-((5-(furan-3-yl)-1H-pyrazolo[4,3-d]pyrimidin-7-yl)amino)-1H-pyrazol-1-yl)propanoic acid

Example 487

5-(furan-3-yl)-N-(1-(1-phenylethyl)-1H-pyrazol-4-yl)-1H-pyrazolo[4,3-d]pyrimidin-7-amine

Example 488

6-((5-(furan-3-yl)-1H-pyrazolo[4,3-d]pyrimidin-7-yl)amino)-4-methyl-2H-benzo[b][1,4]oxazin-3(4H)-one

Example 489

N-(3-ethylphenyl)-5-(furan-3-yl)-1H-pyrazolo[4,3-d]pyrimidin-7-amine

Example 490 cyclopropyl(7-((5-(furan-3-yl)-1H-pyrazolo[4,3-d]pyrimidin-7-yl)amino)-3,4-dihydroquinolin-1(2H)-yl)methanone

Example 491

5-(2,2-dimethylcyclopropyl)-N-(1-(tetrahydro-2H-pyran-4-yl)-1H-pyrazol-4-yl)-1H-pyrazolo[4,3-d]pyrimidin-7-amine

Example 492

5-(2,2-dimethylcyclopropyl)-N-(3-methoxy-4-morpholinophenyl)-1H-pyrazolo[4,3-d]pyrimidin-7-amine

Example 493

2-(4-((5-(1H-indazol-6-yl)-1H-pyrazolo[4,3-d]pyrimidin-7-yl)amino)-1H-pyrazol-1-yl)propanoic acid

Example 494

5-((5-(1H-indazol-6-yl)-1H-pyrazolo[4,3-d]pyrimidin-7-yl)amino)-1H-pyrazole-3-carboxylic acid

Example 495

N-(1-(1-(tert-butyl)piperidin-4-yl)-1H-pyrazol-4-yl)-5-(4,5,6,7-tetrahydrobenzo[d]thiazol-2-yl)-1H-pyrazolo[4,3-d]pyrimidin-7-amine

Example 496

N-(1-(tetrahydro-2H-pyran-4-yl)-1H-pyrazol-4-yl)-5-(4,5,6,7-tetrahydrobenzo[d]thiazol-2-yl)-1H-pyrazolo[4,3-d]pyrimidin-7-amine

Example 497

6-((5-cyclopropyl-1H-pyrazolo[4,3-d]pyrimidin-7-yl)amino)-4-methyl-2H-benzo[b][1,4]oxazin-3(4H)-one

Example 498

5-cyclopropyl-N-(1-(3-methylbutan-2-yl)-1H-pyrazol-4-yl)-1H-pyrazolo[4,3-d]pyrimidin-7-amine

Example 499

5-((5-cyclopropyl-1H-pyrazolo[4,3-d]pyrimidin-7-yl)amino)-1H-pyrazole-3-carboxylic acid

Example 500

(4-((5-(2,6-difluorophenyl)-1H-pyrazolo[4,3-d]pyrimidin-7-yl)amino)phenyl)(4-methylpiperazin-1-yl)methanone

Example 501

2-(4-(4-((5-(2,6-difluorophenyl)-1H-pyrazolo[4,3-d]pyrimidin-7-yl)amino)phenyl)piperazin-1-yl)ethan-1-ol

Example 502

5-((5-(2,6-difluorophenyl)-1H-pyrazolo[4,3-d]pyrimidin-7-yl)amino)-2-morpholinobenzonitrile

Example 503 cyclopropyl(7-((5-cyclopropyl-1H-pyrazolo[4,3-d]pyrimidin-7-yl)amino)-3,4-dihydroquinolin-1(2H)-yl)methanone

Example 504

2-(4-((5-cyclopropyl-1H-pyrazolo[4,3-d]pyrimidin-7-yl)amino)-1H-pyrazol-1-yl)propanoic acid

Example 505

5-(1H-indazol-6-yl)-N-(1-(tetrahydro-2H-pyran-3-yl)-1H-pyrazol-4-yl)-1H-pyrazolo[4,3-d]pyrimidin-7-amine

Example 506

2-((5-(1H-indazol-6-yl)-1H-pyrazolo[4,3-d]pyrimidin-7-yl)amino)phenol

Example 507

N1-(5-(1H-indazol-6-yl)-1H-pyrazolo[4,3-d]pyrimidin-7-yl)-4,5-dimethoxybenzene-1,2-diamine

Example 508

N-(3-methoxy-4-morpholinophenyl)-5-((1S,2S)-2-phenylcyclopropyl)-1H-pyrazolo[4,3-d]pyrimidin-7-amine

Example 509

N-(3,4-dimethoxyphenyl)-5-((1S,2S)-2-phenylcyclopropyl)-1H-pyrazolo[4,3-d]pyrimidin-7-amine

Example 510

N-(4-morpholinophenyl)-5-((1S,2S)-2-phenylcyclopropyl)-1H-pyrazolo[4,3-d]pyrimidin-7-amine

Example 511

N-(3,4-dimethoxyphenyl)-5-(1-(3-methylbutan-2-yl)-1H-pyrazol-4-yl)-1H-pyrazolo[4,3-d]pyrimidin-7-amine

Example 512

N-(3-methoxy-4-morpholinophenyl)-5-(1-(3-methylbutan-2-yl)-1H-pyrazol-4-yl)-1H-pyrazolo[4,3-d]pyrimidin-7-amine

Example 513

5-(2-chloro-6-fluorophenyl)-N-(3,4-dimethoxyphenyl)-1H-pyrazolo[4,3-d]pyrimidin-7-amine

Example 514

5-(2-chloro-6-fluorophenyl)-N-(3-methoxy-4-morpholinophenyl)-1H-pyrazolo[4,3-d]pyrimidin-7-amine

Example 515

5-(1H-indazol-6-yl)-N-(4-(phenylthio)phenyl)-1H-pyrazolo[4,3-d]pyrimidin-7-amine

Example 516

8-((5-(1H-indazol-6-yl)-1H-pyrazolo[4,3-d]pyrimidin-7-yl)amino)-4,5-dihydro-1H-benzo[b]azepin-2(3H)-one

Example 517

5-(1H-indazol-6-yl)-N-(1-(2,2,2-trifluoroethyl)-1H-pyrazol-4-yl)-1H-pyrazolo[4,3-d]pyrimidin-7-amine

Example 518

1-(4-((5-(1H-indazol-6-yl)-1H-pyrazolo[4,3-d]pyrimidin-7-yl)amino)phenyl)piperidin-4-ol

Example 519

6-((5-(1H-indazol-6-yl)-1H-pyrazolo[4,3-d]pyrimidin-7-yl)amino)-2H-benzo[b][1,4]oxazin-3(4H)-one

Example 520

6-((5-(1H-indazol-6-yl)-1H-pyrazolo[4,3-d]pyrimidin-7-yl)amino)-2H-benzo[b][1,4]thiazin-3(4H)-one

Example 521

8-((5-(2,6-difluorophenyl)-1H-pyrazolo[4,3-d]pyrimidin-7-yl)amino)-4,5-dihydro-1H-benzo[b]azepin-2(3H)-one

Example 522

1-(4-((5-(2,6-difluorophenyl)-1H-pyrazolo[4,3-d]pyrimidin-7-yl)amino)phenyl)piperidin-4-ol

Example 523

N-(5-((5-(2,6-difluorophenyl)-1H-pyrazolo[4,3-d]pyrimidin-7-yl)amino)-2-methoxyphenyl)acetamide

Example 524

5-(2,6-difluorophenyl)-N-(1-(2,2,2-trifluoroethyl)-1H-pyrazol-4-yl)-1H-pyrazolo[4,3-d]pyrimidin-7-amine

Example 525

3-(7-((2-oxo-2,3,4,5-tetrahydro-1H-benzo[b]azepin-8-yl)amino)-1H-pyrazolo[4,3-d]pyrimidin-5-yl)benzenesulfonamide

Example 526

3-(7-((1-(2-hydroxyethyl)-1H-pyrazol-4-yl)amino)-1H-pyrazolo[4,3-d]pyrimidin-5-yl)benzenesulfonamide

Example 527

5-(2-(methylsulfonyl)phenyl)-N-(4-morpholinophenyl)-1H-pyrazolo[4,3-d]pyrimidin-7-amine

Example 528

8-((5-(2-(methylsulfonyl)phenyl)-1H-pyrazolo[4,3-d]pyrimidin-7-yl)amino)-4,5-dihydro-1H-benzo[b]azepin-2(3H)-one

Example 529

N-(3-(7-((2-oxo-2,3,4,5-tetrahydro-1H-benzo[b]azepin-8-yl)amino)-1H-pyrazolo[4,3-d]pyrimidin-5-yl)phenyl)methanesulfonamide

Example 533

N-(1-(1-methylpiperidin-4-yl)-1H-pyrazol-4-yl)-5-(2-(methylsulfonyl)phenyl)-1H-pyrazolo[4,3-d]pyrimidin-7-amine

Example 534

5-(2-(methylsulfonyl)phenyl)-N-(1-(tetrahydro-2H-pyran-4-yl)-1H-pyrazol-4-yl)-1H-pyrazolo[4,3-d]pyrimidin-7-amine

Example 535

N-(1-(1-methylpiperidin-4-yl)-1H-pyrazol-4-yl)-5-(thiazol-2-yl)-1H-pyrazolo[4,3-d]pyrimidin-7-amine

Example 536

(5-((5-(1H-indazol-6-yl)-1H-pyrazolo[4,3-d]pyrimidin-7-yl)amino)-2-(4-methylpiperazin-1-yl)phenyl)methanol

Example 537

N-(5-(2,6-difluorophenyl)-1H-pyrazolo[4,3-d]pyrimidin-7-yl)-3,4-dihydro-2H-benzo[b][1,4]oxazin-6-amine

Example 538

N-(2-(4-acetylpiperazin-1-yl)-5-((5-(2,6-difluorophenyl)-1H-pyrazolo[4,3-d]pyrimidin-7-yl)amino)phenyl)acetamide

Example 539

N-(3-chloro-4-(4-methylpiperazin-1-yl)phenyl)-5-(2,6-difluorophenyl)-1H-pyrazolo[4,3-d]pyrimidin-7-amine

Example 540

2,6-dichloro-4-((5-(2,6-difluorophenyl)-1H-pyrazolo[4,3-d]pyrimidin-7-yl)amino)phenol

Example 541

5-(2,6-difluorophenyl)-N-(3-ethoxy-4-methoxyphenyl)-1H-pyrazolo[4,3-d]pyrimidin-7-amine

Example 7

5-(3-aminophenyl)-N-(3,4-dimethoxyphenyl)-1H-pyrazolo[4,3-d]pyrimidin-7-amine 7-chloro-2-(4-methoxybenzyl)-5-(3-nitrophenyl)-2H-pyrazolo[4,3-d]pyrimidine (0.16 mmol) and 3,4-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated. The reaction mixture was dissolved in methanol (3 mL). Pd/C was added (20 mg) and the reaction was stirred overnight under N2 at room temperature. After filtration with celite the reaction mixture was concentrated and purified by semi-preparative HPLC-MS and freeze dried from water/t-BuOH 4/1.

exact mass: 362.1744 g/mol
HPLC-MS: analytical method A
rt: 3.60 min—found mass: 363.2 (m/z+H)

The following examples were synthesized according to the protocol of Example 7:

Example 14

1-(4-(4-((5-(3-aminophenyl)-1H-pyrazolo[4,3-d]pyrimidin-7-yl)amino)phenyl)piperazin-1-yl)ethan-1-one

Example 530

5-(3-aminophenyl)-N-(1-(tetrahydro-2H-pyran-4-yl)-1H-pyrazol-4-yl)-1H-pyrazolo[4,3-d]pyrimidin-7-amine

Example 531

5-(2-aminophenyl)-N-(1-(tetrahydro-2H-pyran-4-yl)-1H-pyrazol-4-yl)-2H-pyrazolo[4,3-d]pyrimidin-7-amine

Example 532

5-(2-amino-6-fluorophenyl)-N-(1-(tetrahydro-2H-pyran-4-yl)-1H-pyrazol-4-yl)-1H-pyrazolo[4,3-d]pyrimidin-7-amine

Example 105

5-(7-((4-morpholinophenyl)amino)-1H-pyrazolo[4,3-d]pyrimidin-5-yl)isoxazole-3-carboxylic acid 5-(7-chloro-2-(4-methoxybenzyl)-2H-pyrazolo[4,3-d]pyrimidin-5-yl)isoxazole-3-carboxylic acid ethyl ester (0.16 mmol) and 4-morpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was evaporated and 2N NaOH (3 mL, aq.) was added. The reaction mixture was irradiated in a microwave reactor for 5 min at 140° C. The reaction mixture was concentrated and purified by semi-preparative HPLC-MS and freeze dried from water/t-BuOH 4/1.

exact mass: 407.1556 g/mol
HPLC-MS: analytical method A
rt: 3.53 min—found mass: 408.2 (m/z+H)

The following examples were synthesized according to the protocol of Example 105:

Example 141

5-(7-((4-morpholinophenyl)amino)-1H-pyrazolo[4,3-d]pyrimidin-5-yl)isoxazole-3-carboxylic acid

Example 217

3-(7-((1-(tetrahydro-2H-pyran-4-yl)-1H-pyrazol-4-yl)amino)-1H-pyrazolo[4,3-d]pyrimidin-5-yl)benzoic acid Biological Data
SYK Activities:
  IC50 lower than 10 nM:
  Example 12; Example 18; Example 22; Example 35; Example 45; Example 50; Example 54; Example 69; Example 106; Example 112; Example 120; Example 134; Example 1-(2; Example 146; Example 148; Example 156; Example 170; Example 189; Example 192; Example 196; Example 198; Example 200; Example 202; Example 204; Example 206; Example 214; Example 215; Example 220; Example 221; Example 223; Example 229; Example 239; Example 241; Example 242; Example 244; Example 245; Example 291; Example 328; Example 410; Example 411; Example 417; Example 418; Example 433; Example 447; Example 456; Example 458; Example 462; Example 468; Example 519; Example 536; Example 412; Example 413;
  IC50 between 10 nM and 100 nM:
  Example 9; Example 10; Example 19; Example 21; Example 25; Example 29; Example 46; Example 49; Example 51; Example 52; Example 77; Example 85; Example 86; Example 87; Example 94; Example 96; Example 97; Example 101; Example 107; Example 110; Example 111; Example 113; Example 115; Example 117; Example 118;

Example 119; Example 121; Example 122; Example 131; Example 132; Example 133; Example 137; Example 143; Example 147; Example 149; Example 151; Example 153; Example 154; Example 155; Example 157; Example 158; Example 167; Example 168; Example 169; Example 178; Example 179; Example 187; Example 190; Example 191; Example 195; Example 205; Example 207; Example 212; Example 216; Example 218; Example 222; Example 224; Example 228; Example 230; Example 233; Example 237; Example 238; Example 240; Example 243; Example 246; Example 247; Example 259; Example 260; Example 264; Example 267; Example 269; Example 278; Example 282; Example 283; Example 296; Example 361; Example 362; Example 363; Example 367; Example 374; Example 377; Example 394; Example 407; Example 408; Example 409; Example 414; Example 415; Example 416; Example 419; Example 420; Example 421; Example 422; Example 423; Example 425; Example 426; Example 428; Example 429; Example 430; Example 431; Example 432; Example 437; Example 442; Example 443; Example 445; Example 446; Example 448; Example 449; Example 450; Example 451; Example 454; Example 459; Example 460; Example 465; Example 466; Example 469; Example 476; Example 482; Example 483; Example 488; Example 495; Example 496; Example 498; Example 501; Example 502; Example 505; Example 514; Example 516; Example 517; Example 522; Example 525; Example 526; Example 530; Example 535; Example 537; Example 539; Example 540;

IC50 between 100 nM and 1000 nM:

Example 2; Example 8; Example 11; Example 13; Example 14; Example 17; Example 23; Example 24; Example 26; Example 28; Example 33; Example 34; Example 37; Example 38; Example 39; Example 41; Example 48; Example 53; Example 55; Example 67; Example 68; Example 70; Example 71; Example 72; Example 73; Example 74; Example 75; Example 76; Example 80; Example 84; Example 95; Example 98; Example 99; Example 100; Example 102; Example 103; Example 108; Example 114; Example 126; Example 127; Example 128; Example 129; Example 130; Example 135; Example 136; Example 138; Example 139; Example 144; Example 150; Example 162; Example 163; Example 164; Example 165; Example 166; Example 175; Example 177; Example 180; Example 181; Example 182; Example 184; Example 185; Example 186; Example 188; Example 193; Example 194; Example 197; Example 199; Example 201; Example 203; Example 208; Example 211; Example 213; Example 217; Example 219; Example 225; Example 226; Example 231; Example 234; Example 249; Example 250; Example 251; Example 252; Example 253; Example 254; Example 255; Example 256; Example 257; Example 258; Example 261; Example 262; Example 263; Example 265; Example 266; Example 268; Example 270; Example 273; Example 287; Example 290; Example 292; Example 293; Example 294; Example 295; Example 297; Example 300; Example 301; Example 304; Example 308; Example 312; Example 319; Example 321; Example 325; Example 364; Example 369; Example 375; Example 383; Example 386; Example 388; Example 393; Example 403; Example 404; Example 406; Example 424; Example 427; Example 436; Example 439; Example 440; Example 444; Example 452; Example 453; Example 455; Example 461; Example 463; Example 467; Example 470; Example 472; Example 473; Example 474; Example 475; Example 477; Example 481; Example 484; Example 485; Example 486; Example 487; Example 493; Example 497; Example 500; Example 503; Example 504; Example 506; Example 508; Example 511; Example 513;

Example 515; Example 520; Example 521; Example 523; Example 529; Example 531; Example 538;

LRRK2 Activities:

IC50 lower than 10 nM:

Example 2; Example 50; Example 110; Example 118; Example 131; Example 133; Example 134; Example 146; Example 154; Example 167; Example 169; Example 170; Example 191; Example 196; Example 198; Example 200; Example 202; Example 204; Example 206; Example 212; Example 214; Example 218; Example 219; Example 220; Example 221; Example 222; Example 223; Example 224; Example 227; Example 228; Example 229; Example 232; Example 239; Example 241; Example 242; Example 267; Example 278; Example 282; Example 287; Example 291; Example 292; Example 293; Example 294; Example 295; Example 297; Example 300; Example 301; Example 304; Example 308; Example 312; Example 325; Example 347; Example 361; Example 362; Example 363; Example 367; Example 395; Example 410; Example 413; Example 505; Example 519; Example 525; Example 527;

IC50 between 10 nM and 100 nM: Example 1; Example 3; Example 12; Example 18; Example 19; Example 29; Example 30; Example 35; Example 45; Example 46; Example 53; Example 54; Example 85; Example 87; Example 94; Example 96; Example 99; Example 101; Example 102; Example 103; Example 106; Example 107; Example 111; Example 112; Example 113; Example 117; Example 119; Example 120; Example 122; Example 127; Example 132; Example 135; Example 137; Example 138; Example 139; Example 1-(2; Example 143; Example 147; Example 148; Example 149; Example 153; Example 155; Example 156; Example 158; Example 163; Example 168; Example 178; Example 179; Example 182; Example 185; Example 189; Example 192; Example 195; Example 197; Example 199; Example 201; Example 203; Example 205; Example 207; Example 208; Example 211; Example 213; Example 215; Example 216; Example 217; Example 225; Example 230; Example 233; Example 234; Example 235; Example 236; Example 237; Example 238; Example 240; Example 243; Example 244; Example 245; Example 246; Example 247; Example 248; Example 249; Example 250; Example 251; Example 252; Example 253; Example 254; Example 256; Example 257; Example 258; Example 259; Example 260; Example 261; Example 262; Example 263; Example 265; Example 268; Example 269; Example 270; Example 273; Example 274; Example 275; Example 280; Example 281; Example 283; Example 284; Example 285; Example 286; Example 288; Example 289; Example 290; Example 298; Example 299; Example 302; Example 303; Example 306; Example 307; Example 310; Example 311; Example 313; Example 314; Example 315; Example 316; Example 324; Example 327; Example 328; Example 330; Example 334; Example 338; Example 340; Example 341; Example 342; Example 343; Example 345; Example 346; Example 349; Example 353; Example 354; Example 358; Example 360; Example 364; Example 365; Example 368; Example 369; Example 374; Example 375; Example 377; Example 380; Example 386; Example 387; Example 388; Example 389; Example 393; Example 394; Example 398; Example 399; Example 401; Example 402; Example 406; Example 407; Example 408; Example 409; Example 411; Example 412; Example 416; Example 417; Example 418; Example 422; Example 423; Example 425; Example 426; Example 428; Example 429; Example 430; Example 431; Example 432; Example 433; Example 437; Example 442; Example 443; Example 446; Example 447; Example 448; Example 449; Example 451; Example 453; Example 454;

Example 455; Example 456; Example 458; Example 460; Example 461; Example 462; Example 463; Example 468; Example 469; Example 470; Example 473; Example 475; Example 476; Example 477; Example 482; Example 483; Example 484; Example 493; Example 497; Example 498; Example 504; Example 514; Example 516; Example 517; Example 520; Example 522; Example 526; Example 530; IC50 between 100 nM and 1000 nM: Example 8; Example 9; Example 10; Example 11; Example 13; Example 17; Example 20; Example 21; Example 22; Example 24; Example 25; Example 26; Example 28; Example 31; Example 33; Example 34; Example 37; Example 38; Example 48; Example 52; Example 55; Example 67; Example 68; Example 69; Example 70; Example 71; Example 72; Example 73; Example 74; Example 75; Example 76; Example 77; Example 80; Example 81; Example 82; Example 84; Example 89; Example 95; Example 97; Example 98; Example 100; Example 108; Example 109; Example 114; Example 115; Example 116; Example 121; Example 126; Example 128; Example 129; Example 130; Example 136; Example 144; Example 145; Example 150; Example 151; Example 152; Example 157; Example 162; Example 164; Example 165; Example 166; Example 175; Example 177; Example 180; Example 181; Example 183; Example 184; Example 186; Example 187; Example 188; Example 190; Example 193; Example 194; Example 209; Example 226; Example 231; Example 255; Example 264; Example 266; Example 271; Example 272; Example 296; Example 305; Example 309; Example 317; Example 318; Example 322; Example 323; Example 331; Example 332; Example 335; Example 336; Example 339; Example 352; Example 356; Example 357; Example 366; Example 371; Example 372; Example 381; Example 382; Example 383; Example 384; Example 385; Example 390; Example 391; Example 392; Example 396; Example 397; Example 400; Example 403; Example 404; Example 405; Example 421; Example 424; Example 427; Example 436; Example 439; Example 440; Example 441; Example 444; Example 445; Example 450; Example 452; Example 459; Example 465; Example 466; Example 467; Example 472; Example 474; Example 481; Example 485; Example 486; Example 487; Example 488; Example 489; Example 490; Example 495; Example 496; Example 500; Example 501; Example 503; Example 506; Example 508; Example 510; Example 511; Example 512; Example 513; Example 521; Example 523; Example 524; Example 529; Example 531; Example 532.

The invention claimed is:
1. A compound of formula (I):

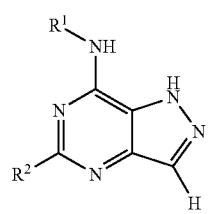

(I)

wherein
R$^1$ is an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group; and R$^2$ is an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group, wherein R$^2$ is bound to the pyrimidine ring of formula (I) via a carbon-carbon bond;

or a pharmaceutically acceptable salt, solvate or hydrate or a pharmaceutically acceptable formulation thereof.

2. The compound of claim 1, wherein R$^1$ is an optionally substituted cycloalkyl, heterocycloalkyl, alkylcycloalkyl, heteroalkylcycloalkyl, aryl, heteroaryl, aralkyl or heteroaralkyl group.

3. The compound of claim 1, wherein R$^1$ is an optionally substituted phenyl or naphthyl group or an optionally substituted heteroaryl group having one or two rings containing 5, 6, 7, 8, 9 or 10 ring atoms, or an optionally substituted arylheterocycloalkyl, heteroarylcycloalkyl or heteroarylheterocycloalkyl group containing two or three rings and 9 to 20 ring atoms.

4. The compound of claim 1, wherein R$^1$ is a group of formula X$^1$-L$^1$-Y$^1$ or a group of formula X$^1$-L$^1$-y$^1$-L$^2$-Z$^1$ wherein X$^1$ is an optionally substituted phenyl group or an optionally substituted heteroaryl group containing 5 or 6 ring atoms and 1, 2, 3 or 4 heteroatoms selected from O, S and N; L$^1$ is a bond or a group of formula —CH$_2$—, —C(=O)—, —SO—, —SO$_2$—, —NH—C(=O)—, —C(=O)—NH—; —C(=O)—O—, —O—C(=O)—, —NH—C(=O)—O—, —O—C(=O)—NH—, —NH—SO$_2$—NH—, —CH$_2$—NH—CH$_2$—, —NH—SO$_2$—, —SO$_2$—NH— or —NH—C(=O)—NH—; Y$^1$ is an optionally substituted phenyl group, an optionally substituted heteroaryl group containing 5 or 6 ring atoms and 1, 2, 3 or 4 heteroatoms selected from O, S and N, an optionally substituted C$_3$-C$_7$ cycloalkyl group or an optionally substituted heterocycloalkyl group containing 3, 4, 5, 6 or 7 ring atoms and 1, 2, 3 or 4 heteroatoms selected from O, S and N; L$^2$ is a bond or a group of formula —CH$_2$—, —C(=O)—, —SO—, —SO$_2$—, —NH—C(=O)—, —C(=O)—NH—; —C(=O)—O—, —O—C(=O)—, —NH—C(=O)—O—, —O—C(=O)—NH—, —NH—SO$_2$—NH—, —CH$_2$—NH—CH$_2$—, —NH—SO$_2$—, —SO$_2$—NH— or —NH—C(=O)—NH—; and Z$^1$ is an optionally substituted phenyl group, an optionally substituted heteroaryl group containing 5 or 6 ring atoms and 1, 2, 3 or 4 heteroatoms selected from O, S and N, an optionally substituted C$_3$-C$_7$ cycloalkyl group or an optionally substituted heterocycloalkyl group containing 3, 4, 5, 6 or 7 ring atoms and 1, 2, 3 or 4 heteroatoms selected from O, S and N.

5. The compound of claim 1, wherein R$^1$ is selected from the following groups:

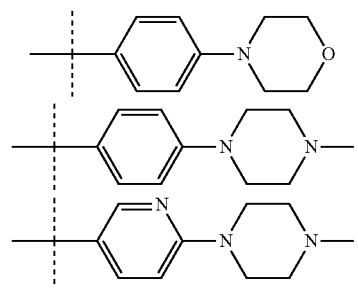

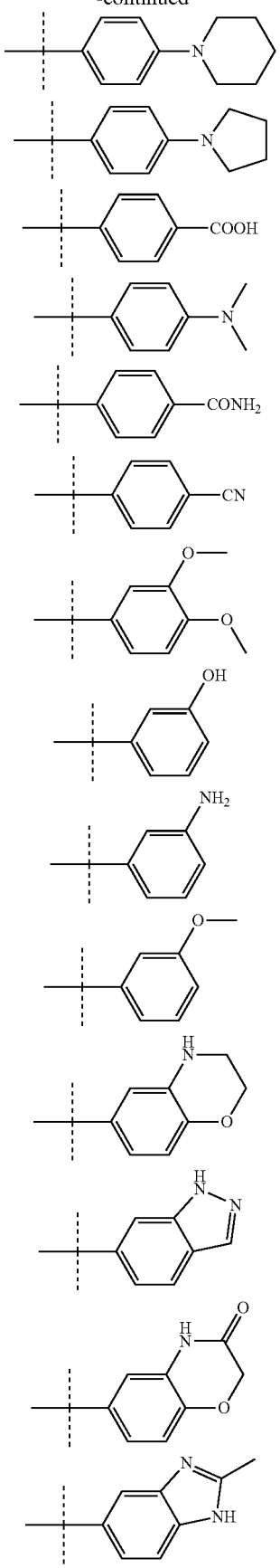
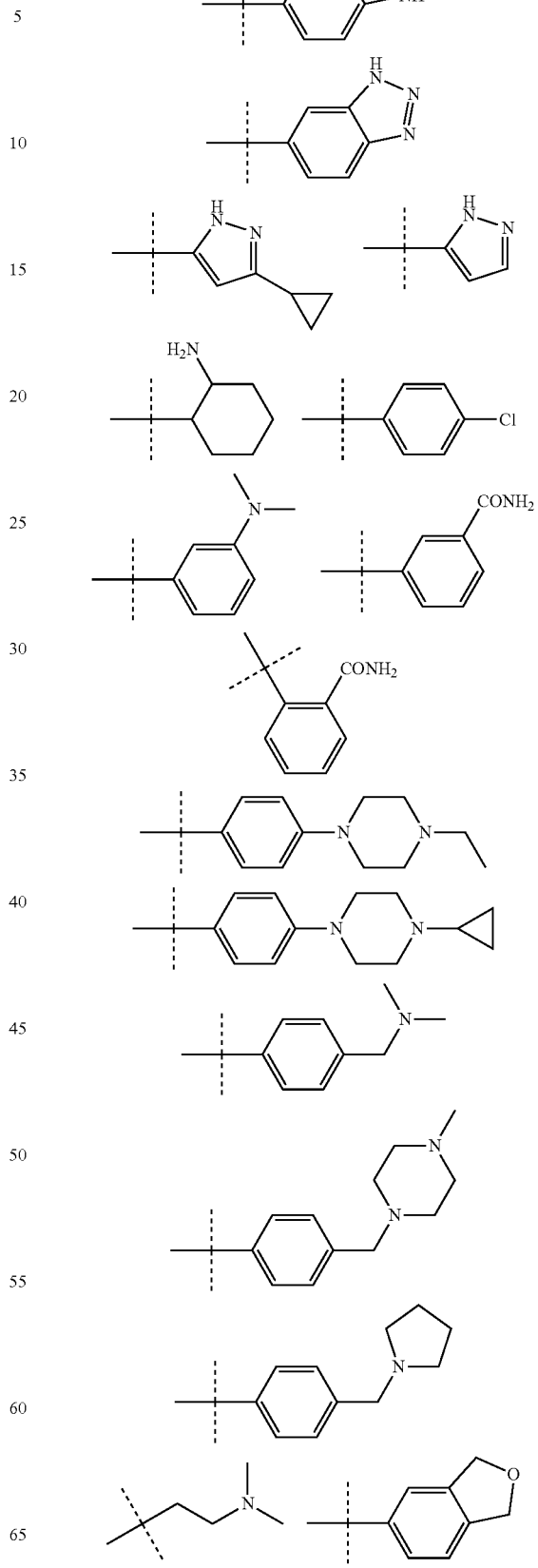

-continued
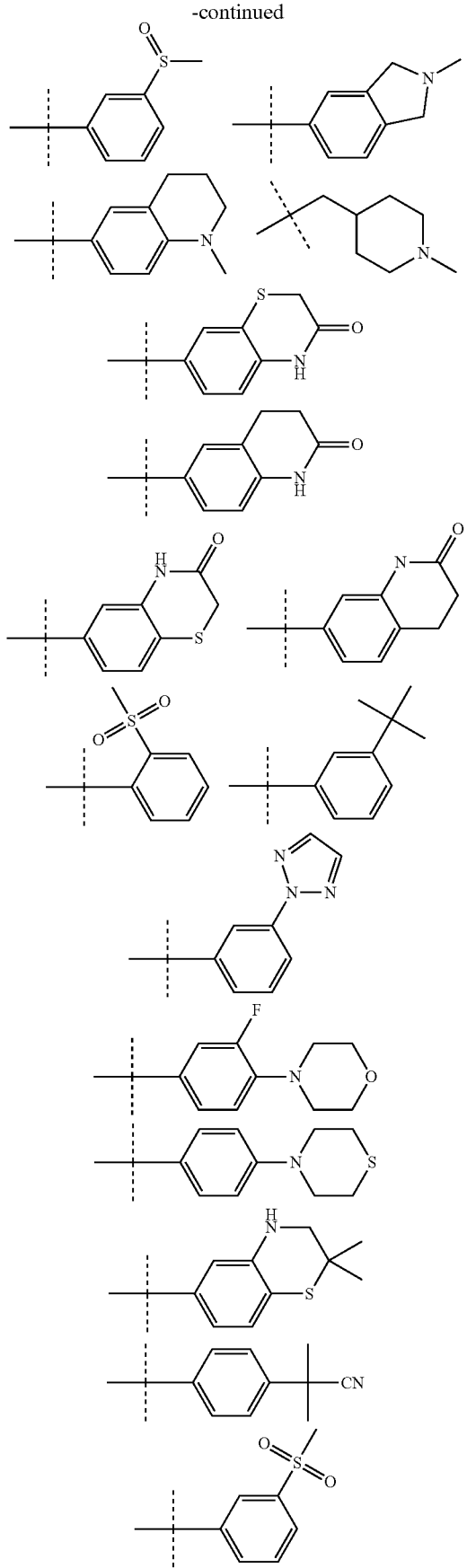
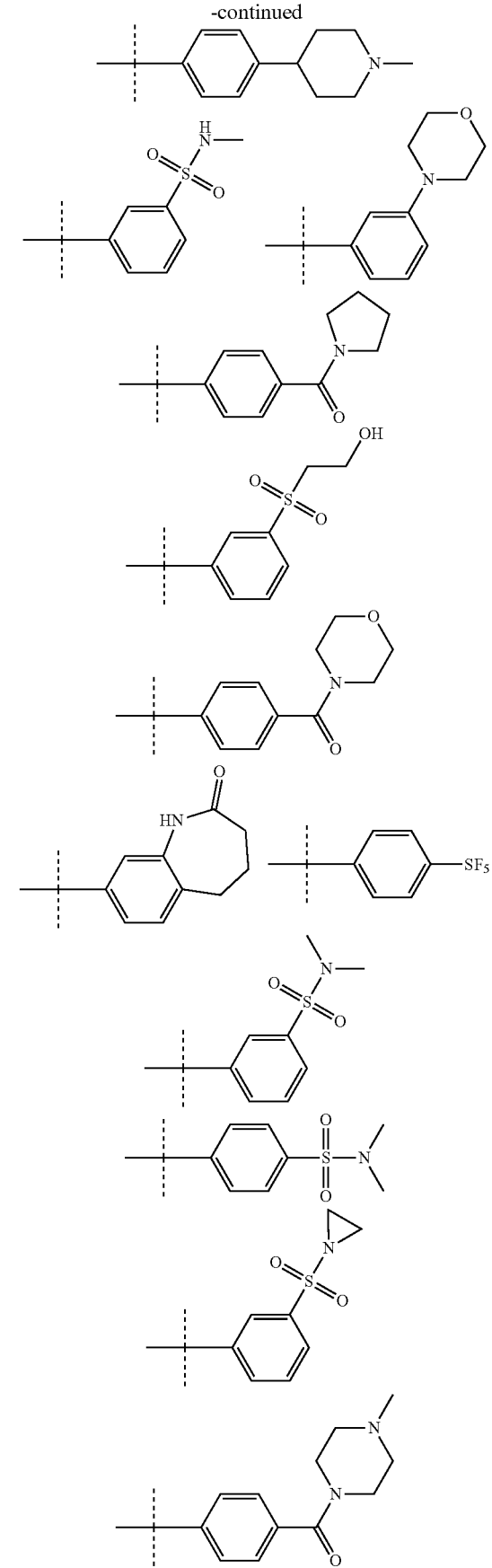

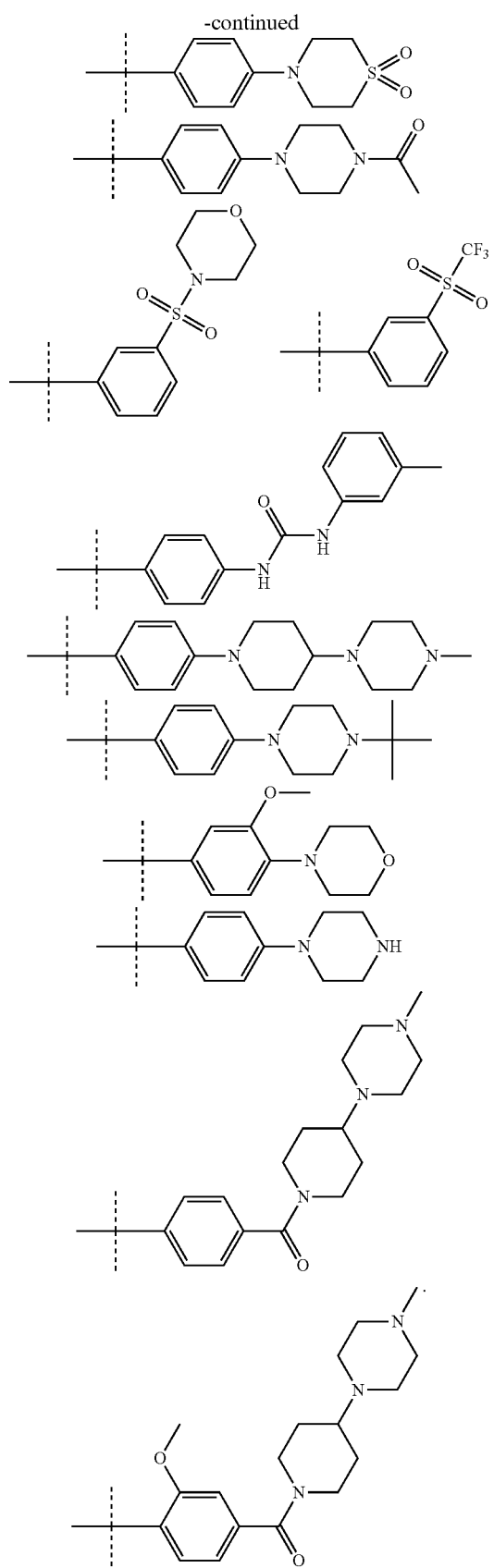
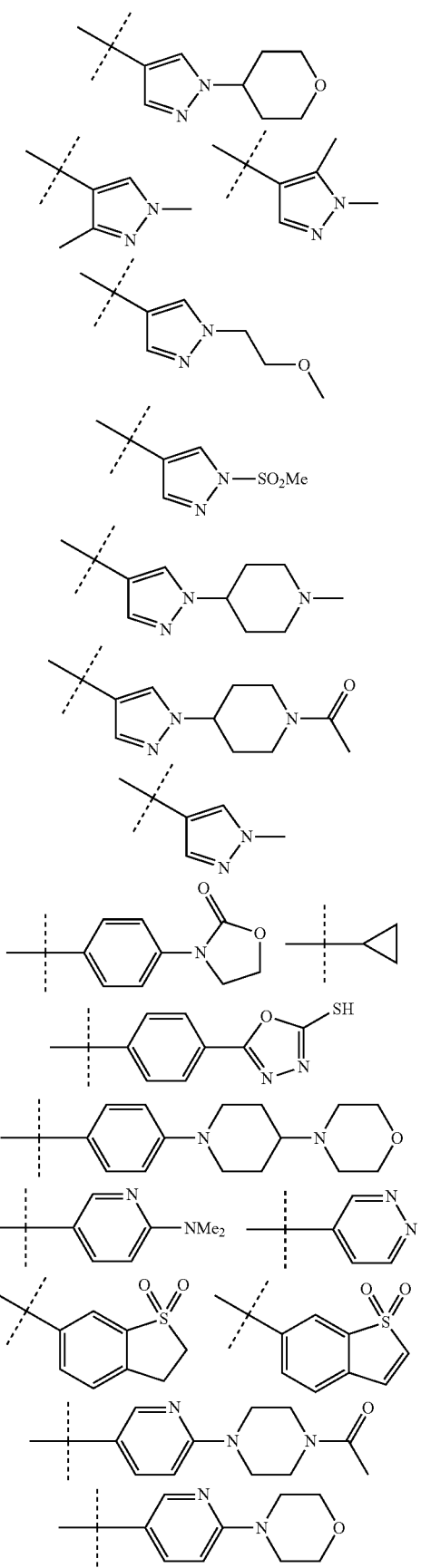
6. The compound according to claim 1, wherein $R^1$ is selected from the following groups:

-continued
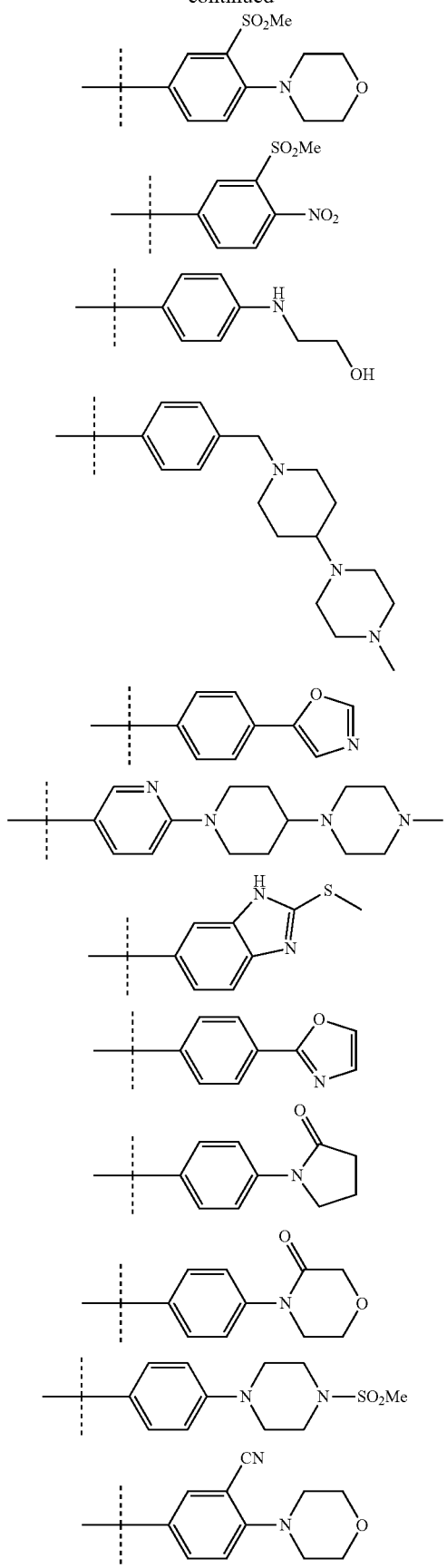
-continued
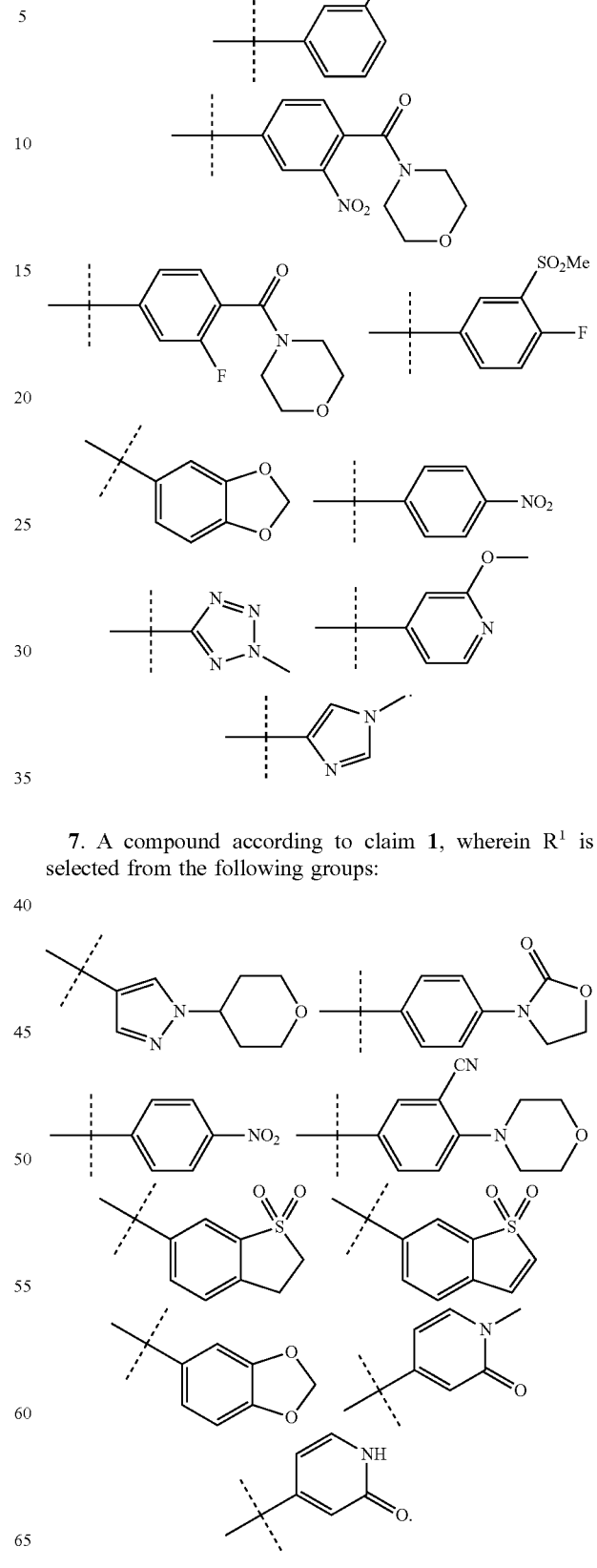
7. A compound according to claim 1, wherein $R^1$ is selected from the following groups:

8. A compound according to claim 1, wherein R[1] is selected from the following groups:
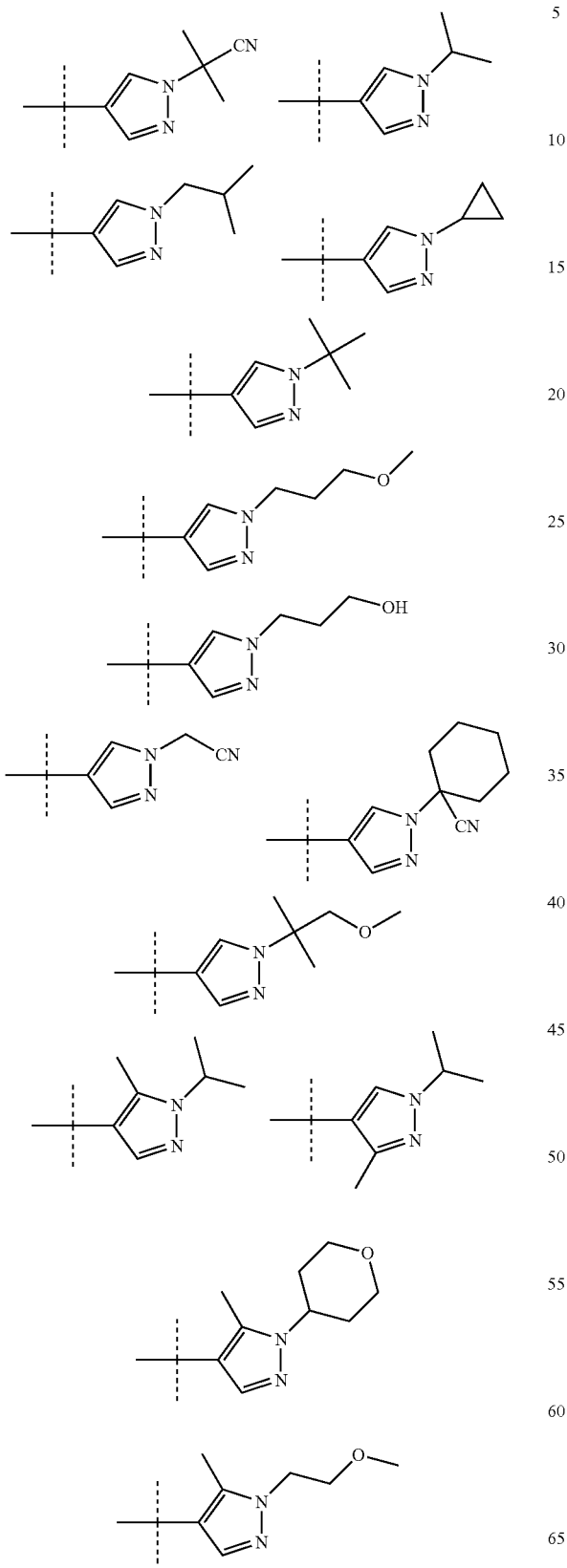
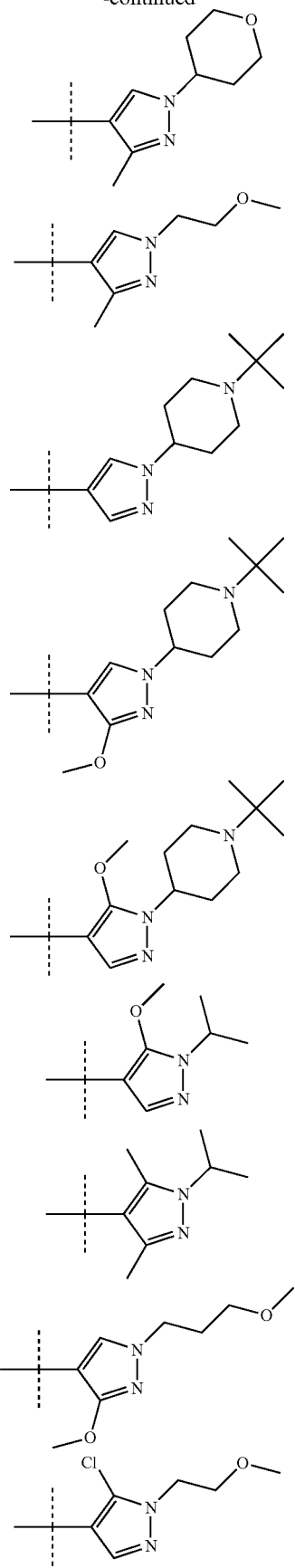

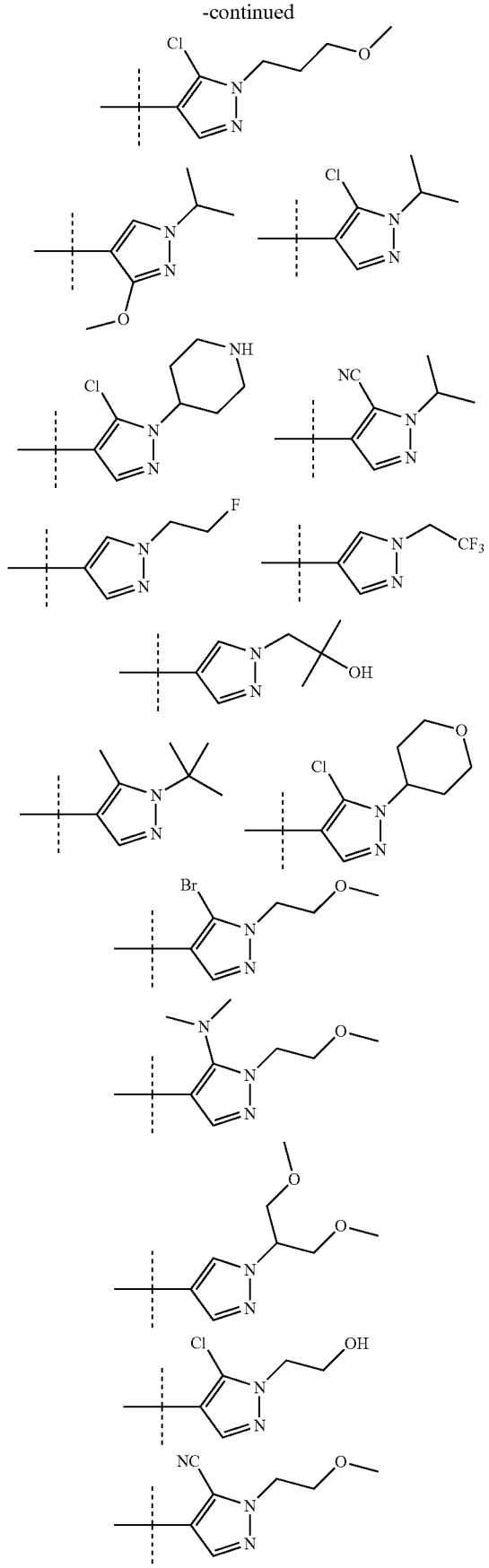
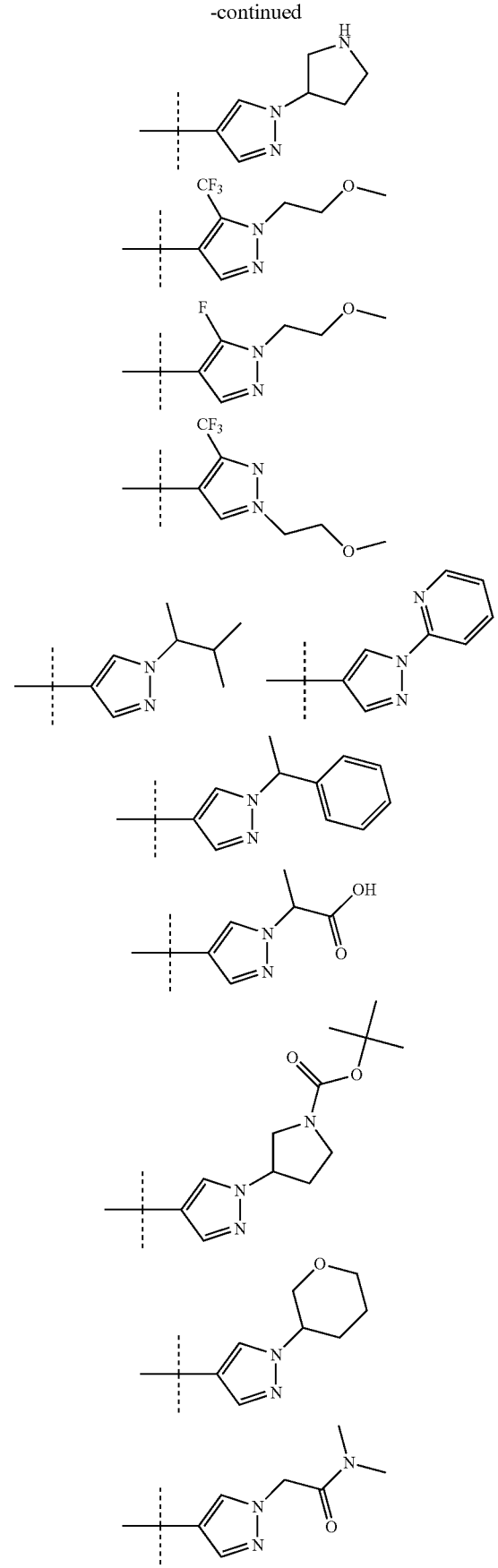

185
-continued
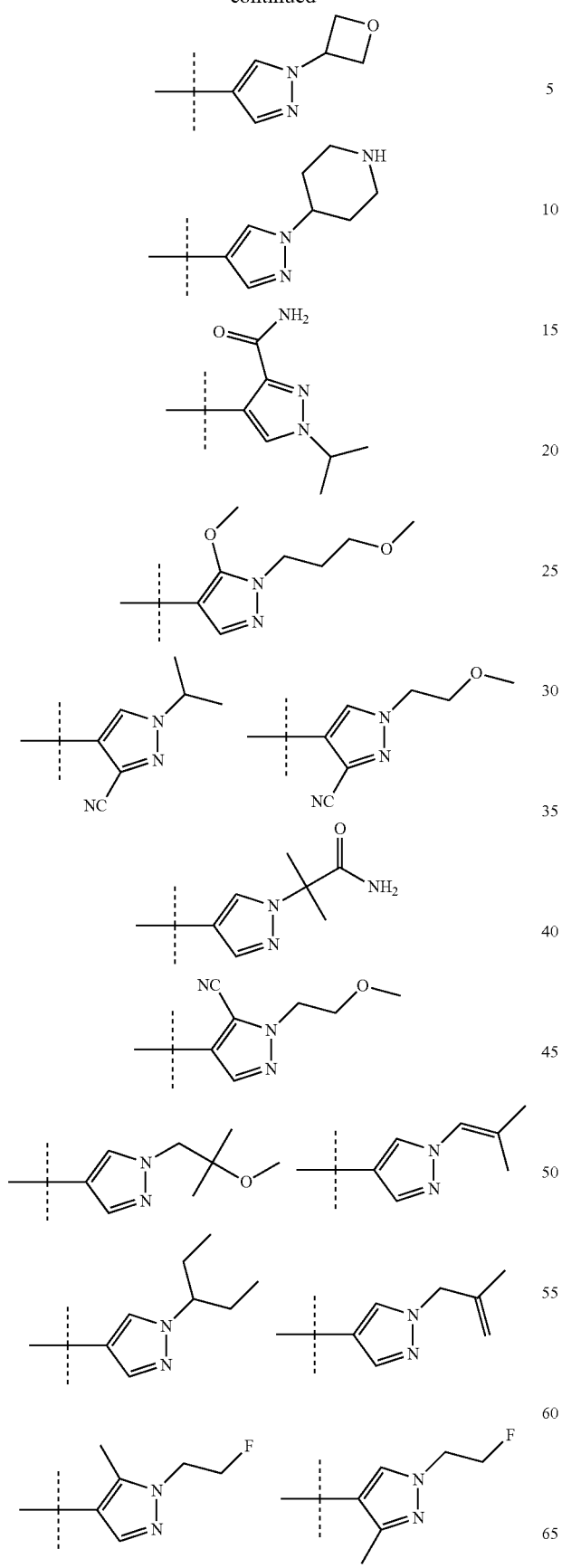
186
-continued
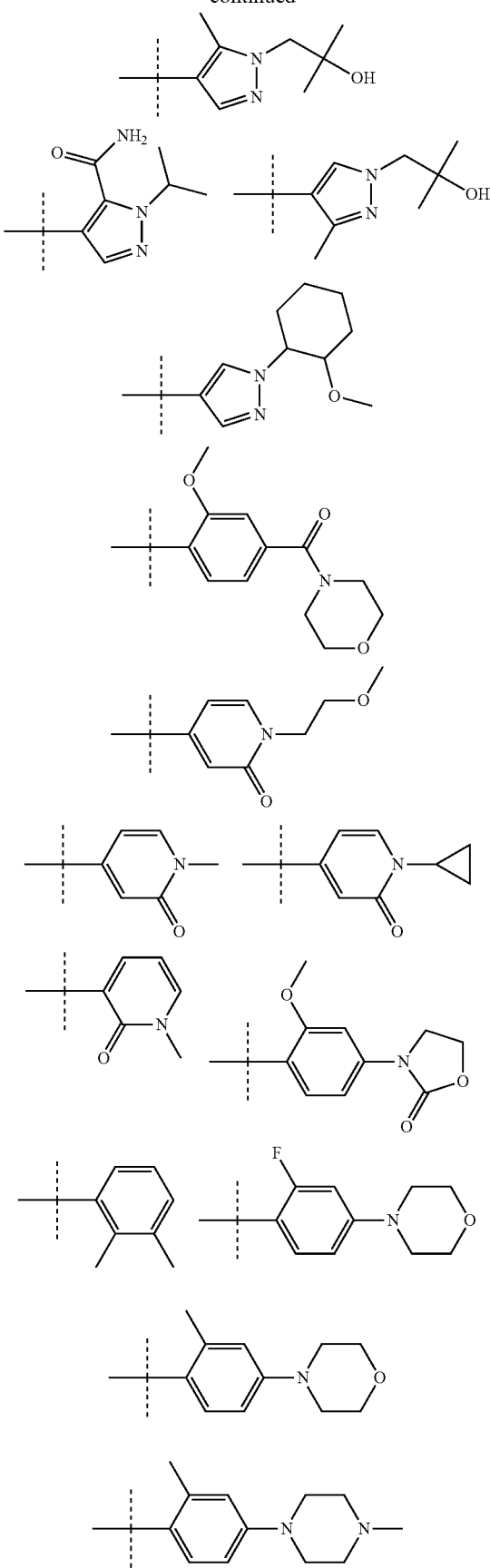

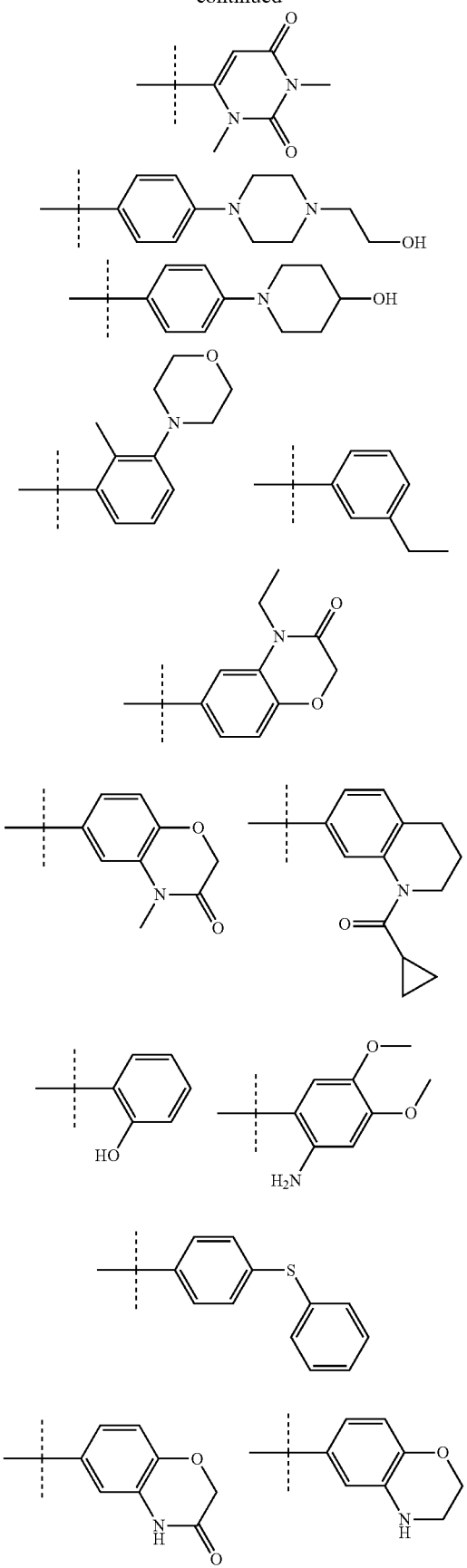
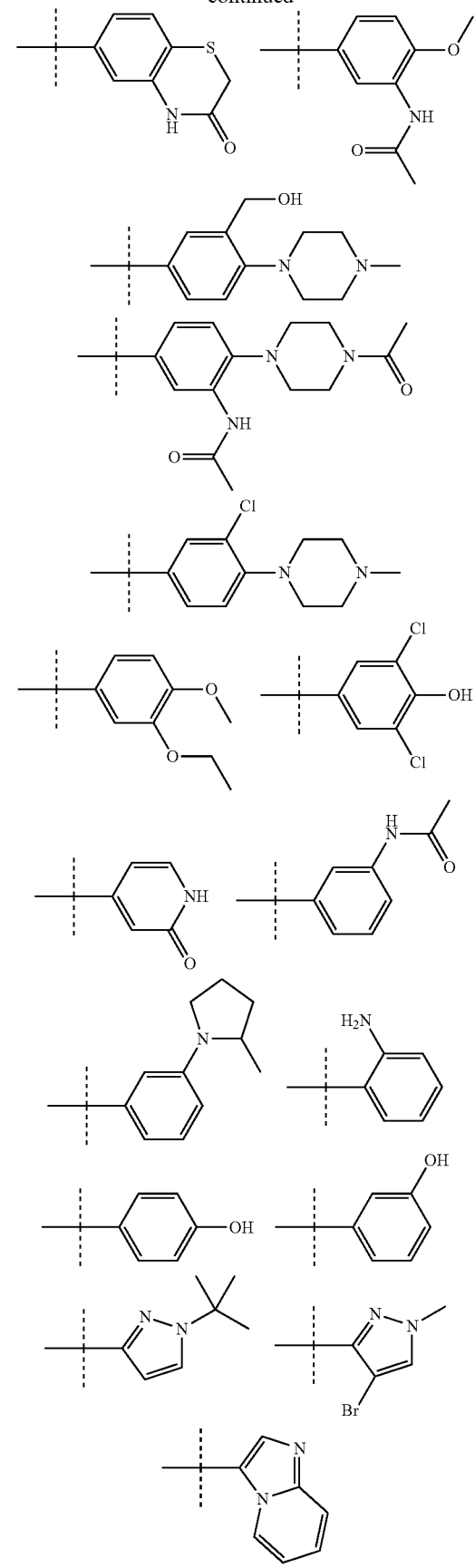

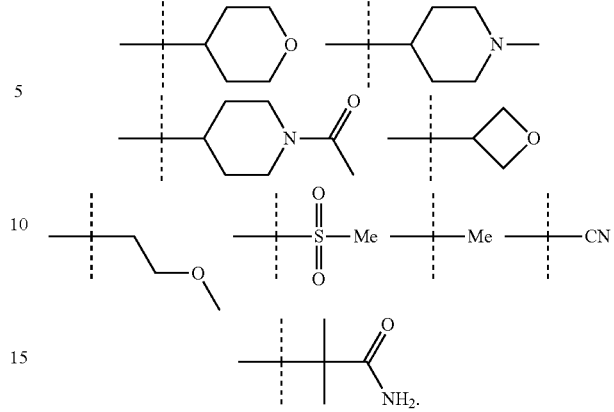

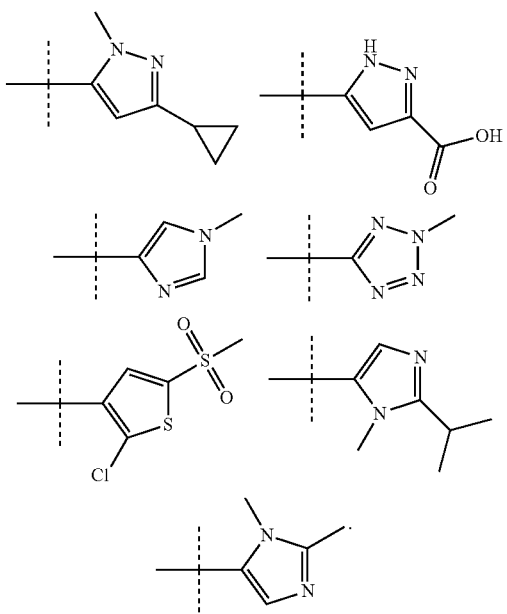

9. The compound according to claim 1, wherein R¹ has the following structure:

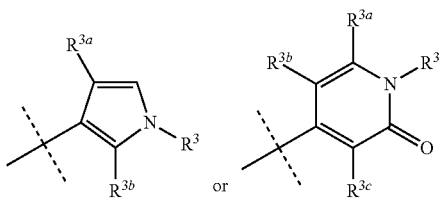

wherein R³ is hydrogen or an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group;

R$^{3a}$ is hydrogen, halogen, OH, SH, NH$_2$, or an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group;

R$^{3b}$ is hydrogen, halogen, OH, SH, NH$_2$, or an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group; and R$^{3c}$ is hydrogen, halogen, OH, SH, NH$_2$, or an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group.

10. The compound of claim 9 wherein R³ is an optionally substituted alkyl, heteroalkyl, cycloalkyl, heterocycloalkyl, alkylcycloalkyl or heteroalkylcycloalkyl group and R$^{3a}$ and R$^{3b}$ are both hydrogen.

11. The compound of claim 9 wherein R$^{3a}$ and R$^{3b}$ are both hydrogen and R³ is selected from the following groups:

12. The compound of claim 1, wherein R² is an optionally substituted aryl, heteroaryl, cycloalkyl, heterocycloalkyl, alkylcycloalkyl, heteroalkylcycloalkyl, aralkyl or heteroaralkyl group.

13. The compound of claim 1, wherein R² is an optionally substituted phenyl or naphthyl group or an optionally substituted heteroaryl group having one or two rings containing 5, 6, 7, 8, 9 or 10 ring atoms, or an optionally substituted arylheterocycloalkyl or heteroarylheterocycloalkyl group containing two or three rings and 9 to 20 ring atoms.

14. The compound of claim 1, wherein R² is a group of formula X²-L³-Y² or a group of formula X²-L³-Y²-L⁴-Z² wherein X² is an optionally substituted phenyl group or an optionally substituted heteroaryl group containing 5 or 6 ring atoms and 1, 2, 3 or 4 heteroatoms selected from O, S and N; L³ is a bond or a group of formula —CH$_2$—, —C(=O)—, —SO—, —SO$_2$—, —NH—C(=O)—, —C(=O)—NH—; —C(=O)—O—, —O—C(=O)—, —NH—C(=O)—O—, —O—C(=O)—NH—, —NH—SO$_2$—NH—, —CH$_2$—NH—CH$_2$—, —NH—SO$_2$—, —SO$_2$—NH— or —NH—C(=O)—NH—; Y² is an optionally substituted phenyl group, an optionally substituted heteroaryl group containing 5 or 6 ring atoms and 1, 2, 3 or 4 heteroatoms selected from O, S and N, an optionally substituted C$_3$-C$_7$ cycloalkyl group or an optionally substituted heterocycloalkyl group containing 3, 4, 5, 6 or 7 ring atoms and 1, 2, 3 or 4 heteroatoms selected from O, S and N; L⁴ is a bond or a group of formula —CH$_2$—, —C(=O)—, —SO—, —SO$_2$—, —NH—C(=O)—, —C(=O)—NH—; —C(=O)—O—, —O—C(=O)—, —NH—C(=O)—O—, —O—C(=O)—NH—, —NH—SO$_2$—NH—, —CH$_2$—NH—CH$_2$—, —NH—SO$_2$—, —SO$_2$—NH— or —NH—C(=O)—NH—; and Z² is an optionally substituted phenyl group, an optionally substituted heteroaryl group containing 5 or 6 ring atoms and 1, 2, 3 or 4 heteroatoms selected from O, S and N, an optionally substituted C$_3$-C$_7$ cycloalkyl group or an optionally substituted heterocycloalkyl group containing 3, 4, 5, 6 or 7 ring atoms and 1, 2, 3 or 4 heteroatoms selected from O, S and N.

15. The compound of claim 1, wherein R² is an optionally substituted alkyl, heteroalkyl, cycloalkyl, heterocycloalkyl, alkylcycloalkyl or heteroalkylcycloalkyl group.

16. The compound of claim 1, wherein R² is a heteroalkyl group containing from 1 to 6 carbon atoms and 1, 2 or 3 heteroatoms selected from O, S and N, or an optionally substituted C$_3$-C$_7$ cycloalkyl group, or an optionally substituted heterocycloalkyl group containing from 2 to 6 carbon atoms and 1, 2 or 3 heteroatoms selected from O, S and N, or an optionally substituted $C_4$-$C_{10}$ alkylcycloalkyl group, or an optionally substituted heteroalkylcycloalkyl group containing from 3 to 10 carbon atoms and from 1 to 4 heteroatoms selected from O, S and N.
17. The compound of claim 1, wherein $R^2$ is selected from the following groups:
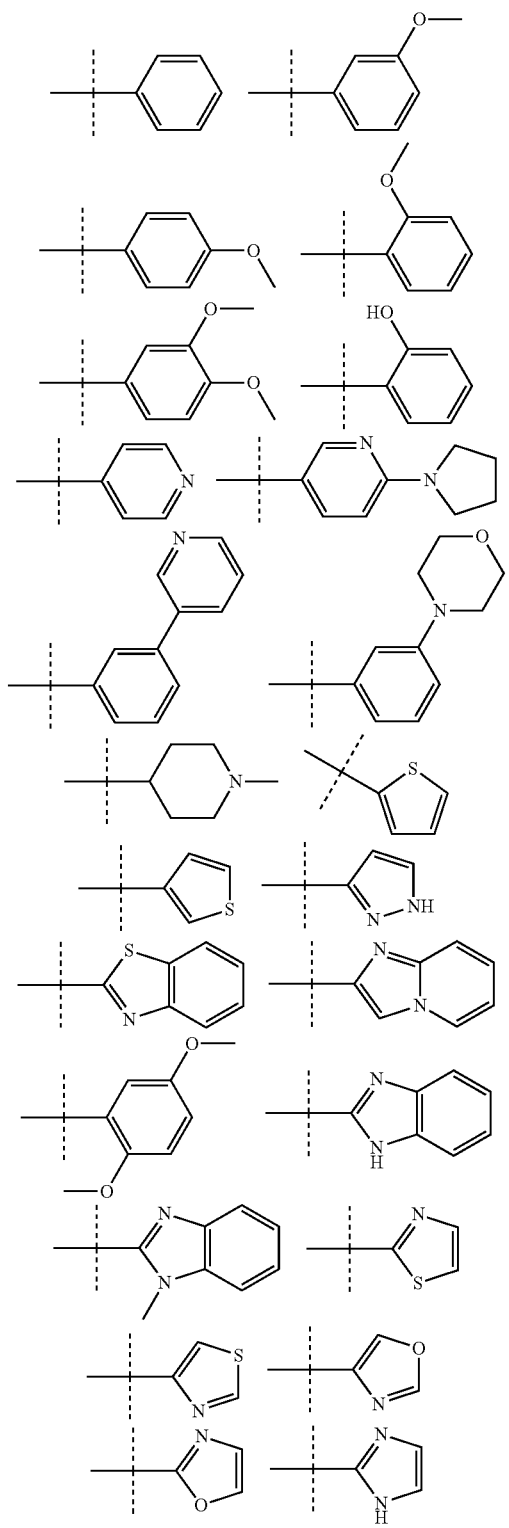
-continued
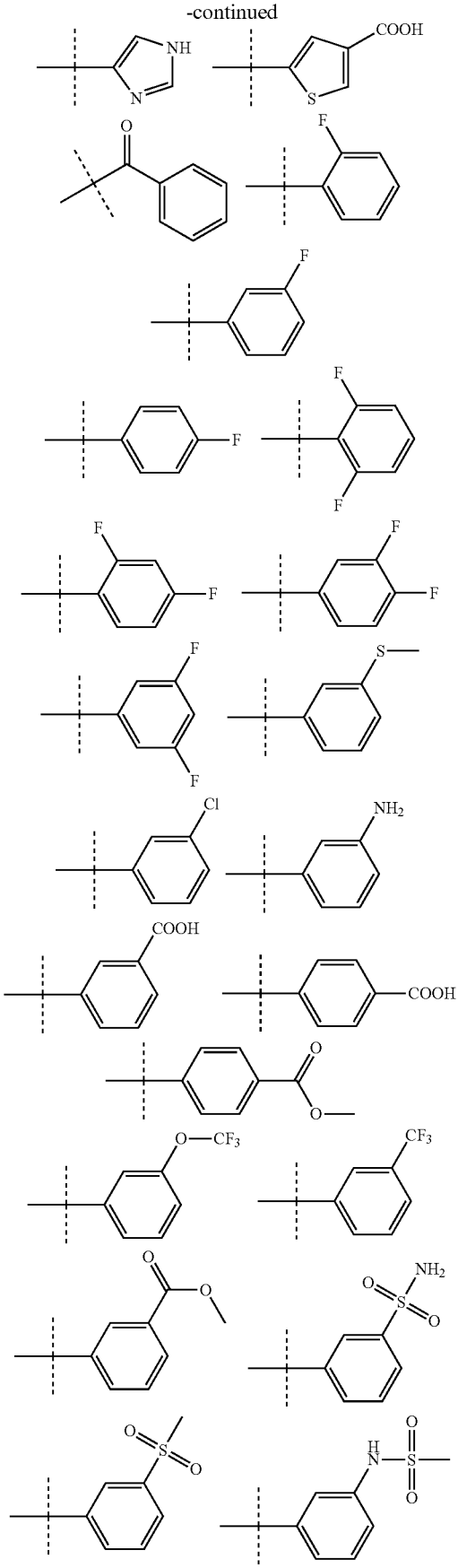

-continued
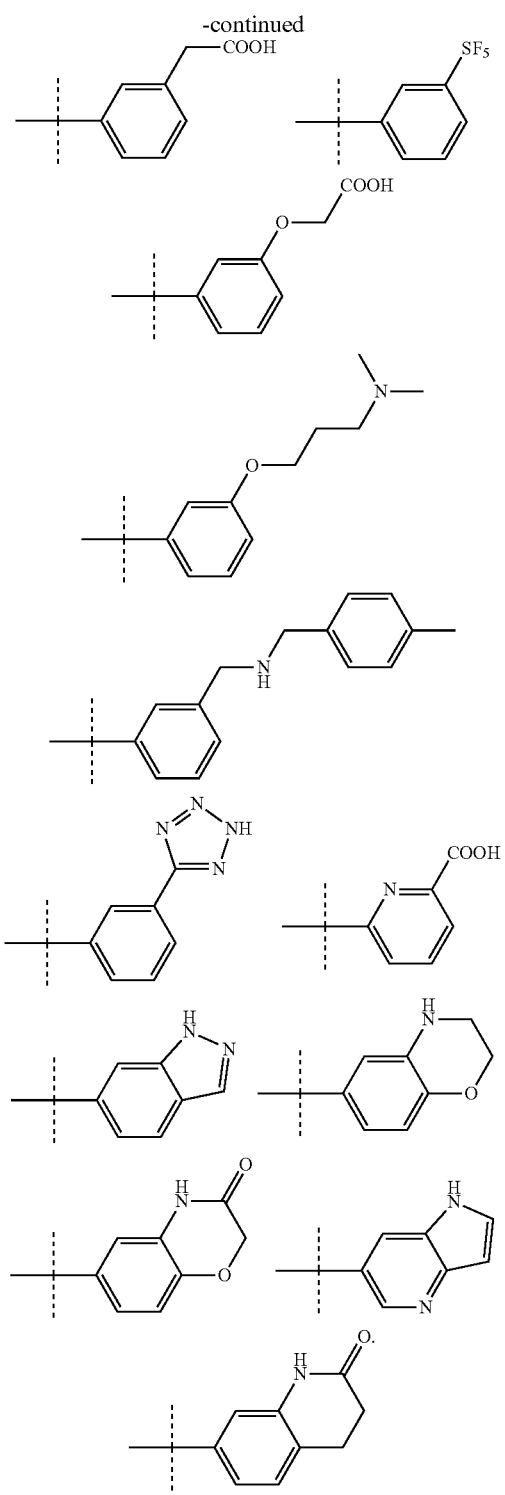
18. The compound of claim 1, wherein $R^2$ is selected from the following groups:
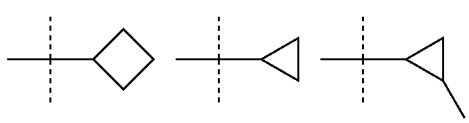
-continued
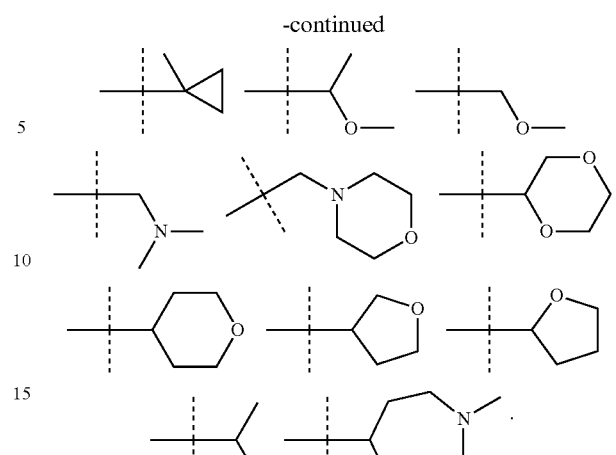
19. The compound of claim 1, wherein $R^2$ is selected from the following groups:
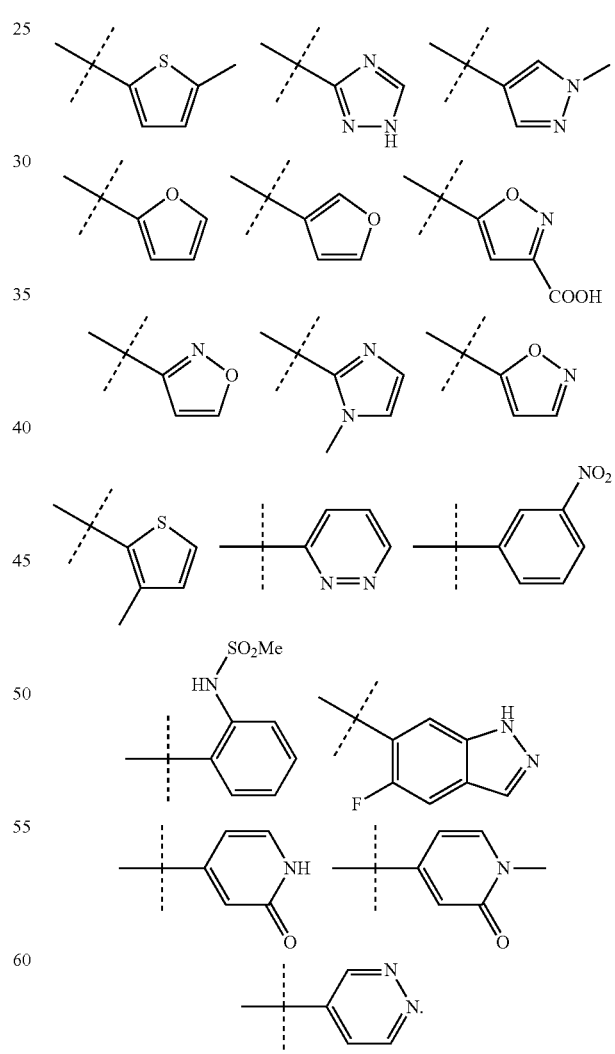
20. The compound of claim 1, wherein $R^2$ is selected from the following groups:

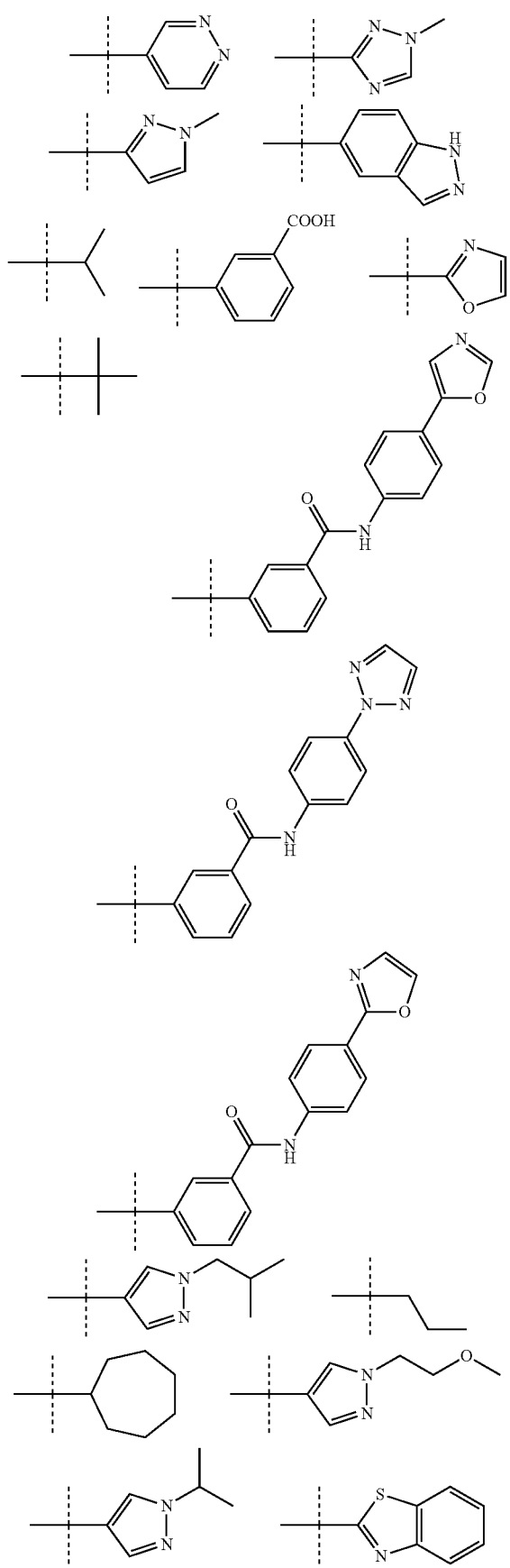
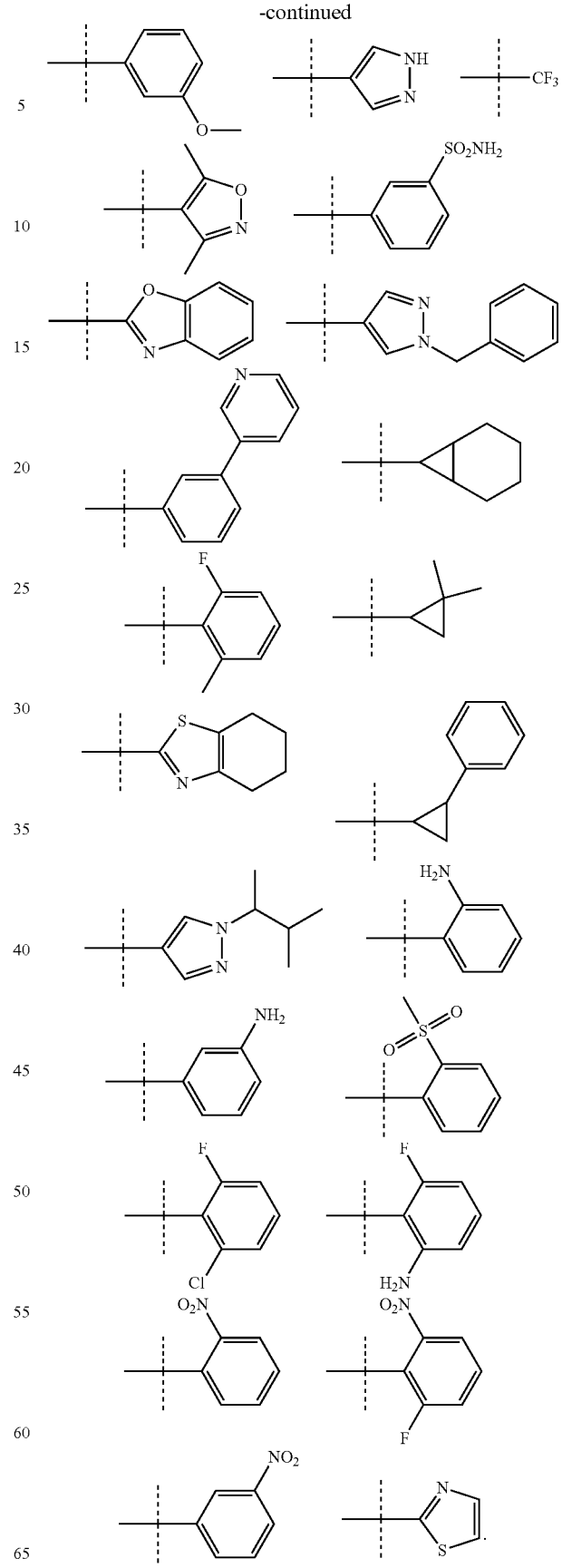

21. The compound of claim 1 selected from the group consisting of: N-(2-(7-((4-morpholinophenyl)amino)-1H-pyrazolo[4,3-d]pyrimidin-5-yl)phenyl)methanesulfonamide; N-(2-(7-((3,4-dimethoxyphenyl)amino)-1H-pyrazolo[4,3-d]pyrimidin-5-yl)phenyl)methanesulfonamide; N-(2-(7-((3-(methylsulfonyl)phenyl)amino)-1H-pyrazolo[4,3-d]pyrimidin-5-yl)phenyl)methanesulfonamide; N-(1H-indazol-6-yl)-5-(3-nitrophenyl)-1H-pyrazolo[4,3-d]pyrimidin-7-amine; N-(4-morpholinophenyl)-5-(3-nitrophenyl)-1H-pyrazolo[4,3-d]pyrimidin-7-amine; 1-(4-(4-((5-(3-nitrophenyl)-1H-pyrazolo[4,3-d]pyrimidin-7-yl)amino)phenyl)piperazin-1-yl)ethan-1-one; 5-(3-aminophenyl)-N-(3,4-dimethoxyphenyl)-1H-pyrazolo[4,3-d]pyrimidin-7-amine; N-(3,4-dimethoxyphenyl)-5-(5-methylthiophen-2-yl)-1H-pyrazolo[4,3-d]pyrimidin-7-amine; 5-(5-methylthiophen-2-yl)-N-(4-morpholinophenyl)-1H-pyrazolo[4,3-d]pyrimidin-7-amine; N-(4-(4-(tert-butyl)piperazin-1-yl)phenyl)-5-(2,6-difluorophenyl)-1H-pyrazolo[4,3-d]pyrimidin-7-amine; 5-(2,6-difluorophenyl)-N-(3-fluoro-4-morpholinophenyl)-1H-pyrazolo[4,3-d]pyrimidin-7-amine; 5-(2,6-difluorophenyl)-N-(3-methoxy-4-morpholinophenyl)-1H-pyrazolo[4,3-d]pyrimidin-7-amine; 1-(4-(4-((5-(2,6-difluorophenyl)-1H-pyrazolo[4,3-d]pyrimidin-7-yl)amino)phenyl)piperazin-1-yl)ethan-1-one; 1-(4-(4-((5-(3-aminophenyl)-1H-pyrazolo[4,3-d]pyrimidin-7-yl)amino)phenyl)piperazin-1-yl)ethan-1-one; methyl 3-(7-(benzo[d][1,3]dioxol-5-ylamino)-1H-pyrazolo[4,3-d]pyrimidin-5-yl)benzoate; N-(benzo[d][1,3]dioxol-5-yl)-5-(3-nitrophenyl)-1H-pyrazolo[4,3-d]pyrimidin-7-amine; 6-((5-(thiophen-2-yl)-1H-pyrazolo[4,3-d]pyrimidin-7-yl)amino)-2,3-dihydrobenzo[b]thiophene 1,1-dioxide; 5-cyclopropyl-N-(4-morpholinophenyl)-1H-pyrazolo[4,3-d]pyrimidin-7-amine; 5-cyclopropyl-N-(3,4-dimethoxyphenyl)-1H-pyrazolo[4,3-d]pyrimidin-7-amine; 5-cyclopropyl-N-(3-(methylsulfonyl)phenyl)-1H-pyrazolo[4,3-d]pyrimidin-7-amine; 6-((5-cyclopropyl-1H-pyrazolo[4,3-d]pyrimidin-7-yl)amino)-2H-benzo[b][1,4]oxazin-3(4H)-one; 7-((5-cyclopropyl-1H-pyrazolo[4,3-d]pyrimidin-7-yl)amino)-3,4-dihydroquinolin-2(1H)-one; N-(4-(4-(tert-butyl)piperazin-1-yl)phenyl)-5-(2-fluorophenyl)-1H-pyrazolo[4,3-d]pyrimidin-7-amine; N-(3-fluoro-4-morpholinophenyl)-5-(2-fluorophenyl)-1H-pyrazolo[4,3-d]pyrimidin-7-amine; 5-(2-fluorophenyl)-N-(3-methoxy-4-morpholinophenyl)-1H-pyrazolo[4,3-d]pyrimidin-7-amine; 1-(4-(4-((5-(2-fluorophenyl)-1H-pyrazolo[4,3-d]pyrimidin-7-yl)amino)phenyl)piperazin-1-yl)ethan-1-one; 2-(4-((5-(2-fluorophenyl)-1H-pyrazolo[4,3-d]pyrimidin-7-yl)amino)phenyl)-2-methylpropanenitrile; 2-(4-((5-(2,6-difluorophenyl)-1H-pyrazolo[4,3-d]pyrimidin-7-yl)amino)phenyl)-2-methylpropanenitrile; N-(2-(7-((4-(4-(4-methylpiperazin-1-yl)piperidin-1-yl)phenyl)amino)-1H-pyrazolo[4,3-d]pyrimidin-5-yl)phenyl)methanesulfonamide; N-(2-(7-((3-oxo-3,4-dihydro-2H-benzo[b][1,4]oxazin-6-yl)amino)-1H-pyrazolo[4,3-d]pyrimidin-5-yl)phenyl)methanesulfonamide; N-(2-(7-((2-oxo-1,2,3,4-tetrahydroquinolin-7-yl)amino)-1H-pyrazolo[4,3-d]pyrimidin-5-yl)phenyl)methanesulfonamide; 5-cyclopropyl-N-(4-(4-(4-methylpiperazin-1-yl)piperidin-1-yl)phenyl)-1H-pyrazolo[4,3-d]pyrimidin-7-amine; 1-(4-(4-((5-cyclopropyl-1H-pyrazolo[4,3-d]pyrimidin-7-yl)amino)phenyl)piperazin-1-yl)ethan-1-one; 5-cyclopropyl-N-(3-fluoro-4-morpholinophenyl)-1H-pyrazolo[4,3-d]pyrimidin-7-amine; 5-cyclopropyl-N-(3-methoxy-4-morpholinophenyl)-1H-pyrazolo[4,3-d]pyrimidin-7-amine; 6-((5-(thiophen-2-yl)-1H-pyrazolo[4,3-d]pyrimidin-7-yl)amino)benzo[b]thiophene 1,1-dioxide; N-(3-methoxy-4-morpholinophenyl)-5-(thiophen-2-yl)-1H-pyrazolo[4,3-d]pyrimidin-7-amine; 3-(4-((5-(thiophen-2-yl)-1H-pyrazolo[4,3-d]pyrimidin-7-yl)amino)phenyl)oxazolidin-2-one; N-(3-(7-((4-(4-(tert-butyl)piperazin-1-yl)phenyl)amino)-1H-pyrazolo[4,3-d]pyrimidin-5-yl)phenyl)methanesulfonamide; N-(3-(7-((3-fluoro-4-morpholinophenyl)amino)-1H-pyrazolo[4,3-d]pyrimidin-5-yl)phenyl)methanesulfonamide; N-(3-(7-((3-methoxy-4-morpholinophenyl)amino)-1H-pyrazolo[4,3-d]pyrimidin-5-yl)phenyl)methanesulfonamide; N-(3-(7-((4-morpholinophenyl)amino)-1H-pyrazolo[4,3-d]pyrimidin-5-yl)phenyl)methanesulfonamide; N-(3-(7-((4-(morpholine-4-carbonyl)phenyl)amino)-1H-pyrazolo[4,3-d]pyrimidin-5-yl)phenyl)methanesulfonamide; N-(3-(7-((4-(2-oxooxazolidin-3-yl)phenyl)amino)-1H-pyrazolo[4,3-d]pyrimidin-5-yl)phenyl)methanesulfonamide; N-(4-(4-(tert-butyl)piperazin-1-yl)phenyl)-5-(1H-indazol-6-yl)-1H-pyrazolo[4,3-d]pyrimidin-7-amine; N-(3-fluoro-4-morpholinophenyl)-5-(1H-indazol-6-yl)-1H-pyrazolo[4,3-d]pyrimidin-7-amine; N-(3-methoxy-4-morpholinophenyl)-5-(oxazol-4-yl)-1H-pyrazolo[4,3-d]pyrimidin-7-amine; N-(4-morpholinophenyl)-5-(oxazol-4-yl)-1H-pyrazolo[4,3-d]pyrimidin-7-amine; N-(4-(4-(tert-butyl)piperazin-1-yl)phenyl)-5-(oxazol-4-yl)-1H-pyrazolo[4,3-d]pyrimidin-7-amine; 1-(4-(4-((5-(1H-indazol-6-yl)-1H-pyrazolo[4,3-d]pyrimidin-7-yl)amino)phenyl)piperazin-1-yl)ethan-1-one; N-(3,4-dimethoxyphenyl)-5-(3-methylthiophen-2yl)-1H-pyrazolo[4,3-d]pyrimidin-7-amine; 5-(3-methylthiophen-2-yl)-N-(4-morpholinophenyl)-1H-pyrazolo[4,3-d]pyrimidin-7-amine; (4-((5-cyclopropyl-1H-pyrazolo[4,3-d]pyrimidin-7-yl)amino)phenyl)(4-(4-methylpiperazin-1-yl)piperidin-1-yl)methanone; 5-(1H-indazol-6-yl)-N-(3-methoxy-4-morpholinophenyl)-1H-pyrazolo[4,3-d]pyrimidin-7-amine; 5-cyclopropyl-N-(4-(piperazin-1-yl)phenyl)-1H-pyrazolo[4,3-d]pyrimidin-7-amine; N-(4-morpholinophenyl)-5-(tetrahydrofuran-2-yl)-1H-pyrazolo[4,3-d]pyrimidin-7-amine; N-(3-fluoro-4-morpholinophenyl)-5-(oxazol-4-yl)-1H-pyrazolo[4,3-d]pyrimidin-7-amine; 3-(4-((5-(oxazol-4-yl)-1H-pyrazolo[4,3-d]pyrimidin-7-yl)amino)phenyl)oxazolidin-2-one; 5-(methoxymethyl)-N-(4-morpholinophenyl)-1H-pyrazolo[4,3-d]pyrimidin-7-amine; N-(3,4-dimethoxyphenyl)-5-(methoxymethyl)-1H-pyrazolo[4,3-d]pyrimidin-7-amine; 5-(methoxymethyl)-N-(4-(4-methylpiperazin-1-yl)piperidin-1-yl)phenyl)-1H-pyrazolo[4,3-d]pyrimidin-7-amine; 5-(methoxymethyl)-N-(3-(methylsulfonyl)phenyl)-1H-pyrazolo[4,3-d]pyrimidin-7-amine; 1-(4-(4-((5-(methoxymethyl)-1H-pyrazolo[4,3-d]pyrimidin-7-yl)amino)phenyl)piperazin-1-yl)ethan-1-one; 5-(1-methoxyethyl)-N-(4-morpholinophenyl)-1H-pyrazolo[4,3-d]pyrimidin-7-amine; 1-(4-(4-((5-(1-methoxyethyl)-1H-pyrazolo[4,3-d]pyrimidin-7-yl)amino)phenyl)piperazin-1-yl)ethan-1-one; N-(3,4-dimethoxyphenyl)-5-(1-methoxyethyl)-1H-pyrazolo[4,3-d]pyrimidin-7-amine; 1-(4-(4-((5-(isoxazol-5-yl)-1H-pyrazolo[4,3-d]pyrimidin-7-yl)amino)phenyl)piperazin-1-yl)ethan-1-one; N-(3,4-dimethoxyphenyl)-5-(isoxazol-5-yl)-1H-pyrazolo[4,3-d]pyrimidin-7-amine; 5-(isoxazol-5-yl)-N-(4-morpholinophenyl)-1H-pyrazolo[4,3-d]pyrimidin-7-amine; N-(3-fluoro-4-morpholinophenyl)-5-(isoxazol-5-yl)-1H-pyrazolo[4,3-d]pyrimidin-7-amine; 5-(isoxazol-5-yl)-N-(3-methoxy-4-morpholinophenyl)-1H-pyrazolo[4,3-d]pyrimidin-7-amine; 1-(4-(4-((5-(isoxazol-3-yl)-1H-pyrazolo[4,3-d]pyrimidin-7-yl)amino)phenyl)piperazin-1-yl)ethan-1-one; N-(3,4-dimethoxyphenyl)-5-(isoxazol-3-yl)-1H-pyrazolo[4,3-d]pyrimidin-7-amine; 5-(isoxazol-3-yl)-N-(4-morpholinophenyl)-1H-pyrazolo[4,3-d]pyrimidin-7-amine; N-(3-fluoro-4-morpholinophenyl)-5-(isoxazol-3-yl)-1H -pyrazolo[4,3-d]pyrimidin-7-amine; 5-(isoxazol-3-yl)-N-(3-methoxy-4-morpholinophenyl)-1H-pyrazolo[4,3-d]pyrimidin-7-amine; 5-(5-fluoro-1H-indazol-6-yl)-N-(4-morpholinophenyl)-1H-pyrazolo[4,3-d]pyrimidin-7-amine; N-(3,4-dimethoxyphenyl)-5-(tetrahydrofuran-2-yl)-1H-pyrazolo[4,3-d]pyrimidin-7-amine; N-(4-morpholinophenyl)-5-(tetrahydrofuran-3-yl)-1H-pyrazolo[4,3-d]pyrimidin-7-amine; N-(3,4-dimethoxyphenyl)-5-(tetrahydrofuran-3-yl)-1H-pyrazolo[4,3-d]pyrimidin-7-amine; N-(3,4-dimethoxyphenyl)-5-(tetrahydro-2H-pyran-4-yl)-1H-pyrazolo[4,3-d]pyrimidin-7-amine; N-(4-morpholinophenyl)-5-(tetrahydro-2H-pyran-4-yl)-1H-pyrazolo[4,3-d]pyrimidin-7-amine; N-(3,4-dimethoxyphenyl)-5-(1,4-dioxan-2-yl)-1H-pyrazolo[4,3-d]pyrimidin-7-amine; 5-(1,4-dioxan-2-yl)-N-(4-morpholinophenyl)-1H-pyrazolo[4,3-d]pyrimidin-7-amine; 5-((5-(1H-indazol-6-yl)-1H-pyrazolo[4,3-d]pyrimidin-7-yl)amino)-2-morpholinobenzonitrile; 5-(furan-2-yl)-N-(4-morpholinophenyl)-1H-pyrazolo[4,3-d]pyrimidin-7-amine; N-(3,4-dimethoxyphenyl)-5-(furan-2-yl)-1H-pyrazolo[4,3-d]pyrimidin-7-amine; 5-(1H-indazol-6-yl)-N-(4-nitrophenyl)-1H-pyrazolo[4,3-d]pyrimidin-7-amine; (4-methylpiperazin-1-yl)(4-((5-(3-nitrophenyl)-1H-pyrazolo[4,3-d]pyrimidin-7-yl)amino)phenyl)methanone; 5-(1-methyl-1H-imidazol-2-yl)-N-(4-morpholinophenyl)-1H-pyrazolo[4,3-d]pyrimidin-7-amine; 1-(4-(4-((5-(1-methyl-1H-imidazol-2-yl)-1H-pyrazolo[4,3-d]pyrimidin-7-yl)amino)phenyl)piperazin-1-yl)ethan-1-one; 5-(morpholinomethyl)-N-(4-morpholinophenyl)-1H-pyrazolo[4,3-d]pyrimidin-7-amine; 1-(4-(4-((5-(morpholinomethyl)-1H-pyrazolo[4,3-d]pyrimidin-7-yl)amino)phenyl)piperazin-1-yl)ethan-1-one; 5-(furan-3-yl)-N-(4-morpholinophenyl)-1H-pyrazolo[4,3-d]pyrimidin-7-amine; N-(3,4-dimethoxyphenyl)-5-(furan-3-yl)-1H-pyrazolo[4,3-d]pyrimidin-7-amine; 1-(4-(4-((5-(furan-3-yl)-1H-pyrazolo[4,3-d]pyrimidin-7-yl)amino)phenyl)piperazin-1-yl)ethan-1-one; N-(4-(4-(tert-butyl)piperazin-1-yl)phenyl)-5-(furan-3-yl)-1H-pyrazolo[4,3-d]pyrimidin-7-amine; 3-(4-((5-(furan-3-yl)-1H-pyrazolo[4,3-d]pyrimidin-7-yl)amino)phenyl)oxazolidin-2-one; 5-(1-methylcyclopropyl)-N-(4-morpholinophenyl)-1H-pyrazolo[4,3-d]pyrimidin-7-amine; 1-(4-(4-((5-(1-methylcyclopropyl)-1H-pyrazolo[4,3-d]pyrimidin-7-yl)amino)phenyl)piperazin-1-yl)ethan-1-one; 5-(2-methylcyclopropyl)-N-(4-morpholinophenyl)-1H-pyrazolo[4,3-d]pyrimidin-7-amine; 1-(4-(4-((5-(2-methylcyclopropyl)-1H-pyrazolo[4,3-d]pyrimidin-7-yl)amino)phenyl)piperazin-1-yl)ethan-1-one; 5-(2-methylcyclopropyl)-N-(1-(tetrahydro-2H-pyran-4-yl)-1H-pyrazol-4-yl)-1H-pyrazolo[4,3-d]pyrimidin-7-amine; 5-((dimethylamino)methyl)-N-(4-morpholinophenyl)-1H-pyrazolo[4,3-d]pyrimidin-7-amine; 5-(7-((4-morpholinophenyl)amino)-1H-pyrazolo[4,3-d]pyrimidin-5-yl)isoxazole-3-carboxylic acid; 5-(furan-3-yl)-N-(4-(4-(4-methylpiperazin-1-yl)piperidin-1-yl)phenyl)-1H-pyrazolo[4,3-d]pyrimidin-7-amine; 8-((5-(furan-3-yl)-1H-pyrazolo[4,3-d]pyrimidin-7-yl)amino)-4,5-dihydro-1H-benzo[b]azepin-2(3H)-one; 5-(furan-3-yl)-N-(6-(4-methylpiperazin-1-yl)pyridin-3-yl)-1H-pyrazolo[4,3-d]pyrimidin-7-amine; 5-(furan-3-yl)-N-(3-(methylsulfonyl)phenyl)-1H-pyrazolo[4,3-d]pyrimidin-7-amine; 5-(furan-3-yl)-N-(1-(tetrahydro-2H-pyran-4-yl)-1H-pyrazol-4-yl)-1H-pyrazolo[4,3-d]pyrimidin-7-amine; 1-(4-(4-((5-(furan-2-yl)-1H-pyrazolo[4,3-d]pyrimidin-7-yl)amino)phenyl)piperazin-1-yl)ethan-1-one; N-(4-(4-(tert-butyl)piperazin-1-yl)phenyl)-5-(furan-2-yl)-1H-pyrazolo[4,3-d]pyrimidin-7-amine; 8-((5-(furan-2-yl)-1H-pyrazolo[4,3-d]pyrimidin-7-yl)amino)-4,5-dihydro-1H-benzo[b]azepin-2(3H)-one; 5-(furan-2-yl)-N-(6-(4-methylpiperazin-1-yl)pyridin-3-yl)-1H-pyrazolo[4,3-d]pyrimidin-7-amine; 3-(4-((5-(furan-2-yl)-1H-pyrazolo[4,3-d]pyrimidin-7-yl)amino)phenyl)oxazolidin-2-one; 5-(furan-2-yl)-N-(3-(methylsulfonyl)phenyl)-1H-pyrazolo[4,3-d]pyrimidin-7-amine; 5-(furan-2-yl)-N-(1-(tetrahydro-2H-pyran-4-yl)-1H-pyrazol-4-yl)-1H-pyrazolo[4,3-d]pyrimidin-7-amine; 5-cyclopropyl-N-(1-(tetrahydro-2H-pyran-4-yl)-1H-pyrazol-4-yl)-1H-pyrazolo[4,3-d]pyrimidin-7-amine; 5-cyclobutyl-N-(1-(tetrahydro-2H-pyran-4-yl)-1H-pyrazol-4-yl)-1H-pyrazolo[4,3-d]pyrimidin-7-amine; 5-cyclobutyl-N-(4-morpholinophenyl)-1H-pyrazolo[4,3-d]pyrimidin-7-amine; 5-(1-methyl-1H-pyrazol-4-yl)-N-(4-morpholinophenyl)-1H-pyrazolo[4,3-d]pyrimidin-7-amine; 5-(1-methyl-1H-pyrazol-4-yl)-N-(1-(tetrahydro-2H-pyran-4-yl)-1H-pyrazol-4-yl)-1H-pyrazolo[4,3-d]pyrimidin-7-amine; N-(4-morpholinophenyl)-5-(1H-1,2,4-triazol-3-yl)-2H-pyrazolo[4,3-d]pyrimidin-7-amine; 5-(pyridazin-3-yl)-N-(1-(tetrahydro-2H-pyran-4-yl)-1H-pyrazol-4-yl)-1H-pyrazolo[4,3-d]pyrimidin-7-amine; N-(4-morpholinophenyl)-5-(pyridazin-3-yl)-1H-pyrazolo[4,3-d]pyrimidin-7-amine; N-(6-morpholinopyridin-3-yl)-5-(pyridin-3-yl)-1H-pyrazolo[4,3-d]pyrimidin-7-amine; 5-(oxazol-4-yl)-N-(1-(tetrahydro-2H-pyran-4-yl)-1H-pyrazol-4-yl)-1H-pyrazolo[4,3-d]pyrimidin-7-amine; N-(1-(2-methoxyethyl)-1H-pyrazol-4-yl)-5-(oxazol-4-yl)-1H-pyrazolo[4,3-d]pyrimidin-7-amine; N-(1-(1-methylpiperidin-4-yl)-1H-pyrazol-4-yl)-5-(oxazol-4-yl)-1H-pyrazolo[4,3-d]pyrimidin-7-amine; 1-(4-(4-((5-(oxazol-4-yl)-1H-pyrazolo[4,3-d]pyrimidin-7-yl)amino)-1H-pyrazol-1-yl)piperidin-1-yl)ethan-1-one; 5-(1H-indazol-6-yl)-N-(1-(2-methoxyethyl)-1H-pyrazol-4-yl)-1H-pyrazolo[4,3-d]pyrimidin-7-amine; 5-(1H-indazol-6-yl)-N-(1-(1-methylpiperidin-4-yl)-1H-pyrazol-4-yl)-1H-pyrazolo[4,3-d]pyrimidin-7-amine; 1-(4-(4-((5-(1H-indazol-6-yl)-1H-pyrazolo[4,3-d]pyrimidin-7-yl)amino)-1H-pyrazol-1-yl)piperidin-1-yl)ethan-1-one; and 5-(1H-indazol-6-yl)-N-(1-(tetrahydro-2H-pyran-4-yl)-1H-pyrazol-4-yl)-1H-pyrazolo[4,3-d]pyrimidin-7-amine;

or a pharmaceutically acceptable salt, ester, solvate or hydrate or a pharmaceutically acceptable formulation thereof.

22. The compound of claim 1 selected from the group consisting of: 5-(1-methylcyclopropyl)-N-(4-morpholinophenyl)-1H-pyrazolo[4,3-d]pyrimidin-7-amine; 1-(4-(4-((5-(1-methylcyclopropyl)-1H-pyrazolo[4,3-d]pyrimidin-7-yl)amino)phenyl)piperazin-1-yl)ethan-1-one; 5-(2-methylcyclopropyl)-N-(4-morpholinophenyl)-1H-pyrazolo[4,3-d]pyrimidin-7-amine; 1-(4-(4-((5-(2-methylcyclopropyl)-1H-pyrazolo[4,3-d]pyrimidin-7-yl)amino)phenyl)piperazin-1-yl)ethan-1-one; 5-(2-methylcyclopropyl)-N-(1-(tetrahydro-2H-pyran-4-yl)-1H-pyrazol-4-yl)-1H-pyrazolo[4,3-d]pyrimidin-7-amine; 5-((dimethylamino)methyl)-N-(4-morpholinophenyl)-1H-pyrazolo[4,3-d]pyrimidin-7-amine; 5-(7-((4-morpholinophenyl)amino)-1H-pyrazolo[4,3-d]pyrimidin-5-yl)isoxazole-3-carboxylic acid; 5-(furan-3-yl)-N-(4-(4-(4-methylpiperazin-1-yl)piperidin-1-yl)phenyl)-1H-pyrazolo[4,3-d]pyrimidin-7-amine; 8-((5-(furan-3-yl)-1H-pyrazolo[4,3-d]pyrimidin-7-yl)amino)-4,5-dihydro-1H-benzo[b]azepin-2(3H)-one; 5-(furan-3-yl)-N-(6-(4-methylpiperazin-1-yl)pyridin-3-yl)-1H-pyrazolo[4,3-d]pyrimidin-7-amine; 5-(furan-3-yl)-N-(3-(methylsulfonyl)phenyl)-1H-pyrazolo[4,3-d]pyrimidin-7-amine; 5-(furan-3-yl)-N-(1-(tetrahydro-2H-pyran-4-yl)-1H-pyrazol-4-yl)-1H-pyrazolo[4,3-d]pyrimidin-7-amine; 1-(4-(4-((5-(furan-2-yl)-1H-pyrazolo[4,3-d]pyrimidin-7-yl)amino)phenyl)piperazin-1-yl)ethan-1-one; N-(4-(4-(tert-butyl)piperazin-1-yl)phenyl)-5-(furan-2-yl)-

1H-pyrazolo[4,3-d]pyrimidin-7-amine; 8-((5-(furan-2-yl)-1H-pyrazolo[4,3-d]pyrimidin-7-yl)amino)-4,5-dihydro-1H-benzo[b]azepin-2(3H)-one; 5-(furan-2-yl)-N-(6-(4-methylpiperazin-1-yl)pyridin-3-yl)-1H-pyrazolo[4,3-d]pyrimidin-7-amine; 3-(4-((5-(furan-2-yl)-1H-pyrazolo[4,3-d]pyrimidin-7-yl)amino)phenyl)oxazolidin-2-one; 5-(furan-2-yl)-N-(3-(methylsulfonyl)phenyl)-1H-pyrazolo[4,3-d]pyrimidin-7-amine; 5-(furan-2-yl)-N-(1-(tetrahydro-2H-pyran-4-yl)-1H-pyrazol-4-yl)-1H-pyrazolo[4,3-d]pyrimidin-7-amine; 5-cyclopropyl-N-(1-(tetrahydro-2H-pyran-4-yl)-1H-pyrazol-4-yl)-1H-pyrazolo[4,3-d]pyrimidin-7-amine; 5-cyclobutyl-N-(1-(tetrahydro-2H-pyran-4-yl)-1H-pyrazol-4-yl)-1H-pyrazolo[4,3-d]pyrimidin-7-amine; 5-cyclobutyl-N-(4-morpholinophenyl)-1H-pyrazolo[4,3-d]pyrimidin-7-amine; 5-(1-methyl-1H-pyrazol-4-yl)-N-(4-morpholinophenyl)-1H-pyrazolo[4,3-d]pyrimidin-7-amine; 5-(1-methyl-1H-pyrazol-4-yl)-N-(1-(tetrahydro-2H-pyran-4-yl)-1H-pyrazol-4-yl)-1H-pyrazolo[4,3-d]pyrimidin-7-amine; N-(4-morpholinophenyl)-5-(1H-1,2,4-triazol-3-yl)-2H-pyrazolo[4,3-d]pyrimidin-7-amine; 5-(pyridazin-3-yl)-N-(1-(tetrahydro-2H-pyran-4-yl)-1H-pyrazol-4-yl)-1H-pyrazolo[4,3-d]pyrimidin-7-amine; N-(4-morpholinophenyl)-5-(pyridazin-3-yl)-1H-pyrazolo[4,3-d]pyrimidin-7-amine; N-(4-morpholinophenyl)-5-(pyridin-3-yl)-2H-pyrazolo[4,3-d]pyrimidin-7-amine; 5-(oxazol-4-yl)-N-(1-(tetrahydro-2H-pyran-4-yl)-1H-pyrazol-4-yl)-1H-pyrazolo[4,3-d]pyrimidin-7-amine; N-(1-(2-methoxyethyl)-1H-pyrazol-4-yl)-5-(oxazol-4-yl)-1H-pyrazolo[4,3-d]pyrimidin-7-amine; N-(1-(1-methylpiperidin-4-yl)-1H-pyrazol-4-yl)-5-(oxazol-4-yl)-1H-pyrazolo[4,3-d]pyrimidin-7-amine; 1-(4-(4-((5-(oxazol-4-yl)-1H-pyrazolo[4,3-d]pyrimidin-7-yl)amino)-1H-pyrazol-1-yl)piperidin-1-yl)ethan-1-one; 5-(1H-indazol-6-yl)-N-(1-(2-methoxyethyl)-1H-pyrazol-4-yl)-1H-pyrazolo[4,3-d]pyrimidin-7-amine; 5-(1H-indazol-6-yl)-N-(1-(1-methylpiperidin-4-yl)-1H-pyrazol-4-yl)-1H-pyrazolo[4,3-d]pyrimidin-7-amine; 1-(4-(4-((5-(1H-indazol-6-yl)-1H-pyrazolo[4,3-d]pyrimidin-7-yl)amino)-1H-pyrazol-1-yl)piperidin-1-yl)ethan-1-one; 5-(1H-indazol-6-yl)-N-(1-(tetrahydro-2H-pyran-4-yl)-1H-pyrazol-4-yl)-1H-pyrazolo[4,3-d]pyrimidin-7-amine; N-(4-morpholinophenyl)-5-(pyridazin-4-yl)-1H-pyrazolo[4,3-d]pyrimidin-7-amine; 5-(1-methyl-1H-1,2,4-triazol-3-yl)-N-(4-morpholinophenyl)-2H-pyrazolo[4,3-d]pyrimidin-7-amine; 5-(1-methyl-1H-pyrazol-3-yl)-N-(4-morpholinophenyl)-1H-pyrazolo[4,3-d]pyrimidin-7-amine; 5-(1-methyl-1H-pyrazol-3-yl)-N-(1-(tetrahydro-2H-pyran-4-yl)-1H-pyrazol-4-yl)-1H-pyrazolo[4,3-d]pyrimidin-7-amine; 2-(4-((5-cyclopropyl-1H-pyrazolo[4,3-d]pyrimidin-7-yl)amino)-1H-pyrazol-1-yl)-2-methylpropanenitrile; 5-(1H-indazol-5-yl)-N-(1-(tetrahydro-2H-pyran-4-yl)-1H-pyrazol-4-yl)-1H-pyrazolo[4,3-d]pyrimidin-7-amine; 5-(1H-indazol-5-yl)-N-(4-morpholinophenyl)-1H-pyrazolo[4,3-d]pyrimidin-7-amine; 1-(4-(4-((5-isopropyl-1H-pyrazolo[4,3-d]pyrimidin-7-yl)amino)phenyl)piperazin-1-yl)ethan-1-one; 5-isopropyl-N-(4-morpholinophenyl)-1H-pyrazolo[4,3-d]pyrimidin-7-amine; 5-isopropyl-N-(1-(tetrahydro-2H-pyran-4-yl)-1H-pyrazol-4-yl)-1H-pyrazolo[4,3-d]pyrimidin-7-amine; (2-fluoro-4-((5-isopropyl-1H-pyrazolo[4,3-d]pyrimidin-7-yl)amino)phenyl)(morpholino)methanone; 5-isopropyl-N-(1-(1-methylpiperidin-4-yl)-1H-pyrazol-4-yl)-1H-pyrazolo[4,3-d]pyrimidin-7-amine; 5-isopropyl-N-(1-(2-methoxyethyl)-1H-pyrazol-4-yl)-1H-pyrazolo[4,3-d]pyrimidin-7-amine; 1-(4-(4-((5-isopropyl-1H-pyrazolo[4,3-d]pyrimidin-7-yl)amino)-1H-pyrazol-1-yl)piperidin-1-yl)ethan-1-one; 1-(4-(4-((5-(1-methyl-1H-pyrazolo[4,3-d]pyrimidin-7-yl)amino)phenyl)piperazin-1-yl)ethan-1-one; N-(1-(2-methoxyethyl)-1H-pyrazol-4-yl)-5-(1-methyl-1H-pyrazol-4-yl)-1H-pyrazolo[4,3-d]pyrimidin-7-amine; 1-(4-(4-((5-(1-methyl-1H-pyrazol-4-yl)-1H-pyrazolo[4,3-d]pyrimidin-7-yl)amino)-1H-pyrazol-1-yl)piperidin-1-yl)ethan-1-one; 5-(1-methyl-1H-pyrazol-4-yl)-N-(1-(1-methylpiperidin-4-yl)-1H-pyrazol-4-yl)-1H-pyrazolo[4,3-d]pyrimidin-7-amine; 5-cyclobutyl-N-(1-(2-methoxyethyl)-1H-pyrazol-4-yl)-1H-pyrazolo[4,3-d]pyrimidin-7-amine; 1-(4-(4-((5-cyclobutyl-1H-pyrazolo[4,3-d]pyrimidin-7-yl)amino)phenyl)piperazin-1-yl)ethan-1-one; (4-((5-cyclobutyl-1H-pyrazolo[4,3-d]pyrimidin-7-yl)amino)-2-fluorophenyl)(morpholino)methanone; 5-cyclopropyl-N-(1-(2-methoxyethyl)-1H-pyrazol-4-yl)-1H-pyrazolo[4,3-d]pyrimidin-7-amine; 5-(furan-2-yl)-N-(1-(2-methoxyethyl)-1H-pyrazol-4-yl)-1H-pyrazolo[4,3-d]pyrimidin-7-amine; 1-(4-(4-((5-(furan-2-yl)-1H-pyrazolo[4,3-d]pyrimidin-7-yl)amino)-1H-pyrazol-1-yl)piperidin-1-yl)ethan-1-one; (2-fluoro-4-((5-(furan-2-yl)-1H-pyrazolo[4,3-d]pyrimidin-7-yl)amino)phenyl)(morpholino)methanone; 5-(furan-2-yl)-N-(1-(1-methylpiperidin-4-yl)-1H-pyrazol-4-yl)-1H-pyrazolo[4,3-d]pyrimidin-7-amine; 5-(furan-3-yl)-N-(1-(2-methoxyethyl)-1H-pyrazol-4-yl)-1H-pyrazolo[4,3-d]pyrimidin-7-amine; 1-(4-(4-((5-(furan-3-yl)-1H-pyrazolo[4,3-d]pyrimidin-7-yl)amino)-1H-pyrazol-1-yl)piperidin-1-yl)ethan-1-one; (2-fluoro-4-((5-(furan-3-yl)-1H-pyrazolo[4,3-d]pyrimidin-7-yl)amino)phenyl)(morpholino)methanone; 5-(furan-3-yl)-N-(1-(1-methylpiperidin-4-yl)-1H-pyrazol-4-yl)-1H-pyrazolo[4,3-d]pyrimidin-7-amine; 2-(4-((5-(furan-3-yl)-1H-pyrazolo[4,3-d]pyrimidin-7-yl)amino)-1H-pyrazol-1-yl)-2-methylpropanenitrile; 1-(4-(4-((5-cyclopropyl-1H-pyrazolo[4,3-d]pyrimidin-7-yl)amino)-1H-pyrazol-1-yl)piperidin-1-yl)ethan-1-one; 1-(4-(4-((5-cyclobutyl-1H-pyrazolo[4,3-d]pyrimidin-7-yl)amino)-1H-pyrazol-1-yl)piperidin-1-yl)ethan-1-one; 5-cyclobutyl-N-(1-(1-methylpiperidin-4-yl)-1H-pyrazol-4-yl)-1H-pyrazolo[4,3-d]pyrimidin-7-amine; 5-cyclopropyl-N-(1-(1-methylpiperidin-4-yl)-1H-pyrazol-4-yl)-1H-pyrazolo[4,3-d]pyrimidin-7-amine; (4-((5-cyclopropyl-1H-pyrazolo[4,3-d]pyrimidin-7-yl)amino)-2-fluorophenyl)(morpholino)methanone; 4-((5-cyclobutyl-1H-pyrazolo[4,3-d]pyrimidin-7-yl)amino)-1-methylpyridin-2(1H)-one; 4-((5-cyclopropyl-1H-pyrazolo[4,3-d]pyrimidin-7-yl)amino)-1-methylpyridin-2(1H)-one; 2-(4-((5-(furan-2-yl)-1H-pyrazolo[4,3-d]pyrimidin-7-yl)amino)-1H-pyrazol-1-yl)-2-methylpropanenitrile; N-(1-(tert-butyl)-1H-pyrazol-4-yl)-5-(furan-2-yl)-1H-pyrazolo[4,3-d]pyrimidin-7-amine; 1-(4-((5-(furan-2-yl)-1H-pyrazolo[4,3-d]pyrimidin-7-yl)amino)-1H-pyrazol-1-yl)cyclohexanecarbonitrile; 5-(furan-2-yl)-N-(1-isopropyl-1H-pyrazol-4-yl)-1H-pyrazolo[4,3-d]pyrimidin-7-amine; 5-(furan-2-yl)-N-(1-(3-methoxypropyl)-1H-pyrazol-4-yl)-1H-pyrazolo[4,3-d]pyrimidin-7-amine; methyl 3-(7-((1-(tetrahydro-2H-pyran-4-yl)-1H-pyrazol-4-yl)amino)-1H-pyrazolo[4,3-d]pyrimidin-5-yl)benzoate; 3-(7-((1-(tetrahydro-2H-pyran-4-yl)-1H-pyrazol-4-yl)amino)-1H-pyrazolo[4,3-d]pyrimidin-5-yl)benzoic acid; N-(1-(tert-butyl)-1H-pyrazol-4-yl)-5-(furan-3-yl)-1H-pyrazolo[4,3-d]pyrimidin-7-amine; 1-(4-((5-(furan-3-yl)-1H-pyrazolo[4,3-d]pyrimidin-7-yl)amino)-1H-pyrazol-1-yl)cyclohexanecarbonitrile; 5-(furan-3-yl)-N-(1-isopropyl-1H-pyrazol-4-yl)-1H-pyrazolo[4,3-d]pyrimidin-7-amine; 5-(furan-3-yl)-N-(1-(3-methoxypropyl)-1H-pyrazol-4-yl)-1H-pyrazolo[4,3-d]pyrimidin-7-amine; N-(1-(tert-butyl)-1H-pyrazol-4-yl)-5-cyclobutyl-1H-pyrazolo[4,3-d]pyrimidin-7-amine; 5-cyclobutyl-N-(1-isopropyl-1H-pyrazol-4-yl)-1H-pyrazolo[4,3-d]pyrimidin-7-amine; 5-cyclobutyl-N-(1-(3-methoxypropyl)-1H-pyrazol-4-yl)-1H-pyrazolo[4,3-d]pyrimidin-7- amine; 2-(4-((5-cyclobutyl-1H-pyrazolo[4,3-d]pyrimidin-7-yl)amino)-1H-pyrazol-1-yl)-2-methylpropanenitrile; 4-((5-cyclobutyl-1H-pyrazolo[4,3-d]pyrimidin-7-yl)amino)-1-(2-methoxyethyl)pyridin-2(1H)-one; (4-((5-cyclobutyl-1H-pyrazolo[4,3-d]pyrimidin-7-yl)amino)-3-methoxyphenyl)(morpholino)methanone; N-(1-(tert-butyl)-1H-pyrazol-4-yl)-5-cyclopropyl-1H-pyrazolo[4,3-d]pyrimidin-1-amine; 5-cyclopropyl-N-(1-isopropyl-1H-pyrazol-4-yl)-1H-pyrazolo[4,3-d]pyrimidin-7-amine; 5-cyclopropyl-N-(1-(3-methoxypropyl)-1H-pyrazol-4-yl)-1H-pyrazolo[4,3-d]pyrimidin-7-amine; 4-((5-cyclopropyl-1H-pyrazolo[4,3-d]pyrimidin-7-yl)amino)-1-(2-methoxyethyl)pyridin-2(1H)-one; (4-((5-cyclopropyl-1H-pyrazolo[4,3-d]pyrimidin-7-yl)amino)-3-methoxyphenyl)(morpholino)methanone; 5-cyclopropyl-N-(1-isobutyl-1H-pyrazol-4-yl)-1H-pyrazolo[4,3-d]pyrimidin-7-amine; 5-cyclobutyl-N-(1-isobutyl-1H-pyrazol-4-yl)-1H-pyrazolo[4,3-d]pyrimidin-7-amine; 5-cyclopropyl-N-(1,5-dimethyl-1H-pyrazol-4-yl)-1H-pyrazolo[4,3-d]pyrimidin-7-amine; 5-cyclopropyl-N-(1,3-dimethyl-1H-pyrazol-4-yl)-1H-pyrazolo[4,3-d]pyrimidin-7-amine; 1-(4-(5-((5-cyclopropyl-1H-pyrazolo[4,3-d]pyrimidin-7-yl)amino)pyridin-2-yl)piperazin-1-yl)ethan-1-one; 5-(furan-2-yl)-N-(1-isobutyl-1H-pyrazol-4-yl)-1H-pyrazolo[4,3-d]pyrimidin-7-amine; 2-(4-((5-(furan-2-yl)-1H-pyrazolo[4,3-d]pyrimidin-7-yl)amino)-1H-pyrazol-1-yl)ethan-1-ol; 5-(furan-3-yl)-N-(1-isobutyl-1H-pyrazol-4-yl)-1H-pyrazolo[4,3-d]pyrimidin-7-amine; 2-(4-((5-(furan-3-yl)-1H-pyrazolo[4,3-d]pyrimidin-7-yl)amino)-1H-pyrazol-1-yl)acetonitrile; 2-(4-((5-(furan-3-yl)-1H-pyrazolo[4,3-d]pyrimidin-7-yl)amino)-1H-pyrazol-1-yl)ethan-1-ol; N-(1-(tert-butyl)-1H-pyrazol-4-yl)-5-(oxazol-4-yl)-1H-pyrazolo[4,3-d]pyrimidin-7-amine; N-(1-isopropyl-1H-pyrazol-4-yl)-5-(oxazol-4-yl)-1H-pyrazolo[4,3-d]pyrimidin-7-amine; N-(1-(3-methoxypropyl)-1H-pyrazol-4-yl)-5-(oxazol-4-yl)-1H-pyrazolo[4,3-d]pyrimidin-7-amine; N-(1-isobutyl-1H-pyrazol-4-yl)-5-(oxazol-4-yl)-1H-pyrazolo[4,3-d]pyrimidin-7-amine; 2-(4-((5-(oxazol-4-yl)-1H-pyrazolo[4,3-d]pyrimidin-7-yl)amino)-1H-pyrazol-1-yl)ethan-1-ol; (4-((5-(furan-3-yl)-1H-pyrazolo[4,3-d]pyrimidin-7-yl)amino)-3-methoxyphenyl)(morpholino)methanone; N-(1-(tert-butyl)-1H-pyrazol-4-yl)-5-(oxazol-2-yl)-1H-pyrazolo[4,3-d]pyrimidin-7-amine; N-(1-isopropyl-1H-pyrazol-4-yl)-5-(oxazol-2yl)-1H-pyrazolo[4,3-d]pyrimidin-7-amine; N-(1-(3-methoxypropyl)-1H-pyrazol-4-yl)-5-(oxazol-2yl)-1H-pyrazolo[4,3-d]pyrimidin-7-amine; N-(1-isobutyl-1H-pyrazol-4-yl)-5-(oxazol-2-yl)-1H-pyrazolo[4,3-d]pyrimidin-7-amine; 2-(4-((5-(oxazol-2-yl)-1H-pyrazolo[4,3-d]pyrimidin-7-yl)amino)-1H-pyrazol-1-yl)ethan-1-ol; 5-(oxazol-2-yl)-N-(1-(tetrahydro-2H-pyran-4-yl)-1H-pyrazol-4-yl)-1H-pyrazolo[4,3-d]pyrimidin-7-amine; N-(1-(1-methylpiperidin-4-yl)-1H-pyrazol-4-yl)-5-(oxazol-2-yl)-1H-pyrazolo[4,3-d]pyrimidin-7-amine; N-(1-(2-methoxyethyl)-1H-pyrazol-4-yl)-5-(oxazol-2-yl)-1H-pyrazolo[4,3-d]pyrimidin-7-amine; 1-(4-(4-((5-(oxazol-2-yl)-1H-pyrazolo[4,3-d]pyrimidin-7-yl)amino)-1H-pyrazol-1-yl)piperidin-1-yl)ethan-1-one; N-(3-(7-((1-(tert-butyl)-1H-pyrazol-4-yl)amino)-1H-pyrazolo[4,3-d]pyrimidin-5-yl)phenyl)methanesulfonamide; N-(3-(7-((1-isopropyl-1H-pyrazol-4-yl)amino)-1H-pyrazolo[4,3-d]pyrimidin-5-yl)phenyl)methanesulfonamide; N-(3-(7-((1-(3-methoxypropyl)-1H-pyrazol-4-yl)amino)-1H-pyrazolo[4,3-d]pyrimidin-5-yl)phenyl)methanesulfonamide; N-(3-(7-((1-isobutyl-1H-pyrazol-4-yl)amino)-1H-pyrazolo[4,3-d]pyrimidin-5-yl)phenyl)methanesulfonamide; N-(3-(7-((1-(2-hydroxyethyl)-1H-pyrazol-4-yl)amino)-1H-pyrazolo[4,3-d]pyrimidin-5-yl)phenyl)methanesulfonamide; N-(3-(7-((1-(tetrahydro-2H-pyran-4-yl)-1H-pyrazol-4-yl)amino)-1H-pyrazolo[4,3-d]pyrimidin-5-yl)phenyl)methanesulfonamide; N-(3-(7-((1-(1-methylpiperidin-4-yl)-1H-pyrazol-4-yl)amino)-1H-pyrazolo[4,3-d]pyrimidin-5-yl)phenyl)methanesulfonamide; N-(3-(7-((1-(2-methoxyethyl)-1H-pyrazol-4-yl)amino)-1H-pyrazolo[4,3-d]pyrimidin-5-yl)phenyl)methanesulfonamide; N-(3-(7-((1-(1-acetylpiperidin-4-yl)-1H-pyrazol-4-yl)amino)-1H-pyrazolo[4,3-d]pyrimidin-5-yl)phenyl)methanesulfonamide; 5-cyclobutyl-N-(1-cyclopropyl-1H-pyrazol-4-yl)-1H-pyrazolo[4,3-d]pyrimidin-7-amine; 5-(tert-butyl)-N-(1-isobutyl-1H-pyrazol-4-yl)-1H-pyrazolo[4,3-d]pyrimidin-7-amine; 5-(tert-butyl)-N-(1-isopropyl-1H-pyrazol-4-yl)-1H-pyrazolo[4,3-d]pyrimidin-7-amine; 5-(tert-butyl)-N-(1-(3-methoxypropyl)-1H-pyrazol-4-yl)-1H-pyrazolo[4,3-d]pyrimidin-7-amine; 5-(tert-butyl)-N-(1,5-dimethyl-1H-pyrazol-4-yl)-1H-pyrazolo[4,3-d]pyrimidin-7-amine; 5-(tert-butyl)-N-(1,3-dimethyl-1H-pyrazol-4-yl)-1H-pyrazolo[4,3-d]pyrimidin-7-amine; 5-(tert-butyl)-N-(1-cyclopropyl-1H-pyrazol-4-yl)-1H-pyrazolo[4,3-d]pyrimidin-7-amine; 2-(4-((5-(tert-butyl)-1H-pyrazolo[4,3-d]pyrimidin-7-yl)amino)-1H-pyrazol-1-yl)-2-methylpropanenitrile; (4-((5-(tert-butyl)-1H-pyrazolo[4,3-d]pyrimidin-7-yl)amino)-3-methoxyphenyl)(morpholino)methanone; 3-((5-(furan-2-yl)-1H-pyrazolo[4,3-d]pyrimidin-7-yl)amino)-1-methylpyridin-2 (1H)-one; N-(1-(tert-butyl)-1H-pyrazol-3-yl)-5-(furan-2yl)-1H-pyrazolo[4,3-d]pyrimidin-7-amine; N-(1-cyclopropyl-1H-pyrazol-4-yl)-5-(furan-2-yl)-1H-pyrazolo[4,3-d]pyrimidin-7-amine; N-(4-bromo-1-methyl-1H-pyrazol-3-yl)-5-(furan-2yl)-1H-pyrazolo[4,3-d]pyrimidin-7-amine; N-(1,5-dimethyl-1H-pyrazol-4-yl)-5-(furan-2-yl)-1H-pyrazolo[4,3-d]pyrimidin-7-amine; N-(1,3-dimethyl-1H-pyrazol-4-yl)-5-(furan-2yl)-1H-pyrazolo[4,3-d]pyrimidin-7-amine; 5-cyclopropyl-N-(1-cyclopropyl-1H-pyrazol-4-yl)-1H-pyrazolo[4,3-d]pyrimidin-7-amine; 5-cyclopropyl-N-(1-(1-methoxy-2-methylpropan-2yl)-1H-pyrazol-4-yl)-1H-pyrazolo[4,3-d]pyrimidin-7-amine; 5-cyclopropyl-N-(1-(2-methoxyethyl)-3-methyl-1H-pyrazol-4-yl)-1H-pyrazolo[4,3-d]pyrimidin-7-amine; 5-cyclopropyl-N-(1-(2-methoxyethyl)-5-methyl-1H-pyrazol-4-yl)-1H-pyrazolo[4,3-d]pyrimidin-7-amine; 5-cyclopropyl-N-(1-isopropyl-3-methyl-1H-pyrazol-4-yl)-1H-pyrazolo[4,3-d]pyrimidin-7-amine; 5-cyclopropyl-N-(1-isopropyl-5-methyl-1H-pyrazol-4-yl)-1H-pyrazolo[4,3-d]pyrimidin-7-amine; 5-(furan-3-yl)-N-(1-(2-methoxyethyl)-3-methyl-1H-pyrazol-4-yl)-1H-pyrazolo[4,3-d]pyrimidin-7-amine; 5-(furan-3-yl)-N-(1-(2-methoxyethyl)-5-methyl-1H-pyrazol-4-yl)-1H-pyrazolo[4,3-d]pyrimidin-7-amine; 5-(furan-3-yl)-N-(1-(1-methoxy-2-methylpropan-2-yl)-1H-pyrazol-4-yl)-1H-pyrazolo[4,3-d]pyrimidin-7-amine; N-(1-(1-(tert-butyl)piperidin-4-yl)-1H-pyrazol-4-yl)-5-(furan-3-yl)-1H-pyrazolo[4,3-d]pyrimidin-7-amine; 5-(furan-3-yl)-N-(1-isopropyl-3-methyl-1H-pyrazol-4-yl)-1H-pyrazolo[4,3-d]pyrimidin-7-amine; 5-(furan-3-yl)-N-(1-isopropyl-5-methyl-1H-pyrazol-4-yl)-1H-pyrazolo[4,3-d]pyrimidin-7-amine; 5-(furan-3-yl)-N-(3-methyl-1-(tetrahydro-2H-pyran-4-yl)-1H-pyrazol-4-yl)-1H-pyrazolo[4,3-d]pyrimidin-7-amine; 5-(furan-3-yl)-N-(5-methyl-1-(tetrahydro-2H-pyran-4-yl)-1H-pyrazol-4-yl)-1H-pyrazolo[4,3-d]pyrimidin-7-amine; 1-cyclopropyl-4-((5-cyclopropyl-1H-pyrazolo[4,3-d]pyrimidin-7-yl)amino)pyridin-2(1H)-one; N-(5-chloro-1-isopropyl-1H-pyrazol-4-yl)-5-cyclopropyl-1H-pyrazolo[4,3-d]pyrimidin-7-amine; 5-(furan-2-yl)-N-(1-(2-methoxyethyl)-3-methyl-1H-pyrazol-4-yl)-1H-pyrazolo[4,3-d]pyrimidin-7-amine; 5-(furan-2-yl)-N-(1-(2-methoxyethyl)-5-methyl-1H-pyrazol-4-yl)-1H-pyrazolo[4,3-d]pyrimidin-7-amine; 5-(furan-2-yl)-N-(1-isopropyl-3-methyl-1H-pyrazol-4-yl)-1H-pyrazolo[4,3-d]pyrimidin-7- amine; 5-(furan-2-yl)-N-(1-isopropyl-5-methyl-1H-pyrazol-4-yl)-1H-pyrazolo[4,3-d]pyrimidin-7-amine; 5-(furan-2-yl)-N-(1-isopropyl-3-methoxy-1H-pyrazol-4-yl)-1H-pyrazolo[4,3-d]pyrimidin-7-amine; 5-(furan-2-yl)-N-(1-isopropyl-3-methyl-1H-pyrazol-4-yl)-1H-pyrazolo[4,3-d]pyrimidin-7-amine; 5-(furan-2-yl)-N-(1-isopropyl-5-methyl-1H-pyrazol-4-yl)-1H-pyrazolo[4,3-d]pyrimidin-7-amine; N-(1-(1-(tert-butyl)piperidin-4-yl)-3-methoxy-1H-pyrazol-4-yl)-5-(furan-2-yl)-1H-pyrazolo[4,3-d]pyrimidin-7-amine; 5-(furan-3-yl)-N-(1-isopropyl-3-methoxy-1H-pyrazol-4-yl)-1H-pyrazolo[4,3-d]pyrimidin-7-amine; 5-(furan-3-yl)-N-(1-isopropyl-3-methyl-1H-pyrazol-4-yl)-1H-pyrazolo[4,3-d]pyrimidin-7-amine; 5-(furan-3-yl)-N-(1-isopropyl-5-methyl-1H-pyrazol-4-yl)-1H-pyrazolo[4,3-d]pyrimidin-7-amine; N-(1-(1-(tert-butyl)piperidin-4-yl)-3-methoxy-1H-pyrazol-4-yl)-5-(furan-3-yl)-1H-pyrazolo[4,3-d]pyrimidin-7-amine; 5-cyclobutyl-N-(1-isopropyl-3-methoxy-1H-pyrazol-4-yl)-1H-pyrazolo[4,3-d]pyrimidin-7-amine; 5-cyclobutyl-N-(1-isopropyl-5-methoxy-1H-pyrazol-4-yl)-1H-pyrazolo[4,3-d]pyrimidin-7-amine; N-(5-chloro-1-isopropyl-1H-pyrazol-4-yl)-5-cyclobutyl-1H-pyrazolo[4,3-d]pyrimidin-7-amine; 5-cyclopropyl-N-(5-methyl-1-(tetrahydro-2H-pyran-4-yl)-1H-pyrazol-4-yl)-1H-pyrazolo[4,3-d]pyrimidin-7-amine; 5-cyclopropyl-N-(3-methyl-1-(tetrahydro-2H-pyran-4-yl)-1H-pyrazol-4-yl)-1H-pyrazolo[4,3-d]pyrimidin-7-amine; 5-cyclopropyl-N-(1-isopropyl-3-methoxy-1H-pyrazol-4-yl)-1H-pyrazolo[4,3-d]pyrimidin-7-amine; 5-cyclopropyl-N-(1-isopropyl-5-methoxy-1H-pyrazol-4-yl)-1H-pyrazolo[4,3-d]pyrimidin-7-amine; N-(1-(1-(tert-butyl)piperidin-4-yl)-3-methoxy-1H-pyrazol-4-yl)-5-cyclopropyl-1H-pyrazolo[4,3-d]pyrimidin-7-amine; N-(1-(1-(tert-butyl)piperidin-4-yl)-5-methoxy-1H-pyrazol-4-yl)-5-cyclopropyl-1H-pyrazolo[4,3-d]pyrimidin-7-amine; 3-(7-((3,4-dimethoxyphenyl)amino)-1H-pyrazolo[4,3-d]pyrimidin-5-yl)-N-(4-(oxazol-5-yl)phenyl)benzamide; N-(4-(2H-1,2,3-triazol-2-yl)phenyl)-3-(7-((3,4-dimethoxyphenyl)amino)-1H-pyrazolo[4,3-d]pyrimidin-5-yl)benzamide; 3-(7-((3,4-dimethoxyphenyl)amino)-1H-pyrazolo[4,3-d]pyrimidin-5-yl)-N-(4-(oxazol-2-yl)phenyl)benzamide; N-(5-chloro-1-(3-methoxypropyl)-1H-pyrazol-4-yl)-5-(furan-3-yl)-1H-pyrazolo[4,3-d]pyrimidin-7-amine; N-(5-chloro-1-isopropyl-1H-pyrazol-4-yl)-5-(furan-3-yl)-1H-pyrazolo[4,3-d]pyrimidin-7-amine; 5-cyclobutyl-N-(1-isopropyl-3-methyl-1H-pyrazol-4-yl)-1H-pyrazolo[4,3-d]pyrimidin-7-amine; 5-cyclobutyl-N-(1-isopropyl-5-methyl-1H-pyrazol-4-yl)-1H-pyrazolo[4,3-d]pyrimidin-7-amine; 5-cyclobutyl-N-(1-isopropyl-3,5-dimethyl-1H-pyrazol-4-yl)-1H-pyrazolo[4,3-d]pyrimidin-7-amine; N-(5-chloro-1-(3-methoxypropyl)-1H-pyrazol-4-yl)-5-cyclobutyl-1H-pyrazolo[4,3-d]pyrimidin-7-amine; N-(1-(1-(tert-butyl)piperidin-4-yl)-1H-pyrazol-4-yl)-5-cyclopropyl-1H-pyrazolo[4,3-d]pyrimidin-7-amine; 5-cyclopropyl-N-(1-isopropyl-3,5-dimethyl-1H-pyrazol-4-yl)-1H-pyrazolo[4,3-d]pyrimidin-7-amine; N-(5-chloro-1-(3-methoxypropyl)-1H-pyrazol-4-yl)-5-cyclopropyl-1H-pyrazolo[4,3-d]pyrimidin-7-amine; 5-cyclobutyl-N-(imidazo[1,2-a]pyridin-3-yl)-1H-pyrazolo[4,3-d]pyrimidin-7-amine; 5-(furan-2-yl)-N-(1-isopropyl-3,5-dimethyl-1H-pyrazol-4-yl)-1H-pyrazolo[4,3-d]pyrimidin-7-amine; N-(3-cyclopropyl-1-methyl-1H-pyrazol-5-yl)-5-(furan-2yl)-1H-pyrazolo[4,3-d]pyrimidin-7-amine; N-(5-chloro-1-(3-methoxypropyl)-1H-pyrazol-4-yl)-5-(furan-2yl)-1H-pyrazolo[4,3-d]pyrimidin-7-amine; 3-(4-((5-(furan-2-yl)-1H-pyrazolo[4,3-d]pyrimidin-7-yl)amino)-3-methoxyphenyl)oxazolidin-2-one; 5-(furan-3-yl)-N-(1-isopropyl-3,5-dimethyl-1H-pyrazol-4-yl)-1H-pyrazolo[4,3-d]pyrimidin-7-amine; N-(3-cyclopropyl-1-methyl-1H-pyrazol-5-yl)-5-(furan-3-yl)-1H-pyrazolo[4,3-d]pyrimidin-7-amine; 5-(furan-3-yl)-N-(3-methoxy-1-(3-methoxypropyl)-1H-pyrazol-4-yl)-1H-pyrazolo[4,3-d]pyrimidin-7-amine; 5-(furan-3-yl)-N-(imidazo[1,2-a]pyridin-3-yl)-1H-pyrazolo[4,3-d]pyrimidin-7-amine; 3-(4-((5-(furan-3-yl)-1H-pyrazolo[4,3-d]pyrimidin-7-yl)amino)-3-methoxyphenyl)oxazolidin-2-one; N-(5-chloro-1-(2-methoxyethyl)-1H-pyrazol-4-yl)-5-cyclobutyl-1H-pyrazolo[4,3-d]pyrimidin-7-amine; N-(5-chloro-1-(2-methoxyethyl)-1H-pyrazol-4-yl)-5-cyclopropyl-1H-pyrazolo[4,3-d]pyrimidin-7-amine; N-(1-(tert-butyl)-5-methyl-1H-pyrazol-4-yl)-5-cyclopropyl-1H-pyrazolo[4,3-d]pyrimidin-7-amine; 5-cyclopropyl-N-(imidazo[1,2-a]pyridin-3-yl)-1H-pyrazolo[4,3-d]pyrimidin-7-amine; 3-(4-((5-cyclobutyl-1H-pyrazolo[4,3-d]pyrimidin-7-yl)amino)-3-methoxyphenyl)oxazolidin-2-one; 5-(furan-2-yl)-N-(3-methoxy-1-(3-methoxypropyl)-1H-pyrazol-4-yl)-1H-pyrazolo[4,3-d]pyrimidin-7-amine; N-(5-chloro-1-isopropyl-1H-pyrazol-4-yl)-5-(furan-2-yl)-1H-pyrazolo[4,3-d]pyrimidin-7-amine; 5-(furan-2-yl)-N-(imidazo[1,2-a]pyridin-3-yl)-1H-pyrazolo[4,3-d]pyrimidin-7-amine; N-(5-chloro-1-(2-methoxyethyl)-1H-pyrazol-4-yl)-5-(furan-2yl)-1H-pyrazolo[4,3-d]pyrimidin-7-amine; N-(1-(tert-butyl)-5-methyl-1H-pyrazol-4-yl)-5-(oxazol-4-yl)-1H-pyrazolo[4,3-d]pyrimidin-7-amine; N-(5-chloro-1-(2-methoxyethyl)-1H-pyrazol-4-yl)-5-(oxazol-4-yl)-1H-pyrazolo[4,3-d]pyrimidin-7-amine; N-(5-chloro-1-isopropyl-1H-pyrazol-4-yl)-5-(oxazol-4-yl)-1H-pyrazolo[4,3-d]pyrimidin-7-amine; N-(1-isopropyl-5-methyl-1H-pyrazol-4-yl)-5-(oxazol-4-yl)-1H-pyrazolo[4,3-d]pyrimidin-7-amine; N-(1-(tert-butyl)-5-methyl-1H-pyrazol-4-yl)-5-(oxazol-2yl)-1H-pyrazolo[4,3-d]pyrimidin-7-amine; N-(5-chloro-1-(2-methoxyethyl)-1H-pyrazol-4-yl)-5-(oxazol-2-yl)-1H-pyrazolo[4,3-d]pyrimidin-7-amine; N-(5-chloro-1-isopropyl-1H-pyrazol-4-yl)-5-(oxazol-2-yl)-1H-pyrazolo[4,3-d]pyrimidin-7-amine; N-(1-isopropyl-5-methyl-1H-pyrazol-4-yl)-5-(oxazol-2yl)-1H-pyrazolo[4,3-d]pyrimidin-7-amine; 6-((5-(furan-3-yl)-1H-pyrazolo[4,3-d]pyrimidin-7-yl)amino)-1,3-dimethylpyrimidine-2,4(1H,3H)-dione; N-(5-chloro-1-(2-methoxyethyl)-1H-pyrazol-4-yl)-5-(furan-3-yl)-1H-pyrazolo[4,3-d]pyrimidin-7-amine; N-(1-(2-fluoroethyl)-1H-pyrazol-4-yl)-5-(furan-3-yl)-1H-pyrazolo[4,3-d]pyrimidin-7-amine; 5-cyclopropyl-N-(1-(2-fluoroethyl)-1H-pyrazol-4-yl)-1H-pyrazolo[4,3-d]pyrimidin-7-amine; 5-cyclobutyl-N-(1-(2-fluoroethyl)-1H-pyrazol-4-yl)-1H-pyrazolo[4,3-d]pyrimidin-7-amine; N-(5-chloro-1-(piperidin-4-yl)-1H-pyrazol-4-yl)-5-cyclobutyl-1H-pyrazolo[4,3-d]pyrimidin-7-amine; (4-((5-(furan-2-yl)-1H-pyrazolo[4,3-d]pyrimidin-7-yl)amino)-3-methoxyphenyl)(morpholino)methanone; 6-((5-(furan-2-yl)-1H-pyrazolo[4,3-d]pyrimidin-7-yl)amino)-1,3-dimethylpyrimidine-2,4(1H,3H)-dione; N-(1-(2-fluoroethyl)-1H-pyrazol-4-yl)-5-(furan-2-yl)-1H-pyrazolo[4,3-d]pyrimidin-7-amine; N-(5-chloro-1-(tetrahydro-2H-pyran-4-yl)-1H-pyrazol-4-yl)-5-(furan-2-yl)-1H-pyrazolo[4,3-d]pyrimidin-7-amine; 1-(4-((5-(furan-2-yl)-1H-pyrazolo[4,3-d]pyrimidin-7-yl)amino)-1H-pyrazol-1-yl)-2-methylpropan-2-ol; 5-cyclopropyl-N-(2-fluoro-4-morpholinophenyl)-1H-pyrazolo[4,3-d]pyrimidin-7-amine; 5-cyclopropyl-N-(2,3-dimethylphenyl)-1H-pyrazolo[4,3-d]pyrimidin-7-amine; 5-cyclopropyl-N-(2-methyl-4-morpholinophenyl)-1H-pyrazolo[4,3-d]pyrimidin-7-amine; 5-cyclopropyl-N-(2-methyl-4-(4-methylpiperazin-1-yl)phenyl)-1H-pyrazolo[4,3-d]pyrimidin-7-amine; 5-cyclopropyl-N-(1-(2,2,2-trifluoroethyl)-1H-pyrazol-4-yl)-1H-pyrazolo[4,3-d]pyrimidin-7-amine; 5-(furan-3-yl)-N-(1-(2,2,2-trifluoroethyl)-1H-pyrazol-4-yl)-1H-pyrazolo[4,3-d]pyrimidin-7-amine; 5-(furan-3-yl)-N-(2-methyl-4- morpholinophenyl)-1H-pyrazolo[4,3-d]pyrimidin-7-amine; 5-(furan-2-yl)-N-(1-(2,2,2-trifluoroethyl)-1H-pyrazol-4-yl)-1H-pyrazolo[4,3-d]pyrimidin-7-amine; 5-(furan-2-yl)-N-(2-methyl-4-morpholinophenyl)-1H-pyrazolo[4,3-d]pyrimidin-7-amine; 5-(furan-2-yl)-N-(2-methyl-4-(4-methylpiperazin-1-yl)phenyl)-1H-pyrazolo[4,3-d]pyrimidin-7-amine; 4-((5-(furan-2-yl)-1H-pyrazolo[4,3-d]pyrimidin-7-yl)amino)-1-isopropyl-1H-pyrazole-5-carbonitrile; 5-(furan-2-yl)-N-(1-(2-methoxyethyl)-3-(trifluoromethyl)-1H-pyrazol-4-yl)-1H-pyrazolo[4,3-d]pyrimidin-7-amine; 5-(furan-2-yl)-N-(1-(2-methoxyethyl)-5-(trifluoromethyl)-1H-pyrazol-4-yl)-1H-pyrazolo[4,3-d]pyrimidin-7-amine; 5-(1-isobutyl-1H-pyrazol-4-yl)-N-(4-morpholinophenyl)-1H-pyrazolo[4,3-d]pyrimidin-7-amine; (3-methoxy-4-((5-propyl-1H-pyrazolo[4,3-d]pyrimidin-7-yl)amino)phenyl)(morpholino)methanone; N-(3,4-dimethoxyphenyl)-5-propyl-1H-pyrazolo[4,3-d]pyrimidin-7-amine; N-(4-morpholinophenyl)-5-propyl-1H-pyrazolo[4,3-d]pyrimidin-7-amine; (4-((5-cycloheptyl-1H-pyrazolo[4,3-d]pyrimidin-7-yl)amino)-3-methoxyphenyl)(morpholino)methanone; 5-cycloheptyl-N-(3,4-dimethoxyphenyl)-1H-pyrazolo[4,3-d]pyrimidin-7-amine; 5-cycloheptyl-N-(4-morpholinophenyl)-1H-pyrazolo[4,3-d]pyrimidin-7-amine; 2-(5-chloro-4-((5-cyclopropyl-1H-pyrazolo[4,3-d]pyrimidin-7-yl)amino)-1H-pyrazol-1-yl)ethan-1-ol; 5-cyclopropyl-N-(1-(2-methoxyethyl)-3-(trifluoromethyl)-1H-pyrazol-4-yl)-1H-pyrazolo[4,3-d]pyrimidin-7-amine; 5-cyclopropyl-N-(1-(2-methoxyethyl)-5-(trifluoromethyl)-1H-pyrazol-4-yl)-1H-pyrazolo[4,3-d]pyrimidin-7-amine; 5-(1-(2-methoxyethyl)-1H-pyrazol-4-yl)-N-(4-morpholinophenyl)-1H-pyrazolo[4,3-d]pyrimidin-7-amine; N-(4-morpholinophenyl)-5-(1H-pyrazol-4-yl)-1H-pyrazolo[4,3-d]pyrimidin-7-amine; 4-((5-(furan-3-yl)-1H-pyrazolo[4,3-d]pyrimidin-7-yl)amino)-1-isopropyl-1H-pyrazole-5-carbonitrile; 5-(furan-3-yl)-N-(1-(2-methoxyethyl)-3-(trifluoromethyl)-1H-pyrazol-4-yl)-1H-pyrazolo[4,3-d]pyrimidin-7-amine; 5-(furan-3-yl)-N-(1-(2-methoxyethyl)-5-(trifluoromethyl)-1H-pyrazol-4-yl)-1H-pyrazolo[4,3-d]pyrimidin-7-amine; N-(5-bromo-1-(2-methoxyethyl)-1H-pyrazol-4-yl)-5-(furan-3-yl)-1H-pyrazolo[4,3-d]pyrimidin-7-amine; N-(5-fluoro-1-(2-methoxyethyl)-1H-pyrazol-4-yl)-5-(furan-3-yl)-1H-pyrazolo[4,3-d]pyrimidin-7-amine; 5-cyclopropyl-N-(2-methyl-3-morpholinophenyl)-1H-pyrazolo[4,3-d]pyrimidin-7-amine; 5-cyclopropyl-N-(5-ethynyl-1-(2-methoxyethyl)-1H-pyrazol-4-yl)-1H-pyrazolo[4,3-d]pyrimidin-7-amine; N-(5-bromo-1-(2-methoxyethyl)-1H-pyrazol-4-yl)-5-(furan-2-yl)-1H-pyrazolo[4,3-d]pyrimidin-7-amine; N-(5-fluoro-1-(2-methoxyethyl)-1H-pyrazol-4-yl)-5-(furan-2-yl)-1H-pyrazolo[4,3-d]pyrimidin-7-amine; N4-(5-(furan-2-yl)-1H-pyrazolo[4,3-d]pyrimidin-7-yl)-1-(2-methoxyethyl)-N5,N5-dimethyl-1H-pyrazole-4,5-diamine; 5-(furan-2-yl)-N-(2-methyl-3-morpholinophenyl)-1H-pyrazolo[4,3-d]pyrimidin-7-amine; N-(1-cyclopropyl-1H-pyrazol-4-yl)-5-(3-methoxyphenyl)-1H-pyrazolo[4,3-d]pyrimidin-7-amine; N-(1-(1-(tert-butyl)piperidin-4-yl)-1H-pyrazol-4-yl)-5-(3-methoxyphenyl)-1H-pyrazolo[4,3-d]pyrimidin-7-amine; 5-(3-methoxyphenyl)-N-(1-(3-methoxypropyl)-1H-pyrazol-4-yl)-1H-pyrazolo[4,3-d]pyrimidin-7-amine; 5-(3-methoxyphenyl)-N-(1-(tetrahydro-2H-pyran-4-yl)-1H-pyrazol-4-yl)-1H-pyrazolo[4,3-d]pyrimidin-7-amine; 5-(benzo[d]thiazol-2-yl)-N-(1-cyclopropyl-1H-pyrazol-4-yl)-1H-pyrazolo[4,3-d]pyrimidin-7-amine; 5-(benzo[d]thiazol-2-yl)-N-(1-(1-(tert-butyl)piperidin-4-yl)-1H-pyrazol-4-yl)-1H-pyrazolo[4,3-d]pyrimidin-7-amine; 5-(benzo[d]thiazol-2-yl)-N-(1-(3-methoxypropyl)-1H-pyrazol-4-yl)-1H-pyrazolo[4,3-d]pyrimidin-7-amine; 5-(benzo[d]thiazol-2-yl)-N-(1-(tetrahydro-2H-pyran-4-yl)-1H-pyrazol-4-yl)-1H-pyrazolo[4,3-d]pyrimidin-7-amine; 5-(1H-indazol-6-yl)-N-(1-isopropyl-1H-pyrazol-4-yl)-1H-pyrazolo[4,3-d]pyrimidin-7-amine; N-(1-(tert-butyl)-1H-pyrazol-4-yl)-5-(1H-indazol-6-yl)-1H-pyrazolo[4,3-d]pyrimidin-7-amine; 2-(4-((5-(1H-indazol-6-yl)-1H-pyrazolo[4,3-d]pyrimidin-7-yl)amino)-1H-pyrazol-1-yl)-2-methylpropanenitrile; N-(1-(2-fluoroethyl)-1H-pyrazol-4-yl)-5-(1H-indazol-6-yl)-1H-pyrazolo[4,3-d]pyrimidin-7-amine; N-(1-cyclopropyl-1H-pyrazol-4-yl)-5-(1H-indazol-6-yl)-1H-pyrazolo[4,3-d]pyrimidin-7-amine; 5-(1H-indazol-6-yl)-N-(1-(3-methoxypropyl)-1H-pyrazol-4-yl)-1H-pyrazolo[4,3-d]pyrimidin-7-amine; N-(1-isopropyl-1H-pyrazol-4-yl)-5-(1-methyl-1H-pyrazol-4-yl)-1H-pyrazolo[4,3-d]pyrimidin-7-amine; 5-(1-isopropyl-1H-pyrazol-4-yl)-N-(4-morpholinophenyl)-1H-pyrazolo[4,3-d]pyrimidin-7-amine; 2-(4-(4-((5-(1H-indazol-6-yl)-1H-pyrazolo[4,3-d]pyrimidin-7-yl)amino)phenyl)piperazin-1-yl)ethan-1-ol; 5-(1H-indazol-6-yl)-N-(1-isobutyl-1H-pyrazol-4-yl)-1H-pyrazolo[4,3-d]pyrimidin-7-amine; 3-(7-((1-(3-methoxypropyl)-1H-pyrazol-4-yl)amino)-1H-pyrazolo[4,3-d]pyrimidin-5-yl)benzenesulfonamide; 3-(7-((1-(tetrahydro-2H-pyran-4-yl)-1H-pyrazol-4-yl)amino)-1H-pyrazolo[4,3-d]pyrimidin-5-yl)benzenesulfonamide; 3-(7-((1-isopropyl-1H-pyrazol-4-yl)amino)-1H-pyrazolo[4,3-d]pyrimidin-5-yl)benzenesulfonamide; 3-(7-((1-(1-acetylpiperidin-4-yl)-1H-pyrazol-4-yl)amino)-1H-pyrazolo[4,3-d]pyrimidin-5-yl)benzenesulfonamide; 3-(7-((1-isobutyl-1H-pyrazol-4-yl)amino)-1H-pyrazolo[4,3-d]pyrimidin-5-yl)benzenesulfonamide; N-(1-(3-methoxypropyl)-1H-pyrazol-4-yl)-5-(thiophen-2-yl)-1H-pyrazolo[4,3-d]pyrimidin-7-amine; N-(1-(tetrahydro-2H-pyran-4-yl)-1H-pyrazol-4-yl)-5-(thiophen-2-yl)-1H-pyrazolo[4,3-d]pyrimidin-7-amine; N-(1-isopropyl-1H-pyrazol-4-yl)-5-(thiophen-2-yl)-1H-pyrazolo[4,3-d]pyrimidin-7-amine; N-(1-isobutyl-1H-pyrazol-4-yl)-5-(thiophen-2-yl)-1H-pyrazolo[4,3-d]pyrimidin-7-amine; N-(1-(1-methylpiperidin-4-yl)-1H-pyrazol-4-yl)-5-(thiophen-2-yl)-1H-pyrazolo[4,3-d]pyrimidin-7-amine; 5-(3,5-dimethylisoxazol-4-yl)-N-(4-morpholinophenyl)-1H-pyrazolo[4,3-d]pyrimidin-7-amine; 5-(3-methylthiophen-2-yl)-N-(1-(tetrahydro-2H-pyran-4-yl)-1H-pyrazol-4-yl)-1H-pyrazolo[4,3-d]pyrimidin-7-amine; N-(1-(3-methoxypropyl)-1H-pyrazol-4-yl)-5-(1-methyl-1H-pyrazol-4-yl)-1H-pyrazolo[4,3-d]pyrimidin-7-amine; N-(1-isobutyl-1H-pyrazol-4-yl)-5-(1-methyl-1H-pyrazol-4-yl)-1H-pyrazolo[4,3-d]pyrimidin-7-amine; N-(4-morpholinophenyl)-5-(trifluoromethyl)-1H-pyrazolo[4,3-d]pyrimidin-7-amine; 5-(2,6-difluorophenyl)-N-(1-(tetrahydro-2H-pyran-4-yl)-1H-pyrazol-4-yl)-1H-pyrazolo[4,3-d]pyrimidin-7-amine; 5-(2,6-difluorophenyl)-N-(1-isobutyl-1H-pyrazol-4-yl)-1H-pyrazolo[4,3-d]pyrimidin-7-amine; N4-(5-(furan-3-yl)-1H-pyrazolo[4,3-d]pyrimidin-7-yl)-1-(2-methoxyethyl)-N5,N5-dimethyl-1H-pyrazole-4,5-diamine; 2-(4-(4-((5-(furan-3-yl)-1H-pyrazolo[4,3-d]pyrimidin-7-yl)amino)phenyl)piperazin-1-yl)ethan-1-ol; 1-(4-((5-(furan-3-yl)-1H-pyrazolo[4,3-d]pyrimidin-7-yl)amino)phenyl)piperidin-4-ol; 2-(4-((5-(benzo[d]oxazol-2-yl)-1H-pyrazolo[4,3-d]pyrimidin-7-yl)amino)-1H-pyrazol-1-yl)ethan-1-ol; 5-(benzo[d]oxazol-2-yl)-N-(1-(1-methylpiperidin-4-yl)-1H-pyrazol-4-yl)-1H-pyrazolo[4,3-d]pyrimidin-7-amine; 5-(benzo[d]oxazol-2-yl)-N-(1-(tetrahydro-2H-pyran-4-yl)-1H-pyrazol-4-yl)-1H-pyrazolo[4,3-d]pyrimidin-7-amine; 5-(1H-indazol-6-yl)-N-(1-(pyrrolidin-3-yl)-1H-pyrazol-4-yl)-1H-pyrazolo[4,3-d]pyrimidin-7-amine; N-(1-(1,3-dimethoxypropan-2-yl)-1H-pyrazol-4-yl)-5-(1H-indazol-6-yl)-1H-pyrazolo[4,3-d]pyrimidin-7-amine; 1-(4-((5-(1H-indazol-6-yl)-1H- pyrazolo[4,3-d]pyrimidin-7-yl)amino)-1H-pyrazol-1-yl)-2-methylpropan-2-ol; 1-(4-((5-(furan-2-yl)-1H-pyrazolo[4,3-d]pyrimidin-7-yl)amino)phenyl)piperidin-4-ol; 1-(4-((5-(furan-2-yl)-1H-pyrazolo[4,3-d]pyrimidin-7-yl)amino)-1H-pyrazol-1-yl)-2-methylpropan-2-ol; 2-(4-((5-(furan-2-yl)-1H-pyrazolo[4,3-d]pyrimidin-7-yl)amino)-1H-pyrazol-1-yl)-N,N-dimethylacetamide; tert-butyl 3-(4-((5-(furan-2-yl)-1H-pyrazolo[4,3-d]pyrimidin-7-yl)amino)-1H-pyrazol-1-yl)pyrrolidine-1-carboxylate; N-(1-cyclopropyl-1H-pyrazol-4-yl)-5-(furan-2-yl)-1H-pyrazolo[4,3-d]pyrimidin-7-amine; N-(1-(1,3-dimethoxypropan-2-yl)-1H-pyrazol-4-yl)-5-(furan-2-yl)-1H-pyrazolo[4,3-d]pyrimidin-7-amine; 5-(benzo[d]thiazol-2-yl)-N-(1-(2-methoxyethyl)-1H-pyrazol-4-yl)-1H-pyrazolo[4,3-d]pyrimidin-7-amine; 5-(benzo[d]thiazol-2yl)-N-(1-isobutyl-1H-pyrazol-4-yl)-1H-pyrazolo[4,3-d]pyrimidin-7-amine; 1-(4-(4-((5-(benzo[d]thiazol-2-yl)-1H-pyrazolo[4,3-d]pyrimidin-7-yl)amino)-1H-pyrazol-1-yl)piperidin-1-yl)ethan-1-one; 5-(benzo[d]thiazol-2-yl)-N-(1-(1-methylpiperidin-4-yl)-1H-pyrazol-4-yl)-1H-pyrazolo[4,3-d]pyrimidin-7-amine; 5-(1-benzyl-1H-pyrazol-4-yl)-N-(4-morpholinophenyl)-1H-pyrazolo[4,3-d]pyrimidin-7-amine; 2-(4-((5-cyclobutyl-1H-pyrazolo[4,3-d]pyrimidin-7-yl)amino)-1H-pyrazol-1-yl)-N,N-dimethylacetamide; 5-cyclobutyl-N-(1-(pyrrolidin-3-yl)-1H-pyrazol-4-yl)-1H-pyrazolo[4,3-d]pyrimidin-7-amine; 5-cyclobutyl-N-(1-(1,3-dimethoxypropan-2-yl)-1H-pyrazol-4-yl)-1H-pyrazolo[4,3-d]pyrimidin-7-amine; N-(1-(pyridin-2-yl)-1H-pyrazol-4-yl)-5-(3-(pyridin-3-yl)phenyl)-1H-pyrazolo[4,3-d]pyrimidin-7-amine; 5-(3-(pyridin-3-yl)phenyl)-N-(1-(pyrrolidin-3-yl)-1H-pyrazol-4-yl)-1H-pyrazolo[4,3-d]pyrimidin-7-amine; N,N-dimethyl-2-(4-((5-(3-(pyridin-3-yl)phenyl)-1H-pyrazolo[4,3-d]pyrimidin-7-yl)amino)-1H-pyrazol-1-yl)acetamide; N-(1-(1,3-dimethoxypropan-2-yl)-1H-pyrazol-4-yl)-5-(3-(pyridin-3-yl)phenyl)-1H-pyrazolo[4,3-d]pyrimidin-7-amine; N-(1-(1-(tert-butyl)piperidin-4-yl)-1H-pyrazol-4-yl)-5-(1H-indazol-6-yl)-1H-pyrazolo[4,3-d]pyrimidin-7-amine; 5-(1H-indazol-6-yl)-N-(1-(3-methylbutan-2-yl)-1H-pyrazol-4-yl)-1H-pyrazolo[4,3-d]pyrimidin-7-amine; 6-((5-(1H-indazol-6-yl)-1H-pyrazolo[4,3-d]pyrimidin-7-yl)amino)-4-methyl-2H-benzo[b][1,4]oxazin-3(4H)-one; 6-((5-(1H-indazol-6-yl)-1H-pyrazolo[4,3-d]pyrimidin-7-yl)amino)-4-ethyl-2H-benzo[b][1,4]oxazin-3(4H)-one; 5-(1H-indazol-6-yl)-N-(1-(pyridin-2-yl)-1H-pyrazol-4-yl)-1H-pyrazolo[4,3-d]pyrimidin-7-amine; 5-(bicyclo[4.1.0]heptan-7-yl)-N-(1-(tetrahydro-2H-pyran-4-yl)-1H-pyrazol-4-yl)-1H-pyrazolo[4,3-d]pyrimidin-7-amine; 5-(bicyclo[4.1.0]heptan-7-yl)-N-(1-(pyrrolidin-3-yl)-1H-pyrazol-4-yl)-1H-pyrazolo[4,3-d]pyrimidin-1-amine; 5-(bicyclo[4.1.0]heptan-7-yl)-N-(3-methoxy-4-morpholinophenyl)-1H-pyrazolo[4,3-d]pyrimidin-7-amine; 2-(4-((5-(1H-indazol-6-yl)-1H-pyrazolo[4,3-d]pyrimidin-7-yl)amino)-1H-pyrazol-1-yl)ethan-1-ol; 5-(1H-indazol-6-yl)-N-(1-(1-phenylethyl)-1H-pyrazol-4-yl)-1H-pyrazolo[4,3-d]pyrimidin-7-amine; N-(3-ethylphenyl)-5-(1H-indazol-6-yl)-1H-pyrazolo[4,3-d]pyrimidin-7-amine; (7-((5-(1H-indazol-6-yl)-1H-pyrazolo[4,3-d]pyrimidin-7-yl)amino)-3,4-dihydroquinolin-1(2H)-yl)(cyclopropyl)methanone; N-(3,4-dimethoxyphenyl)-5-(2-fluoro-6-methylphenyl)-1H-pyrazolo[4,3-d]pyrimidin-7-amine; 5-(2-fluoro-6-methylphenyl)-N-(3-methoxy-4-morpholinophenyl)-1H-pyrazolo[4,3-d]pyrimidin-7-amine; 5-(furan-3-yl)-N-(1-(3-methylbutan-2-yl)-1H-pyrazol-4-yl)-1H-pyrazolo[4,3-d]pyrimidin-7-amine; 5-(furan-3-yl)-N-(1-(tetrahydro-2H-pyran-3-yl)-1H-pyrazolo[4,3-d]pyrimidin-7-amine; 5-(furan-3-yl)-N-(1-(pyridin-2-yl)-1H-pyrazol-4-yl)-1H-pyrazolo[4,3-d]pyrimidin-7-amine; 4-ethyl-6-((5-(furan-3-yl)-1H-pyrazolo[4,3-d]pyrimidin-7-yl)amino)-2H-benzo[b][1,4]oxazin-3(4H)-one; 2-(4-((5-(furan-3-yl)-1H-pyrazolo[4,3-d]pyrimidin-7-yl)amino)-1H-pyrazol-1-yl)propanoic acid; 5-(furan-3-yl)-N-(1-(1-phenylethyl)-1H-pyrazol-4-yl)-1H-pyrazolo[4,3-d]pyrimidin-7-amine; 6-((5-(furan-3-yl)-1H-pyrazolo[4,3-d]pyrimidin-7-yl)amino)-4-methyl-2H-benzo[b][1,4]oxazin-3(4H)-one; N-(3-ethylphenyl)-5-(furan-3-yl)-1H-pyrazolo[4,3-d]pyrimidin-7-amine; cyclopropyl(7-((5-(furan-3-yl)-1H-pyrazolo[4,3-d]pyrimidin-7-yl)amino)-3,4-dihydroquinolin-1(2H)-yl)methanone; 5-(2,2-dimethylcyclopropyl)-N-(i-(tetrahydro-2H-pyran-4-yl)-1H-pyrazol-4-yl)-1H-pyrazolo[4,3-d]pyrimidin-7-amine; 5-(2,2-dimethylcyclopropyl)-N-(3-methoxy-4-morpholinophenyl)-1H-pyrazolo[4,3-d]pyrimidin-7-amine; 2-(4-((5-(1H-indazol-6-yl)-1H-pyrazolo[4,3-d]pyrimidin-7-yl)amino)-1H-pyrazol-1-yl)propanoic acid; 5-((5-(1H-indazol-6-yl)-1H-pyrazolo[4,3-d]pyrimidin-7-yl)amino)-1H-pyrazole-3-carboxylic acid; N-(1-(1-(tert-butyl)piperidin-4-yl)-1H-pyrazol-4-yl)-5-(4,5,6,7-tetrahydrobenzo[d]thiazol-2-yl)-1H-pyrazolo[4,3-d]pyrimidin-7-amine; N-(1-(tetrahydro-2H-pyran-4-yl)-1H-pyrazol-4-yl)-5-(4,5,6,7-tetrahydrobenzo[d]thiazol-2-yl)-1H-pyrazolo[4,3-d]pyrimidin-7-amine; 6-((5-cyclopropyl-1H-pyrazolo[4,3-d]pyrimidin-7-yl)amino)-4-methyl-2H-benzo[b][1,4]oxazin-3(4H)-one; 5-cyclopropyl-N-(1-(3-methylbutan-2-yl)-1H-pyrazol-4-yl)-1H-pyrazolo[4,3-d]pyrimidin-7-amine; 5-((5-cyclopropyl-1H-pyrazolo[4,3-d]pyrimidin-7-yl)amino)-1H-pyrazole-3-carboxylic acid; (4-((5-(2,6-difluorophenyl)-1H-pyrazolo[4,3-d]pyrimidin-7-yl)amino)phenyl)(4-methylpiperazin-1-yl)methanone; 2-(4-(4-((5-(2,6-difluorophenyl)-1H-pyrazolo[4,3-d]pyrimidin-7-yl)amino)phenyl)piperazin-1-yl)ethan-1-ol; 5-((5-(2,6-difluorophenyl)-1H-pyrazolo[4,3-d]pyrimidin-7-yl)amino)-2-morpholinobenzonitrile; cyclopropyl(7-((5-cyclopropyl-1H-pyrazolo[4,3-d]pyrimidin-7-yl)amino)-3,4-dihydroquinolin-1(2H)-yl)methanone; 2-(4-((5-cyclopropyl-1H-pyrazolo[4,3-d]pyrimidin-7-yl)amino)-1H-pyrazol-1-yl)propanoic acid; 5-(1H-indazol-6-yl)-N-(1-(tetrahydro-2H-pyran-3-yl)-1H-pyrazol-4-yl)-1H-pyrazolo[4,3-d]pyrimidin-7-amine; 2-((5-(1H-indazol-6-yl)-1H-pyrazolo[4,3-d]pyrimidin-7-yl)amino)phenol; N1-(5-(1H-indazol-6-yl)-1H-pyrazolo[4,3-d]pyrimidin-7-yl)-4,5-dimethoxybenzene-1,2-diamine; N-(3-methoxy-4-morpholinophenyl)-5-((1S,2S)-2-phenylcyclopropyl)-1H-pyrazolo[4,3-d]pyrimidin-7-amine; N-(3,4-dimethoxyphenyl)-5-((1S,2S)-2-phenylcyclopropyl)-1H-pyrazolo[4,3-d]pyrimidin-7-amine; N-(4-morpholinophenyl)-5-((1S,2S)-2-phenylcyclopropyl)-1H-pyrazolo[4,3-d]pyrimidin-7-amine; N-(3,4-dimethoxyphenyl)-5-(1-(3-methylbutan-2-yl)-1H-pyrazol-4-yl)-1H-pyrazolo[4,3-d]pyrimidin-7-amine; N-(3-methoxy-4-morpholinophenyl)-5-(1-(3-methylbutan-2-yl)-1H-pyrazol-4-yl)-1H-pyrazolo[4,3-d]pyrimidin-7-amine; 5-(2-chloro-6-fluorophenyl)-N-(3,4-dimethoxyphenyl)-1H-pyrazolo[4,3-d]pyrimidin-7-amine; 5-(2-chloro-6-fluorophenyl)-N-(3-methoxy-4-morpholinophenyl)-1H-pyrazolo[4,3-d]pyrimidin-7-amine; 5-(1H-indazol-6-yl)-N-(4-(phenylthio)phenyl)-1H-pyrazolo[4,3-d]pyrimidin-7-amine; 8-((5-(1H-indazol-6-yl)-1H-pyrazolo[4,3-d]pyrimidin-7-yl)amino)-4,5-dihydro-1H-benzo[b]azepin-2(3H)-one; 5-(1H-indazol-6-yl)-N-(1-(2,2,2-trifluoroethyl)-1H-pyrazol-4-yl)-1H-pyrazolo[4,3-d]pyrimidin-7-amine; 1-(4-((5-(1H-indazol-6-yl)-1H-pyrazolo[4,3-d]pyrimidin-7-yl)amino)phenyl)piperidin-4-ol; 6-((5-(1H-indazol-6-yl)-1H-pyrazolo[4,3-d]pyrimidin-7-yl)amino)-2H-benzo[b][1,4]oxazin-3(4H)-one; 6-((5-(1H-indazol-6-yl)-1H-pyrazolo[4,3-d]pyrimidin-7-yl)amino)-2H-benzo[b][1,4]thiazin-3(4H)-one;

8-((5-(2,6-difluorophenyl)-1H-pyrazolo[4,3-d]pyrimidin-7-yl)amino)-4,5-dihydro-1H-benzo[b]azepin-2(3H)-one; 1-(4-((5-(2,6-difluorophenyl)-1H-pyrazolo[4,3-d]pyrimidin-7-yl)amino)phenyl)piperidin-4-ol; N-(5-((5-(2,6-difluorophenyl)-1H-pyrazolo[4,3-d]pyrimidin-7-yl)amino)-2-methoxyphenyl)acetamide; 5-(2,6-difluorophenyl)-N-(1-(2,2,2-trifluoroethyl)-1H-pyrazol-4-yl)-1H-pyrazolo[4,3-d]pyrimidin-7-amine; 3-(7-((2-oxo-2,3,4,5-tetrahydro-1H-benzo[b]azepin-8-yl)amino)-1H-pyrazolo[4,3-d]pyrimidin-5-yl)benzenesulfonamide; 3-(7-((1-(2-hydroxyethyl)-1H-pyrazol-4-yl)amino)-1H-pyrazolo[4,3-d]pyrimidin-5-yl)benzenesulfonamide; 5-(2-(methylsulfonyl)phenyl)-N-(4-morpholinophenyl)-1H-pyrazolo[4,3-d]pyrimidin-7-amine; 8-((5-(2-(methylsulfonyl)phenyl)-1H-pyrazolo[4,3-d]pyrimidin-7-yl)amino)-4,5-dihydro-1H-benzo[b]azepin-2(3H)-one; N-(3-(7-((2-oxo-2,3,4,5-tetrahydro-1H-benzo[b]azepin-8-yl)amino)-1H-pyrazolo[4,3-d]pyrimidin-5-yl)phenyl)methanesulfonamide; 5-(3-aminophenyl)-N-(1-(tetrahydro-2H-pyran-4-yl)-1H-pyrazol-4-yl)-1H-pyrazolo[4,3-d]pyrimidin-7-amine; 5-(2-aminophenyl)-N-(1-(tetrahydro-2H-pyran-4-yl)-1H-pyrazol-4-yl)-2H-pyrazolo[4,3-d]pyrimidin-7-amine; 5-(2-amino-6-fluorophenyl)-N-(1-(tetrahydro-2H-pyran-4-yl)-1H-pyrazol-4-yl)-1H-pyrazolo[4,3-d]pyrimidin-7-amine; N-(1-(1-methylpiperidin-4-yl)-1H-pyrazol-4-yl)-5-(2-(methylsulfonyl)phenyl)-1H-pyrazolo[4,3-d]pyrimidin-7-amine; 5-(2-(methylsulfonyl)phenyl)-N-(1-(tetrahydro-2H-pyran-4-yl)-1H-pyrazol-4-yl)-1H-pyrazolo[4,3-d]pyrimidin-7-amine; N-(1-(1-methylpiperidin-4-yl)-1H-pyrazol-4-yl)-5-(thiazol-2-yl)-1H-pyrazolo[4,3-d]pyrimidin-7-amine; (5-((5-(1H-indazol-6-yl)-1H-pyrazolo[4,3-d]pyrimidin-7-yl)amino)-2-(4-methylpiperazin-1-yl)phenyl)methanol; N-(5-(2,6-difluorophenyl)-1H-pyrazolo[4,3-d]pyrimidin-7-yl)-3,4-dihydro-2H-benzo[b][1,4]oxazin-6-amine; N-(2-(4-acetylpiperazin-1-yl)-5-((5-(2,6-difluorophenyl)-1H-pyrazolo[4,3-d]pyrimidin-7-yl)amino)phenyl)acetamide; N-(3-chloro-4-(4-methylpiperazin-1-yl)phenyl)-5-(2,6-difluorophenyl)-1H-pyrazolo[4,3-d]pyrimidin-7-amine; 2,6-dichloro-4-((5-(2,6-difluorophenyl)-1H-pyrazolo[4,3-d]pyrimidin-7-yl)amino)phenol; and 5-(2,6-difluorophenyl)-N-(3-ethoxy-4-methoxyphenyl)-1H-pyrazolo[4,3-d]pyrimidin-7-amine.

23. A pharmaceutical composition comprising a compound of claim 1, 21 or 22 or a pharmaceutically acceptable hydrate, solvate or salt thereof, optionally in combination with a pharmaceutically acceptable carrier.

24. A method of treatment of a disease mediated by kinase-activity comprising the administration, to a patient in need thereof, of a therapeutically effective amount of a compound of claim 1, 21 or 22 or a pharmaceutical composition according to claim 23, wherein the kinese is selected from SYK (Spleen Tyrosine Kinase), LRRK2 (Leucine-rich repeat kinase 2), and/or Myosin light chain kinase (MYLK or MLCK) or mutants thereof and wherein the disease is selected from the group consisting of pruritus, eczema, asthma, rhinitis, dry eye, ocular inflammation, allergic conjunctivitis, vernal conjunctivitis, vernal keratoconjunctivitis, giant papillary conjunctivitis, fungal keratitis and uveitis.

25. The method of claim 24, wherein said treatment is systemic or topical.

26. The method of claim 25, wherein said topical administration is to the skin, the eye, by intranasal administration or by inhalation.

* * * * *